United States Patent
Yokota et al.

(10) Patent No.: US 10,196,363 B2
(45) Date of Patent: Feb. 5, 2019

(54) DIHYDROPYRIMIDIN-2-ONE COMPOUNDS AND MEDICAL USE THEREOF

(71) Applicant: JAPAN TOBACCO INC., Tokyo (JP)

(72) Inventors: Masahiro Yokota, Osaka (JP); Taku Ikenogami, Osaka (JP); Eiichi Watanabe, Osaka (JP); Noriyoshi Seki, Osaka (JP); Shingo Fujioka, Osaka (JP); Makoto Shiozaki, Osaka (JP); Masato Noguchi, Kanagawa (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 14/966,120

(22) Filed: Dec. 11, 2015

(65) Prior Publication Data

US 2016/0194290 A1 Jul. 7, 2016

(30) Foreign Application Priority Data

Dec. 12, 2014 (JP) ................................ 2014-251771

(51) Int. Cl.

| | |
|---|---|
| *C07D 239/22* | (2006.01) |
| *C07D 403/04* | (2006.01) |
| *A61K 31/505* | (2006.01) |
| *A61K 31/506* | (2006.01) |
| *A61K 31/695* | (2006.01) |
| *C07D 405/04* | (2006.01) |
| *C07F 7/12* | (2006.01) |
| *C07D 401/04* | (2006.01) |
| *C07D 405/10* | (2006.01) |
| *C07D 413/04* | (2006.01) |
| *C07F 7/08* | (2006.01) |
| *A61P 25/00* | (2006.01) |
| *A61P 27/00* | (2006.01) |
| *A61P 3/00* | (2006.01) |
| *A61P 29/00* | (2006.01) |
| *A61P 37/00* | (2006.01) |
| *A61P 17/00* | (2006.01) |
| *A61P 43/00* | (2006.01) |

(52) U.S. Cl.
CPC .......... *C07D 239/22* (2013.01); *A61K 31/505* (2013.01); *A61K 31/506* (2013.01); *A61K 31/695* (2013.01); *A61P 3/00* (2018.01); *A61P 17/00* (2018.01); *A61P 25/00* (2018.01); *A61P 27/00* (2018.01); *A61P 29/00* (2018.01); *A61P 37/00* (2018.01); *A61P 43/00* (2018.01); *C07D 401/04* (2013.01); *C07D 403/04* (2013.01); *C07D 405/04* (2013.01); *C07D 405/10* (2013.01); *C07D 413/04* (2013.01); *C07F 7/0812* (2013.01); *C07F 7/12* (2013.01)

(58) Field of Classification Search
CPC .. C07D 239/22; C07D 403/04; A61K 31/505; A61K 31/506

USPC ................................ 544/315, 318; 514/274
See application file for complete search history.

(56) References Cited

U.S. PATENT DOCUMENTS

| | | |
|---|---|---|
| 8,604,069 B2 | 12/2013 | Maeba et al. |
| 10,035,790 B2 | 7/2018 | Xu et al. |
| 2012/0322837 A1 | 12/2012 | Maeba et al. |
| 2014/0296306 A1 | 10/2014 | Maeba et al. |
| 2015/0175556 A1 | 6/2015 | Ambroise et al. |
| 2015/0266856 A1 | 9/2015 | Xu et al. |
| 2016/0137639 A1 | 5/2016 | Kotoku et al. |
| 2016/0346256 A1 | 12/2016 | Maeba et al. |

FOREIGN PATENT DOCUMENTS

| | | |
|---|---|---|
| CL | 201701466 A1 | 1/2018 |
| CL | 201701478 A1 | 1/2018 |
| CL | 201701511 A1 | 2/2018 |
| WO | WO 2012/147916 A1 | 11/2012 |
| WO | WO-2014/062938 A1 | 4/2014 |
| WO | WO 2014/065413 A1 | 5/2014 |
| WO | WO 2014/203044 A1 | 12/2014 |
| WO | WO-2016/091346 A1 | 6/2016 |
| WO | WO-2016/091997 A1 | 6/2016 |
| WO | WO-2016/094824 A1 | 6/2016 |

OTHER PUBLICATIONS

Yang et al., Targeting Th17 cells in autoimmune diseases, Trends in Pharmacological Sciences, vol. 35, No. 10, pp. 493-500, Oct. 2014.*

Dubernet et al., "Identification of New Nonsteroidal RORα Ligands; Related Structure-Activity Relationships and Docking Studies," *ACS Medicinal Chemistry Letters*, 4(6): 504-508 (2013).

(Continued)

*Primary Examiner* — Deepak R Rao
(74) *Attorney, Agent, or Firm* — Morrison & Foerster LLP

(57) ABSTRACT

A compound of Formula [I] or a pharmaceutically acceptable salt thereof:

[I]

wherein each symbol is defined as in the specification.

28 Claims, No Drawings

(56) References Cited

OTHER PUBLICATIONS

Kumar et al., "Design and synthesis of 6-methyl-2-oxo-1,2,3,4-tetrahydro-pyrimidine-5-carboxylic acid derivatives as PPARγ activators," *Bioorganic & Medicinal Chemistry Letters*, 17: 4613-4618 (2007).
Lauro et al., "Exploration of the dihydropyrimidine scaffold for development of new potential anti-inflammatory agents blocking prostaglandin E$_2$ synthase-1 enzyme (mPGES-1)," *European Journal of Medicinal Chemistry*, 80: 407-415 (2014).
Terracciano et al., "Structural Insights for the Optimization of Dihydropyrimidin-2(1H)-one Based mPGES-1 Inhibitors," *ACS Medicinal Chemistry Letters*, 6: 187-191 (2015).
Wissel et al., "Exploring the structure-activity relationships of ABCC2 modulators using a screening approach," *Bioorganic & Medicinal Chemistry*, 23: 3513-3525 (2015).
Japanese Patent Office, International Search Report in International Patent Application No. PCT/JP2015/084791 (dated Mar. 15, 2016).
Baeten et al., "Anti-Interleukin-17A Monoclonal Antibody Secukinumab in Treatment of Ankylosing Spondylitis: A Randomised, Double-Blind, Placebo-Controlled Trial," *Lancet*, 382(9906): 1705-1713 (2013).
Contreras-Ruiz et al., "Sjögren's syndrome associated dry eye in a mouse model is ameliorated by topical application of integrin α4 antagonist GW559090," *Experimental Eye Research*, 143: 1-8 (2016).
Crispin et al., "Interleukin-17-producing T cells in lupus," *Current Opinion in Rheumatology*, 22(5): 499-503 (2010).
De Wit et al., "RORγt inhibitors suppress T$_H$17 responses in inflammatory arthritis and inflammatory bowel disease," *J. Allergy Clin. Immunol.*, 137(3): 960-963 (Mar. 2016).
Emamaullee et al., "Inhibition of Th17 Cells Regulates Autoimmune Diabetes in NOD Mice," *Diabetes*, 58: 1302-1311 (2009).
Fauber et al., "Modulators of the Nuclear Receptor Retinoic Acid Receptor-Related Orphan Receptor-γ (RORγ or RORc)," *J. Med. Chem.*, 57: 5871-5892 (Feb. 6, 2014).
Fulton et al., "Attenuation of Acute Graft-versus-Host Disease in the Absence of the Transcription Factor RORγt," *Journal of Immunology*, 189(4): 1765-1772 (2012)
Hueber et al., "Effects of AIN457, a Fully Human Antibody to Interleukin-17A, on Psoriasis, Rheumatoid Arthritis, and Uveitis," *Science Translational Medicine*, 2(52):52ra72 (2010).
Isono et al., "Inhibiting RORγt/Th17 axis for autoimmune disorders," *Drug Discovery Today*, 19(8): 1205-1211 (Aug. 2014).
Ivanov et al., "The Orphan Nuclear Receptor RORγt Directs the Differentiation Program of Proinflammatory IL-17$^+$ T Helper Cells," *Cell*, 126(6): 1121-1133 (2006).
Ji et al., "Novel benzenediamine derivative FC99 ameliorates zymosan-induced arthritis by inhibiting RORγt expression and Th17 cell differentiation," *Acta Biochim. Biophys. Sin.*, 46(10): 829-836 (Sep. 3, 2014).
Kelchtermans et al., "Effector mechanisms of interleukin-17 in collagen-induced arthritis in the absence of interferon-γ and counteraction by interferon-γ," *Arthritis Research & Therapy*, 11(4): R122 (2009).
Kim et al., "Oleanolic acid suppresses ovalbumin-induced airway inflammation and Th2-mediated allergic asthma by modulating the transcription factors T-bet, GATA-3, RORγt and Foxp3 in asthmatic mice," *International Immunopharmacology*, 18: 311-324 (2014).
Lee et al., "Ocotillol, a Majonoside R2 Metabolite, Ameliorates 2,4,6-Trinitrobenzenesulfonic Acid-Induced Colitis in Mice by Restoring the Balance of Th17/Treg Cells," *J. Agric. Food Chem.*, 63: 7024-7031 (2015).
Leppkes et al., "RORγ-Expressing Th17 Cells Induce Murine Chronic Intestinal Inflammation via Redundant Effects of IL-17A and IL-17F," *Gastroenterology*, 136(1): 257-67 (2009).
Lin et al., "Targeting Th17 Cells with Small Molecules and Small Interference RNA," *Mediators of Inflammation*, 2015: Article ID 290657 (Nov. 30, 2015).
Mi et al., "Blocking IL-17A Promotes the Resolution of Pulmonary Inflammation and Fibrosis via TGF-β1-Dependent and—Independent Mechanisms," *Journal of Immunology*, 187: 3003-3014 (2011).
Sanford et al., "Secukinumab: first global approval," *Drugs*, 75(3): 329-338 (2015).
Son et al., "Effect of Retinoic Acid in a Mouse Model of Allergic Rhinitis," *Allergy Asthma Immunol. Res.*, 7(6): 590-598 (Nov. 2015).
Steinmetz et al., "The Th17-Defining Transcription Factor RORγt Promotes Glomerulonephritis," *Journal of the American Society of Nephrology*, 22(3): 472-483 (2011).
Takeda et al., "Retinoic Acid-Related Orphan Receptor γ (RORγ): A Novel Participant in the Diurnal Regulation of Hepatic Gluconeogenesis and Insulin Sensitivity," *PLOS Genetics*, 10(5): e1004331 (May 2014).
U.S. National Institutes of Health, "A Study of Efficacy and Safety of Ustekinumab in Patients With Primary Biliary Cirrhosis (PBC) Who Had an Inadequate Response to Ursodeoxycholic Acid," ClinicalTrials.gov information for Clinical Trials Identifier NCT01389973 (Apr. 2, 2015).
U.S. National Institutes of Health, "Efficacy and Safety Study of Sirukumab in Subjects With Polymyalgia Rheumatica," ClinicalTrials.gov information for Clinical Trials Identifier NCT02899026 (Dec. 9, 2016).
U.S. National Institutes of Health, "The Effects of a Single Intravenous Administration of Secukinumab (AIN457) or Canakinumab (ACZ885) in Dry Eye Patients," ClinicalTrials.gov information for Clinical Trials Identifier NCT01250171 (Dec. 4, 2012).
Wang et al., "Cyclosporine A Suppresses the Activation of the Th17 Cells in Patients with Primary Sjögren's Syndrome," *Iran J. Allergy Asthma Immunol.*, 14(2): 198-207 (Apr. 2015).
Xiao et al., "Small molecule RORγt antagonists inhibit T helper 17 cell transcriptional network by divergent mechanisms," *Immunity*, 40(4): 477-489 (Apr. 17, 2014).
European Extended Search Report dated Aug. 17, 2018 for EP Application No. 15866802.0 filed Dec. 11, 2015, six pages.

\* cited by examiner

DIHYDROPYRIMIDIN-2-ONE COMPOUNDS AND MEDICAL USE THEREOF

TECHNICAL FIELD

The present invention relates to dihydropyrimidin-2-one compounds or pharmaceutically acceptable salts thereof which have inhibitory actions against Retinoid-related Orphan Receptor gamma (RORγ), pharmaceutical compositions comprising the same, and medical uses thereof.

BACKGROUND ART

RORγ is a nuclear receptor which is important for the differentiation and activation of Th17 cells. RORγt is also known as a splice variant of RORγ (Nonpatent literature 1). RORγ and RORγt differ only in their N-terminal domains, and share the same ligand-binding domain and DNA-binding domain. It is reported that RORγ is expressed in other tissues besides Th17 cells (Nonpatent literature 1).

By inhibiting RORγ, the differentiation and activation of Th17 cells can be inhibited. IL-17 produced in Th17 cells is involved in the induction of a variety of chemokines, cytokines, metalloproteases and other inflammatory mediators, and the migration of neutrophil, hence, the inhibition of IL-17 may lead to the inhibition of such induction and migration (Nonpatent literatures 2 and 3).

RORγ in adipose tissues is related to the regulation of adipogenesis, and by inhibiting RORγ, insulin resistance can be improved (Nonpatent literature 4).

It is known that Th17 cells are involved in autoimmune diseases such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease; allergic diseases; dry eye; and fibrosis such as pulmonary fibrosis and primary biliary cirrhosis. It is known that adipose tissues are involved in metabolic diseases.

As for rheumatoid arthritis, for example, it is reported that the administration of anti-IL-17 antibody can improve swelling and joint destruction associated with collagen-induced arthritis (Nonpatent literature 5). Moreover, it is reported that swelling and joint destruction associated with collagen-induced arthritis can be improved in experiments using IL-17-deficient mice (Nonpatent literature 6).

As for psoriasis, it is reported that in a clinical trial, the administration of anti-IL-17 antibody is effective in treating psoriasis (Nonpatent literature 7). Anti IL-17 antibodies have been placed on the market for use in psoriasis (Nonpatent literature 8).

As for inflammatory bowel diseases such as Crohn's disease and ulcerative colitis, in a colitis model induced by the adaptive transfer of T-cells, the adaptive transfer of T-cells derived from RORγ-KO mice does not increase IL-17 in the mucosa, thereby the onset of colitis can be suppressed (Nonpatent literature 9).

As for multiple sclerosis, the disease state of mouse experimental autoimmune encephalomyelitis model which is an animal model of multiple sclerosis can be suppressed in RORγt-KO mice (Nonpatent literature 10).

As for systemic lupus erythematosus, it is reported that the onset of GBM nephritis model which is an animal model of glomerulonephritis can be inhibited in RORγt-KO mice (Nonpatent literature 11). Nephritis associated with SLE may also be suppressed (Nonpatent literature 12).

As for ankylosing spondylitis, it is reported that the administration of anti-IL-17 antibody is effective in treating ankylosing spondylitis (Nonpatent literature 13).

As for uveitis, it is reported that the administration of anti-IL-17 antibody is effective in treating uveitis associated with Behcet's disease, sarcoidosis and Harada disease (Nonpatent literature 7).

As for polymyalgia rheumatica, an efficacy of anti-IL-17 antibody in treatment of polymyalgia rheumatica is currently tested in a clinical trial.

As for type I diabetes, the disease state of NOD mice which is a type I diabetes model can be suppressed by the administration of anti-IL-17 antibody (Nonpatent literature 14).

As for graft versus host disease, it is reported in a mouse transplant model that a survival rate and a rejection in a host would be improved by transfecting RORγKO mouse-derived cells (Nonpatent literature 19).

As for allergic disease such as asthma, in OVA-sensitized model, the attenuated eosinophilic pulmonary inflammation, the reduced numbers of CD4+ lymphocytes, and the decrease of Th2 cytokines/chemokines level are exhibited in RORγ-KO mice, that is, the allergenic reaction can be inhibited in RORγ-KO mice (Nonpatent literature 15).

As for dry eye, it is reported that the Th17 cells increases in an animal model of dry eye, and an efficacy of anti-IL-17 antibody in dry eye patient is currently tested in a clinical trial (Nonpatent literature 16).

As for fibrosis, in a bleomycin-induced pulmonary fibrosis model which is an animal model of pulmonary fibrosis, the administration of anti-IL-17 antibody can inhibit inflammation and fibrosis in lung and can increase survival of the animal (Nonpatent literature 17).

As for primary biliary cirrhosis, it is reported that Th17 cells in the lesion area of a patient with a primary biliary cirrhosis increase, and an efficacy of an antibody to IL-23 which activates Th17 cells is currently tested in a clinical trial (Nonpatent literature 18).

As for metabolic disease, the insulin resistance which is induced by feeding a high-fat diet can be suppressed in RORγ KO mice (Nonpatent literature 4).

On the basis of these findings, RORγ antagonists are thought to be useful for preventing or treating autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease; allergic diseases such as asthma; dry eye; fibrosis such as pulmonary fibrosis and primary biliary cirrhosis; and metabolic diseases such as diabetes.

LIST OF NONPATENT LITERATURES

[Nonpatent literature 1] Anton. 2009 NRS 7, 1-32
[Nonpatent literature 2] Koenders et al. 2006 Ann Rheum Dis 65 (Suppl III), iii29-iii33
[Nonpatent literature 3] Carsten et al. 2007 J Allergy Clin Immunol 120, 247-54
[Nonpatent literature 4] Bettina et al. 2011 EMBO Mol Med 3, 1-15
[Nonpatent literature 5] Hilde et al. 2009 Arthritis Research & Therapy 11: R122
[Nonpatent literature 6] Susumu et al. 2003 J. Immnol 171, 6173-6177
[Nonpatent literature 7] Wolfgang et al. 2010 Sci Transl Med 2, 52ra72

[Nonpatent literature 8] Sanford et al. Drugs (2015) 75: 329-338
[Nonpatent literature 9] Moritz et al. 2009 Gastroenterology 136, 257-67
[Nonpatent literature 10] Ivaylo et al. 2006 Cell 126, 1121-1133
[Nonpatent literature 11] Oliver et al. 2011 J Am Soc Nephrol 22: 472-483
[Nonpatent literature 12] Jose et al. 2010 Curr Opin Rheumatol 22, 499-503
[Nonpatent literature 13] Dominique et al. Lancet 2013, 382(9906): 1705
[Nonpatent literature 14] Juliet et al. 2009 Diabetes 58: 1302-1311
[Nonpatent literature 15] Stephen et al. 2007 J. Immnol 178, 3208-18
[Nonpatent literature 16] ClinicalTrials.gov Identifier: NCT01250171
[Nonpatent literature 17] Su et al. 2011 J. Immnol 187
[Nonpatent literature 18] ClinicalTrials.gov Identifier: NCT01389973
[Nonpatent literature 19] Fulton L M et al. 2012 J. Immunol 15; 189(4): 1765-1772

SUMMARY OF INVENTION

An object of the present invention is to provide dihydropyrimidin-2-one compounds or pharmaceutically acceptable salts thereof which have inhibitory actions against RORγ, pharmaceutical compositions comprising the same, and medical uses thereof.

In particular, the present invention relates to compounds which would inhibit differentiation and activation of T helper 17 (Th17) cells by an inhibitory action for Retinoid-related Orphan Receptor gamma: RORγ and inhibit interleukin-17 (IL-17) production.

The present invention is also directed to provide an agent for preventing or treating autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease; allergic disease such as asthma; dry eye; fibrosis such as pulmonary fibrosis and primary biliary cirrhosis; and metabolic disease such as diabetes.

The present inventors have found dihydropyrimidin-2-one compounds which are RORγ antagonists, thereby have completed the present invention.

That is, the present invention includes the following embodiments.

[01] A compound of Formula [I] or a pharmaceutically acceptable salt thereof:

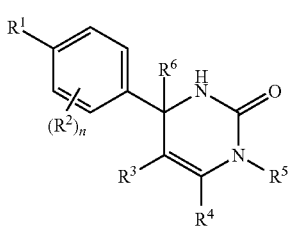

[I]

wherein
$R^1$ is
(1) $C_{4-8}$ alkyl,
(2) $C_{3-8}$ alkyl substituted with one hydroxy,
(3) $C_{4-8}$ alkyl substituted with one halogen,
(4) $C_{4-8}$ alkenyl,
(5) $C_{4-8}$ alkynyl,
(6) $C_{3-7}$ alkyl substituted with one trifluoromethyl,
(7) $C_{1-3}$ alkyl substituted with one substituent selected from Group $X^{a1}$,
(8) $C_{3-6}$ alkoxy,
(9) $C_{2-7}$ alkoxy substituted with one trifluoromethyl,
(10) $C_{1-3}$ alkoxy substituted with one substituent selected from Group $X^{a2}$,
(11) $C_{4-6}$ cycloalkyl,
(12) $C_{3-6}$ cycloalkyl substituted with the same or different one to two $C_{1-5}$ alkyl,
(13) $C_{3-6}$ cycloalkenyl optionally substituted with the same or different one to two $C_{1-4}$ alkyl,
(14) spiro $C_{6-11}$ cycloalkyl,
(15) $C_{1-3}$ alkoxycarbonyl,
(16) $C_{3-6}$ alkylsulfanyl,
(17) $C_{3-6}$ alkylsulfinyl,
(18) $C_{3-6}$ alkylsulfonyl,
(19) $C_{3-6}$ cycloalkylsulfanyl,
(20) $C_{3-6}$ cycloalkylsulfinyl,
(21) $C_{3-6}$ cycloalkylsulfonyl,
(22) cyclobutylidenemethyl,
(23) cyclopentylidenemethyl,
(24) cyclohexylidenemethyl optionally substituted with the same or different one to two $C_{1-3}$ alkyl,
(25) tetrahydropyran-4-ylidenemethyl,
(26) $C_{3-6}$ cycloalkyl substituted with one to the same two halogen, or
(27) $C_{5-6}$ cycloalkenyl substituted with one to the same two halogen;
Group $X^{a1}$ is
(a) $C_{3-6}$ cycloalkyl optionally substituted with the same or different one to three $C_{1-5}$ alkyl,
(b) $C_{3-6}$ cycloalkyl substituted with the same or different one to two halogen,
(c) phenyl,
(d) $C_{2-4}$ alkoxy,
(e) trimethylsilyl,
(f) carboxy, and
(g) tetrahydropyran-4-yl;
Group $X^{a2}$ is
(a) $C_{3-6}$ cycloalkyl,
(b) phenyl, and
(c) $C_{1-4}$ alkoxy;
$R^2$ is
(1) halogen,
(2) $C_{1-6}$ alkyl,
(3) $C_{1-3}$ alkoxy optionally substituted with phenyl, or
(4) trifluoromethyl;
n is an integer of 0, 1 or 2, provided that when n is 2, each $R^2$ may be different with each other;
or
$R^1$ and $R^2$ may combine together with the benzene ring to which they attach to form indanyl where the indanyl may be substituted with the same or different one to two $C_{1-6}$ alkyl;
$R^3$ is
(1) $-Y^b-COO-R^{30}$,
(2) $C_{1-6}$ alkyl optionally substituted with one hydroxy,
(3) $C_{1-6}$ alkyl substituted with one $C_{1-4}$ alkoxy,
(4) $C_{1-6}$ alkyl substituted with one $C_{1-4}$ alkylsulfonyl,
(5) $C_{3-6}$ cycloalkyl optionally substituted with the same or different one to three substituent(s) selected from Group $X^b$, (6) 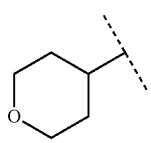

(7) 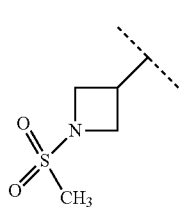

(8) phenyl, (9) 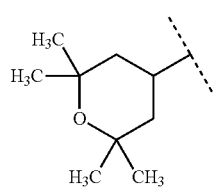

or
(10) $C_{2-3}$ alkenyl;
$Y^b$ is
(a) $C_{1-6}$ alkylene,
(b) $C_{3-6}$ cycloalkylene,
(c) phenylene,
(d) pyridinediyl or (e) 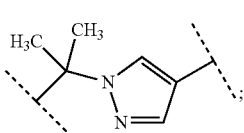

$R^{30}$ is
(a) hydrogen or (b) $C_{1-4}$ alkyl;
Group $X^b$ is
(a) halogen,
(b) $C_{1-6}$ alkyl,
(c) $C_{1-3}$ alkyl substituted with one hydroxy,
(d) $C_{1-3}$ alkyl substituted with one $C_{1-3}$ alkoxy, and
(e) $C_{1-3}$ alkoxy;
$R^4$ is
(1) hydrogen or (2) methyl;
$R^5$ is
(1) —$Y^c$—COO—$R^{50}$,
(2) hydrogen,
(3) $C_{1-4}$ alkyl optionally substituted with one $C_{1-3}$ alkoxy,
(4) $C_{1-4}$ alkyl substituted with one amide,
(5) $C_{1-3}$ alkyl substituted with one $C_{3-6}$ cycloalkyl substituted with the same or different two halogen,
(6) $C_{3-6}$ cycloalkyl optionally substituted with one hydroxy-$C_{1-4}$ alkyl,
(7) $C_{3-6}$ cycloalkyl substituted with one $C_{1-3}$ alkoxy,
(8) $C_{3-6}$ cycloalkyl substituted with one $C_{1-3}$ alkoxy-$C_{1-3}$ alkyl,
(9) $C_{3-6}$ cycloalkyl substituted with the same or different one to two halogen,
(10) $C_{3-6}$ cycloalkyl substituted with the same or different one to two $C_{1-3}$ alkyl,
(11) tetrahydropyran-4-yl or
(12) pyridin-4-yl;
$Y^c$ is
(a) $C_{1-6}$ alkylene optionally substituted with one hydroxy,
(b) $CH_2$—$CH_2$—O—$CH_2$ or
(c) $(CH_2)_m$—$Y^{c1}$—$(CH_2)_w$;
m is an integer of 0, 1 or 2;
w is an integer of 0, 1 or 2;
$Y^{c1}$ is
(a) $C_{3-6}$ cycloalkylene optionally substituted with one $C_{1-3}$ alkyl,
(b) phenylene,
(c) phenylene substituted with one halogen,
(d) phenylene substituted with one $C_{1-3}$ alkyl,
(e) phenylene substituted with one $C_{1-3}$ alkoxy,
(f) phenylene substituted with one trifluoromethyl,
(g) cross-linked $C_{5-8}$ cycloalkylene, (h) 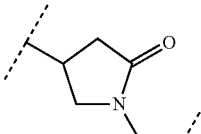

(i) 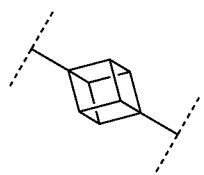

(j) spiro[3.3]heptanediyl,
(k) pyrrolidinediyl,
(l) pyrrolidinediyl substituted with one carboxy,
(m) pyrrolidinediyl substituted with one $C_{1-3}$ alkylcarbonyl,
(n) pyrrolidinediyl substituted with one $C_{1-3}$ alkylsulfonyl,
(o) pyridinediyl,
(p) isoxazolediyl or
(q) pyrazolediyl substituted with one $C_{1-3}$ alkyl;
$R^{50}$ is
(a) hydrogen or (b) $C_{1-4}$ alkyl;
$R^6$ is
(1) hydrogen or (2) methyl;
provided that
when $R^5$ is —$Y^c$—COO—$R^{50}$, $Y^c$ is $(CH_2)_m$—$Y^{c1}$—$(CH_2)_w$, m and w are 0, and $Y^{c1}$ is (b) phenylene, (c) phenylene substituted with one halogen, (d) phenylene substituted with one $C_{1-3}$ alkyl, (e) phenylene substituted with one $C_{1-3}$ alkoxy or (f) phenylene substituted with one trifluoromethyl, then $R^6$ is methyl; and
either $R^3$ or $R^5$ or both of them have "—COO—".

[02] The compound of [01], wherein the compound of Formula [I] is a compound of Formula [II], or a pharmaceutically acceptable salt thereof:

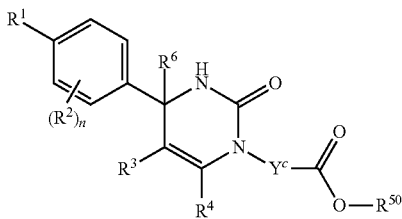

wherein
R³ is
(1) C$_{1-6}$ alkyl optionally substituted with one hydroxy,
(2) C$_{1-6}$ alkyl substituted with one C$_{1-4}$ alkoxy,
(3) C$_{1-6}$ alkyl substituted with one C$_{1-4}$ alkylsulfonyl,
(4) C$_{3-6}$ cycloalkyl optionally substituted with the same or different one to three substituent(s) selected from Group X$^b$, (5)

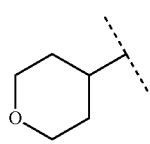

(6)

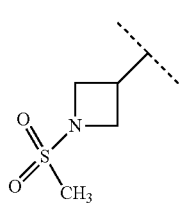

(7) phenyl, (8)

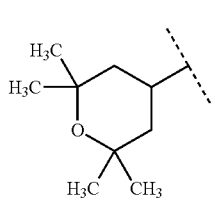

or
(9) C$_{2-3}$ alkenyl; and the other symbols have the same meanings as defined in [01].
[03] The compound of [01], wherein the compound of Formula [I] is a compound of Formula [III], or a pharmaceutically acceptable salt thereof:

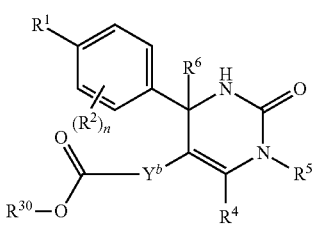

wherein
R⁵ is
(1) hydrogen,
(2) C$_{1-4}$ alkyl optionally substituted with one C$_{1-3}$ alkoxy,
(3) C$_{1-4}$ alkyl substituted with one amide,
(4) C$_{1-3}$ alkyl substituted with one C$_{3-6}$ cycloalkyl substituted with the same or different two halogen,
(5) C$_{3-6}$ cycloalkyl optionally substituted with one hydroxy-C$_{1-4}$ alkyl,
(6) C$_{3-6}$ cycloalkyl substituted with one C$_{1-3}$ alkoxy,
(7) C$_{3-6}$ cycloalkyl substituted with one C$_{1-3}$ alkoxy-C$_{1-3}$ alkyl,
(8) C$_{3-6}$ cycloalkyl substituted with the same or different one to two halogen,
(9) C$_{3-6}$ cycloalkyl substituted with the same or different one to two C$_{1-3}$ alkyl,
(10) tetrahydropyran-4-yl or
(11) pyridin-4-yl; and the other symbols have the same meanings as defined in [01].
[04] The compound of [01], wherein the compound of Formula [I] is a compound of Formula [IV], or a pharmaceutically acceptable salt thereof:

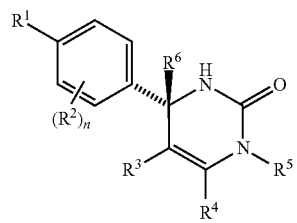

wherein each symbol has the same meaning as defined in [01].
[05] The compound of any one of [01] to [04], wherein R⁶ is methyl, or a pharmaceutically acceptable salt thereof.
[06] The compound of any one of [01] to [05], wherein R⁴ is hydrogen, or a pharmaceutically acceptable salt thereof.
[07] The compound of any one of [01] to [06], wherein n is an integer of 1 or 2, or a pharmaceutically acceptable salt thereof.
[08] The compound of any one of [01] to [07], wherein R² is halogen or trifluoromethyl, or a pharmaceutically acceptable salt thereof.
[09] The compound of any one of [01], [02], [04] to [07] or [08], wherein Y$^c$ is
(a) C$_{1-6}$ alkylene or
(b) (CH$_2$)$_m$—Y$^{c1}$—(CH$_2$)$_w$;
m is an integer of 0 or 1;
w is an integer of 0 or 1;
Y$^{c1}$ is
(a) C$_{3-6}$ cycloalkylene optionally substituted with one C$_{1-3}$alkyl,
(b) phenylene,
(c) phenylene substituted with one halogen,
(d) phenylene substituted with one C$_{1-3}$ alkyl,
(e) phenylene substituted with one C$_{1-3}$ alkoxy,
(f) phenylene substituted with one trifluoromethyl,
(g) cross-linked C$_{5-8}$ cycloalkylene,
(h) pyridinediyl or
(i) pyrazolediyl substituted with one C$_{1-3}$ alkyl; and
R³ is
(1) C$_{1-6}$ alkyl optionally substituted with one hydroxy,
(2) C$_{1-6}$ alkyl substituted with one C$_{1-4}$ alkoxy or (3) C$_{3-6}$ cycloalkyl optionally substituted with the same or different one to three substituent(s) selected from Group X$^b$, or a pharmaceutically acceptable salt thereof.

[10] The compound of [02], wherein R$^{50}$ is hydrogen, or a pharmaceutically acceptable salt thereof.

[11] The compound of [01], wherein the compound of Formula [I] is any one of the compounds of Formulae [IV-B-A] to [IV-B-N], or a pharmaceutically acceptable salt thereof:

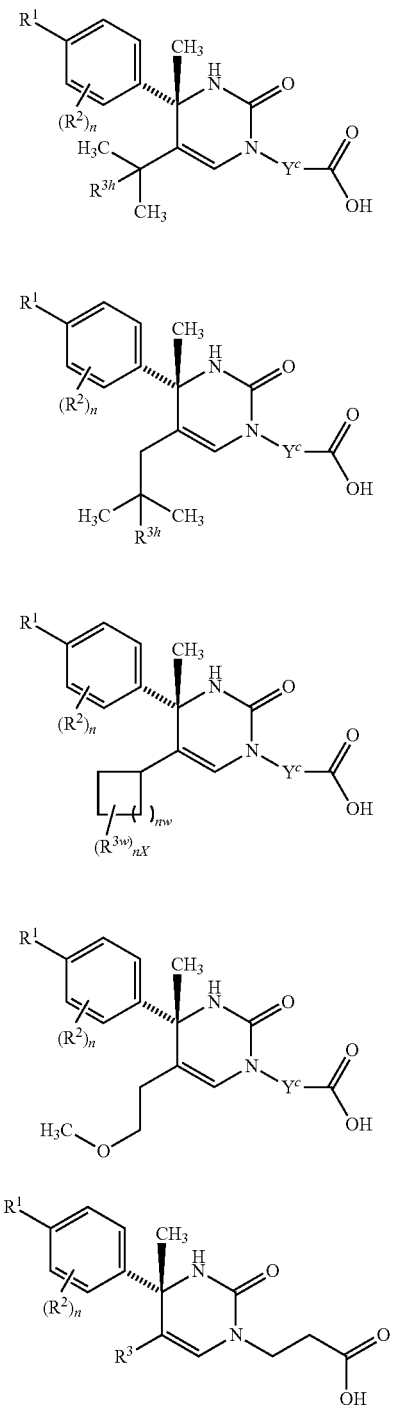
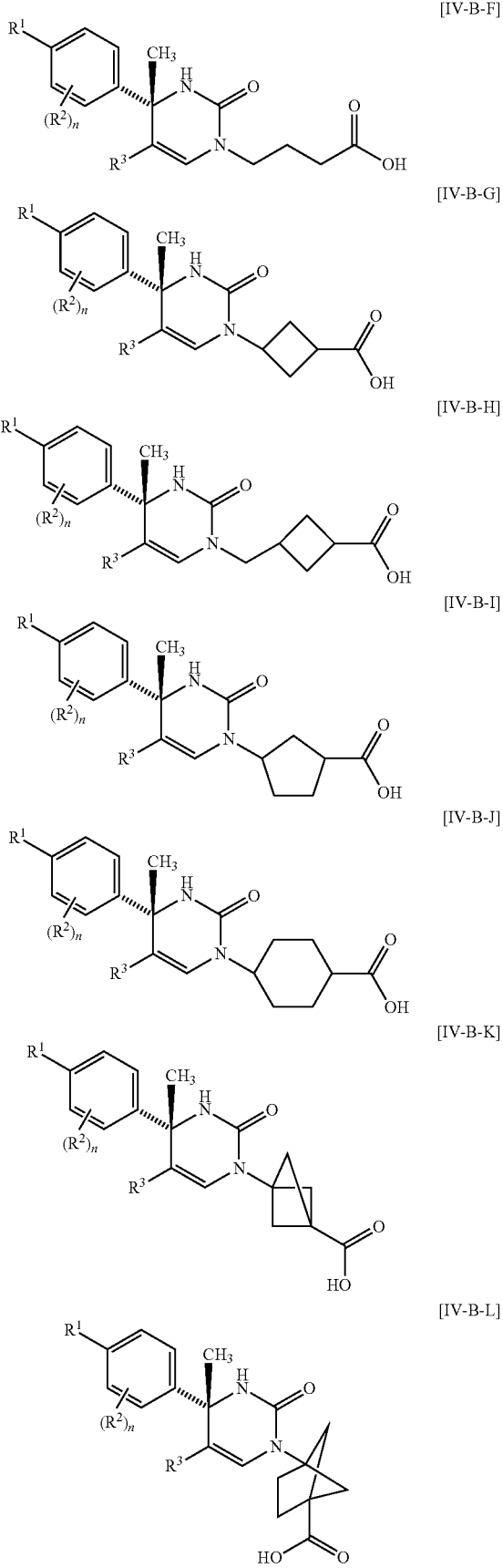

-continued

[IV-B-M]

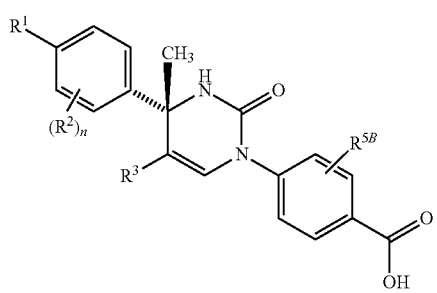

[IV-B-N]

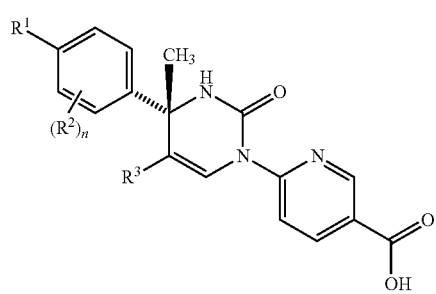

wherein
$R^{3h}$ is hydrogen or methyl;
$R^{3w}$ is methyl or fluoro;
$n^x$ is an integer of 0 or 2;
$n^w$ is an integer of 0, 1, 2 or 3;
$R^3$ is $C_{1-6}$ alkyl optionally substituted with one hydroxy, $C_{1-6}$ alkyl substituted with one $C_{1-4}$ alkoxy or
$C_{3-6}$ cycloalkyl optionally substituted with the same or different one to three substituent(s) selected from Group $X^b$;
$R^{5B}$ is hydrogen, halogen, $C_{1-3}$ alkyl, $C_{1-3}$ alkoxy or trifluoromethyl; and the other symbols have the same meanings as defined in [01].

[12] The compound of [01], selected from the group consisting of the following formulae, or a pharmaceutically acceptable salt thereof.

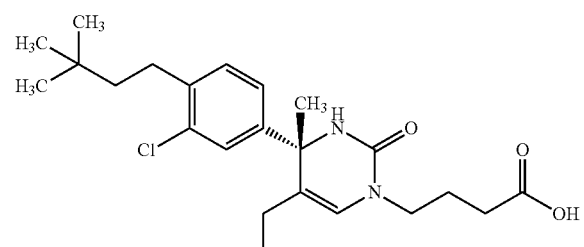

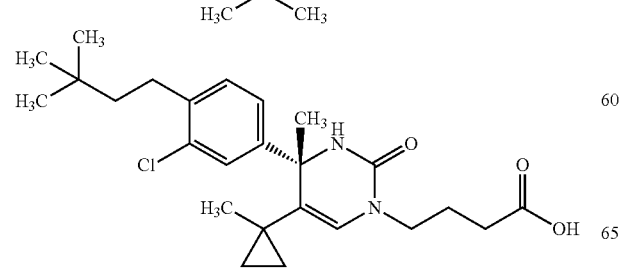

-continued

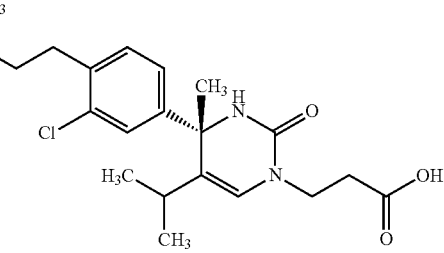

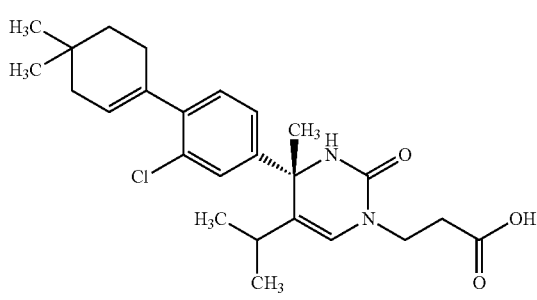

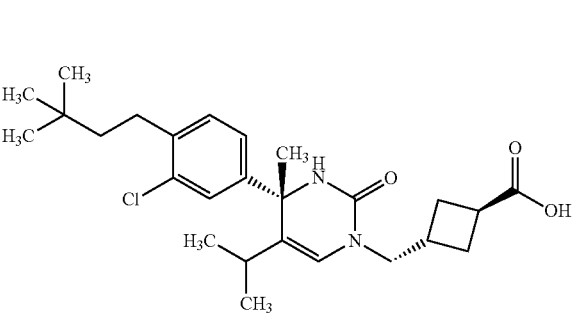

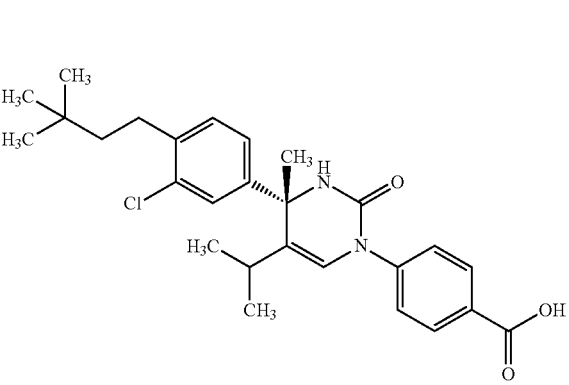

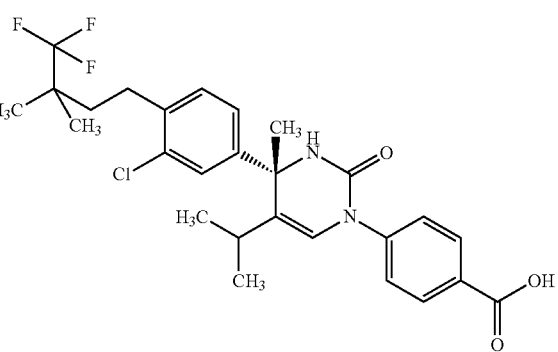

13
-continued
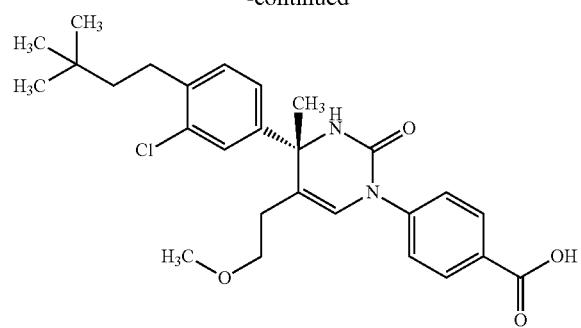
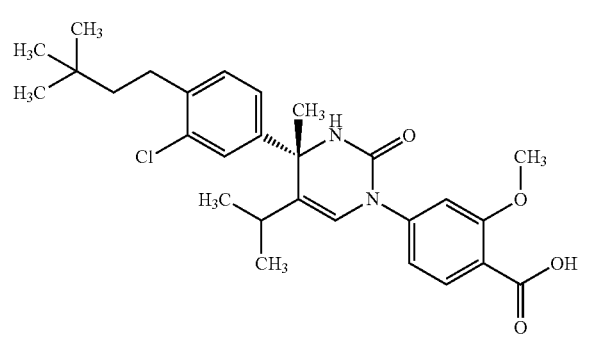
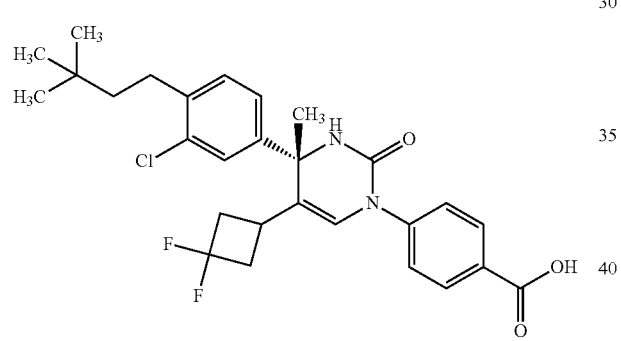
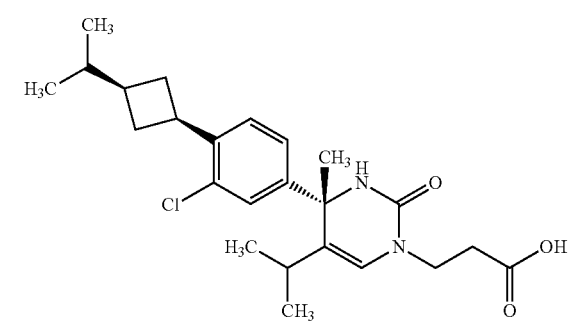
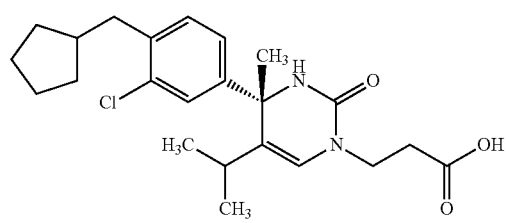
14
-continued
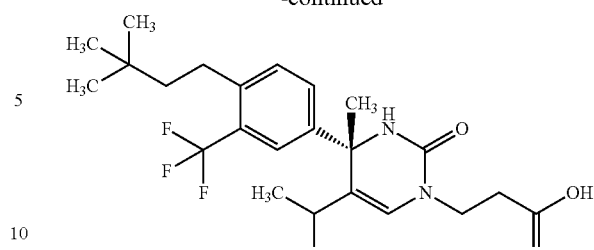
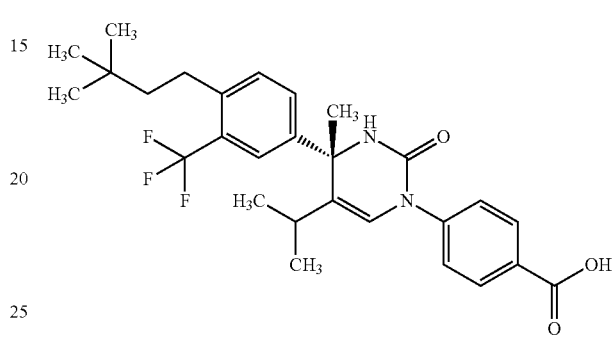
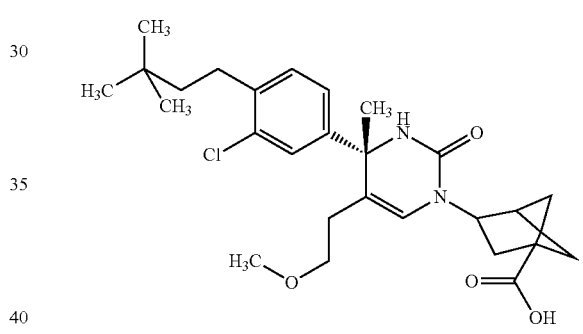
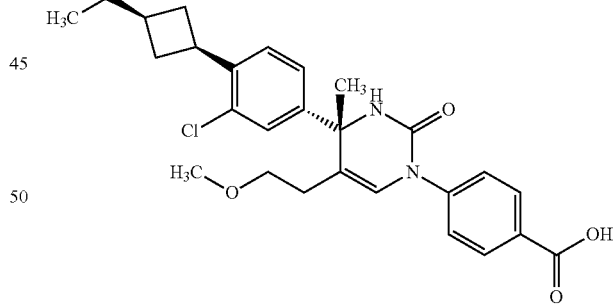
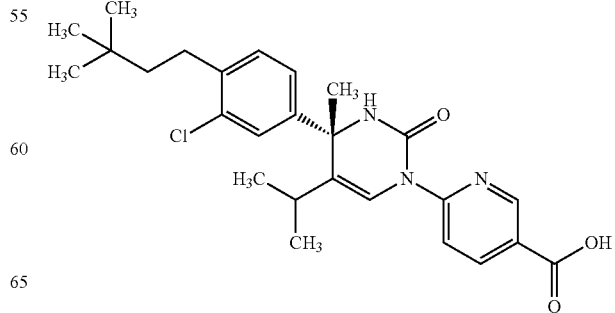

-continued
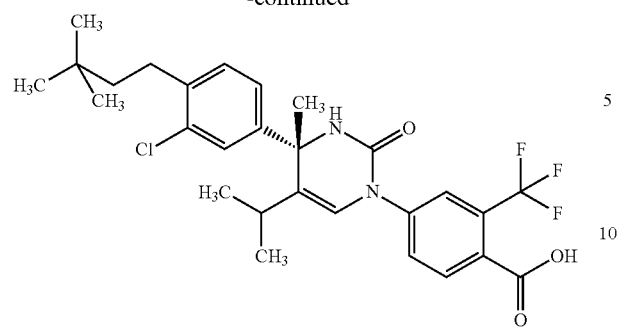
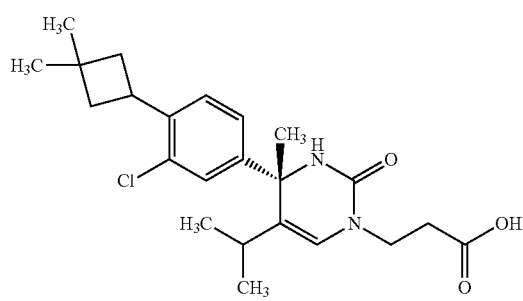
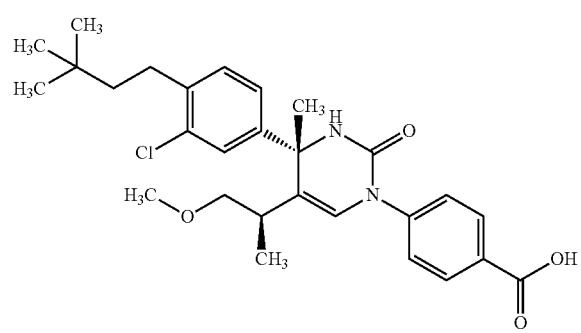
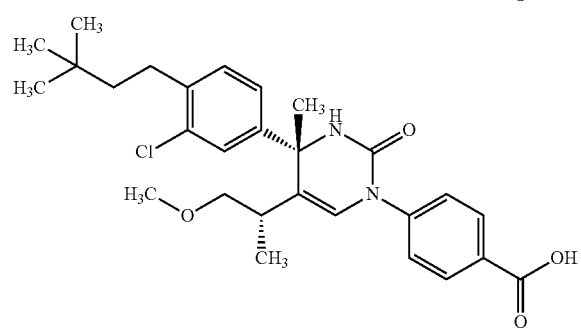
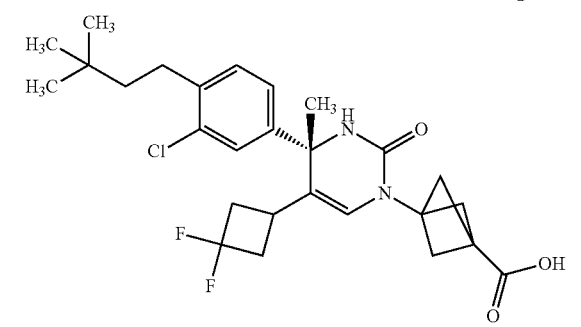
-continued
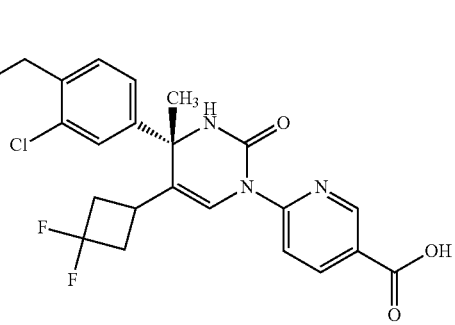
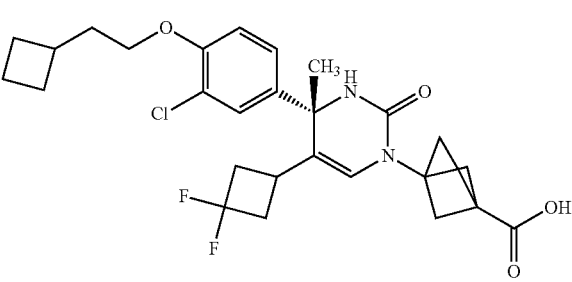
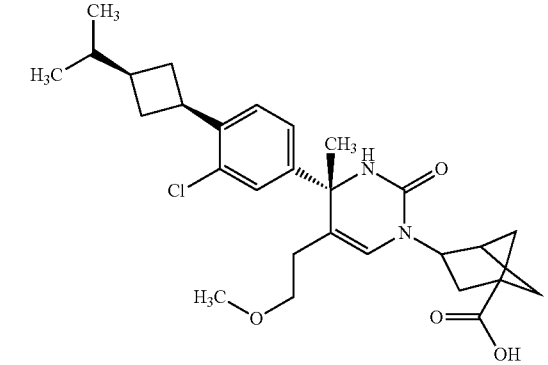
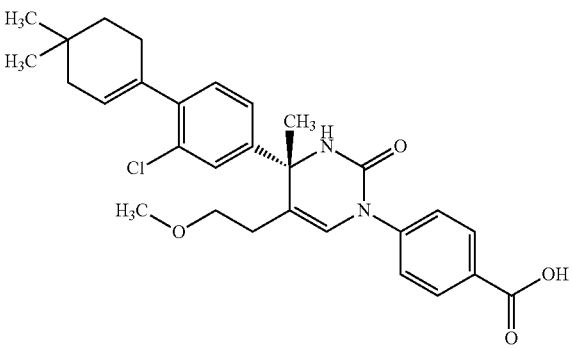
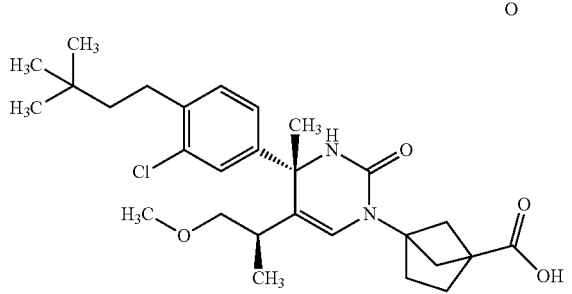

-continued

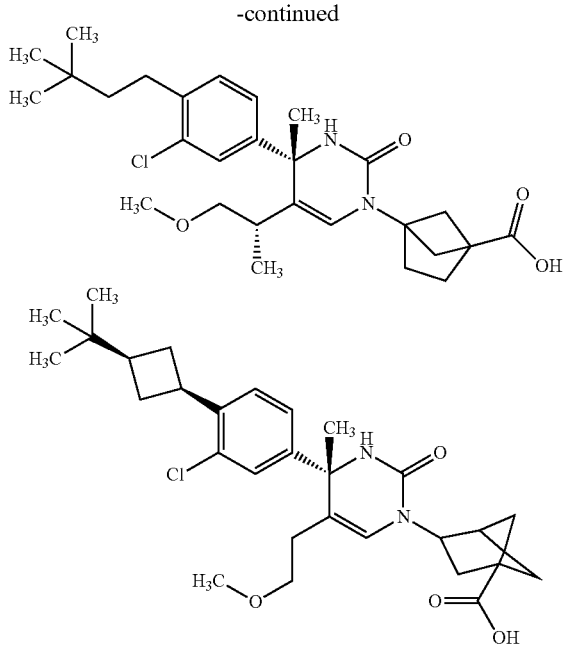

[13] A pharmaceutical composition comprising the compound of any one of [01] to [12] or a pharmaceutically acceptable salt thereof and a pharmaceutically acceptable carrier.
[14] An RORγ antagonist comprising the compound of any one of [01] to [12] or a pharmaceutically acceptable salt thereof and a pharmaceutically acceptable carrier.
[15] An agent for treating or preventing a disease selected from the group consisting of autoimmune disease, allergic disease, dry eye, fibrosis, and metabolic disease, comprising the compound of any one of [01] to [12] or a pharmaceutically acceptable salt thereof.
[16] The agent of [15], wherein the disease is autoimmune disease.
[17] The agent of [16], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease.
[18] The agent of [15], wherein the disease is metabolic disease.
[19] The agent of [18], wherein the metabolic disease is diabetes.
[20] A method of inhibiting RORγ, comprising administering to a mammal a therapeutically effective amount of the compound of any one of [01] to [12] or a pharmaceutically acceptable salt thereof.
[21] A method of treating or preventing a disease selected from the group consisting of autoimmune disease, allergic disease, dry eye, fibrosis, and metabolic disease, comprising administering to a mammal an effective amount of the compound of any one of [01] to [12] or a pharmaceutically acceptable salt thereof.
[22] The method of [21], wherein the disease is autoimmune disease.
[23] The method of [22], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease.
[24] The method of [21], wherein the disease is metabolic disease.
[25] The method of [24], wherein the metabolic disease is diabetes.
[26] Use of the compound of any one of [01] to [12] or a pharmaceutically acceptable salt thereof for the manufacture of an RORγ antagonist.
[27] Use of the compound of any one of [01] to [12] or a pharmaceutically acceptable salt thereof for the manufacture of an agent for treating or preventing a disease selected from the group consisting of autoimmune disease, allergic disease, dry eye, fibrosis, and metabolic disease.
[28] The use of [27], wherein the disease is autoimmune disease.
[29] The use of [28], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease.
[30] The use of [27], wherein the disease is metabolic disease.
[31] The use of [30], wherein the metabolic disease is diabetes.
[32] A compound of any one of [01] to [12] or a pharmaceutically acceptable salt thereof for use as an RORγ antagonist.
[33] A compound of any one of [01] to [12] or a pharmaceutically acceptable salt thereof for use as an agent for treating or preventing a disease selected from the group consisting of autoimmune disease, allergic disease, dry eye, fibrosis, and metabolic disease.
[34] The compound of [33], wherein the disease is autoimmune disease, or a pharmaceutically acceptable salt thereof.
[35] The compound of [34], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease, or a pharmaceutically acceptable salt thereof.
[36] The compound of [33], wherein the disease is metabolic disease, or a pharmaceutically acceptable salt thereof.
[37] The compound of [36], wherein the metabolic disease is diabetes, or a pharmaceutically acceptable salt thereof.

Dihydropyrimidin-2-one compounds and pharmaceutically acceptable salts thereof of the present invention is useful as an agent for prevention or treatment of autoimmune diseases such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease, allergic diseases such as asthma, dry eye, fibrosis such as pulmonary fibrosis and primary biliary cirrhosis, and metabolic diseases such as diabetes.

DESCRIPTION OF EMBODIMENTS

Definitions of terms used herein are as follows.
"Halogen" includes fluoro, chloro, bromo or iodo. A preferable "halogen" is fluoro or chloro.
"Alkyl" means a straight or branched chain saturated hydrocarbon group, and includes, for example, "$C_{1-3}$ alkyl", "$C_{1-4}$ alkyl", "$C_{1-5}$ alkyl", "$C_{1-6}$ alkyl", "$C_{4-6}$ alkyl", "$C_{4-8}$ alkyl", and "$C_{5-8}$ alkyl", each of which means alkyl with 1 to 3 of carbon atom(s), 1 to 4 of carbon atom(s), 1 to 5 of carbon atom(s), 1 to 6 of carbon atom(s), 4 to 6 of carbon atoms, 4 to 8 of carbon atoms, and 5 to 8 of carbon atoms, respectively.

An illustrative example of "$C_{1-3}$ alkyl" includes, for example, methyl, ethyl, propyl, and isopropyl. A preferable "$C_{1-3}$ alkyl" is methyl.

An illustrative example of "$C_{1-4}$ alkyl" includes, for example, methyl, ethyl, propyl, isopropyl, butyl, isobutyl, sec-butyl, tert-butyl, and 1-methylpropyl. A preferable "$C_{1-4}$ alkyl" is methyl or ethyl.

An illustrative example of "$C_{1-5}$ alkyl" includes, for example, methyl, ethyl, propyl, isopropyl, butyl, isobutyl, sec-butyl, tert-butyl, 1-methylpropyl, pentyl, isopentyl, neopentyl, 1,2-dimethylpropyl, and 1-ethylpropyl. A preferable "$C_{1-5}$ alkyl" is methyl.

An illustrative example of "$C_{1-6}$ alkyl" includes, for example, methyl, ethyl, propyl, isopropyl, butyl, isobutyl, sec-butyl, tert-butyl, 1-methylpropyl, pentyl, isopentyl, neopentyl, 1,2-dimethylpropyl, 1-ethylpropyl, hexyl, isohexyl, 1,2,2-trimethylpropyl, 1,1-dimethylbutyl, 2,2-dimethylbutyl, 3,3-dimethylbutyl, and 2-ethylbutyl. A preferable "$C_{1-6}$ alkyl" is methyl, ethyl, isopropyl, isobutyl, tert-butyl, isopentyl, neopentyl, 1-methylpropyl or 1,1-dimethylbutyl.

An illustrative example of "$C_{4-6}$ alkyl" includes, for example, butyl, isobutyl, sec-butyl, tert-butyl, 1-methylpropyl, pentyl, isopentyl, neopentyl, 1,2-dimethylpropyl, 1-ethylpropyl, hexyl, isohexyl, 1,2,2-trimethylpropyl, 1,1-dimethylbutyl, 2,2-dimethylbutyl, 3,3-dimethylbutyl, and 2-ethylbutyl. A preferable one is isobutyl or isopentyl.

An illustrative example of "$C_{4-8}$ alkyl" includes, for example, butyl, isobutyl, sec-butyl, tert-butyl, 1-methylpropyl, pentyl, isopentyl, neopentyl, 1,2-dimethylpropyl, 1-ethylpropyl, hexyl, isohexyl, 1,2,2-trimethylpropyl, 1,1-dimethylbutyl, 2,2-dimethylbutyl, 3,3-dimethylbutyl, 2-ethylbutyl, heptyl, 4,4-dimethylpentyl, 1-methyl-3,3-dimethylbutyl, octyl, and 2-propylpentyl. A preferable one is butyl, isobutyl, pentyl, isopentyl, 3,3-dimethylbutyl, 2-ethylbutyl, 4,4-dimethylpentyl, 1-methyl-3,3-dimethylbutyl or 2-propylpentyl.

An illustrative example of "$C_{5-8}$ alkyl" includes, for example, pentyl, isopentyl, neopentyl, 1,2-dimethylpropyl, 1-ethylpropyl, hexyl, isohexyl, 1,2,2-trimethylpropyl, 1,1-dimethylbutyl, 2,2-dimethylbutyl, 3,3-dimethylbutyl, 2-ethylbutyl, heptyl, 4,4-dimethylpentyl, 1-methyl-3,3-dimethylbutyl, octyl, and 2-propylpentyl. A preferable one is pentyl, isopentyl, 3,3-dimethylbutyl, 2-ethylbutyl, 4,4-dimethylpentyl, 1-methyl-3,3-dimethylbutyl or 2-propylpentyl.

"$C_{1-6}$ alkyl optionally substituted with one hydroxy" means "$C_{1-6}$ alkyl substituted with one hydroxy" or "unsubstituted $C_{1-6}$ alkyl".

"$C_{1-3}$ alkyl substituted with one hydroxy" means "alkyl", with 1 to 3 of carbon atom(s), substituted at any position with one hydroxy. In particular, it includes, for example, hydroxymethyl.

"$C_{5-8}$ alkyl substituted with one hydroxy" means "alkyl", with 5 to 8 of carbon atoms, substituted with at any position with one hydroxy. In particular, it includes, for example, 3,3-dimethyl-3-hydroxypropyl, 3,3-dimethyl-2-hydroxybutyl, and 3,3-dimethyl-4-hydroxybutyl.

"$C_{5-8}$ alkyl substituted with one halogen" means "alkyl", with 5 to 8 of carbon atoms, substituted with at any position with one halogen. In particular, it includes, for example, 3-fluoro-3-methylbutyl.

"$C_{3-7}$ alkyl substituted with one trifluoromethyl" means "alkyl", with 3 to 7 of carbon atoms, substituted at any position with one trifluoromethyl. In particular, it includes, for example, 4,4,4-trifluorobutyl and 4,4,4-trifluoro-3,3-dimethylbutyl.

"Alkenyl" means a straight or branched chain unsaturated hydrocarbon group with one or more double bond(s) between carbon atoms, and includes, for example, "$C_{2-3}$ alkenyl" and "$C_{4-8}$ alkenyl" which "$C_{2-3}$ alkenyl" means alkenyl with 2 to 3 of carbon atoms and "$C_{4-8}$ alkenyl" means alkenyl with 4 to 8 of carbon atoms. A preferable "$C_{4-8}$ alkenyl" is "$C_{4-6}$ alkenyl" with one double bond between carbon atoms.

An illustrative example of "$C_{2-3}$ alkenyl" includes, for example, ethenyl and isopropenyl. A preferable one is isopropenyl.

An illustrative example of "$C_{4-8}$ alkenyl" includes, for example, 2-methyl-prop-1-enyl, 3,3-dimethyl-but-1-enyl, and 3-methyl-but-2-enyl. A preferable one is 2-methyl-prop-1-enyl or 3,3-dimethyl-but-1-enyl.

"Alkynyl" means a straight or branched chain unsaturated hydrocarbon group with one or more triple bond(s) between carbon atoms, and includes, for example, "$C_{4-8}$ alkynyl" which means alkynyl with 4 to 8 carbon atoms. A preferable "$C_{4-8}$ alkynyl" is "$C_{4-6}$ alkynyl" with one triple bond between carbon atoms.

An illustrative example of "$C_{4-8}$ alkynyl" includes, for example, 3,3-dimethyl-but-1-ynyl, 3-methyl-but-1-ynyl, and 3-ethyl-pent-1-ynyl. A preferable one is 3,3-dimethyl-but-1-ynyl.

"Alkoxy" means a group where a straight or branched chain saturated hydrocarbon group attaches to oxygen atom, and includes, for example, "$C_{1-3}$ alkoxy", "$C_{1-4}$ alkoxy", "$C_{2-4}$ alkoxy", "$C_{3-6}$ alkoxy", and "$C_{2-7}$ alkoxy", each of which means alkoxy with 1 to 3 of carbon atom(s), 1 to 4 of carbon atom(s), 2 to 4 of carbon atoms, 3 to 6 of carbon atoms, and 2 to 7 of carbon atoms, respectively.

An illustrative example of "$C_{1-3}$ alkoxy" includes, for example, methoxy, ethoxy, propoxy, and isopropoxy. A preferable one is methoxy or ethoxy.

An illustrative example of "$C_{1-4}$ alkoxy" includes, for example, methoxy, ethoxy, propoxy, isopropoxy, butoxy, isobutoxy, sec-butoxy, and tert-butoxy. A preferable one is methoxy.

An illustrative example of "$C_{2-4}$ alkoxy" includes, for example, ethoxy, propoxy, isopropoxy, butoxy, isobutoxy, sec-butoxy, and tert-butoxy. A preferable one is isopropoxy or tert-butoxy.

An illustrative example of "$C_{3-6}$ alkoxy" includes, for example, propoxy, isopropoxy, butoxy, isobutoxy, sec-butoxy, tert-butoxy, pentyloxy, isopentyloxy, 2-methylbutoxy, 1,1-dimethylpropoxy, neopentyloxy, 3,3-dimethylbutoxy, 1-ethylpropoxy, and hexyloxy. A preferable one is isobutoxy, isopentyloxy, neopentyloxy or 3,3-dimethylbutoxy.

An illustrative example of "$C_{2-7}$ alkoxy" includes, for example, ethoxy, propoxy, isopropoxy, butoxy, isobutoxy, sec-butoxy, and tert-butoxy. A preferable one is isopropoxy or tert-butoxy.

"$C_{2-7}$ alkoxy substituted with one trifluoromethyl" means "alkoxy", with 2 to 7 carbon atoms, substituted at any position with one "trifluoromethyl". Its illustrative example includes, for example, 3,3,3-trifluoropropoxy, 4,4,4-trifluorobutoxy, 5,5,5-trifluoropentyloxy, 6,6,6-trifluorohexyloxy, 7,7,7-trifluoroheptyloxy, and 8,8,8-trifluorooctyloxy. A preferable one includes, for example, 3,3,3-trifluoropropoxy.

"$C_{1-3}$ alkyl substituted with one $C_{1-3}$ alkoxy" means "alkyl", with 1 to 3 of carbon atom(s), substituted at any position with one $C_{1-3}$ alkoxy. In particular, it includes, for example, methoxymethyl.

"$C_{1-6}$ alkyl substituted with one $C_{1-4}$ alkoxy" means "alkyl", with 1 to 6 of carbon atom(s), substituted at any position with one $C_{1-4}$ alkoxy. In particular, it includes, for example, 2-methoxyethyl, 1-methyl-2-methoxyethyl, 2-methoxypropyl, 4-methoxy-2,2-dimethylbutyl, and 3-tert-butoxypropyl.

"Cycloalkyl" means a monocyclic saturated hydrocarbon group, and includes, for example, "$C_{3-6}$ cycloalkyl" and "$C_{4-6}$ cycloalkyl", each of which means cycloalkyl with 3 to 6 of carbon atoms, and 4 to 6 of carbon atoms, respectively.

An illustrative example of "$C_{3-6}$ cycloalkyl" includes, for example, cyclopropyl, cyclobutyl, cyclopentyl, and cyclohexyl.

An illustrative example of "$C_{4-6}$ cycloalkyl" includes, for example, cyclobutyl, cyclopentyl, and cyclohexyl.

"$C_{3-6}$ cycloalkyl substituted with one $C_{1-3}$ alkoxy" means "cycloalkyl", with 3 to 6 of carbon atoms, substituted at any position with one $C_{1-3}$ alkoxy. In particular, it includes, for example, 3-methoxycyclobutyl.

"$C_{3-6}$ cycloalkyl substituted with one $C_{1-3}$ alkoxy-$C_{1-3}$ alkyl" means "cycloalkyl", with 3 to 6 of carbon atoms, substituted at any position with one $C_{1-3}$ alkoxy-$C_{1-3}$ alkyl. In particular, it includes, for example, 1-methoxymethylcyclopropyl and 3-methoxymethylcyclobutyl.

"Cycloalkenyl" means a monocyclic unsaturated hydrocarbon group with one or more double bond(s) between carbon atoms, and includes, for example, "$C_{5-6}$ cycloalkenyl", which means cycloalkenyl with 5 to 6 of carbon atoms.

A preferable "$C_{5-6}$ cycloalkenyl" is "$C_{5-6}$ cycloalkenyl" with one double bond between carbon atoms.

An illustrative example of "$C_{5-6}$ cycloalkenyl" includes, for example, cyclopentenyl and cyclohexenyl. A preferable one is cyclopent-1-enyl or cyclohex-1-enyl.

"Spiro cycloalkyl" means a cyclic saturated hydrocarbon group with one spiro atom, and includes, for example, "spiro $C_{6-11}$ cycloalkyl", which means spiro cycloalkyl with one spiro atom and 6 to 11 of carbon atoms.

An illustrative example of "spiro $C_{6-11}$ cycloalkyl" includes, for example, spiro [3.3]heptyl, spiro [4.4]nonyl, and spiro [5.5]undecyl. A preferable one is spiro [3.3]heptyl.

"Alkylcarbonyl" means "alkyl"-attached carbonyl, and includes "$C_{1-3}$ alkylcarbonyl".

An illustrative example of "$C_{1-3}$ alkylcarbonyl" includes carbonyl which attaches to the "$C_{1-3}$ alkyl". A preferable one is methylcarbonyl.

"Alkylsulfanyl" means "alkyl"-attached sulfanyl, and includes "$C_{4-6}$ alkylsulfanyl".

An illustrative example of "$C_{4-6}$ alkylsulfanyl" includes sulfanyl which attaches to the "$C_{4-6}$ alkyl". A preferable one is isobutylsulfanyl or isopentylsulfanyl.

"Alkylsulfinyl" means "alkyl"-attached sulfinyl, and includes "$C_{4-6}$ alkylsulfinyl".

An illustrative example of "$C_{4-6}$ alkylsulfinyl" includes sulfinyl which attaches to the "$C_{4-6}$ alkyl". A preferable one is isobutylsulfinyl or isopentylsulfinyl.

"Alkylsulfonyl" means "alkyl"-attached sulfonyl, and includes "$C_{1-3}$ alkylsulfonyl", "$C_{1-4}$ alkylsulfonyl", and "$C_{4-6}$ alkylsulfonyl".

An illustrative example of "$C_{1-3}$ alkylsulfonyl" includes sulfonyl which attaches to the "$C_{1-3}$ alkyl". A preferable one is methylsulfonyl.

An illustrative example of "$C_{1-4}$ alkylsulfonyl" includes sulfonyl which attaches to the "$C_{1-4}$ alkyl". A preferable one is methylsulfonyl.

An illustrative example of "$C_{4-6}$ alkylsulfonyl" includes sulfonyl which attaches to the "$C_{4-6}$ alkyl". A preferable one is isobutylsulfonyl or isopentylsulfonyl.

"$C_{1-6}$ alkyl substituted with one $C_{1-4}$ alkylsulfonyl" means "alkyl", with 1 to 6 of carbon atom(s), substituted at any position with one $C_{1-4}$ alkylsulfonyl. In particular, it includes, for example, 2-methylsulfonylethyl.

"Alkoxycarbonyl" means carbonyl which attaches to "alkoxy", and includes, for example, "$C_{1-3}$ alkoxycarbonyl".

An illustrative example of "$C_{1-3}$ alkoxycarbonyl" includes, for example, methoxycarbonyl, ethoxycarbonyl, and propoxycarbonyl. A preferable one is ethoxycarbonyl.

"Cycloalkylsulfanyl" means "cycloalkyl"-attached sulfanyl, and includes "$C_{3-6}$ cycloalkylsulfanyl".

An illustrative example of "$C_{3-6}$ cycloalkylsulfanyl" includes sulfanyl which attaches to the "$C_{3-6}$ cycloalkyl". A preferable one is cyclopentylsulfanyl.

"Cycloalkylsulfinyl" means "cycloalkyl"-attached sulfinyl, and includes "$C_{3-6}$ cycloalkylsulfinyl".

An illustrative example of "$C_{3-6}$ cycloalkylsulfinyl" includes, for example, sulfinyl which attaches to the "$C_{3-6}$ cycloalkyl". A preferable one is cyclopentylsulfinyl.

"Cycloalkylsulfonyl" means "cycloalkyl"-attached sulfonyl, and includes "$C_{3-6}$ cycloalkylsulfonyl".

An illustrative example of "$C_{3-6}$ cycloalkylsulfanyl" includes sulfonyl which attaches to the "$C_{3-6}$ cycloalkyl". A preferable one is cyclopentylsulfonyl.

"Alkylene" means a divalent group derived from straight or branched chain saturated hydrocarbon, and includes, for example, "$C_{1-3}$ alkylene" and "$C_{1-6}$ alkylene", each of which means alkylene with 1 to 3 of carbon atom(s) and 1 to 6 of carbon atom(s), respectively.

An illustrative example of "$C_{1-3}$ alkylene" includes, for example, methylene, ethylene, trimethylene, and $-C(CH_3)_2-$. A preferable one is methylene or ethylene.

An illustrative example of "$C_{1-6}$ alkylene" includes, for example, methylene, ethylene, trimethylene, butylene, pentylene, hexylene, $-C(CH_3)_2-$, $-C(CH_3)_2-CH_2-$, $-(CH_2)_2-CH(CH_3)-$, $-CH_2-C(CH_3)_2-CH_2-$, $-(CH_2)_3-C(CH_3)_2-$, and $-(CH_2)_2-C(CH_3)_2-$. A preferable one is methylene, ethylene, trimethylene, butylene, $-C(CH_3)_2-$, $-C(CH_3)_2-CH_2-$, $-(CH_2)_2-CH(CH_3)-$, $-CH_2-C(CH_3)_2-CH_2-$, $-(CH_2)_3-C(CH_3)_2-$ or $-(CH_2)_2-C(CH_3)_2-$.

"$C_{1-6}$ alkylene optionally substituted with one hydroxy" means "$C_{1-6}$ alkylene substituted with one hydroxy" or "unsubstituted $C_{1-6}$ alkylene".

"Cycloalkylene" means a divalent group derived from monocyclic saturated hydrocarbon, and includes, for example, "$C_{3-6}$ cycloalkylene", which means cycloalkylene with 3 to 6 of carbon atoms.

An illustrative example of "$C_{3-6}$ cycloalkylene" includes, for example, cyclopropylene, cyclobutylene, cyclopentylene, and cyclohexylene. A preferable "$C_{3-6}$ cycloalkylene" is "$C_{4-6}$ cycloalkylene".

"Cross-linked cycloalkylene" means a divalent group derived from polycyclic saturated hydrocarbon with a cross-linked structure of carbon atoms, and includes, for example, "cross-linked $C_{5-8}$ cycloalkylene", which means cross-linked cycloalkylene with 5 to 8 of carbon atoms.

An illustrative example of "cross-linked $C_{5-8}$ cycloalkylene" includes, for example, bicyclo[1.1.1]pentylene, bicyclo[2.1.1]hexylene, bicyclo[2.2.1]heptylene, and bicyclo[2.2.2]octylene. A preferable "cross-linked $C_{5-8}$ cycloalkylene" is "cross-linked $C_{5-6}$ cycloalkylene", in particular bicyclo[1.1.1]pentylene or bicyclo[2.1.1]hexylene.

"Phenylene substituted with one halogen" means phenylene substituted at any position with one halogen. In particular, it includes, for example, 2-fluorophenylene and 4-fluorophenylene.

"Phenylene substituted with one $C_{1-3}$ alkyl" means phenylene substituted at any position with one $C_{1-3}$ alkyl. In particular, it includes, for example, 2-methylphenylene and 3-methylphenylene.

"Phenylene substituted with one $C_{1-3}$ alkoxy" means phenylene substituted at any position with one $C_{1-3}$ alkoxy. In particular, it includes, for example, 2-methoxyphenylene and 3-methoxyphenylene.

"Phenylene substituted with one trifluoromethyl" means phenylene substituted at any position with one trifluoromethyl. In particular, it includes, for example, 3-trifluorophenylene.

"Pyrrolidinediyl substituted with one carboxy" means pyrrolidinediyl substituted at any position with one carboxy. In particular, it includes, for example, 3-carboxypyrrolidine-1,4-diyl.

"Pyrrolidinediyl substituted with one $C_{1-3}$ alkylcarbonyl" means pyrrolidinediyl substituted at any position with one $C_{1-3}$ alkylcarbonyl. In particular, it includes, for example, 1-methylcarbonylpyrrolidine-3,4-diyl.

"Pyrrolidinediyl substituted with one $C_{1-3}$ alkylsulfonyl" means pyrrolidinediyl substituted at any position with one $C_{1-3}$ alkylsulfonyl. In particular, it includes, for example, 1-methylsulfonylpyrrolidine-3,4-diyl.

"Pyrazolediyl substituted with one $C_{1-3}$ alkyl" means pyrazolediyl substituted at any position with one $C_{1-3}$ alkyl. In particular, it includes, for example, 1-methylpyrazole-3,5-diyl.

Embodiments of each group in the above formulae are illustrated as below.

A preferable "$C_{4-8}$ alkyl" in $R^1$ particularly includes butyl, isobutyl, sec-butyl, tert-butyl, 1-methylpropyl, pentyl, isopentyl, neopentyl, 1,2-dimethylpropyl, 1-ethylpropyl, hexyl, isohexyl, 1,2,2-trimethylpropyl, 1,1-dimethylbutyl, 2,2-dimethylbutyl, 3,3-dimethylbutyl, 2-ethylbutyl, heptyl, 4,4-dimethylpentyl, 1-methyl-3,3-dimethylbutyl, octyl, and 2-propylpentyl. A further preferable one is butyl, isobutyl, pentyl, isopentyl, 3,3-dimethylbutyl, 2-ethylbutyl, 4,4-dimethylpentyl, 1-methyl-3,3-dimethylbutyl or 2-propylpentyl.

A preferable "$C_{4-8}$ alkenyl" in $R^1$ is "$C_{4-6}$ alkenyl", and particularly includes 2-methyl-propenyl, 3,3-dimethyl-but-1-enyl, and 3-methyl-but-2-enyl. A further preferable one is 2-methyl-propenyl or 3,3-dimethyl-but-1-enyl.

A preferable "$C_{4-8}$ alkynyl" in $R^1$ is "$C_{4-6}$ alkynyl", and particularly includes 3,3-dimethyl-but-1-ynyl, and 3-methyl-but-1-ynyl. A further preferable one is "$C_6$ alkynyl", in particular 3,3-dimethyl-but-1-ynyl.

A preferable "$C_{3-7}$ alkyl substituted with one trifluoromethyl" in $R^1$ is "$C_{3-5}$ alkyl substituted with one trifluoromethyl", and particularly includes 4,4,4-trifluorobutyl, 5,5,5-trifluoropentyl, 6,6,6-trifluorohexyl, and 4,4,4-trifluoro-3,3-dimethylbutyl. A further preferable one is 4,4,4-trifluorobutyl or 4,4,4-trifluoro-3,3-dimethylbutyl.

A preferable "$C_{1-4}$ alkyl" in "$C_{1-4}$ alkyl substituted with one substituent selected from Group $X^{a1}$" in $R^1$ is "$C_{1-2}$ alkyl", in particular methyl or ethyl.

A preferable "$C_{3-6}$ alkoxy" in $R^1$ is "$C_{4-6}$ alkoxy", and particularly includes propoxy, isopropoxy, butoxy, isobutoxy, sec-butoxy, tert-butoxy, pentyloxy, isopentyloxy, 2-methylbutoxy, 1,1-dimethylpropoxy, neopentyloxy, 3,3-dimethylbutoxy, 1-ethylpropoxy, and hexyloxy. A further preferable one is isobutoxy, isopentyloxy, neopentyloxy or 3,3-dimethylbutoxy.

A preferable "$C_{2-7}$ alkoxy substituted with one trifluoromethyl" in $R^1$ is "$C_2$ alkoxy substituted with one trifluoromethyl", in particular 3,3,3-trifluoropropoxy.

A preferable "$C_{1-3}$ alkoxy" in "$C_{1-3}$ alkoxy substituted with one substituent selected from Group $X^{a2}$" in $R^1$ is "$C_{1-2}$ alkoxy", in particular methoxy or ethoxy.

A preferable "$C_{4-6}$ cycloalkyl" in $R^1$ is in particular cyclobutyl, cyclopentyl or cyclohexyl.

A preferable "$C_{3-6}$ cycloalkyl substituted with one to two $C_{1-4}$ alkyl" in $R^1$ is "$C_{3-6}$ cycloalkyl substituted with the same or different one or two $C_{1-4}$ alkyl", more preferably "cyclopropyl or cyclohexyl substituted with the same or different one or two methyl, isopropyl or tert-butyl". In particular, it is 2-isopropylcyclopropyl, 2-tert-butylcyclopropyl or 3,3-dimethylcyclohexyl.

A preferable "$C_{5-6}$ cycloalkenyl optionally substituted with one to two $C_{1-4}$ alkyl" in $R^1$ is "$C_{5-6}$ cycloalkenyl optionally substituted with the same or different two $C_{1-4}$ alkyl", more preferably "1-cyclopentenyl or 1-cyclohexenyl, optionally substituted with the same or different two methyl". In particular, it is 1-cyclopentenyl, 1-cyclohexenyl, 3,3-dimethylcyclohex-1-enyl or 4,4-dimethylcyclohex-1-enyl.

A preferable "spiro $C_{6-11}$ cycloalkyl" in $R^1$ is "spiro $C_{6-8}$ cycloalkyl", more preferably "spiro $C_7$ cycloalkyl". In particular, it is spiro [3.3]heptyl.

A preferable "$C_{1-3}$ alkoxycarbonyl" in $R^1$ is "$C_{1-2}$ alkoxycarbonyl", more preferably ethoxycarbonyl.

A preferable "halogen" in $R^2$ is fluoro or chloro.

A preferable "$C_{1-6}$ alkyl" in $R^2$ is "$C_{1-2}$ alkyl", more preferably methyl.

A preferable "$C_{1-3}$ alkoxy optionally substituted with phenyl" in $R^2$ is "$C_{1-2}$ alkoxy optionally substituted with phenyl", more preferably benzyloxy.

A preferable "n" is an integer of 0 to 2. In Formula [I], the following partial structure:

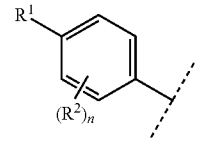

includes the following embodiments.

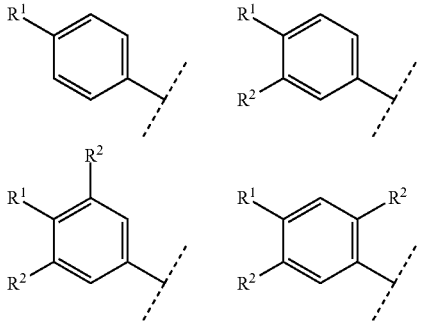

A further preferable "n" is an integer of 1 or 2. In Formula [I], the following partial structure:

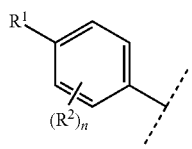

includes the following embodiments.

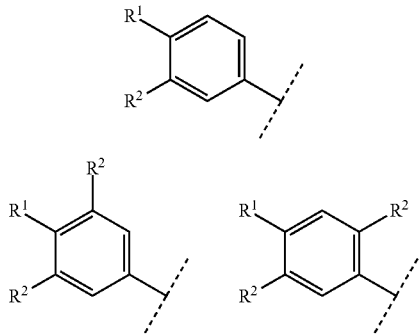

In the above embodiments, when R² is halogen, the following moieties are illustrated.

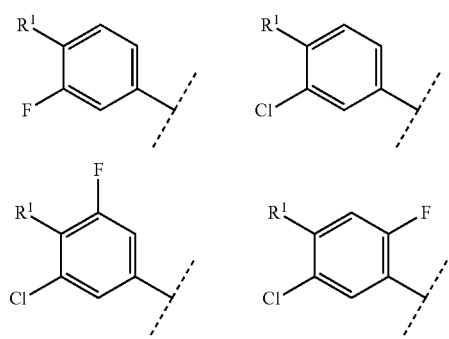

The above structure also includes the following embodiments.

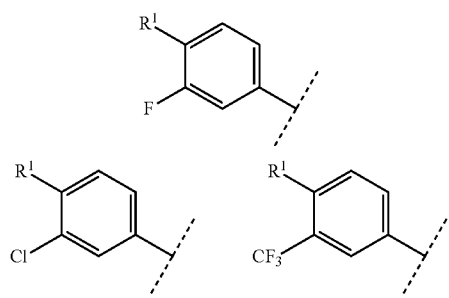

An embodiment of "R¹ and R² may combine together with the benzene ring to which they attach to form indanyl where the indanyl may be substituted with the same or different one to two $C_{1-6}$ alkyl" includes, when "n" is 1, the following embodiments.

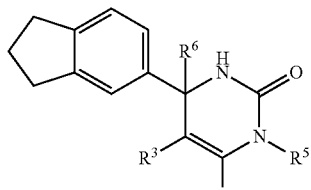

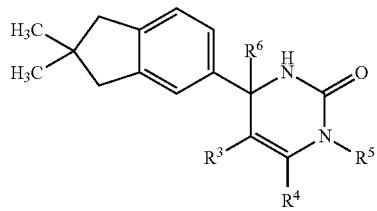

A preferable "—$Y^b$—COO—$R^{30}$" in $R^3$ is —($C_{3-5}$ alkylene)-COOH or —$C_4$ cycloalkylene-COOH, in particular —C(CH₃)₂—COOH, —C(CH₃)₂—CH₂—COOH, —C(CH₃)₂—(CH₂)₂—COOH or -cyclobutylene-COOH.

"$C_{1-6}$ alkyl optionally substituted with one hydroxy" in $R^3$ is "$C_{1-6}$ alkyl substituted with one hydroxy" or "unsubstituted $C_{1-6}$ alkyl". A preferable "$C_{1-6}$ alkyl substituted with one hydroxy" is "$C_6$ alkyl substituted with one hydroxy". An illustrative example of "$C_{1-6}$ alkyl optionally substituted with one hydroxy" includes methyl, ethyl, isopropyl, isobutyl, tert-butyl, 1-methylpropyl, isopentyl, neopentyl or 4-hydroxy-1,1-dimethylbutyl.

A preferable "$C_{3-6}$ cycloalkyl optionally substituted with the same or different one to three substituent(s) selected from Group $X^b$" in $R^3$ is "$C_{3-6}$ cycloalkyl optionally substituted with the same or different one to two substituent(s) selected from fluoro or methyl", in particular cyclopropyl, cyclobutyl, 1-methylcyclopropyl, 3,3-difluorocyclobutyl or cyclohexyl.

One preferable embodiment of $R^3$ is —$Y^b$—COO—$R^{30}$, and includes any of the following structures.

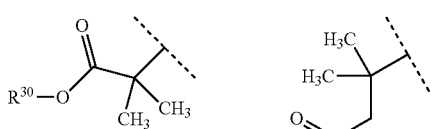

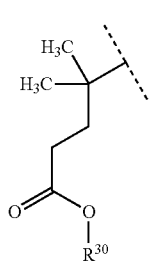

Another preferable embodiment of $R^3$ is —$Y^b$—COO—$R^{30}$ wherein $Y^b$ is

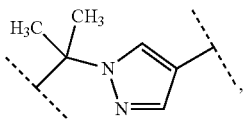

and in this case, one preferable embodiment of Formula [I] includes an embodiment having the following structure.

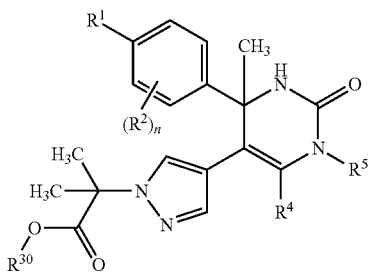

A preferable $R^4$ is hydrogen.

An illustrative example of "$C_{1-6}$ alkylene optionally substituted with one hydroxy" in $Y^c$ in "—$Y^c$—COO—$R^{50}$" in $R^5$ includes, for example, methylene, ethylene, trimethylene, butylene, $(CH_2)_2$—$CH(CH_3)$, $CH(CH_3)$—$(CH_2)_2$, $(CH_2)_2$—$C(CH_3)_2$, $CH_2$—$C(CH_3)_2$—$CH_2$, $C(CH_3)_2$—$(CH_2)_2$, $(CH_2)_3$—$C(CH_3)_2$, and $(CH_2)_2$—$CH(OH)$.

A preferable m is an integer of 0 to 2, and a preferable w is an integer of 0 to 1.

A preferable "$(CH_2)_m$—$Y^{c1}$—$(CH_2)_w$" in $Y^c$ in "—$Y^c$—COO—$R^{50}$" in $R^5$ is $Y^{c1}$, $Y^{c1}$—$CH_2$, $CH_2$—$Y^{c1}$, $CH_2$—$Y^{c1}$—$CH_2$, $(CH_2)_2$—$Y^{c1}$ or $(CH_2)_2$—$Y^{c1}$—$CH_2$.

A preferable "$C_{3-6}$ cycloalkylene optionally substituted with one $C_{1-3}$ alkyl" in $Y^{c1}$ is "cyclopropylene, cyclobutylene, cyclopentylene or cyclohexylene, optionally substituted with one methyl".

A preferable "cross-linked $C_{5-8}$ cycloalkylene" in $Y^{c1}$ is "cross-linked $C_5$ cycloalkylene", and for example has the following structure.

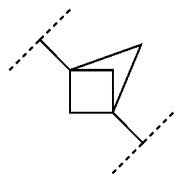

When $Y^{c1}$ is

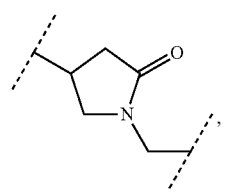

one preferable embodiment of Formula [I] includes embodiments having the following structures in the case where m is 0 and w is 0.

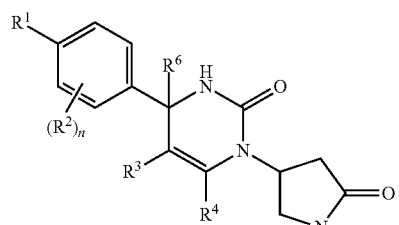

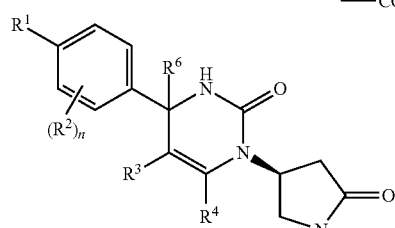

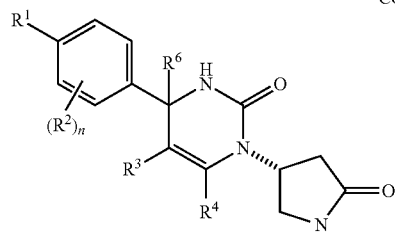

In this case, a preferable $R^{50}$ is hydrogen or methyl.

When $Y^{c1}$ is "pyrazolediyl substituted with one $C_{1-3}$ alkyl", one preferable embodiment of Formula [I] includes an embodiment having the following structure in the case where m is 0 and w is 0.

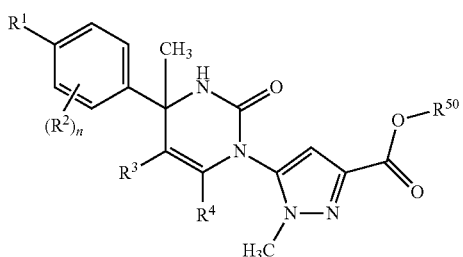

In this case, a preferable $R^{50}$ is hydrogen or methyl.

When $Y^{c1}$ is "isoxazolediyl", one preferable embodiment of Formula [I] includes an embodiment having the following structure in the case where m is 0 and w is 0.

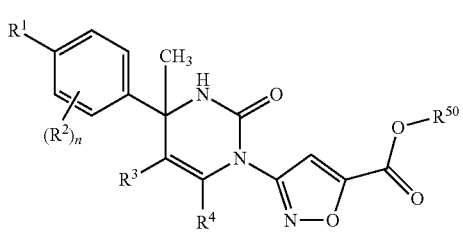

In this case, a preferable $R^{50}$ is hydrogen or methyl.

A preferable "$C_{1-4}$ alkyl optionally substituted with one $C_{1-3}$ alkoxy" in $R^5$ is "$C_{1-3}$ alkyl optionally substituted with one $C_{1-3}$ alkoxy", more preferably "ethyl or isopropyl, optionally substituted with one methoxy". In particular, it is methoxyethyl or isopropyl.

A preferable "$C_{3-6}$ cycloalkyl optionally substituted with one hydroxy-$C_{1-4}$ alkyl" in $R^5$ is "cyclobutyl optionally substituted with one hydroxymethyl". In particular, it is cyclobutyl or 3-hydroxymethylcyclobutyl.

One preferable embodiment of $R^5$ is —$Y^c$—COO—$R^{50}$, and includes any of the following structures.

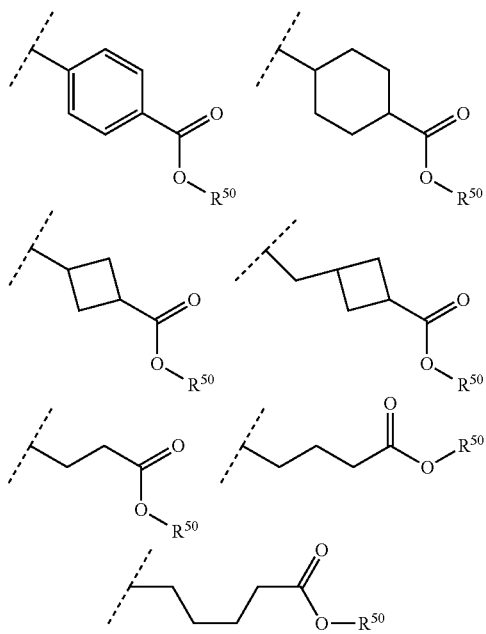

A preferable $R^6$ is methyl.

In [01], the expression "when $R^5$ is —$Y^c$—COO—$R^{50}$, $Y^c$ is $(CH_2)_m$—$Y^{c1}$—$(CH_2)_w$, m and w are 0, and $Y^{c1}$ is phenylene, then $R^6$ is methyl" means an embodiment where $R^6$ is methyl when $R^5$ moiety attaches to a dihydropyrimidine ring via phenylene. An illustrative example includes the following embodiment.

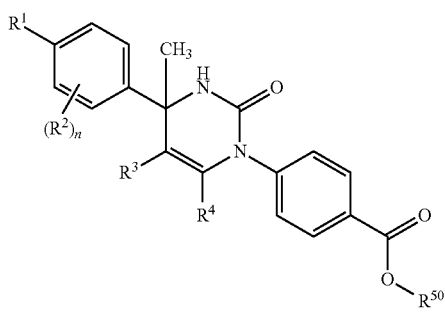

In [01], the expression "either $R^3$ or $R^5$ or both of them have "—COO—" includes the following embodiments.

An embodiment where when $R^1$ is (1) —$Y^b$—COO—$R^{30}$, then $R^5$ is (1) $Y^c$—COO—$R^{50}$,
(2) hydrogen,
(3) $C_{1-4}$ alkyl optionally substituted with one $C_{1-3}$ alkoxy or (4) $C_{3-6}$ cycloalkyl optionally substituted with one hydroxy-$C_{1-4}$ alkyl; or an embodiment where when $R^3$ is
(1) $C_{1-6}$ alkyl optionally substituted with one hydroxy,
(2) $C_{3-6}$ cycloalkyl optionally substituted with the same or different one to three substituent(s) selected from Group $X^b$, (3)

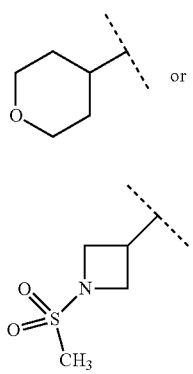

or (4)

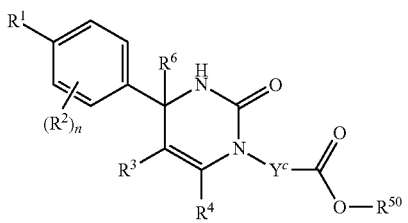

then $R^5$ is (1) —$Y^c$—COO—$R^{50}$.

A compound of Formula [I] includes any compound of the following Formula [II], [III] or [VI].

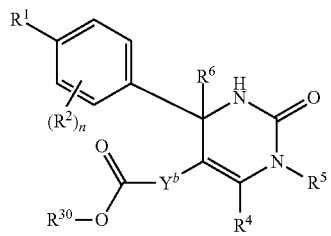

[II]

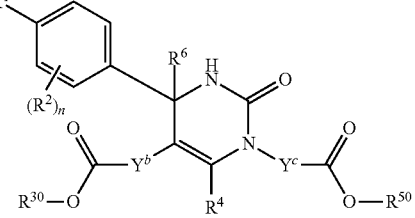

[III]

[VI]

One preferable embodiment of the compound of Formula [I] includes the compounds of the following general formulae.

Each symbol in the following each formula has the same meaning as defined in the above [01] unless otherwise specified.

[I-A]
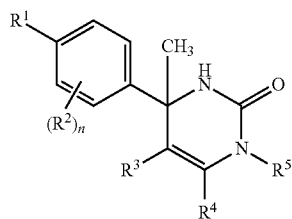

[I-B]
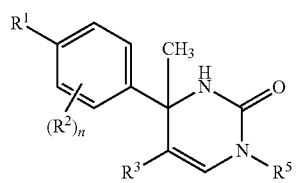

[I-C]
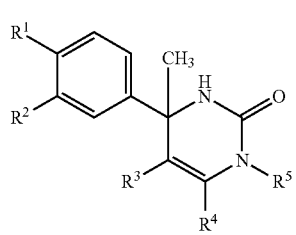

[I-D]
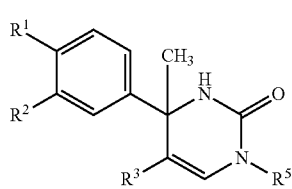

[I-Ca]
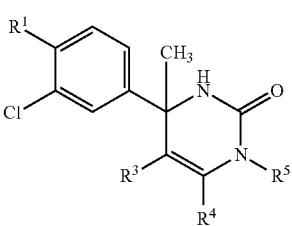

Another preferable embodiment of the compound of Formula [I] is a compound of Formula [I],
wherein $R^1$ is
(1) $C_{4-8}$ alkyl,
(2) $C_{4-6}$ alkenyl,
(3) $C_{4-6}$ alkynyl,
(4) $C_{3-5}$ alkyl substituted with one trifluoromethyl,
(5) $C_{1-4}$ alkyl substituted with one substituent selected from Group $X^{a1}$,
(6) $C_{3-6}$ alkoxy,
(7) $C_{2-7}$ alkoxy substituted with one trifluoromethyl,
(8) $C_{1-3}$ alkoxy substituted with one substituent selected from Group $X^{a2}$,
(9) $C_{4-6}$ cycloalkyl,
(10) $C_{3-6}$ cycloalkyl substituted with one to two $C_{1-4}$ alkyl,
(11) $C_{5-6}$ cycloalkenyl optionally substituted with one to two $C_{1-4}$ alkyl,
(12) spiro $C_{6-8}$ cycloalkyl or
(13) $C_{1-3}$ alkoxycarbonyl;
Group $X^{a1}$ is
(a) $C_{3-6}$ cycloalkyl optionally substituted with the same or different one to three $C_{1-5}$ alkyl,
(b) phenyl,
(c) $C_{2-4}$ alkoxy, and
(d) trimethylsilyl;
Group $X^{a2}$ is
(a) $C_{3-6}$ cycloalkyl,
(b) phenyl, and
(c) $C_{1-4}$ alkoxy;
$R^2$ is
(1) halogen,
(2) $C_{1-6}$ alkyl or
(3) $C_{1-3}$ alkoxy optionally substituted with phenyl;
n is an integer of 0, 1 or 2, provided that when n is 2, each $R^2$ may be different with each other; or
$R^1$ and $R^2$ may combine together with the benzene ring to which they attach to form indanyl where the indanyl may be substituted with the same or different one to two $C_{1-6}$ alkyl;
$R^3$ is
(1) $-Y^b-COO-R^{30}$,
(2) $C_{1-6}$ alkyl optionally substituted with one hydroxy,
(3) $C_{3-6}$ cycloalkyl optionally substituted with the same or different one to three substituent(s) selected from Group $X^b$, (4)

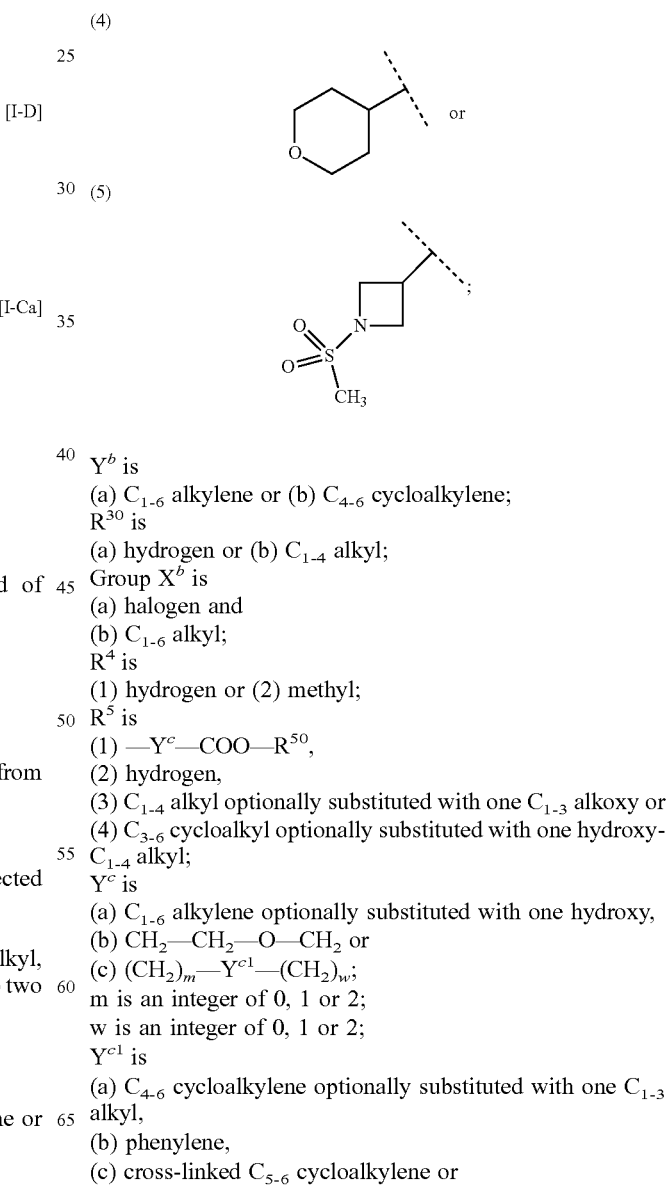

$Y^b$ is
(a) $C_{1-6}$ alkylene or (b) $C_{4-6}$ cycloalkylene;
$R^{30}$ is
(a) hydrogen or (b) $C_{1-4}$ alkyl;
Group $X^b$ is
(a) halogen and
(b) $C_{1-6}$ alkyl;
$R^4$ is
(1) hydrogen or (2) methyl;
$R^5$ is
(1) $-Y^c-COO-R^{50}$,
(2) hydrogen,
(3) $C_{1-4}$ alkyl optionally substituted with one $C_{1-3}$ alkoxy or
(4) $C_{3-6}$ cycloalkyl optionally substituted with one hydroxy-$C_{1-4}$ alkyl;
$Y^c$ is
(a) $C_{1-6}$ alkylene optionally substituted with one hydroxy,
(b) $CH_2-CH_2-O-CH_2$ or
(c) $(CH_2)_m-Y^{c1}-(CH_2)_w$;
m is an integer of 0, 1 or 2;
w is an integer of 0, 1 or 2;
$Y^{c1}$ is
(a) $C_{4-6}$ cycloalkylene optionally substituted with one $C_{1-3}$ alkyl,
(b) phenylene,
(c) cross-linked $C_{5-6}$ cycloalkylene or (d)

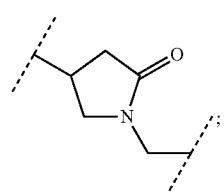

$R^{50}$ is
(a) hydrogen or (b) $C_{1-4}$ alkyl;
$R^6$ is
(1) hydrogen or (2) methyl,
provided that
when $R^5$ is —$Y^c$—COO—$R^{50}$, $Y^c$ is $(CH_2)_m$—$Y^{c1}$—$(CH_2)_w$, m and w are 0, and $Y^{c1}$ is phenylene, then $R^6$ is methyl; and
either $R^3$ or $R^5$ or both of them have "—COO—".

Another preferable embodiment of the compound of Formula [I] is a compound of Formula [I],
wherein $R^1$ is
(1) $C_{4-8}$ alkyl,
(2) $C_{4-6}$ alkenyl,
(3) $C_6$ alkynyl,
(4) trifluoromethyl-$C_{3-5}$ alkyl,
(5) $C_{1-2}$ alkyl substituted with one substituent selected from Group $X^{a1}$,
(6) $C_{4-6}$ alkoxy,
(7) trifluoromethyl-$C_2$ alkoxy,
(8) $C_{1-2}$ alkoxy substituted with one substituent selected from Group $X^{a2}$,
(9) $C_{4-6}$ cycloalkyl,
(10) $C_{3-6}$ cycloalkyl substituted with one to two $C_{1-4}$ alkyl,
(11) $C_{5-6}$ cycloalkenyl optionally substituted with one to two $C_{1-4}$ alkyl,
(12) spiro $C_7$ cycloalkyl or
(13) ethoxycarbonyl;
Group $X^{a1}$ is
(a) $C_{3-6}$ cycloalkyl optionally substituted with one to two methyl,
(b) phenyl,
(c) $C_{3-4}$ alkoxy, and
(d) trimethylsilyl;
Group $X^2$ is
(a) cyclohexyl,
(b) phenyl, and
(c) methoxy;
$R^2$ is
(1) fluoro or chloro,
(2) $C_{1-6}$ alkyl or
(3) methoxy optionally substituted with phenyl;
n is an integer of 0, 1 or 2, provided that n is 2, each $R^2$ may be different with each other; or
$R^1$ and $R^2$ may combine together with the benzene ring to which they attach to form indanyl optionally substituted with two methyl;
$R^3$ is
(1) —$Y^b$—COO—$R^{30}$,
(2) $C_{1-6}$ alkyl optionally substituted with one hydroxy,
(3) $C_{3-6}$ cycloalkyl optionally substituted with the same or different one to two substituent(s) selected from Group $X^b$, (4)

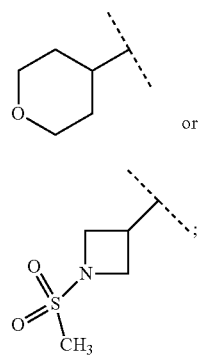

or (5)

$Y^b$ is
(a) $C_{3-5}$ alkylene or (b) $C_4$ cycloalkylene;
$R^{30}$ is hydrogen;
Group $X^b$ is
(a) fluoro and
(b) methyl;
$R^4$ is
(1) hydrogen or (2) methyl;
$R^5$ is
(1) —$Y^c$—COO—$R^{50}$,
(2) hydrogen,
(3) $C_{2-3}$ alkyl optionally substituted with one $C_{1-3}$ alkoxy or
(4) $C_4$ cycloalkyl optionally substituted with one hydroxy-$C_{1-4}$ alkyl;
$Y^c$ is
(a) $C_{1-6}$ alkylene optionally substituted with one hydroxy,
(b) $CH_2$—$CH_2$—O—$CH_2$ or
(c) $(CH_2)$—$Y^{c1}$—$(CH_2)_w$;
m is an integer of 0, 1 or 2;
w is an integer of 0 or 1;
$Y^{c1}$ is
(a) $C_{3-6}$ cycloalkylene optionally substituted with one methyl,
(b) phenylene,
(c) cross-linked $C_5$ cycloalkylene or (d)

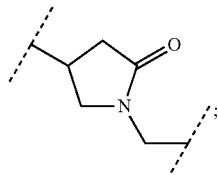

$R^{50}$ is
(a) hydrogen or (b) methyl;
$R^6$ is
(1) hydrogen or (2) methyl,
provided that
when $R^5$ is —$Y^c$—COO—$R^{50}$, $Y^c$ is (ethylene)-$Y^{c1}$-(methylene), and $Y^{c1}$ is phenylene, then $R^6$ is methyl; and
either $R^3$ or $R^5$ or both of them have "—COO—".

Another preferable embodiment of the compound of Formula [I] is a compound of the following Formula [II]:

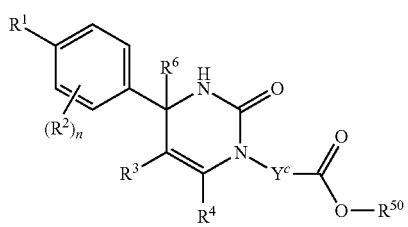

[II]

wherein
R¹ is
(1) $C_{4-8}$ alkyl,
(2) $C_{3-6}$ alkoxy or
(3) $C_{5-6}$ cycloalkenyl optionally substituted with one to two $C_{1-4}$ alkyl;
$R^2$ is fluoro or chloro;
n is 1;
$R^3$ is $C_{1-6}$ alkyl;
$R^4$ is
(1) hydrogen or (2) methyl;
$Y^c$ is $C_{1-6}$ alkylene;
$R^{50}$ is
(a) hydrogen or (b) $C_{1-4}$ alkyl;
$R^6$ is
(1) hydrogen or (2) methyl.

A more preferable embodiment of the compound of Formula [I] is a compound of Formula [II-A] which $R^6$ is methyl in Formula [II]:

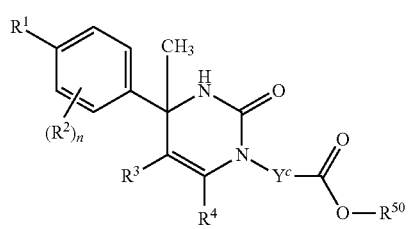

[II-A]

Another more preferable embodiment of the compound of Formula [I] is a compound of Formula [II-B] which $R^4$ is hydrogen and $R^6$ is methyl in Formula [II]:

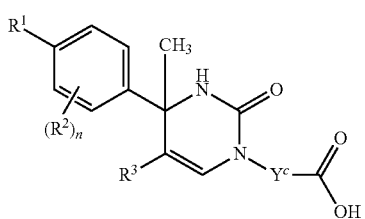

[II-B]

Another preferable embodiment of the compound of Formula [I] is a compound of Formula [III]:

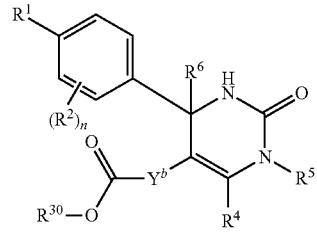

[III]

wherein
R¹ is
(1) $C_{4-8}$ alkyl,
(2) $C_{3-6}$ alkoxy or
(3) $C_{5-6}$ cycloalkenyl optionally substituted with one to two $C_{1-4}$ alkyl;
$R^2$ is fluoro or chloro;
n is 1;
$Y^b$ is $C_{1-6}$ alkylene;
$R^{30}$ is
(a) hydrogen or (b) $C_{1-4}$ alkyl;
$R^4$ is
(1) hydrogen or (2) methyl;
$R^5$ is
(1) hydrogen,
(2) $C_{1-4}$ alkyl optionally substituted with one $C_{1-3}$ alkoxy or
(3) $C_{3-6}$ cycloalkyl optionally substituted with one hydroxy-$C_{1-4}$ alkyl;
$R^6$ is
(1) hydrogen or (2) methyl.

A more preferable embodiment of the compound of Formula [I] is a compound of Formula [III-A] which $R^6$ is methyl in Formula [III]:

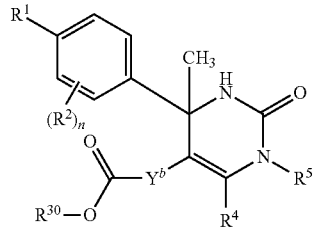

[III-A]

Another more preferable embodiment of the compound of Formula [I] is a compound of Formula [III-B] which $R^4$ is hydrogen and $R^6$ is methyl in Formula [III]:

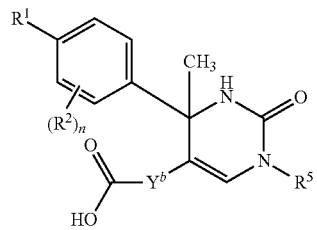

[III-B]

Another preferable embodiment of the compound of Formula [I] is a compound of the following Formula [IV]:

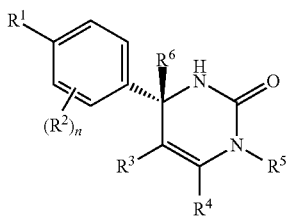

[IV]

A more preferable embodiment of the compound of Formula [I] is a compound of Formula [IV-A] which $R^6$ is methyl in Formula [IV]:

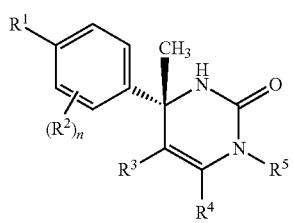

[IV-A]

Another more preferable embodiment of the compound of Formula [I] is a compound of Formula [IV-B] which $R^4$ is hydrogen and $R^6$ is methyl in Formula [IV]:

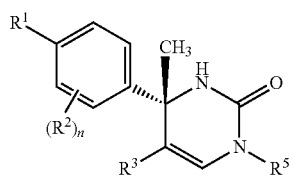

[IV-B]

Another more preferable embodiment is a compound of the following formula:

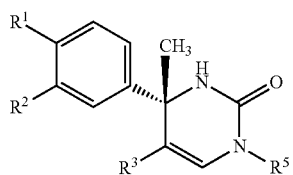

[IV-C]

Another preferable embodiment of the compound of Formula [I] is a compound of Formula [IV-D] which $R^4$ is hydrogen in Formula [IV]:

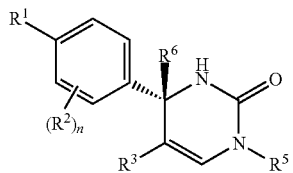

[IV-D]

Another preferable embodiment of the compound of Formula [I] is a compound of the following Formula [E-IV]:

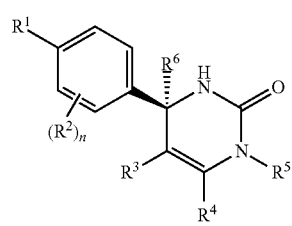

[E-IV]

A more preferable embodiment of the compound of Formula [I] is a compound of Formula [E-IV-A] which $R^6$ is methyl in Formula [E-IV]:

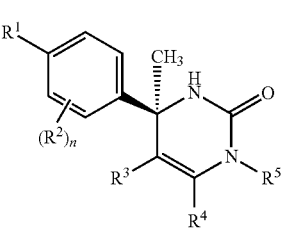

[E-IV-A]

Another more preferable embodiment of the compound of Formula [I] is a compound of Formula [E-IV-B] which $R^4$ is hydrogen in Formula [E-IV-A]:

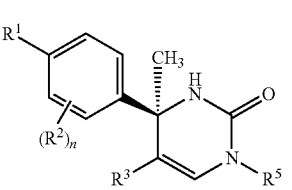

[E-IV-B]

A particularly preferable embodiment of the compound of Formula [E-IV] is a compound of the following formula:

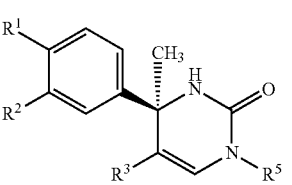

[E-IV-C]

Another preferable embodiment of the compound of Formula [I] is a compound of the following Formula [V]:

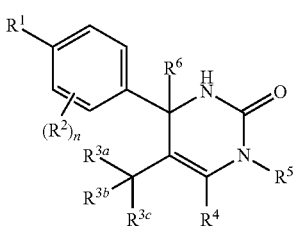

[V]

wherein
R³ is
(1) hydrogen or
(2) $C_{1-6}$ alkyl optionally substituted with the same or different one to three substituent(s) selected from the group consisting of hydroxy, halogen, hydroxycarbonyl, and $C_{1-3}$ alkoxycarbonyl;
$R^{3b}$ is
(1) hydrogen or (2) $C_{1-6}$ alkyl;
$R^{3c}$ is
(1) hydrogen or (2) $C_{1-6}$ alkyl; and the other symbols have the same meanings as defined in [01],
provided that
when $R^5$ is $-Y^c-COO-R^{50}$, $Y^c$ is $(CH_2)_m-Y^{c1}-(CH_2)_w$, m and w are 0, and $Y^{c1}$ is phenylene, then $R^6$ is methyl; and
either a structure of the formula:

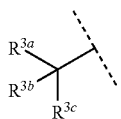

or $R^5$ or both of them have "—COO—".

Another embodiment of the compound of Formula [V] is the following compound:

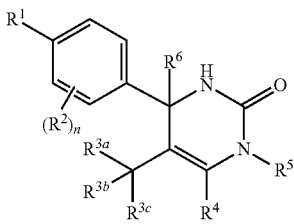

[V]

wherein
$R^{3a}$ and $R^{3b}$ may combine together with the carbon atom to which they attach to form
(1) a $C_{3-6}$ cycloalkane ring optionally substituted with the same or different one to three substituent(s) selected from the group consisting of hydroxy, halogen, hydroxycarbonyl, and $C_{1-3}$ alkoxycarbonyl,
(2) a tetrahydropyran ring or
(3) a 1-methanesulfonylazetidine ring;
R³ is (1) hydrogen or (2) $C_{1-6}$ alkyl; and the other symbols have the same meanings as defined in [01],
provided that
when $R^5$ is $-Y^c-COO-R^{50}$, $Y^c$ is $(CH_2)_m-Y^{c1}-(CH_2)_w$, m and w are 0, and $Y^{c1}$ is phenylene, then $R^6$ is methyl;

either a structure of the formula:

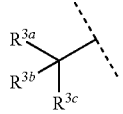

or $R^5$ or both of them have "—COO—".

A more preferable embodiment of the compound of Formula [V] includes the compounds of the following general formulae.

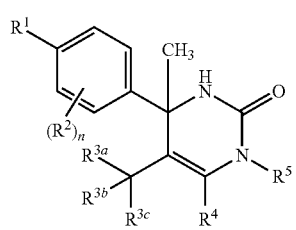

[V-A]

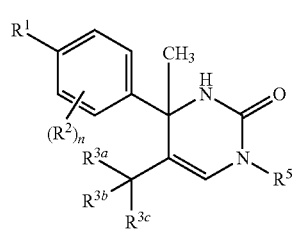

[V-B]

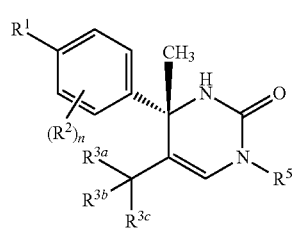

[V-C]

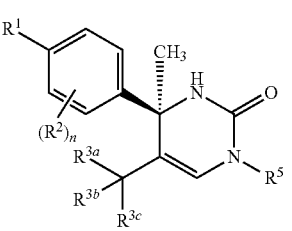

[E-V-C]

Another preferable embodiment of the compound of Formula [I] is a compound of the following Formula [VI]:

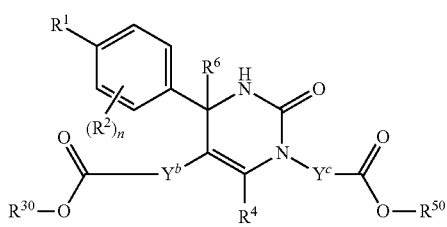

[VI]

A further preferable embodiment of a compound of Formula [I] is any one of compounds of the following formulae:

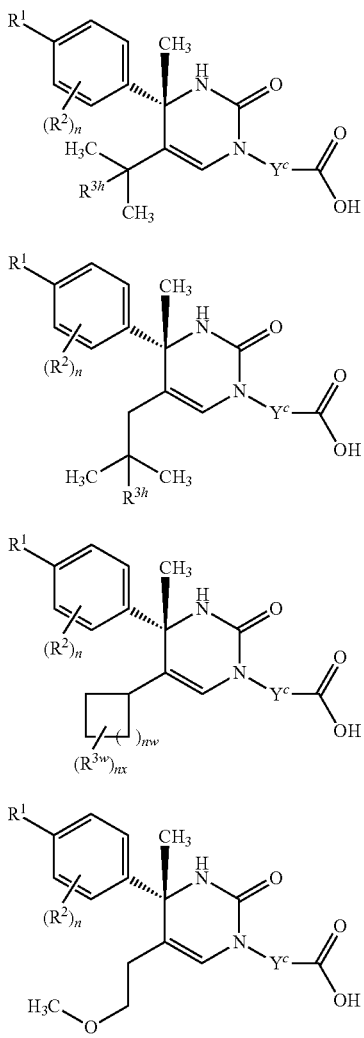

[IV-B-A]

[IV-B-B]

[IV-B-C]

[IV-B-D]

wherein
$R^{3h}$ is hydrogen or methyl;
$R^{3w}$ is methyl or fluoro;
$n^x$ is an inter of 0 or 2;
$n^w$ is an integer of 0, 1, 2 or 3; and
the other symbols have the same meanings as defined in [01].

In the Formulae [IV-B-A] to [IV-B-D], a more preferable one is any one of compounds wherein $R^2$ is chloro or trifluoromethyl.

In the Formulae [IV-B-A] to [IV-B-D], a still more preferable one is any one of compounds wherein
$Y^c$ is
(a) $C_{1-6}$ alkylene optionally substituted with one hydroxy or
(b) $(CH_2)_m$—$Y^{c1}$—$(CH_2)_w$;
m is an integer of 0, 1 or 2;
w is an integer of 0, 1 or 2; and
$Y^{c1}$ is
(a) $C_{3-6}$ cycloalkylene optionally substituted with one $C_{1-3}$ alkyl,
(b) phenylene,
(c) phenylene substituted with one halogen,
(d) phenylene substituted with one $C_{1-3}$ alkyl,
(e) phenylene substituted with one $C_{1-3}$ alkoxy,
(f) phenylene substituted with one trifluoromethyl,
(g) cross-linked $C_{5-8}$ cycloalkylene,
(h) pyrrolidinediyl,
(i) pyrrolidinediyl substituted with one carboxy,
(j) pyrrolidinediyl substituted with one $C_{1-3}$ alkylcarbonyl,
(k) pyrrolidinediyl substituted with one $C_{1-3}$ alkylsulfonyl or
(l) pyridinediyl.

A still more preferable one is any one of compounds of Formula [IV-B-A] to [IV-B-D] wherein
$Y^c$ is $C_{1-6}$ alkylene, phenylene, cross-linked $C_{5-8}$ cycloalkylene or pyridinediyl.

Another further preferable embodiment of a compound of Formula [I] is any one of compounds of the following formulae:

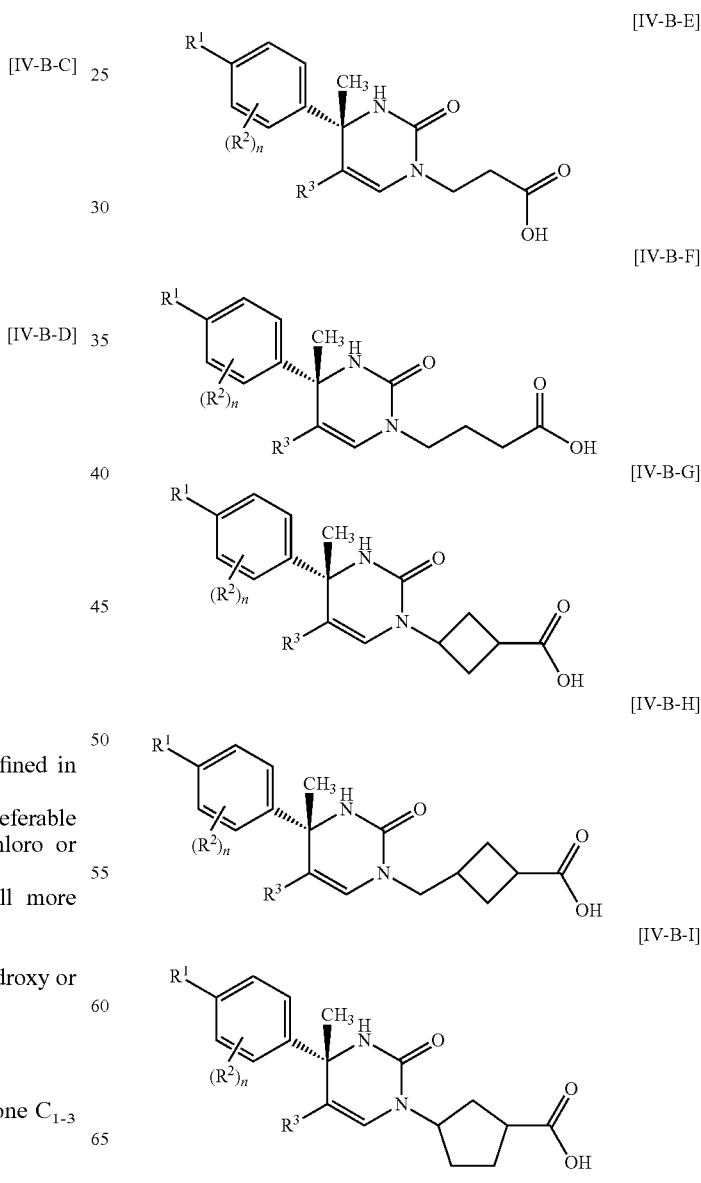

[IV-B-E]

[IV-B-F]

[IV-B-G]

[IV-B-H]

[IV-B-I]

-continued

[IV-B-J]
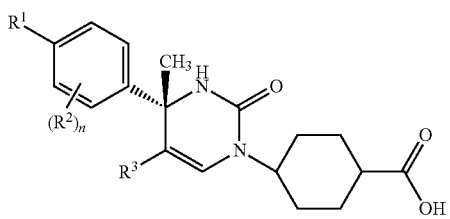

[IV-B-K]
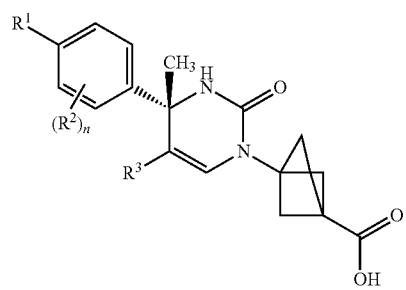

[IV-B-L]
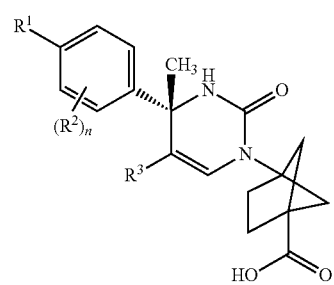

[IV-B-M]
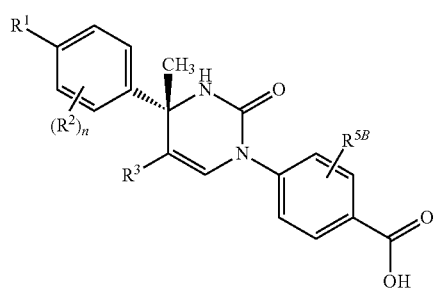

[IV-B-N]
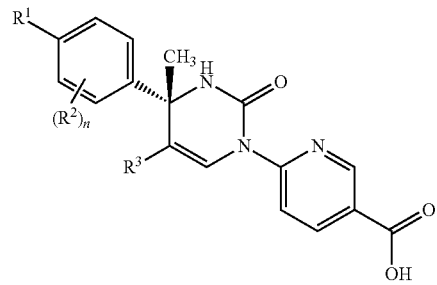

wherein
$R^1$ is $C_{1-6}$ alkyl optionally substituted with one hydroxy, $C_{1-6}$ alkyl substituted with one $C_{1-4}$ alkoxy or
$C_{3-6}$ cycloalkyl optionally substituted with the same or different one to three substituent(s) selected from Group $X^b$;
$R^{5B}$ is hydrogen, halogen, $C_{1-3}$ alkyl, $C_{1-3}$ alkoxy or trifluoromethyl; and
the other symbols have the same meanings as defined in [01].

In the Formulae [IV-B-A] to [IV-B-N], a more preferable one is any one of compounds wherein
$R^1$ is
$C_{4-8}$ alkyl,
$C_{3-7}$ alkyl substituted with one trifluoromethyl,
$C_{1-5}$ alkyl substituted with one substituent selected from Group $X^{a1}$,
$C_{3-6}$ alkoxy,
$C_{2-7}$ alkoxy substituted with one trifluoromethyl,
$C_{1-3}$ alkoxy substituted with one substituent selected from Group $X^{a2}$,
$C_{4-6}$ cycloalkyl,
$C_{3-6}$ cycloalkyl substituted with the same or different one to two $C_{1-5}$ alkyl,
$C_{5-6}$ cycloalkenyl optionally substituted with the same or different one to two $C_{1-4}$ alkyl, cyclohexylidenemethyl optionally substituted with the same or different one to two $C_{1-3}$ alkyl, tetrahydropyran-4-ylidenemethyl,
$C_{3-6}$ cycloalkyl substituted with one to the same two halogen or
$C_{5-6}$ cycloalkenyl substituted with one to the same two halogen; and
$R^2$ is fluoro, chloro or trifluoromethyl.

In the Formulae [IV-B-A] to [IV-B-N], a still more preferable one is any one of compounds wherein
$R^1$ is
$C_{4-8}$ alkyl,
$C_{3-7}$ alkyl substituted with one trifluoromethyl,
$C_{1-5}$ alkyl substituted with one substituent selected from Group $X^{a1}$,
$C_{3-6}$ alkoxy,
$C_{4-6}$ cycloalkyl substituted with the same or different one to two $C_{1-5}$ alkyl,
$C_{5-6}$ cycloalkenyl optionally substituted with the same or different one to two $C_{1-4}$ alkyl,
$C_6$ cycloalkyl substituted with one to the same two halogen or
$C_6$ cycloalkenyl substituted with one to the same two halogen; and
$R^2$ is chloro or trifluoromethyl.

In a still more preferable embodiment of the Formulae [IV-B-A] to [IV-B-N], $R^1$ is any one of the following substituents.

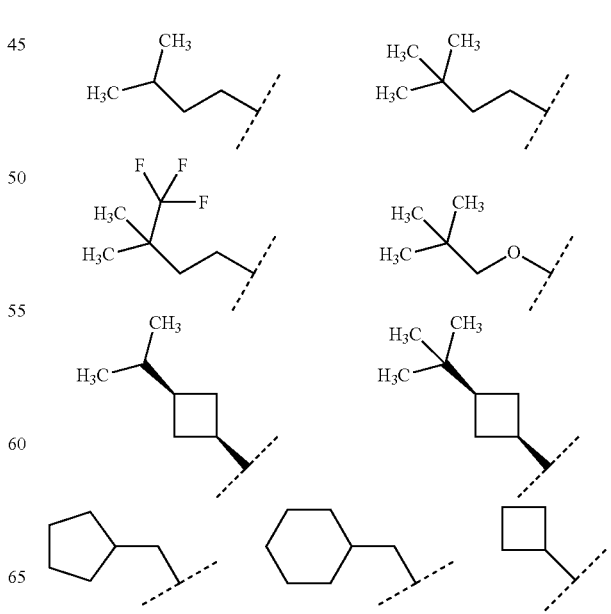

-continued

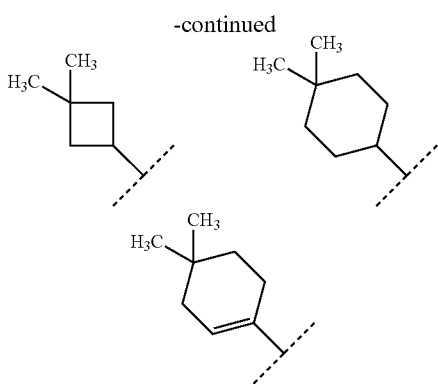

Another embodiment of the present invention also includes the following embodiments.

[01a] A compound of Formula [I] or a pharmaceutically acceptable salt thereof:

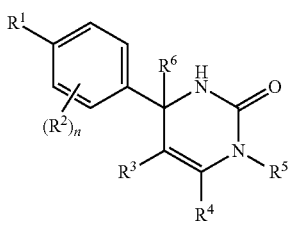

[I]

wherein
$R^1$ is
(1) $C_{4-8}$ alkyl,
(2) $C_{4-8}$ alkenyl,
(3) $C_{4-8}$ alkynyl,
(4) $C_{3-7}$ alkyl substituted with one trifluoromethyl,
(5) $C_{1-4}$ alkyl substituted with one substituent selected from Group $X^{a1}$,
(6) $C_{3-6}$ alkoxy,
(7) $C_{2-7}$ alkoxy substituted with one trifluoromethyl,
(8) $C_{1-3}$ alkoxy substituted with one substituent selected from Group $X^{a2}$,
(9) $C_{4-6}$ cycloalkyl,
(10) $C_{3-6}$ cycloalkyl substituted with one to two $C_{1-4}$ alkyl,
(11) $C_{5-6}$ cycloalkenyl optionally substituted with one to two $C_{1-4}$ alkyl,
(12) spiro $C_{6-11}$ cycloalkyl or
(13) $C_{1-3}$ alkoxycarbonyl;
Group $X^{a1}$ is
(a) $C_{3-6}$ cycloalkyl optionally substituted with the same or different one to three $C_{1-5}$ alkyl,
(b) phenyl,
(c) $C_{2-4}$ alkoxy, and
(d) trimethylsilyl;
Group $X^{a2}$ is
(a) $C_{3-6}$ cycloalkyl,
(b) phenyl, and
(c) $C_{1-4}$ alkoxy;
$R^2$ is
(1) halogen,
(2) $C_{1-6}$ alkyl, or
(3) $C_{1-3}$ alkoxy optionally substituted with phenyl;
n is an integer of 0, 1 or 2, provided that when n is 2, each $R^2$ may be different with each other; or $R^1$ and $R^2$ may combine together with the benzene ring to which they attach to form indanyl where the indanyl may be substituted with the same or different one to two $C_{1-6}$ alkyl;
$R^3$ is
(1) —$Y^b$—COO—$R^{30}$,
(2) $C_{1-6}$ alkyl optionally substituted with one hydroxy,
(3) $C_{3-6}$ cycloalkyl optionally substituted with the same or different one to three substituent(s) selected from Group $X^b$, (4)

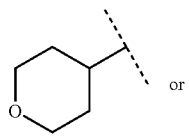

or (5)

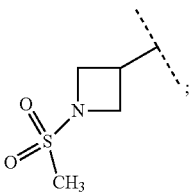

;

$Y^b$ is
(a) $C_{1-6}$ alkylene or (b) $C_{3-6}$ cycloalkylene;
$R^{30}$ is
(a) hydrogen or (b) $C_{1-4}$ alkyl;
Group $X^b$ is
(a) halogen and
(b) $C_{1-6}$ alkyl;
$R^4$ is
(1) hydrogen or (2) methyl;
$R^5$ is
(1) —$Y^c$—COO—$R^{50}$,
(2) hydrogen,
(3) $C_{1-4}$ alkyl optionally substituted with one $C_{1-3}$ alkoxy or
(4) $C_{3-6}$ cycloalkyl optionally substituted with one hydroxy-$C_{1-4}$ alkyl;
$Y^c$ is
(a) $C_{1-6}$ alkylene optionally substituted with one hydroxy,
(b) CH$_2$—CH$_2$—O—CH$_2$ or
(c) (CH$_2$)$_m$—$Y^{c1}$—(CH$_2$)$_w$;
m is an integer of 0, 1 or 2;
w is an integer of 0, 1 or 2;
$Y^{c1}$ is
(a) $C_{3-6}$ cycloalkylene optionally substituted with one $C_{1-3}$ alkyl,
(b) phenylene,
(c) cross-linked $C_{5-8}$ cycloalkylene or (d)

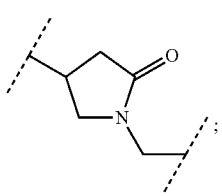

;

R⁵⁰ is
(a) hydrogen or (b) C₁₋₄ alkyl;
R⁶ is
(1) hydrogen or (2) methyl;
provided that
when R⁵ is —Y^c—COO—R⁵⁰, Y^c is (CH₂)_m—Y^{c1}—(CH₂)_w, m and w are 0, and Y^{c1} is phenylene, then R⁶ is methyl; and
either R³ or R⁵ or both of them have "—COO—".

[02a] The compound of [01a], wherein the compound of Formula [I] is a compound of Formula [II], or a pharmaceutically acceptable salt thereof.

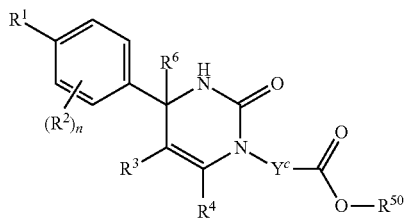

[03a] The compound of [01a], wherein the compound of Formula [I] is a compound of Formula [III], or a pharmaceutically acceptable salt thereof.

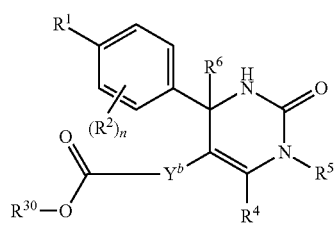

[04a] The compound of [01a], wherein the compound of Formula [I] is a compound of Formula [IV], or a pharmaceutically acceptable salt thereof.

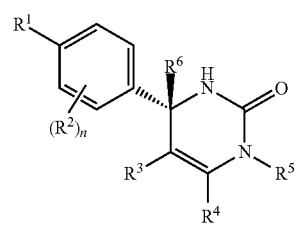

[05a] The compound of any one of [01a] to [04a], wherein R⁶ is methyl, or a pharmaceutically acceptable salt thereof.
[06a] The compound of any one of [01a] to [05a], wherein R⁴ is hydrogen, or a pharmaceutically acceptable salt thereof.
[07a] The compound of any one of [01a] to [06a], wherein n is an integer of 1 or 2, or a pharmaceutically acceptable salt thereof.
[08a] The compound of any one of [01a] to [07a], wherein R² is halogen, or a pharmaceutically acceptable salt thereof.
[09a] The compound of [08a], wherein R² is chloro or fluoro, or a pharmaceutically acceptable salt thereof.

[10a] The compound of [02a], wherein R⁵⁰ is hydrogen, or a pharmaceutically acceptable salt thereof.
[11a] The compound of [03a], wherein R³⁰ is hydrogen, or a pharmaceutically acceptable salt thereof.
[12a] A pharmaceutical composition comprising the compound of any one of [01a] to [11a] or a pharmaceutically acceptable salt thereof and a pharmaceutically acceptable carrier.
[13a] An RORγ antagonist comprising the compound of any one of [01a] to [11a] or a pharmaceutically acceptable salt thereof and a pharmaceutically acceptable carrier.
[14a] An agent for treating or preventing a disease selected from the group consisting of autoimmune disease, allergic disease, dry eye, fibrosis, and metabolic disease, comprising the compound of any one of [01a] to [11a] or a pharmaceutically acceptable salt thereof.
[15a] The agent of [14a], wherein the disease is autoimmune disease.
[16a] The agent of [15a], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes.
[17a] The agent of [14a], wherein the disease is metabolic disease.
[18a] The agent of [17a], wherein the metabolic disease is diabetes.
[19a] A method of inhibiting RORγ, comprising administering to a mammal a therapeutically effective amount of the compound of any one of [01a] to [11a] or a pharmaceutically acceptable salt thereof.
[20a] A method of treating or preventing a disease selected from the group consisting of autoimmune disease, allergic disease, dry eye, fibrosis, and metabolic disease, comprising administering to a mammal an effective amount of the compound of any one of [01a] to [11a] or a pharmaceutically acceptable salt thereof.
[21a] The method of [20a], wherein the disease is autoimmune disease.
[22a] The method of [21a], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes.
[23a] The method of [20a], wherein the disease is metabolic disease.
[24a] The method of [23a], wherein the metabolic disease is diabetes.
[25a] Use of the compound of any one of [01a] to [11a] or a pharmaceutically acceptable salt thereof for the manufacture of an RORγ antagonist.
[26a] Use of the compound of any one of [01a] to [11a] or a pharmaceutically acceptable salt thereof for the manufacture of an agent for treatment or prevention of a disease selected from the group consisting of autoimmune disease, allergic disease, dry eye, fibrosis, and metabolic disease.
[27a] The use of [26a], wherein the disease is autoimmune disease.
[28a] The use of [27a], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes.
[29a] The use of [26a], wherein the disease is metabolic disease.

[30a] The use of [29a], wherein the metabolic disease is diabetes.

[31a] A compound of any one of [01a] to [11a] or a pharmaceutically acceptable salt thereof for use as an RORγ antagonist.

[32a] A compound of any one of [01a] to [11a] or a pharmaceutically acceptable salt thereof for use as an agent for treating or preventing a disease selected from the group consisting of autoimmune disease, allergic disease, dry eye, fibrosis, and metabolic disease.

[33a] The compound of [32a], wherein the disease is autoimmune disease, or a pharmaceutically acceptable salt thereof.

[34a] The compound of [33a], wherein the autoimmune disease is selected from the group consisting of rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, and type I diabetes, or a pharmaceutically acceptable salt thereof.

[35a] The compound of [32a], wherein the disease is metabolic disease, or a pharmaceutically acceptable salt thereof.

[36a] The compound of [35a], wherein the metabolic disease is diabetes, or a pharmaceutically acceptable salt thereof.

The term "pharmaceutically acceptable salt" may be any salts without excess toxicity known in the art.

In particular, it includes, for example, a salt with an inorganic acid, a salt with an organic acid, a salt with an inorganic base, and a salt with an organic base. Various forms of pharmaceutically acceptable salts are well known in the art, and are listed in the following references, for example.

(a) Berge et al., J. Pharm. Sci., 66, p 1-19 (1977),
(b) Stahl et al., "Handbook of Pharmaceutical Salt: Properties, Selection, and Use" (Wiley-VCH, Weinheim, Germany, 2002),
(c) Paulekuhn et al., J. Med. Chem., 50, p 6665-6672 (2007)

The salt with an organic acid or inorganic acid includes a salt with acetic acid, adipic acid, alginic acid, 4-aminosalicylic acid, anhydromethylenecitric acid, benzoic acid, benzenesulfonic acid, calcium edetate, camphor acid, camphor-10-sulfonic acid, carbonic acid, citric acid, edetic acid, ethane-1,2-disulfonic acid, dodecylsulfonic acid, ethanesulfonic acid, fumaric acid, glucoheptonic acid, gluconic acid, glucuronic acid, glucoheptonic acid, glycollylarsanilic acid, hexylresorcylic acid, hydrobromic acid, hydrochloric acid, hydrofluoric acid, hydroiodic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, nitric acid, oleic acid, oxalic acid, pamoic acid, pantothenic acid, pectic acid, phosphoric acid, picric acid, propionic acid, polygalacturonic acid, salicylic acid, stearic acid, succinic acid, sulfuric acid, tannic acid, tartaric acid, teoclic acid, thiocyanic acid, trifluoroacetic acid, p-toluenesulfonic acid, undecanoic acid, asparaginic acid or glutamic acid.

A preferable salt with an organic acid includes a salt with oxalic acid, maleic acid, citric acid, fumaric acid, lactic acid, malic acid, succinic acid, tartaric acid, acetic acid, trifluoroacetic acid, benzoic acid, glucuronic acid, oleic acid or pamoic acid. Alternatively, a salt with methanesulfonic acid, benzenesulfonic acid, p-toluenesulfonic acid or 2-hydroxy-1-ethanesulfonic acid is illustrated.

A preferable salt with an inorganic acid includes a salt with hydrochloric acid, nitric acid, sulfuric acid, phosphoric acid or hydrobromic acid.

The salt with an organic base includes a salt with arecoline, betaine, choline, clemizole, ethylenediamine, N-methylglucamine, N-benzylphenethylamine, tris(hydroxymethyl)methylamine, arginine or lysine.

A preferable salt with an organic base includes a salt with tris(hydroxymethyl)methylamine, N-methylglucamine or lysine.

The salt with an inorganic base includes a salt with ammonium, aluminum, barium, bismuth, calcium, lithium, magnesium, potassium, sodium or zinc.

A preferable salt with an inorganic base includes a salt with sodium, potassium, calcium, magnesium or zinc.

According to known methods, each pharmaceutically acceptable salt may be obtained by reacting a compound of Formula [I] with an inorganic base, an organic base, an inorganic acid or an organic acid.

A preferable salt of a compound of Formula [I] includes a salt with sodium, potassium or calcium.

Another preferable salt of a compound of Formula [I] includes a salt with sodium, potassium, L-lysine, tris(hydroxymethyl)methylamine, diethylamine, piperazine or dicyclohexylamine.

A compound of Formula [I] or a pharmaceutically acceptable salt thereof may exist in its solvate.

The term "solvate" means a compound where a solvent molecule is coordinated with a compound of Formula [I] or a pharmaceutically acceptable salt thereof, and includes a hydrate.

A pharmaceutically acceptable solvate is preferred as the solvate, and includes, for example, a hydrate, an ethanolate, and a dimethylsulfoxidate of a compound of Formula [I] or a pharmaceutically acceptable salt thereof.

In particular, it includes, for example, a hemihydrate, 1 hydrate, 2 hydrate or 1 ethanolate of a compound of Formula [I], or a monohydrate of a sodium salt of a compound of Formula [I] or a ½ ethanolate of dihydrochloride thereof.

According to known methods, the solvates may be obtained.

A compound of Formula [I] may exist as a tautomer. In that case, a compound of Formula [I] may exist as an individual tautomer or a mixture of tautomers.

A compound of Formula [I] may have a carbon-carbon double bond. In that case, a compound of Formula [I] may exist as an E-isomer, a Z-isomer or a mixture of E- and Z-isomers.

A compound of Formula [I] may exist as a stereoisomer which should be recognized as a cis/trans isomer. In that case, a compound of Formula [I] may exist as a cis-isomer, a trans-isomer or a mixture of cis- and trans-isomers.

A compound of Formula [I] may have one or more asymmetric carbon atom(s). In that case, a compound of Formula [I] may exist as a single enantiomer, a single diastereomer, a mixture of enantiomers or a mixture of diastereomers.

A compound of Formula [I] may exist as an atropisomer. In that case, a compound of Formula [I] may exist as an individual atropisomer or a mixture of atropisomers.

A compound of Formula [I] may simultaneously have multiple structural features which can provide the above isomers. A compound of Formula [I] may also contain the above isomers in any ratios.

Formulae, chemical structures or chemical names without specifying a stereochemistry herein include all the above isomers which may exist, unless otherwise specified.

Diastereomer mixtures may be isolated into each diastereomer by a conventional method such as chromatography or crystallization. Each diastereomer may be also prepared by using a starting material which is a single isomer in terms of stereochemistry or by a synthetic method using a stereoselective reaction.

A mixture of enantiomers may be isolated into each single enantiomer by a well known method in the art.

For example, a mixture of enantiomers may be reacted with a substantially pure enantiomer which is known as a chiral auxiliary to form a mixture of diastereomers, which may be then isolated into a diastereomer with an enhanced isomeric ratio or a substantially pure single diastereomer by a common method such as fractionated crystallization or chromatography. The added chiral auxiliary may be removed from the isolated diastereomer by a cleavage reaction to give a desirable enantiomer.

A mixture of enantiomers may be also directly separated by a well known chromatography in the art using a chiral stationary phase.

Alternatively, either of enantiomers may be also obtained by using a substantially pure and optically active starting material or a stereoselective synthesis (i.e., asymmetric induction) from a prochiral intermediate with a chiral auxiliary or asymmetric catalyst.

An absolute configuration may be determined by X-ray crystallographic analysis of a crystalline product or intermediate. In that case, a crystalline product or intermediate which is induced by an agent having an asymmetric center with a known configuration may be used if needed.

A compound of Formula [I] may be labeled with an isotope atom such as $^2H$, $^3H$, $^{14}C$, and $^{35}S$.

A compound of Formula [I] or a pharmaceutically acceptable salt thereof is preferably a substantially purified compound of Formula [I] or pharmaceutically acceptable salt thereof. A more preferable one is a compound of Formula [I] or a pharmaceutically acceptable salt thereof purified in an 80% or more purity.

According to known methods in the art of pharmaceutical formulation, a pharmaceutical composition in the present invention may be prepared by optionally mixing a compound of Formula [I] or a pharmaceutically acceptable salt thereof with at least one or more pharmaceutically acceptable carrier(s) in any amount. A content of a compound of Formula [I] or a pharmaceutically acceptable salt thereof in the pharmaceutical composition depends on dosage forms and doses, and is for example 0.1 to 100% by weight of the composition.

A dosage form of a compound of Formula [I] or a pharmaceutically acceptable salt thereof includes an oral preparation such as a tablet, a capsule, a granule, a powder, a lozenge, a syrup, an emulsion, and a suspension or an parenteral preparation such as an external preparation, a suppository, an injection, an eye drop, a nasal preparation, and a pulmonary preparation.

The term "pharmaceutically acceptable carrier" includes various common organic or inorganic carrier substances as a formulation material, and includes excipients, disintegrants, binders, fluidizers, and lubricants in a solid formulation, solvents, solubilizing agents, suspending agents, tonicity agents, buffers, and soothing agents in a liquid formulation, and bases, emulsifying agents, wetting agents, stabilizers, stabilizing agents, dispersants, plasticizers, pH regulators, absorption promoters, gelators, preservatives, fillers, solubilizers, solubilizing agents, and suspending agents in a semisolid formulation.

A preserving agent, an antioxidant agent, a colorant or a sweetening agent may be also optionally used as an additive.

The term "excipient" includes, for example, lactose, white soft sugar, D-mannitol, D-sorbitol, cornstarch, dextrin, microcrystalline cellulose, crystalline cellulose, carmellose, carmellose calcium, sodium carboxymethylstarch, low substituted hydroxypropylcellulose, and gum arabic.

The term "disintegrant" includes, for example, carmellose, carmellose calcium, carmellose sodium, sodium carboxymethylstarch, croscarmellose sodium, crospovidone, low substituted hydroxypropylcellulose, hydroxypropylmethylcellulose, and crystalline cellulose.

The term "binder" includes, for example, hydroxypropylcellulose, hydroxypropylmethylcellulose, povidone, crystalline cellulose, white soft sugar, dextrin, starch, gelatin, carmellose sodium, and gum arabic.

The term "fluidizer" includes, for example, light anhydrous silicic acid and magnesium stearate.

The term "lubricant" includes, for example, magnesium stearate, calcium stearate, and talc.

The term "solvent" includes, for example, purified water, ethanol, propyleneglycol, macrogol, sesame oil, corn oil, and olive oil.

The term "solubilizing agent" includes, for example, propyleneglycol, D-mannitol, benzyl benzoate, ethanol, triethanolamine, sodium carbonate, and sodium citrate.

The term "suspending agent" includes, for example, benzalkonium chloride, carmellose, hydroxypropylcellulose, propyleneglycol, povidone, methylcellulose, and glyceryl monostearate.

The term "tonicity agent" includes, for example, glucose, D-sorbitol, sodium chloride, and D-mannitol.

The term "buffer" includes, for example, sodium hydrogen phosphate, sodium acetate, sodium carbonate, and sodium citrate.

The term "soothing agent" includes, for example, benzyl alcohol.

The term "base" includes, for example, water, animal or vegetable oils such as olive oil, corn oil, arachis oil, sesame oil, and castor oil, lower alcohols such as ethanol, propanol, propylene glycol, 1,3-butylene glycol, and phenol, higher fatty acid and an ester thereof, waxes, higher alcohols, polyalcohols, hydrocarbons such as white petrolatum, liquid paraffin, and paraffin, hydrophilic petrolatum, purified lanolin, absorptive ointment, hydrous lanolin, hydrophilic ointment, starch, pullulan, gum arabic, tragacanth gum, gelatin, dextran, cellulose derivatives such as methylcellulose, carboxymethylcellulose, hydroxyethylcellulose, and hydroxypropylcellulose, synthetic polymers such as carboxyvinyl polymer, sodium polyacrylate, polyvinyl alcohol, and polyvinylpyrrolidone, propylene glycol, macrogol such as macrogol 200 to 600, and a combination of two or more of them.

The term "preserving agent" includes, for example, ethyl parahydroxybenzoate, chlorobutanol, benzyl alcohol, sodium dehydroacetate, and sorbic acid.

The term "antioxidant agent" includes, for example, sodium sulfite and ascorbic acid.

The term "colorant" includes, for example, food dye such as Food Red No. 2 and No. 3, and Food Yellow No. 4 and No. 5, and β-carotene.

The term "sweetening agent" includes, for example saccharin sodium, dipotassium glycyrrhizate, and aspartame.

A pharmaceutical composition in the present invention may be administered to human as well as mammals other than human such as mice, rats, hamsters, guinea pigs, rabbits, cats, dogs, pigs, cattle, horses, sheep, and monkeys orally or parenterally such as locally, rectally, intravenously, intramuscularly, and subcutaneously. While a dose may vary depending on subjects, diseases, symptoms, dosage forms, routes of administration and the like, for example when it is administered orally to an adult patient the dose of a compound of Formula [I] as the active ingredient ranges generally from about 0.01 mg to about 1 g per day, which may be administered once to several times in a divided amount.

A compound of Formula [I] or a pharmaceutically acceptable salt thereof has an inhibitory activity of Retinoid-related Orphan Receptor γ (RORγ), and is useful for treating or preventing various diseases or conditions which are expected to be improved by adjusting the RORγ inhibitory activity, e.g. autoimmune diseases such as rheumatoid arthritis, psoriasis, inflammatory bowel diseases such as Crohn's disease and ulcerative colitis, multiple sclerosis, systemic lupus erythematosus (SLE), ankylosing spondylitis, uveitis, polymyalgia rheumatica, type I diabetes, and graft versus host disease, allergic diseases such as asthma, dry eye, fibrosis such as lung fibrosis and primary biliary cirrhosis, and metabolic diseases such as diabetes.

The term "RORγ antagonist" means a compound having an ability which inhibits the function of Retinoid-related Orphan Receptor γ (RORγ) to make the activity thereof disappear or reduced.

To "inhibit RORγ" means that a function of RORγ is inhibited to make the activity thereof disappear or reduced, which includes, for example, the function of RORγ is inhibited according to Test Example 1 described hereafter. To "inhibit RORγ" preferably includes "inhibiting human RORγ". Inhibiting the function or disappearing or reducing the activity may be preferably carried out during clinical indication in human.

The term "RORγ inhibitor" means any substance which inhibits RORγ, and may be a low molecular compound, a nucleic acid, polypeptide, protein, antibody, vaccine and the like. A preferable "RORγ inhibitor" is "human RORγ inhibitor".

The term "treating" used herein includes improving symptoms, preventing severe diseases, maintaining a remission, preventing exacerbation as well as preventing relapse.

The term "preventing" used herein means suppressing pathogenesis of symptoms.

The term "autoimmune disease" means a generic name of diseases where an immune system overreacts to and attacks normal cells and tissues thereof to cause symptoms, and in particular, includes rheumatoid arthritis, psoriasis, inflammatory bowel diseases such as Crohn's disease and ulcerative colitis, multiple sclerosis, systemic lupus erythematosus, Behcet's disease, sarcoidosis, Harada disease, ankylosing spondylitis, uveitis, polymyalgia rheumatica, type I diabetes, and graft versus host disease.

The term "allergic disease" means a disease derived from the condition where an immune reaction excessively occurs against a certain antigen, and in particular, includes atopic dermatitis, allergic rhinitis such as pollen allergy, allergic conjunctivitis, allergic gastroenteritis, bronchial asthma, infantile asthma, food allergy, medication allergy, and hives.

The term "fibrosis" means a condition with increased fibroconnective tissues, and in particular, includes lung fibrosis and primary biliary cirrhosis.

The term "metabolic disease" means a disease caused by abnormality of metabolic turnover or a disease which includes metabolic abnormality as an element that constitutes pathogenesis, and includes, for example, diabetes such as type I diabetes or type II diabetes.

Herein, the proposal of preferences and options in respect of different features of the compounds, methods, uses, and compositions comprises the proposal of combinations of those preferences and options for the different features, insofar as they are combinable and compatible.

Methods for preparing a compound of Formula [I] or a pharmaceutically acceptable salt thereof are illustrated as below. A method for preparing a compound of Formula [I] or a pharmaceutically acceptable salt thereof is not however intended to be limited thereto.

Each compound obtained in each step may be isolated and/or purified by known methods such as distillation, recrystallization, and column chromatography, if necessary, but a reaction may optionally proceed to a sequential step without isolation and purification.

In particular, a compound of Formula [I] may be prepared according to the following Preparation Methods 1 to 5, for example:

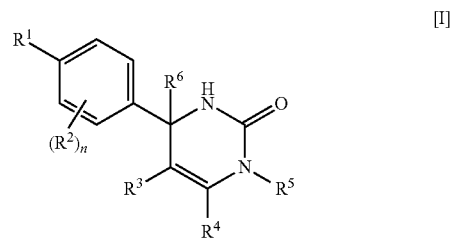

Each definition of each substituent in schemes in each Preparation Method is illustrative and is not limited thereto.

Preparation Method 1

A Method for Preparing dihydropyrimidin-2-one Compounds Via Claisen Reaction (1)

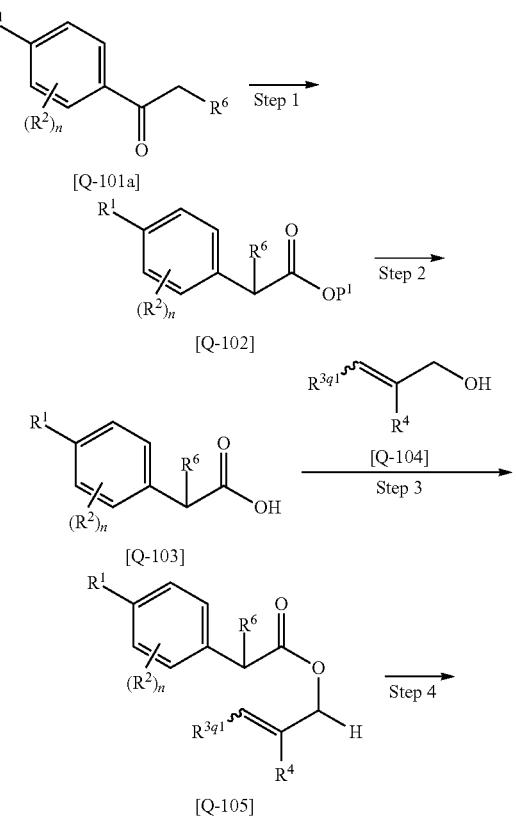

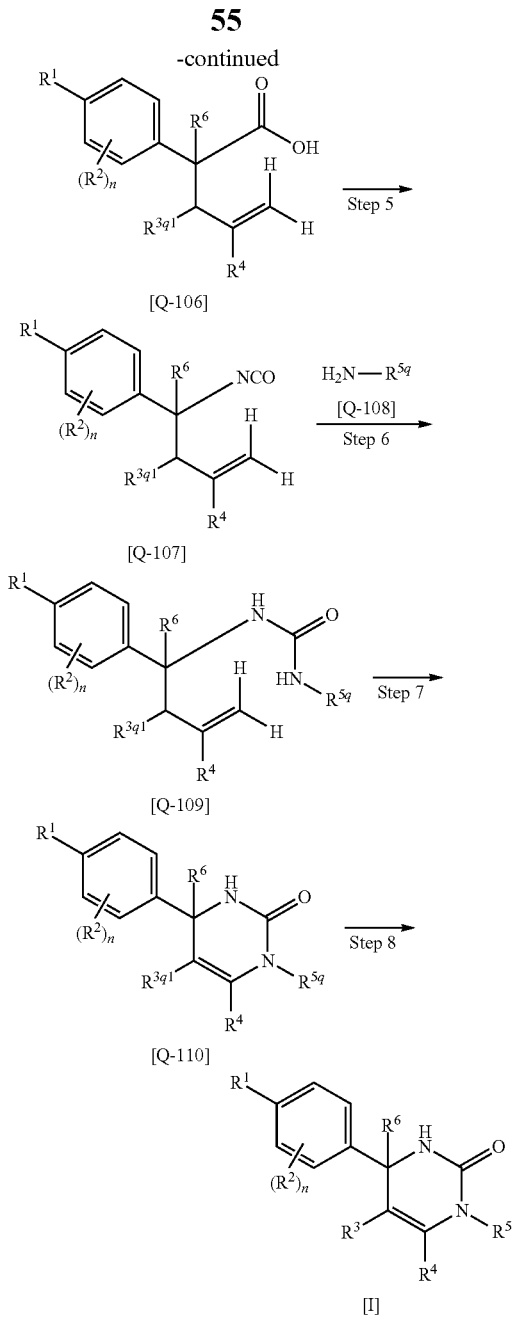

In the formula,
P¹ is for example $C_{1-4}$ alkyl;
$R^{3q1}$ is for example —$Y^b$—$CH_2OP^2$ (in which P² is a protective group such as trimethylsilyl (TMS) and tert-butyldimethylsilyl (TBDMS)), $C_{1-6}$ alkyl optionally substituted with hydroxy protected with one P², $C_{3-6}$ cycloalkyl optionally substituted with the same or different one to three substituent(s) selected from Group $X^b$, 4-tetrahydropyranyl or 1-methanesulfonyl-3-azetidinyl;
$Y^b$ is for example $C_{1-6}$ alkylene or $C_{3-6}$ cycloalkylene;
Group $X^b$ is for example halogen or $C_{1-6}$ alkyl;
$R^{5q}$ is for example —$Y^c$—COO—$R^{q50}$ (in which $R^{50}$ is $C_{1-4}$ alkyl), hydrogen, $C_{1-4}$ alkyl optionally substituted with one $C_{1-3}$ alkoxy or $C_{3-6}$ cycloalkyl optionally substituted with hydroxy-$C_{1-4}$ alkyl protected with one P²;
$Y^c$ is $C_{1-6}$ alkylene optionally substituted with hydroxy protected with one P², $CH_2$—$CH_2$—O—$CH_2$ or $(CH_2)_m$—$Y^{c1}$—$(CH_2)_w$;

m is an integer of 0, 1 or 2;
w is an integer of 0, 1 or 2;
$Y^{c1}$ is for example $C_{3-6}$ cycloalkylene optionally substituted with one $C_{1-3}$ alkyl, phenylene, cross-linked $C_{5-8}$ cycloalkylene or

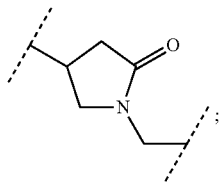

and
the other symbols have the same meanings as defined in [01].

Step 1

A compound of Formula [Q-102] may be prepared from a compound of Formula [Q-101a] by a rearrangement reaction with diacetoxyiodobenzene (e.g. a method described in Chem. Pharm. Bull., 1985, 33, 1097-1103).
A compound of Formula [Q-101a] may be prepared by Preparation Method 6 described below.

Step 2

A compound of Formula [Q-103] may be prepared from a compound of Formula [Q-102] by hydrolysis with a base.
The base includes sodium hydroxide, potassium hydroxide, and lithium hydroxide. A preferable base is sodium hydroxide.
A solvent includes methanol, ethanol, isopropanol, tetrahydrofuran, and water, and may be used alone or by mixture of two or more of them. A preferable solvent is a mixed solvent with ethanol and water.
A reaction temperature includes from room temperature to 100° C. A preferable reaction temperature is room temperature.

Step 3

A compound of Formula [Q-105] may be prepared by a condensation reaction of a compound of Formula [Q-103] with a compound of Formula [Q-104].
A condensation agent includes aqueous carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). For example, 1-hydroxy-1H-benzotriazole monohydrate (HOBt.H₂O) or 4-dimethylaminopyridine (DMAP) may be optionally added thereto. A preferable condensation agent is a mixture of aqueous carbodiimide (WSC.HCl: 1-ethyl-3-(3-dimethylaminopropyl)carbodiimide hydrochloride) and 4-dimethylaminopyridine (DMAP).
A solvent includes toluene, dichloromethane, chloroform, tetrahydrofuran, dioxane, N,N-dimethylformamide, dimethylsulfoxide, acetonitrile, and acetone, and may be used alone or by mixture of two or more of them. A preferable solvent is dichloromethane.
A reaction temperature includes from 0° C. to 100° C. A preferable reaction temperature is room temperature.

A compound of Formula [Q-104] may be prepared by Preparation Method 7-1 described below.

Step 4

A compound of Formula [Q-106] may be prepared from a compound of Formula [Q-105] in the presence of a base and a chlorosilane compound by Ireland Claisen rearrangement reaction (e.g. a method described in Org. Lett., 2007, 9, 4431-4434).

The base includes lithium diisopropylamide (LDA), lithium hexamethyldisilazide (LHMDS), and lithium 2,2,6,6-tetramethylpiperidide (LiTMP). A preferable base is lithium diisopropylamide (LDA).

The chlorosilane compound includes trimethylsilyl chloride and tert-butyldimethylsilyl chloride. A preferable chlorosilane compound is trimethylsilyl chloride.

Hexamethylphosphoric triamide (HMPA) or N,N'-dimethylpropyleneurea (DMPU) may be added as an additive.

A solvent includes an ether type solvent such as diethyl ether, tetrahydrofuran, 1,2-dimethoxyethane. A preferable solvent is tetrahydrofuran.

A reaction temperature includes from −78° C. to 80° C. A preferable reaction temperature is from −78° C. to room temperature.

Step 5

A compound of Formula [Q-107] may be prepared from a compound of Formula [Q-106] in the presence of a base by an azidation reaction followed by Curtius rearrangement reaction.

An azidation agent includes DPPA.

The base includes triethylamine and diisopropylethylamine. A preferable base is triethylamine.

A solvent includes benzene, toluene, and xylene. A preferable solvent is toluene.

A reaction temperature includes from 0° C. to 140° C. A preferable reaction temperature is 110° C.

Step 6

A compound of Formula [Q-109] may be prepared from a compound of Formula [Q-107] and a compound of Formula [Q-108]. When a compound of Formula [Q-108] is hydrochloride, one or more equivalent(s) of a base such as triethylamine may be optionally added.

A solvent includes benzene, toluene, dichloromethane, chloroform, diethyl ether, tetrahydrofuran, 1,2-dimethoxyethane, ethyl acetate, N,N-dimethylformamide, dimethylsulfoxide, acetonitrile, and acetone, and may be used alone or by mixture of two or more of them. A preferable solvent is tetrahydrofuran.

A reaction temperature includes from 0° C. to 80° C. A preferable reaction temperature is from 0° C. to room temperature.

A compound of Formula [Q-108] may be prepared by Preparation Method 8-2 described below.

Step 7

A compound of Formula [Q-110] may be prepared by an oxidative cleavage reaction of exo-olefin of a compound of Formula [Q-109], followed by a cyclization reaction with an acid.

The oxidative cleavage reaction includes ozone oxidation by reductive treatment. A reducing agent used in the oxidative cleavage reaction includes dimethyl sulfide and triphenylphosphine. A preferable reducing agent is dimethyl sulfide.

The acid used in the cyclization reaction includes hydrochloric acid, acetic acid, hydrobromic acid, sulfuric acid, trifluoroacetic acid, and p-toluenesulfonic acid. A preferable acid is hydrochloric acid. The acid used in the cyclization reaction may be mixed with reactants from the beginning or may be added to the reaction system after completion of the oxidative cleavage reaction.

A solvent includes methanol, ethanol, isopropyl alcohol, tert-butanol, dichloromethane, and chloroform, and may be used alone or by mixture of two or more of them. A preferable solvent is methanol, or a mixed solvent of methanol with dichloromethane.

A reaction temperature includes from −100° C. to 80° C. A preferable reaction temperature is from −78° C. to room temperature.

Step 8

A compound of Formula [I] may be prepared from a compound of Formula [Q-110] by the following method. For example, a compound which $R^3$ or $R^5$ has a hydroxyl group as a substituent in a compound of Formula [I] and the hydroxyl group is protected with $P^2$ may be prepared by a deprotection reaction of $P^2$. The deprotection reaction may be carried out from the compound obtained in the cyclization reaction by a method described in a reference (e.g. a method described in Peter G. M. Wuts (2007). Green's Protective Groups in Organic Synthesis Fourth Edition, Weinheim, Germany, Wiley-VCH, 165-215). Alternatively, the reaction may be carried out under an acidic condition simultaneously with the cyclization reaction.

A compound which $R^3$ has a carboxyl group as a substituent in a compound of Formula [I] may be prepared by oxidizing a compound which $R^{3q1}$ has a primary hydroxyl group as a substituent with Dess-Martin reagent to an aldehyde (e.g. a method described in J. Org. Chem., 2000, 65, 5498-5505), followed by an oxidation reaction of the aldehyde with 2,2,6,6-tetramethylpiperidine 1-oxyl (TEMPO) and chlorous acid (e.g. a method described in J. Org. Chem., 1999, 64, 2564-2566). Alternatively, a compound which $R^3$ has a carboxyl group as a substituent may be prepared from a compound which $R^{3q1}$ has an ester as a substituent by a hydrolysis reaction. The hydrolysis reaction may be carried out by a method of the above Step 2 or a hydrolysis reaction with an acid such as trifluoroacetic acid.

A compound which $R^5$ has a carboxyl group as a substituent in a compound of Formula [I] may be prepared by an oxidation reaction of a hydroxyl group or a hydrolysis reaction of an ester according to the Preparation Method of the compound which $R^3$ has a carboxyl group as a substituent.

For example, when $R^5$ is "—$Y^c$—COO—$R^{50}$", the compound may be prepared by the following hydrolysis reaction:

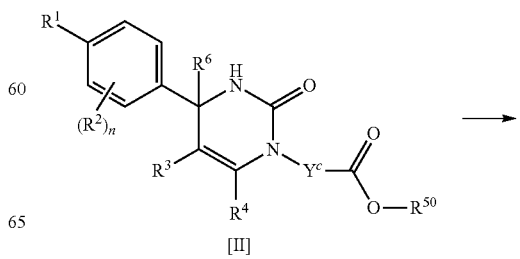

[II]

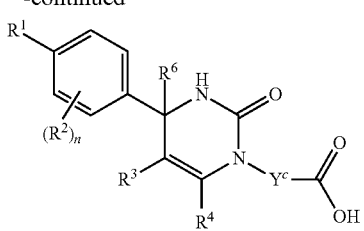

wherein $R^{50}$ is for example $C_{1-4}$ alkyl and the other symbols have the same meanings as defined above.

For example when $R^3$ is "—$Y^b$—COO—$R^{30}$", the compound may be prepared by the following hydrolysis reaction:

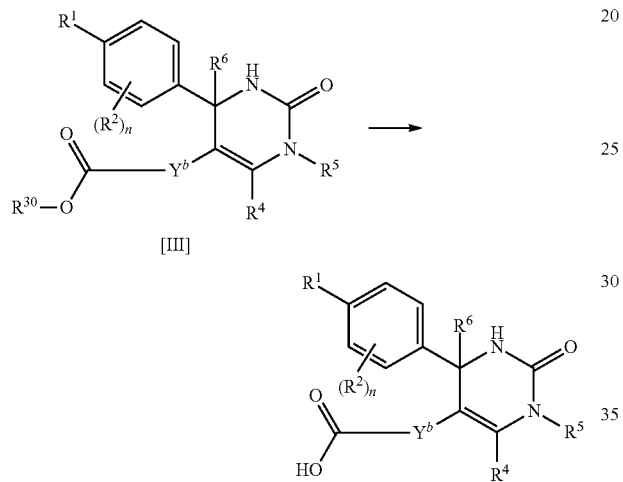

wherein $R^{30}$ is for example $C_{1-4}$ alkyl and the other symbols have the same meanings as defined above.

For example, when $R^3$ is "—$Y^b$—COO—$R^{30}$" in which $R^{30}$ is hydrogen, the compound may be prepared by the following oxidation reaction:

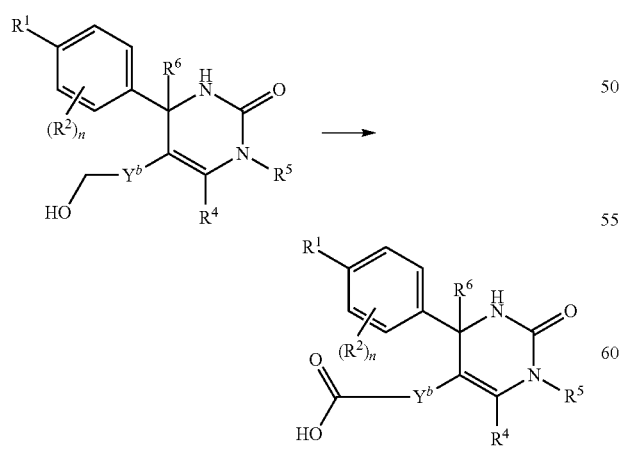

wherein each symbol has the same meaning as defined above.

An example of Preparation Method 1 is as follows.

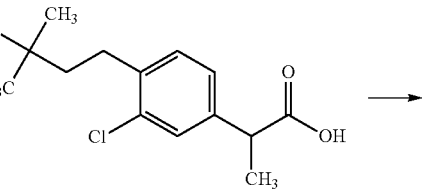

Preparation Method 2
A Method for Preparing dihydropyrimidin-2-one Compounds Via Claisen Reaction (2)

A compound of Formula [I] may be also prepared from a compound of Formula [(Q-201] prepared from a compound of Formula [Q-101b] according to Preparation Method 1.

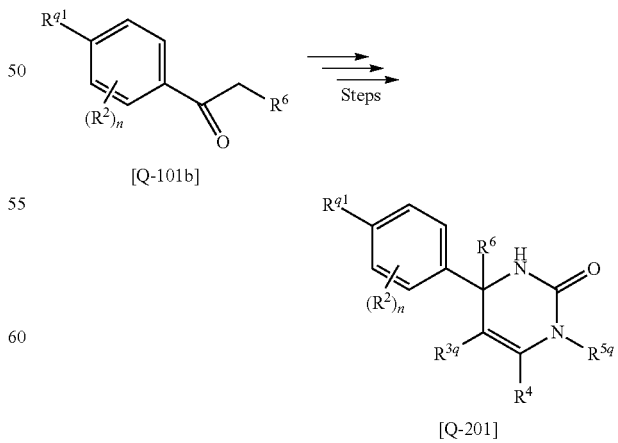

In the formula, $R^{q1}$ is for example bromo, iodo or benzyloxy, $R^{3q}$ is for example —$Y^b$—COO—$R^{q30}$ (in which $R^{q30}$ is $C_{1-4}$ alkyl), $C_{1-4}$ alkyl optionally substituted with one $C_{1-3}$ alkoxy or $C_{3-6}$ cycloalkyl optionally substituted with hydroxy-$C_{1-4}$ alkyl protected with one $P^2$, and the other symbols have the same meanings as defined above.

Preparation Method 2-1

A compound which $R^1$ is $C_{3-6}$ alkoxy, $C_{2-7}$ alkoxy substituted with one trifluoromethyl or $C_{1-3}$ alkoxy substituted with one substituent selected from Group $X^{a2}$ in Formula [I] may be prepared by the following method.

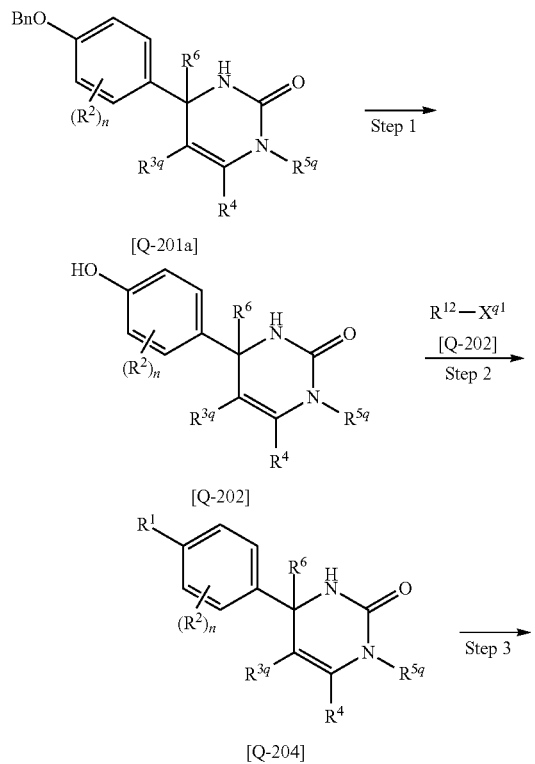

In the formula, Bn is benzyl, $X^{q1}$ is a leaving group such as halogen or a hydroxyl group, $R^{12}$ is a substituent (e.g. $C_{3-6}$ alkyl) which combines together with the oxygen atom on the benzene ring to form $C_{3-6}$ alkoxy, $C_{2-7}$ alkoxy substituted with one trifluoromethyl or $C_{1-3}$ alkoxy substituted with one substituent selected from Group $X^{a2}$, $R^1$ is for example $C_{3-6}$ alkoxy or $C_{2-7}$ alkoxy substituted with one trifluoromethyl, and the other symbols have the same meanings as defined above.

Step 1

A compound of Formula [Q-202] may be prepared by deprotecting the benzyl group of a compound of Formula [Q-201a] according to a method described in a reference (e.g. a method described in Peter G. M. Wuts (2007) Green's Protective Groups in Organic Synthesis Fourth Edition, Weinheim, Germany, Wiley-VCH, p 102-120). For example, the benzyl group may be removed by a reaction in the presence of Lewis acid in the step.

Lewis acid includes boron tribromide, boron trichloride, and trimethylsilyl iodide. A preferable Lewis acid is boron tribromide.

A solvent includes benzene, toluene, dichloromethane, and chloroform. A preferable solvent is dichloromethane.

A reaction temperature includes from −78° C. to 80° C. A preferable reaction temperature is −78° C.

Step 2

A compound of Formula [Q-204] may be prepared from a compound of Formula [Q-202] and a compound of Formula [Q-203].

When $X^{q1}$ is a Leaving Group Such as Halogen (Alkylation Reaction):

A compound of Formula [Q-202] may be coupled with a compound of Formula [Q-203] in the presence of a base to give a compound of Formula [Q-204].

The base includes sodium carbonate, potassium carbonate, cesium carbonate, and sodium hydrogencarbonate. A preferable base is cesium carbonate.

A solvent includes diethyl ether, tetrahydrofuran, dioxane, 1,2-dimethoxyethane, benzene, toluene, methylene chloride, chloroform, ethyl acetate, acetone, N,N-dimethylformamide, and dimethylsulfoxide. A preferable solvent is N,N-dimethylformamide.

A reaction temperature is from room temperature to 120° C. A preferable reaction temperature is 100° C.

When $X^{q1}$ is a Hydroxyl Group (Mitsunobu Reaction):

A compound of Formula [Q-202] may be subjected under Mitsunobu reaction with a compound of Formula [Q-203] in a solvent in the presence of bis(2-methoxyethyl)azodicarboxylate and triphenylphosphine to give a compound of Formula [Q-204].

The solvent includes methylene chloride, chloroform, tetrahydrofuran, and toluene. A preferable solvent is tetrahydrofuran.

A reaction temperature includes from 0° C. to 100° C. A preferable reaction temperature is from room temperature to 60° C.

Step 3

A compound of Formula [I] may be prepared from a compound of Formula [Q-204] according to Preparation Method 1 Step 8.

An example of Preparation Method 2-1 is as follows.

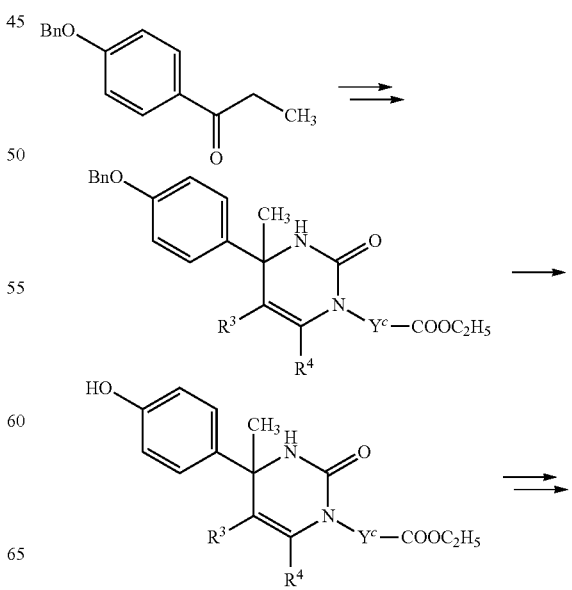

-continued

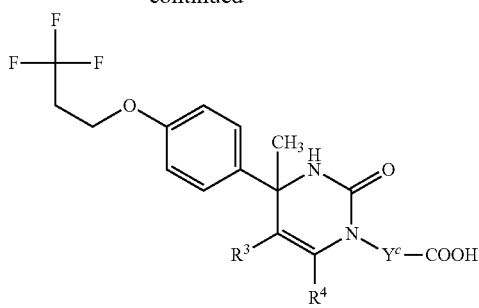

Preparation Method 2-2

A compound which $R^1$ is, for example, $C_{4-8}$ alkyl or $C_{1-4}$ alkyl substituted with one substituent selected from Group $X^{a1}$ in Formula [I] (provided that $R^1$ is not $C_{3-6}$ alkoxy, $C_{2-7}$ alkoxy substituted with one trifluoromethyl or $C_{1-3}$ alkoxy substituted with one substituent selected from Group $X^{a2}$) may be prepared from a compound of Formula [Q-201b] by a cross coupling reaction or an insertion reaction of carbon monoxide:

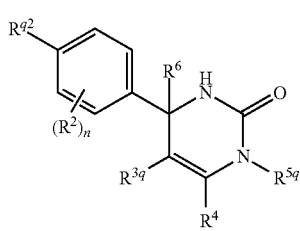

[Q-201b]

wherein $R^{q2}$ is for example bromo, iodo or trifluoromethane sulfonyloxy and the other symbols have the same meanings as defined above.

The cross coupling reaction includes a method described in a reference (e.g. a method described in F. Diederich, P. J. Stang (1998). Metal-catalyzed Cross-coupling Reactions, Weinheim, Germany, Wiley-VCH), and the insertion reaction of carbon monoxide includes a method described in a reference (e.g. M. Schlosser (1994). Organometallics in Synthesis, Weinheim, Germany, Wiley-VCH).

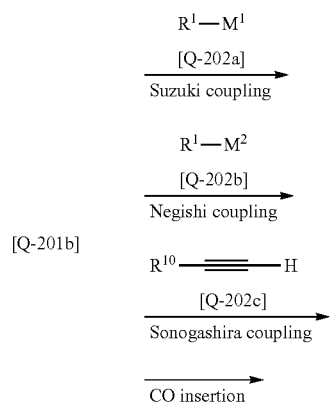

-continued

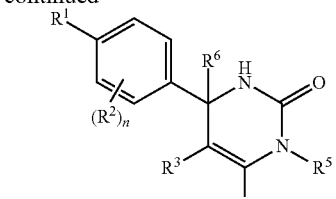

[I]

In the formula, $R^1$ is for example $C_{4-8}$ alkyl or $C_{1-4}$ alkyl substituted with one substituent selected from Group $X^{a1}$ (provided that $R^1$ is not $C_{3-6}$ alkoxy, $C_{2-7}$ alkoxy substituted with one trifluoromethyl or $C_{1-3}$ alkoxy substituted with one substituent selected from Group $X^{a2}$), $R^{10}$ is for example $C_{2-6}$ alkyl, $M^1$ is boronic acid, boronic acid ester or trifluoroborate salt, $M^2$ is zinc or zinc halide, and the other symbols have the same meanings as defined above.

For compounds of Formula [Q-202a], Formula [Q-202b], and Formula [Q-202c], a commercially available product (e.g. isobutylboronic acid, 1-hexylboronic acid pinacol ester, potassium (3,3-dimethylbutyl)trifluoroborate, butylzinc bromide, cyclohexylacetylene) may be used or they may be for example prepared from a commercially available $R^1$—$X^{qq}$ (e.g. 1-chloro-3,3-dimethyl-butane, bromomethyl-cyclohexane; $X^{qq}$ is chloro, bromo or iodo) according to known methods.

For example, a compound of Formula [Q-202a] may be prepared by the following method.

A compound which $M^1$ is boronic acid may be prepared by preparing Grignard reagent from a commercially available compound such as $R^1$—Br and magnesium to react with trimethyl borate, triisopropyl borate, for example.

A compound which $M^1$ is boronic acid ester may be prepared by reacting a boronic acid compound with pinacol.

A compound which $M^1$ is trifluoroborate salt may be prepared by reacting a boronic acid compound with potassium hydrogen fluoride.

For example, a compound of Formula [Q-202b] may be prepared from a commerically available compound such as $R^1$—I and zinc.

An activating agent of zinc includes iodine, trimethylsilyl chloride and 1,2-dibromoethane, and may be used alone or by mixture of two or more of them. A preferable activating agent is trimethylsilyl chloride or 1,2-dibromoethane.

A solvent includes tetrahydrofuran, N,N-dimethylformamide, and N,N-dimethylacetamide. A preferable solvent is tetrahydrofuran or dimethylacetamide.

A reaction temperature includes from room temperature to 80° C. A preferable reaction temperature is room temperature.

For example, a commerically available product such as 3,3-dimethyl-1-butyne, cyclohexylacetylene, and phenylacetylene may be used for a compound of Formula [Q-202c].

An alkynylene compound of Formula [I] obtained by Sonogashira reaction may be converted into an alkyl compound by a catalytic hydrogen addition reaction with a catalyst such as palladium on carbon, platinum on carbon, and rhodium-alumina.

In the insertion reaction of carbon monoxide, a compound of Formula [Q-201b] may be reacted in an alcohol solvent such as ethanol to convert into an ester corresponding to the alcohol.

In a compound of Formula [I], a compound which R³ or R⁵ has a hydroxyl group as a substituent, a compound which R³ has a carboxyl group as a substituent or a compound which R⁵ has a carboxyl group as a substituent may be prepared according to Preparation Method 2-1 Step 3.

An example of Preparation Method 2-2 is as follows.

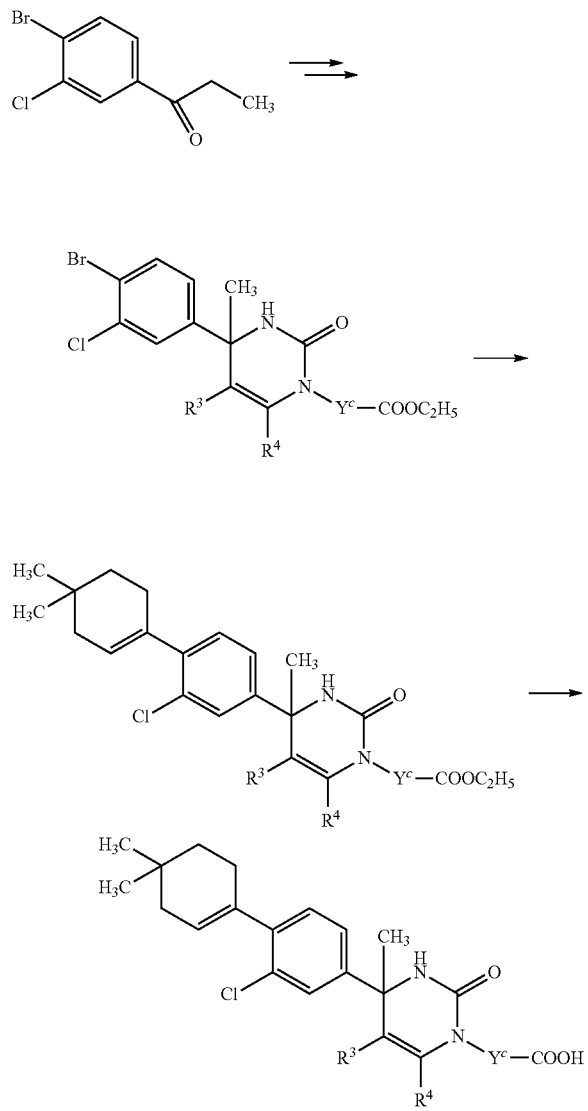

Preparation Method 3

A Method for Preparing dihydropyrimidin-2-one Compounds Via Biginelli Reaction

A compound which R⁶ is hydrogen in a compound of Formula [I] may be prepared by Biginelli reaction

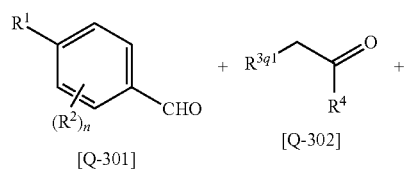

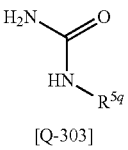
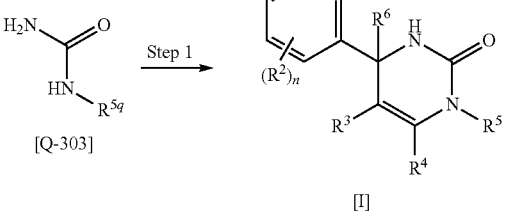

In the formula, R⁶ is hydrogen and each symbol has the same meaning as defined above.

Step 1

A compound of Formula [I] may be prepared by reacting a compound of Formula [Q-301], a compound of Formula [Q-302], and a compound of Formula [Q-303] in the presence of an acid.

The acid includes hydrochloric acid, acetic acid, trimethylchlorosilane, and p-toluenesulfonic acid. A preferable acid is trimethylchlorosilane.

A solvent includes toluene, dichloromethane, chloroform, tetrahydrofuran, dioxane, N,N-dimethylformamide, dimethylsulfoxide, acetonitrile, and acetone, and may be used alone or by mixture of two or more of them. A preferable solvent in the reaction is a mixed solvent of acetonitrile and N,N-dimethylformamide.

A reaction temperature includes from 0° C. to 140° C. A preferable reaction temperature is from room temperature to 120° C.

A compound of Formula [Q-301] may be prepared by Preparation Method 6 described below.

A compound of Formula [Q-302] may be prepared by Preparation Method 7-2 described below.

A compound of Formula [Q-303] may be prepared by Preparation Method 8-3 described below.

A compound which R³ or R⁵ has a hydroxyl group as a substituent, a compound which R³ has a carboxyl group as a substituent or a compound which R⁵ has a carboxyl group as a substituent in a compound of Formula [I] may be prepared according to Preparation Method 2-1 Step 3.

Preparation Method 4

A Method for Preparing dihydropyrimidin-2-one Compounds Using Optically Active Sulfinyl Amide (1)

A compound of Formula [IV-D] wherein R⁴ is hydrogen in a compound of Formula [I]:

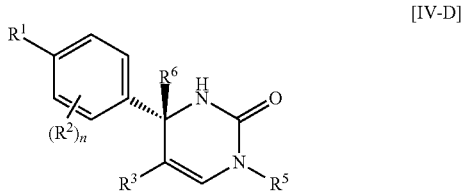

may be prepared under an asymmetric synthesis with optically active sulfinyl amide.

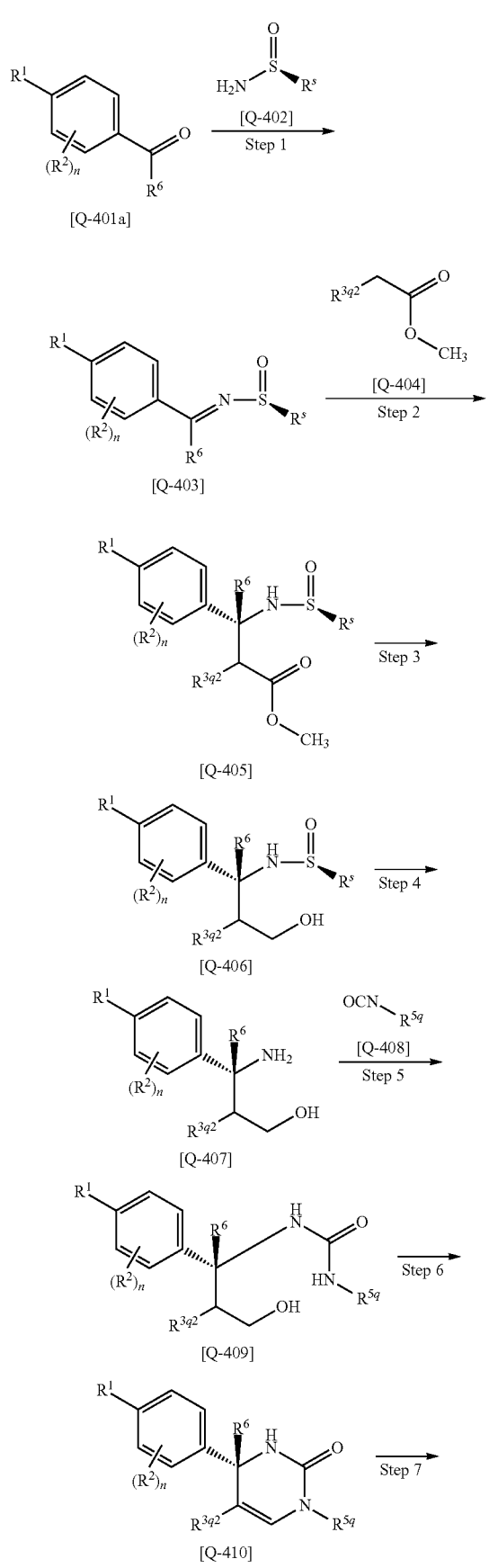

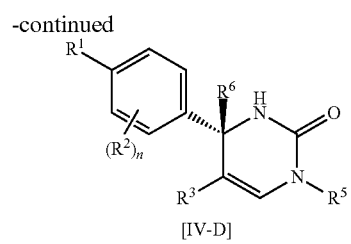

[IV-D]

In the formula, $R^{3q2}$ is for example —$Y^b$—$CH_2OP^3$ (in which $P^3$ is a protective group such as tert-butyldiphenylsilyl (TBDPS) and benzyl), $C_{1-6}$ alkyl optionally substituted with a hydroxyl group protected with one $P^3$, $C_{3-6}$ cycloalkyl optionally substituted with the same or different one to three substituent(s) selected from Group $X^b$, 4-tetrahydropyranyl or 1-methanesulfonyl-3-azetidinyl; $R^s$ is for example tert-butyl; and the other symbols have the same meanings as defined above.

Step 1

A compound of Formula [Q-403] may be prepared by reacting a compound of Formula [Q-401a] and a compound of Formula [Q-402] in the presence of Lewis acid according to a method described in a reference (e.g. a method described in G. K. Datta; J. A. Ellman, J. Org. Chem. 2010, 75, 6283-6285).

An illustrative example of a compound of Formula [Q-402] includes the following compound.

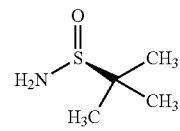

Lewis acid includes Lewis acid such as tetraalkyl orthotitanate. A preferable Lewis acid is tetraethyl orthotitanate.

A solvent includes benzene, toluene, dichloromethane, chloroform, tetrahydrofuran, dioxane, 1,2-dimethoxyethane, and cyclopentylmethyl ether. A preferable solvent is cyclopentylmethyl ether.

A reaction temperature includes from room temperature to 120° C. A preferable reaction temperature is 110° C.

A commercially available product may be used for a compound of Formula [Q-401a] or it may be prepared by known methods or Preparation Method 6.

Step 2

A compound of Formula [Q-405] may be prepared by reacting a compound of Formula [Q-403] and a compound of Formula [Q-404] in the presence of a base according to a method described in a reference (e.g. a method described in T. P. Tang; J. A. Ellman, J. Org. Chem. 2002, 67, 7819-7832).

The base includes lithium diisopropylamide (LDA), lithium hexamethyldisilazide (LHMDS), and lithium 2,2,6,6-tetramethylpiperidide (LiTMP). A preferable base is lithium diisopropylamide (LDA) or lithium hexamethyldisilazide (LHMDS).

A solvent includes benzene, toluene, xylene, hexane, tetrahydrofuran, dioxane, and 1,2-dimethoxyethane, and may be used alone or by mixture of two or more of them. A preferable solvent is tetrahydrofuran.

A reaction temperature includes from −78° C. to room temperature. A preferable reaction temperature is from −78° C. to 0° C.

To improve diastereoselectivity, an additive such as titanium (IV) chlorotriisopropoxy may be also added.

An equivalent amount of the base includes from 1 to 3 equivalent(s). A preferable amount is 2.1 equivalents.

A commercially available product may be used for a compound of Formula [Q-404] or it may be prepared by known methods or Preparation Method 6.

Step 3

A compound of Formula [Q-406] may be prepared by reacting a compound of Formula [Q-405] with a reducing agent.

The reducing agent includes diisobutylaluminum hydride, lithium aluminum hydride, and lithium borohydride. A preferable reducing agent is diisobutylaluminum hydride.

A solvent includes toluene, dichloromethane, diethyl ether, and tetrahydrofuran. A preferable solvent is toluene.

A reaction temperature includes from −78° C. to room temperature. A preferable reaction temperature is from −78° C. to 0° C.

Step 4

A compound of Formula [Q-407] may be prepared by hydrolyze a compound of Formula [Q-406] under an acidic condition.

The acid includes hydrochloric acid, hydrobromic acid, sulfuric acid, trifluoroacetic acid, and p-toluenesulfonic acid. A preferable acid is hydrochloric acid.

A solvent includes tetrahydrofuran, methanol, ethanol, and isopropyl alcohol, and may be used alone or by mixture of two or more of them. A preferable solvent is methanol.

A reaction temperature includes from 0° C. to 60° C. A preferable reaction temperature is from 0° C. to room temperature.

Step 5

A compound of Formula [Q-409] may be prepared from a compound of Formula [Q-407] and a compound of Formula [Q-408].

A solvent includes benzene, toluene, dichloromethane, chloroform, diethyl ether, tetrahydrofuran, 1,2-dimethoxyethane, ethyl acetate, N,N-dimethylformamide, dimethylsulfoxide, acetonitrile, and acetone, and may be used alone or by mixture of two or more of them. A preferable solvent is tetrahydrofuran.

A reaction temperature includes from 0° C. to 80° C. A preferable reaction temperature is from 0° C. to room temperature.

Step 6

A compound of Formula [Q-410] may be prepared by an oxidation reaction of a compound of Formula [Q-409], followed by a cyclization reaction.

The oxidizing agent includes 2-azaadamantane-N-oxyl (AZADO), 2,2,6,6-tetramethyl-1-piperidinyloxy radical (TEMPO), and Dess-Martin reagent (DMP). Diacetoxyiodobenzene or sodium hydrochlorite, for example, may be optionally added as a co-oxidizing agent. A preferable oxidizing agent in the reaction is a mixture of 2,2,6,6-tetramethyl-1-piperidinyloxy radical (TEMPO) and diacetoxyiodobenzene.

The acid in the cyclization reaction includes hydrochloric acid, trifluoroacetic acid, and p-toluenesulfonic acid. A preferable acid is trifluoroacetic acid.

A solvent includes tert-butanol, benzene, toluene, dichloromethane, chloroform, ethyl acetate, and acetonitrile. A preferable solvent in the reaction is dichloromethane or chloroform.

A reaction temperature includes from 0° C. to 80° C. A preferable reaction temperature is from 0° C. to room temperature.

Step 7

A compound which $R^3$ or $R^5$ has a hydroxyl group as a substituent, a compound which $R^3$ has a carboxyl group as a substituent or a compound which $R^5$ has a carboxyl group as a substituent in a compound of Formula [IV-D] may be prepared according to Preparation Method 1 Step 8.

The following compound of Formula [E-IV-D] may be prepared using an enantiomer (i.e., a compound of Formula [E-Q-402]) of a compound of Formula [Q-402] according to Preparation Method 4.

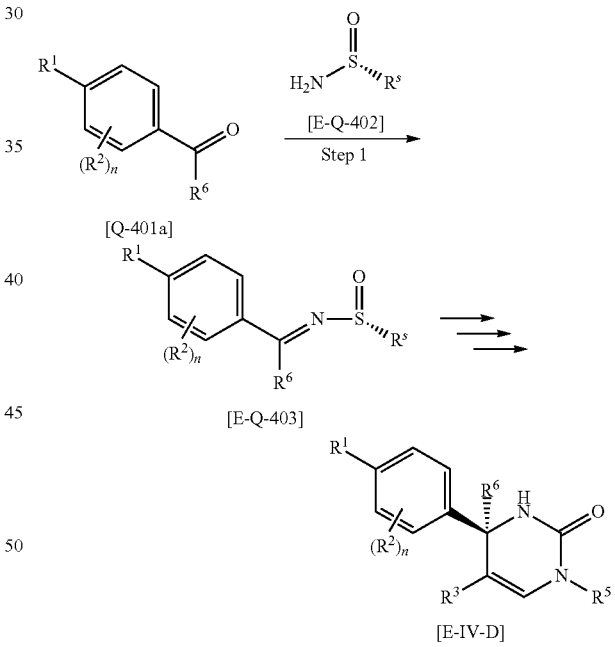

Preparation Method 5

A Method for Preparing dihydropyrimidin-2-one Compounds Using Optically Active Sulfinyl Amide (2)

Alternative Method for Preparing a Compound of Formula [IV-D]

A compound of Formula [Q-501] may be prepared from a compound of Formula [Q-401b] and a compound of Formula [Q-402] according to Preparation Method 4. A compound of Formula [IV-D] may be prepared from a compound of Formula [Q-501] according to the following Preparation Method 5-1 or 5-2.

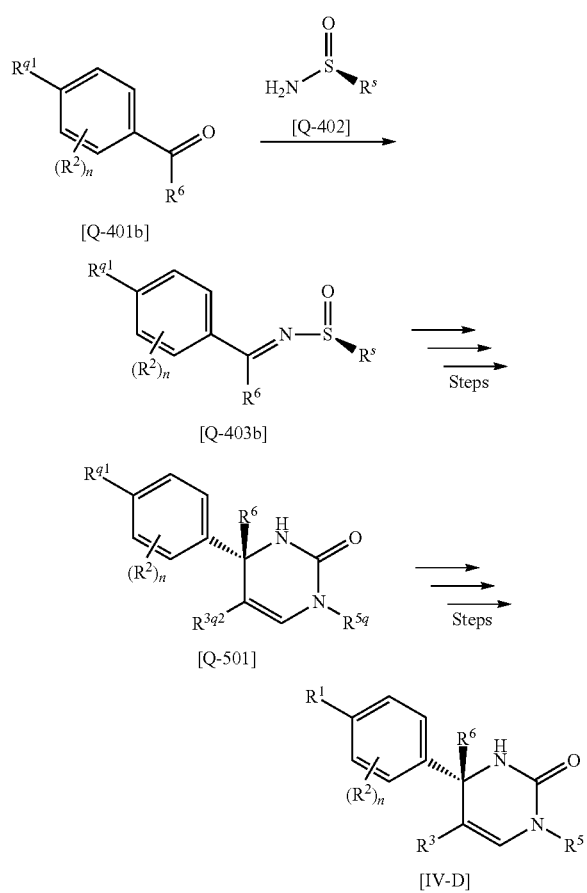

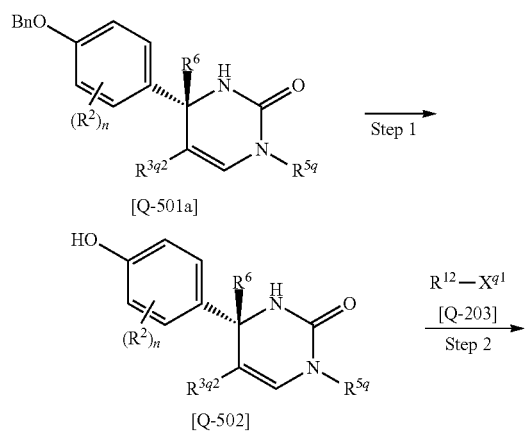

In the formula, each symbol has the same meaning as defined above.

Preparation Method 5-1

When $R^{q1}$ is for Example a Hydroxyl Group in a Compound of Formula [Q-501]:

For example, a compound of Formula [Q-503] which $R^1$ is $C_{3-6}$ alkoxy, $C_{2-7}$ alkoxy substituted with one trifluoromethyl or $C_{1-3}$ alkoxy substituted with one substituent selected from Group $X^{a2}$ in Formula [IV-D] may be prepared by the following method.

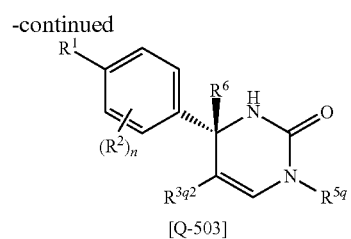

In the formula, $R^1$ is $C_{3-6}$ alkoxy, $C_{2-7}$ alkoxy substituted with one trifluoromethyl or $C_{1-3}$ alkoxy substituted with one substituent selected from Group $X^{a2}$, and the other symbols have the same meanings as defined above.

A compound of Formula [Q-501a] may be prepared from a compound which $R^{q1}$ is a benzyl ether group in a compound of Formula [Q-401b] according to Preparation Method 4.

A compound of Formula [Q-503] may be prepared from a compound of Formula [Q-501a] according to Preparation Method 2-1.

Preparation Method 5-2

When $R^{q1}$ is for Example Bromo, Iodo or Trifluoromethanesulfonyloxy Group in a Compound of Formula [Q-501]:

A compound which $R^1$ is a substituent such as $C_{4-8}$ alkyl and $C_{1-4}$ alkyl substituted with one substituent selected from Group $X^{a1}$ in Formula [IV-D] (provided that $R^1$ is not $C_{3-6}$ alkoxy, $C_{2-7}$ alkoxy substituted with one trifluoromethyl or $C_{1-3}$ alkoxy substituted with one substituent selected from Group $X^{a2}$) may be prepared from a compound of the following Formula [Q-501b] by a cross coupling reaction or an insertion reaction of carbon monoxide.

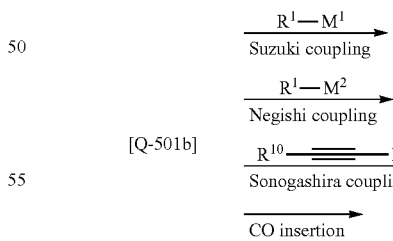

In the formula, each symbol has the same meaning as defined above.

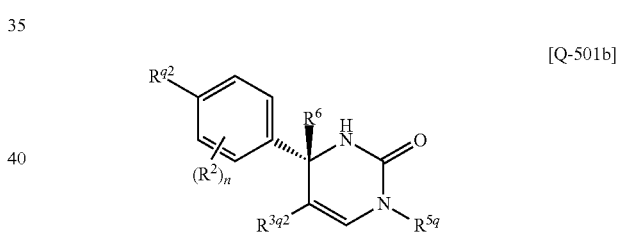

In the formula, each symbol has the same meaning as defined above.

A compound of Formula [IV-D] may be prepared from a compound of Formula [Q-501b] according to Preparation Method 2-2.

In particular, Preparation Method 5-2 (Suzuki coupling) is for example as follows. A compound of Formula [$R^1$-$M^1$] may be synthesized by a common procedure.

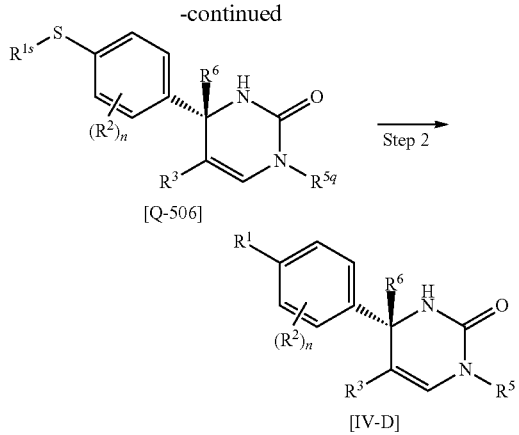

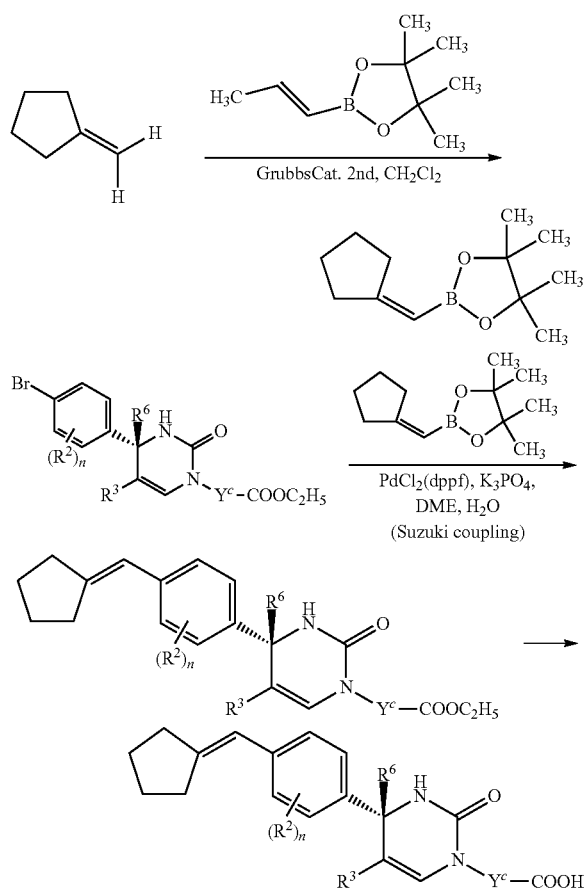

In the formula, GrubbsCat.2nd means a second-generation Grubbs catalyst, (1,3-bis(2,4,6-trimethylphenyl)-2-imidazo-lidinylidene)dichloro(phenylmethylene)(tricyclohexylphosphine)-ruthenium, and the other symbols have the same meanings as defined above.

Preparation Method 5-3

When $R^{q1}$ is bromo in a compound of Formula [Q-501] (i.e., a compound of Formula [Q-504]):

A compound which $R^1$ is $C_{3-6}$ alkylsulfanyl, $C_{3-6}$ alkylsulfinyl, $C_{3-6}$ alkylsulfonyl, $C_{3-6}$ cycloalkylsulfanyl, $C_{3-6}$ cycloalkylsulfinyl or $C_{3-6}$ cycloalkylsulfonyl in Formula [IV-D] may be prepared by the following method.

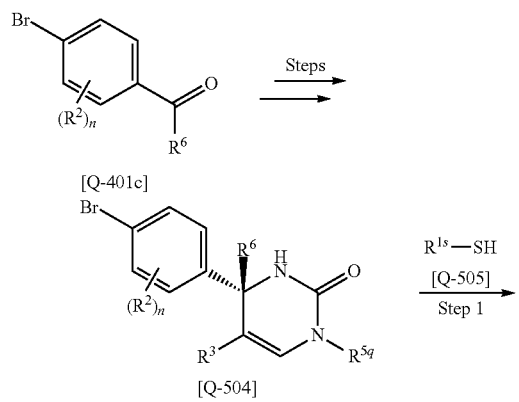

In the formula,
$R^{1s}$ is $C_{3-6}$ alkyl or $C_{3-6}$ cycloalkyl,
$R^1$ is $C_{3-6}$ alkylsulfanyl or $C_{3-6}$ cycloalkylsulfanyl,
$R^{5q}$ is —$Y^c$—COOR$^{q50}$ wherein $Y^c$ is $C_{1-6}$ alkylene optionally substituted with one hydroxy and
$R^{q50}$ is hydrogen or $C_{1-4}$ alkyl,
$R^5$ is —$Y^c$—COOH,
$R^6$ is methyl, and the other symbols have the same meanings as defined above.

A compound of Formula [Q-504] may be prepared from a compound of Formula [Q-401c] using Preparation Method 5.

Step 1

A compound of Formula [Q-506] may be prepared by a coupling reaction of a compound of Formula [Q-504] and a compound of Formula [Q-505] according to a method described in a literature such as a method described in Org. Lett. 2004, 6, 4587-4590, for example.

Step 2

A compound of Formula [IV-D] may be prepared from a compound of Formula [Q-506] according to Preparation Method 1 Step 8.

For example, an illustrative example of Preparation Method 5-3 includes the following reactions:

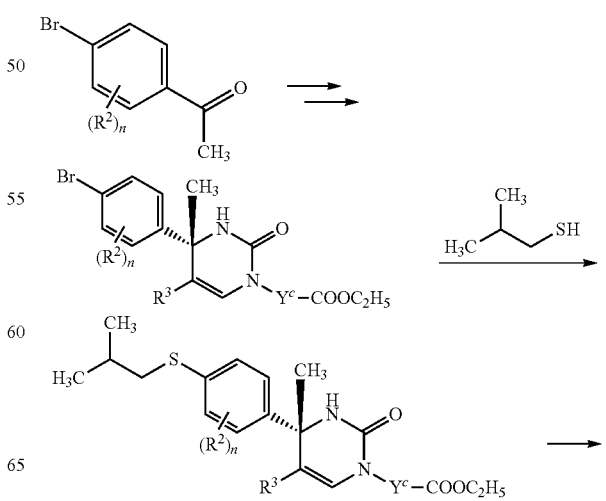

-continued

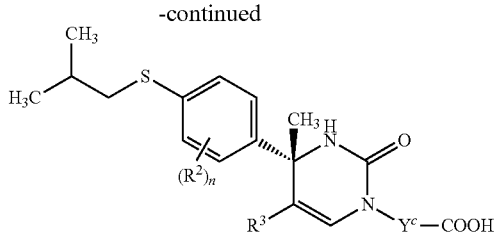

Preparation Method 5-3-A

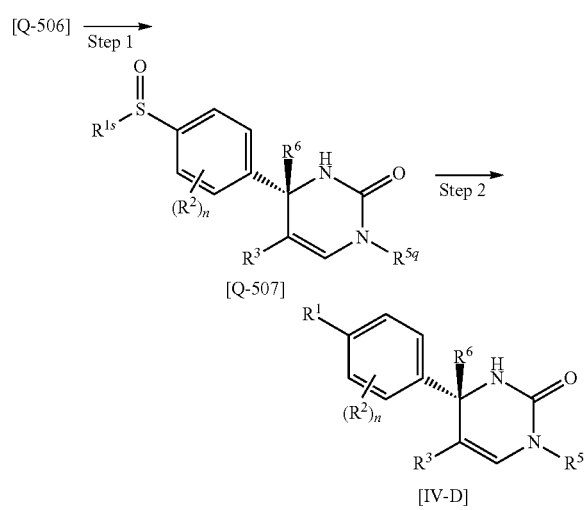

In the formula,
$R^{1s}$ is $C_{3-6}$ alkyl or $C_{3-6}$ cycloalkyl,
$R^1$ is $C_{3-6}$ alkylsulfinyl or $C_{3-6}$ cycloalkylsulfinyl,
$R^{5q}$ is —$Y^c$—COOR$^{q50}$ wherein $Y^c$ is $C_{1-6}$ alkylene optionally substituted with one hydroxy and
$R^{q50}$ is hydrogen or $C_{1-4}$ alkyl,
$R^5$ is —$Y^c$—COOH,
$R^6$ is methyl, and the other symbols have the same meanings as defined above.

Step 1

A compound of Formula [Q-507] may be prepared by an oxidation reaction of sulfide of a compound of Formula [Q-506].

An oxidizing agent includes hydrogen peroxide, peracetic acid, hydroperoxide, permanganate, meta-chloroperbenzoic acid, and sodium hypochlorite. A preferable oxidizing agent is meta-chloroperbenzoic acid.

A solvent includes benzene, dichloromethane, acetonitrile, and water, and may be used alone or by mixture of two or more of them. A preferable solvent is dichloromethane.

A reaction temperature includes from −78° C. to room temperature. A preferable reaction temperature is −78° C.

Step 2

A compound of Formula [IV-D] may be prepared from a compound of Formula [Q-507] according to Preparation Method 1 Step 8.

Preparation Method 5-3-B

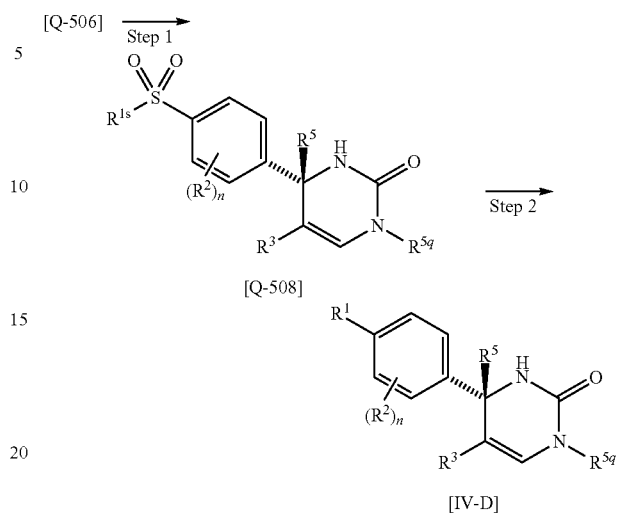

In the formula,
$R^{1s}$ is $C_{3-6}$ alkyl or $C_{3-6}$ cycloalkyl,
$R^1$ is $C_{3-6}$ alkylsulfonyl or $C_{3-6}$ cycloalkylsulfonyl,
$R^{5q}$ is —$Y^c$—COOR$^{q50}$ wherein $Y^c$ is $C_{1-6}$ alkylene optionally substituted with one hydroxy and
$R^{q50}$ is hydrogen or $C_{1-4}$ alkyl,
$R^5$ is —$Y^c$—COOH,
$R^6$ is methyl, and the other symbols have the same meanings as defined above.

Step 1

A compound of Formula [Q-508] may be prepared by an oxidation reaction of sulfide of a compound of Formula [Q-506].

An oxidizing agent includes oxone, meta-chloroperbenzoic acid, and potassium permanganate. A preferable oxidizing agent is meta-chloroperbenzoic acid.

A solvent includes benzene, dichloromethane, acetonitrile, and water, and may be used alone or by mixture of two or more of them. A preferable solvent is dichloromethane.

A reaction temperature includes from −78° C. to room temperature. A preferable reaction temperature is room temperature.

Step 2

A compound of Formula [IV-D] may be prepared from a compound of Formula [Q-508] according to Preparation Method 1 Step 8.

Preparation Method 5-4

Preparation Method of dihydropyrimidin-2-one Compounds Using Optically Active Sulfinylamide (4) (i.e., an Alternative Method for Preparing a Compound of Formula [IV-D] Using p-Nitrophenyl Chloroformate)

A compound of Formula [Q-520] may be prepared from a compound of Formula [Q-401a] according to Preparation Method 4. A compound of Formula [IV-D] may be prepared from a compound of Formula [Q-520] using cross-coupling reaction.

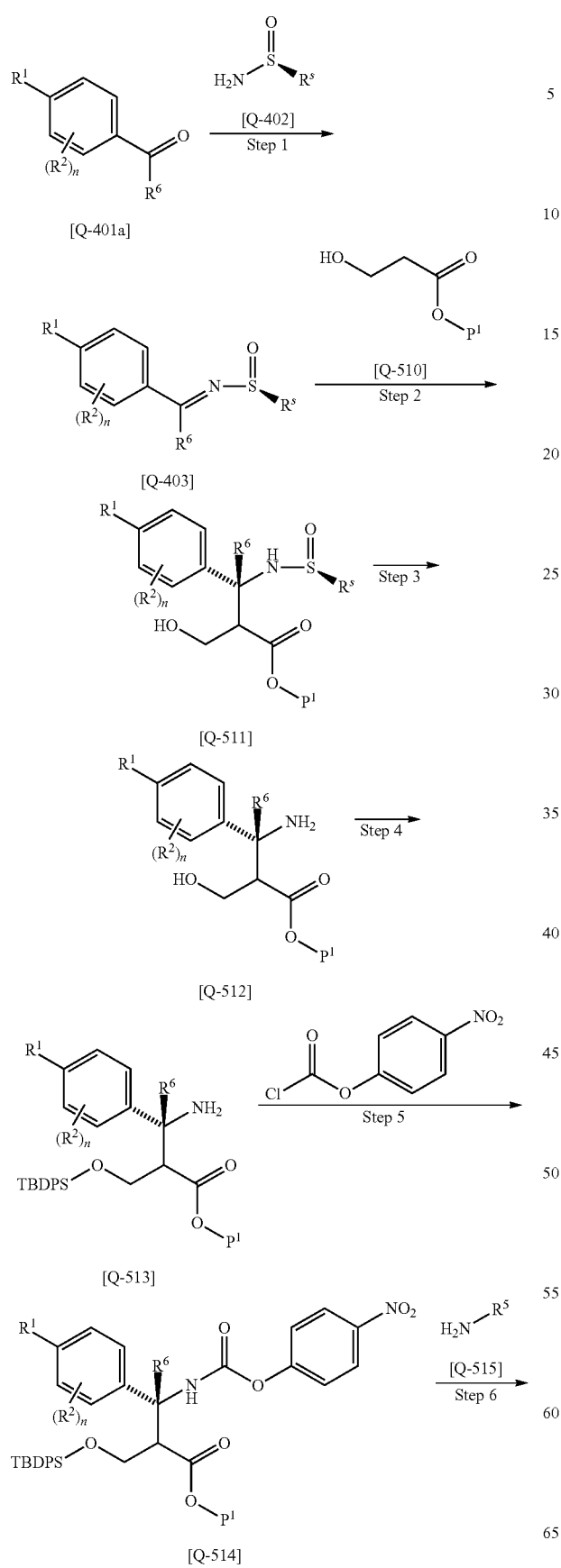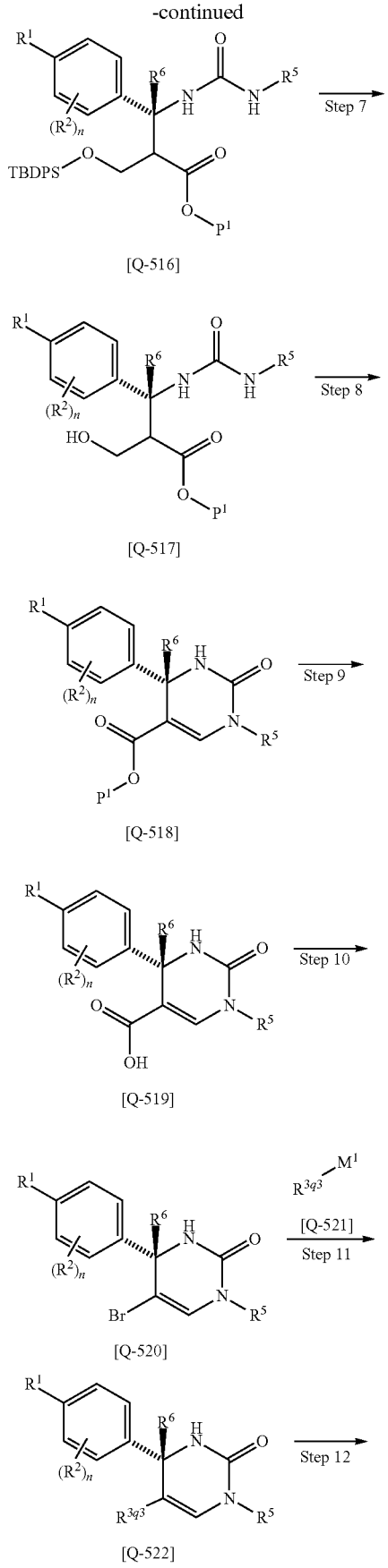

-continued

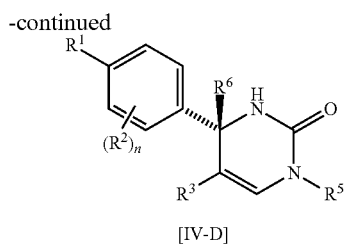

[IV-D]

In the formula, $R^{3q3}$ is —$Y^b$—COOR$^{q30}$ wherein $Y^b$ is phenyl and $R^{q30}$ is hydrogen or $C_{1-4}$ alkyl, $R^6$ is methyl, and the other symbols have the same meanings as defined above.

Step 1

The reaction is carried out in a similar way to Preparation Method 4 Step 1.

Step 2

A compound of Formula [Q-511] may be prepared by reacting a compound of Formula [Q-403] with a compound of Formula [Q-510] under a basic condition.

A base includes lithium diisopropylamide (LDA), lithium hexamethyldisilazide (LHMDS), and lithium 2,2,6,6-tetramethylpiperidide (LiTMP). A preferable base is lithium diisopropylamide (LDA) or lithium hexamethyldisilazide (LHMDS).

A solvent includes benzene, toluene, xylene, hexane, tetrahydrofuran, dioxane, and 1,2-dimethoxyethane, and may be used alone or by mixture of two or more of them. A preferable solvent is tetrahydrofuran.

A reaction temperature includes from −78° C. to room temperature. A preferable reaction temperature is from −78° C. to 0° C.

To improve a diastereoselectivity, an additive such as chlorotriisopropoxy titanium (IV) may be further added.

An equivalent amount of a base includes from 1 to 3 equivalent amount(s). A preferable equivalent amount is 2.1 equivalent amounts.

As a compound of Formula [Q-510], a commercially available product such as 3-hydroxy-propionic acid methyl ester, 3-hydroxy-propionic acid ethyl ester, and 3-hydroxy-propionic acid t-butyl ester may be used.

Step 3

A compound of Formula [Q-512] may be prepared by hydrolyzing a compound of Formula [Q-511] under an acidic condition.

An acid includes hydrochloric acid, hydrobromic acid, sulfuric acid, trifluoroacetic acid, and p-toluenesulfonic acid. A preferable acid is hydrochloric acid.

A solvent includes tetrahydrofuran, methanol, ethanol, and isopropyl alcohol, and may be used alone or by mixture of two or more of them. A preferable solvent is methanol.

A reaction temperature includes from 0° C. to 60° C. A preferable reaction temperature is from 0° C. to room temperature.

Step 4

A compound of Formula [Q-513] may be prepared by protecting a compound of Formula [Q-512] with tert-butyldiphenylsilyl (TBDPS) according to a method described in a literature (e.g. a method described in Peter G. M. Wuts (2007). Green's Protective Groups in Organic Synthesis Fourth Edition, Weinheim, Germany, Wiley-VCH, 141-144).

Step 5

A compound of Formula [Q-514] may be prepared by reacting a compound of Formula [Q-513] with p-nitrophenyl chloroformate under a basic condition.

A base includes triethylamine, diisopropylethylamine, pyridine, N-methylmorpholine, and potassium carbonate. A preferable base is triethylamine.

A solvent includes chloroform, dichloromethane, toluene, tetrahydrofuran, and acetonitrile. A preferable solvent is chloroform.

A reaction temperature includes from 0° C. to 85° C. A preferable reaction temperature is 0° C.

Step 6

A compound of Formula [Q-516] may be prepared by reacting a compound of Formula [Q-514] with a compound of Formula [Q-515] under a basic condition.

A base includes triethylamine and diisopropylethylamine. A preferable base is triethylamine.

A solvent includes chloroform, dichloromethane, and tetrahydrofuran. A preferable solvent is chloroform.

A reaction temperature includes from room temperature to 60° C. A preferable reaction temperature is 60° C.

Step 7

A compound of Formula [Q-517] may be prepared by deprotecting tert-butyldiphenylsilyl (TBDPS) of a compound of Formula [Q-516] according to a method described in a literature (e.g. a method described in Peter G. M. Wuts (2007). Green's Protective Groups in Organic Synthesis Fourth Edition, Weinheim, Germany, Wiley-VCH, 142-143).

Step 8

A compound of Formula [Q-518] may be prepared from a compound of Formula [Q-517] according to Preparation Method 4 Step 6.

Step 9

A compound of Formula [Q-519] may be prepared by deprotecting tert-butyl ester from a compound of Formula [Q-518] wherein $P^1$ is for example tert-butyl according to a method described in a literature (e.g. a method described in Peter G. M. Wuts. Protective Groups in Organic Synthesis Third Edition, Wiley-Interscience, 406-407).

Step 10

A compound of Formula [Q-520] may be prepared by brominating a compound of Formula [Q-519] according to a method described in a literature (e.g. a method described in A. J. Zych; H. Wang; S. A. Sakwa, Tetrahedron Lett. 2010, 51, 5103-5105).

Step 11

A compound of Formula [Q-522] may be prepared from a compound of Formula [Q-520] and a compound of Formula [Q-521] according to Preparation Method 2-2 (including cross-coupling).

Step 12

A compound of Formula [IV-D] may be prepared for example by hydrolyzing a compound of Formula [Q-522].

In Preparation Method 5-4, Step 11 (coupling reaction) and Step 12 (hydrolysis reaction) are illustrated as follows.

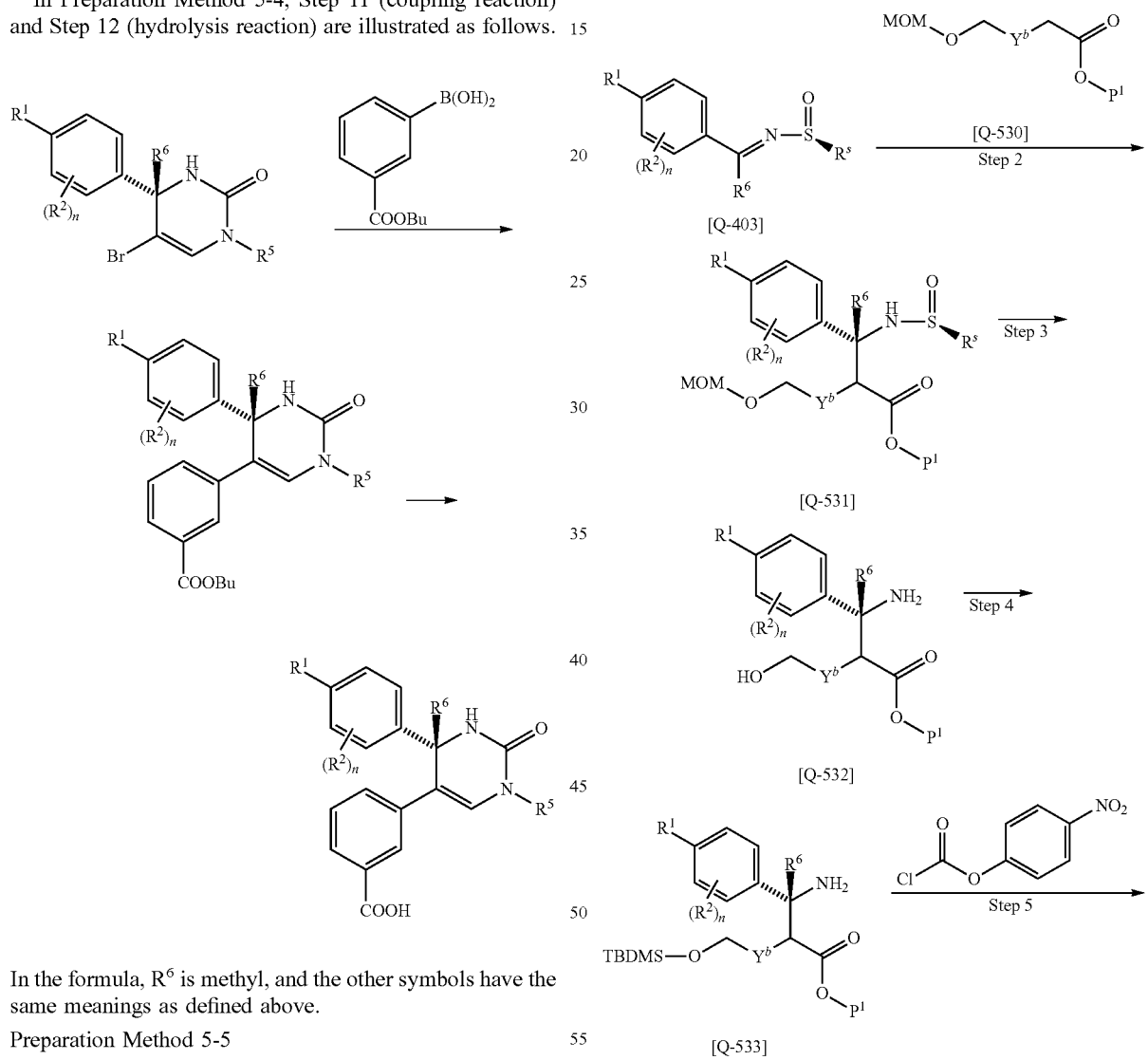

In the formula, $R^6$ is methyl, and the other symbols have the same meanings as defined above.

Preparation Method 5-5

Preparation Method of dihydropyrimidin-2-one Compounds Using Optically Active Sulfinylamide (5) (i.e., an Alternative Method for Preparing a Compound of Formula [IV-D])

A compound of Formula [Q-536] may be prepared from a compound of Formula [Q-401a] using Preparation Methods 4 and 5-4. A compound of Formula [IV-D] may be prepared from a compound of Formula [Q-536] by a cyclization reaction under a basic condition, a reduction reaction using Schwartz's reagent, an oxidation reaction using Dess-Martin reagent into an aldehyde compound, followed by Pinnic Oxidation into a carboxylic acid compound.

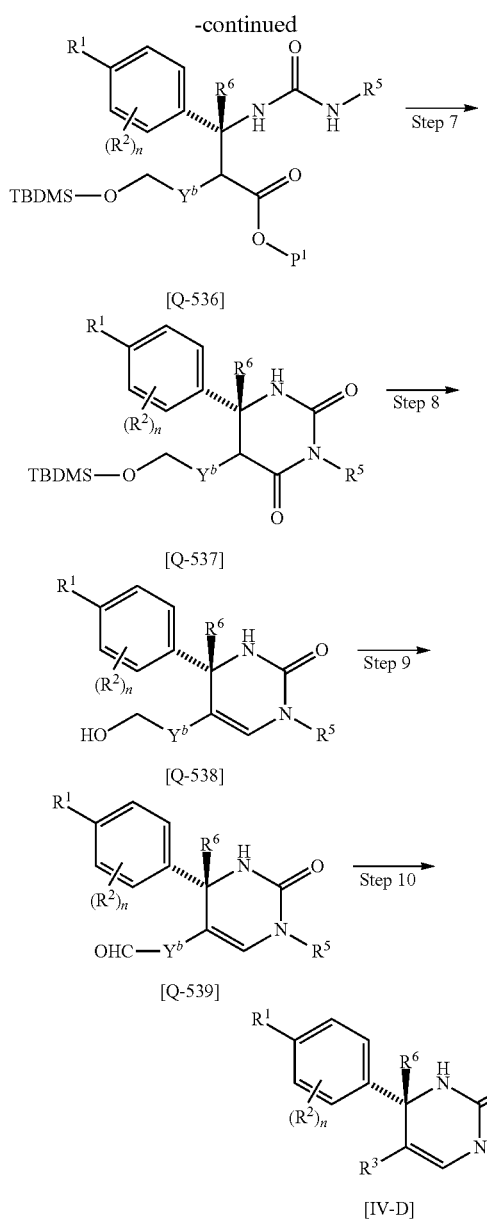

[Q-536]

[Q-537]

[Q-538]

[Q-539]

[IV-D]

In the formula, $Y^b$ is $C_{3-6}$ cycloalkylene, $R^3$ is —$Y^b$—COOH, $R^6$ is methyl; and the other symbols have the same meanings as defined above.

Protective groups in the formula may be optionally changed. For example, TBDMS (tert-butyldimethylsilyl) may be replaced with TBDPS (tert-butyldiphenylsilyl), and MOM (methoxymethyl) may be replaced with methyl.

Step 1

A compound of Formula [Q-403] may be prepared from a compound of Formula [Q-401a] according to Preparation Method 4 Step 1.

Step 2

A compound of Formula [Q-531] may be prepared from a compound of Formula [Q-403] and a compound of Formula [Q-530] according to Preparation Method 4 Step 2. A compound of Formula [Q-530] may be commercially available or synthesized by a method described in a literature (e.g. a method described in WO 2009/019174).

Step 3

A compound of Formula [Q-403] may be prepared from a compound of Formula [Q-401a] according to Preparation Method 4 Step 4.

Step 4

A compound of Formula [Q-533] may be prepared by protecting a compound of Formula [Q-532] with tert-butyldimethylsilyl (TBDMS) according to a method described in a literature (e.g. a method described in Peter G. M. Wuts. Protective Groups in Organic Synthesis Third Edition, Wiley-Interscience, 127-131).

Step 5

A compound of Formula [Q-534] may be prepared from a compound of Formula [Q-533] according to Preparation Method 5 Step 5.

Step 6

A compound of Formula [Q-536] may be prepared from a compound of Formula [Q-534] and a compound of Formula [Q-535] according to Preparation Method 5 Step 6.

Step 7

A compound of Formula [Q-537] may be prepared by cyclizing a compound of Formula [Q-536] according to a method described in a literature (e.g. a method described in R. Patino-Molina; I. Cubero-Lajo; M. J. P. Vega; M. T. Garcia-Lopez, Tetrahedron Lett. 2007, 48, 3615-3616).

Step 8

A compound of Formula [Q-538] may be prepared by reducing a compound of Formula [Q-537] with Schwartz's reagent according to a method described in for example S. R. Dandepally; R. Elgoummadi; A. L. Williams, Tetrahedron Lett. 2013, 54, 925-928.

Step 9

A compound of Formula [Q-539] may be prepared by oxidizing a compound of Formula [Q-538] with Dess-Martin reagent (e.g. a method described in E. Vedejs; D. W. Piotrowski; F. C. Tucci, J. Org. Chem. 2000, 65, 5498-5505).

Step 10

A compound of Formula [IV-D] may be prepared from a compound of Formula [Q-539] by Pinnick oxidation (e.g. a method described in G. A. Kraus; B. Roth, J. Org. Chem. 1980, 45, 4825-4830).

Preparation Method 5-5 is illustrated in the following reactions when chemical name: (3-methoxymethoxymethyl-cyclobutyl)-acetic acid methyl ester is used as a compound of Formula [Q-530] and chemical name: 3,3-difluoro-cyclobutylamine is used as a compound of Formula [Q-535].

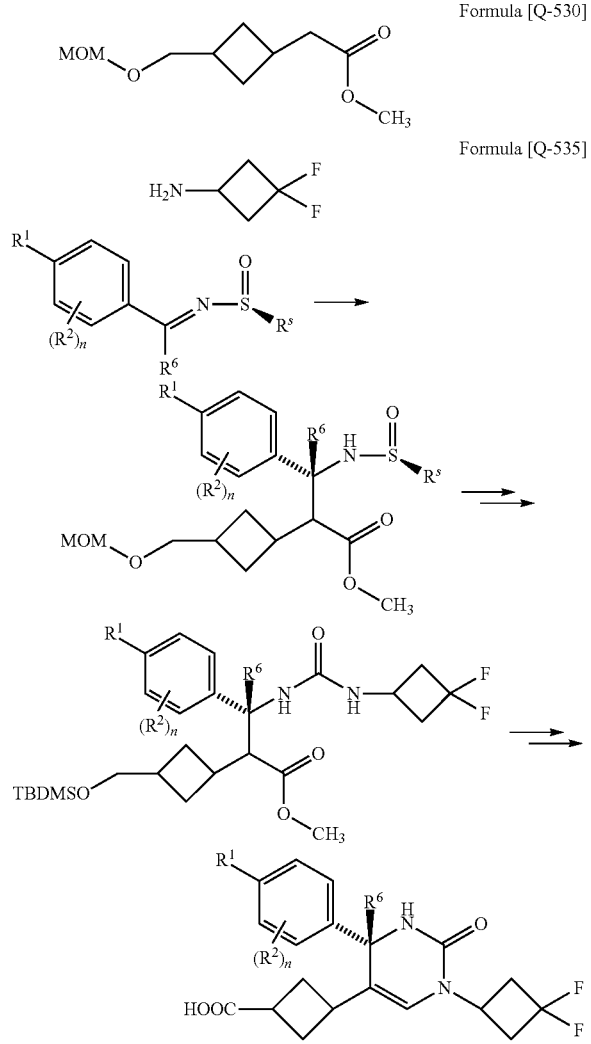

In the formula, R⁶ is methyl, and the other symbols have the same meanings as defined above.

Preparation Method 6

Methods for Preparing Starting Materials of Preparation Methods 1 to 5

Preparation Method 6-1

A compound of Formula [Q-101b], Formula [Q-301a] or [Q-401b] which is a starting material of Preparation Method 2 or 5 is represented by the following general formula:

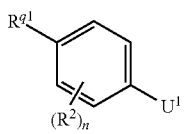

wherein $U^1$ is formyl, acetyl or ethylcarbonyl (which means each embodiment of —(C=O)—H, —(C=O)—R⁶ or —(C=O)—CH₂—R⁶ wherein R⁶ is hydrogen or methyl, respectively), and the other symbols have the same meanings as defined above. A commercially available product (e.g. 4-bromo-3-chloro-benzaldehyde, 1-(4-bromo-3-chloro-phenyl)-ethanone, 1-(4-bromo-3-chloro-phenyl)-propan-1-one) may be used for the compound or it may be prepared by known methods.

For example, it may be prepared by the following method.

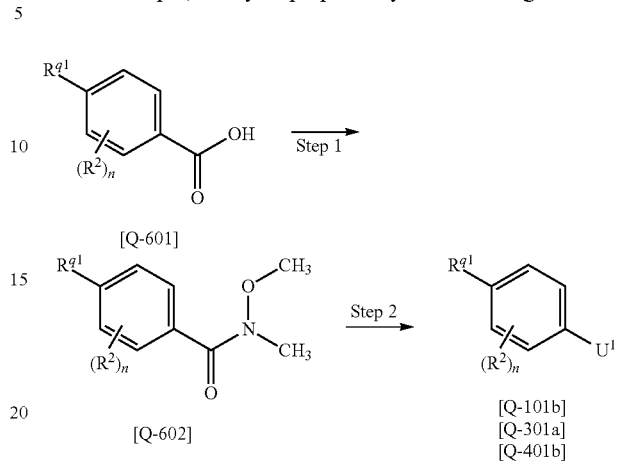

In the formula, each symbol has the same meaning as defined above.

Step 1

A compound of Formula [Q-602] may be prepared by a condensation reaction of a compound of Formula [Q-601] with N,O-dimethylhydroxylamine or N,O-dimethylhydroxylamine hydrochloride.

The condensation agent includes aqueous carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), and carbonyldiimidazole (CDI). For example, 1-hydroxy-1H-benzotriazole monohydrate (HOBt.H₂O) or 4-dimethylaminopyridine (DMAP) may be optionally added. A preferable condensation agent in the step is a mixture of aqueous carbodiimide (WSC.HCl: 1-ethyl-3-(3-dimethylaminopropyl)carbodiimide hydrochloride) and 1-hydroxy-1H-benzotriazole monohydrate (HOBt.H₂O).

A solvent includes toluene, dichloromethane, chloroform, tetrahydrofuran, dioxane, N,N-dimethylformamide, dimethylsulfoxide, acetonitrile, and acetone, and may be used alone or by mixture of two or more of them. A preferable solvent in the reaction is N,N-dimethylformamide or acetonitrile.

Step 2

A compound of Formula [Q-101b] or Formula [Q-401b] may be prepared by reacting a compound of Formula [Q-602] with Grignard reagent such as MeMgX and EtMgX (wherein X is chloro or bromo).

A solvent includes an ether solvent such as diethyl ether, tetrahydrofuran (THF), and 1,2-dimethoxyethane (DME). A preferable solvent is THF.

A compound of Formula [Q-301a] may be prepared by reacting a compound of Formula [Q-602] with a reducing agent such as diisobutylaluminum hydride (DIBAL-H).

For example, a compound which $U^1$ is formyl or ketone may be also prepared from a commercially available compound such as 2,2-dimethyl-indane-5-carboxylic acid in place of a compound of Formula [Q-601] by the above Steps 1 and 2.

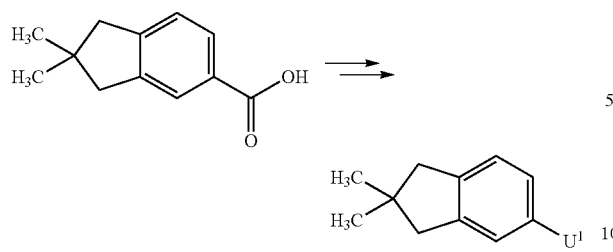

In the formula, $U^1$ is formyl, acetyl or ethylcarbonyl and each symbol has the same meaning as defined above.

Preparation Method 6-2

Preparation Method 6-2A

Synthesis of the Starting Material in Preparation Method 1, 3 or 4

A compound of Formula [Q-101a], a starting material of Preparation Method 1, a compound of Formula [Q-301], a starting material of Preparation Method 3, and a compound of Formula [Q-401a], a starting material of Preparation Method 4, are represented by the following general formula:

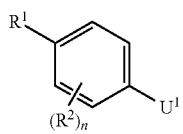

wherein each symbol has the same meaning as defined above.

The above compound may be for example prepared according to the following method.

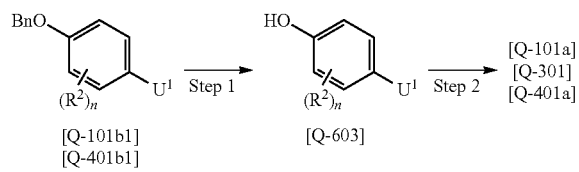

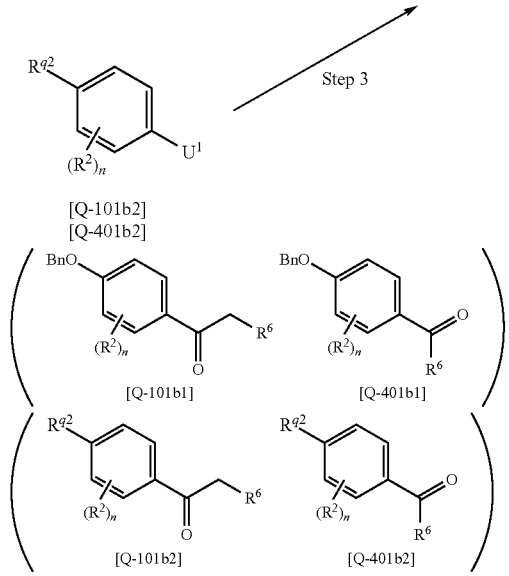

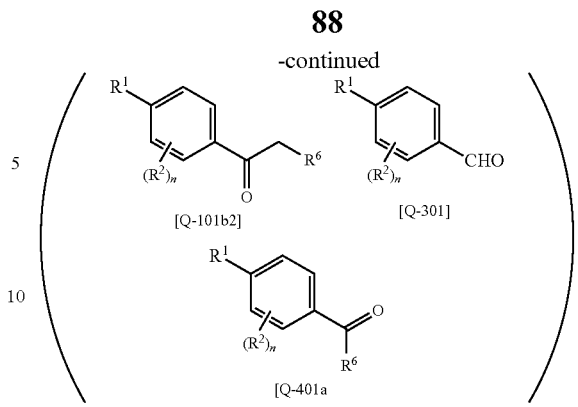

In the formula, each symbol has the same meaning as defined above.

Step 1 to Step 2

For example, a compound of Formula [Q-101a], Formula [Q-301] or Formula [Q-401a] wherein $R^1$ is $C_{3-6}$ alkoxy, $C_{2-7}$ alkoxy substituted with one trifluoromethyl or $C_{1-3}$ alkoxy substituted with one substituent selected from Group $X^{a2}$ may be prepared from a compound of Formula [Q-101b1] or Formula [Q-401b1] via a compound of Formula [Q-603].

Each Step may be carried out according to Preparation Method 2-1 Step 1 (a deprotection reaction of benzyl group) and Step 2 (a reaction with a compound of Formula [Q-203]).

Step 3

For example, a compound of Formula [Q-101a], Formula [Q-301] or Formula [Q-401a] wherein $R^1$ is $C_{4-8}$ alkyl or $C_{1-4}$ alkyl substituted with one substituent selected from Group $X^{a1}$ but $R^1$ is not $C_{3-6}$ alkoxy, $C_{2-7}$ alkoxy substituted with one trifluoromethyl or $C_{1-3}$ alkoxy substituted with one substituent selected from Group $X^{a2}$ may be prepared from a compound of Formula [Q-101b2] or Formula [Q-401b2].

In the step, a cross-coupling reaction using palladium (including Suzuki reaction) may be carried out according to Preparation Method 2-2.

Preparation Method 6-2B

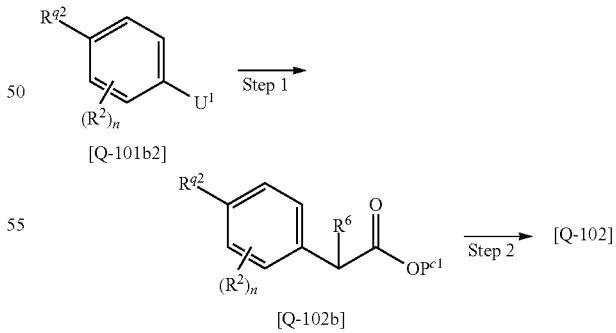

In the formula, $U^1$ is acetyl or ethylcarbonyl, and each symbol has the same meaning as defined above.

Step 1

A compound of Formula [Q-102b] may be prepared from 2-(3-chloro-4-trifluoromethanesulfonyloxy-phenyl)-propionic-acid-methyl-ester prepared from known 2-(3-chloro-4-hydroxy-phenyl)-propionic-acid-methyl-ester or a compound of the following Formula [Q-101b2] according to Preparation Method 1 Step 1.

Step 2

A compound of Formula [Q-102] may be prepared from a compound of Formula [Q-102b] according to Preparation Method 2-2.

Preparation Method 6-3

A compound of Formula [Q-101a], [Q-301] or [Q-401a] which is a starting material of Preparation Method 1, 3 or 4:

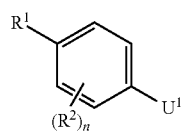

wherein each symbol has the same meaning as defined above
may be prepared by the following method, for example.

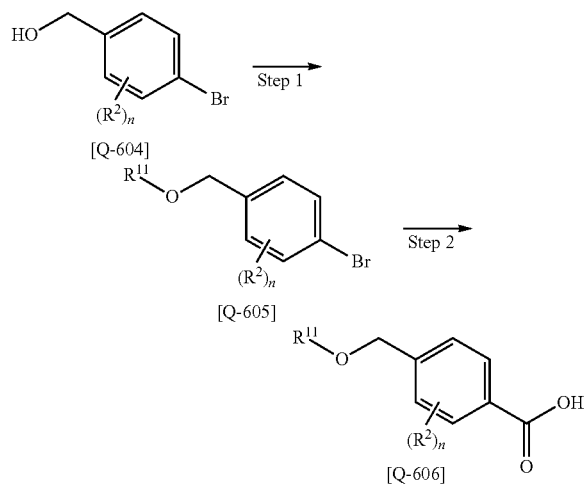

In the formula, $R^{11}$ is for example $C_{2-4}$ alkyl, and the other symbols have the same meanings as defined above.

Step 1

As a compound of Formula [Q-604], a commercially available compound such as (4-bromo-3-chloro-phenyl)-methanol, (4-bromo-3,5-dimethyl-phenyl)-methanol, and (4-bromo-2-methoxy-phenyl)-methanol may be used. A compound of Formula [Q-605] may be prepared by reacting a compound of Formula [Q-604] with a commercially available compound such as $R^{11}$—Br in the presence of a base such as sodium hydride.

A solvent includes N,N-dimethylformamide.

A compound of Formula [Q-605] wherein $R^{11}$ is tert-butyl may be prepared by reacting a compound of Formula [Q-604] with di-tert-butyl dicarbonate in the presence of magnesium perchlorate (e.g. a method described in Org. Lett., 2005, 7, 427-430).

Step 2

A compound of Formula [Q-606] may be prepared from a compound of Formula [Q-605] according to an insertion reaction of carbon monoxide in Preparation Method 2-2.

A solvent includes a mixed solvent of toluene and water.

The corresponding formyl, acetyl or ethylcarbonyl compound of Formula [Q-101a], [Q-301] or [Q-401a] may be prepared from a compound of Formula [Q-606] according to Preparation Method 6-1.

Preparation Method 6-4

A compound of Formula [Q-101a], [Q-301] or [Q-401a] which is a starting material of Preparation Method 1, 3 or 4:

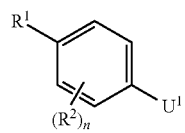

wherein each symbol has the same meaning as defined above
may be also prepared by a formation reaction of carbon-carbon bond of a compound of the following Formula [Q-607] and the compound having ketone or formyl.

As a compound of Formula [Q-607], a commercially available product such as 4-bromo-2-chloro-1-iodobenzene, 5-bromo-1,3-difluoro-2-iodobenzene, 4-bromo-2-ethyliodobenzene, and 5-bromo-2-iodo-m-xylene may be used. Alternatively, 2-benzyloxy-4-bromo-1-iodo-benzene which a commercially available 5-bromo-2-iodophenol is benzylated by a known method is also illustrated.

The compound having ketone or formyl includes the compound having ketone such as spiro-$C_{6-11}$ cycloalkanone and $C_{4-6}$ cycloalkanone or the compound having formyl such as $C_{4-8}$ alkylaldehyde.

For example, when spiro-$C_{6-11}$ cycloalkanone as the compound having ketone or formyl is spiro[3.3]heptan-2-one, a compound of Formula [Q-607] may be reacted as follows to prepare a compound of the following Formula [Q-612].

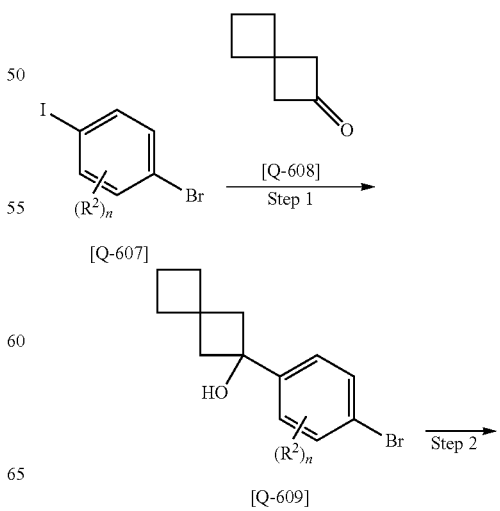

-continued

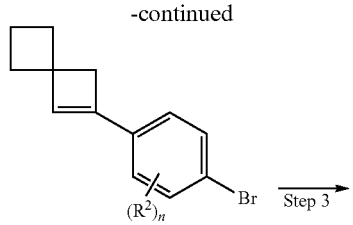
[Q-610]

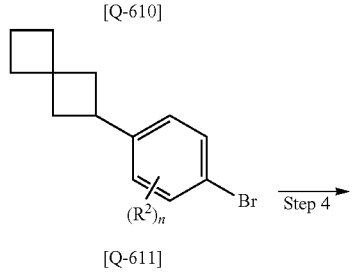
[Q-611]

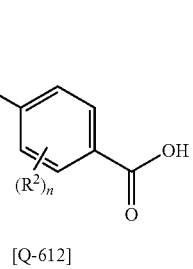
[Q-612]

In the formula, each symbol has the same meaning as defined above.

Step 1

A compound of Formula [Q-609] may be prepared by a halogen-metal exchange reaction of a compound of Formula [Q-607] with isopropylmagnesium chloride and the like, followed by an addition reaction with a compound of Formula [Q-608].

A solvent includes THF and DME. A reaction temperature includes from −45° C. to room temperature.

Step 2

A compound of Formula [Q-610] may be prepared by a mesylation reaction of a compound of Formula [Q-609] in the presence of a base.

A mesylating agent includes methanesulfonyl chloride.

A base includes triethylamine and diisopropylethylamine. A preferable base is triethylamine. A catalytic amount of trimethylamine hydrochloride and the like may be added if needed.

A solvent includes benzene, toluene, dichloromethane, chloroform, tetrahydrofuran, acetonitrile, and acetone. A preferable solvent is toluene.

A reaction temperature includes from 0° C. to 60° C. A preferable reaction temperature is from 0° C. to room temperature.

Step 3

A compound of Formula [Q-611] may be prepared by a catalytic hydrogenation of a compound of Formula [Q-610] in the presence of a catalyst.

A catalyst includes palladium carbon, platinum carbon, rhodium carbon, and rhodium-alumina. A preferable catalyst is rhodium carbon.

A solvent includes methanol, ethanol, isopropanol, tetrahydrofuran, 1,2-dimethoxyethane, and ethyl acetate, and may be used alone or by mixture of two or more of them. A preferable solvent is a mixed solvent of methanol and tetrahydrofuran.

A compound of Formula [Q-611] may be also prepared by reducing a compound of Formula [Q-609] in the presence of Lewis acid.

Lewis acid includes boron trifluoride diethyl ether.

A reducing agent includes triethylsilane.

A solvent includes dichloromethane and tetrahydrofuran. A preferable solvent is dichloromethane.

A reaction temperature includes from −78° C. to room temperature. A preferable reaction temperature is from −78° C. to room temperature.

Step 4

A compound of Formula [Q-612] may be prepared from a compound of Formula [Q-611] according to an insertion reaction of carbon monoxide in Preparation Method 6-3.

The corresponding formyl, acetyl or ethylcarbonyl compound of Formula [Q-101a], [Q-301] or [Q-401a] may be prepared from a compound of Formula [Q-612] according to Preparation Method 6-1.

The following compound may be prepared with a ketone compound of "$C_{3-6}$ cycloalkyl substituted with the same or different one to two $C_{1-5}$ alkyl", e.g. 3-isopropyl-cyclobutanone, as described above.

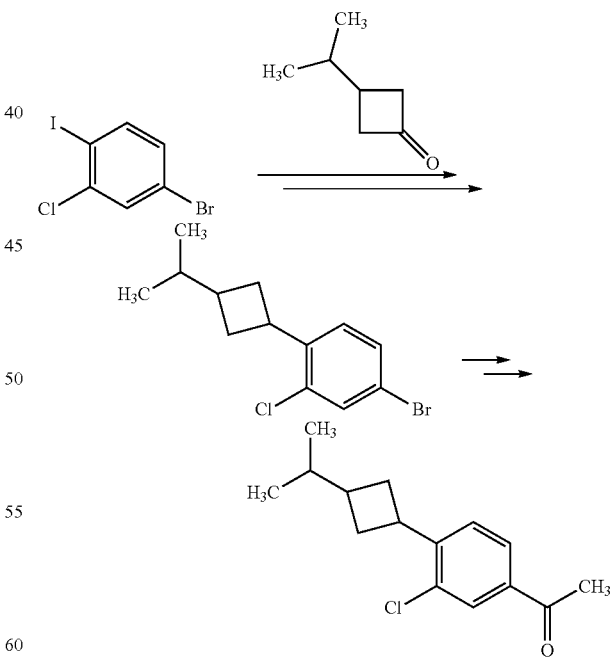

Preparation Method 6-5

A compound of Formula [Q-102], an intermediate of Preparation Method 1, e.g. a compound of Formula [Q-617] wherein $R^2$ is chloro and $R^6$ is methyl and the like, may be prepared by the following method.

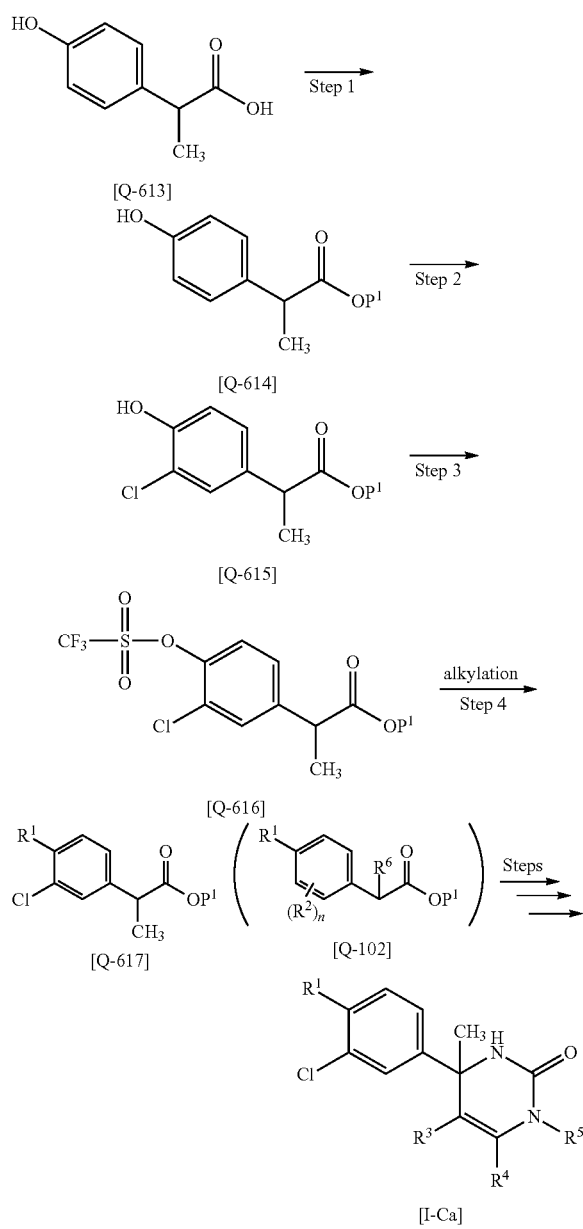

[Q-613]
[Q-614]
[Q-615]
[Q-616]
[Q-617]
[Q-102]
[I-Ca]

Step 1

A compound of Formula [Q-614] may be prepared by esterifying a compound of Formula [Q-613]. For example, when thionyl chloride and methanol are used, methyl ester may be obtained. As a compound of Formula [Q-613], a commercially available product such as 2-(4-hydroxy-phenyl)-propionic acid may be used.

Step 2

A compound of Formula [Q-615] may be prepared by chlorination of a compound of Formula [Q-614] with N-chlorosuccinimide (NCS) and the like.

A solvent includes acetonitrile and N,N-dimethylformamide. A preferable solvent is N,N-dimethylformamide.

Step 3

A compound of Formula [Q-616] may be prepared by reacting a compound of Formula [Q-615] with trifluoromethanesulfonic anhydride in the presence of a base.

A base includes triethylamine and pyridine. A preferable base is pyridine.

A solvent includes toluene, dichloromethane, chloroform, and tetrahydrofuran. A preferable solvent is dichloromethane.

A reaction temperature includes from 0° C. to room temperature. A preferable reaction temperature is 0° C.

Step 4

A compound of Formula [Q-617] may be prepared from a compound of Formula [Q-616] by a cross-coupling reaction (e.g. Suzuki reaction and Sonogashira reaction) as described in Preparation Method 2-2.

When Sonogashira reaction is carried out, the resulted alkynylene compound may be converted into an alkylene compound by a catalytic hydrogenation with a catalyst such as palladium carbon, platinum carbon, and rhodium-alumina.

Steps after Step 4

A compound of Formula [I] wherein $R^2$ is chloro and $R^6$ is methyl and the like (i.e., a compound of Formula [I-Ca]) may be prepared with a compound of Formula [Q-617] by the reactions described in Preparation Method 1.

Preparation Method 7

A Method for Preparing Starting Materials (1)

Preparation Method 7-1

As a compound of Formula [Q-104]:

[Q-104]

wherein each symbol has the same meaning as defined above, a commercially available compound such as 4-methyl-2-pentan-1-ol, 4-methyl-2-hexen-1-ol, 4,4-dimethyl-2-penten-1-ol, and 2,4-dimethyl-2-penten-1-ol may be used, which may be alternatively prepared by the following method.

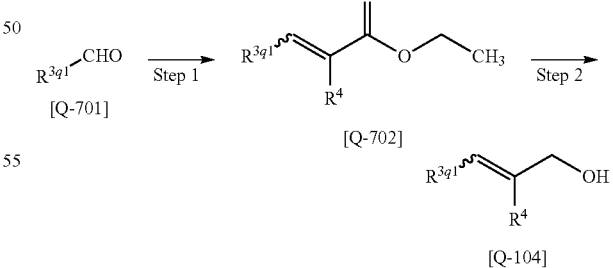

[Q-701]
[Q-702]
[Q-104]

In the formula, each symbol has the same meaning as defined above.

Step 1

A compound of Formula [Q-702] may be prepared from a compound of Formula [Q-701] and alkylphosphonic diester such as triethyl phosphonoacetate under Horner-Wadsworth-Emmons Reaction.

Step 2

A compound of Formula [Q-104] may be prepared from a compound of Formula [Q-702] by DIBAL reduction according to Preparation Method 6-1 Step 2.

As a compound of Formula [Q-701], a commercially available aldehyde such as 2-methylpropylaldehyde, isovaleraldehyde, 3,3-dimethylbutylaldehyde, and 4-methylpentylaldehyde may be used, which may be alternatively prepared by a known method.

A Method for Preparing a Compound of Formula [Q-701] (1)

For example, a compound of Formula [Q-701a] may be prepared from a compound of Formula [Q-703].

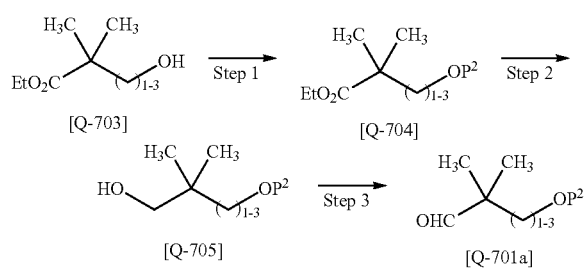

In the formula, each symbol has the same meaning as defined above.

Step 1

A compound of Formula [Q-704] may be prepared by protecting a hydroxyl group of a compound of Formula [Q-703] (e.g. a commerically available compound such as 2,2-dimethyl-3-hydroxypropanoic acid methyl ester, 4-hydroxy-2,2-dimethyl-butanoic acid methyl ester, and 5-hydroxy-2,2-dimethyl-pentanoic acid methyl ester) with trimethylsilyl (TMS), tert-butyldimethylsilyl (TBS) and the like according to a method described in a literature (e.g. a method described in Peter G. M. Wuts (2007). Green's Protective Groups in Organic Synthesis Fourth Edition, Weinheim, Germany, Wiley-VCH, 165-215).

Step 2

A compound of Formula [Q-705] may be prepared from a compound of Formula [Q-704] under DIBAL reduction according to Preparation Method 6-1 Step 2.

Step 3

A compound of Formula [Q-701a] may be for example prepared by Parikh-Doering oxidation reaction of a compound of Formula [Q-705] with SO$_3$.Py.

A Method for Preparing a Compound of Formula [Q-701] (2)

[Q-701]

A compound of Formula [Q-701b] may be also prepared from C$_{3-6}$ cycloalkanone optionally substituted with the same or different one to three substituent(s) selected from Group X$^b$ and Wittig reagent according to a method described in a literature (e.g. a method described in Bioorg. Med. Chem. Lett. 2004, 14(20), 5199-5203). For example, when R$^{3q}$ is cyclohexyl, the following is illustrated.

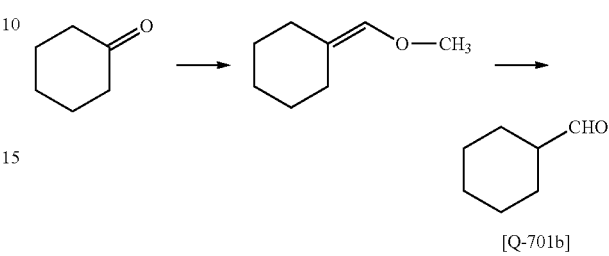

Preparation Method 7-2

As a compound of Formula [Q-302]:

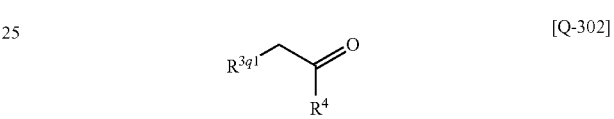

wherein each symbol has the same meaning as defined above, a commerically available aldehyde or ketone such as 3,3-dimethyl-butylaldehyde, 4-methyl-pentanal, cyclohexyl-acetaldehyde, and 2-butanone may be used, which may be alternatively prepared by a known method. For example, a compound of Formula [Q-302] wherein R$^4$ is H (i.e., an aldehyde compound) may be prepared from a compound of Formula [Q-701] under a carburation reaction according to a method described in a literature (e.g. a method described in Bioorg. Med. Chem. Lett. 2004, 14 (20), 5199-5203). For example, a compound of Formula [Q-302] wherein R$^4$ is methyl (i.e., a ketone compound) may be prepared from a compound of Formula [Q-701] under a carburation reaction according to a method described in a literature (e.g. a method described in Tetrahedron Lett. 2009, 50, 1276-1278).

Preparation Method 7-3

As a compound of Formula [Q-404]:

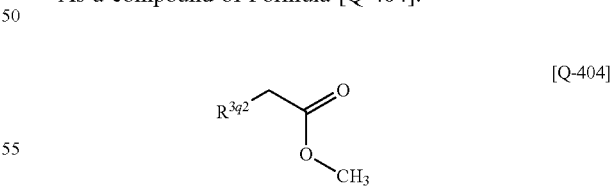

wherein each symbol has the same meaning as defined above, a commerically available ester such as 3-methyl-butanoic acid methyl ester, 4-methylvaleric acid methyl ester (i.e., 4-Methyl-pentanoic acid methyl ester), and 5-methyl-hexanoic acid methyl ester may be used, which may be alternatively prepared by a known method.

A methyl ester of a compound of Formula [Q-404] may be replaced with an ethyl ester.

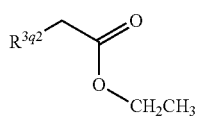

The ester compound may be, for example, prepared from a compound where a hydroxyl group of $C_{3-6}$ cycloalkanone optionally substituted with the same or different one to three substituent(s) selected from Group $X^b$ or a commerically available product such as 1-hydroxypropan-2-one, 1-hydroxybutan-2-one, and 1-hydroxypentan-2-one is protected with TBDPS, benzyl and the like under Horner-Wadsworth-Emmons Reaction and the like using alkylphosphonic diester.

For example, a compound of Formula [Q-404a] may be synthesized by the following preparation method.

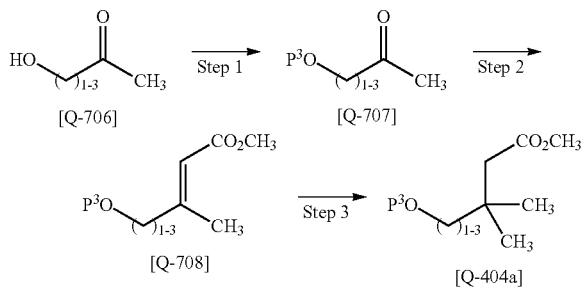

In the formula, each symbol has the same meaning as defined above.

Step 1

A compound of Formula [Q-707] may be prepared from a compound of Formula [Q-706] by a protecting reaction of alcohol according to Preparation Method 7-1.

Step 2

A compound of Formula [Q-708] may be prepared from a compound of Formula [Q-707] under Horner-Wadsworth-Emmons Reaction according to Preparation Method 7-1 Step 1.

Step 3

A compound of Formula [Q-404a] may be prepared from a compound of Formula [Q-708] by 1,4-addition reaction with methyllithium in the presence of a copper catalyst (e.g. a method described in J. Am. Chem. Soc. 2009, 131(44), 16016-16017).

Preparation Method 8
A Method for Preparing Starting Materials (2)
Preparation Method 8-1
As a compound of Formula [Q-408]:

wherein each symbol has the same meaning as defined above, a commercially available product such as 6-isocyanate-hexanoic acid ethyl ester, 2-isocyanate-2-methyl-propionic acid methyl ester, 3-isocyanate-propionic acid methyl ester, 4-isocyanate-cyclohexanecarboxylic acid methyl ester, and 4-isocyanatebenzoic acid ethyl ester may be used, which may be alternatively prepared by a known method.

For example, a compound of Formula [Q-408] may be prepared by the following method.

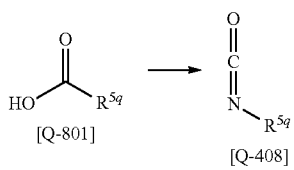

In the formula, each symbol has the same meaning as defined above.

A compound of Formula [Q-408] may be prepared from a compound of Formula [Q-801] (e.g. a commerically available product such as 3-(methoxycarbonyl)bicyclo[1.1.1]pentane-1-carboxylic acid, 1-(2-methoxy-2-oxo-ethyl)-5-oxopyrrolidine-3-carboxylic acid, and 3-[1-(ethoxycarbonyl)cyclopropyl]propanoic acid) by an azidation reaction, followed by Curtius rearrangement reaction according to Preparation Method 1 Step 5.

Preparation Method 8-2
As a compound of Formula [Q-108]:

wherein each symbol has the same meaning as defined above, a commercially available product such as methyl 3-aminopropanoate, methyl 3-aminocyclopentanecarboxylate, tert-butyl 2-(2-aminoethoxy)acetate, ethyl 4-aminobenzoate, and methyl 3-aminobicyclo[1.1.1]pentane-1-carboxylate hydrochloride may be used, which may be alternatively prepared by a known method.

For example, a compound of Formula [Q-108] may be prepared by reacting a compound of Formula [Q-408] with benzyl alcohol or t-BuOH to protect an amino group with tert-butoxycarbonyl group (Boc group) or benzyloxycarbonyl group (Cbz group), followed by deprotection of the Boc group or Cbz group according to a known method (e.g. a method described in Peter G. M. Wuts (2007). Green's Protective Groups in Organic Synthesis Fourth Edition, Weinheim, Germany, Wiley-VCH, 725-735, 748-756).

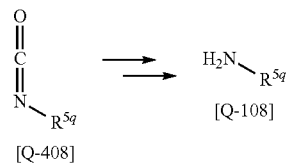

In the formula, each symbol has the same meaning as defined above.

Preparation Method 8-3

As a compound of Formula [Q-303]:

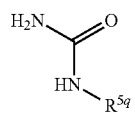

[Q-303]

wherein each symbol has the same meaning as defined above, a commerically available urea compound such as ureido-acetic acid ethyl ester, 2,2-dimethyl-3-ureido-propionic acid ethyl ester, 3-ureido-cyclohexanecarboxylic acid ethyl ester, and 4-ureido-benzoic acid ethyl ester may be used, which may be alternatively prepared by a known method.

For example, a compound of Formula [Q-303] may be prepared by the following method.

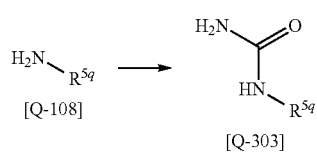

In the formula, each symbol has the same meaning as defined above.

A compound of Formula [Q-303] may be prepared from a compound of Formula [Q-108] and trimethylsilyl isocyanate.

A base includes triethylamine, diisopropylethylamine, and dimethylaminopyridine (DMAP), and may be used alone or by mixture of two or more of them. A preferable base is a mixture of triethylamine and dimethylaminopyridine.

A solvent includes benzene, toluene, tetrahydrofuran, dichloromethane, chloroform, ethyl acetate, and acetonitrile. A preferable solvent is tetrahydrofuran.

A reaction temperature includes from under ice cooling to 120° C. A preferable reaction temperature is 80° C.

Preparation Method 9

A racemate of Formula [I] obtained in Preparation Method 1, 2 or 3 or a racemate of Formula [Q-110] or Formula [Q-201], an intermediate of a compound of Formula [I], may be separated into a desirable enantiomer by liquid chromatography using a chiral stationary phase.

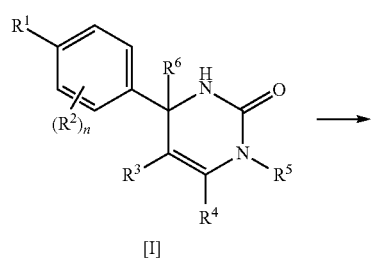

[I]

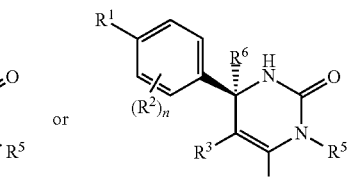

[IV] or [E-IV]

For example, a racemate [Q-901] which "$R^6$ is methyl" and "$R^5$ is —$Y^c$—COO—$C_2H_5$" in the following formula may be separated and isolated into a compound of Formula [Q-902] and a compound of Formula [Q-E-902] by liquid chromatography using a chiral stationary phase, followed by hydrolysis of each isolated enantiomer to give a desirable compound.

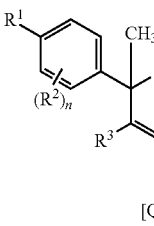

[Q-901]

Racemate

Column Chromatography →

[Q-902] or [Q-E-902]

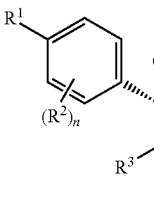

[Q-902]

Hydrolysis →

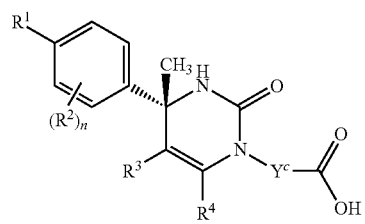

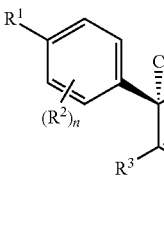

[Q-E-902]

Hydrolysis →

-continued

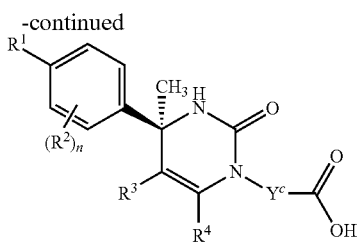

A separation condition is for example any of the followings. A mobile phase may be optionally adjusted depending on polarities of compounds and a mixing ratio of each solvent may be modified.

Separation Condition A:

Separation instrument; Recycling preparative chromatograph LC-9225 NEXT SERIES Japan Analytical Industry Co., Ltd.

Column; DAICEL CHIRALPAK IA 2.0 cmφ×25 cm

Mobile phase; hexane:2-propanol=90:10

Flow rate; 10.0 mL/min

Detection; UV (254 nm)

Separation Condition B:

Separation instrument; Recycling preparative chromatograph LC-9225 NEXT SERIES Japan Analytical Industry Co., Ltd.

Column; Japan Analytical Industry Co., Ltd. JAIGEL-ODS-AP, SP-120-10, 2.0 cmφ×25 cm Mobile phase; acetonitrile:$H_2O$:formic acid=90:10:0.1

Flow rate; 10.0 mL/min

Detection; UV (220 nm)

The following abbreviations may be for example used herein:

DMF: dimethylformamide

TBAF: tetrabutylammonium fluoride

NMP: N-methylpyrrolidone

Grubbs Cat. 2nd: (1,3-bis(2,4,6-trimethylphenyl)-2-imidazolidinylidene)dichloro-(phenylmethylene)tricyclohexylphosphine)ruthenium $PdCl_2$(dppf): dichloro[1,1'-bis(diphenylphosphino)ferrocene]palladium

EXAMPLES

In particular, a method for preparing a compound of Formula [I] or a pharmaceutically acceptable salt thereof is illustrated by Examples. A method for preparation of a compound of Formula [I] or a pharmaceutically acceptable salt thereof is however not limited to the method for preparation.

For example, to "purify through silica gel column chromatography (ethyl acetate:hexane=1:50→1:5)" means a procedure for elution with a mixed solution with a mixed ratio of 1:50 (ethyl acetate:hexane), followed by elution with a mixed solution with a mixed ratio of 1:5 (ethyl acetate:hexane) in a purification through silica gel column chromatography. "d.r." means a diastereomer ratio. A melting point is determined by a melting point determination apparatus (Yanaco MP-500D, manufactured by Yanagimoto Seisakujo).

Example 5

Preparation of 4-{5-tert-butyl-4-[3-chloro-4-(2,2-dimethylpropoxy)-phenyl]-2-oxo-3,4-dihydro-2H-pyrimidin-1-yl}-butanoic Acid (Optically Active Compound)

Step 1

3-chloro-4-(2,2-dimethylpropoxy)-benzaldehyde

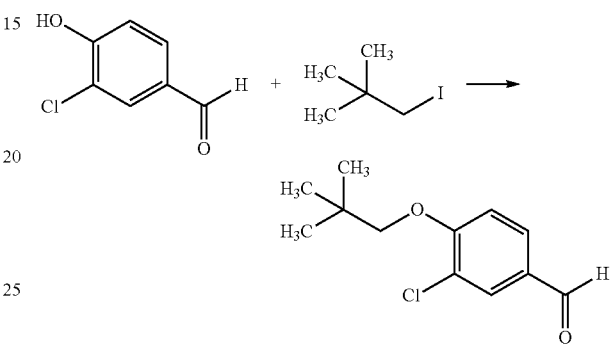

3-Chloro-4-hydroxybenzaldehyde (5 g) and 1-iodo-2,2-dimethylpropane (8.5 mL) were mixed in N,N-dimethylformamide (25 mL). To the reaction solution was added cesium carbonate (4.43 g), and the reaction solution was stirred at 100° C. overnight. To the reaction solution was added water, and then the mixture was extracted with ethyl acetate. The organic layer was sequentially washed with water and aqueous saturated sodium chloride solution, and dried over magnesium sulfate. After removing magnesium sulfate on a filter, the filtrate was concentrated under reduced pressure to give the titled compound (4.82 g).

Step 2

4-Carbamoylaminobutanoic Acid ethyl Ester

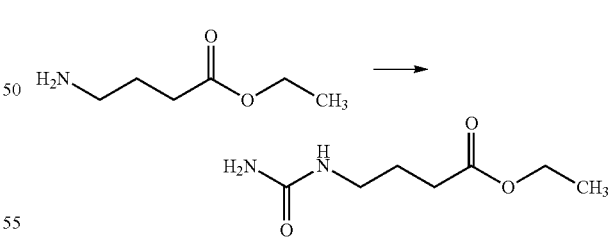

4-Aminobutyric acid ethyl hydrochloride (3.00 g), triethylamine (2.49 mL), and 4-dimethylaminopyridine (218 mg) were mixed in tetrahydrofuran (40 mL). To the reaction solution was added trimethylsilyl isocyanate (2.37 mL), and the reaction solution was stirred at 80° C. for 3.5 hours. To the reaction solution was added ethyl acetate under ice cooling. After removing an insoluble on a filter, the filtrate was concentrated under reduced pressure. The solid precipitated by adding diisopropylether to the resulted residue was filtered to give the titled compound (2.48 g).

Step 3

4-{5-tert-Butyl-4-[3-chloro-4-(2,2-dimethyl-propoxy)-phenyl]-2-oxo-3,4-dihydro-2H-pyrimidin-1-yl}-butanoic Acid ethyl Ester (Optically Active Compound)

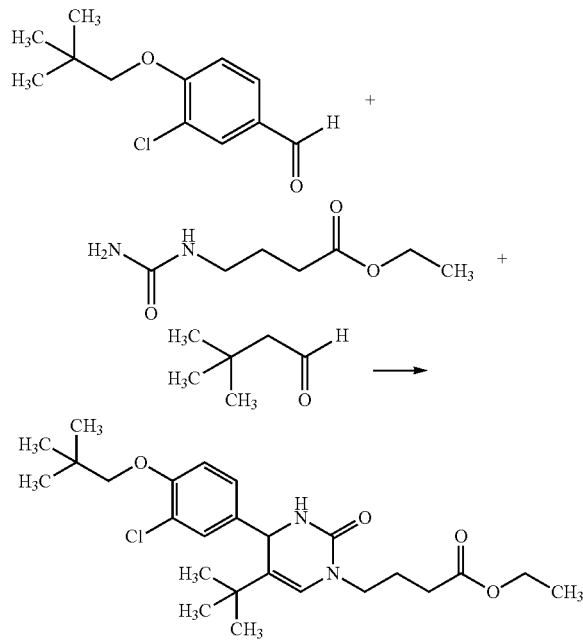

3-Chloro-4-(2,2-dimethylpropoxy)-benzaldehyde (510 mg) and 4-carbamoylaminobutanoic acid ethyl ester (261 mg) were mixed in acetonitrile (1.6 mL) and N,N-dimethylformamide (0.8 mL). To the reaction solution was added trimethylchlorosilane (0.19 mL), and the reaction solution was stirred for 30 minutes. To the reaction solution was added 3,3-dimethylbutylaldehyde (0.19 mL), and the reaction solution was stirred at 80° C. for 2.5 hours. Water was added to the reaction solution at room temperature, which was then extracted with ethyl acetate. The organic layer was sequentially washed with water and aqueous saturated sodium chloride solution, and dried over magnesium sulfate. After removing magnesium sulfate on a filter, the filtrate was concentrated under reduced pressure. The resulted residue was purified through silica gel chromatography (ethyl acetate:chloroform=1:2), followed by thin layer silica gel chromatography (ethyl acetate:chloroform=1:2), to give a racemate of the titled compound (147.4 mg). The racemate was separated and purified by recycling preparative chromatograph.

The titled compound (64.5 mg) was obtained as a compound in a fraction eluted earlier in recycling preparative chromatograph (separation condition A1). The compound was analyzed by analytical column DAICEL CHIRALPAK IA-3 (analytical condition B1) to determine 6.6 min as the retention time and >99% ee as the optical purity.

An enantiomer of the titled compound (i.e., an ethyl ester of Example 6) was obtained as a compound in a fraction eluted later in recycling preparative chromatograph (separation condition A1). The compound was analyzed by analytical column DAICEL CHIRALPAK IA-3 (analytical condition B1) to determine 9.5 min as the retention time and >99% ee as the optical purity.

The separation condition was as follows.

(Separation Condition A1)
Separation instrument; Recycling preparative chromatograph LC-9225 NEXT SERIES Japan Analytical Industry Co., Ltd.
Column; DAICEL CHIRALPAK IA 2.0 cmφ×25 cm
Mobile phase; hexane:2-propanol=70:30
Flow rate; 10.0 mL/min
Detection; UV (220 nm)

The analytical condition used in the chiral column was as follows.

(Analytical Condition B1)
Measuring instrument; HPLC system Shimadzu Corporation high-performance liquid chromatograph prominence
Column; DAICEL CHIRALPAK IA-3 0.46 cmφ×15 cm
Column temperature; 40° C.
Mobile phase; hexane:2-propanol=80:20
Flow rate; 1.0 mL/min
Detection; UV (220 nm)

Step 4

4-{5-tert-Butyl-4-[3-chloro-4-(2,2-dimethyl-propoxy)-phenyl]-2-oxo-3,4-dihydro-2H-pyrimidin-1-yl}-butanoic Acid (Optically Active Compound)

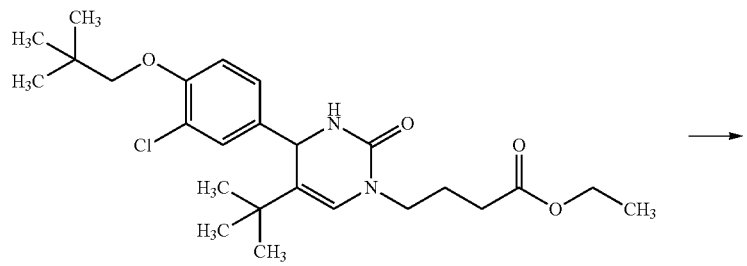

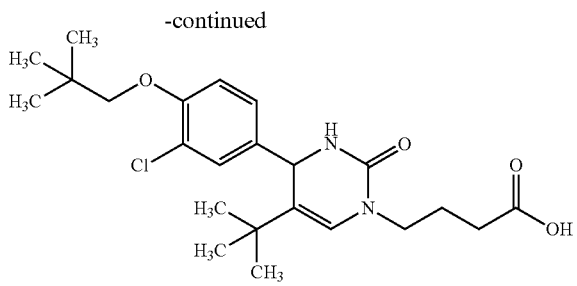

4-{5-tert-Butyl-4-[3-chloro-4-(2,2-dimethylpropoxy)-phenyl]-2-oxo-3,4-dihydro-2H-pyrimidin-1-yl}-butanoic acid ethyl ester (63 mg) obtained in Step 3 was mixed in ethanol (0.5 mL). To the reaction solution was added 4M aqueous lithium hydroxide solution (0.07 mL), and the reaction solution was stirred at room temperature for 3.5 hours. To the reaction solution were added 2M aqueous hydrochloric acid solution and water under ice cooling, which was then extracted with ethyl acetate. The organic layer was washed with aqueous saturated sodium chloride solution, and dried over magnesium sulfate. After removing magnesium sulfate on a filter, the filtrate was concentrated under reduced pressure. To the resulted residue was added a mixed solvent of hexane-diisopropylether (1:1), and the precipitated solid was filtered to give the titled compound (47.8 mg).

The resulted compounds were analyzed with a chiral column to determine 13.5 min as the retention time and >99% ee as the optical purity of the resulted enantiomer compound. The retention time of the other enantiomer was 16.7 min.

The analytical condition used in the chiral column was as follows.
Measuring instrument; HPLC system Shimadzu Corporation high-performance liquid chromatograph prominence
Column; DAICEL CHIRALPAK AS-3R 0.46 cmφ×15 cm
Column temperature; 40° C.
Mobile phase; water:acetonitrile:trifluoroacetic acid=30:70: 0.1
Flow rate; 0.5 mL/min
Detection; UV (220 nm)

Example 87

Preparation of 3-{(S)-4-[3-chloro-4-(3,3-dimethyl-butyl)-phenyl]-5-isopropyl-4-methyl-2-oxo-3,4-dihydro-2H-pyrimidin-1-yl}-propionic Acid A Method for Preparation Using an Optically Active Sulfinamide

Step 1

4-Bromo-3-chloro-N-methoxy-N-methyl-benzamide

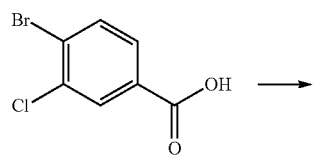

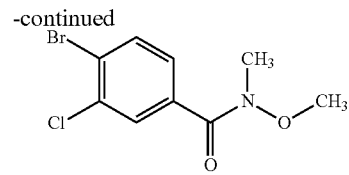

4-Bromo-3-chloro-benzoic acid (100 g), N,O-dimethyl-hydroxylamine hydrochloride (49.7 g), 1-hydroxybenzotri-azole monohydrate (13.0 g), and diisopropylethylamine (103.8 mL) were mixed in acetonitrile (800 mL). To the reaction solution was added 1-ethyl-3-(3-dimethylamino-propyl)carbodiimide hydrochloride (97.6 g) in four batches under ice cooling, and the reaction solution was stirred at room temperature overnight. To the reaction solution were added toluene (1 L) and water (500 mL), and the mixture was separated, and then the aqueous layer was extracted with toluene (500 ml) twice. The resulted organic layer was collected and washed sequentially with 1M hydrochloric acid, water, saturated aqueous sodium hydrogen carbonate solution, and aqueous saturated sodium chloride solution, and dried over magnesium sulfate. After removing magnesium sulfate on a filter, the filtrate was concentrated under reduced pressure to give the titled compound (115.8 g) as a crude product.

$^1$H-NMR (400 MHz, CDCl$_3$) 3.36 (s, 3H), 3.55 (s, 3H), 7.47 (dd, J=8.32, 1.85 Hz, 1H), 7.66 (d, J=8.32 Hz, 1H), 7.81 (d, J=1.85 Hz, 1H)

Step 2

1-(4-Bromo-3-chloro-phenyl)-ethanone

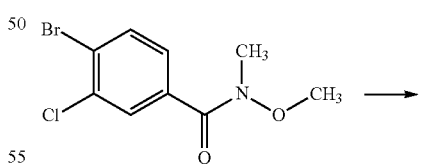

4-Bromo-3-chloro-N-methoxy-N-methyl-benzamide (115 g) was mixed in tetrahydrofuran (575 mL). To the reaction solution was added dropwise 1M methylmagnesium bromide/tetrahydrofuran solution (516 mL) under ice cooling, and the reaction solution was stirred for 2 hours under ice cooling. To the reaction solution was added dropwise 1M hydrochloric acid (550 mL) under ice cooling, and then to the mixture was added ethyl acetate (500 ml). The mixed solution was separated, and the aqueous layer was then extracted with ethyl acetate. The resulted organic layer was collected and washed sequentially with water and aqueous saturated sodium chloride solution, and dried over magnesium sulfate. After removing magnesium sulfate on a filter, the filtrate was concentrated under reduced pressure. To the resulted residue were added diisopropylether and hexane, and the precipitated solid was filtered to give the titled compound (91.5 g).

$^1$H-NMR (400 MHz, CDCl$_3$) 2.59 (s, 3H), 7.68 (dd, J=8.32, 1.85 Hz, 1H), 7.74 (d, J=8.32 Hz, 1H), 8.02 (d, J=1.85 Hz, 1H)

Step 3

1-[3-Chloro-4-(3,3-dimethyl-but-1-ynyl)-phenyl]-ethanone

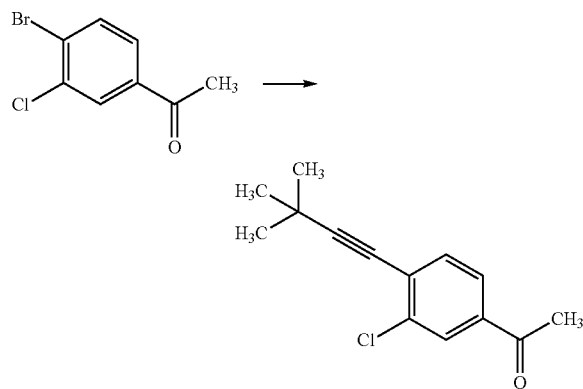

1-(4-Bromo-3-chloro-phenyl)-ethanone (78 g), triethylamine (390 mL), 3,3-dimethyl-but-1-yne (53.2 mL), and copper iodide (6.4 g) were mixed in N,N-dimethylformamide (46 mL) under argon gas. To the reaction solution was added bis(triphenylphosphine)palladium (II) dichloride (23.5 g), and the reaction solution was stirred at 90° C. for 2 hours. To the reaction solution were added saturated ammonium chloride water, a mixed solution of ethyl acetate-hexane (1:1), and Celite at room temperature, and the mixture was stirred for 10 minutes. After removing an insoluble on a filter, the filtrate was extracted with a mixed solution of ethyl acetate-hexane (1:1). The organic layer was sequentially washed with aqueous saturated ammonium chloride solution, 0.5M hydrochloric acid, water, and aqueous saturated sodium chloride solution, and dried over magnesium sulfate. After removing magnesium sulfate on a filter, the filtrated was concentrated under reduced pressure. The resulted residue was purified through silica gel column chromatography (ethyl acetate:hexane=1:30→1:13) to give the titled compound (75.37 g).

$^1$H-NMR (400 MHz, CDCl$_3$) 1.35 (s, 9H), 2.58 (s, 3H), 7.49 (d, J=7.97 Hz, 1H), 7.74 (dd, J=7.97, 1.69 Hz, 1H), 7.95 (d, J=1.69 Hz, 1H)

Step 4

1-[3-Chloro-4-(3,3-dimethyl-butyl)-phenyl]-ethanone

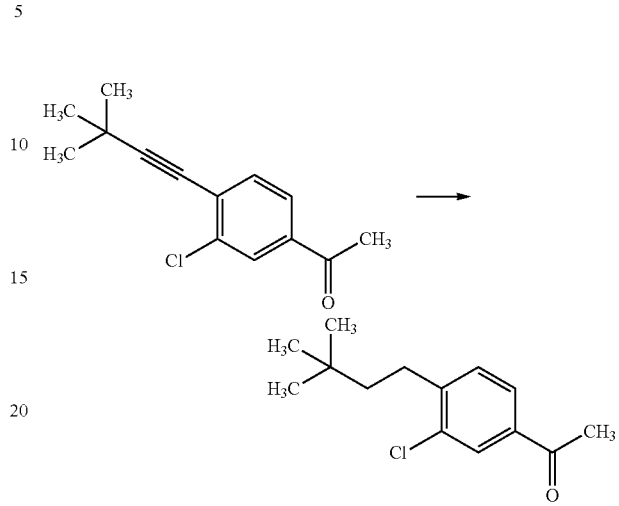

1-[3-Chloro-4-(3,3-dimethyl-but-1-ynyl)-phenyl]-ethanone (22.3 g) was mixed in tetrahydrofuran (112 mL) and methanol (112 mL). To the reaction solution was added 5 w/w % rhodium/alumina (2.23 g), and the reaction solution was stirred for 8.5 hours under hydrogen gas at ordinary pressure. After removing rhodium/alumina on a filter, the filtrate was concentrated under reduced pressure. The procedure was repeated two more times, and the resulted residue was collected and purified through silica gel chromatography (ethyl acetate:hexane=1:50) to give the titled compound (58.0 g).

$^1$H-NMR (400 MHz, CDCl$_3$) 0.98 (s, 9H), 1.45-1.48 (m, 2H), 1.54 (s, 3H), 2.57 (s, 3H), 2.72-2.76 (m, 2H), 7.31 (d, J=7.92 Hz, 1H), 7.76 (dd, J=7.92, 1.79 Hz, 1H), 7.92 (d, J=1.79 Hz, 1H)

Step 5

(S)-2-Methyl-propane-2-sulfinic acid [1-[3-chloro-4-(3,3-dimethyl-butyl)-phenyl]-eth-(E)-ylidene]-amide

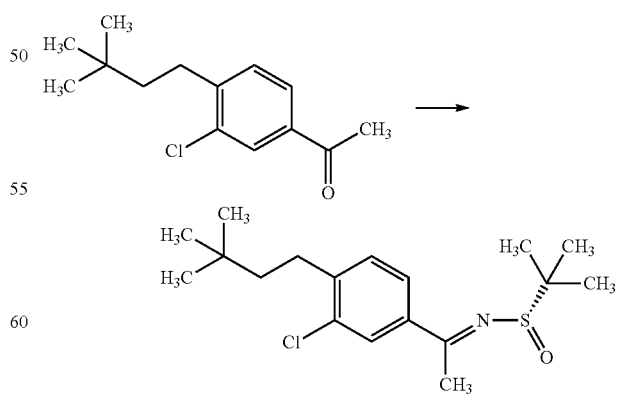

1-[3-Chloro-4-(3,3-dimethyl-butyl)-phenyl]-ethanone (56.1 g) and (S)-(−)-2-methyl-propane-2-sulfinic acid amide (29.05 g) were mixed in cyclopentylmethyl ether (234 mL).

To the reaction solution was added tetraethyl orthotitanate (98.3 mL), and the reaction solution was stirred at 110° C. for 4.5 hours. The solution was added dropwise to a mixed solution of 10 w/w % aqueous ammonium chloride solution (300 mL)-ethyl acetate (200 mL) under ice cooling, and the mixed solution was stirred at room temperature for 30 minutes. To the mixed solution was added Celite, and the mixed solution was stirred for additional 30 minutes at room temperature. After removing an insoluble on a filter, the filtrate was washed sequentially with 30 w/w % aqueous ammonium chloride solution and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:50→1:33→1:20→1:10→1:5) to give the titled compound (69.86 g).

$^1$H-NMR (400 MHz, CDCl$_3$) 0.99 (s, 9H), 1.32 (s, 9H), 1.45-1.47 (m, 2H), 2.70-2.75 (m, 2H), 2.73 (s, 3H), 7.26 (d, J=8.09 Hz, 1H), 7.68 (dd, J=8.09, 1.74 Hz, 1H), 7.84 (d, J=1.74 Hz, 1H)

Step 6

(R)-3-[3-Chloro-4-(3,3-dimethyl-butyl)-phenyl]-2-isopropyl-3-((S)-2-methyl-propane-2-sulfinylamino)-butanoic Acid methyl Ester

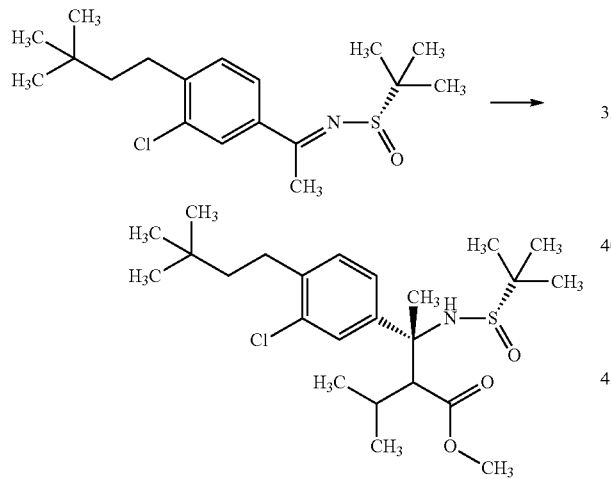

Diisopropylamine (52.7 mL) was mixed in tetrahydrofuran (341 mL) under argon gas. To the reaction solution was added dropwise 1.63 M n-butyllithium/hexane solution (220 mL) at −78° C., and the reaction solution was stirred at −78° C. for 40 minutes. To the reaction solution was added dropwise a mixed solution of 3-methyl-butanoic acid methyl ester (45 mL) in tetrahydrofuran (34 mL), and the reaction solution was stirred at −78° C. for additional 1 hour. To the reaction solution was added dropwise 1 M chloro titanium (IV) triisopropoxide/hexane solution (682 mL), and the reaction solution was stirred at −78° C. for additional 30 minutes. To the reaction solution was added dropwise a mixed solution of (S)-2-methyl-propane-2-sulfinic acid [1-[3-chloro-4-(3,3-dimethyl-butyl)-phenyl]-eth-(E)-ylidene]-amide (60.73 g) in tetrahydrofuran (34 mL), and the reaction solution was stirred at −78° C. for 10 minutes, then at −40° C. for additional 2 hours. The reaction solution was cooled to −78° C. and was dropped under ice cooling to aqueous ammonium chloride solution. The resulted mixed solution was stirred under ice cooling for 1 hour, and then an insoluble was removed on a filter. The filtrate was separated, and the organic layer was washed sequentially with ammonium chloride water and aqueous sodium chloride solution and dried over sodium sulfate. After removing sodium sulfate on a filter, the filtrate was concentrated under reduced pressure. The resulted residue was purified through silica gel column chromatography (ethyl acetate:hexane=1:20→1:10→1:4→1:3) to give the titled compound (64.91 g) as a mixture of diastereomers generated by isopropyl group at α-position of ester (d.r.=90:10).

$^1$H-NMR (400 MHz, CDCl$_3$) 0.72 (d, J=6.82 Hz, 0.3H), 0.92 (d, J=2.31 Hz, 2.7H), 0.93 (d, J=2.31 Hz, 2.7H), 0.98 (s, 8.1H), 0.99 (s, 0.9H), 1.01 (d, J=6.82 Hz, 0.3H), 1.25 (s, 8.1H), 1.34 (s, 0.9H), 1.44-1.49 (m, 2H), 1.86 (s, 0.3H), 1.89 (s, 2.7H), 2.01-2.11 (m, 1H), 2.46 (d, J=3.93 Hz, 0.1H), 2.63-2.72 (m, 2H), 2.83 (d, J=3.93 Hz, 0.9H), 3.59 (s, 2.7H), 3.70 (s, 0.3H), 5.04 (brs, 0.9H), 5.42 (brs, 0.1H), 7.13-7.27 (m, 2H), 7.39 (d, J=2.08 Hz, 0.9H), 7.43 (d, J=1.85 Hz, 0.1H)

Step 7

(S)-2-Methyl-propane-2-sulfinic acid {(R)-1-[3-chloro-4-(3,3-dimethyl-butyl)-phenyl]-2-hydroxymethyl-1,3-dimethyl-butyl}amide

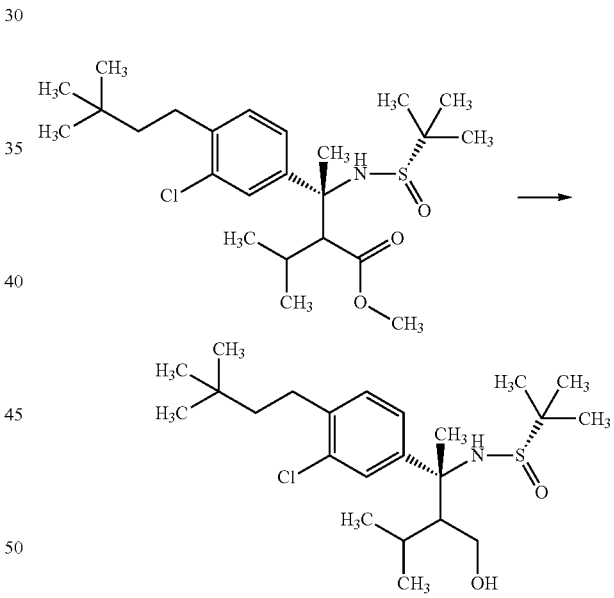

(R)-3-[3-Chloro-4-(3,3-dimethyl-butyl)-phenyl]-2-isopropyl-3-((S)-2-methyl-propane-2-sulfinylamino)-butanoic acid methyl ester (54.9 g) was mixed in toluene (384 mL) under argon gas. To the reaction was added dropwise 1 M diisobutylaluminum hydride/toluene solution (415 mL) at −78° C., and the reaction solution was stirred at −78° C. for 50 minutes, then gradually warmed to 0° C. to stir for 3 hours. To the reaction solution was added dropwise under ice cooling methanol, then aqueous Rochelle salt solution. To the mixed solution was added ethyl acetate, and then the mixture was stirred at room temperature for 3 hours. The resulted solution was extracted with ethyl acetate. The organic layer was washed sequentially with water and aqueous saturated sodium chloride solution, and dried over sodium sulfate. After removing sodium sulfate on a filter, the filtrate was concentrated under reduced pressure. To the resulted residue was added diisopropylether, and the precipitated solid was filtered to give the titled compound (42.0 g, d.r.=95:5).

$^1$H-NMR (400 MHz, CDCl$_3$) 0.70 (d, J=7.06 Hz, 3H), 0.75 (d, J=7.06 Hz, 3H), 0.99 (s, 9H), 1.15 (s, 9H), 1.17-1.26 (m, 1H), 1.47-1.52 (m, 2H), 1.94 (s, 3H), 2.04-2.09 (m, 1H), 2.65-2.71 (m, 2H), 3.91-3.96 (m, 1H), 3.99-4.06 (m, 1H), 4.75 (s, 1H), 6.63 (s, 1H), 7.17 (d, J=8.04 Hz, 1H), 7.23 (dd, J=8.04, 1.91 Hz, 1H), 7.40 (d, J=1.91 Hz, 1H) (for the major isomer)

An absolute configuration of the quaternary asymmetric carbon in the titled compound was determined by purification of the major isomer of the titled compound (i.e. the following compound), followed by single crystal X-ray structural analysis thereof.

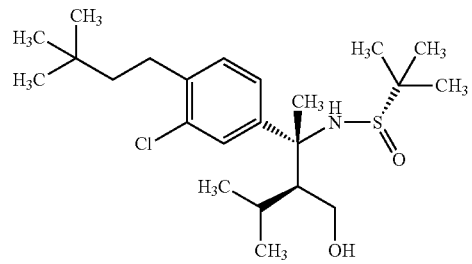 [SMILES: CC(C)[C@H](CO)[C@@](C)(N[S@@](=O)C(C)(C)C)c1ccc(CCC(C)(C)C)c(Cl)c1]

Step 8

(R)-3-Amino-3-[3-chloro-4-(3,3-dimethyl-butyl)-phenyl]-2-isopropyl-butan-1-ol

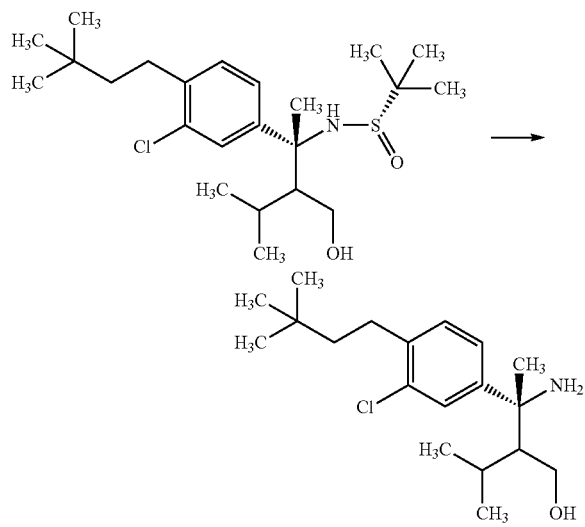

(S)-2-Methyl-propane-2-sulfinic acid {(R)-1-[3-chloro-4-(3, 3-dimethyl-butyl)-phenyl]-2-hydroxymethyl-1,3-dimethyl-butyl}amide (41.4 g) was mixed in methanol (207 mL) and tetrahydrofuran (21 ml). To the reaction solution was added dropwise 2M hydrogen chloride/methanol solution (193 mL) under ice cooling, and the reaction solution was stirred at room temperature for three hours. The reaction solution was concentrated under reduced pressure, and chloroform was added to the residue. An aqueous sodium carbonate solution was added to the mixed solution under ice cooling so that the aqueous layer was adjusted to pH 10. The mixed solution was extracted with chloroform. The organic layer was washed with aqueous saturated sodium chloride solution, and dried over sodium sulfate. After removing sodium sulfate on a filter, the filtrate was concentrated under reduced pressure to give the titled compound (29.0 g, d.r.=95:5) as a crude product.

$^1$H-NMR (400 MHz, CDCl$_3$) 0.80 (d, J=7.00 Hz, 3H), 0.85 (d, J=7.00 Hz, 3H), 0.98 (s, 9H), 1.35-1.42 (m, 1H), 1.43-1.49 (m, 2H), 1.60 (s, 3H), 1.86-1.91 (m, 1H), 2.65-2.70 (m, 2H), 3.70 (dd, J=11.59, 3.38 Hz, 5H), 3.92 (dd, J=11.59, 9.18 Hz, 1H), 7.21-7.22 (m, 2H), 7.36 (d, J=1.69 Hz, 1H) (for the major isomer)

Step 9

3-(3-{(R)-1-[3-Chloro-4-(3,3-dimethyl-butyl)-phenyl]-2-hydroxymethyl-1,3-dimethyl-butyl}-ureido)-propionic Acid ethyl Ester

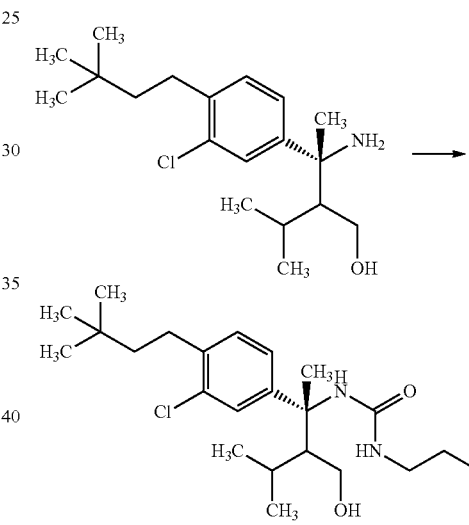

(R)-3-Amino-3-[3-chloro-4-(3,3-dimethyl-butyl)-phenyl]-2-isopropyl-butan-1-ol (29.0 g) was mixed in tetrahydrofuran (203 mL). To the reaction solution was added 3-isocyanatopropionic acid ethyl ester (11.8 mL) under ice cooling, and the reaction solution was stirred at room temperature for 100 minutes. To the reaction solution was added 3-isocyanatopropionic acid ethyl ester (1.18 mL) under ice cooling, and the reaction solution was stirred at room temperature for 75 minutes. To the reaction solution was added 3-isocyanatopropionic acid ethyl ester (0.59 mL) at room temperature, and the reaction solution was stirred at room temperature for 2 hours. To the mixed solution was added N,N,N'-trimethylethylenediamine (1.73 mL), and the mixture was stirred at room temperature for 40 minutes. To the reaction solution was added 0.1M hydrochloric acid, which was extracted with ethyl acetate. The organic layer was washed sequentially with water, aqueous saturated sodium chloride solution, and aqueous sodium chloride solution, and dried over sodium sulfate. After removing sodium sulfate on a filter, the reaction solution was concentrated under reduced pressure, and the resulted residue was purified through silica gel column chromatography (ethyl acetate:chloroform=1:10→1:5→1:3) to give the titled compound (41.6 g, d.r.=95:5).

¹H-NMR (400 MHz, CDCl₃) 0.77 (d, J=6.94 Hz, 3H), 0.83 (d, J=6.94 Hz, 3H), 0.98 (s, 9H), 1.25 (t, J=7.03 Hz, 3H), 1.48 (dt, J=9.02, 4.05 Hz, 2H), 1.52-1.58 (m, 1H), 1.71-1.74 (m, 1H), 1.79 (s, 3H), 2.33-2.45 (m, 2H), 2.63-2.68 (m, 2H), 2.82 (brs, 1H), 3.31 (q, J=6.17 Hz, 2H), 3.80 (d, J=11.10 Hz, 1H), 3.90-3.95 (m, 1H), 4.12 (q, J=7.03 Hz, 2H), 4.49 (t, J=6.01 Hz, 1H), 7.13 (brs, 1H), 7.16 (d, J=8.15 Hz, 1H), 7.25 (dd, J=8.15, 2.03 Hz, 1H), 7.38 (d, J=2.03 Hz, 1H) (for the major isomer)

Step 10

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic Acid ethyl Ester

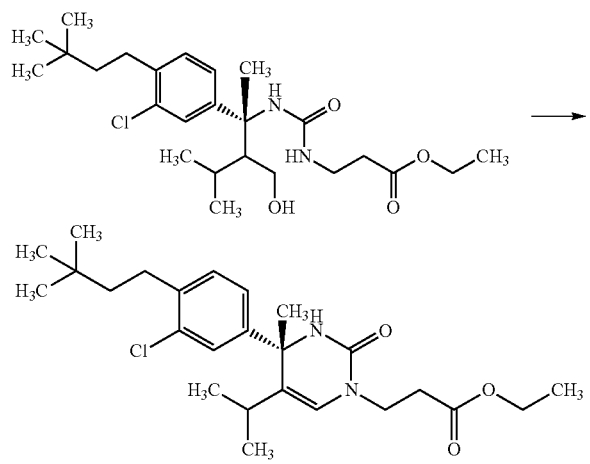

3-(3-{(R)-1-[3-Chloro-4-(3,3-dimethyl-butyl)-phenyl]-2-hydroxymethyl-1,3-dimethyl-butyl}-ureido)-propionic acid ethyl ester (17.1 g) and iodobenzene diacetate (13.3 g) were mixed in dichloromethane (143 mL). To the reaction solution was added a mixed solution of 2,2,6,6-tetramethylpiperidine 1-oxyl free radical (17.5 mg) in dichloromethane (2 ml) under ice cooling, and the reaction solution was stirred at room temperature for 18 hours. To the reaction solution was added trifluoroacetic acid (10.78 mL) under ice cooling, and then the reaction solution was stirred at room temperature for 1 hour. To the reaction solution was added aqueous sodium sulfite solution under ice cooling, and then thereto was added aqueous potassium hydrogen carbonate solution. The resulted mixed solution was extracted with ethyl acetate. The organic layer was washed sequentially with water and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:20→1:9→1:7→1:4→1:3) to give the titled compound (18.3 g).

¹H-NMR (400 MHz, CDCl₃) 0.71 (d, J=6.94 Hz, 3H), 0.98 (s, 9H), 1.04 (d, J=6.94 Hz, 3H), 1.28 (t, J=7.17 Hz, 4H), 1.41-1.48 (m, 2H), 1.68 (s, 3H), 1.83-1.90 (m, 1H), 2.64-2.69 (m, 4H), 3.78 (t, J=6.59 Hz, 2H), 4.16 (q, J=7.17 Hz, 3H), 4.61 (s, 1H), 5.90 (s, 1H), 7.16 (d, J=8.04 Hz, 1H), 7.24 (dd, J=7.94, 2.02 Hz, 1H), 7.38 (d, J=2.02 Hz, 1H)

Step 11

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic Acid

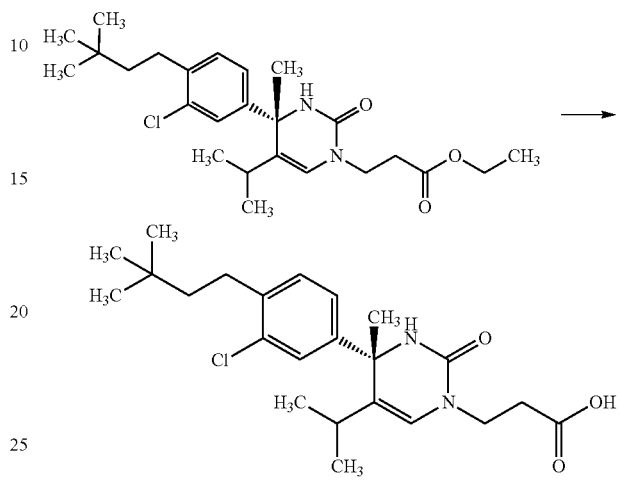

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic acid ethyl ester (34.8 g) obtained by repeating Example 87 (a method for preparation using an optically active sulfinamide) Steps 1 to 10 was mixed in ethanol (350 mL). To the reaction solution was added dropwise 4M aqueous sodium hydroxide solution (38.7 mL) under ice cooling, and the reaction solution was stirred at room temperature for 2 hours. The reaction solution was concentrated under reduced pressure, and then water was added to the residue. To the mixed solution was added 6M hydrochloric acid (25.8 mL) under ice cooling. The precipitated solid was dissolved in ethyl acetate, and then extracted with ethyl acetate. The organic layer was washed with aqueous saturated sodium chloride solution, and then dried over magnesium sulfate. After removing sodium sulfate on a filter, the reaction solution was concentrated under reduced pressure. To the resulted residue was added ethanol (500 mL), which was again concentrated under reduced pressure. The resulted residue was mixed in water (600 mL). To the reaction solution was added 4M aqueous sodium hydroxide solution (26.85 mL) under ice cooling. To the reaction solution was added 6M hydrochloric acid (17.9 mL) under ice cooling, and the reaction solution was stirred under ice cooling for 30 minutes. Then 6M hydrochloric acid was added to the solution so that the reaction solution was adjusted to pH 2, and the reaction solution was stirred under ice cooling for 30 minutes. The precipitated solid was filtered and dried to give the titled compound (28.9 g).

A specific optical rotation of the resulted compound was $[\alpha]_D^{25}$=+112.6° (c=1.00, methanol).

The resulted compound was analyzed with a chiral column, and the retention time of the resulted titled compound (S-enantiomer) was 9.0 minutes, the optical purity of which was >99% ee.

The analytical condition using a chiral column was as follows.

Measuring instrument; HPLC system Shimadzu Corporation high-performance liquid chromatograph prominence Column; DAICEL CHIRALPAK AD-3R 0.46 cmφ×15 cm
Column temperature; 40° C.
Mobile phase; water:acetonitrile:formic acid=30:70:0.1
Flow rate; 0.5 mL/min
Detection; UV (220 nm)

The resulted solid (20 mg) was mixed in a mixed solvent of 2-propanol-water (1:20, 0.21 mL), and the suspension was stirred at 60° C. for 1.5 hours. The suspension was cooled to room temperature over 1 hour, and then the precipitated solid was filtered to give a crystal of the titled compound (18 mg). The melting point of the crystal was 117.5-118.7° C.

Example 87

Preparation of 3-{(S)-4-[3-chloro-4-(3,3-dimethyl-butyl)-phenyl]-5-isopropyl-4-methyl-2-oxo-3,4-dihydro-2H-pyrimidin-1-yl}-propionic Acid A Method for Preparation Using Cleisen Reaction Step 1

2-(4-Hydroxy-phenyl)-propionic Acid methyl Ester

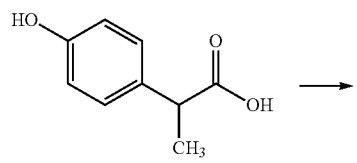

2-(4-Hydroxyphenyl)propionic acid (75 g) was mixed in methanol (750 mL). To the reaction solution was added dropwise thionyl chloride (49 mL), and the reaction solution was stirred at 60° C. for 3 hours. The reaction solution was concentrated under reduced pressure, and water was added to the residue, which was then extracted with ethyl acetate. The organic layer was washed sequentially with water and aqueous saturated sodium chloride solution, and dried over magnesium sulfate. After removing magnesium sulfate on a filter, the filtrate was concentrated under reduced pressure to give the titled compound (97 g) as a crude product.
$^1$H-NMR (400 MHz, CDCl$_3$) 1.45 (d, J=7.40 Hz, 3H), 3.64-3.66 (m, 4H), 5.08 (s, 1H), 6.75-6.78 (m, 2H), 7.14-7.15 (m, 2H)

Step 2

2-(3-Chloro-4-hydroxy-phenyl)-propionic Acid methyl Ester

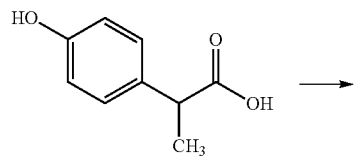

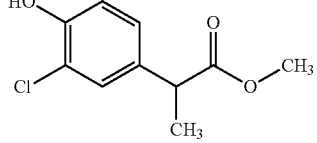

2-(4-Hydroxy-phenyl)-propionic acid methyl ester (97.0 g) was mixed in N,N-dimethylformamide (450 mL). To the reaction solution was added N-chlorosuccinimide (60.1 g), and the reaction solution was stirred at 80° C. for 4 hours. To the reaction solution was added water, which was then extracted with toluene. The organic layer was washed with water and aqueous saturated sodium chloride solution, and dried over magnesium sulfate. After removing magnesium sulfate on a filter, the filtrated was concentrated under reduced pressure to give the titled compound (101.5 g) as a crude product.
$^1$H-NMR (400 MHz, CDCl$_3$) 1.45 (d, J=7.17 Hz, 3H), 3.61-3.66 (m, 4H), 5.58 (s, 1H), 6.95 (d, J=8.55 Hz, 1H), 7.09 (dd, J=8.44, 1.97 Hz, 1H), 7.25 (d, J=8.55 Hz, 1H)

Step 3

2-(3-Chloro-4-trifluoromethanesulfonyloxyphenyl) propionic Acid methyl Ester

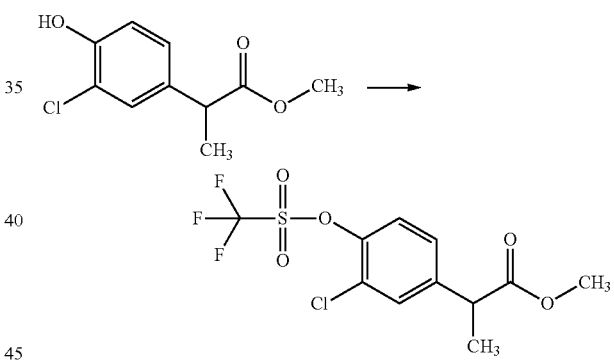

2-(3-Chloro-4-hydroxy-phenyl)-propionic acid methyl ester (101.5 g) was mixed in methylene chloride (600 mL) and pyridine (73 mL) under argon gas. To the reaction solution was added dropwise trifluoromethanesulfonic anhydride (91 mL) under ice cooling, and the reaction solution was stirred at room temperature for 6.5 hours. Then to the reaction solution was added trifluoromethanesulfonic anhydride (11.4 mL), and the reaction solution was stirred at room temperature overnight. To the reaction solution was added water, which was then extracted with chloroform. The organic layer was washed sequentially with 1M hydrochloric acid, saturated aqueous sodium hydrogen carbonate solution, and aqueous saturated sodium chloride solution, and dried over magnesium sulfate. After removing magnesium sulfate on a filter, the filtrate was concentrated under reduced pressure to give the titled compound (156.69 g) as a crude product.
$^1$H-NMR (400 MHz, CDCl$_3$) 1.50 (d, J=7.17 Hz, 3H), 3.67-3.71 (m, 4H), 7.27-7.28 (m, 1H), 7.46 (d, J=1.85 Hz, 1H)

Step 4

2-[3-Chloro-4-(3,3-dimethyl-but-1-ynyl)-phenyl]-propionic Acid methyl Ester

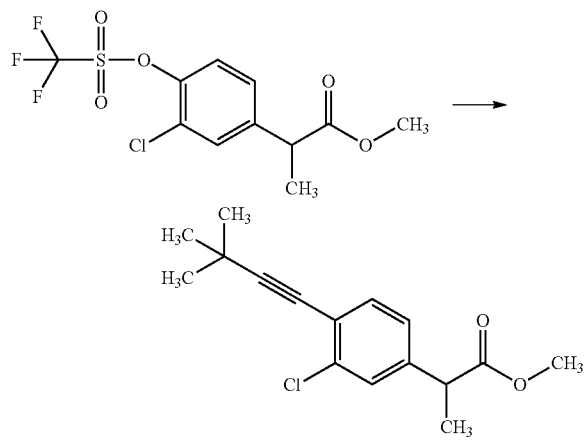

2-(3-Chloro-4-trifluoromethanesulfonyloxyphenyl)propionic acid methyl ester (60 g), tetrabutylammonium iodide (128 g), 3,3-dimethyl-but-1-yne (42.4 mL), triethylamine (60 mL), bis(triphenylphosphine)palladium (II) dichloride (12.2 g), and copper iodide (9.88 g) were mixed in N,N-dimethylformamide (300 mL) under argon gas. The reaction solution was stirred at 70° C. for 1 hour. To the reaction solution was added water, which was then extracted with toluene. The organic layer was washed sequentially with 1M hydrochloric acid, water, saturated aqueous sodium hydrogen carbonate solution, and saturated sodium chloride water, and dried over magnesium sulfate. After removing magnesium sulfate on a filter, the filtrate was concentrated under reduced pressure. The resulted residue was purified through silica gel column chromatography (ethyl acetate:hexane=1:30→1:20) to give the titled compound (37.15 g).

$^1$H-NMR (400 MHz, CDCl$_3$) 1.31 (s, 9H), 1.45 (d, J=7.17 Hz, 3H), 3.62-3.67 (m, 4H), 7.08 (dd. J=7.86, 1.85 Hz, 1H), 7.29 (d, J=1.62 Hz, 1H), 7.34 (d, J=8.09 Hz, 1H)

Step 5

2-[3-Chloro-4-(3,3-dimethyl-butyl)-phenyl]-propionic Acid methyl Ester

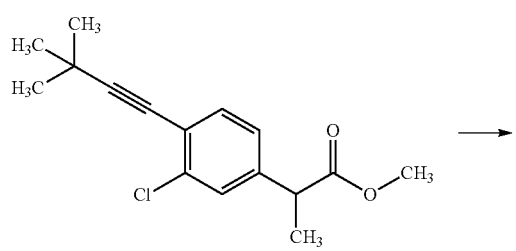

-continued

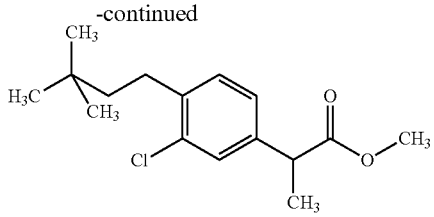

2-[3-Chloro-4-(3,3-dimethyl-but-1-ynyl)-phenyl]-propionic acid methyl ester (18.5 g) was mixed in methanol (185 mL). To the mixed solution was added 5 w/w % platinum/activated carbon (1.85 g), and the reaction solution was stirred for 9 hours under hydrogen gas at 4 atm. Removal from the reaction solution platinum/activated carbon on a filter gave a filtrate (referred to as Filtrate A hereinafter).

According to the reduction procedure, 2-[3-chloro-4-(3,3-dimethyl-but-1-ynyl)-phenyl]-propionic acid methyl ester (18.5 g) was treated to give a filtrate (referred to as Filtrate B hereinafter).

Filtrate A and Filtrate B were combined and concentrated under reduced pressure to give a residue (34.08 g/referred to as Residue C hereinafter).

Residue C was analyzed ($^1$H-NMR measurement), which showed that the reduction reaction was not completed (i.e. a starting material was existed), and the reduction reaction was repeated.

Residue C (34 g) was divided into two halves of Residue D (17 g) and Residue E (17 g). Residue D (17 g) was mixed in methanol (185 mL). To the mixed solution was added 5 w/w % platinum/activated carbon (1.85 g), and the reaction solution was stirred for 5 hours under hydrogen gas at 4 atm. Then platinum/activated carbon was removed from the reaction solution on a filter to give a filtrate (referred to as Filtrate F hereinafter).

Residue E (17 g) was treated according to the reduction procedure to give a filtrate (referred to as Filtrate G hereinafter).

The resulted Filtrate F and Filtrate G were combined and concentrated under reduced pressure to give the titled compound (35.06 g) as a crude product.

$^1$H-NMR (400 MHz, CDCl$_3$) 0.97 (s, 9H), 1.42-1.48 (m, 5H), 2.63-2.68 (m, 2H), 3.65-3.66 (m, 4H), 7.10 (dd, J=7.85, 1.81 Hz, 1H), 7.16 (d, J=7.97 Hz, 1H), 7.26-7.27 (m, 1H)

Step 6

2-[3-Chloro-4-(3,3-dimethyl-butyl)-phenyl]-propionic Acid

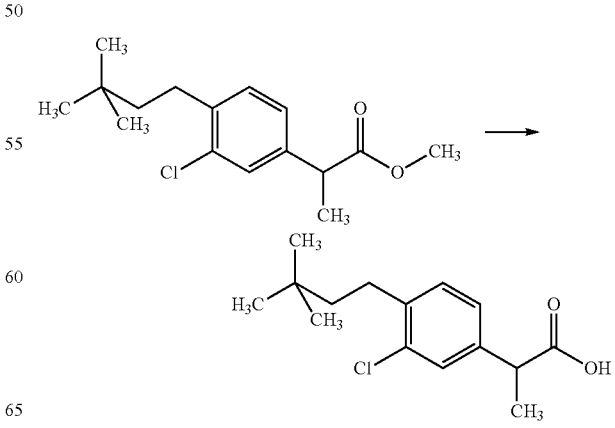

2-[3-Chloro-4-(3,3-dimethyl-butyl)-phenyl]-propionic acid methyl ester (35.0 g) was mixed in tetrahydrofuran (110 mL) and methanol (110 ml). To the reaction solution was added dropwise 4M aqueous sodium hydroxide solution (93 mL) under ice cooling, and the reaction solution was stirred at room temperature for 2 hours. Then to the reaction solution was added dropwise 2M hydrochloric acid (186 mL) under ice cooling, and the resulted mixed solution was extracted with ethyl acetate. The organic layer was washed sequentially with water and saturated sodium chloride water, and then dried over sodium sulfate. After removing sodium sulfate on a filter, the filtrate was concentrated under reduced pressure. To the resulted residue was added a mixed solution of hexane-diisopropylether (10:1), and then the precipitated solid was filtered. The resulted filtrate was concentrated under reduced pressure, and to the residue was added again a mixed solution of hexane-diisopropylether (10:1), and the precipitated solid was filtered. The resulted solid was collected to give the titled compound (30.4 g).

$^1$H-NMR (400 MHz, CDCl$_3$) 0.96 (s, 9H), 1.42-1.44 (m, 2H), 1.48 (d, J=7.17 Hz, 3H), 2.63-2.65 (m, 2H), 3.67 (q, J=7.17 Hz, 1H), 7.11 (dd, J=7.98, 1.73 Hz, 1H), 7.15 (d, J=8.09 Hz, 1H), 7.28 (d, J=1.85 Hz, 1H)

Step 7

(E)-4-Methyl-pent-2-en-1-ol

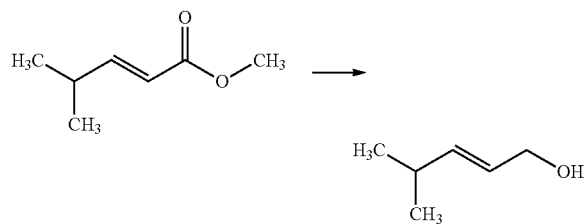

(E)-4-Methyl-pent-2-enoic acid methyl ester (16.72 g) was mixed in dichloromethane (50 mL). To the reaction solution was added dropwise 1M diisobutylaluminum hydride/dichloromethane solution (300 mL) at −78° C., and the reaction solution was stirred at −78° C. for 1 hour. The reaction solution was added dropwise to 1.5M aqueous sulfuric acid solution (350 mL) under ice cooling, and then the mixed solution was stirred under ice cooling for 1.5 hours. The reaction solution was extracted with dichloromethane, and the organic layer was washed sequentially with 1M aqueous sulfuric acid solution, water, and aqueous saturated sodium chloride solution, and dried over magnesium sulfate. After removing magnesium sulfate on a filter, the filtrate was concentrated under reduced pressure to give the titled compound in dichloromethane solution (73.3 w/w %, 18.81 g).

$^1$H-NMR (400 MHz, CDCl$_3$) 1.00 (d, J=6.94 Hz, 6H), 1.25 (s, 1H), 2.31 (td, J=13.58, 6.78 Hz, 1H), 4.09 (d, J=5.78 Hz, 2H), 5.59 (tdd, J=10.63, 5.20, 0.89 Hz, 1H), 5.67 (ddt, J=15.26, 6.17, 0.90 Hz, 1H)

Step 8

2-[3-Chloro-4-(3,3-dimethyl-butyl)-phenyl]-propionic acid (E)-4-methyl-pent-2-enyl Ester

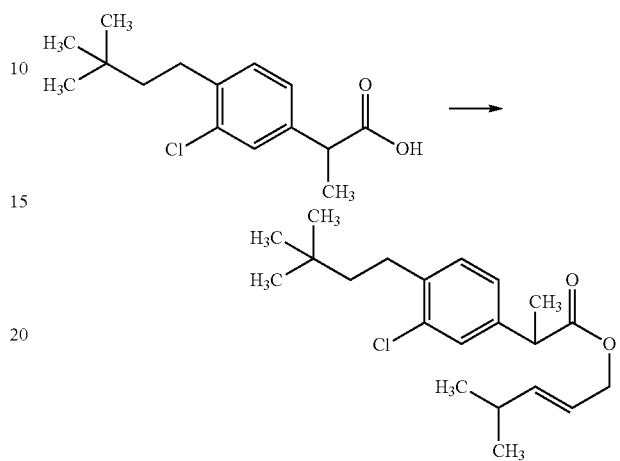

73.3 w/w % of (E)-4-methyl-pent-2-en-1-ol/dichloromethane solution (5.33 g), 2-[3-chloro-4-(3,3-dimethyl-butyl)-phenyl]-propionic acid (10.0 g), and 4-dimethylaminopyridine (1.36 g) were mixed in chloroform (150 mL). To the reaction solution was added 1-ethyl-3-(3-dimethylaminopropyl)carbodiimide hydrochloride (4.7 g) under ice cooling, and the reaction solution was stirred at room temperature overnight. To the reaction solution were added ethyl acetate and 1M hydrochloric acid, which was then extracted with ethyl acetate. The organic layer was washed sequentially with water, aqueous sodium hydrogen carbonate solution, and aqueous saturated sodium chloride solution, and dried over magnesium sulfate. After removing magnesium sulfate on a filter, the filtrate was concentrated under reduced pressure to give the titled compound (13.0 g) as a crude product.

$^1$H-NMR (400 MHz, CDCl$_3$) 0.92-1.04 (m, 10H), 1.37-1.51 (m, 5H), 1.56 (s, 3H), 2.22-2.33 (m, 1H), 2.59-2.72 (m, 2H), 3.61-3.70 (m, 1H), 4.42-4.60 (m, 2H), 5.45 (tt, J=10.87, 3.38 Hz, 1H), 5.65 (dd, J=15.45, 6.52 Hz, 1H), 7.08-7.17 (m, 2H), 7.27-7.30 (m, 1H)

Step 9

2-[3-Chloro-4-(3,3-dimethyl-butyl)-phenyl]-3-isopropyl-2-methyl-pent-4-enoic Acid

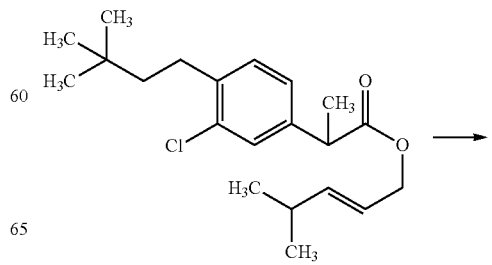

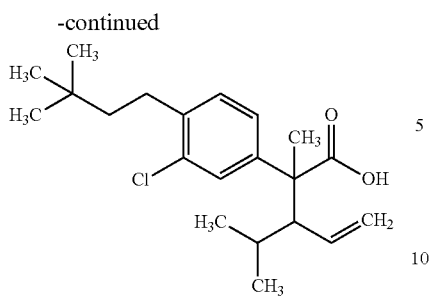

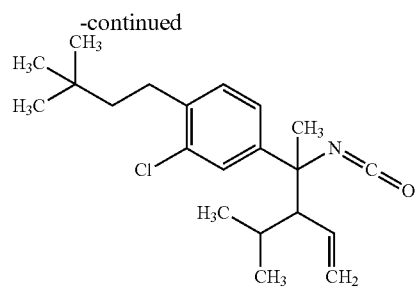

Diisopropylamine (10.9 mL) was mixed in tetrahydrofuran (130 mL). To the reaction solution was added dropwise 1.64M n-butyllithium/hexane solution (45.2 mL) at −78° C., and the reaction solution was stirred at −78° C. for 20 minutes. To the reaction solution was added dropwise a mixed solution of 2-[3-chloro-4-(3,3-dimethyl-butyl)-phenyl]-propionic acid (E)-4-methyl-pent-2-enyl ester (13.0 g) in tetrahydrofuran (130 mL) over 30 minutes at −78° C., and the reaction solution was stirred under ice cooling for 60 minutes. Then thereto was added dropwise chlorotrimethylsilane (9.87 mL) at −78° C., and the reaction solution was stirred at −78° C. for 30 minutes, which was then stirred under ice cooling for 130 minutes, then at room temperature for 150 minutes. To the reaction solution was added 1 M hydrochloric acid under ice cooling, which was then extracted with ethyl acetate. The organic layer was washed sequentially with water and aqueous saturated sodium chloride solution, and dried over magnesium sulfate. After removing magnesium sulfate on a filter, the filtrate was concentrated under reduced pressure. The resulted residue was purified through silica gel chromatography (ethyl acetate:hexane=1:30→1:15→1:7) to give the titled compound (14.49 g).

$^1$H-NMR (400 MHz, CDCl$_3$) 0.67 (d, J=6.94 Hz, 2H), 0.74 (d, J=6.70 Hz, 2H), 0.83 (d, J=6.70 Hz, 1H), 0.95 (t, J=4.05 Hz, 10H), 1.39-1.47 (m, 3H), 1.58 (s, 3H), 2.60-2.65 (m, 2H), 2.79-2.83 (m, 1H), 4.69 (dd, J=16.88, 2.08 Hz, 0.3H), 4.83 (dd, J=10.17, 2.08 Hz, 0.3H), 5.12 (dd, J=7.86, 2.31 Hz, 0.7H), 5.16 (s, 0.7H), 5.31 (dt, J=19.34, 8.44 Hz, 0.3H), 5.65-5.74 (m, 0.7H), 7.09 (d, J=8.09 Hz, 0.3H), 7.15 (d, J=8.32 Hz, 0.3H), 7.19 (dd, J=8.21, 1.97 Hz, 0.3H), 7.31 (dt, J=12.10, 4.28 Hz, 0.3H), 7.43 (d, J=2.08 Hz, 0.3H)

Step 10

2-Chloro-1-(3,3-dimethyl-butyl)-4-(1-isocyanato-2-isopropyl-1-methyl-but-3-enyl)-benzene

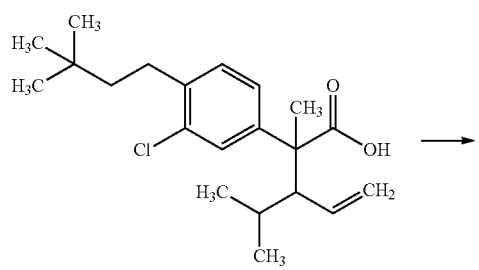

2-[3-Chloro-4-(3,3-dimethyl-butyl)-phenyl]-3-isopropyl-2-methyl-pent-4-enoic acid (12.0 g) and triethylamine (7.2 mL) were mixed in toluene (120 mL). To the reaction solution was added diphenyl phosphoryl azide (11.1 mL), and the reaction solution was stirred at 120° C. for 7.5 hours. The reaction solution was concentrated under reduced pressure, and the resulted residue was purified through silica gel chromatography (ethyl acetate:hexane=1:30) to give the titled compound (9.6 g).

$^1$H-NMR (400 MHz, CDCl$_3$) 0.64 (d, J=6.70 Hz, 2H), 0.67 (d, J=6.94 Hz, 1H), 0.82 (d, J=6.94 Hz, 1H), 0.84 (d, J=6.70 Hz, 2H), 0.98 (s, 6H), 0.98 (s, 3H), 1.46 (m, 2H), 1.62 (s, 1H), 1.74 (s, 2H), 1.99-2.01 (m, 0.65H), 2.17-2.20 (m, 1H), 2.35 (brs, 0.35H), 2.64-2.70 (m, 2H), 4.88-4.93 (m, 0.65H), 5.12-5.17 (m, 1H), 5.34-5.36 (m, 0.35H), 5.60-5.64 (m, 0.65H), 5.81-5.88 (m, 0.35H), 7.15-7.15 (m, 1H), 7.17-7.18 (m, 1H), 7.31-7.32 (m, 0.65H), 7.35-7.36 (m, 0.35H)

Step 11

3-{3-[1-(3-Chloro-4-(3,3-dimethyl-butyl)-phenyl)-2-isopropyl-1-methyl-but-3-enyl]-ureido}-propionic Acid ethyl Ester

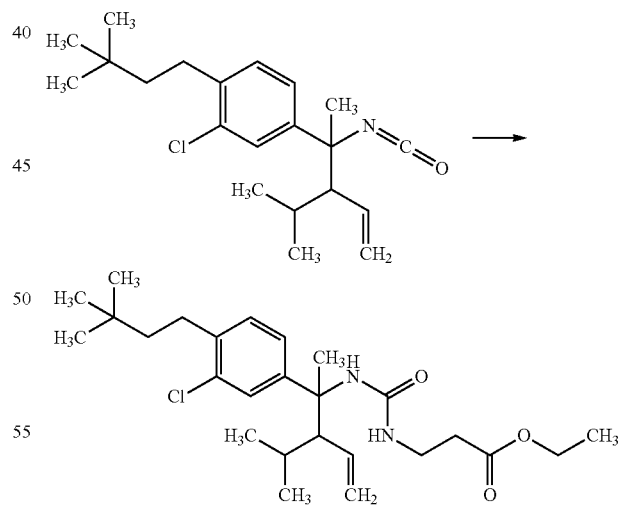

2-Chloro-1-(3,3-dimethyl-butyl)-4-(1-isocyanato-2-isopropyl-1-methyl-but-3-enyl)-benzene (400 mg) and 3-amino-propionic acid ethyl ester hydrochloride (194 mg) were mixed in 1,4-dioxane (4 mL). To the reaction solution was added triethylamine (0.18 mL), and the reaction solution was stirred at 60° C. for about 40 minutes. The reaction solution was concentrated under reduced pressure, and the resulted residue was purified through silica gel column chromatography (methanol:chloroform=1:99→2:98→4:96) to give the titled compound (478 mg).

¹H-NMR (400 MHz, CDCl₃) 0.21-0.26 (m, 0.33H), 0.54-0.60 (m, 0.67H), 0.70-0.75 (m, 0.67H), 0.80-0.84 (m, 0.33H), 0.97-0.99 (m, 9H), 1.40-1.53 (m, 2H), 1.66-1.69 (m, 2H), 1.79-1.82 (m, 1H), 1.64-1.83 (m, 3H), 1.84-2.04 (m, 1H), 2.25-2.45 (m, 2H), 2.61-2.72 (m, 2H), 3.22-3.38 (m, 2H), 4.01-4.14 (m, 2H), 4.35-4.59 (m, 1H), 4.87-5.41 (m, 1H), 5.53-5.88 (m, 1H), 7.10-7.43 (m, 2H)

Step 12

3-{4-[3-Chloro-4-(3,3-dimethyl-butyl)-phenyl]-5-isopropyl-4-methyl-2-oxo-3,4-dihydro-2H-pyrimidin-1-yl}-propionic Acid ethyl Ester

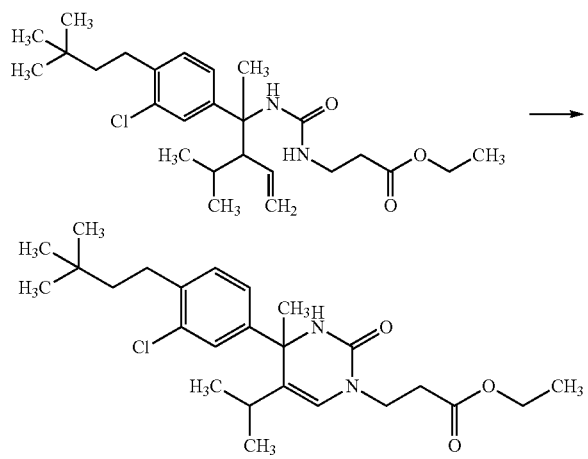

3-{3-[1-(3-Chloro-4-(3,3-dimethyl-butyl)-phenyl)-2-isopropyl-1-methyl-but-3-enyl]-ureido}-propionic acid ethyl ester (478 mg) was mixed in methanol (8 mL). The reaction solution was stirred at −78° C. for 30 minutes under ozone flow. Then the reaction solution was stirred at −78° C. for 3 minutes under nitrogen flow. Then to the reaction solution were added methylsulfide (0.76 mL) at −78° C. and methanol (4 mL) at room temperature. The reaction solution was concentrated under reduced pressure, and to the residue was added 2M hydrogen chloride/methanol solution (1 mL), and the reaction solution was stirred at room temperature for 2 hours. The reaction solution was concentrated under reduced pressure, and the resulted residue was purified through silica gel chromatography (methanol:chloroform=4:96) twice to give the titled compound (191 mg).

¹H-NMR (400 MHz, CDCl₃) 0.67-0.72 (m, 3H), 0.96 (s, 9H), 1.00-1.05 (m, 3H), 1.22-1.29 (m, 3H), 1.40-1.46 (m, 2H), 1.67 (s, 3H), 1.80-1.89 (m, 1H), 2.62-2.69 (m, 4H), 3.74-3.79 (m, 2H), 4.11-4.18 (m, 2H), 4.61 (brs, 1H), 5.88 (s, 1H), 7.13-7.17 (m, 1H), 7.20-7.24 (m, 1H), 7.35-7.37 (m, 1H)

Step 13

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic Acid ethyl Ester

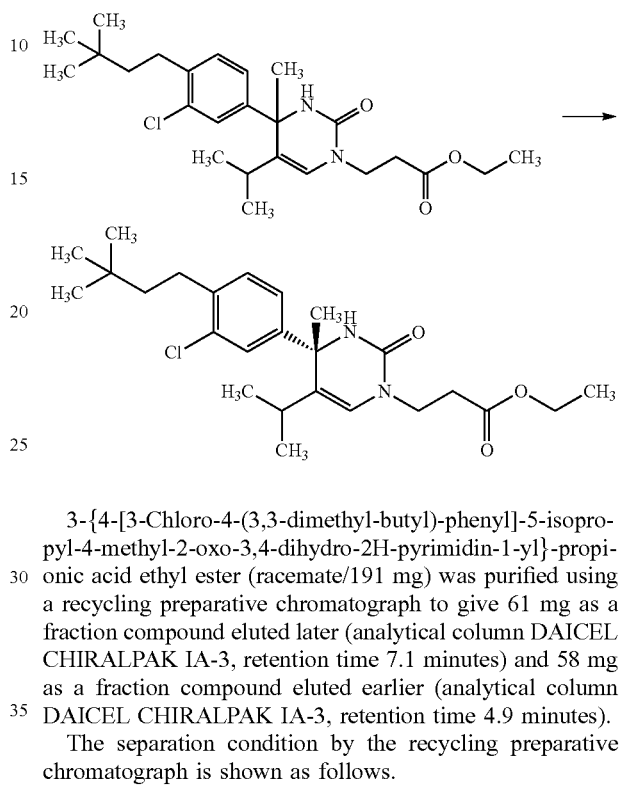

3-{4-[3-Chloro-4-(3,3-dimethyl-butyl)-phenyl]-5-isopropyl-4-methyl-2-oxo-3,4-dihydro-2H-pyrimidin-1-yl}-propionic acid ethyl ester (racemate/191 mg) was purified using a recycling preparative chromatograph to give 61 mg as a fraction compound eluted later (analytical column DAICEL CHIRALPAK IA-3, retention time 7.1 minutes) and 58 mg as a fraction compound eluted earlier (analytical column DAICEL CHIRALPAK IA-3, retention time 4.9 minutes).

The separation condition by the recycling preparative chromatograph is shown as follows.
Separation instrument; Recycling preparative chromatograph LC-9225 NEXT SERIES Japan Analytical Industry Co., Ltd.
Column; DAICEL CHIRALPAK IA 2.0 cmφ×25 cm
Mobile phase; hexane:2-propanol=90:10
Flow rate; 10.0 mL/min
Detection; UV (254 nm)
The analytical condition using a chiral column is as follows.
Measuring instrument; HPLC system Shimadzu Corporation high-performance liquid chromatograph prominence
Column; DAICEL CHIRALPAK IA-3 0.46 cmφ×15 cm
Column temperature; 40° C.
Mobile phase; hexane:2-propanol=90:10
Flow rate; 1.0 mL/min
Detection; UV (254 nm)
The ethyl ester compound obtained as a fraction eluted later was converted into a carboxylic acid compound in the next step (Step 14, hydrolysis reaction). The retention time and NMR spectrum of the carboxylic acid compound in a chiral column coincided with those in a chiral column of the carboxylic acid compound (S-enantiomer) obtained in the method using the optically active sulfinamide.

The ester compound obtained as a fraction eluted later was thus estimated as an S-enantiomer.
(S-Enantiomer)

¹H-NMR (400 MHz, CDCl₃) 0.67-0.72 (m, 3H), 0.96 (s, 9H), 1.00-1.05 (m, 3H), 1.22-1.29 (m, 3H), 1.40-1.46 (m, 2H), 1.67 (s, 3H), 1.80-1.89 (m, 1H), 2.62-2.69 (m, 4H), 3.74-3.79 (m, 2H), 4.11-4.18 (m, 2H), 4.61 (brs, 1H), 5.88 (s, 1H), 7.13-7.17 (m, 1H), 7.20-7.24 (m, 1H), 7.35-7.37 (m, 1H)

(R-Enantiomer)

$^1$H-NMR (400 MHz, CDCl$_3$) 0.67-0.72 (m, 3H), 0.96 (s, 9H), 1.00-1.05 (m, 3H), 1.22-1.29 (m, 3H), 1.40-1.46 (m, 2H), 1.67 (s, 3H), 1.80-1.89 (m, 1H), 2.62-2.69 (m, 4H), 3.74-3.79 (m, 2H), 4.11-4.18 (m, 2H), 4.61 (brs, 1H), 5.88 (s, 1H), 7.13-7.17 (m, 1H), 7.20-7.24 (m, 1H), 7.35-7.37 (m, 1H)

Step 14

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic Acid

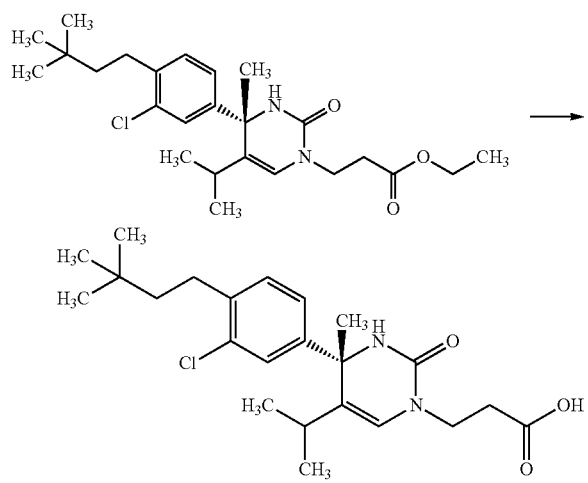

3-{(S)-4-[3-Chloro-4-(3,3-dimethyl-butyl)-phenyl]-5-isopropyl-4-methyl-2-oxo-3,4-dihydro-2H-pyrimidin-1-yl}-propionic acid ethyl ester (57 mg) was mixed in methanol (2 mL). To the reaction solution was added 2M aqueous sodium hydroxide solution (0.25 mL), and the reaction solution was stirred at 60° C. The reaction solution was concentrated under reduced pressure, and then water was added thereto. To the resulted mixed solution was added 2M hydrochloric acid (0.25 mL), which was then stirred at room temperature. The precipitated solid was filtered to give the titled compound (49 mg).

The resulted compound was analyzed by a chiral column, and the retention time of the resulted titled compound (S-enantiomer) was 9.0 minutes, the optical purity of which was >99% ee. The analytical condition in the chiral column was as follows.

Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 0.5 mL/min
Detection; UV (220 nm)

Example 86

The Enantiomer of Example 87

3-{(R)-4-[3-Chloro-4-(3,3-dimethyl-butyl)-phenyl]-5-isopropyl-4-methyl-2-oxo-3,4-dihydro-2H-pyrimidin-1-yl}-propionic Acid

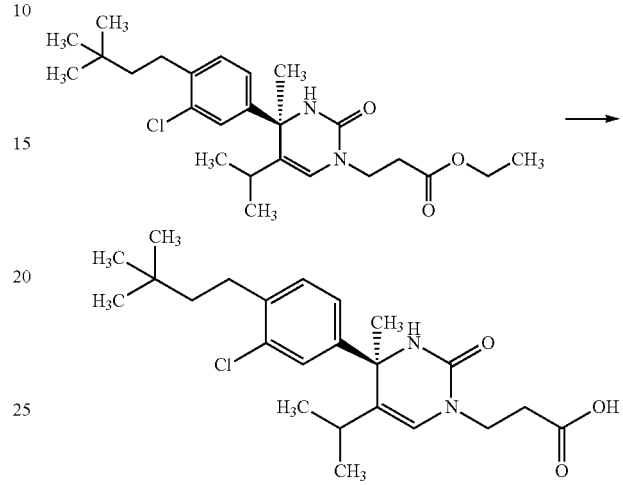

3-{(R)-4-[3-Chloro-4-(3,3-dimethyl-butyl)-phenyl]-5-isopropyl-4-methyl-2-oxo-3,4-dihydro-2H-pyrimidin-1-yl}-propionic acid ethyl ester obtained in Example 87 Step 13 was treated according to the reaction in Example 87 Step 14 to give the titled compound (36 mg). The retention time of the resulted enantiomer (R-enantiomer) was 6.0 minutes.

The analytical condition in a chiral column was as follows.
Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 1.0 mL/min
Detection; UV (220 nm)

Example 116

Preparation of 3-{(S)-4-[3-chloro-4-(4,4-dimethyl-cyclohex-1-enyl)-phenyl]-5-isopropyl-4-methyl-2-oxo-3,4-dihydro-2H-pyrimidin-1-yl}-propionic Acid A Method for Preparation Using an Optically Active Sulfinamide Step 1

(S)-2-Methyl-propane-2-sulfinic acid [1-(4-bromo-3-chloro-phenyl)-eth-(E)-ylidene]-amide

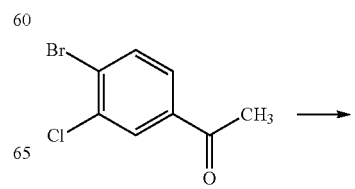

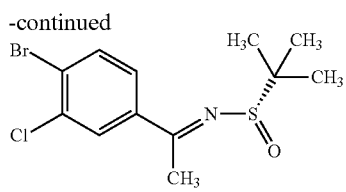

1-(4-Bromo-3-chloro-phenyl)-ethanone (20 g) prepared according to Example 87 (a method for preparation using an optically active sulfinamide) Steps 1 to 2 and (S)-(-)-2-methyl-propane-2-sulfinic acid amide (11.4 g) were mixed in cyclopentylmethyl ether (100 mL). To the reaction solution was added tetraethyl orthotitanate (23.3 mL), and the reaction solution was stirred at 100° C. for 5 hours. To the reaction solution was added 25 w/w % aqueous citric acid solution under ice cooling, and the mixed solution was stirred at room temperature. After removing an insoluble on a filter, the filtrate was extracted with toluene. The organic layer was washed sequentially with water and aqueous saturated sodium chloride solution, and then concentrated under reduced pressure. The resulted residue was purified through silica gel column chromatography (ethyl acetate:hexane=1:20→1:10→1:5) to give the titled compound (23 g).

$^1$H-NMR (400 MHz, CDCl$_3$) 1.30 (s, 9H), 2.72 (s, 3H), 7.56-7.61 (m, 1H), 7.66 (d, J=8.55 Hz, 1H), 7.91 (d, J=2.08 Hz, 1H)

Step 2

(R)-3-(4-Bromo-3-chloro-phenyl)-2-isopropyl-3-((S)-2-methyl-propane-2-sulfinylamino)-butanoic Acid methyl Ester

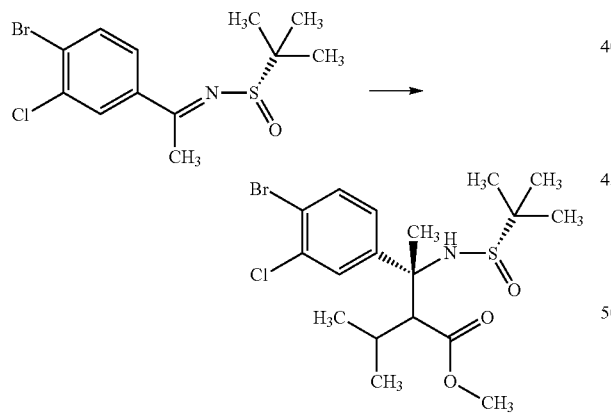

Diisopropylamine (21.1 mL) was mixed in THF (138 mL) under argon gas. To the reaction solution was added dropwise 1.63M n-butyllithium/hexane solution (88 mL) at -78° C., and the reaction solution was stirred at -78° C. for 20 minutes. To the reaction solution was added dropwise 3-methyl-butanoic acid methyl ester (18 mL), and the reaction solution was stirred at -78° C. for 30 minutes. To the reaction solution were added dropwise 1M chloro titanium (IV) triisopropoxide/hexane solution (100 mL) and then a mixed solution of chloro titanium (IV) triisopropoxide (48.7 g) in tetrahydrofuran (80 mL), and the reaction solution was stirred at -78° C. for 30 minutes. To the reaction solution was added dropwise a mixed solution of (S)-2-methyl-propane-2-sulfinic acid [1-(4-bromo-3-chloro-phenyl)-eth-(E)-ylidene]-amide (23 g) in THF (138 mL), and the reaction solution was stirred at -78° C. for 75 minutes and then at -45° C. for 2 hours. The reaction solution was added dropwise saturated aqueous Rochelle salt solution. The mixed solution was extracted with ethyl acetate. The organic layer was washed sequentially with water and aqueous saturated sodium chloride solution, and then dried over sodium sulfate. After removing sodium sulfate on a filter, the filtrate was concentrated under reduced pressure. The resulted residue was purified through silica gel column chromatography (ethyl acetate:hexane=1:10) to give the titled compound (16 g) as a mixture of diastereomers generated by the isopropyl group at α-position of ester (d.r.=72:28).

$^1$H-NMR (400 MHz, CDCl$_3$) 0.75-1.01 (m, 6H), 1.25 (s, 6H), 1.33 (s, 3H), 1.87-1.88 (m, 3H), 2.04-2.12 (m, 1H), 2.46 (d, J=4.11 Hz, 0.3H), 2.80 (d, J=3.86 Hz, 0.7H), 3.60 (t, J=6.64 Hz, 2H), 3.71 (s, 1H), 5.13 (s, 0.7H), 5.42 (s, 0.3H), 7.14-7.22 (m, 1H), 7.52-7.56 (m, 1H), 7.57-7.59 (m, 1H)

Step 3

(S)-2-Methyl-propane-2-sulfinic acid [(R)-1-(4-bromo-3-chloro-phenyl)-2-hydroxymethyl-1,3-dimethyl-butyl]amide

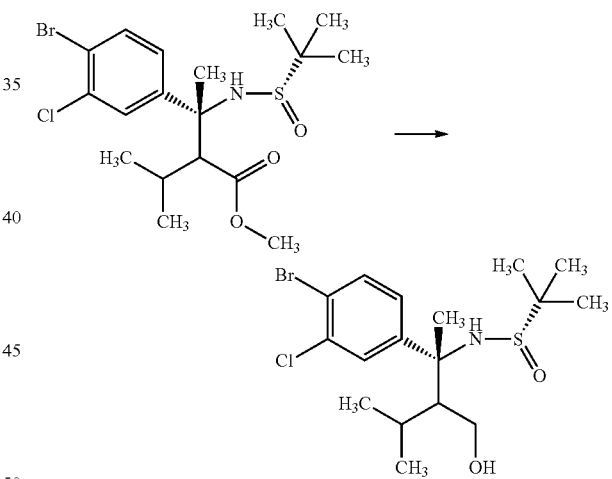

(R)-3-(4-Bromo-3-chloro-phenyl)-2-isopropyl-3-((S)-2-methyl-propane-2-sulfinylamino)-butanoic acid methyl ester (16 g) was mixed in toluene (160 mL) under argon gas. To the reaction solution was added dropwise 1.01M diisobutylaluminum hydride/toluene solution (140 mL) at -78° C., and the reaction solution was stirred at -78° C. for 30 minutes, and then gradually warmed to 0° C., and then stirred for 1 hour. To the reaction solution were added dropwise methanol and then aqueous Rochelle salt solution under ice cooling, and then the mixed solution was extracted with ethyl acetate. The organic layer was washed sequentially with water and aqueous saturated sodium chloride solution, and then dried over sodium sulfate. After removing sodium sulfate on a filter, the filtrate was concentrated under reduced pressure. The resulted residue was purified through silica gel column chromatography (ethyl acetate:hexane=1:

5→1:3→1:1, then ethyl acetate only, then methanol:chloroform=1:20) to give the titled compound (11.5 g).
¹H-NMR (400 MHz, CDCl₃) 0.66-0.85 (m, 6H), 1.13 (s, 7H), 1.29 (s, 2H), 1.69-1.81 (m, 2H), 1.89-2.00 (m, 3H), 2.01-2.12 (m, 1H), 3.83-4.12 (m, 2H), 5.06-5.28 (m, 1H), 6.81-6.93 (m, 1H), 7.12-7.23 (m, 1H), 7.50-7.62 (m, 2H)

Step 4

(R)-3-Amino-3-(4-bromo-3-chloro-phenyl)-2-isopropyl-butan-1-ol

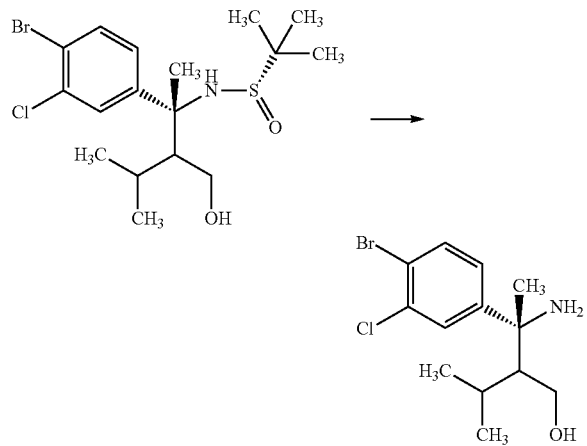

(S)-2-Methyl-propane-2-sulfinic acid [(R)-1-(4-bromo-3-chloro-phenyl)-2-hydroxymethyl-1,3-dimethyl-butyl]amide (11.5 g) was mixed in methanol (66 mL). To the reaction solution was added dropwise 2M hydrogen chloride/methanol solution (54 mL) under ice cooling, and the reaction solution was left to stand at room temperature overnight. The reaction solution was concentrated under reduced pressure, and aqueous sodium carbonate solution was added to the residue so that the aqueous layer was adjusted to pH 10, and then the reaction solution was extracted with chloroform. The organic layer was washed sequentially with water and aqueous saturated sodium chloride solution, and then dried over sodium sulfate. After removing sodium sulfate on a filter, the filtrate was concentrated under reduced pressure to give the titled compound (14 g) as a crude product.
¹H-NMR (400 MHz, CDCl₃) 0.66-0.89 (m, 6H), 1.34-1.49 (m, 1H), 1.58-1.61 (m, 3H), 1.62-1.76 (m, 1H), 1.83-1.88 (m, 1H), 3.65-3.72 (m, 1H), 3.87-4.00 (m, 1H), 7.12-7.25 (m, 3H), 7.48-7.55 (m, 1H), 7.55-7.63 (m, 1H)

Step 5

3-{3-[(R)-1-(4-Bromo-3-chloro-phenyl)-2-hydroxymethyl-1,3-dimethyl-butyl]-ureido}-propionic Acid ethyl Ester

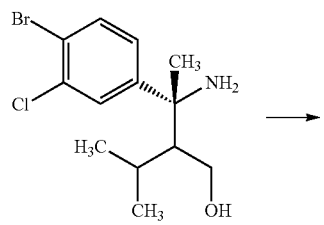

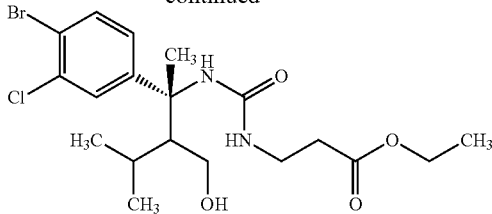

(R)-3-Amino-3-(4-bromo-3-chloro-phenyl)-2-isopropyl-butan-1-ol (14 g) was mixed in tetrahydrofuran (50 mL). To the reaction solution was added a mixed solution of 3-isocyanate-propionic acid ethyl ester (3.56 mL) in tetrahydrofuran (50 mL) under ice cooling, and the reaction solution was stirred under ice cooling for 1.5 hours. To the reaction solution was added water, which was then extracted with ethyl acetate. The organic layer was washed sequentially with 0.1M hydrochloric acid, water, and aqueous saturated sodium chloride solution, and then dried over sodium sulfate. After removing sodium sulfate on a filter, the filtrate was concentrated under reduced pressure. The resulted residue was purified through silica gel column chromatography (ethyl acetate:hexane=1:10→1:5→1:3→1:1, then methanol:chloroform=1:20) to give the titled compound (13.7 g).
¹H-NMR (400 MHz, CDCl₃) 0.26-0.80 (m, 3H), 0.80-0.97 (m, 3H), 1.23-1.31 (m, 3H), 1.46-1.55 (m, 1H), 1.64-1.71 (m, 1H), 1.79-1.90 (m, 3H), 2.38-2.48 (m, 2H), 3.28-3.39 (m, 2H), 3.76-3.85 (m, 1H), 3.88-3.99 (m, 1H), 4.08-4.18 (m, 2H), 4.55-4.71 (m, 1H), 7.06-7.13 (m, 1H), 7.14-7.22 (m, 1H), 7.43-7.58 (m, 2H)

Step 6

3-[(S)-4-(4-Bromo-3-chloro-phenyl)-5-isopropyl-4-methyl-2-oxo-3,4-dihydro-2H-pyrimidin-1-yl]-propionic Acid ethyl Ester

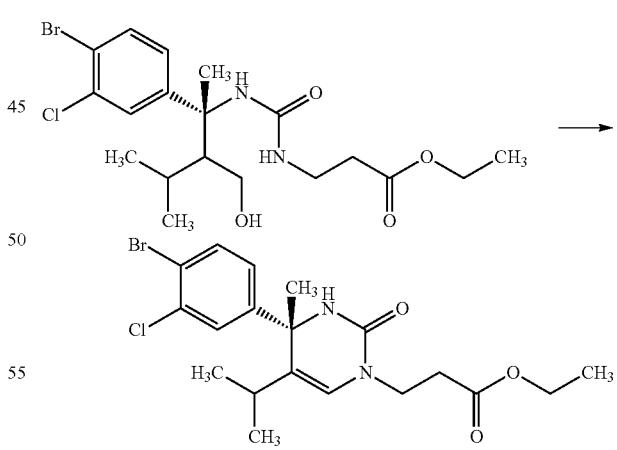

3-{3-[(R)-1-(4-Bromo-3-chloro-phenyl)-2-hydroxymethyl-1,3-dimethyl-butyl]-ureido}-propionic acid ethyl ester (9.49 g) and iodobenzene diacetate (7.26 g) were mixed in dichloromethane (95 mL). To the reaction solution was added 2,2,6,6-tetramethylpiperidine 1-oxyl free radical (319 mg) under ice cooling, and the reaction solution was stirred at room temperature for 3.5 hours. To the reaction solution was added TFA (6.1 mL) under ice cooling, and the reaction solution was stirred at room temperature for 3.5 hours. To the reaction solution were added 20 w/w % aqueous sodium sulfite solution and 25 w/w % aqueous potassium hydrogen carbonate solution, and then the mixed solution was extracted with chloroform. The organic layer was washed sequentially with 25 w/w % aqueous potassium hydrogen carbonate solution and aqueous saturated sodium chloride solution, and then dried over magnesium sulfate. After removing magnesium sulfate on a filter, the filtrate was concentrated under reduced pressure. The resulted residue was purified through silica gel column chromatography (ethyl acetate:hexane=1:6→1:3→1:2) to give the titled compound (7.77 g).

$^1$H-NMR (400 MHz, CDCl$_3$) 0.68-0.74 (m, 3H), 1.00-1.07 (m, 3H), 1.26 (s, 3H), 1.68 (s, 3H), 1.80-1.89 (m, 1H), 2.60-2.67 (m, 2H), 3.72-3.78 (m, 2H), 4.08-4.19 (m, 2H), 4.82 (brs, 1H), 5.91 (s, 1H), 7.15-7.21 (m, 1H), 7.47-7.51 (m, 1H), 7.53-7.58 (m, 1H)

Step 7

3-{(S)-4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic Acid ethyl Ester

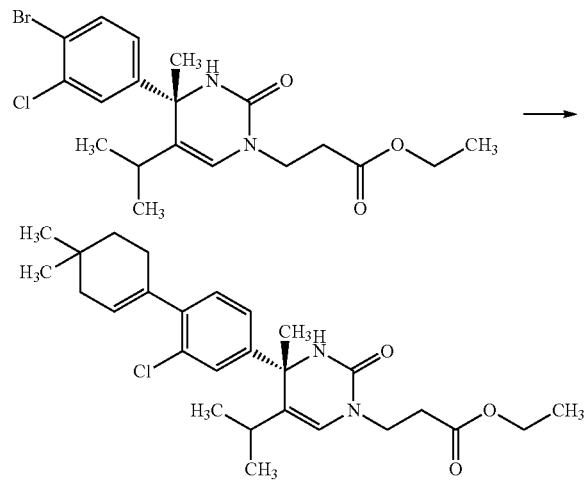

3-[(S)-4-(4-Bromo-3-chloro-phenyl)-5-isopropyl-4-methyl-2-oxo-3,4-dihydro-2H-pyrimidin-1-yl]-propionic acid ethyl ester (58.1 g) prepared according to Example 116 (a method for preparation using an optically active sulfinamide) Steps 1 to 6, 3-[(S)-4-(4-bromo-3-chloro-phenyl)-5-isopropyl-4-methyl-2-oxo-3,4-dihydro-2H-pyrimidin-1-yl]-propionic acid ethyl ester obtained in the previous step 6 (2.9 g), 2-(4,4-dimethyl-1-cyclohexenyl)-4,4,5,5-tetramethyl-[1,3,2]dioxaborolane (48.9 g), and tripotassium phosphate (87.7 g) were mixed in 1,2-dimethoxyethane (777 mL) and water (194 mL) under argon gas. To the reaction solution was added bis(triphenylphosphine)palladium (II) dichloride (5.6 g), and the reaction solution was stirred at 100° C. for 4 hours. To the reaction solution was added ethyl acetate at room temperature, and then an insoluble was removed on a filter. The filtrate was extracted with ethyl acetate, washed with aqueous saturated sodium chloride solution, and then dried over sodium sulfate. After removing sodium sulfate on a filter, the filtrate was concentrated under reduced pressure.

The resulted residue was purified twice through silica gel chromatography to give the titled compound (48.3 g).

$^1$H-NMR (400 MHz, CDCl$_3$) 0.73 (d, J=6.76 Hz, 3H), 1.00 (s, 6H), 1.05 (d, J=7.00 Hz, 3H), 1.27 (t, J=7.00 Hz, 2H), 1.50 (t, J=6.52 Hz, 2H), 1.69 (s, 3H), 1.85-1.92 (m, 1H), 1.95-1.97 (m, 2H), 2.28-2.32 (m, 2H), 2.67 (t, J=6.64 Hz, 2H), 3.78 (t, J=6.64 Hz, 2H), 4.13-4.19 (m, 2H), 4.62 (s, 1H), 5.58-5.61 (m, 1H), 5.91 (s, 1H), 7.11 (d, J=7.97 Hz, 1H), 7.25 (dd, J=7.97, 1.93 Hz, 1H), 7.38 (d, J=1.93 Hz, 1H)

Step 8

3-{(S)-4-[3-Chloro-4-(4,4-dimethyl-cyclohex-1-enyl)-phenyl]-5-isopropyl-4-methyl-2-oxo-3,4-dihydro-2H-pyrimidin-1-yl}-propionic Acid

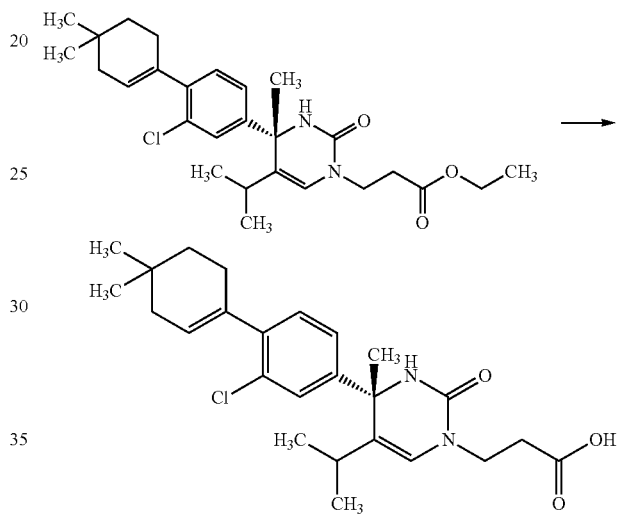

3-{(S)-4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic acid ethyl ester (48.3 g) was mixed in ethanol (480 mL). To the reaction solution was added 4M aqueous sodium hydroxide solution (51 mL) under ice cooling, and the reaction solution was stirred at room temperature overnight. The reaction solution was concentrated under reduced pressure, and then thereto was added water (960 mL). To the reaction solution was added 2M hydrochloric acid (102 mL) under ice cooling, and the reaction solution was stirred under ice cooling for 3 hours. The precipitated solid was filtered to give the titled compound (41 g) as a crystal. The specific optical rotation of the resulted compound was $[\alpha]_D^{25}$=+106.10 (c=1.00, methanol). The melting point of the resulted crystal was 90-95° C.

The resulted compound was analyzed using a chiral column, and the retention time of the resulted titled compound (S-enantiomer) was 9.2 minutes, the optical purity of which was >99% ee.

The analytical condition in the chiral column is shown as follows.
Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 1.0 mL/min
Detection; UV (220 nm)

Example 116

Preparation of 3-{(S)-4-[3-chloro-4-(4,4-dimethyl-cyclohex-1-enyl)-phenyl]-5-isopropyl-4-methyl-2-oxo-3,4-dihydro-2H-pyrimidin-1-yl}-propionic Acid A Method for Preparation Using Cleisen Reaction Step 1

4-Bromo-3-chloro-N-methoxy-N-methylbenzamide

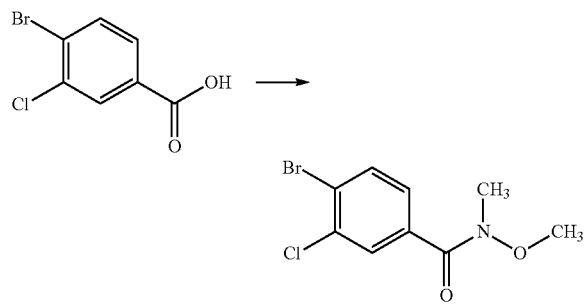

4-Bromo-3-chlorobenzoic acid (25.0 g), N,O-dimethylhydroxylamine hydrochloride (12.4 g), 1-hydroxybenzotriazolemonohydrate (19.5 g), and triethylamine (22.2 mL) were mixed in N,N-dimethylformamide (100 mL). To the reaction solution was added 1-ethyl-3-(3-dimethylaminopropyl)carbodiimide hydrochloride (24.4 g) under ice cooling, and the reaction solution was stirred at room temperature overnight. To the reaction solution was added 5 w/v % aqueous sodium hydrogen carbonate solution, which was then extracted with ethyl acetate. The organic layer was washed sequentially with water and aqueous saturated sodium chloride solution, and dried over magnesium sulfate. After removing magnesium sulfate on a filter, the filtrate was concentrated under reduced pressure to give the titled compound (31 g) as a crude product.

$^1$H-NMR (400 MHz, CDCl$_3$) 3.36 (d, J=1.16 Hz, 3H), 3.55 (d, J=0.92 Hz, 3H), 7.47 (dt, J=8.17, 1.50 Hz, 1H), 7.66 (dd, J=8.32, 1.16 Hz, 1H), 7.81 (t, J=1.50 Hz, 1H)

Step 2

1-(4-Bromo-3-chloro-phenyl)-propan-1-one

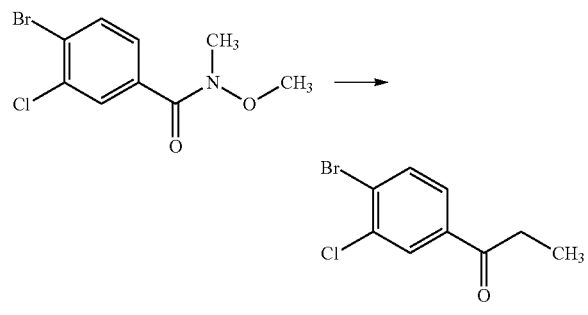

4-Bromo-3-chloro-N-methoxy-N-methylbenzamide (31 g) was mixed in tetrahydrofuran (60 mL). To the reaction solution was added dropwise 0.97M ethylmagnesium bromide/tetrahydrofuran solution (141 mL) under ice cooling, and the reaction solution was stirred at room temperature for 1.5 hours. To the reaction solution was added 2M hydrochloric acid (140 mL) under ice cooling, which was then extracted with toluene. The organic layer was washed sequentially with water and aqueous saturated sodium chloride solution, and dried over magnesium sulfate. After removing magnesium sulfate on a filter, the filtrate was concentrated under reduced pressure to give the titled compound (26.80 g) as a crude product.

$^1$H-NMR (400 MHz, CDCl$_3$) 1.22 (t, J=7.17 Hz, 3H), 2.96 (q, J=7.17 Hz, 2H), 7.68 (dd, J=8.44, 1.97 Hz, 1H), 7.72 (d, J=8.32 Hz, 1H), 8.02 (d, J=1.85 Hz, 1H)

Step 3

2-(4-Bromo-3-chloro-phenyl)-propionic Acid methyl Ester

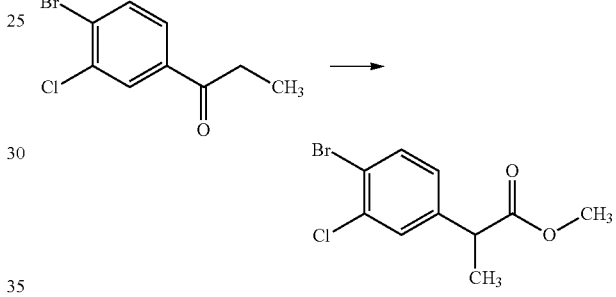

1-(4-Bromo-3-chloro-phenyl)-propan-1-one (26.80 g) and iodobenzene diacetate (36.9 g) were mixed in trimethyl orthoformate (250 mL). To the reaction solution was slowly added concentrated sulfuric acid (11.1 mL) under water cooling, and the reaction solution was stirred at 60° C. for 3 hours. To the reaction solution was added water, which was then extracted with ethyl acetate. The organic layer was washed sequentially with aqueous sodium sulfite solution, water, and aqueous saturated sodium chloride solution, and dried over magnesium sulfate. After removing magnesium sulfate on a filter, the filtrate was concentrated under reduced pressure to give the titled compound (55.3 g) as a crude product.

$^1$H-NMR (400 MHz, CDCl$_3$) 1.48 (d, J=7.17 Hz, 3H), 3.23 (dd, J=7.40, 0.46 Hz, 1H), 3.67 (d, J=0.46 Hz, 3H), 7.06 (dd, J=8.32, 2.08 Hz, 1H), 7.40 (d, J=2.08 Hz, 1H), 7.55 (d, J=8.32 Hz, 1H)

Step 4

2-(4-Bromo-3-chloro-phenyl)-propionic Acid

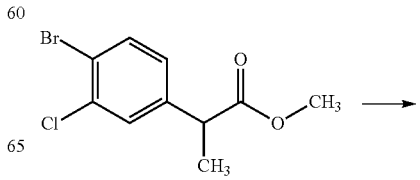

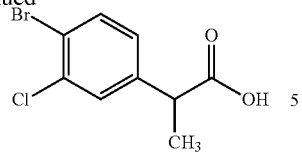

2-(4-Bromo-3-chloro-phenyl)-propionic acid methyl ester (55.3 g) was mixed in tetrahydrofuran (100 mL) and methanol (100 mL). To the reaction solution was added 2M aqueous sodium hydroxide solution (150 mL), and the reaction solution was stirred at 60° C. for 1.5 hours. To the reaction solution was added 2M aqueous sodium hydroxide solution (50 mL), and the reaction solution was further stirred for 3.5 hours. The reaction solution was concentrated under reduced pressure, and to the resulted residue was added hexane (150 mL), which was separated. The aqueous layer was washed again with hexane (150 mL), and then thereto was added 2M hydrochloric acid (200 mL), which was extracted with ethyl acetate. The organic layer was washed sequentially with water and aqueous saturated sodium chloride solution, and dried over magnesium sulfate. After removing magnesium sulfate on a filter, a mixed solution which toluene was added to the filtrate was concentrated under reduced pressure to give the titled compound (21.6 g) as a crude product.

$^1$H-NMR (400 MHz, CDCl$_3$) 1.51 (d, J=7.17, 3H), 3.70 (q, J=7.17 Hz, 1H), 7.08 (dd, J=8.21, 2.20 Hz, 1H), 7.42 (d, J=2.08 Hz, 1H), 7.57 (t, J=6.01 Hz, 1H), 10.63 (s, 1H)

Step 5

(E)-4-Methyl-pent-2-en-1-ol

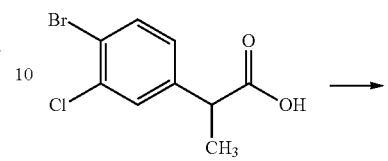

(E)-4-methyl-pent-2-enoic acid methyl ester (20.7 g) was mixed in dichloromethane (50 mL). To the reaction solution was added dropwise 1M diisobutylaluminum hydride/dichloromethane solution (300 mL) at −78° C., and the reaction solution was stirred at −78° C. for 1 hour. To the reaction solution was added methanol (45 mL), and then the reaction solution was warmed to room temperature. The reaction solution was added dropwise to 1M aqueous sulfuric acid solution (150 mL), and then extracted with dichloromethane. The organic layer was washed with aqueous saturated sodium chloride solution and dried over sodium sulfate. After removing sodium sulfate on a filter, the filtrate was concentrated under reduced pressure to give the titled compound in dichloromethane solution (35.1 w/w %, 57.3 g).

$^1$H-NMR (400 MHz, CDCl$_3$) 1.00 (d, J=6.94 Hz, 6H), 1.25 (s, 1H), 2.31 (td, J=13.58, 6.78 Hz, 1H), 4.09 (d, J=5.78 Hz, 2H), 5.59 (tdd, J=10.63, 5.20, 0.89 Hz, 1H), 5.67 (dtt, J=15.26, 6.17, 0.90 Hz, 1H)

Step 6

2-(4-Bromo-3-chloro-phenyl)-propionic acid (E)-4-methyl-pent-2-enyl Ester

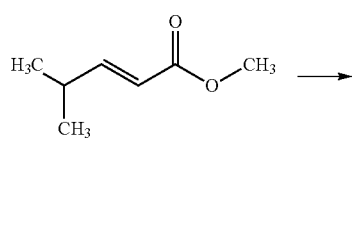

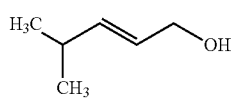

35.1 w/w % of (E)-4-methyl-pent-2-en-1-ol/dichloromethane solution (28.8 g) and 4-dimethylaminopyridine (11.4 g) were mixed in dichloromethane (200 mL). To the reaction solution was added 1-ethyl-3-(3-dimethylaminopropyl)carbodiimide hydrochloride (17.9 g) under ice cooling, and the reaction solution was stirred for 30 minutes. To the reaction solution was added a mixed solution of 2-(4-bromo-3-chloro-phenyl)-propionic acid (22.0 g) in dichloromethane (100 mL), and the reaction solution was stirred at room temperature overnight. To the reaction solution was added water (200 mL), which was then extracted with chloroform. The organic layer was washed sequentially with 1M aqueous hydrochloric acid solution, 5 w/v % aqueous sodium hydrogen carbonate solution, water, and aqueous saturated sodium chloride solution, and dried over magnesium sulfate. After removing magnesium sulfate on a filter, the filtrate was concentrated under reduced pressure. The resulted residue was purified through silica gel chromatography (toluene:hexane=1:2) to give the titled compound (20.8 g).

$^1$H-NMR (400 MHz, CDCl$_3$) 0.97 (d, J=6.47 Hz, 6H), 1.48 (d, J=7.17 Hz, 3H), 2.28 (td, J=13.35, 6.70 Hz, 1H), 3.66 (q, J=7.24 Hz, 1H), 4.51 (dd, J=6.59, 3.35 Hz, 2H), 5.44 (dtd, J=15.45, 6.36, 1.35 Hz, 1H), 5.66 (ddt, J=15.49, 6.47, 1.18 Hz, 1H), 7.07 (dd, J=8.32, 2.08 Hz, 1H), 7.41 (d, J=2.08 Hz, 1H), 7.55 (d, J=8.09 Hz, 1H)

Step 7

2-(4-Bromo-3-chloro-phenyl)-3-isopropyl-2-methyl-pent-4-enoic Acid

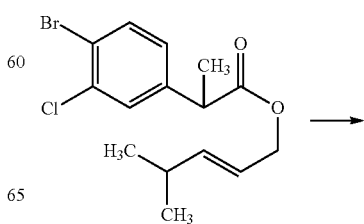

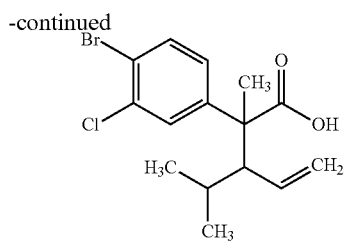

2-(4-Bromo-3-chloro-phenyl)-propionic acid (E)-4-methyl-pent-2-enyl ester (17.5 g) was mixed in tetrahydrofuran (200 mL). To the reaction solution was added dropwise 1.17M lithium hexamethyldisilazane/tetrahydrofuran solution (45.3 mL) at −41° C., and the reaction solution was stirred at −41° C. for 1 hour. To the reaction solution was added dropwise chlorotrimethylsilane (12.8 mL), and then the reaction solution was stirred at −41° C. for 30 minutes and then stirred at room temperature overnight. To the reaction solution was added 1M aqueous hydrochloric acid solution, which was then extracted with ethyl acetate. The organic layer was concentrated under reduced pressure to give the titled compound (18.0 g) as a crude product.

$^1$H-NMR (400 MHz, CDCl$_3$) 0.71 (d, J=6.70 Hz, 2.01H), 0.76 (d, J=6.70 Hz, 2.01H), 0.86 (d, J=6.70 Hz, 0.99H), 0.96 (d, J=6.70 Hz, 0.99H), 1.57 (ddd, J=13.47, 6.65, 3.99 Hz, 0.67H), 1.60 (s, 2.01H), 1.61 (s, 0.99H), 1.78 (ddd, J=13.47, 6.65, 3.99 Hz, 0.33H), 2.78 (dd, J=9.13, 2.89 Hz, 0.33H), 2.81 (dd, J=10.06, 2.66 Hz, 0.67H), 4.71 (dd, J=16.88, 1.62 Hz, 0.33H), 4.87 (dd, J=10.17, 2.08 Hz, 0.33H), 5.15 (dd. J=13.87, 2.31 Hz, 0.67H), 5.18 (dd, J=7.28, 2.20 Hz, 0.67H), 5.31 (dt, J=19.42, 8.50 Hz, 0.33H), 5.70 (dt, J=19.19, 8.38 Hz. 0.67H), 7.17 (dd. J=8.32, 2.31 Hz, 0.33H), 7.28 (dd, J=8.67, 2.43 Hz. 0.67H), 7.48 (d, J=2.31 Hz, 0.33H), 7.50 (d, J=8.55 Hz, 0.33H), 7.57 (d. J=8.55 Hz, 0.67H), 7.59 (d. J=2.31 Hz. 0.67H), 10.3 (s, 1H)

Step 8

1-Bromo-2-chloro-4-(1-isocyanato-2-isopropyl-1-methyl-but-3-enyl)-benzene

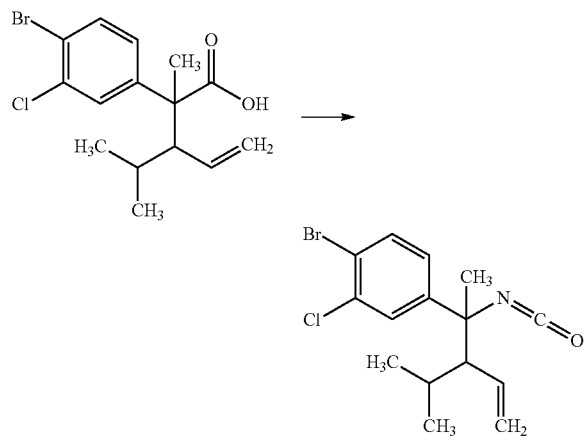

2-(4-Bromo-3-chloro-phenyl)-3-isopropyl-2-methyl-pent-4-enoic acid (18.0 g) and triethylamine (10.6 mL) were mixed in toluene (300 mL). To the reaction solution was added diphenyl phosphoryl azide (16.3 mL), and the reaction solution was stirred at 70° C. for 2 hours. The reaction solution was concentrated under reduced pressure, and the resulted residue was purified through silica gel chromatography (chloroform:hexane=1:4) to give the titled compound (15.5 g).

$^1$H-NMR (400 MHz, CDCl$_3$) 0.69 (d, J=6.47 Hz, 1.05H), 0.70 (d, J=6.94 Hz, 1.95H), 0.83 (d, J=6.94 Hz, 1.05H), 0.86 (d, J=6.94 Hz, 1.95H), 1.40-1.48 (m, 0.35H), 1.63 (s, 1.05H), 1.76 (s, 1.95H), 1.99-2.06 (m, 0.65H), 2.16 (dd, J=−10.17, 2.31 Hz, 0.65H), 2.20 (dd, J=9.94, 2.54 Hz, 0.35H), 4.88 (dd, J=16.99, 1.97 Hz, 0.65H), 5.13 (dd, J=10.29, 1.97 Hz, 0.65H), 5.18 (dd, J=16.88, 2.08 Hz, 0.35H), 5.38 (dd, J=10.29, 1.97 Hz, 0.35H), 5.60 (dt, J=19.27, 8.50 Hz, 0.65H), 5.84 (dt, J=19.03, 8.44 Hz, 0.35H), 7.10 (dd, J=8.55, 2.31 Hz, 0.65H), 7.14 (dd, J=8.55, 2.31 Hz, 0.35H), 7.45 (d, J=2.31 Hz, 0.65H), 7.51 (d, J=2.31 Hz, 0.35H), 7.55 (d, J=8.32 Hz, 0.65H), 7.59 (d, J=8.32 Hz, 0.35H)

Step 9

3-{3-[1-(4-Bromo-3-chloro-phenyl)-2-isopropyl-1-methyl-but-3-enyl]-ureido}-propionic Acid ethyl Ester

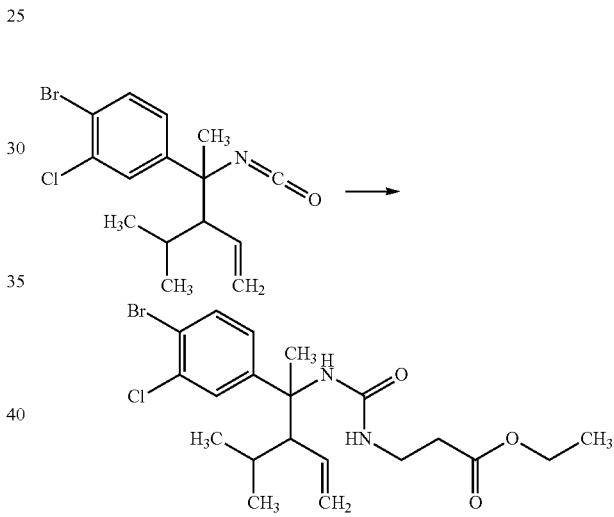

1-Bromo-2-chloro-4-(1-isocyanato-2-isopropyl-1-methyl-but-3-enyl)-benzene (13.76 g) and triethylamine (11.2 mL) were mixed in tetrahydrofuran (100 mL). To the reaction solution was added 3-amino-propionic acid ethyl ester hydrochloride (7.4 g) under ice cooling, and the reaction solution was stirred at room temperature overnight. To the reaction solution was added 1M aqueous hydrochloric acid solution (100 mL), which was then extracted with ethyl acetate. The organic layer was washed sequentially with 1M hydrochloric acid, 5 w/v % aqueous sodium hydrogen carbonate solution, water, and aqueous saturated sodium chloride solution, and dried over magnesium sulfate. The organic layer was concentrated under reduced pressure to give the titled compound (18.5 g) as a crude product.

$^1$H-NMR (400 MHz, CDCl$_3$) 0.32 (d, J=6.70 Hz, 1.02H), 0.59 (d, J=6.70 Hz, 1.98H), 0.76 (d, J=6.70 Hz, 1.98H), 0.84 (d, J=6.94 Hz, 1.02H), 1.25 (t, J=7.05 Hz, 1.98H), 1.25 (t, J=7.17 Hz, 1.02H), 1.45-1.53 (m, 1H), 1.71 (s, 1.98H), 1.83 (s, 1.02H), 1.98 (dd, J=10.52, 1.97 Hz, 0.66H), 1.99 (dd, J=10.52, 1.50 Hz, 0.34H), 2.38 (td, J=5.84, 1.77 Hz, 1.32H), 2.42 (t, J=5.90 Hz, 0.68H), 3.25-3.41 (m, 2H), 4.11 (q, J=7.17 Hz, 1.32H), 4.11 (q, J=7.17 Hz, 0.68H), 4.57 (t,

J=6.01 Hz, 0.66H), 4.66 (t, J=6.13 Hz, 0.34H), 4.93 (s, 1H), 5.07 (dd, J=16.88, 1.85 Hz, 0.34H), 5.22 (dd, J=17.34, 2.54 Hz, 0.66H), 5.26 (dd, J=10.87, 2.31 Hz, 0.34H), 5.37 (dd, J=10.06, 1.97 Hz, 0.66H), 5.59 (dt, J=19.50, 8.44 Hz, 0.34H), 5.79 (dt, J=19.42, 8.50 Hz, 0.66H), 7.09 (dd, J=8.55, 2.31 Hz, 0.34H), 7.20 (dd, J=8.32, 2.31 Hz, 0.66H), 7.41 (d, J=2.31 Hz, 0.34H), 7.51 (d, J=2.31 Hz, 0.66H), 7.53 (d, J=8.32 Hz, 0.34H), 7.56 (d, J=8.32 Hz, 0.66H)

Step 10

3-[4-(4-Bromo-3-chloro-phenyl)-5-isopropyl-4-methyl-2-oxo-3,4-dihydro-2H-pyrimidin-1-yl]-propionic Acid ethyl Ester

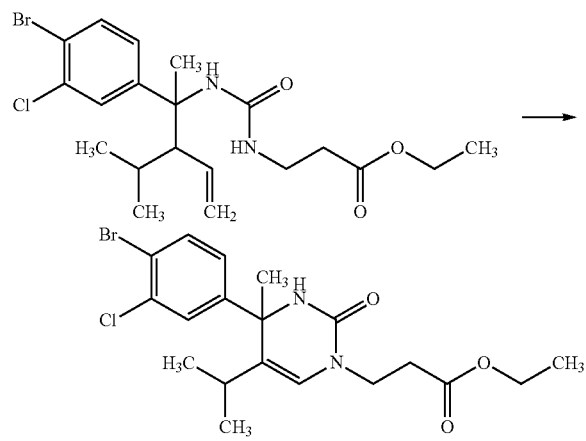

3-{3-[1-(4-Bromo-3-chloro-phenyl)-2-isopropyl-1-methyl-but-3-enyl]-ureido}-propionic acid ethyl ester (18.5 g) was mixed in methanol (100 mL) and dichloromethane (50 mL). The reaction solution was stirred at −78° C. for 3 hours under ozone flow. The reaction solution was then stirred at −78° C. for 30 minutes under nitrogen flow. To the reaction solution was added methylsulfide (15 mL) at −78° C., and the reaction solution was warmed to room temperature. To the reaction solution was added ethanol (50 mL), and the mixed solution was concentrated under reduced pressure. To the resulted residue was added 2M hydrogen chloride/ethanol solution (50 mL), and the reaction solution was stirred at room temperature for 1 hour. The reaction solution was concentrated under reduced pressure, and the resulted residue was purified through silica gel chromatography (ethyl acetate:chloroform-1:4) and then recrystallized from a mixed solution of hexane-diisopropylether (1:1) to give the titled compound (6.19 g).

$^1$H-NMR (400 MHz, CDCl$_3$) 0.68-0.74 (m, 3H), 1.00-1.07 (m, 3H), 1.26 (s, 3H), 1.68 (s, 3H), 1.80-1.89 (m, 1H), 2.60-2.67 (m, 2H), 3.72-3.78 (m, 2H), 4.08-4.19 (m, 2H), 4.82 (brs, 1H), 5.91 (s, 1H), 7.15-7.21 (m, 1H), 7.47-7.51 (m, 1H), 7.53-7.58 (m, 1H)

Step 11

3-{4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic Acid ethyl Ester

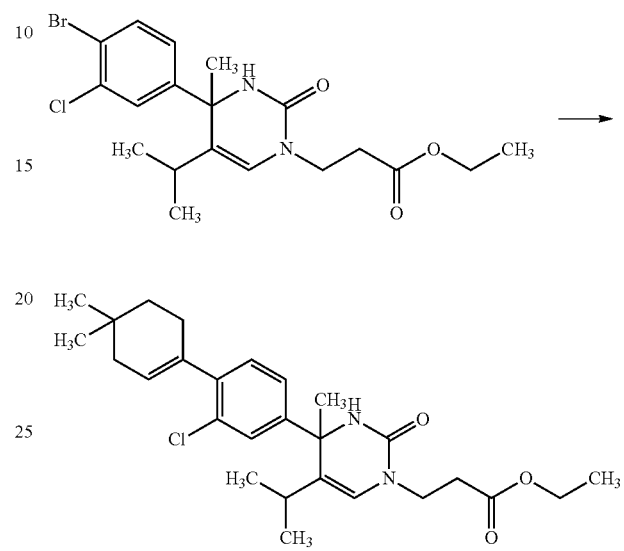

3-[4-(4-Bromo-3-chloro-phenyl)-5-isopropyl-4-methyl-2-oxo-3,4-dihydro-2H-pyrimidin-1-yl]-propionic acid ethyl ester (200 mg), 2-(4,4-dimethyl-1-cyclohexenyl)-4,4,5,5-tetramethyl-[1,3,2]dioxaborolane (160 mg) and tripotassium phosphate (287 mg) were mixed in 1,2-dimethoxyethane (4 mL) and water (1 mL) under argon gas. To the reaction solution was added bis(triphenylphosphine)palladium (II) dichloride (16 mg), and the reaction solution was stirred at 100° C. overnight. To the reaction solution was added ethyl acetate at room temperature, and then an insoluble was removed on a filter. The filtrate was washed sequentially with water and aqueous saturated sodium chloride solution, and then dried over sodium sulfate. After removing sodium sulfate on a filter, the filtrate was concentrated under reduced pressure. The resulted residue was purified through silica gel chromatography (ethyl acetate:hexane=1:3), followed by thin layer silica gel chromatography (methanol:chloroform=1:30) to give the titled compound (180 mg).

$^1$H-NMR (400 MHz, CDCl$_3$) 0.73 (d, J=6.76 Hz, 3H), 1.00 (s, 6H), 1.05 (d, J=7.00 Hz, 3H), 1.27 (t, J=7.00 Hz, 2H), 1.50 (t, J=6.52 Hz, 2H), 1.69 (s, 3H), 1.85-1.92 (m, 1H), 1.95-1.97 (m, 2H), 2.28-2.32 (m, 2H), 2.67 (t, J=6.64 Hz, 2H), 3.78 (t, J=6.64 Hz, 2H), 4.13-4.19 (m, 2H), 4.62 (s, 1H), 5.58-5.61 (m, 1H), 5.91 (s, 1H), 7.11 (d, J=7.97 Hz, 1H), 7.25 (dd, J=7.97, 1.93 Hz, 1H), 7.38 (d, J=1.93 Hz, 1H)

Step 12

3-{(S)-4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic Acid ethyl Ester

Step 13

3-{(S)-4-[3-Chloro-4-(4,4-dimethyl-cyclohex-1-enyl)-phenyl]-5-isopropyl-4-methyl-2-oxo-3,4-dihydro-2H-pyrimidin-1-yl}-propionic Acid

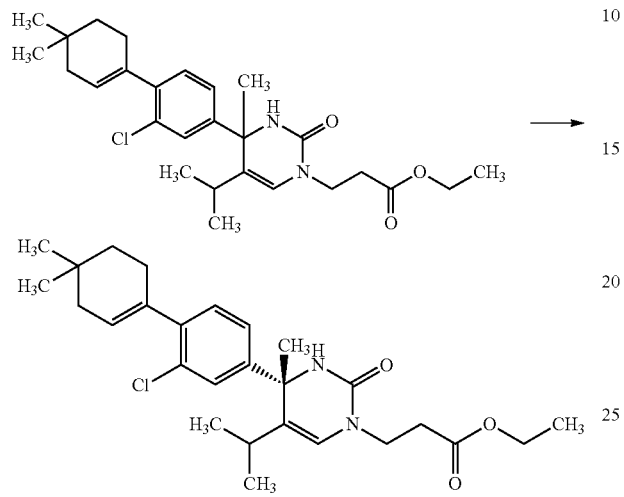

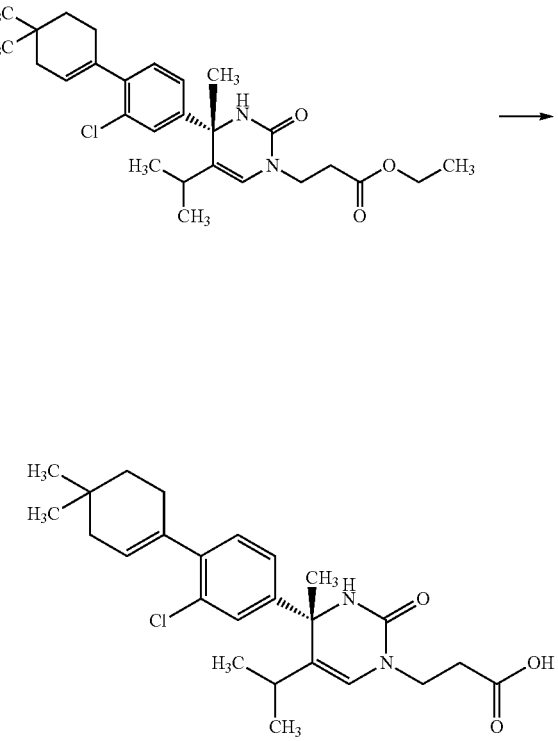

3-{4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic acid ethyl ester (racemate/190 mg) was purified with recycling preparative chromatograph to give 71 mg as a fraction compound eluted later (analytical column DAICEL CHIRALPAK IA-3, retention time 6.4 minutes) and 75 mg as a fraction compound eluted earlier (analytical column DAICEL CHIRALPAK IA-3, retention time 4.1 minutes).

The separation condition in the recycling preparative chromatograph is shown as follows.

Separation instrument; Recycling preparative chromatograph LC-9225 NEXT SERIES Japan Analytical Industry Co., Ltd.
Column; DAICEL CHIRALPAK IA 2.0 cmφ×25 cm
Mobile phase; hexane:2-propanol=90:10
Flow rate; 10.0 mL/min
Detection; UV (254 nm)

The analytical condition in a chiral column is shown as follows.
Measuring instrument; HPLC system Shimadzu Corporation high-performance liquid chromatograph prominence
Column; DAICEL CHIRALPAK IA-3 0.46 cmφ×15 cm
Column temperature; 40° C.
Mobile phase; hexane:2-propanol=90:10
Flow rate; 1.0 mL/min
Detection; UV (254 nm)

The retention time of the compound obtained in the next step by hydrolysis of the compound as a fraction eluted later in a chiral column coincided with that in the chiral column of the compound obtained by the method using the optically active sulfinamide in Example 116 Step 8. The compound obtained as a fraction eluted later was thus estimated as an S-enantiomer.

3-{(S)-4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic acid ethyl ester (25 mg) was mixed in tetrahydrofuran (0.5 mL) and methanol (1 mL), and thereto was added 1M aqueous sodium hydroxide solution (0.16 mL) at room temperature. The reaction solution was stirred at 50° C. for 8 hours. The reaction solution was concentrated under reduced pressure, and then thereto was added water. To the mixed solution was added 1M hydrochloric acid (0.2 mL) under ice cooling, and then the mixed solution was stirred at room temperature. The precipitated solid was filtered to give the titled compound (19 mg). The resulted compound was analyzed by a chiral column, and the retention time of the resulted titled compound (S-enantiomer) was 9.2 minutes, the optical purity of which was >99% ee.

The analytical condition in the chiral column is shown as follows.
Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid-30:70:0.1
Flow rate; 1.0 mL/min
Detection; UV (220 nm)

Example 115

The Enantiomer of Example 116

3-{(R)-4-[3-Chloro-4-(4,4-dimethyl-cyclohex-1-enyl)-phenyl]-5-isopropyl-4-methyl-2-oxo-3,4-dihydro-2H-pyrimidin-1-yl}-propionic Acid

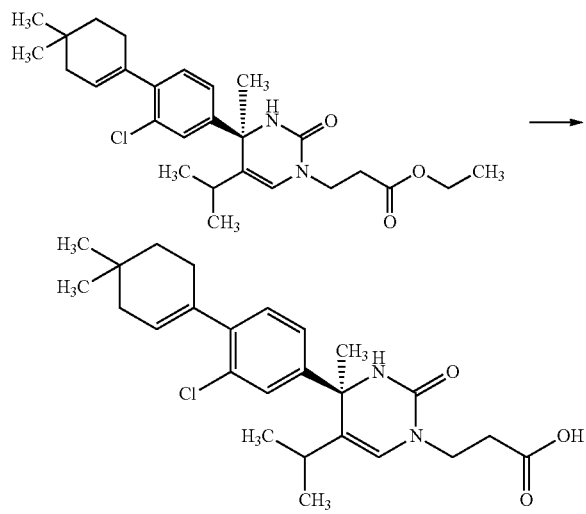

3-{(R)-4-[3-Chloro-4-(4,4-dimethyl-1-cyclohex-1-enyl)-phenyl]-5-isopropyl-4-methyl-2-oxo-3,4-dihydro-2H-pyrimidin-1-yl}-propionic acid ethyl ester obtained by Example 116 Step 12 was treated according to Example 116 Step 13 to give the titled compound (25 mg). The retention time of the resulted enantiomer (R-enantiomer) was 6.0 minutes.

The analytical condition in the chiral column is shown as follows.
Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 1.0 mL/min
Detection; UV (220 nm)

Example 130

Preparation of 4-{4-[3-chloro-4-(3,3-dimethyl-butyl)-phenyl]-4-methyl-2-oxo-1,2,3,4-tetrahydro-pyrimidin-5-yl}-4-methyl-pentanoic Acid (an Optically Active Compound)

Step 1

5-(tert-Butyl-dimethyl-silanyloxy)-2,2-dimethyl-pentanoic Acid ethyl Ester

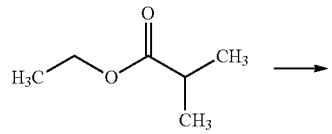

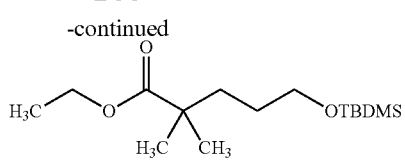

Diisopropylamine (14.3 mL) and tetrahydrofuran (70 mL) were mixed under argon gas. To the reaction solution was added dropwise 1.55M n-butyllithium/hexane solution (65.8 mL) at −78° C., and the reaction solution was stirred for 10 minutes under ice cooling. To the reaction solution was added dropwise a mixed solution of isobutanoic acid ethyl ester (13.6 mL) in tetrahydrofuran (70 mL) at −78° C., and the reaction solution was stirred at −78° C. for 1.5 hours. To the reaction solution was added dropwise a mixed solution of 3-bromopropoxy-tert-butyldimethylsilane (23.9 mL) in tetrahydrofuran (30 mL) at −78° C. and the reaction solution was stirred at −78° C. for 5.5 hours and then stirred at room temperature for 3 days. To the reaction solution was added aqueous saturated ammonium chloride solution, which was then extracted with ethyl acetate. The organic layer was washed with aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:20) to give the titled compound (26.4 g).

$^1$H-NMR (400 MHz, CDCl$_3$) 0.04 (s, 6H), 0.89 (s, 9H), 1.17 (s, 6H), 1.24 (t, J=7.25 Hz, 3H), 1.41-1.50 (m, 2H), 1.56-1.51 (m, 2H), 3.58 (t, J=6.45 Hz, 2H), 4.11 (q, J=6.85 Hz, 2H)

Step 2

5-(tert-Butyl-dimethyl-silanyloxy)-2,2-dimethyl-pentan-1-ol

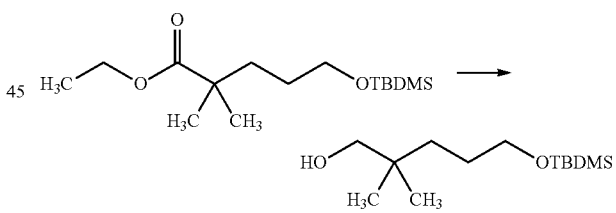

5-(tert-Butyl-dimethyl-silanyloxy)-2,2-dimethyl-pentanoic acid ethyl ester (26.5 g) was mixed in tetrahydrofuran (200 mL) under argon gas. To the reaction solution was added dropwise 1 M diisobutylaluminum hydride/toluene solution (210 mL) at −78° C., and the reaction solution was stirred at −78° C. for 40 minutes. To the reaction solution were added ethyl acetate and 1M aqueous Rochelle salt solution (500 mL), and the reaction solution was stirred at room temperature for 30 minutes. The reaction solution was extracted with ethyl acetate. The organic layer was washed sequentially with 0.5M hydrochloric acid (2×200 mL), water (2×200 mL), saturated aqueous sodium hydrogen carbonate solution, and aqueous saturated sodium chloride solution, and dried over sodium sulfate. After removing sodium sulfate on a filter, the filtrate was concentrated to give the titled compound (24.3 g).

$^1$H-NMR (400 MHz, CDCl$_3$) 0.06 (s, 6H), 0.87 (s, 6H), 0.90 (s, 9H), 1.25-1.29 (m, 2H), 1.46-1.56 (m, 2H), 3.32 (s, 2H), 3.60 (t, J=6.45 Hz, 2H)

Step 3

5-(tert-Butyl-dimethyl-silanyloxy)-2,2-dimethyl-pentanal

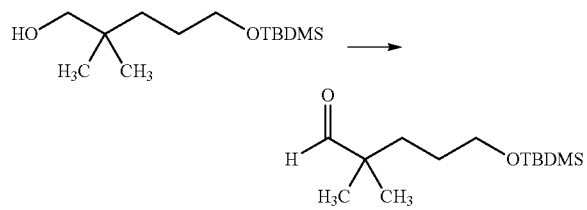

5-(tert-Butyl-dimethyl-silanyloxy)-2,2-dimethyl-pentan-1-ol (24.3 g) and triethylamine (38.2 mL) were mixed in dichloromethane (100 mL). To the reaction solution was added dropwise a mixed solution of sulfur trioxide pyridine complex (20.1 g) in DMSO (130 mL) under ice cooling, and the reaction solution was stirred at room temperature for 2 hours. To the reaction solution was added saturated aqueous sodium hydrogen carbonate solution (100 mL), which was then extracted with ethyl acetate. The organic layer was washed sequentially with 0.5M hydrochloric acid (3×200 mL), water (150 mL), saturated aqueous sodium hydrogen carbonate solution (100 mL), and aqueous saturated sodium chloride solution, and dried over sodium sulfate. After removing sodium sulfate on a filter, the filtrate was concentrated to give the titled compound (25.2 g).

$^1$H-NMR (400 MHz, CDCl$_3$) 0.04 (s, 6H), 0.89 (s, 9H), 1.05 (s, 6H), 1.47-1.41 (m, 2H), 1.54-1.48 (m, 2H), 3.59 (t, J=6.45 Hz, 2H), 9.45 (s, 1H)

Step 4

(E)-7-(tert-Butyl-dimethyl-silanyloxy)-4,4-dimethyl-hept-2-enoic Acid ethyl Ester

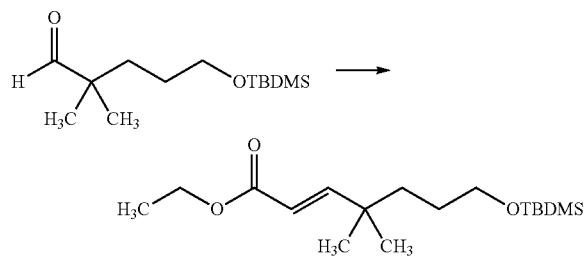

Sodium hydride (60 w/w %) (4.40 g) was mixed in tetrahydrofuran (100 mL) under argon gas. To the reaction solution was added dropwise ethyl diethylphosphonoacetate (21.8 mL) under ice cooling, and the reaction solution was stirred at room temperature for 40 minutes. To the reaction solution was added dropwise a mixed solution of 5-(tert-butyl-dimethyl-silanyloxy)-2,2-dimethyl-pentanal (21.9 g) in tetrahydrofuran (50 mL) under ice cooling, and the reaction solution was stirred at room temperature for 75 minutes. To the reaction solution was added aqueous saturated ammonium chloride solution (150 mL) under ice cooling, which was extracted with ethyl acetate. The organic layer was washed sequentially with water (150 mL) and aqueous saturated sodium chloride solution, and dried over sodium sulfate. After removing sodium sulfate on a filter, the filtrate was concentrated. The resulted residue was purified through silica gel column chromatography (ethyl acetate: hexane=1:20) to give the titled compound (27.1 g).

$^1$H-NMR (400 MHz, CDCl$_3$) 0.04 (s, 6H), 0.89 (s, 9H), 1.05 (s, 6H), 1.29 (t, J=7.05 Hz, 3H), 1.36-1.47 (m, 4H), 3.56 (t, J=6.04 Hz, 2H), 4.19 (q, J=7.25 Hz, 2H), 5.72 (d, J=16.12 Hz, 1H), 6.90 (d, J=16.12 Hz, 1H)

Step 5

(E)-7-(tert-Butyl-dimethyl-silanyloxy)-4,4-dimethyl-hept-2-en-1-ol

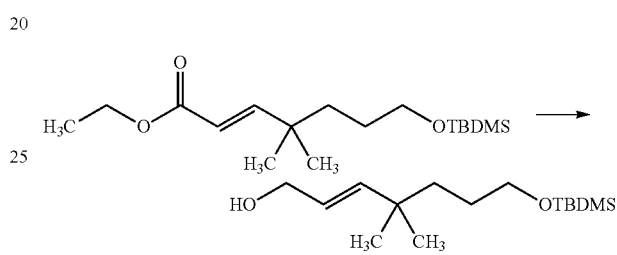

(E)-7-(tert-Butyl-dimethyl-silanyloxy)-4,4-dimethyl-hept-2-enoic acid ethyl ester (27.1 g) was mixed in tetrahydrofuran (200 mL) under argon gas. To the reaction solution was added dropwise 1M diisobutylaluminum hydride/toluene solution (190 mL) at −78° C., and the reaction solution was stirred at −78° C. for 1.5 hours. To the reaction solution was added 0.5M hydrochloric acid (200 mL), which was then extracted with ethyl acetate (500 mL). The organic layer was washed sequentially with 0.5M hydrochloric acid (2×150 mL), water (150 mL), saturated aqueous sodium hydrogen carbonate solution (100 mL), and aqueous saturated sodium chloride solution, and dried over sodium sulfate. After removing sodium sulfate on a filter, the filtrate was concentrated to give the titled compound (23.6 g).

$^1$H-NMR (400 MHz, CDCl$_3$) 0.04 (s, 6H), 0.89 (s, 9H), 0.99 (s, 6H), 1.22 (brs, 1H), 1.31-1.27 (m, 2H), 1.40-1.48 (m, 2H), 3.56 (t, J=6.85 Hz, 2H), 4.11 (d, J=5.24 Hz, 2H), 5.53 (dt, J=15.72, 5.64 Hz, 1H), 5.63 (dt, J=15.72, 0.81 Hz, 1H)

Step 6

2-[3-Chloro-4-(3,3-dimethyl-butyl)-phenyl]-propionic acid (E)-7-(tert-butyl-dimethyl-silanyloxy)-4,4-dimethyl-hept-2-enyl Ester

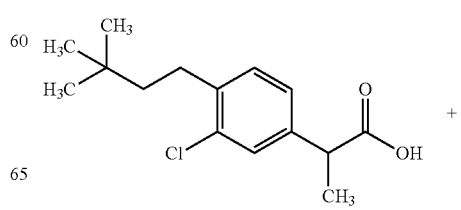

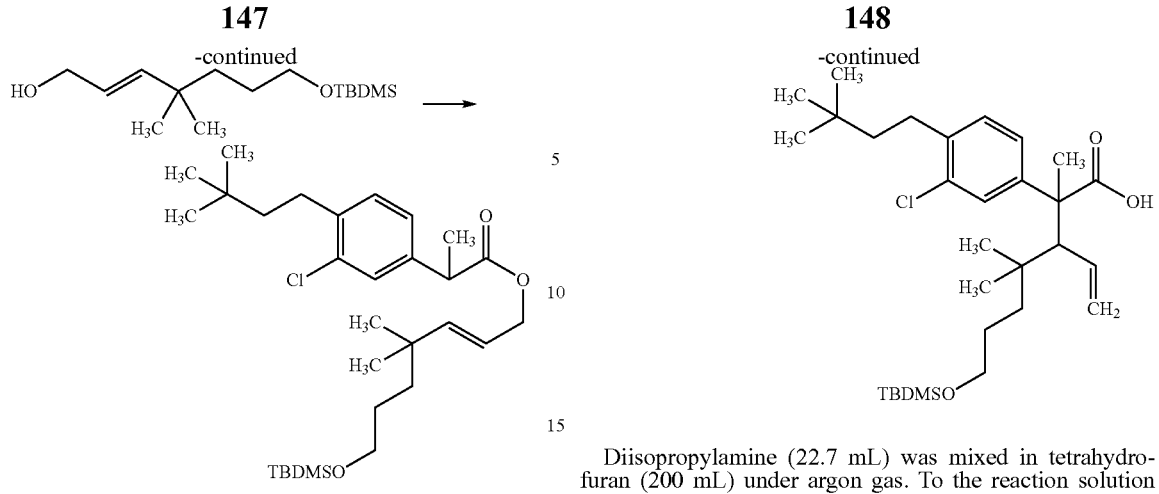

2-[3-Chloro-4-(3,3-dimethylbutyl)phenyl]propionic acid (21.3 g), 7-(tert-butyldimethylsilyloxy)-4,4-dimethyl-2-heptenol (21.6 g), and 4-dimethylaminopyridine (11.6 g) were mixed in dichloromethane (250 mL). To the reaction solution was added 1-ethyl-3-(3-dimethylaminopropyl)carbodiimide hydrochloride (18.2 g) under ice cooling, and the reaction solution was stirred at room temperature for 16 hours. The reaction solution was concentrated under reduced pressure, and to the residue was added water (150 mL), which was then extracted with ethyl acetate (500 mL). The organic layer was washed sequentially with water (150 mL) and aqueous saturated sodium chloride solution, and dried over sodium sulfate. After removing sodium sulfate on a filter, the filtrate was concentrated. The resulted residue was purified through silica gel column chromatography (ethyl acetate:hexane=1:20) to give the titled compound (40.1 g).

$^1$H-NMR (400 MHz, CDCl$_3$) 0.04 (s, 6H), 0.89 (s, 9H), 0.95 (s, 6H), 0.97 (s, 9H), 1.23-1.27 (m, 2H), 1.35-1.47 (m, 4H), 1.47 (d, J=7.25 Hz, 3H), 2.63-2.67 (m, 2H), 3.55 (t, J=6.45 Hz, 2H), 3.66 (q, J=7.12 Hz, 1H), 4.52 (dt, J=6.45, 1.21 Hz, 2H), 5.38 (dt, J=15.72, 6.45 Hz, 1H), 5.59 (dt, J=15.72, 1.21 Hz, 1H), 7.11 (dd, J=7.66, 1.61 Hz, 1H), 7.15 (d, J=8.06 Hz, 1H), 7.28 (d, J=1.61 Hz, 1H)

Step 7

7-(tert-Butyl-dimethyl-silanyloxy)-2-[3-chloro-4-(3,3-dimethyl-butyl)-phenyl]-2,4,4-trimethyl-3-vinyl-heptanoic Acid

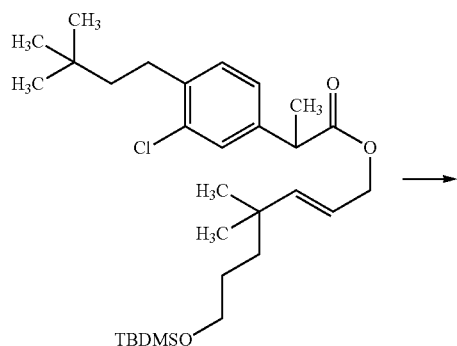

Diisopropylamine (22.7 mL) was mixed in tetrahydrofuran (200 mL) under argon gas. To the reaction solution was added dropwise 1.55M n-butyllithium/hexane solution (100 mL) at −78° C., and the reaction solution was stirred under ice cooling for 20 minutes. To the reaction solution was added dropwise a mixed solution of 2-[3-chloro-4-(3,3-dimethyl-butyl)-phenyl]-propionic acid (E)-7-(tert-butyl-dimethyl-silanyloxy)-4,4-dimethyl-hept-2-enyl ester (40.1 g) in tetrahydrofuran (250 mL) at −78° C., and the reaction solution was stirred under ice cooling for 1 hour. To the reaction solution was added chlorotrimethylsilane (20.8 mL) at −78° C., and the reaction solution was stirred at −78° C. for 1.5 hours and then stirred at room temperature for 19.5 hours. To the reaction solution was added 1M hydrochloric acid (312 mL) under ice cooling, which was then extracted with ethyl acetate (500 mL). The organic layer was washed sequentially with 18 w/v % aqueous sodium chloride solution (300 mL) and aqueous saturated sodium chloride solution, and dried over sodium sulfate. After removing sodium sulfate on a filter, the filtrate was concentrated. The resulted residue was purified through silica gel column chromatography (ethyl acetate:hexane=1:4) to give the titled compound (14.5 g).

$^1$H-NMR (400 MHz, CDCl$_3$) 0.03 (s, 3.0H), 0.05 (s, 3.0H), 0.51 (s, 1.5I), 0.78 (s, 1.5H), 0.89 (s, 4.5H), 0.90 (s, 4.5H), 0.93 (s, 1.5H), 0.95 (s, 4.5H), 0.97 (s, 4.5H), 1.02 (s, 1.5H), 1.20-1.60 (m, 6.0H), 1.71 (s, 1.5H), 1.72 (s, 1.5H), 2.59-2.67 (m, 2.0H), 3.07-3.11 (m, 1.0H), 3.45 (t, J=6.851 Hz, 1.0H), 3.57 (t, J=7.25 Hz, 1.0H), 4.56 (dd, J=16.92, 2.01 Hz, 0.5H), 4.74 (dd, J=10.28, 2.22 Hz, 0.5H), 5.13-5.17 (m, 1.0H), 5.24-5.34 (m, 0.5H), 5.84-5.93 (m, 0.5H), 7.07 (d, J=8.06 Hz, 0.5H), 7.13 (d, J=8.46 Hz, 0.5H), 7.28-7.24 (m, 0.5H), 7.39 (d, J=2.01 Hz, 0.5H), 7.46 (dd, J=8.46, 2.01 Hz, 0.5H), 7.58 (d, J=2.01 Hz, 0.5H)

Step 8 tert-Butyl-(5-{1-[3-chloro-4-(3,3-dimethyl-butyl)-phenyl]-1-isocyanatoethyl}-4,4-dimethyl-hept-6-enyloxy)-dimethyl-silane

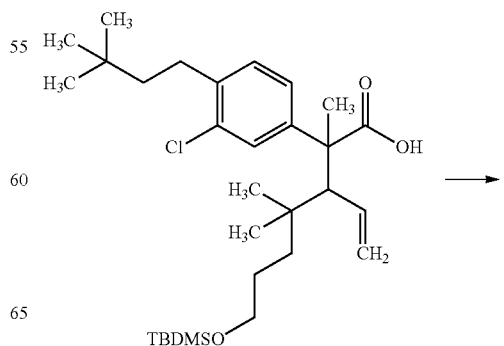

149

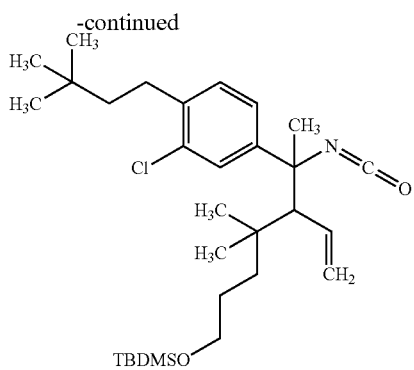

7-(tert-Butyl-dimethyl-silanyloxy)-2-[3-chloro-4-(3,3-dimethyl-butyl)-phenyl]-2,4,4-trimethyl-3-vinyl-heptanoic acid (7.17 g) and triethylamine (2.86 mL) were mixed in toluene (100 mL). To the reaction solution was added diphenyl phosphoryl azide (4.42 mL), and the reaction solution was stirred at 110° C. for 3 hours. The reaction solution was concentrated under reduced pressure, and the resulted residue was purified through silica gel column chromatography (ethyl acetate:hexane=1:60) to give the titled compound (5.12 g).

$^1$H-NMR (400 MHz, CDCl$_3$) 0.02 (s, 3.0H), 0.04 (s, 3.0H), 0.53 (s, 1.5H), 0.75 (s, 1.5H), 0.81 (s, 1.5H), 0.88 (s, 4.5H), 0.89 (s, 4.5H), 0.91 (s, 1.5H), 0.98 (s, 4.5H), 0.98 (s, 4.5H), 1.12-1.48 (m, 6.0H), 1.60 (s, 1.5H), 1.81 (s, 1.5H), 2.34-2.42 (m, 1.0H), 2.64-2.69 (m, 2.0H), 3.36-3.41 (m, 1.0H), 3.49 (t, J=6.45 Hz, 1.0H), 4.77 (dd, J=17.13, 1.81 Hz, 0.5H), 5.06-5.12 (m, 1.0H), 5.29 (dd, J=10.07, 2.01 Hz, 0.5H), 5.74-5.83 (m, 0.5H), 5.88-5.98 (m, 0.5H), 7.28-7.13 (m, 2.0H), 7.33 (d, J=2.01 Hz, 0.5H), 7.37 (d, J=2.01 Hz, 0.5H)

Step 9

{6-(tert-Butyl-dimethyl-silanyloxy)-1-[3-chloro-4-(3,3-dimethyl-butyl)-phenyl]-1,3,3-trimethyl-3-vinyl-hexyl}-urea

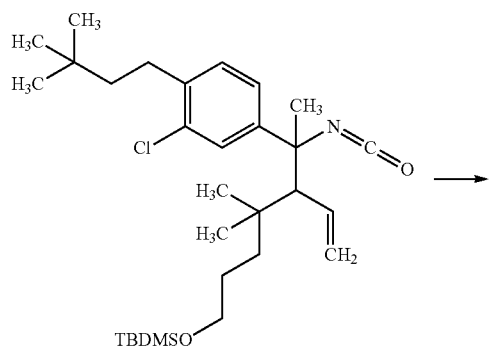

150

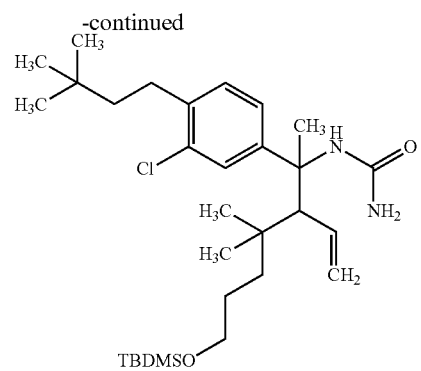

tert-Butyl-(5-{1-[3-chloro-4-(3,3-dimethyl-butyl)-phenyl]-1-isocyanatoethyl}-4,4-dimethyl-hept-6-enyloxy)-dimethyl-silane (552 mg) was mixed in tetrahydrofuran (10 mL). To the reaction solution was added 2M ammonia/methanol solution (3.18 mL), and the reaction solution was stirred at room temperature for 18.5 hours. The reaction solution was concentrated under reduced pressure, and the resulted residue was purified through silica gel column chromatography (ethyl acetate:hexane=2:1) to give the titled compound (574 mg).

$^1$H-NMR (400 MHz, CDCl$_3$) 0.02 (s, 3.0H), 0.03 (s, 3.0H), 0.51 (s, 1.5H), 0.74 (s, 1.5H), 0.76 (s, 1.5H), 0.84 (s, 1.5H), 0.88 (s, 4.5H), 0.88 (s, 4.5H), 0.97 (s, 4.5H), 0.98 (s, 4.5H), 1.13-1.48 (m, 6.0H), 1.84 (s, 1.5H), 1.88 (s, 1.5H), 2.22 (d, J=10.48 Hz, 0.5H), 2.34 (d, J=10.88 Hz, 0.5H), 2.63-2.69 (m, 2.0H), 3.35-3.41 (m, 1.0H), 3.46 (t, J=5.91 Hz, 1.0H), 3.95 (s, 1.0H), 4.15 (s, 1.0H), 4.85 (dd, J=17.13, 1.81 Hz, 0.5H), 5.09 (dd, J=10.07, 2.01 Hz, 0.5H), 5.23-5.31 (m, 1.0H), 5.39-5.43 (m, 1.0H), 5.70-5.80 (m, 0.5H), 5.94-6.04 (m, 0.5H), 7.13-7.20 (m, 1.5H), 7.36-7.32 (m, 1.0H), 7.49 (d, J=1.61 Hz, 0.5H)

Step 10

4-[3-Chloro-4-(3,3-dimethyl-butyl)-phenyl]-5-(4-hydroxy-1,1-dimethyl-butyl)-4-methyl-3,4-dihydro-1H-pyrimidin-2-one (Optically Active Compound)

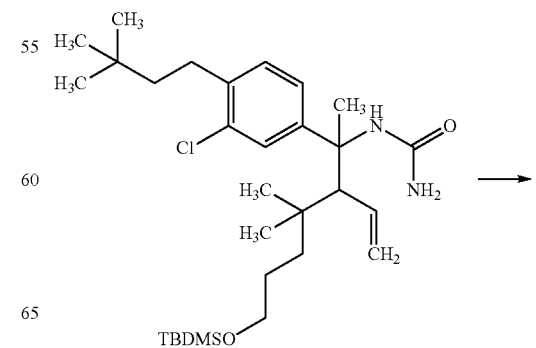

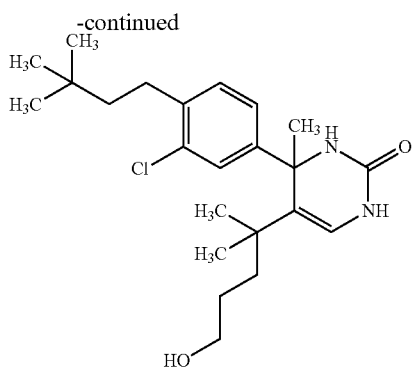

{6-(tert-Butyl-dimethyl-silanyloxy)-1-[3-chloro-4-(3,3-dimethyl-butyl)-phenyl]-1,3,3-trimethyl-3-vinyl-hexyl}-urea (574 mg) was mixed in methanol (10 mL). The reaction solution was stirred at −78° C. for 1 hour under ozone flow. To the reaction solution were added dimethylsulfide (0.785 mL) at −78° C. and then 2M hydrochloric acid/methanol solution (1.06 mL) under ice cooling. The reaction solution was stirred overnight, which was then concentrated. To the resulted residue was added saturated aqueous sodium hydrogen carbonate solution, which was then extracted with ethyl acetate. The organic layer was washed sequentially with water and aqueous saturated sodium chloride solution, and dried over sodium sulfate. After removing sodium sulfate on a filter, the filtrate was concentrated. The resulted residue was purified through silica gel column chromatography (methanol:chloroform=1:10) to give a racemate of the titled compound (257 mg).

The racemate was separated and purified by a recycling preparative chromatograph.

The titled compound (103 mg) was obtained as a compound in a fraction eluted later in a recycling preparative chromatograph (separation condition A2).

The compound was analyzed in the analytical condition B2, and the retention time was 5.6 minutes and the optical purity was >99% ee.

The enantiomer of the titled compound was obtained as a compound in a fraction eluted earlier in a recycling preparative chromatograph (separation condition A2).

The compound was analyzed in the analytical condition B2, and the retention time was 3.8 minutes.

The separation condition is shown as follows.
(Separation Condition A2)
Separation instrument; Recycling preparative chromatograph LC-9225 NEXT SERIES Japan Analytical Industry Co., Ltd.
Column; DAICEL CHIRALPAK IA 2.0 cmφ×25 cm
Mobile phase; hexane:2-propanol=80:20
Flow rate; 10.0 mL/min
Detection; UV (254 nm)

The analytical condition in the chiral column is shown as follows.
(Analytical Condition B2)
Measuring instrument; HPLC system Shimadzu Corporation high-performance liquid chromatograph prominence
Column; DAICEL CHIRALPAK IA-3 0.46 cmφ×15 cm
Column temperature; 40° C.
Mobile phase; hexane:2-propanol=80:20
Flow rate; 1.0 mL/min
Detection; UV (254 nm)

$^1$H-NMR (400 MHz, CDCl$_3$) 0.84 (s, 3H), 0.97 (s, 3H), 0.98 (s, 9H), 1.24-1.48 (m, 6H), 1.84 (s, 3H), 2.65-2.69 (m, 2H), 3.55-3.45 (m, 2H), 4.66 (s, 1H), 6.07 (d, J=5.24 Hz, 1H), 6.60 (s, 1H), 7.17 (d, J=8.061 Hz, 1H), 7.31 (dd, J=8.06, 2.01 Hz, 1H), 7.46 (d, J=2.01 Hz, 1H)

Step 1

4-{4-[3-Chloro-4-(3,3-dimethyl-butyl)-phenyl]-4-methyl-2-oxo-1,2,3,4-tetrahydro-pyrimidin-5-yl}-4-methyl-pentanal (Optically Active Compound)

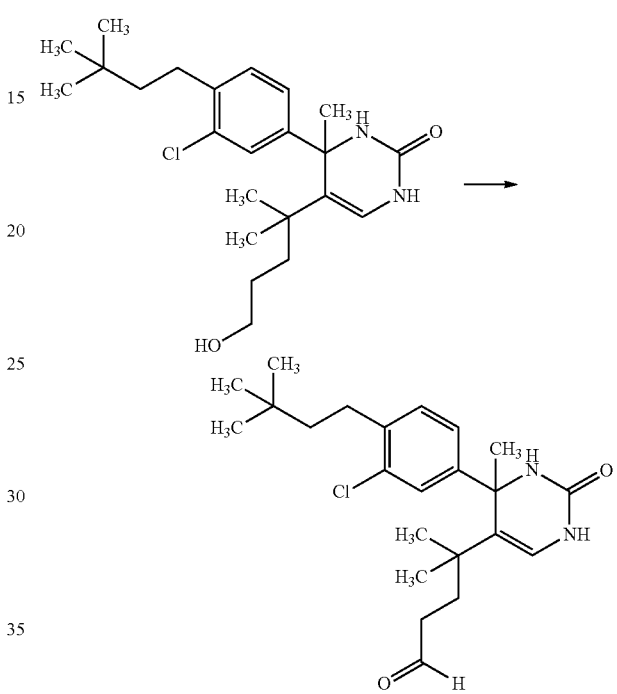

4-[3-Chloro-4-(3,3-dimethyl-butyl)-phenyl]-5-(4-hydroxy-1,1-dimethyl-butyl)-4-methyl-3,4-dihydro-1H-pyrimidin-2-one (22.6 mg) obtained in the previous step was mixed in chloroform (2.0 mL). To the reaction solution was added Dess-Martin Periodinane (67.7 mg) under ice cooling, and the reaction solution was stirred under ice cooling for 1 hour. To the reaction solution were added 10 w/v % aqueous sodium sulfite solution and saturated aqueous sodium hydrogen carbonate solution, which was then extracted with ethyl acetate. The organic layer was washed sequentially with saturated aqueous sodium hydrogen carbonate solution and aqueous saturated sodium chloride solution, and dried over sodium sulfate. After removing sodium sulfate on a filter, the filtrate was concentrated to give the titled compound (25.1 mg).

$^1$H-NMR (400 MHz, CDCl$_3$) 0.86 (s, 3H), 0.98 (s, 9H), 0.99 (s, 3H), 1.27-1.19 (m, 1H), 1.42-1.47 (m, 2H), 1.49-1.56 (m, 1H), 1.84 (s, 3H), 2.24-2.32 (m, 2H), 2.65-2.69 (m, 2H), 4.62 (s, 1H), 6.07 (d, J=5.24 Hz, 1H), 6.43 (s, 1H), 7.17 (d, J=8.06 Hz, 1H), 7.30 (dd, J=8.06, 2.01 Hz, 1H), 7.46 (d, J=2.01 Hz, 1H), 9.66 (t, J=1.21 Hz, 1H)

153

Step 12

4-{(4-[3-Chloro-4-(3,3-dimethyl-butyl)-phenyl]-4-methyl-2-oxo-1,2,3,4-tetrahydro-pyrimidin-5-yl}-4-methyl-pentanoic Acid (Optically Active Compound)

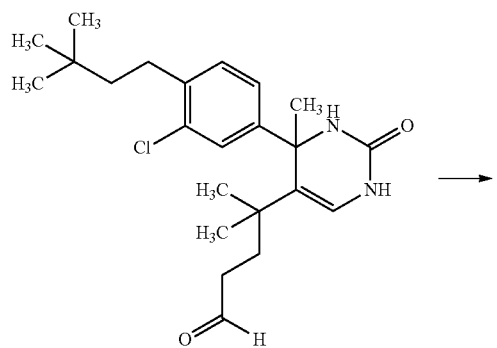

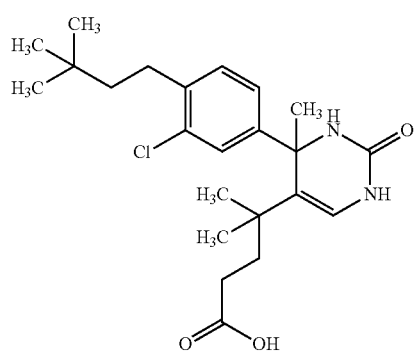

4-{4-[3-Chloro-4-(3,3-dimethyl-butyl)-phenyl]-4-methy-2-oxo-1,2,3,4-tetrahydro-pyrimidin-5-yl}-4-methyl-pentanal (25.1 mg) obtained in the previous step, 2-methyl-2-butene (0.0588 mL), and 1M aqueous sodium dihydrogenphosphate solution (0.555 mL) were mixed in tert-butanol (1.5 mL) and acetonitrile (3.0 mL). To the reaction solution was added 0.166M aqueous sodium chlorite solution (0.500 mL), and the reaction solution was stirred at room temperature for 2.5 hours. To the reaction solution were added 10 w/v % aqueous sodium sulfite solution and 1 M hydrochloric acid, which was then extracted with ethyl acetate. The organic layer was washed with aqueous saturated sodium chloride solution, and dried over sodium sulfate. After removing sodium sulfate on a filter, the filtrate was concentrated. The resulted residue was purified through thin layer silica gel chromatography (methanol:chloroform=1:9) to give the titled compound (13.4 mg).

154

Example 154

Preparation of 3-{(S)-4-[3-chloro-4-(3,3-dimethyl-butyl)-phenyl]-5-isopropyl-4-methyl-2-oxo-3,4-dihydro-2H-pyrimidin-1-ylmethyl}-cyclobutanecarboxylic acid Step 1

4-Benzyloxy-butylaldehyde

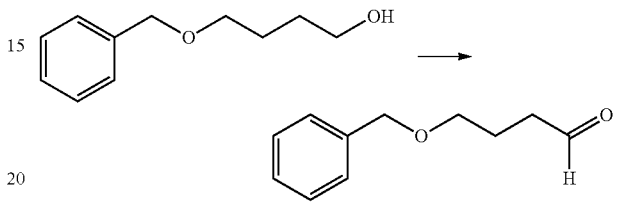

4-Benzyloxy-butan-1-ol (5.0 g), potassium bromide (0.66 g), and 2,2,6,6-tetramethylpiperidine 1-oxyl free radical (43.1 mg) were mixed in toluene (15 mL), ethyl acetate (15 mL), and water (3 mL). To the reaction solution were added dropwise a mixed solution of potassium hydrogen carbonate (5.55 g) in water (15 mL) and then 15 w/w/o aqueous sodium hypochlorite solution (16.5 mL) under ice cooling. The reaction solution was stirred under ice cooling for 1.5 hours. To the reaction solution was added 15 w/w % aqueous sodium hypochlorite solution (4 mL), and the reaction solution was stirred for additional 2 hours. The reaction solution was extracted with toluene. The organic layer was washed sequentially with water, a mixed solution of potassium iodide (73 mg) in 1M hydrochloric acid (5 mL), a mixed solution of sodium thiosulfate (2.3 g) and potassium carbonate (4.02 g) in water (8.3 mL), and aqueous saturated sodium chloride solution, and dried over magnesium sulfate. After removing magnesium sulfate on a filter, the filtrate was concentrated under reduced pressure to give the titled compound (4.08 g) as a crude product.

$^1$H-NMR (400 MHz, CDCl$_3$) 1.91-1.99 (m, 2H), 2.55 (td, J=7.05, 1.62 Hz, 2H), 3.51 (t, J=6.13 Hz, 2H), 4.49 (s, 2H), 7.15-7.37 (m, 5H), 9.79 (t, J=1.62 Hz, 1H)

Step 2

1-((E)-4-Benzyloxy-but-1-enyl)-piperidine

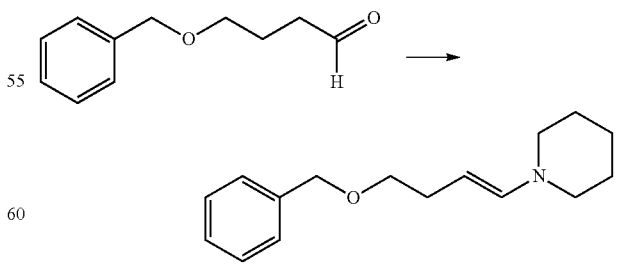

4-Benzyloxy-butylaldehyde (4.08 g) and Molecular Sieves 4A (15.8 g) were mixed in toluene (55 mL). To the reaction solution was added a mixed solution of piperidine (1.36 mL) in toluene (15 mL) under ice cooling, and the reaction solution was stirred at room temperature overnight. After removing an insoluble on a filter, the filtrate was concentrated under reduced pressure to give the titled compound (5.24 g) as a crude product.

$^1$H-NMR (400 MHz, DMSO-D$_6$) 1.38-1.65 (m, 6H), 2.13-2.20 (m, 2H), 2.69 (t, J=5.09 Hz, 4H), 3.35 (t, J=7.05 Hz, 2H), 4.17-4.25 (m, 1H), 4.44 (s, 2H), 5.86 (d, J=13.87 Hz, 1H), 7.14-7.36 (m, 5H)

Step 3

3-(2-Benzyloxy-ethyl)-2-piperidin-1-yl-cyclobutan-ecarboxylic Acid ethyl Ester

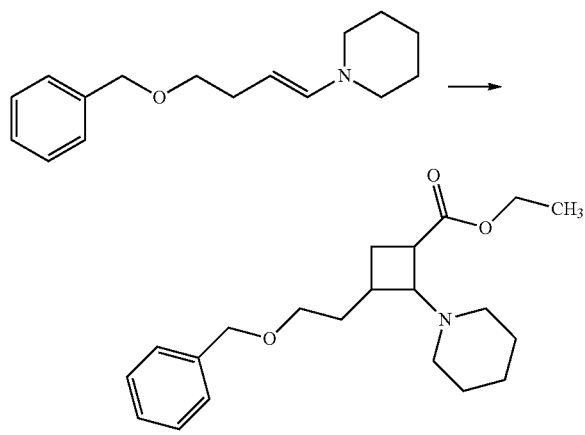

1-((E)-4-Benzyloxy-but-1-enyl)-piperidine (5.24 g) and hydroquinone (13.2 mg) were mixed in acetonitrile (3.45 mL). To the reaction solution was added ethyl acrylate (1.89 mL), and the reaction solution was stirred at 85° C. overnight. The reaction solution was concentrated under reduced pressure to give the titled compound (6.45 g) as a crude product.

$^1$H-NMR (400 MHz, DMSO-D$_6$) 1.15 (t, J=7.05 Hz, 3H), 1.30-2.35 (m, 16H), 2.65-2.79 (m, 1H), 3.36-3.45 (m, 3H), 4.00-4.08 (m, 2H), 4.42 (s, 2H), 7.16-7.36 (m, 5H)

Step 4

3-(2-Benzyloxy-ethyl)-cyclobut-1-enecarboxylic Acid

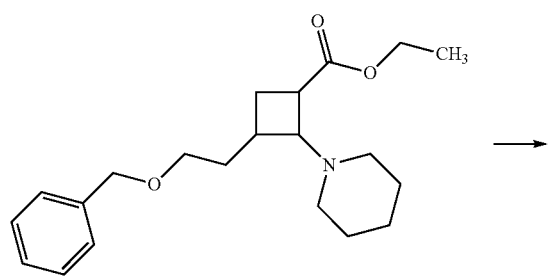

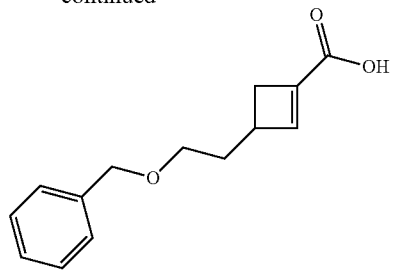

3-(2-Benzyloxy-ethyl)-2-piperidin-1-yl-cyclobutanecarboxylic acid ethyl ester (6.45 g) was mixed in methyl p-toluenesulfonate (1.92 mL). The reaction solution was stirred at 105° C. for 1 hour. The reaction solution was cooled to 50° C., and water (13.5 mL) was added thereto. To the reaction solution was added potassium hydroxide (3.04 g, 85%) under ice cooling, and then the reaction solution was stirred at 45° C. overnight. The reaction solution was washed sequentially with diethylether and a mixed solution of diethylether-hexane solution (1:1). Concentrated hydrochloric acid was added to the aqueous layer under ice cooling so that the aqueous layer was adjusted to pH 1, which was then extracted with ethyl acetate. The organic layer was washed sequentially with water and aqueous saturated sodium chloride solution, and dried over magnesium sulfate. After removing magnesium sulfate on a filter, the filtrate was concentrated under reduced pressure to give the titled compound (4.57 g) as a crude product.

$^1$H-NMR (400 MHz, CDCl$_3$) 1.82-1.88 (m, 8H), 2.50 (t, J=7.17 Hz, 1H), 2.84-2.93 (m, 2H), 3.51-3.56 (m, 2H), 4.51 (s, 3H), 6.98 (d, J=0.92 Hz, 1H), 7.26-7.38 (m, 5H)

Step 5 trans-3-(2-Benzyloxy-ethyl)-cyclobutanecarboxylic Acid

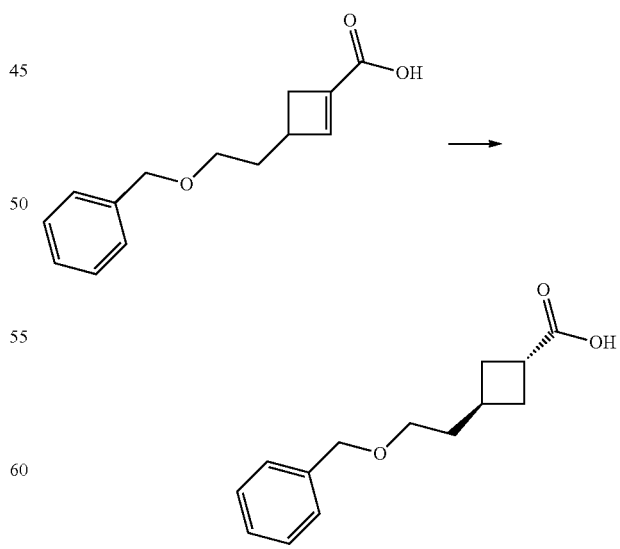

3-(2-Benzyloxy-ethyl)-cyclobut-1-enecarboxylic acid (4.57 g) and zinc (4.17 g) were mixed in tetrahydrofuran (53 mL) and water (21.2 mL). To the reaction solution was added dropwise concentrated hydrochloric acid (31.8 mL) under ice cooling, and the reaction solution was stirred at room temperature for 2.5 hours. Tetrahydrofuran was distilled away under reduced pressure, which was then extracted with ethyl acetate. The organic layer was washed sequentially with water and aqueous saturated sodium chloride solution, and dried over magnesium sulfate. After removing magnesium sulfate on a filter, the filtrate was concentrated under reduced pressure. The resulted residue was purified through silica gel column chromatography (acetone:hexane=1:9→1:6) to give the titled compound (2.93 g).

1H-NMR (400 MHz, CDCl$_3$) 1.78 (q, J=6.73 Hz, 2H), 1.92-2.01 (m, 3H), 2.38-2.59 (m, 5H), 3.09-3.17 (m, 1H), 3.43 (t, J=6.73 Hz, 2H), 4.48 (s, 2H), 7.26-7.36 (m, 5H)

Step 6 trans-3-(2-Benzyloxy-ethyl)-cyclobutanecarboxylic Acid ethyl Ester

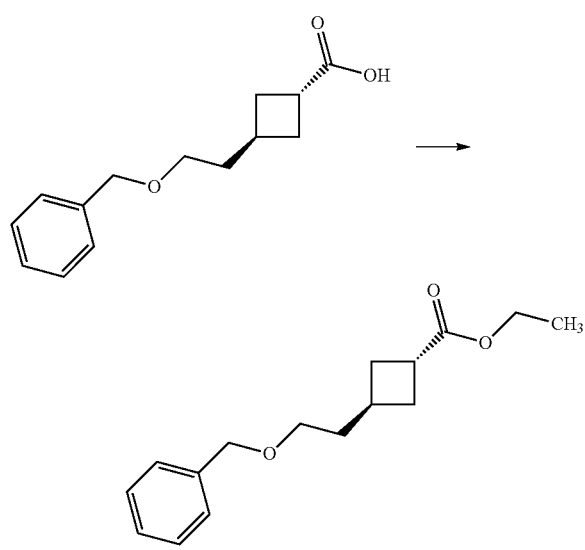

trans-3-(2-Benzyloxy-ethyl)-cyclobutanecarboxylic acid (2.93 g), 4-dimethylaminopyridine (0.15 g), 1-hydroxybenzotriazole monohydrate, and ethanol (0.86 mL) were mixed in chloroform. To the reaction solution was added 1-ethyl-3-(3-dimethylaminopropyl)carbodiimide hydrochloride (2.84 g) under ice cooling, and the reaction solution was stirred at room temperature overnight. The reaction solution was concentrated under reduced pressure and water was added to the resulted residue, which was extracted with ethyl acetate. The organic layer was washed sequentially with water and aqueous saturated sodium chloride solution, and dried over magnesium sulfate. After removing magnesium sulfate on a filter, the filtrate was concentrated under reduced pressure. The resulted residue was purified through silica gel column chromatography (ethyl acetate:hexane=1:16) to give the titled compound (2.37 g).

$^1$H-NMR (400 MHz, CDCl$_3$) 1.26 (t, J=7.13 Hz, 4H), 1.78 (q, J=6.82 Hz, 2H), 1.89-1.96 (m, 2H), 2.35-2.44 (m, 2H), 2.47-2.54 (m, 1H), 3.03-3.11 (m, 1H), 3.42 (t, J=6.82 Hz, 2H), 4.14 (q, J=7.13 Hz, 3H), 4.48 (s, 2H), 7.24-7.36 (m, 11H)

Step 7 trans-3-(2-Hydroxy-ethyl)-cyclobutanecarboxylic Acid ethyl Ester

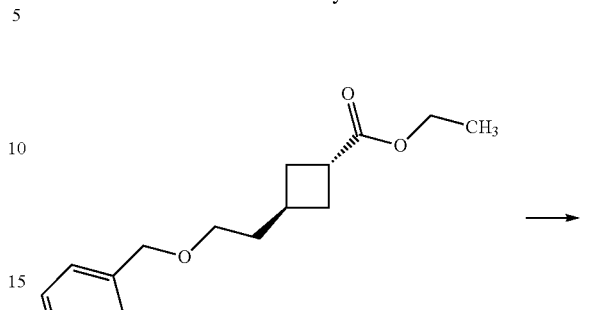

trans-3-(2-Benzyloxy-ethyl)-cyclobutanecarboxylic acid ethyl ester (2.37 g) was mixed in tetrahydrofuran (24 mL). To the reaction solution was added 10 w/w % palladium hydroxide/activated carbon (0.24 g), and the reaction solution was stirred at room temperature for 3.5 hours at an ordinary pressure under hydrogen gas. After removing palladium hydroxide/activated carbon on a filter, the filtrate was concentrated under reduced pressure. The resulted residue was purified through silica gel column chromatography (ethyl acetate:hexane=1:4→1:3→1:1.5) to give the titled compound (1.24 g).

$^1$H-NMR (400 MHz, CDCl$_3$) 1.19 (brs, 1H), 1.26 (t, J=7.17 Hz, 3H), 1.74 (q, J=6.94 Hz, 2H), 1.87-1.97 (m, 2H), 2.37-2.45 (m, 2H), 2.46-2.55 (m, 1H), 3.04-3.13 (m, 1H), 3.57-3.64 (m, 2H), 4.14 (q, J=7.17 Hz, 3H)

Step 8 trans-3-Carboxymethyl-cyclobutanecarboxylic Acid ethyl Ester

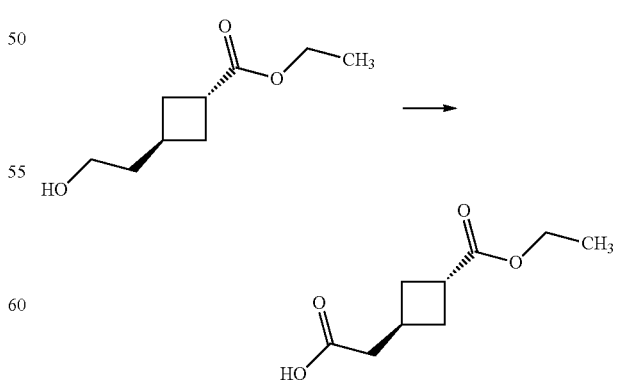

trans-3-(2-Hydroxy-ethyl)-cyclobutanecarboxylic acid ethyl ester (1.24 g) and 2,2,6,6-tetramethylpiperidine-1-oxyl free radical (39 mg) were mixed in acetonitrile (12 mL) and 1M phosphate buffer (5.5 mL). To the reaction solution were added sodium chlorite (0.91 g) and 15 w/w % aqueous sodium hypochlorite solution (74 piL) under ice cooling, and the reaction solution was stirred under ice cooling for 5 minutes and then stirred at room temperature for 4 hours. To the reaction solution was added aqueous sodium sulfite solution under ice cooling, and the reaction solution was stirred at room temperature for 30 minutes. An aqueous potassium hydrogensulfate solution was added to the reaction solution so that the aqueous layer was adjusted to pH 2, which was then extracted with ethyl acetate. The organic layer was washed with aqueous saturated sodium chloride solution, and dried over magnesium sulfate. After removing magnesium sulfate on a filter, the filtrate was concentrated under reduced pressure. The resulted residue was purified through silica gel column chromatography (methanol:chloroform=1:20) to give the titled compound (1.18 g).

$^1$H-NMR (400 MHz, CDCl$_3$) 1.26 (t, J=7.17 Hz, 4H), 1.98-2.05 (m, 2H), 2.46-2.53 (m, 2H), 2.61-2.65 (m, 1H), 2.67-2.71 (m, 1H), 2.75-2.87 (m, 1H), 3.06-3.14 (m, 1H), 4.15 (q, J=7.17 Hz, 2H)

Step 9 trans-3-(Benzyloxycarbonylaminomethyl)-cyclobutanecarboxylic Acid ethyl Ester

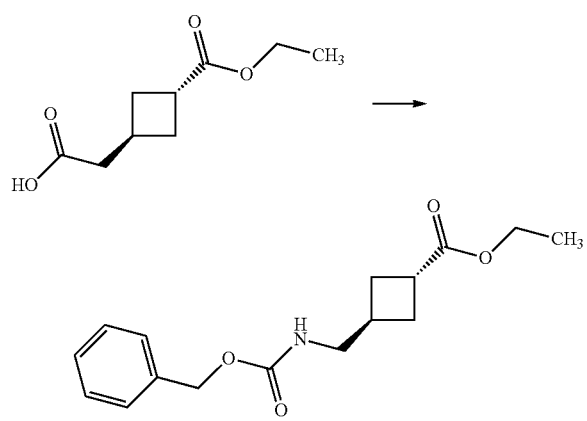

trans-3-Carboxymethyl-cyclobutanecarboxylic acid ethyl ester (1.18 g), benzylalcohol (1.05 mL), and triethylamine (3.8 mL) were mixed in toluene (12 mL). To the reaction solution was added diphenyl phosphoryl azide (1.6 mL) under ice cooling, and the reaction solution was stirred at room temperature for 15 minutes, then at 100° C. for 1 hour, and then at 70° C. for 7 hours. To the reaction solution was added water at room temperature, which was then extracted with ethyl acetate. The organic layer was washed sequentially with water, aqueous potassium hydrogensulfate solution, aqueous sodium hydrogen carbonate solution, and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:9→1:4→1:3) to give the titled compound (0.85 g).

$^1$H-NMR (400 MHz, CDCl$_3$) 1.25 (t, J=7.17 Hz, 3H), 1.93-2.00 (m, 2H), 2.33-2.40 (m, 2H), 2.50-2.55 (m, 1H), 3.06-3.13 (m, 1H), 3.27-3.31 (m, 2H), 4.14 (q, J=7.17 Hz, 3H), 4.72 (brs, 1H), 5.10 (s, 2H), 7.30-7.38 (m, 5H)

Step 10 trans-3-Aminomethyl-cyclobutanecarboxylic Acid ethyl Ester

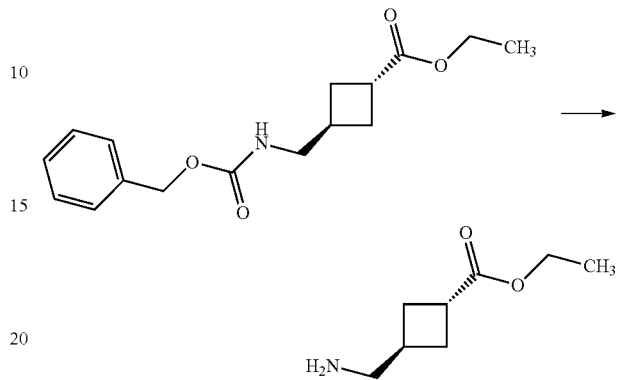

trans-3-(Benzyloxycarbonylaminomethyl)-cyclobutanecarboxylic acid ethyl ester (400 mg) was mixed in ethanol. To the reaction solution was added 10 w/w % palladium/activated carbon (60 mg), and the reaction solution was stirred at room temperature overnight at an ordinary pressure under hydrogen gas overnight. After removing palladium/activated carbon on a filter, the filtrate was concentrated under reduced pressure to give the titled compound (232 mg) as a crude product.

$^1$H-NMR (400 MHz, CDCl$_3$) 1.26 (t, J=7.17 Hz, 3H), 1.92-1.98 (m, 2H), 2.34-2.43 (m, 3H), 2.76-2.79 (m, 2H), 3.04-3.12 (m, 1H), 4.15 (q, J=7.17 Hz, 3H)

Step 11 trans-3-Isocyanatomethyl-cyclobutanecarboxylic Acid ethyl Ester

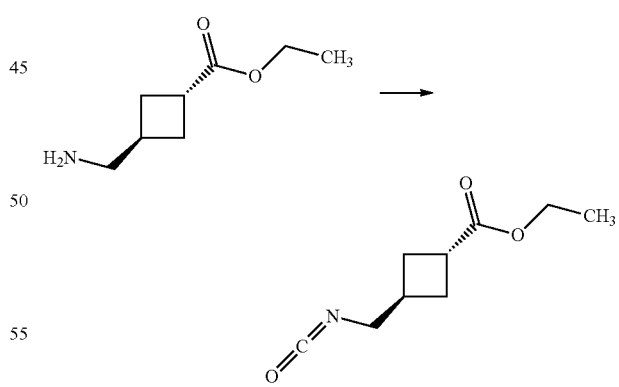

3-Aminomethyl-cyclobutanecarboxylic acid ethyl ester (232 mg) was mixed in dichloromethane (5.5 mL) and saturated aqueous sodium hydrogen carbonate solution (5.5 mL). To the reaction solution was added triphosgene (134 mg) under ice cooling, and the reaction solution was stirred under ice cooling for 3 hours. The reaction solution was extracted with chloroform. The organic layer was washed with aqueous saturated sodium chloride solution, and dried over sodium sulfate. After removing sodium sulfate on a filter, the filter, the filtrate was concentrated under reduced pressure to give the titled compound (236 mg) as a crude product.

$^1$H-NMR (400 MHz, CDCl$_3$) 1.27 (t, J=7.11 Hz, 3H), 2.01-2.08 (m, 2H), 2.37-2.45 (m, 2H), 2.58-2.68 (m, 1H), 3.04-3.13 (m, 1H), 3.36 (d, J=6.70 Hz, 2H), 4.16 (q, J=7.11 Hz, 2H)

Step 12

3-(3-{(R)-1-[3-Chloro-4-(3,3-dimethyl-butyl)-phenyl]-2-hydroxymethyl-1,3-dimethyl-butyl}-ureidomethyl)-cyclobutanecarboxylic Acid ethyl Ester

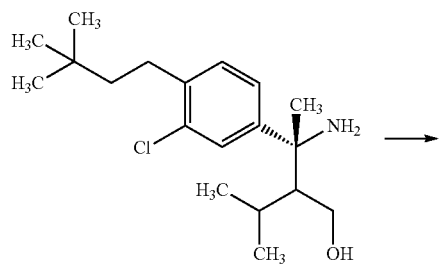

(R)-3-amino-3-[3-chloro-4-(3,3-dimethyl-butyl)-phenyl]-2-isopropyl-butan-1-ol (130 mg) obtained according to Example 87 (a method for preparation using an optically active sulfinamide) Steps 1 to 8 was mixed in tetrahydrofuran (0.5 mL). To the reaction solution was added a mixed solution of trans-3-isocyanatomethyl-cyclobutanecarboxylic acid ethyl ester (56 mg) in tetrahydrofuran (0.5 mL) under ice cooling, and the reaction solution was stirred at room temperature overnight. To the reaction solution was added N,N,N'-trimethylethylenediamine (10 μl), which was then concentrated under reduced pressure. The resulted residue was purified through silica gel column chromatography (acetone:chloroform=1:6) to give the titled compound (128 mg, d.r.=79:21).

$^1$H-NMR (400 MHz, CDCl$_3$) 0.22 (d, J=6.94 Hz, 0.69H), 0.75 (d, J=6.94 Hz, 2.31H), 0.80 (d, J=6.94 Hz, 2.31H), 0.95 (d, J=6.94 Hz, 0.69H), 0.97 (s, 2.07H), 0.98 (s, 6.93H), 1.25 (t, J=7.17 Hz, 3H), 1.40-1.49 (m, 2.77H), 1.64-1.87 (m, 6.23H), 2.14-2.40 (m, 3H), 2.63-2.69 (m, 2H), 2.94-3.19 (m, 3H), 3.71-4.03 (m, 3H), 4.09-4.15 (m, 2H), 7.15-7.21 (m, 1H), 7.24-7.30 (m, 1H), 7.35-7.43 (m, 2H)

Step 13

3-{(S)-4-[3-Chloro-4-(3,3-dimethyl-butyl)-phenyl]-5-isopropyl-4-methyl-2-oxo-3,4-dihydro-2H-pyrimidin-1-ylmethyl}-cyclobutanecarboxylic Acid ethyl Ester

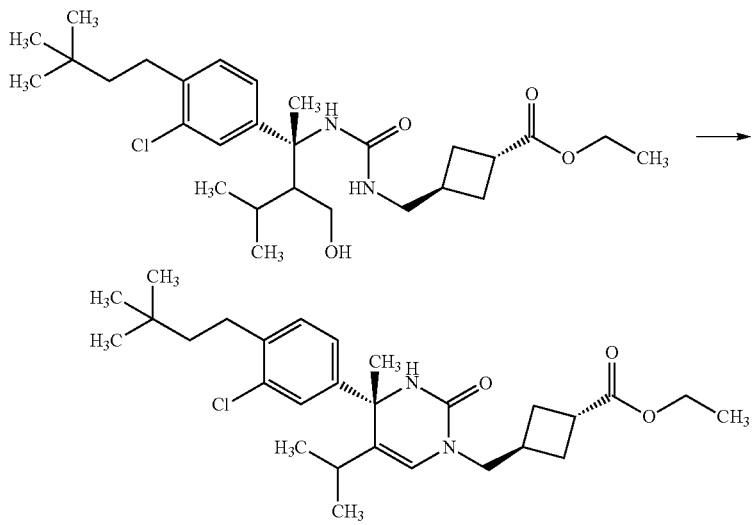

-continued

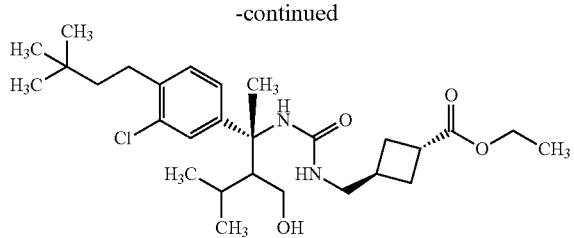

3-(3-{(R)-1-[3-Chloro-4-(3,3-dimethyl-butyl)-phenyl]-2-hydroxymethyl-1,3-dimethyl-butyl}-ureidomethyl)-cyclobutanecarboxylic acid ethyl ester (128 mg) and iodobenzene diacetate (90 mg) were mixed in dichloromethane (1.3 mL). To the reaction solution was added 2,2,6,6-tetramethylpiperidine-1-oxyl free radical (2 mg) under ice cooling, and the reaction solution was stirred at room temperature for 2 hours. To the reaction solution was added trifluoroacetic acid (0.74 μl), and the reaction solution was stirred for 1 hour. To the reaction solution was added dropwise aqueous sodium sulfite solution under ice cooling, and then thereto was added dropwise aqueous sodium hydrogen carbonate solution so that the aqueous layer was adjusted to pH 6. The resulted mixed solution was extracted with ethyl acetate. The organic layer was washed sequentially with water and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:3), followed by purification by recycling preparative chromatograph to give the titled compound (72 mg).

The separation condition is shown as follows.
Separation instrument; Recycling preparative chromatograph LC-9225 NEXT SERIES Japan Analytical Industry Co., Ltd.
Column; DAICEL CHIRALPAK IA-3 2.0 cmφ×25 cm
Mobile phase; hexane:2-propanol=90:10
Flow rate; 10.0 mL/min
Detection; UV (220 nm)

$^1$H-NMR (400 MHz, CDCl$_3$) 0.72 (d, J=6.82 Hz, 3H), 0.98 (s, 9H), 1.05 (d, J=6.82 Hz, 3H), 1.26 (t, J=7.13 Hz, 3H), 1.42-1.47 (m, 2H), 1.68 (s, 3H), 1.86-1.94 (m, 1H), 2.04-2.11 (m, 2H), 2.35-2.42 (m, 2H), 2.63-2.77 (m, 3H), 3.09-3.18 (m, 1H), 3.58 (d, J=7.63 Hz, 2H), 4.15 (q, J=7.09 Hz, 2H), 4.62 (brs, 1H), 5.81 (s, 1H), 7.16 (d, J=8.04 Hz, 1H), 7.23 (dd, J=8.04, 1.91 Hz, 1H), 7.37 (d, J=1.81 Hz, 11H)

Step 14

3-{(S)-4-[3-Chloro-4-(3,3-dimethyl-butyl)-phenyl]-5-isopropyl-4-methyl-2-oxo-3,4-dihydro-2H-pyrimidin-1-ylmethyl}-cyclobutanecarboxylic Acid 3-{(S)-4-[3-Chloro-4-(3,3-dimethyl-butyl)-phenyl]-5-isopropyl-4-methyl-2-oxo-3,4-dihydro-2H-pyrimidin-1-yl-methyl}-cyclobutanecarboxylic acid ethyl ester (72 mg) was mixed in tetrahydrofuran (360 μl) and methanol (360 μl). To the reaction solution was added dropwise 2M aqueous sodium hydroxide solution (296 μl) under ice cooling, and the reaction solution was stirred at room temperature overnight. The reaction solution was concentrated under reduced pressure, and thereto was added water. To the mixed solution was added 1M hydrochloric acid (590 μl) under ice cooling, and then the mixed solution was stirred at room temperature. The precipitated solid was filtered to give the titled compound (59 mg).

The specific optical rotation of the resulted compound was $[\alpha]_D^{25}$=+141.2° (c=0.05, methanol).

The resulted compound was analyzed by a chiral column, and the retention time of the resulted titled compound was 10.1 minutes.

The analytical condition in the chiral column is shown as follows.
Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 1.0 mL/min
Detection; UV (220 nm)

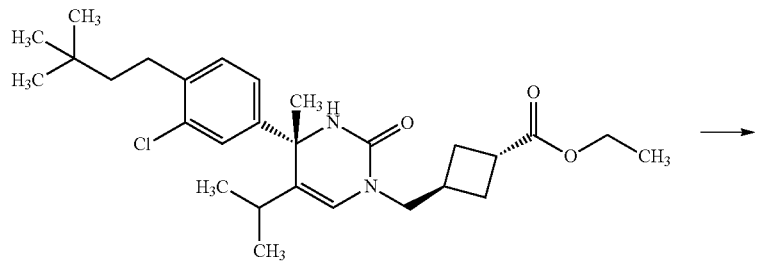

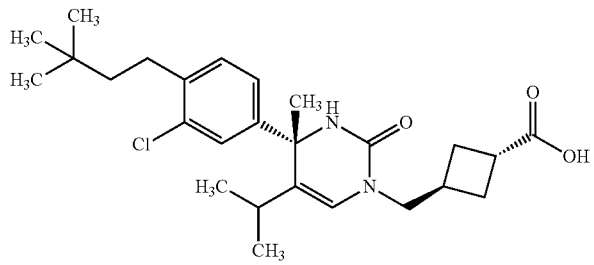

Example 159

Preparation of 4-{(S)-4-[3-chloro-4-(3,3-dimethyl-butyl)-phenyl]-5-isopropyl-4-methyl-2-oxo-3,4-dihydro-2H-pyrimidin-1-yl}-benzoic Acid

Step 1

(S)-2-Methyl-propane-2-sulfinic acid {(R)-1-[3-chloro-4-(3,3-dimethyl-butyl)-phenyl]-2-hydroxymethyl-1,3-dimethyl-butyl}amide

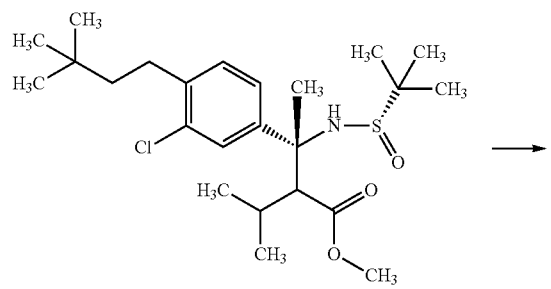

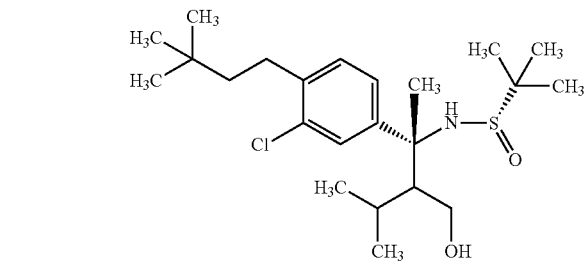

(R)-3-[3-Chloro-4-(3.3-dimethyl-butyl)-phenyl]-2-isopropyl-3-((S)-2-methyl-propane-sulfinylamino)-butyric acid methyl ester (3.39 g) prepared according to Example 87 (a method for preparation using an optically active sulfinamide) Steps 1 to 6 was mixed in tetrahydrofuran (30 mL). To the reaction solution was added dropwise 1M isobutylaluminum hydride/toluene solution (22.4 mL) at −78° C., and the reaction solution was stirred under ice cooling for 2.5 hours. To the reaction solution was added saturated aqueous Rochelle salt solution, which was then extracted with ethyl acetate. The organic layer was washed sequentially with aqueous saturated sodium chloride solution and water, and then concentrated under reduced pressure. The resulted residue was purified through silica gel column chromatography (ethyl acetate:hexane=1:2) to give the titled compound (3.01 g).

Step 2

(R)-3-Amino-3-[3-chloro-4-(3,3-dimethyl-butyl)-phenyl]-2-isopropyl-butan-1-ol

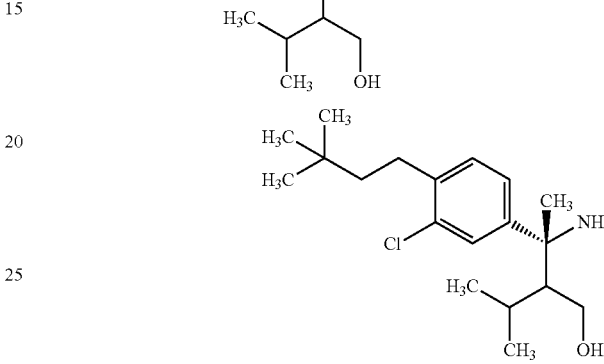

(S)-2-Methyl-propane-2-sulfinic acid {(R)-1-[3-chloro-4-(3,3-dimethyl-butyl)-phenyl]-2-hydroxymethyl-1,3-dimethyl-butyl}amide (3.0 g) was mixed in methanol (15 mL). To the reaction solution was added 2M hydrogen chloride/methanol solution (11.2 mL) under ice cooling, and the reaction solution was left to stand at room temperature overnight. The reaction solution was concentrated under reduced pressure, and to the residue was added saturated sodium carbonate solution under ice cooling so that the aqueous layer was adjusted to be alkaline. The mixed solution was extracted with chloroform, and the organic layer was dried over sodium sulfate. After removing sodium sulfate on a filter, the filtrate was concentrated under reduced pressure to give the titled compound (2.37 g) as a crude product.

Step 3

4-(3-{(R)-1-[3-Chloro-4-(3.3-dimethyl-butyl)-phenyl]-2-hydroxymethyl-1,3-dimethyl-butyl}-ureido)-benzoic Acid ethyl Ester

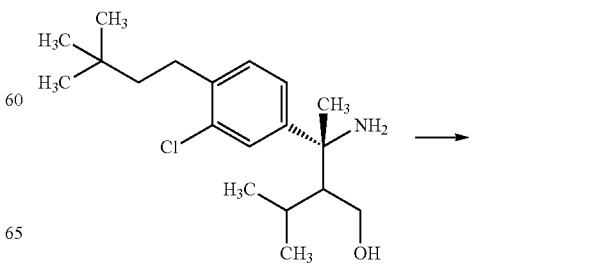

-continued

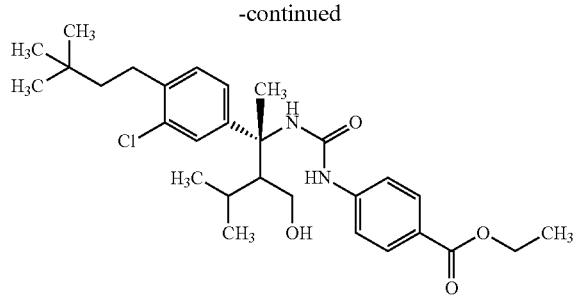

(R)-3-Amino-3-[3-chloro-4-(3,3-dimethyl-butyl)-phenyl]-2-isopropyl-butan-1-ol (100 mg) was mixed in tetrahydrofuran (1.5 mL). To the reaction solution was added 4-isocyanatebenzoic acid ethyl ester (59 mg) under ice cooling, and the reaction solution was stirred at room temperature for 1 hour. To the reaction solution was added 4-isocyanatebenzoic acid ethyl ester (34 mg), and the reaction solution was concentrated under reduced pressure. The resulted residue was purified through silica gel column chromatography (methanol:chloroform=5:95) to give the titled compound (139 mg).

$^1$H-NMR (400 MHz, CDCl$_3$) 0.74-0.83 (m, 3H), 0.83-0.88 (m, 3H), 0.92-1.01 (m, 9H), 1.30-1.49 (m, 5H), 1.85-2.03 (m, 5H), 2.54-2.67 (m, 1H), 3.76-4.02 (m, 1H), 4.28-4.40 (m, 2H), 6.24-6.42 (m, 1H), 7.10-7.56 (m, 5H), 7.85-8.03 (m, 2H)

Step 4

4-{(S)-4-[3-Chloro-4-(3,3-dimethyl-butyl)-phenyl]-5-isopropyl-4-methyl-2-oxo-3,4-dihydro-2H-pyrimidin-1-yl}-benzoic Acid ethyl Ester

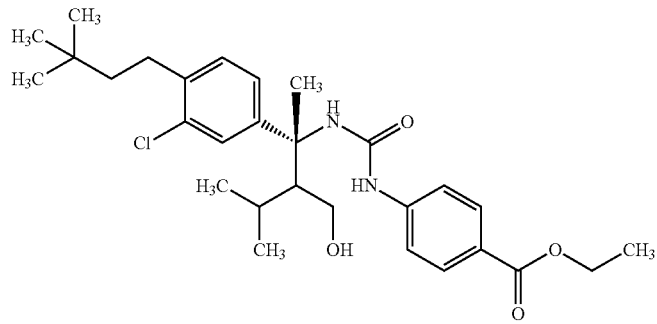

4-(3-{(R)-1-[3-Chloro-4-(3,3-dimethyl-butyl)-phenyl]-2-hydroxymethyl-1,3-dimethyl-butyl}-ureido)-benzoic acid ethyl ester (139 mg) and iodobenzene diacetate (182 mg) were mixed in dichloromethane (3.0 mL). To the reaction solution was added 2,2,6,6-tetramethylpiperidine 1-oxyl (4.0 mg) under ice cooling, and the reaction solution was stirred at room temperature for 3 hours. To the reaction solution was added saturated aqueous sodium sulfite solution under ice cooling, which was then extracted with chloroform. The organic layer was dried over sodium sulfate. After removing sodium sulfate on a filter, the filtrate was concentrated under reduced pressure. The resulted residue was purified through silica gel column chromatography (ethyl acetate:hexane=3:1) to give the titled compound (33 mg).

$^1$H-NMR (400 MHz, CDCl$_3$) 0.70-0.78 (m, 3H), 0.97 (s, 9H), 1.06-1.12 (m, 3H), 1.34-1.41 (m, 3H), 1.42-1.49 (m, 2H), 1.79 (s, 3H), 1.92-2.03 (m, 1H), 2.63-2.71 (m, 2H), 4.30-4.42 (m, 2H), 5.07 (brs, 1H), 6.18 (s, 1H), 7.13-7.23 (m, 1H), 7.27-7.34 (m, 1H), 7.38-7.49 (m, 3H), 8.00-8.11 (m, 2H)

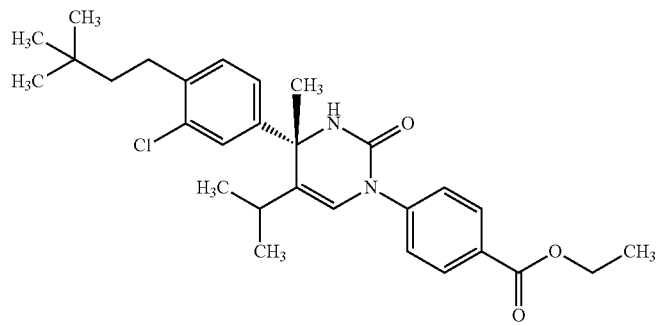

Step 5

4-{(S)-4-[3-Chloro-4-(3,3-dimethyl-butyl)-phenyl]-5-isopropyl-4-methyl-2-oxo-3,4-dihydro-2H-pyrimidin-1-yl}-benzoic Acid

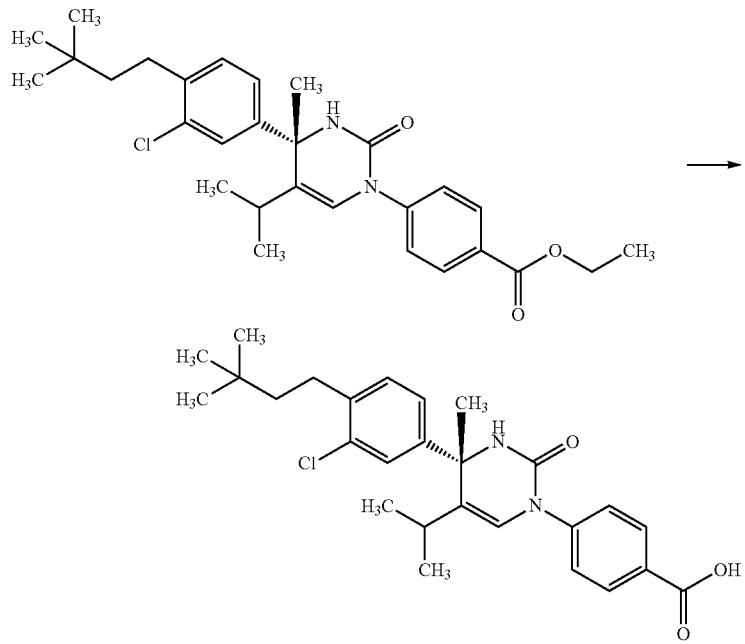

4-{(S)-4-[3-Chloro-4-(3,3-dimethyl-butyl)-phenyl]-5-isopropyl-4-methyl-2-oxo-3,4-dihydro-2H-pyrimidin-1-yl}-benzoic acid ethyl ester (33 mg) was mixed in ethanol (1.0 mL) and tetrahydrofuran (1.0 mL). To the reaction solution was added 2M aqueous sodium hydroxide solution (0.132 mL), and the reaction solution was stirred at room temperature for 90 minutes, and then stirred at 70° C. so that the reaction solution became cloudy. The reaction solution was concentrated under reduced pressure, and then thereto was added 2M aqueous hydrochloric acid solution (0.132 mL). The precipitated solid was filtered to give the titled compound (21 mg).

The specific optical rotation of the resulted compound was $[\alpha]_D^{25} = +87.5°$ (c=0.25, methanol).

The resulted compound was analyzed by a chiral column, and the retention time of the resulted titled compound was 16.2 minutes.

The analytical condition in a chiral column is shown as follows.

Measuring instrument; HPLC system Shimadzu Corporation high-performance liquid chromatograph prominence
Column; DAICEL CHIRALPAK AD-3R 0.46 cmφ×15 cm
Column temperature; 40° C.
Mobile phase; water:acetonitrile:formic acid=30:70:0.1
Flow rate; 1.0 mL/min
Detection; UV (220 nm)

Example 226

Step 1

4-(3-{(R)-1-[3-Chloro-4-(3.3-dimethyl-butyl)-phenyl]-2-hydroxymethyl-1,3-dimethyl-butyl}-ureido)-2-methoxy-benzoic Acid methyl Ester

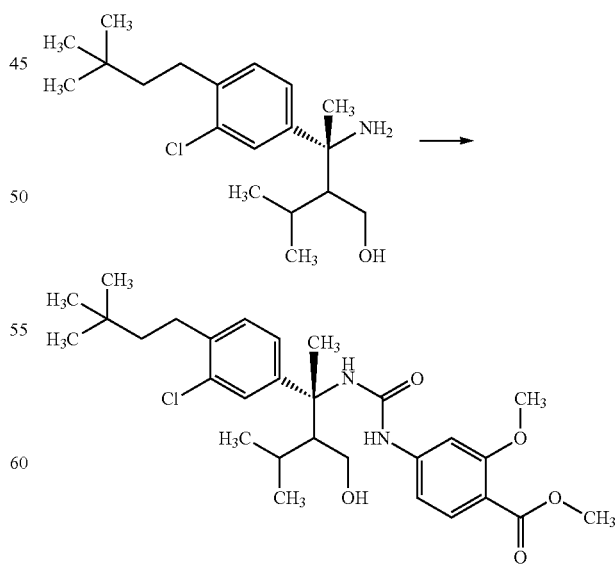

(R)-3-Amino-3-[3-chloro-4-(3,3-dimethyl-butyl)-phenyl]-2-isopropyl-butan-1-ol (181 mg, corresponding to 0.5 mmol) prepared according to Example 159 (a method for preparation using an optically active sulfinamide) Steps 1 to 2 was mixed in tetrahydrofuran (5.0 mL), and thereto was added 4-isocyanate-2-methoxy-benzoic acid methyl ester (114 mg) under ice cooling. A cooling bath was removed, and the reaction solution was stirred at room temperature overnight. The resulted solution was then concentrated under reduced pressure.

The resulted residue was purified through silica gel column chromatography (ethyl acetate:hexane=4:1) to give the titled compound (139 mg).

Step 2

4-{(S)-4-[3-Chloro-4-(3,3-dimethyl-butyl)-phenyl]-5-isopropyl-4-methyl-2-oxo-3,4-dihydro-2H-pyrimidin-1-yl}-2-methoxy-benzoic Acid methyl Ester

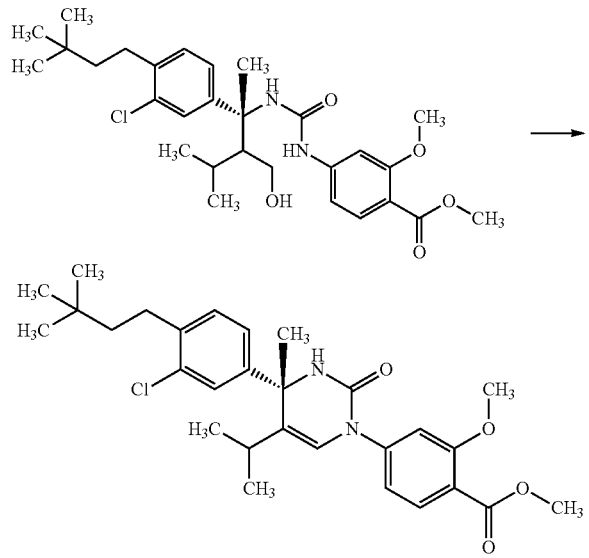

4-(3-{(R)-1-[3-Chloro-4-(3.3-dimethyl-butyl)-phenyl]-2-hydroxymethyl-1,3-dimethyl-butyl}-ureido)-2-methoxy-benzoic acid methyl ester (139 mg) and dichloromethane (2.0 mL) were mixed, and thereto were added 2,2,6,6-tetramethylpiperidine 1-oxyl (4.0 mg) and iodobenzene diacetate (92 mg) under ice cooling. A cooling bath was removed, and the reaction solution was stirred for about 3 hours. Then trifluoroacetic acid (119 mg) was added to the reaction solution. The reaction solution was stirred at room temperature for 80 minutes, and then thereto were added saturated aqueous sodium sulfite solution and chloroform, which was separated. The organic layer was dried over sodium sulfate. After filtered through sodium sulfate, the filtrate was concentrated under reduced pressure. The resulted residue was purified through silica gel column chromatography (ethyl acetate:hexane=2:3), followed by purification by thin layer silica gel chromatography (ethyl acetate:hexane=1:1) to give the titled compound (81 mg).

Step 3

4-{(S)-4-[3-Chloro-4-(3,3-dimethyl-butyl)-phenyl]-5-isopropyl-4-methyl-2-oxo-3,4-dihydro-2H-pyrimidin-1-yl}-2-methoxy-benzoic Acid

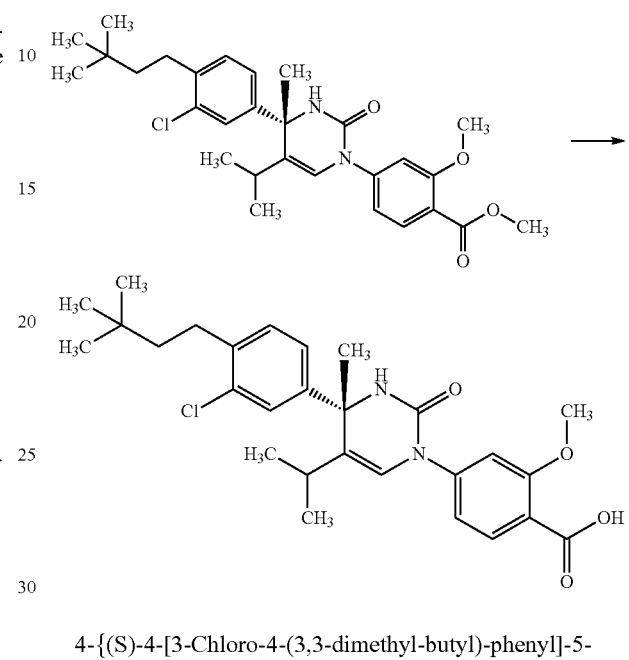

4-{(S)-4-[3-Chloro-4-(3,3-dimethyl-butyl)-phenyl]-5-isopropyl-4-methyl-2-oxo-3,4-dihydro-2H-pyrimidin-1-yl}-2-methoxy-benzoic acid methyl ester (68 mg), methanol (2.0 mL), and tetrahydrofuran (1.0 mL) were mixed. To the reaction solution was added 2M aqueous sodium hydroxide solution (0.2 mL) at room temperature, which was stirred at 70° C. for about 3 hours. The reaction solution was concentrated under reduced pressure, and then thereto was added 2M aqueous hydrochloric acid solution (0.2 mL). The precipitated solid was filtered and dried at 60° C. to give the titled compound (58 mg).

Example 229

Step 1 cis-(3-Hydroxymethyl-cyclobutyl)-acetic Acid tert-butyl Ester

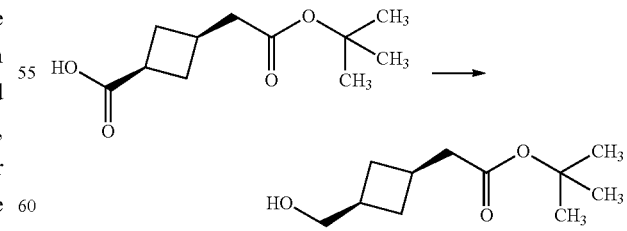

cis-3-tert-Butoxycarbonylmethyl-cyclobutanoic acid (10.0 g) was mixed with tetrahydrofuran (100 mL), and thereto was added dropwise 0.85M borane-tetrahydrofuran/tetrahydrofuran solution (82 mL) at −16° C. The reaction solution was stirred for 23 hours with naturally warming to room temperature, and then thereto was added 6M hydrochloric acid (20 mL). The reaction solution was concentrated, and then thereto were added ethyl acetate and water, which was separated. The organic layer was washed sequentially with water (3 times) and aqueous saturated sodium chloride solution, and dried over magnesium sulfate. After removing magnesium sulfate on a filter, the filtrate was concentrated under reduced pressure to give the titled compound (8.93 g).

$^1$H-NMR (400 MHz, CDCl$_3$) 1.43 (s, 9H), 1.45-1.51 (m, 2H), 2.18-2.25 (m, 2H), 2.29 (d, J=7.25 Hz, 2H), 2.36-2.43 (m, 1H), 2.58-2.48 (m, 1H), 3.55 (d, J=6.45 Hz, 2H)

Step 2 cis-(3-Hydroxymethyl-cyclobutyl)-acetic Acid methyl Ester

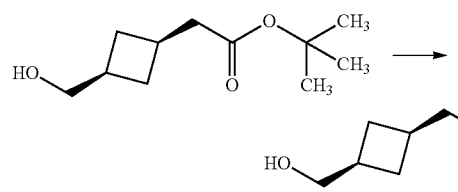

cis-(3-Hydroxymethyl-cyclobutyl)-acetic acid tert-butyl ester (1.25 g) was mixed with chloroform (6.0 mL), and then thereto was added trifluoroacetic acid (3.0 mL) at room temperature. The mixture was stirred for 71 hours, and then thereto was added trifluoroacetic acid (3.0 mL). The mixture was stirred at 60° C. for 1.5 hours, and then concentrated. After azeotropy with toluene (twice), the residue was mixed with methanol (9.0 mL), and thereto was added 2M trimethylsilyldiazomethane n-hexane solution (9.4 mL). The reaction solution was stirred for 1 hour at room temperature, and then thereto was added acetic acid (80 mL), which was concentrated. The resulted residue was purified through silica gel column chromatography (ethyl acetate:hexane=1:20→1:10→1:5→1:2→1:1)) to give the titled compound (983 mg).

$^1$H-NMR (400 MHz, CDCl$_3$) 1.43-1.52 (m, 2H), 2.18-2.27 (m, 2H), 2.34-2.46 (m, 3H), 2.52-2.62 (m, 1H), 3.55 (d, J=6.28 Hz, 2H), 3.65 (s, 3H)

Step 3 cis-(3-Methoxymethoxymethyl-cyclobutyl)-acetic Acid methyl Ester

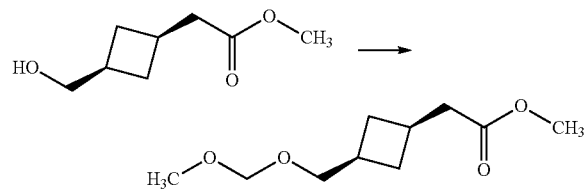

cis-(3-Hydroxymethyl-cyclobutyl)-acetic acid methyl ester (500 mg) was mixed with chloroform (5.0 mL), and thereto were added chloromethyl methyl ether (0.323 mL) and diisopropylethylamine (0.739 mL) under ice cooling. The reaction solution was stirred for 20 hours at room temperature, and then thereto were added ethyl acetate and 0.5M hydrochloric acid, which was separated. The organic layer was washed sequentially with 0.5N hydrochloric acid, water, aqueous sodium hydrogen carbonate solution, and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:15→1:10) to give the titled compound (364 mg).

$^1$H-NMR (400 MHz, CDCl$_3$) 1.44-1.53 (m, 2H), 2.22-2.29 (m, 2H), 2.39 (d, J=7.25 Hz, 2H), 2.43-2.49 (m, 1H), 2.52-2.62 (m, 1H), 3.35 (s, 3H), 3.44 (d, J=6.45 Hz, 2H), 3.65 (s, 3H), 4.60 (s, 2H)

Step 4

(R)-3-[3-Chloro-4-(3,3-dimethyl-butyl)-phenyl]-2-(3-methoxymethoxymethyl-cyclobutyl)-3-((S)-2-methyl-propane-2-sulfinylamino)-butanoic Acid methyl Ester

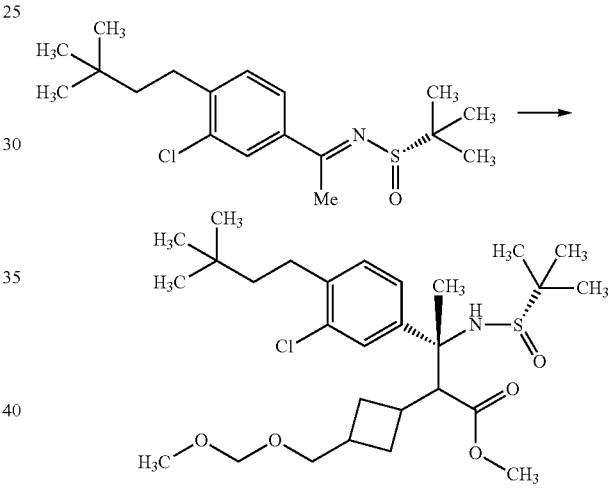

Diisopropylamine (0.280 mL) was mixed in tetrahydrofuran (1.0 mL) under argon gas. To the reaction solution was added dropwise 1.63M n-butyllithium/hexane solution (1.20 mL) at −78° C., and the reaction solution was stirred at 0° C. for 10 minutes. To the reaction solution was added dropwise a mixed solution of (3-methoxymethoxymethyl-cyclobutyl)-acetic acid methyl ester (363 mg) in tetrahydrofuran (2.0 mL) at −78° C., which was stirred at −20° C. for additional 1.5 hours. To the reaction solution was added dropwise 1 M chloro titanium (IV) triisopropoxide/hexane solution (3.70 mL) at −78° C., which was stirred at −78° C. for additional 1 hour. To the reaction solution was added dropwise a mixed solution of (S)-2-methyl-propane-2-sulfinic acid [1-[3-chloro-4-(3,3-dimethyl-butyl)-phenyl]-eth-(E)-ylidene]-amide (307 mg) in tetrahydrofuran (2.0 mL), which was stirred at −78° C. for 4 hours. To the reaction solution was added acetic acid (0.212 mL) at −78° C. To the reaction solution were added 10 wt/v % aqueous citric acid solution and ethyl acetate at room temperature, which was separated. The organic layer was washed sequentially with 10 wt/wt % aqueous citric acid solution and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:2→1:1→2:1) to give the titled compound (429 mg) as a diastereomer mixture.

$^1$H-NMR (400 MHz, CDCl$_3$) 0.97-0.98 (m, 9H), 1.28-1.34 (m, 9H), 1.42-1.52 (m, 3H), 1.74-1.83 (m, 3H), 1.85-1.91 (m, 1H), 2.01-2.11 (m, 1H), 2.28-2.55 (m, 2H), 2.61-2.71 (m, 3H), 2.85-2.96 (m, 1H), 3.29-3.35 (m, 5H), 3.53-3.65 (m, 3H), 4.53-4.60 (m, 2H), 5.03-5.28 (m, 1H), 7.12-7.21 (m, 2H), 7.41-7.37 (m, 1H)

Step 5

(R)-3-Amino-3-[3-chloro-4-(3,3-dimethyl-butyl)-phenyl]-2-(3-hydroxymethyl-cyclobutyl)-butanoic Acid methyl Ester

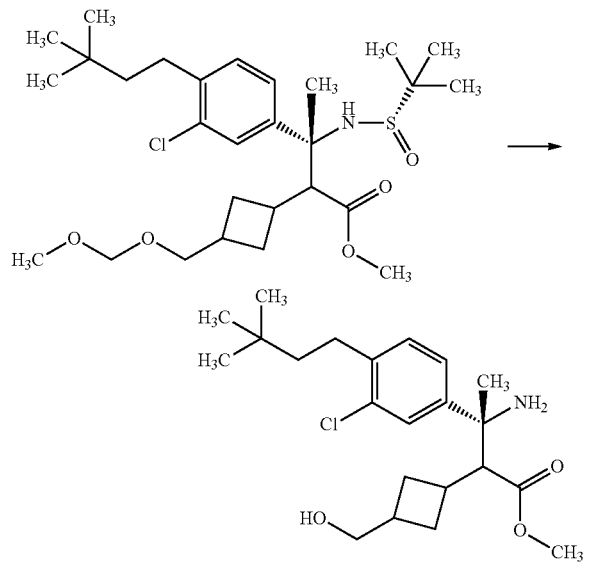

(R)-3-[3-Chloro-4-(3,3-dimethyl-butyl)-phenyl]-2-(3-methoxymethoxymethyl-cyclobutyl)-3-((S)-2-methyl-propane-2-sulfinylamino)-butanoic acid methyl ester (315 mg) was mixed with methanol (3.0 mL), and thereto was added 2M hydrogen chloride/methanol solution (0.458 mL) under ice cooling. The reaction solution was stirred at room temperature for 21 hours, and then thereto were added 2N aqueous sodium hydroxide solution (0.910 mL) and saturated aqueous sodium hydrogen carbonate solution under ice cooling. To the reaction solution was added ethyl acetate, which was separated. Then the organic layer was washed with aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=2:1→4:1→ethyl acetate:methanol=20:1) to give a diastereomer compound A of the titled compound (57.5 mg) and a diastereomer compound B of the titled compound (60.3 mg), respectively.

(Diastereomer Compound A of the Titled Compound)

$^1$H-NMR (400 MHz, CDCl$_3$) 0.81-0.89 (m, 1H), 0.97 (s, 9H), 1.39-1.49 (m, 7H), 1.93-2.01 (m, 1H), 2.13-2.21 (m, 1H), 2.46-2.53 (m, 1H), 2.64-2.68 (m, 2H), 2.79 (d, J=9.27 Hz, 1H), 3.37 (d, J=6.04 Hz, 2H), 3.68 (s, 3H), 7.14 (d, J=8.06 Hz, 1H), 7.25 (dd, J=8.06, 2.01 Hz, 1H), 7.47 (d, J=2.01 Hz, 1H)

(Diastereomer Compound B of the Titled Compound)

$^1$H-NMR (400 MHz, CDCl$_3$) 0.97 (s, 9H), 1.41-1.46 (m, 7H), 2.00-2.15 (m, 2H), 2.30-2.41 (m, 1H), 2.63-2.68 (m, 3H), 2.81 (d, J=9.67 Hz, 1H), 3.41 (s, 3H), 3.50 (d, J=6.04 Hz, 2H), 7.13 (d, J=8.06 Hz, 1H), 7.22 (dd, J=8.06, 2.01 Hz, 1H), 7.40 (d, J=3=2.01 Hz, 1H)

Step 6

(R)-3-Amino-2-[3-(tert-butyl-dimethyl-silanyloxymethyl)-cyclobutyl]-3-[3-chloro-4-(3,3-dimethyl-butyl)-phenyl]-butanoic Acid methyl Ester

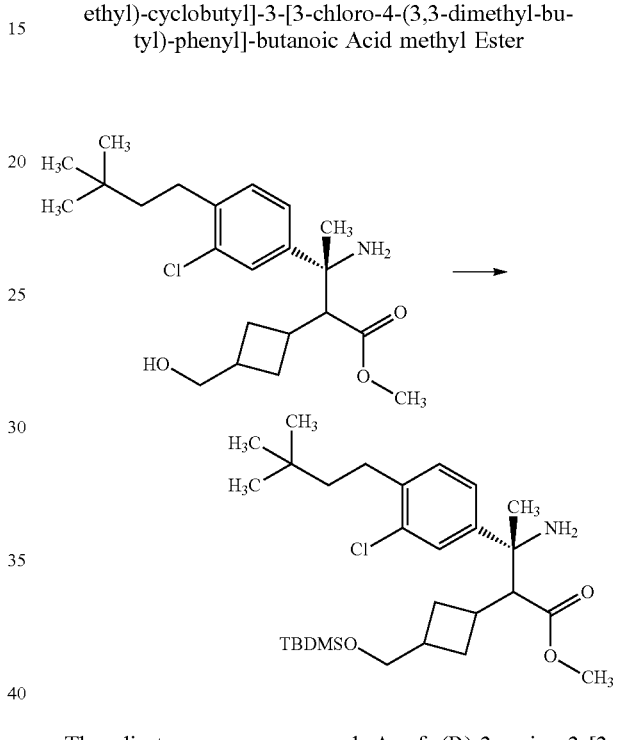

The diastereomer compound A of (R)-3-amino-3-[3-chloro-4-(3,3-dimethyl-butyl)-phenyl]-2-(3-hydroxymethyl-cyclobutyl)-butanoic acid methyl ester (57.0 mg) was mixed with dimethylformamide (1.0 mL), and thereto were added t-butyldimethylchlorosilane (34.3 mg) and imidazole (15.5 mg) at room temperature. The mixture was stirred for 16.5 hours, and then thereto were added ethyl acetate and water, which was separated. The organic layer was washed sequentially with water (3 times) and aqueous saturated sodium chloride solution, and dried over sodium sulfate. After removing sodium sulfate on a filter, the filtrate was concentrated under reduced pressure. The resulted residue was purified through silica gel column chromatography (ethyl acetate:hexane=1:4) to give a diastereomer compound A of the titled compound (68.6 mg).

$^1$H-NMR (400 MHz, CDCl$_3$) 0.04 (s, 6H), 0.79-0.88 (m, 1H), 0.85 (s, 9H), 0.97 (s, 9H), 1.29-1.36 (m, 1H), 1.40 (s, 3H), 1.42-1.50 (m, 3H), 1.84-1.92 (m, 1H), 2.06-2.15 (m, 1H), 2.38-2.49 (m, 1H), 2.63-2.67 (m, 2H), 2.78 (d, J=9.67 Hz, 1H), 3.31 (d, J=5.64 Hz, 2H), 3.68 (s, 3H), 7.13 (d, J=8.06 Hz, 1H), 7.26-7.24 (m, 1H), 7.45 (d, J=2.01 Hz, 1H)

The diastereomer compound B of (R)-3-amino-3-[3-chloro-4-(3,3-dimethyl-butyl)-phenyl]-2-(3-hydroxymethyl-cyclobutyl)-butanoic acid methyl ester (60.0 mg) was treated in a similar way to the diastereomer compound A of (R)-3-amino-3-[3-chloro-4-(3,3-dimethyl-butyl)-phenyl]-2-

(3-hydroxymethyl-cyclobutyl)-butanoic acid methyl ester to give a diastereomer compound B of the titled compound (65.0 mg).

¹H-NMR (400 MHz, CDCl₃) 0.02 (s, 6H), 0.89 (s, 9H), 0.97 (s, 9H), 1.38-1.45 (m, 6H), 1.50-1.58 (m, 1H), 1.92-2.03 (m, 2H), 2.24-2.32 (m, 1H), 2.57-2.66 (m, 3H), 2.79 (d, J=9.67 Hz, 1H), 3.40 (s, 3H), 3.44 (dd, J=5.64, 1.61 Hz, 2H), 7.12 (d, J=8.06 Hz, 1H), 7.22 (dd, J=8.06, 2.01 Hz, 1H), 7.40 (d, J=2.01 Hz, 1H)

Step 7

(R)-2-[3-(tert-Butyl-dimethyl-silanyloxymethyl)-cyclobutyl]-3-[3-chloro-4-(3,3-dimethyl-butyl)-phenyl]-3-(4-nitro-phenoxycarbonylamino)-butanoic Acid methyl Ester

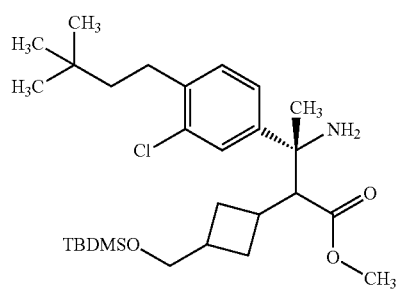

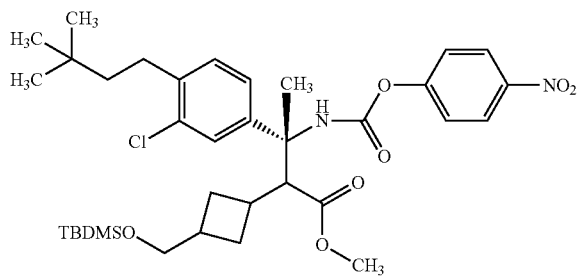

The diastereomer compound A (31.3 mg) and the diastereomer compound B (28.0 mg) of (R)-3-amino-2-[3-(tert-butyl-dimethyl-silanyloxymethyl)-cyclobutyl]-3-[3-chloro-4-(3,3-dimethyl-butyl)-phenyl]-butanoic acid methyl ester were mixed with chloroform (1.5 mL), and thereto were added diisopropylethylamine (0.0434 mL) and a solution of chloroformic acid p-nitrophenyl ester (50.4 mg) in chloroform (0.5 mL) at room temperature. The reaction solution was stirred for 3 hours, and then concentrated under reduced pressure. The resulted residue was purified through thin layer silica gel column chromatography (ethyl acetate: hexane=1:6) to give the titled compound (51.4 mg).

Step 8

(R)-2-[3-(tert-Butyl-dimethyl-silanyloxymethyl)-cyclobutyl]-3-[3-chloro-4-(3,3-dimethyl-butyl)-phenyl]-3-(3-fluoro-3-methyl-cyclobutyloxycarbonylamino)-butanoic Acid methyl Ester

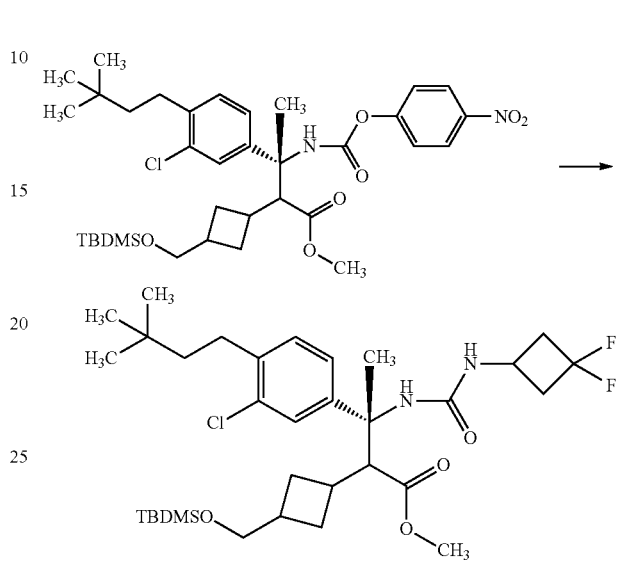

(R)-2-[3-(tert-Butyl-dimethyl-silanyloxymethyl)-cyclobutyl]-3-[3-chloro-4-(3,3-dimethyl-butyl)-phenyl]-3-(4-nitro-phenoxycarbonylamino)-butanoic acid methyl ester (51.4 mg) was mixed with chloroform (1.0 mL), and thereto were added 3,3-difluorocyclobutylamine hydrochloride (32.9 mg) and triethylamine (0.0478 mL). The reaction solution was stirred for 17.5 hours at 60° C., and then concentrated under reduced pressure. The resulted residue was purified through silica gel column chromatography (ethyl acetate:hexane=1:8→1:6) to give the titled compound (51.3 mg).

Step 9

(R)-5-[3-(tert-Butyl-dimethyl-silanyloxymethyl)-cyclobutyl]-6-[3-chloro-4-(3,3-dimethyl-butyl)-phenyl]-3-(3,3-difluoro-cyclobutyl)-6-methyl-dihydro-pyrimidine-2,4-dione

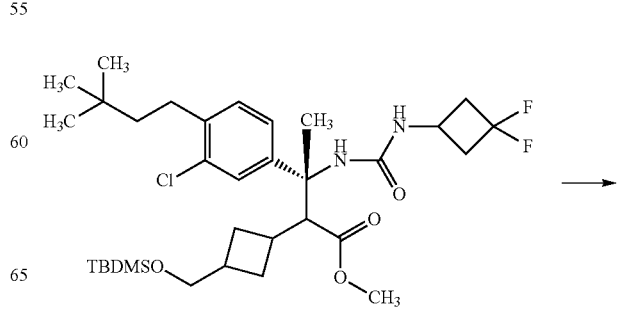

-continued

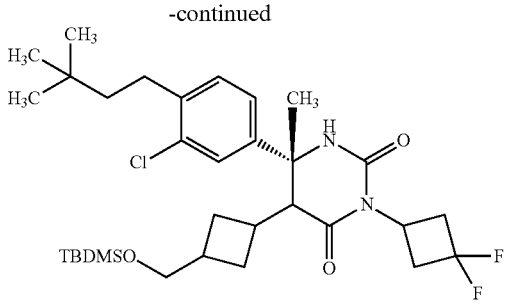

(R)-2-[3-(tert-Butyl-dimethyl-silanyloxymethyl)-cyclobutyl]-3-[3-chloro-4-(3,3-dimethyl-butyl)-phenyl]-3-(3-fluoro-3-methyl-cyclobutyloxycarbonylamino)-butanoic acid methyl ester (51.3 mg) was mixed with tetrahydrofuran (2.0 mL) under argon gas, and thereto was added potassium t-butoxide (12.8 mg) under ice cooling. The reaction solution was stirred for 40 minutes under ice cooling, and then thereto was added water. To the reaction solution was added ethyl acetate, which was separated. The organic layer was washed sequentially with water and aqueous saturated sodium chloride solution, and dried over sodium sulfate. After removing sodium sulfate on a filter, the filtrate was concentrated under reduced pressure. The resulted residue was purified through thin layer silica gel chromatography (ethyl acetate:hexane=1:4) to give the titled compound (36.0 mg) as a mixture of diastereomers.

$^1$H-NMR (400 MHz, CDCl$_3$) −0.03-0.04 (m, 6H), 0.85-0.91 (m, 9H), 0.97-0.98 (m, 9H), 1.40-1.65 (m, 6H), 1.76-2.23 (m, 3H), 2.54-2.89 (m, 6H), 3.05-3.19 (m, 1H), 3.29-3.52 (m, 4H), 4.70-4.98 (m, 1H), 5.40 (brs, 1H), 7.28-7.06 (m, 3H)

Step 10

(S)-4-[3-Chloro-4-(3,3-dimethyl-butyl)-phenyl]-1-(3,3-difluoro-cyclobutyl)-5-(3-hydroxymethyl-cyclobutyl)-4-methyl-3,4-dihydro-1H-pyrimidin-2-one

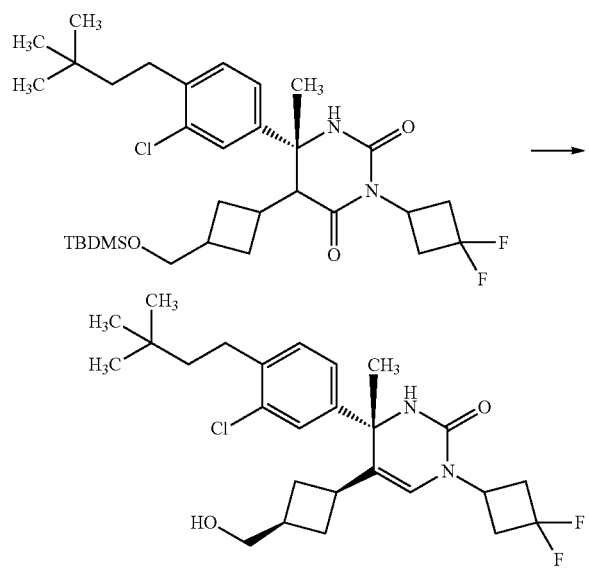

Bis(cyclopentadienyl)zirconium (IV) chloride hydride (73.6 mg) was mixed with tetrahydrofuran (3.0 mL) under argon gas. To the suspension was added a solution of (R)-5-[3-(tert-butyl-dimethyl-silanyloxymethyl)-cyclobutyl]-6-[3-chloro-4-(3,3-dimethyl-butyl)-phenyl]-3-(3,3-difluoro-cyclobutyl)-6-methyl-dihydro-pyrimidine-2,4-dione (36.0 mg) in tetrahydrofuran (6.0 ml) at room temperature, which was then stirred. To the reaction solution was added bis(cyclopentadienyl)zirconium (IV) chloridehydride (75.0 mg), and the mixture was stirred for 20 hours. To the reaction solution was added 2N hydrochloric acid (1.0 mL) at room temperature. The reaction solution was stirred for 3 days, and then thereto were added ethyl acetate and water, which was then separated. The organic layer was washed sequentially with saturated aqueous sodium hydrogen carbonate solution and aqueous saturated sodium chloride solution, and dried over sodium sulfate. After removing sodium sulfate on a filter, the filtrate was concentrated under reduced pressure. The resulted residue was purified through thin layer silica gel chromatography (methanol:chloroform=1:15) to give the titled compound (10.6 mg).

$^1$H-NMR (400 MHz, CDCl$_3$) 0.98 (s, 9H), 1.34-1.47 (m, 3H), 1.58-1.70 (m, 5H), 2.09-2.28 (m, 2H), 2.39-2.48 (m, 11H), 2.65-2.69 (m, 2H), 2.76-2.89 (m, 2H), 2.93-3.03 (m, 2H), 3.49 (d, J=5.64 Hz. 2H), 4.76-4.70 (m, 1H), 4.87 (s, 1H), 5.89 (d, J=1.21 Hz, 1H), 7.17 (d, J=8.06 Hz, 1H), 7.20 (dd, J=8.06, 1.61 Hz, 1H), 7.34 (d, J=1.61 Hz, 1H)

Step 11

3-[(S)-4-[3-Chloro-4-(3,3-dimethyl-butyl)-phenyl]-1-(3,3-difluoro-cyclobutyl)-4-methyl-2-oxo-1,2,3,4-tetrahydro-pyrimidin-5-yl]-cyclobutanoic Acid

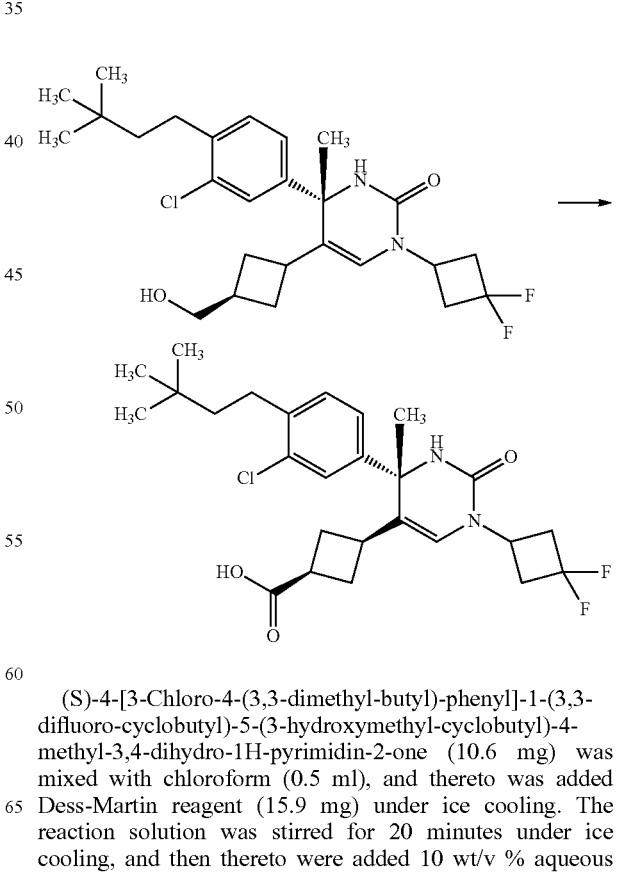

(S)-4-[3-Chloro-4-(3,3-dimethyl-butyl)-phenyl]-1-(3,3-difluoro-cyclobutyl)-5-(3-hydroxymethyl-cyclobutyl)-4-methyl-3,4-dihydro-1H-pyrimidin-2-one (10.6 mg) was mixed with chloroform (0.5 ml), and thereto was added Dess-Martin reagent (15.9 mg) under ice cooling. The reaction solution was stirred for 20 minutes under ice cooling, and then thereto were added 10 wt/v % aqueous sodium sulfite solution and saturated aqueous sodium hydrogen carbonate solution, then ethyl acetate. After separation, the organic layer was washed sequentially with saturated aqueous sodium hydrogen carbonate solution and aqueous saturated sodium chloride solution, and dried over sodium sulfate. After removing sodium sulfate on a filter, the filtrate was concentrated under reduced pressure. The residue was mixed with t-butanol (0.7 mL) and acetonitrile (1.4 mL), and thereto were added 1M aqueous sodium dihydrogenphosphate solution (0.22 mL) and an aqueous solution (0.25 mL) of 2-methyl-2-butene, sodium chlorite (3.8 mg) at room temperature. The reaction solution was stirred for 15.5 hours at room temperature, and then thereto were added sequentially 10 wt/v % aqueous sodium sulfite solution and 2N hydrochloric acid, then ethyl acetate. After separation, the organic layer was washed with aqueous saturated sodium chloride solution, and dried over sodium sulfate. After removing sodium sulfate on a filter, the filtrate was concentrated under reduced pressure. The resulted residue was purified through thin layer silica gel column chromatography (methanol:chloroform=1:10) to give the titled compound (7.5 mg).

Example 258

Step 1

1-(4-Bromo-2-chloro-phenyl)-3-isopropyl-cyclobutanol

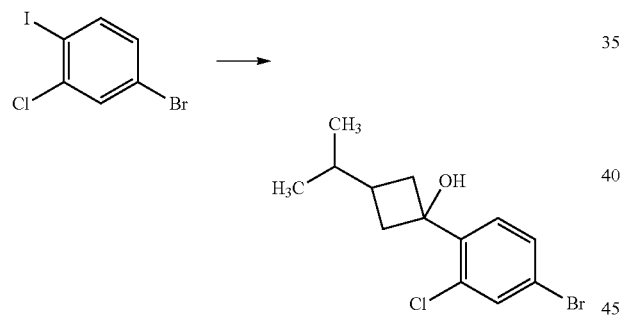

4-Bromo-2-chloro-1-iodobenzene (3.68 g) was mixed in tetrahydrofuran (17.8 mL). To the reaction solution was added dropwise 2M isopropylmagnesium chloride/tetrahydrofuran (5.8 mL) at −30° C., and the reaction solution was stirred at −30° C. for 40 minutes. To the reaction solution were added dropwise 0.6M lanthanum chloride bis(lithium chloride) complex/tetrahydrofuran (4.5 mL) and then a mixed solution of 3-isopropyl-cyclobutanone (1.00 g) in tetrahydrofuran (8.9 mL), and the reaction solution was stirred at −30° C. for 4 hours. To the reaction solution was added 20% aqueous ammonium chloride solution, which was then extracted with tert-butylmethylether. The organic layer was washed sequentially with 20% aqueous ammonium chloride solution, water, and 20% aqueous sodium chloride solution, and dried over magnesium sulfate. After removing magnesium sulfate on a filter, the filtrate was concentrated under reduced pressure. The resulted residue was purified through silica gel column chromatography (ethyl acetate:hexane=0:100→10:90) to give the titled compound (2.72 g) as a mixture of cis- and trans-isomers.

Step 2

4-Bromo-2-chloro-1-(3-isopropyl-cyclobut-1-enyl)-benzene

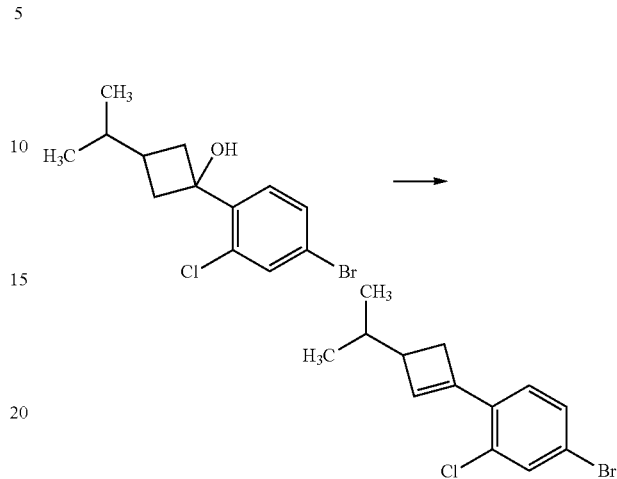

1-(4-Bromo-2-chloro-phenyl)-3-isopropyl-cyclobutanol (2.42 g) and pentafluoroanilinium trifluoromethanesulfonate (133 mg) were mixed in toluene (16.0 mL). The reaction solution was stirred at 80° C. for 2 hours. The reaction solution was concentrated under reduced pressure, and the resulted residue was purified through silica gel column chromatography (hexane) to give the titled compound (2.02 g).

$^1$H-NMR (400 MHz, CDCl$_3$) 0.95 (d, J=6.70 Hz, 3H), 0.98 (d, J=6.47 Hz, 3H), 1.59-1.68 (m, 1H), 2.42-2.52 (m, 2H), 2.91 (dd, J=12.72, 4.39 Hz, 1H), 6.74 (s, 1H), 7.12 (d, J=8.32 Hz, 1H), 7.34 (dd, J=8.32, 1.97 Hz, 1H), 7.50 (d, J=1.97 Hz, 1H)

Step 3

4-bromo-2-chloro-1-(3-isopropyl-cyclobutyl)-benzene

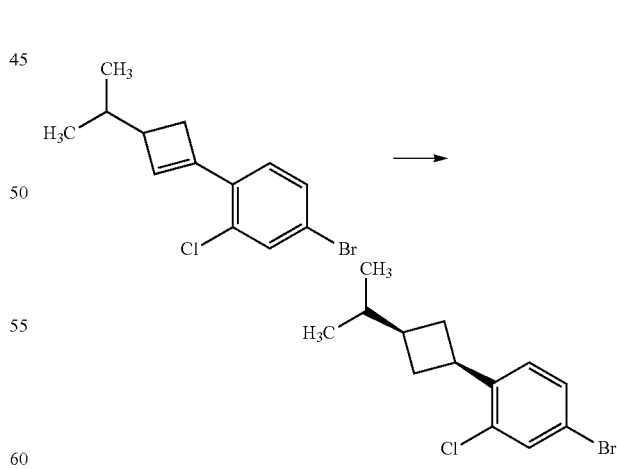

4-bromo-2-chloro-1-(3-isopropyl-cyclobut-1-enyl)-benzene (2.02 g) was mixed in a mixed solution of tetrahydrofuran (10.0 mL) and methanol (10.0 mL). To the reaction solution was added 5 w/w % rhodium/activated carbon (203 mg), and the reaction solution was stirred for 3 hours at 1 atm under hydrogen gas. After removing rhodium/activated carbon on a filter, the filtrate was concentrated under reduced pressure. The resulted residue was purified through silica gel column chromatography (hexane) to give the titled compound (1.94 g). The relative configurations of substituents on the cyclobutane ring were estimated as cis-configuration by NOESY measurement.

$^1$H-NMR (400 MHz, CDCl$_3$) 0.83 (d, J=6.70 Hz, 6H), 1.37-1.46 (m, 1H), 1.59-1.68 (m, 2H), 1.85-1.96 (m, 1H), 2.46-2.54 (m, 2H), 3.39-3.48 (m, 1H), 7.11 (d, J=8.27 Hz, 1H), 7.34 (dd, J=8.27, 2.03 Hz, 1H), 7.46 (d, J=2.03 Hz, 1H)

Step 4

1-[3-Chloro-4-(3-isopropyl-cyclobutyl)-phenyl]-ethanone

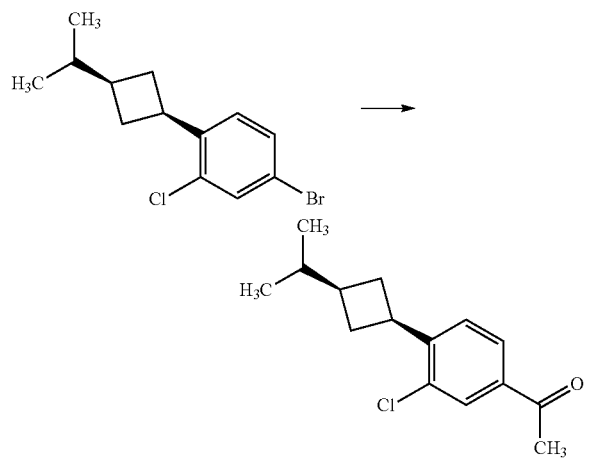

4-Bromo-2-chloro-1-(3-isopropyl-cyclobutyl)-benzene (1.85 g), palladium acetate (30 mg) and 1,3-bis(diphenylphosphino)propane (103 mg) were mixed in 2-ethoxyethanol (13.0 mL) under argon gas. The reaction solution was stirred at room temperature for 10 minutes, and then to the reaction solution were added N,N-diisopropylethylamine (2.8 mL) and ethyleneglycol monovinyl ether (1.8 mL). The reaction solution was stirred at 145° C. for 2.5 hours. To the reaction solution was added 6M hydrochloric acid (3.2 mL) under ice cooling, and the reaction solution was stirred at room temperature overnight. To the reaction solution was added water, which was then extracted with tert-butylmethylether. The organic layer was washed sequentially with water and 25% aqueous sodium chloride solution, and dried over magnesium sulfate. After removing magnesium sulfate on a filter, the filtrate was concentrated under reduced pressure. The resulted residue was purified through silica gel column chromatography (ethyl acetate:hexane=0:100→10:90) to give the titled compound (1.24 g).

$^1$H-NMR (400 MHz, CDCl$_3$) 0.84 (d, J=6.70 Hz, 6H), 1.43 (d, J=34.91 Hz, 1H), 1.70 (d, J=36.07 Hz, 2H), 1.94 (d, J=42.08 Hz, 1H), 2.54-2.58 (m, 2H), 2.57 (s, 3H), 3.50-3.59 (m, 1H), 7.35 (d, J=7.98 Hz, 1H), 7.80 (dd, J=7.98, 1.74 Hz, 1H), 7.89 (d, J=1.74 Hz, 1H)

Step 5

3-{(S)-4-[3-Chloro-4-(3-isopropyl-cyclobutyl)-phenyl]-5-isopropyl-4-methyl-2-oxo-3,4-dihydro-2H-pyrimidin-1-yl}-propionic Acid

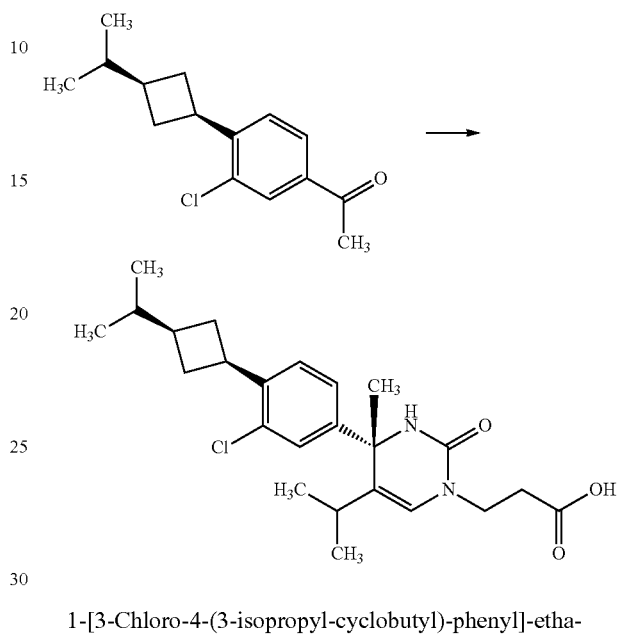

1-[3-Chloro-4-(3-isopropyl-cyclobutyl)-phenyl]-ethanone was treated as a starting material in a similar manner to Example 87 (a method for preparation using an optically active sulfinamide) Steps 5 to 11 to give the titled compound (73 mg).

Example 271

Step 1

4-(3,3-Dimethyl-but-1-ynyl)-3-trifluoromethyl-benzoic Acid

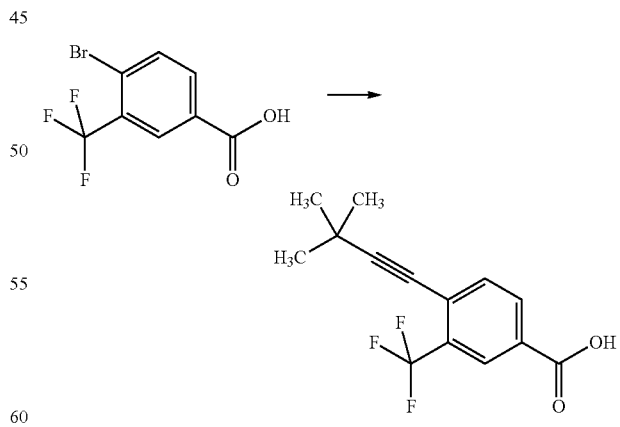

4-Bromo-3-trifluoromethyl-benzoic acid (5.2 g), bis(triphenylphosphine)palladium (II) dichloride (678 mg), and copper iodide (185 mg) were mixed in N-methylpyrrolidone (32 mL) under argon gas. The reaction system was vacuated to replace with argon three times, and then thereto were added diisopropylamine (10.9 mL) and 3,3-dimethyl-but-1- yne (3.55 mL). The reaction solution was stirred at 60° C. overnight, and then warmed to room temperature, and to the reaction solution was added toluene (30 mL). Then thereto were added 2M aqueous sodium hydroxide solution (12 mL) and water, which wash then extracted with toluene. The resulted aqueous layer was acidified by adding 6M aqueous hydrochloric acid solution (20 mL), and ethyl acetate was added thereto, and the mixture was separated. The organic layer was washed with brine, and then dried over magnesium sulfate. After removing magnesium sulfate on a filter, the filtrate was concentrated under reduced pressure. The resulted residue was purified through silica gel column chromatography (ethyl acetate:methanol=90:10). Hexane was then added to the resulted solid, and the resulted slurry was stirred and then filtered to give the titled compound (2.4 g). The filtrate was concentrated under reduced pressure, and purified through silica gel column chromatography (ethyl acetate:hexane=1:9→10:0) to give the titled compound (1.47 g).

$^1$H-NMR (400 MHz, CDCl$_3$) 1.33 (s, 9H), 7.57-7.62 (m, 1H), 8.12-8.17 (m, 1H), 8.32-8.35 (m, 1H)

Step 2

4-(3,3-Dimethyl-butyl)-3-trifluoromethyl-benzoic Acid

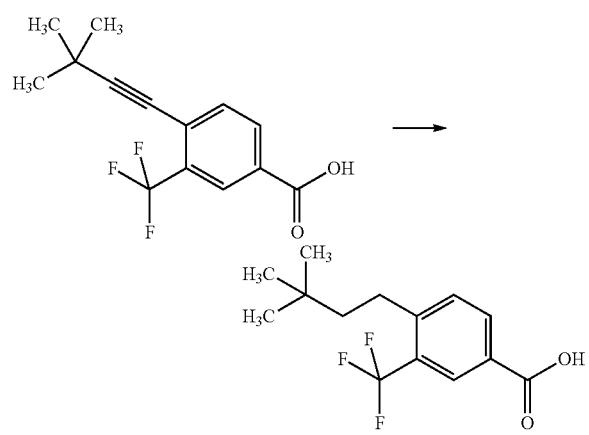

4-(3,3-Dimethyl-but-1-ynyl)-3-trifluoromethyl-benzoic acid (3.9 g) was mixed in methanol (40 mL). To the mixed solution was added 5 w/w % platinum/activated carbon (1.16 g), and the reaction solution was stirred for two days overnight at 1 atm under hydrogen gas. After removing platinum/activated carbon on a filter from the reaction solution, the filtrate was concentrated under reduced pressure to give the titled compound (7.32 g).

$^1$H-NMR (400 MHz, CDCl$_3$) 0.97 (s, 9H), 1.44-1.52 (m, 2H), 2.76-2.84 (m, 2H), 7.39-7.45 (m, 1H), 8.12-8.18 (m, 1H), 8.34 (brs, 1H)

Step 3

4-(3,3-Dimethyl-butyl)-N-methoxy-N-methyl-3-trifluoromethyl-benzamide

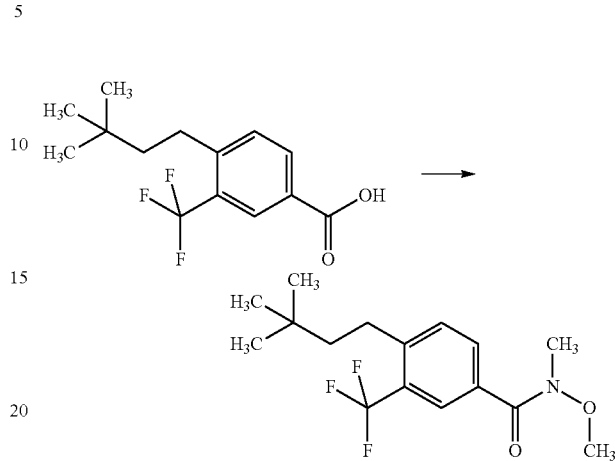

4-(3,3-Dimethyl-butyl)-3-trifluoromethyl-benzoic acid, a crude product, (3.78 g), N,O-dimethylhydroxylamine hydrochloride (1.48 g), 1-hydroxybenzotriazolemonohydrate (211 mg), and sodium hydrogen carbonate (1.28 g) were mixed in N,N-dimethylformamide (22 mL). Then thereto was added WSC.HCl (3.04 g), and the mixture was stirred at room temperature for 3 hours and then left to stand at room temperature overnight. To the reaction solution were added water, hexane, and ethyl acetate, which was then separated, and then the aqueous layer was extracted with ethyl acetate twice. After azeotropy of the organic layer with a denatured ethanol solution, the resulted residue was purified through silica gel chromatography (ethyl acetate:hexane=8:92→1:1) to give the titled compound (4.29 g).

$^1$H-NMR (400 MHz, CDCl$_3$) 0.96 (s, 9H), 1.44-1.50 (m, 2H), 2.72-2.79 (m, 2H), 3.36 (s, 3H), 3.54 (s, 3H), 7.31-7.36 (m, 1H), 7.76-7.81 (m, 1H), 7.95-7.98 (m, 1H)

Step 4

1-[4-(3,3-Dimethyl-butyl)-3-trifluoromethyl-phenyl]-ethanone

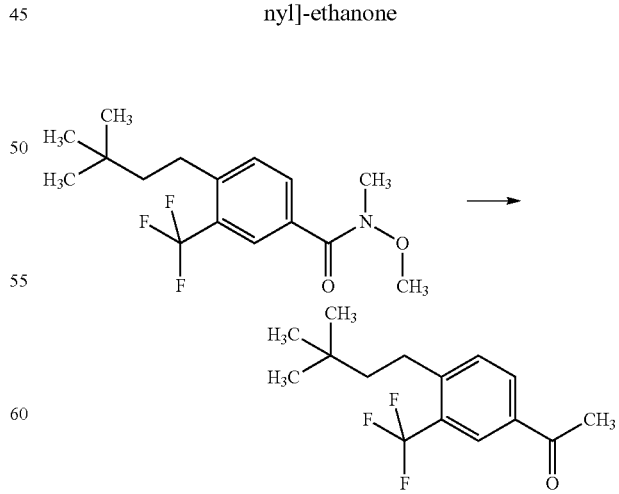

4-(3,3-Dimethyl-butyl)-N-methoxy-N-methyl-3-trifluoromethyl-benzamide (4.29 g) was mixed in tetrahydrofuran (25 mL). To the reaction solution was added dropwise 0.91M methylmagnesium bromide/tetrahydrofuran solution (22.3 mL) under ice cooling, and the reaction solution was stirred under ice cooling for 40 minutes. To the reaction solution were added dropwise 1M hydrochloric acid (32 mL) and water under ice cooling, and then thereto was added ethyl acetate. After the mixed solution was separated, the aqueous layer was extracted with ethyl acetate. The resulted organic layer was dried over magnesium sulfate. After removing magnesium sulfate on a filter, the filtrate was concentrated under reduced pressure to give the titled compound (3.6 g).

Step 5

4-{(S)-4-[4-(3,3-Dimethyl-butyl)-3-trifluoromethyl-phenyl]-5-isopropyl-4-methyl-2-oxo-3,4-dihydro-2H-pyrimidin-1-yl}-benzoic Acid

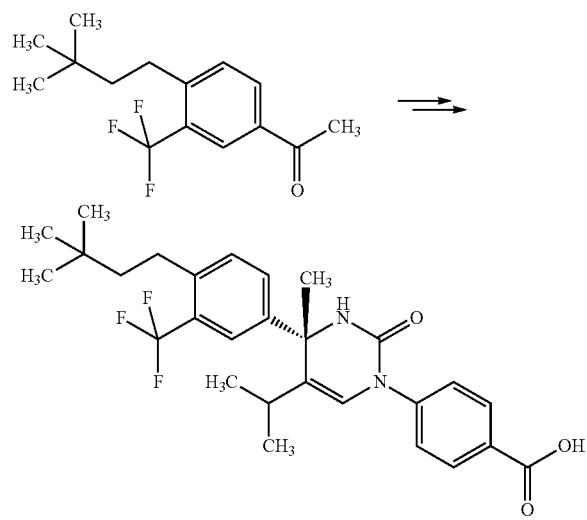

1-[4-(3,3-Dimethyl-butyl)-3-trifluoromethyl-phenyl]-ethanone was treated as a starting material in a similar manner to Example 87 (a method for preparation using an optically active sulfinamide) Steps 5 to 11 to give the titled compound (29 mg).

Example 281

Step 1

(R)-2-(tert-Butyl-diphenyl-silanyloxymethyl)-1-[3-chloro-4-(3,3-dimethyl-butyl)-phenyl]-1,3-dimethyl-butylamine

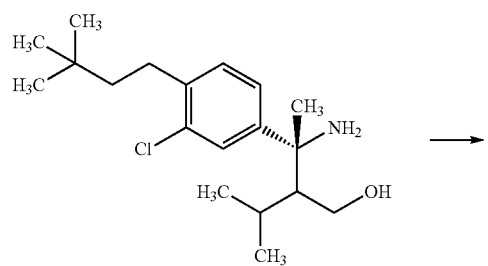

-continued

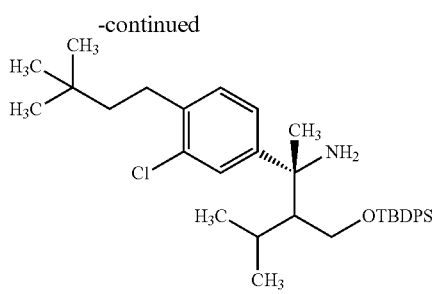

(R)-3-Amino-3-[3-chloro-4-(3,3-dimethyl-butyl)-phenyl]-2-isopropyl-butan-1-ol (1.98 g) obtained according to Example 159 (a method for preparation using an optically active sulfinamide) Steps 1 to 2 was mixed with dimethylformamide (50 ml), and to the mixed solution were mixed chloro-t-butyldiphenylsilane (2.36 ml) and imidazole (620 mg) under ice cooling. The reaction solution was stirred at room temperature for 20 hours. To the reaction solution were added ethyl acetate and water, which was then separated. The organic layer was washed with water and aqueous saturated sodium chloride solution, and dried over sodium sulfate. After removing sodium sulfate on a filter, the reaction solution was concentrated under reduced pressure, and the resulted residue was purified through silica gel column chromatography (ethyl acetate:n-hexane) to give the titled compound (2.77 g).

$^1$H-NMR (400 MHz, CDCl$_3$) 0.79 (d, J=7.25 Hz, 3H), 0.81 (d, J=7.25 Hz, 3H), 0.98 (s, 9H), 1.06 (s, 9H), 1.37 (s, 3H), 1.43-1.47 (m, 2H), 1.68-1.75 (m, 1H), 1.79-1.82 (m, 1H), 2.62-2.67 (m, 2H), 3.81 (d, J=5.24 Hz, 2H), 7.10 (d, J=8.06 Hz, 1H), 7.18 (dd, J=8.06, 2.01 Hz, 1H), 7.37-7.46 (m, 7H), 7.69-7.66 (m, 4H)

Step 2

6-(4-Nitro-phenoxycarbonylamino)-nicotinic Acid methyl Ester

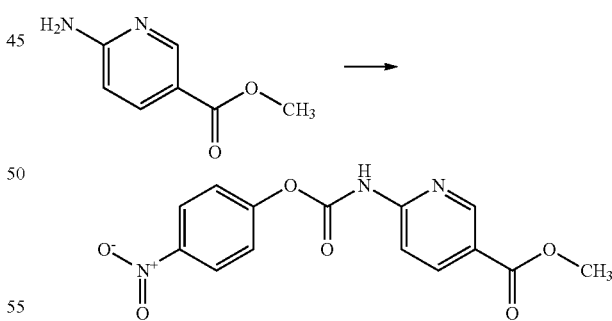

6-Amino-nicotinic acid methyl ester (100 mg) was mixed with dichloromethane (5.0 mL) and tetrahydrofuran (3.0 mL). To the mixed solution were added p-nitrophenyl chloroformate (146 mg) and pyridine (0.0798 mL) under ice cooling, which was then stirred for 1 hour. The mixture was stirred at room temperature for 15 minutes, and then a solid was filtered. The resulted solid was washed sequentially with water, tetrahydrofuran, and n-hexane, and then dried under reduced pressure to give the titled compound (57.3 mg).

¹H-NMR (400 MHz, DMSO-D₆) 3.76 (s, 3H), 6.45 (dd, J=8.87, 0.81 Hz, 1H), 6.93 (td, J=6.35, 3.90 Hz, 2H), 7.82 (dd, J=8.87, 2.82 Hz, 1H), 8.12 (td, J=6.35, 3.90 Hz, 2H), 8.50 (dd, J=2.42, 0.81 Hz, 1H), 11.04 (s, 1H)

Step 3

6-(3-{(R)-2-(tert-Butyl-diphenyl-silanyloxymethyl)-1-[3-chloro-4-(3,3-dimethyl-butyl)-phenyl]-1,3-dimethyl-butyl}-ureido)-nicotinic Acid methyl Ester

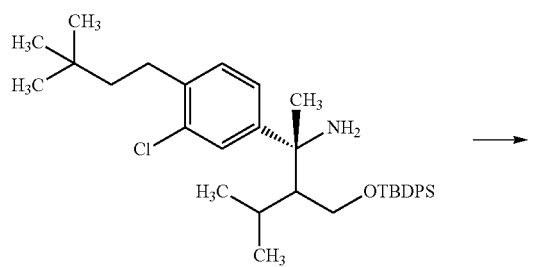

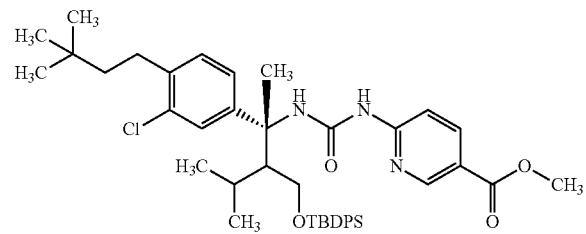

(R)-2-(tert-Butyl-diphenyl-silanyloxymethyl)-1-[3-chloro-4-(3,3-dimethyl-butyl)-phenyl]-1,3-dimethyl-butylamine (71.7 mg) was mixed with chloroform (1.5 ml), and to the mixed solution were added 6-(4-nitro-phenoxycarbonylamino)-nicotinic acid methyl ester (57.3 mg) and triethylamine (0.0252 ml) at room temperature. The reaction solution was stirred at 60° C. for 3 hours, and then concentrated. The residue was purified through thin layer silica gel chromatography (chloroform:methanol=20:1) to give the titled compound (105 mg).

¹H-NMR (400 MHz, CDCl₃) 0.97 (s, 9H), 0.99 (s, 9H), 1.04 (d, J=6.85 Hz, 3H), 1.21 (d, J=6.85 Hz, 3H), 1.34-1.39 (m, 2H), 1.78 (s, 3H), 1.98-2.01 (m, 1H), 2.11-2.18 (m, 1H), 2.53-2.66 (m, 2H), 3.47 (dd, J=10.88, 4.03 Hz, 1H), 3.67 (dd, J=10.88, 8.87 Hz, 1H), 3.93 (s, 3H), 6.36 (d, J=8.87 Hz, 1H), 7.01 (d, J=8.06 Hz, 1H), 7.07 (dd, J=8.06, 1.61 Hz, 1H), 7.26-7.30 (m, 3H), 7.33-7.42 (m, 4H), 7.48 (dd, J=8.06, 1.61 Hz, 2H), 7.57 (dd, J=7.66, 1.61 Hz, 2H), 8.03 (dd, J=8.87, 2.01 Hz, 1H), 8.66 (s, 1H), 8.73 (d, J=2.01 Hz, 1H), 10.05 (s, 1H)

Step 4

6-(3-{(R)-1-[3-Chloro-4-(3,3-dimethyl-butyl)-phenyl]-2-hydroxymethyl-1,3-dimethyl-butyl}-ureido)-nicotinic Acid methyl Ester

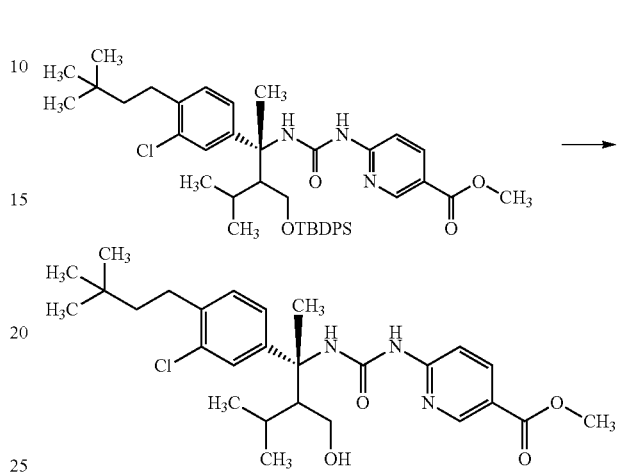

6-(3-{(R)-2-(tert-Butyl-diphenyl-silanyloxymethyl)-1-[3-chloro-4-(3,3-dimethyl-butyl)-phenyl]-1,3-dimethyl-butyl}-ureido)-nicotinic acid methyl ester (105 mg) was mixed with tetrahydrofuran (1.0 ml). To the mixed solution was added at room temperature an 1 M solution of tetrabutylammonium fluoride in tetrahydrofuran (0.191 ml). The mixture was stirred for 15 hours at room temperature, and then concentrated. The residue was purified through thin layer silica gel column chromatography (chloroform:methanol=20:1) to give the titled compound (62.0 mg).

¹H-NMR (400 MHz, CDCl₃) 0.93 (d, J=6.85 Hz, 3H), 0.96 (s, 9H), 1.15 (d, J=6.85 Hz, 3H), 1.43 (dd, J=8.87, 8.46 Hz, 2H), 1.87-1.90 (m, 1H), 1.92 (s, 3H), 2.12-2.19 (m, 1H), 2.58-2.71 (m, 2H), 3.61-3.72 (m, 2H), 3.93 (s, 3H), 6.39 (d, J=8.46 Hz, 1H), 7.16 (d, J=8.06 Hz, 1H), 7.23 (dd, J=8.06, 2.01 Hz, 1H), 7.39 (d, J=2.01 Hz, 1H), 8.05 (dd, J=8.46, 2.42 Hz, 1H), 8.79 (d, J=2.42 Hz, 1H), 8.97 (s, 1H), 10.20 (s, 1H)

Step 5

6-{(S)-4-[3-Chloro-4-(3,3-dimethyl-butyl)-phenyl]-5-isopropyl-4-methyl-2-oxo-3,4-dihydro-2H-pyrimidin-1-yl}-nicotinic Acid methyl Ester

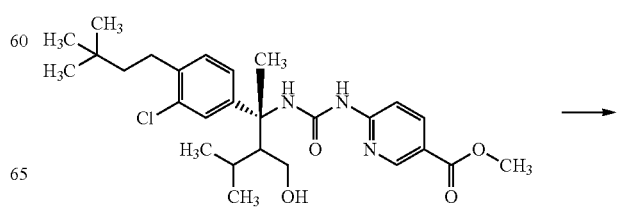

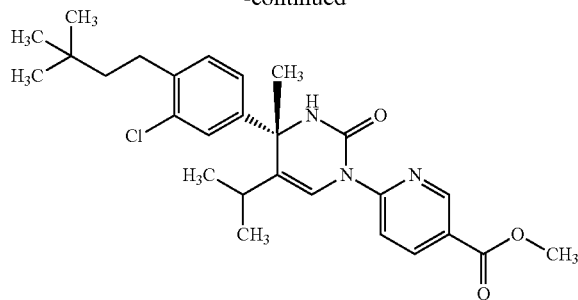

6-(3-{(R)-1-[3-Chloro-4-(3,3-dimethyl-butyl)-phenyl]-2-hydroxymethyl-1,3-dimethyl-butyl}-ureido)-nicotinic acid methyl ester (62.0 mg) and iodobenzene diacetate (43.6 mg) were mixed in dichloromethane (1.0 mL). To the reaction solution was added 2,2,6,6-tetramethylpiperidine 1-oxyl free radical (1.9 mg) under ice cooling, and the reaction solution was stirred at room temperature for 18 hours. To the reaction solution was added trifluoroacetic acid (0.0182 mL) under ice cooling, which was then stirred at room temperature for 4.5 hours. To the reaction solution were added aqueous sodium sulfite solution and then aqueous sodium hydrogen carbonate solution at room temperature. The resulted mixed solution was extracted with ethyl acetate. The organic layer was washed with aqueous saturated sodium chloride solution, and dried over sodium sulfate. After removing sodium sulfate on a filter, the filtrate was concentrated under reduced pressure. The resulted residue was purified through thin layer silica gel column chromatography (chloroform:methanol=20:1).

The resulted compound was mixed with chloroform, and thereto was added trifluoroacetic acid. The reaction solution was stirred at 50° C. for 3.5 hours, and then concentrated. The residue was mixed with ethyl acetate, and washed sequentially with aqueous sodium hydrogen carbonate solution, and aqueous saturated sodium chloride solution, and dried over sodium sulfate. After removing sodium sulfate on a filter, the filtrate was concentrated under reduced pressure to give the titled compound (22.5 mg).

$^1$H-NMR (400 MHz, CDCl$_3$) 0.84 (d, J=6.85 Hz, 3H), 0.98 (s, 9H), 1.17 (d, J=6.85 Hz, 3H), 1.42-1.46 (m, 2H), 1.81 (s, 3H), 1.95-2.02 (m, 1H), 2.65-2.69 (m, 2H), 3.95 (s, 3H), 5.22 (s, 1H), 7.19 (d, J=8.06 Hz, 1H), 7.30 (dd, J=8.06, 2.01 Hz, 1H), 7.39 (s, 1H), 7.44 (d, J=2.01 Hz, 1H), 8.12 (d, J=8.87 Hz, H), 8.25 (dd, J=8.87, 2.42 Hz, 1H), 9.01 (d, J=2.42 Hz, 1H)

Step 6

6-{(S)-4-[3-Chloro-4-(3,3-dimethyl-butyl)-phenyl]-5-isopropyl-4-methyl-2-oxo-3,4-dihydro-2H-pyrimidin-1-yl}-nicotinic Acid hydrochloride

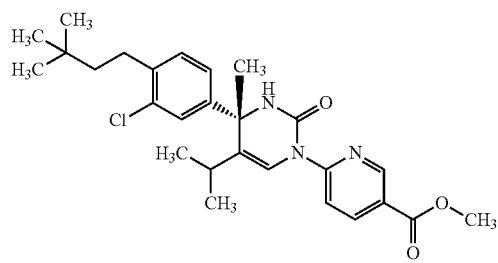

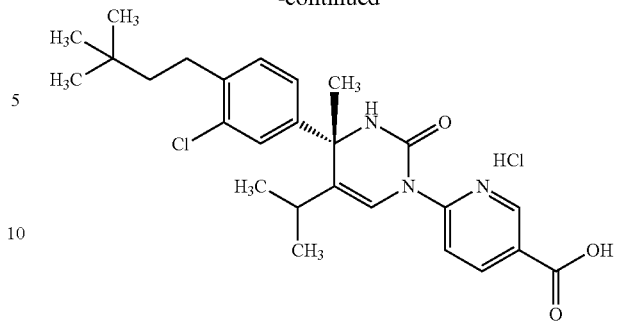

6-{(S)-4-[3-Chloro-4-(3,3-dimethyl-butyl)-phenyl]-5-isopropyl-4-methyl-2-oxo-3,4-dihydro-2H-pyrimidin-1-yl}-nicotinic acid methyl ester (22.5 mg) was mixed with ethanol (1.0 mL) and tetrahydrofuran (0.25 mL). To the reaction solution was added dropwise 2M aqueous sodium hydroxide solution (0.0465 mL) at room temperature, and the reaction solution was stirred at room temperature for 14.5 hours. To the reaction solution was added 2M hydrochloric acid at room temperature, which was then concentrated. To the residue was added a mixed solution of ethyl acetate and methanol (ethyl acetate:methanol=10:1), and an insoluble was removed on a filter. The filtrate was concentrated to give the titled compound (22.0 mg).

Examples 263 and 264

According to the following reaction scheme, the compounds of Examples 263 and 264 were prepared. In the reaction scheme, 3-[(S)-4-(4-bromo-3-chloro-phenyl)-5-isopropyl-4-methyl-2-oxo-3,4-dihydro-2H-pyrimidin-1-yl]-propionic acid ethyl ester was synthesized in Example 116 Step 6.

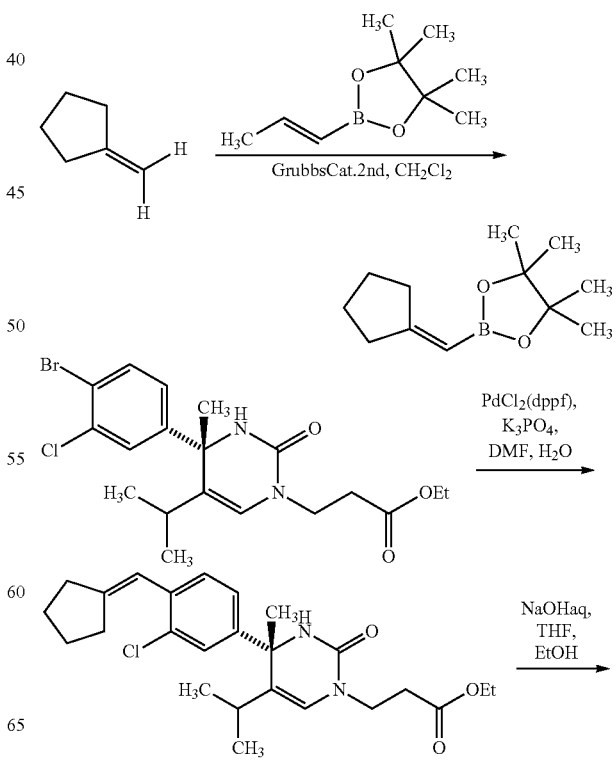

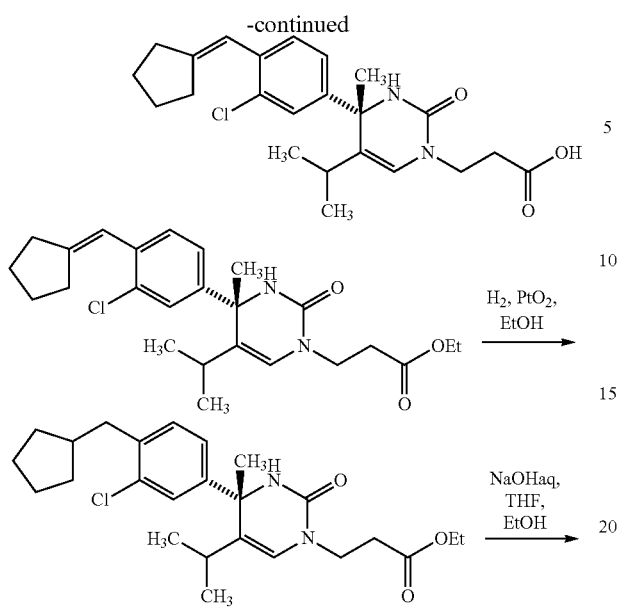
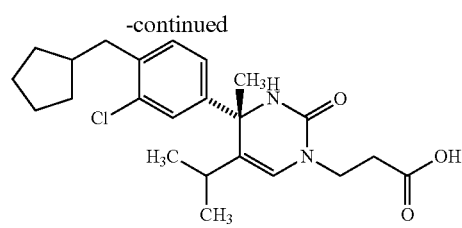
In the formula, GrubbsCat.2nd means a second-generation Grubbs catalyst, (1,3-bis(2,4,6-trimethylphenyl)-2-imidazolidinylidene)dichloro(phenylmethylene)(tricyclohexylphosphine)-ruthenium.
Example 273
The compound of Example 273 was prepared using an optically active sulfinic acid as follows.
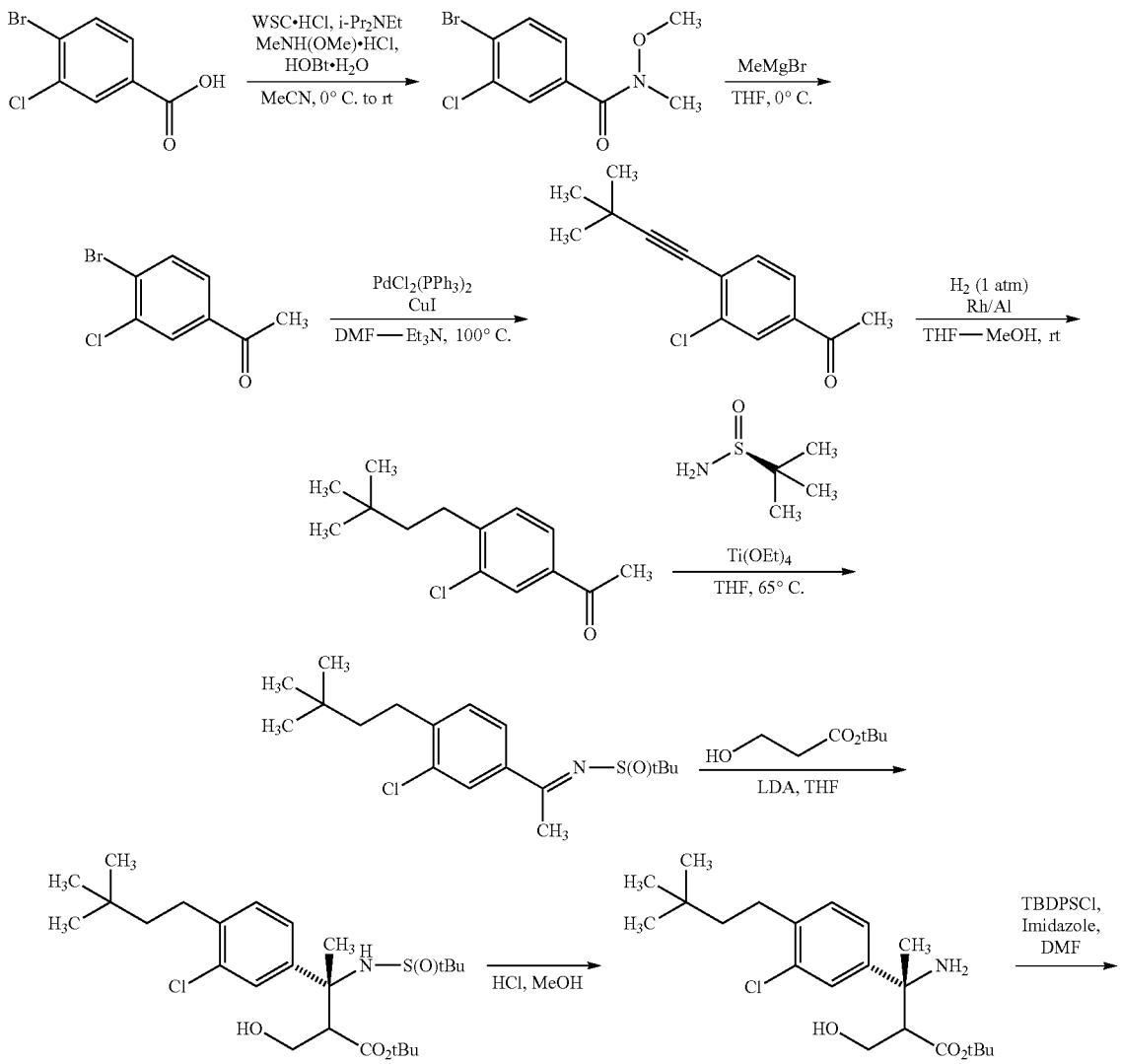

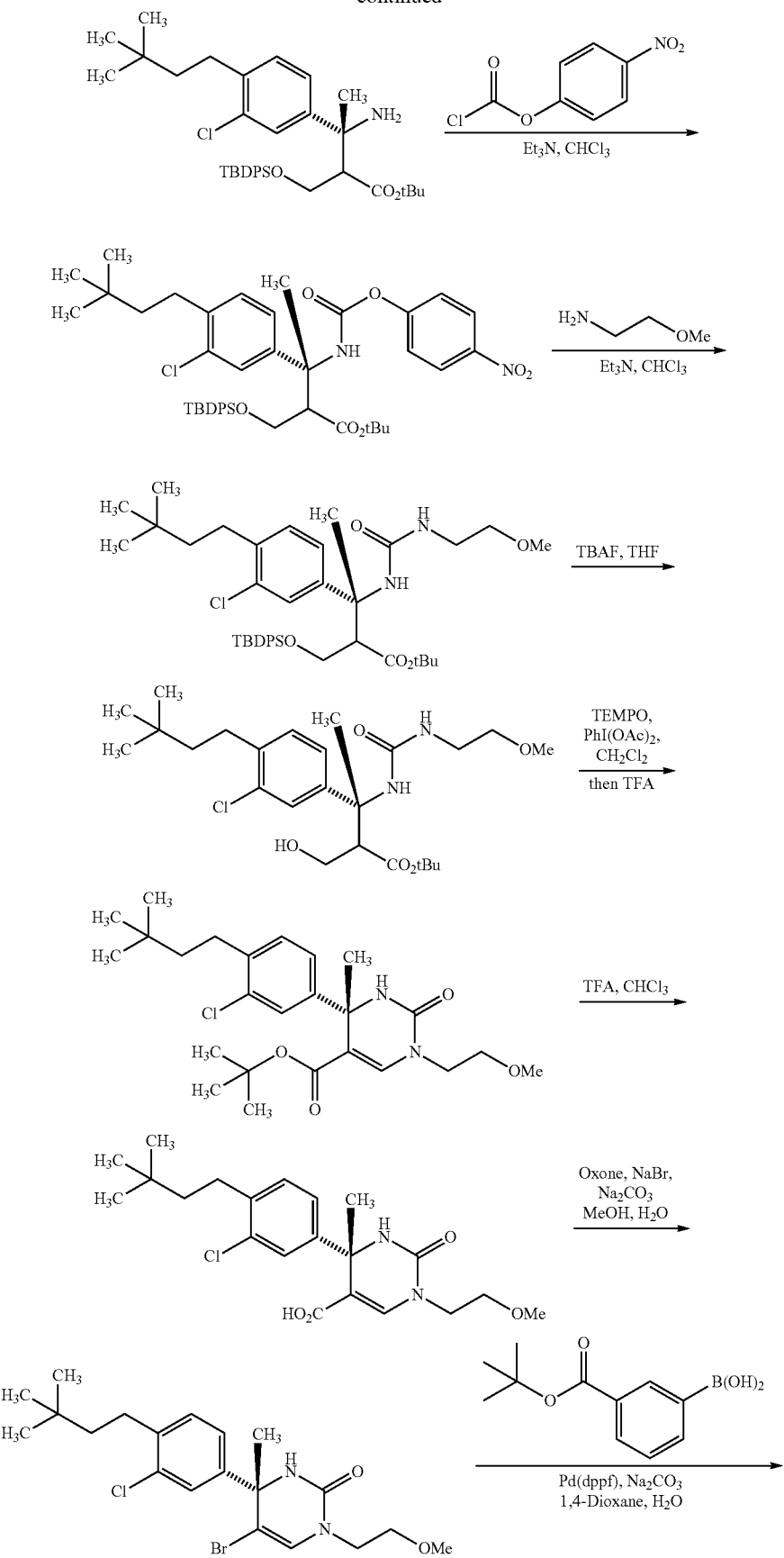

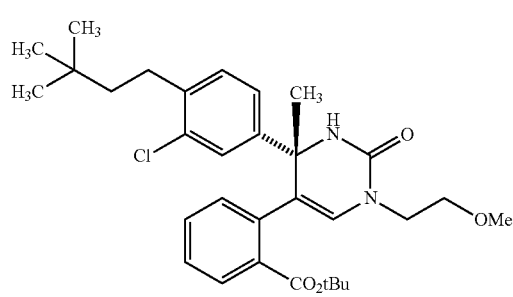

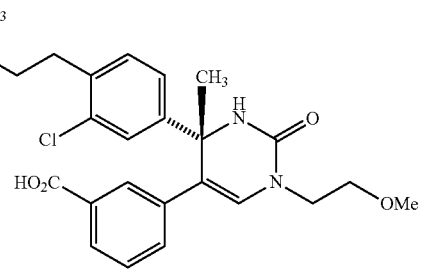

TFA, CHCl₃ →

Example 292

The compound of Example 292 was prepared according to the following reaction scheme.

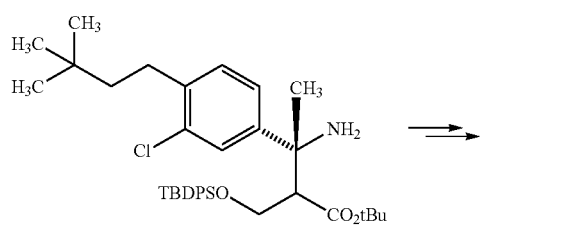

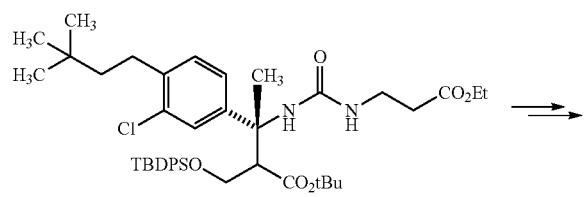

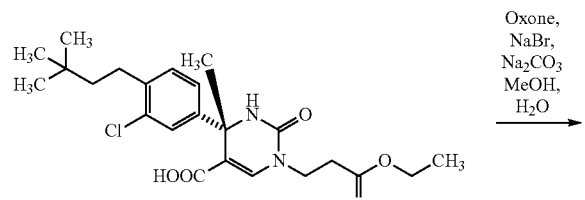

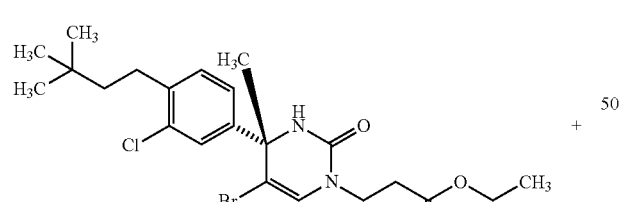

Oxone, NaBr, Na₂CO₃, MeOH, H₂O →

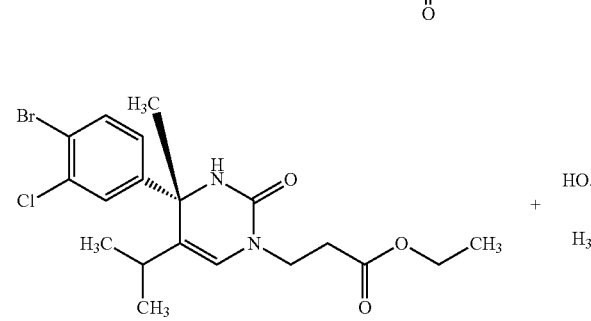

-continued

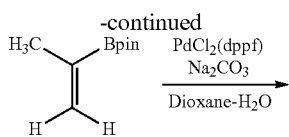

PdCl₂(dppf), Na₂CO₃
Dioxane-H₂O →

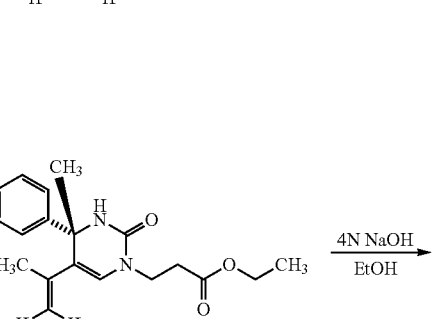

4N NaOH / EtOH →

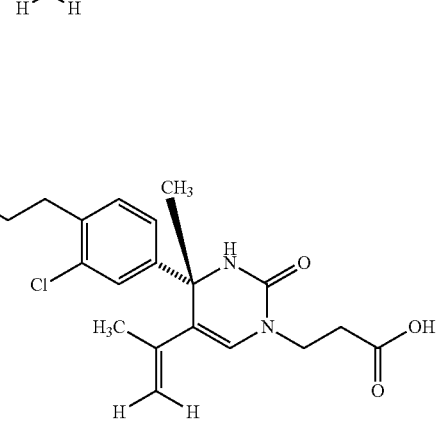

Examples 293 and 294

The compounds of Examples 293 and 294 were prepared using the bromo product obtained in Step 10 of the method using Cleisen reaction in Example 116 and 2-methyl-but-3-yn-2-ol.

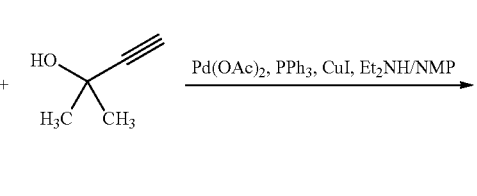

Pd(OAc)₂, PPh₃, CuI, Et₂NH/NMP →

-continued
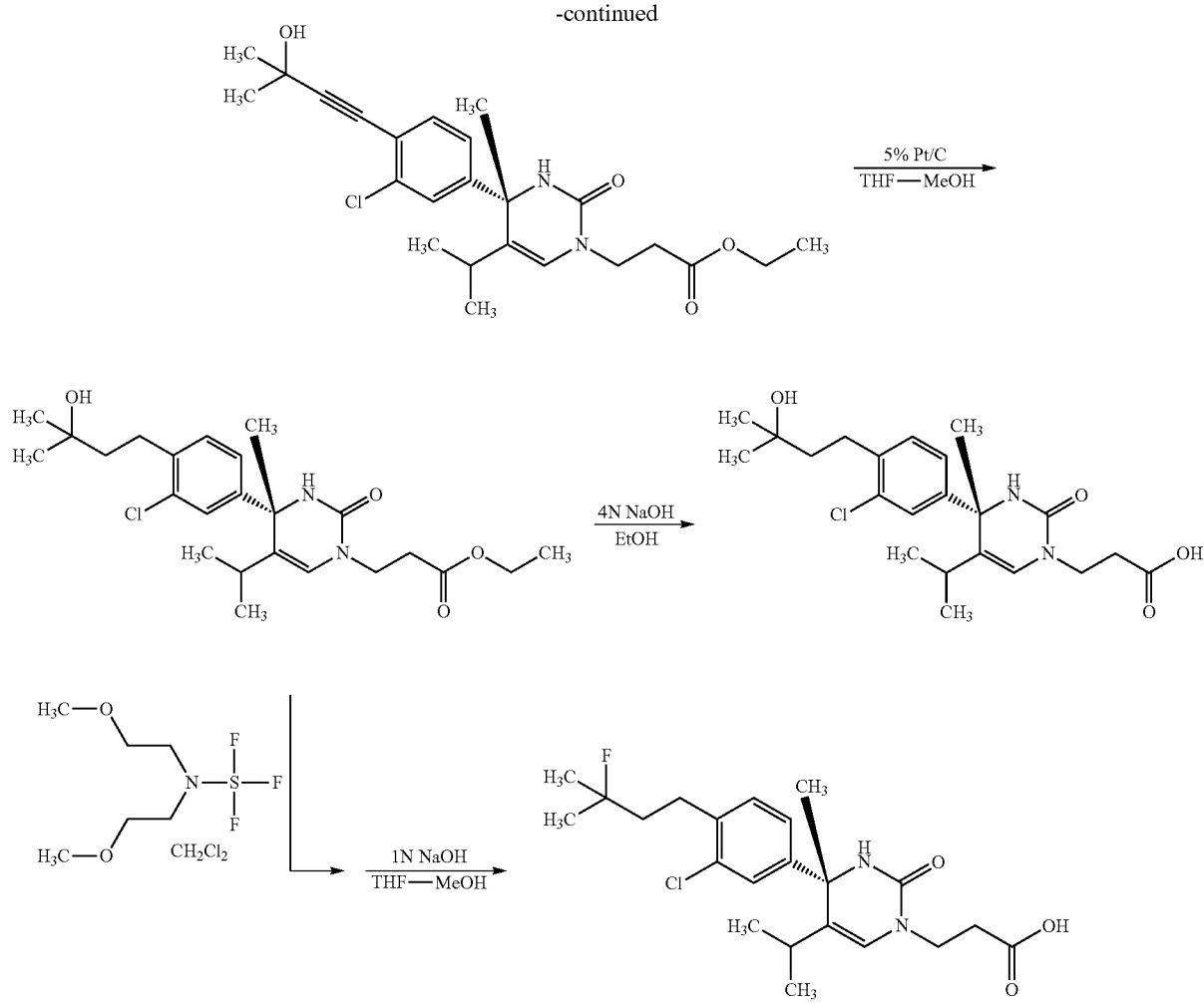
Example 296
The compound of Example 296 was prepared according to the following reaction scheme.
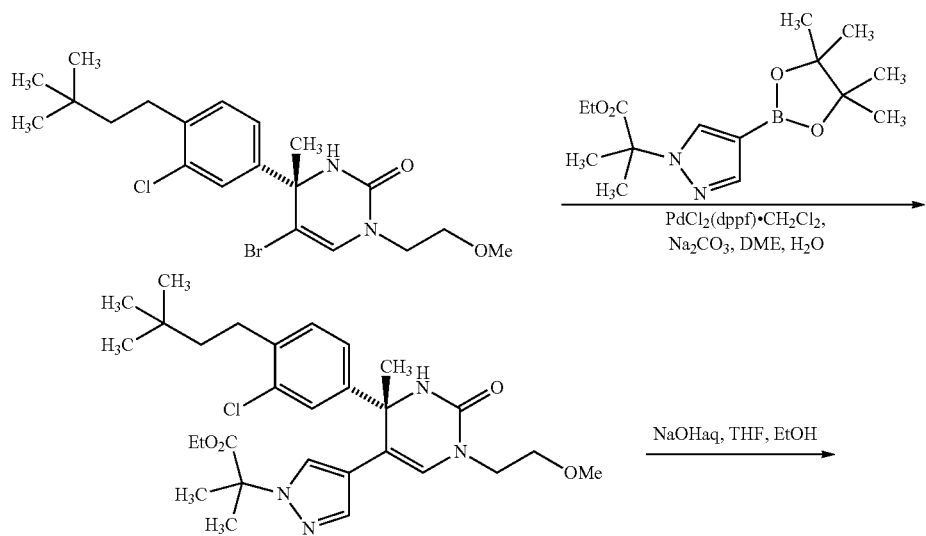

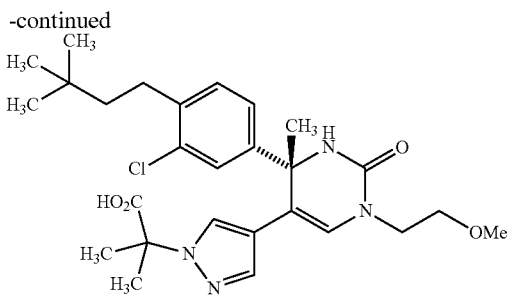

Example 298

The compound of Example 298 was prepared according to the following reaction scheme. In the following reaction scheme, 3-[(S)-4-(4-bromo-3-chloro-phenyl)-5-isopropyl-4-methyl-2-oxo-3,4-dihydro-2H-pyrimidin-1-yl]-propionic acid ethyl ester was synthesized in Example 116 Step 6.

Example 316

The compound of Example 316 was prepared using (3,3-difluoro-cyclobutyl)-acetic acid methyl ester as follows according to the method of Example 229.

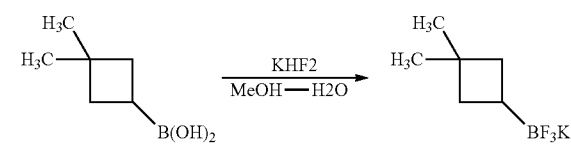

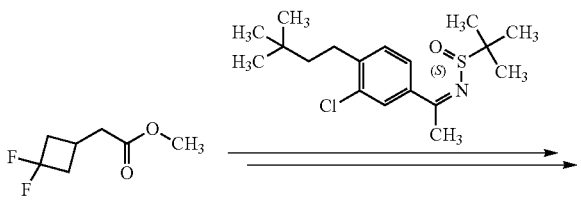

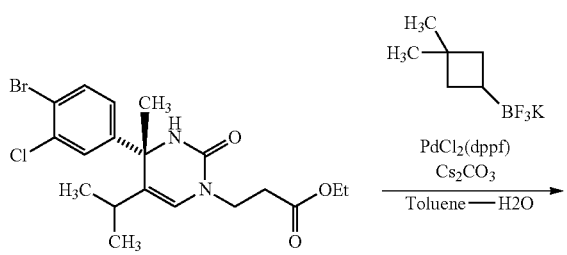

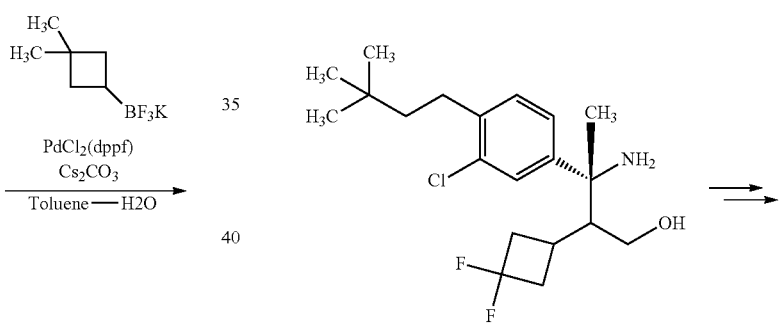

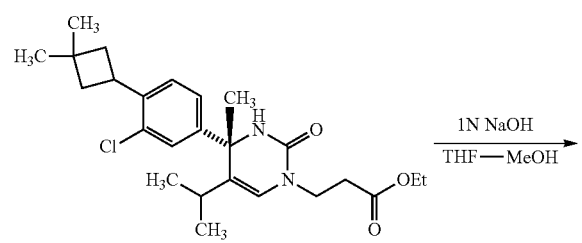

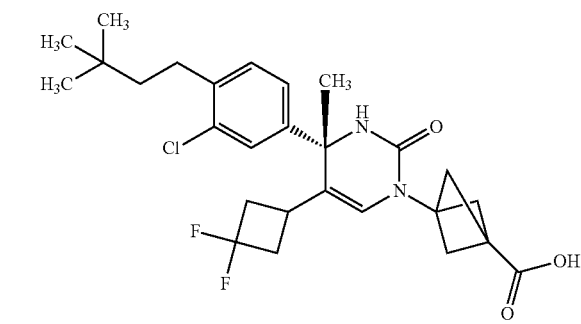

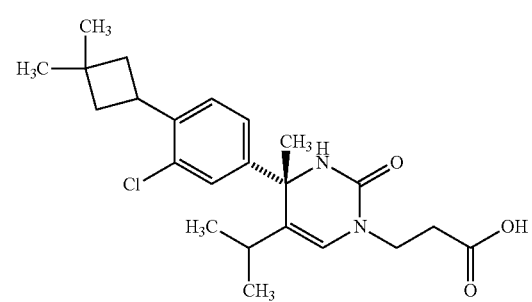

Example 320

The compound of Example 320 was prepared using (3,3-difluoro-cyclobutyl)-acetic acid methyl ester as follows according to the method of Example 271.

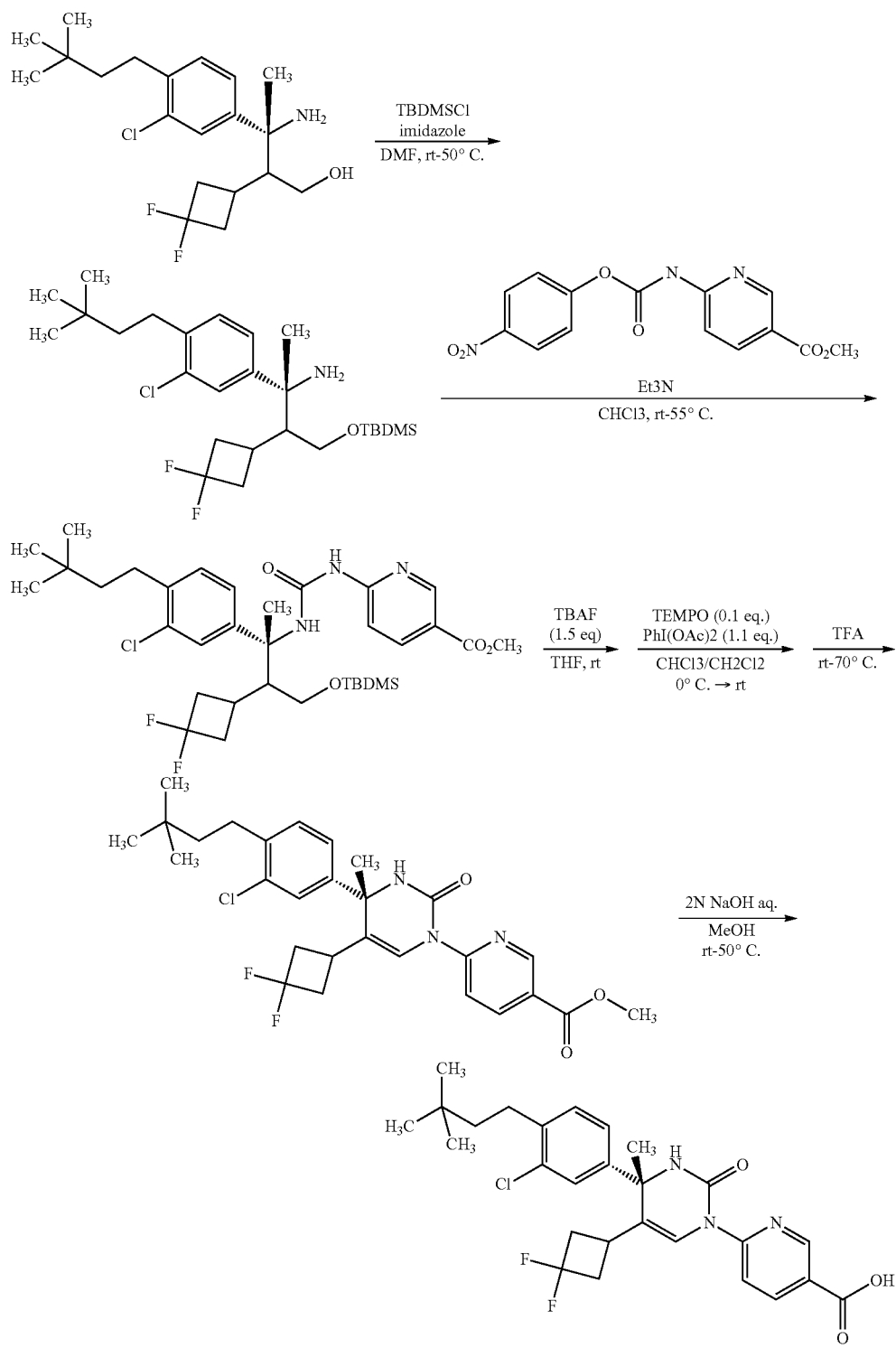

According to the method of Example 87, Example 116, Example 154 or Example 159 using an optically active sulfinic acid amide (i.e., (S)-(−)-2-methyl-propane-2-sulfinic acid amide), the following Example compounds were prepared.
Example 38, Example 113, Example 125, Example 126, Example 127, Example 137, Example 140, Example 147, Example 150, Example 157, Example 158. Example 161, Example 162, Example 163, Example 164, Example 165, Example 173, Example 175, Example 176, Example 177, Example 178, Example 179, Example 183, Example 185, Example 189

According to the method using the reaction of an optically active sulfinic acid amide the following Example compounds were prepared.

Example 190 to Example 357, other than Example 190, Example 191, Example 197, Example 198, Example 199, Example 200, Example 205, Example 212, Example 213, and Example 312

According to the method of Example 87, Example 116 or Example 130 using Cleisen reaction, the following Example compounds were prepared.
Example 9, Example 12, Example 13, Example 14, Example 15, Example 16, Example 17, Example 18, Example 19, Example 20, Example 21, Example 22, Example 23, Example 24, Example 25, Example 26, Example 27, Example 28, Example 29, Example 30, Example 31, Example 32, Example 33, Example 34, Example 35, Example 36, Example 37, Example 38, Example 39, Example 40, Example 41, Example 42, Example 43, Example 44, Example 45, Example 46, Example 47, Example 48, Example 49, Example 50, Example 143, Example 144, Example 145, Example 146, Example 148, Example 149, Example 151, Example 152, Example 153, Example 155, Example 156, Example 160, Example 166, Example 167, Example 168, Example 169, Example 170, Example 171, Example 172, Example 174, Example 180, Example 181, Example 182, Example 184, Example 186, Example 188

According to the method using the Cleisen reaction, the following Example compounds were prepared.
Example 190, Example 191, Example 197, Example 198, Example 199, Example 200, Example 205, Example 312

When an Example compound is an optically active product, a desirable enantiomer was obtained by a chiral column separation and purification of a racemate intermediate (e.g. an ethyl ester intermediate).

For example, the following example is illustrated (see Example 87, Steps 13 and 14, a method for preparation using Cleisen reaction).

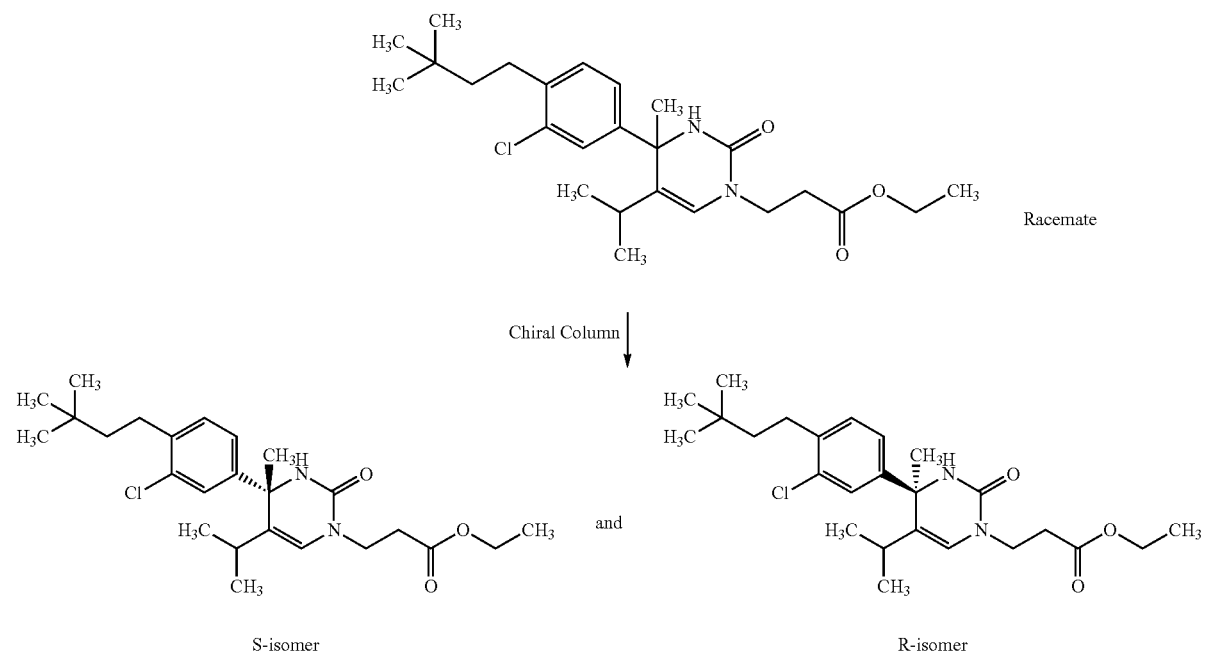

Example 51, Example 52, Example 53, Example 54, Example 55, Example 56, Example 57, Example 58, Example 59, Example 60, Example 61, Example 63, Example 64, Example 65, Example 66, Example 67, Example 68, Example 69, Example 70, Example 71, Example 72, Example 73, Example 74, Example 75, Example 76, Example 77, Example 78, Example 79, Example 80, Example 81, Example 82, Example 83, Example 84, Example 85, Example 86, Example 88, Example 89, Example 90, Example 91, Example 92, Example 93, Example 94, Example 95, Example 96, Example 97, Example 98, Example 99, Example 100, Example 103, Example 104, Example 105, Example 106, Example 107, Example 108, Example 109, Example 110, Example 111, Example 112, Example 114, Example 115, Example 117, Example 118, Example 119, Example 120, Example 121, Example 122, Example 123, Example 124, Example 128, Example 129, Example 131, Example 132, Example 133, Example 134, Example 135, Example 136, Example 138, Example 139, Example 141, Example 142, Each absolute configuration of each enantiomer was estimated on the basis of the followings:

1) A consistency of the retention times in a chiral column of an optically active product obtained in the method using an optically active sulfinic acid amide and an optically active product obtained by the method using Cleisen reaction and a separation using a chiral column;

2) A certain regularity in the retention times in a chiral column of a methyl ester intermediate or an ethyl ester intermediate of a compound in the present invention and the like;

3) A certain regularity in the strength of the biological activity value of each enantiomer of a compound in the present invention (Test Example 1); and/or 4) Results of X-ray structural analysis of a co-crystal of a compound having an RORγ antagonist activity (i.e. a related compound having the same 4-phenyl-3,4-dihydro-1H-pyrimidin-2-one skeleton as the compound of the present invention) and RORγ.

Absolute configurations of parts of Example compounds and the intermediates were determined by single crystal X-ray structural analysis.

According to Example 5, the following Example compounds were prepared using Biginelli reaction.
Example 1, Example 2, Example 3, Example 4, Example 6, Example 7, Example 8, Example 10, Example 11, Example 62, Example 101, Example 102, Example 187

Chemical structures and structural information of Example compounds prepared as above are shown in the following tables.

In the tables, i) refers to a stereochemistry of the Example compound, ii) refers to physical data (such as the retention time in a chiral column) and analytical conditions for the Example compound, or physical data (such as the retention time in a chiral column) and analytical conditions for a precursor or intermediate such as an ester of the Example compound.

In the tables,
"Chiral column IA-3" refers to CHIRALPAK IA-3 0.46 cmφ×15 cm manufactured by DAICEL Corporation, "Chiral column IC" refers to CHIRALPAK IC 0.46 cmφ×25 cm manufactured by DAICEL Corporation, "Chiral column IF-3" refers to CHIRALPAK IF-3 0.46 cmφ×15 cm manufactured by DAICEL Corporation, "Chiral column AD-3R" refers to CHIRALPAK AD-3R 0.46 cmφ×15 cm manufactured by DAICEL Corporation, and "Chiral column AS-3R" refers to CHIRALPAK AS-3R 0.46 cmφ×15 cm manufactured by DAICEL Corporation.

In the tables, "JAIGEL-ODS-AP-A" refers to an analytical column JAIGEL-ODS-AP-A, SP-120-10, φ6×25 cm of Japan Analytical Industry Co., Ltd.

In the tables, for example, "Chiral column IC, IPA/Hexane=3/7, 1 ml/min, Retention time 8.1 min" refers to "Chiral column, Mobile phase, Flow rate, Retention time, used in the measurement". "IPA" refers to isopropanol. "Hex" or "hexane" refers to n-hexane. "TFA" refers to trifluoroacetic acid.

In the tables, for example, "the optical purity of a methyl ester of Example 32 was >99% ee" refers to "HPLC analysis using a chiral column for a methyl ester, a synthetic precursor, of Example 32 showed that the optical purity was >99% ee".

Example 32

Methyl ester of Example 32

In the tables, HPLC analyses of Examples 38, 87, and 116 using a chiral column were determined with samples synthesized by a method using Cleisen reaction.

The specific optical rotations were determined with samples synthesized by a method using an optically active sulfinic acid amide.

In the tables, Example 64, Example 278, Example 279, and Example 280 are different with each other and any one of the following isomeric compounds, respectively.

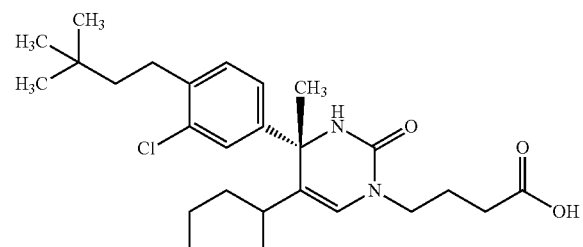

TABLE 1

| Example | Chemical Structural Formula | Structural Information |
|---|---|---|
| 1 | | i) Racemate |
| 2 | | i) Racemate |
| 3 | | i) Racemate |
| 4 | | i) Racemate |
| 5 | | i) Optically active product of Example 1 Enantiomer of Example 6<br>ii) Optical purity was >99% ee Chiral column AS-3R, $H_2O$/MeCN/TFA = 30/70/0.1, Flow rate 0.5 ml/min, Retention time 13.5 min |

TABLE 1-continued

| Example | Chemical Structural Formula | Structural Information |
|---|---|---|
| 6 | | i) Optically active product of Example 1 Enantiomer of Example 5<br>ii) Optical purity was >99% ee Chiral column AS-3R, H₂O/MeCN/TFA = 30/70/0.1, Flow rate 0.5 ml/min, Retention time 16.7 min |
| 7 | | i) Racemate |
| 8 | | i) Racemate |
| 9 | | i) Racemate |
| 10 | | i) Optically active product of Example 8 Enantiomer of Example 11<br>ii) Optical purity was >99% ee Chiral column AS-3R, H₂O/MeCN/TFA = 30/70/0.1, Flow rate 0.5 ml/min, Retention time 13.6 min |

TABLE 1-continued

| Example | Chemical Structural Formula | Structural Information |
|---|---|---|
| 11 | | i) Optically active product of Example 8. Optical purity was >99% ee<br>Enantiomer of Example 10<br>ii) Chiral column AS-3R, $H_2O$/MeCN/TFA = 30/70/0.1, Flow rate 0.5 ml/min, Retention time 12.6 min |
| 12 | | i) Optically active product of Example 9<br>Enantiomer of Example 13<br>ii) Optical purity of methyl ester of Example 12 was 99.9% ee<br>Chiral column IC, IPA/hexane = 30/70, 1 ml/min, Retention time 7.1 min |
| 13 | | i) Optically active product of Example 9<br>Enantiomer of Example 12<br>ii) Optical purity of methyl ester of Example 13 was 98.9% ee<br>Chiral column IC, IPA/hexane = 30/70, 1 ml/min, Retention time 8.1 min |
| 14 | | i) Enantiomer of Example 15<br>ii) Optical purity was >99% ee<br>Chiral column AS-3R, $H_2O$/MeCN/TFA = 40/60/0.1, Flow rate = 0.5 ml/min, Retention time 11.4 min |
| 15 | | i) Enantiomer of Example 14<br>ii) Optical purity was >99% ee<br>Chiral column AS-3R, $H_2O$/MeCN/TFA = 40/60/0.1, Flow rate = 0.5 ml/min, Retention time 12.7 min |

TABLE 1-continued

| Example | Chemical Structural Formula | Structural Information |
|---|---|---|
| 16 | | i) Racemate |
| 17 | | i) Racemate |
| 18 | | i) Racemate |
| 19 | | i) Single enantiomer<br>Example 19, Example 20, and Example 21 are diastereomers with each other<br>ii) 96.7% d.e<br>Chiral column IC,<br>IPA/hexane/TFA = 3/7/0.1, 1 ml/min,<br>Retention time 5.8 min, |
| 20 | | i) Single enantiomer<br>Example 19, Example 20, and Example 21 are diastereomers with each other<br>ii) 96.2% d.e<br>Chiral column IC,<br>IPA/hexane/TFA = 3/7/0.1, 1 ml/min,<br>Retention time 5.3 min |

TABLE 1-continued

| Example | Chemical Structural Formula | Structural Information |
|---|---|---|
| 21 | 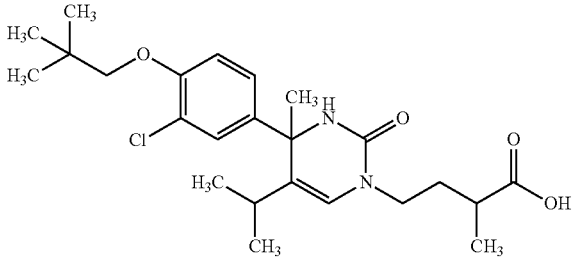 [SMILES: CC(C)C1=CN(CCC(C)C(=O)O)C(=O)NC1(C)c1ccc(OCC(C)(C)C)c(Cl)c1] | i) A mixture of two diastereomers Example 19, Example 20, and Example 21 are diastereomer with each other ii) Chiral column IC, IPA/hexane/TFA = 1/9/0.1, 1 ml/min, Retention time 12.9 min, 13.3 min |
| 22 | 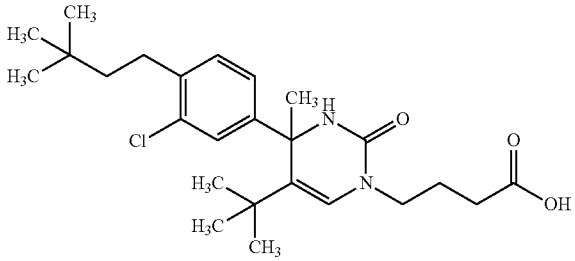 [SMILES: CC(C)(C)CCc1ccc(C2(C)NC(=O)N(CCCC(=O)O)C=C2C(C)(C)C)cc1Cl] | i) Racemate |
| 23 | 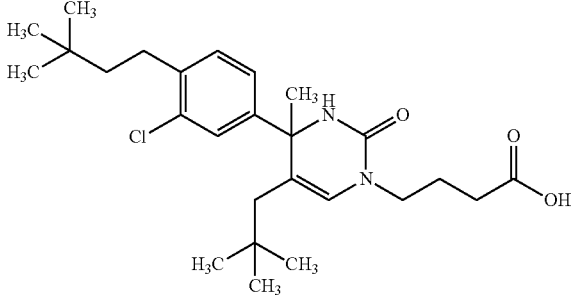 [SMILES: CC(C)(C)CCc1ccc(C2(C)NC(=O)N(CCCC(=O)O)C=C2CC(C)(C)C)cc1Cl] | i) Racemate |
| 24 | 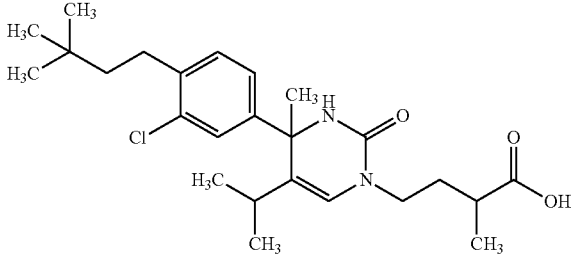 [SMILES: CC(C)C1=CN(CCC(C)C(=O)O)C(=O)NC1(C)c1ccc(CCC(C)(C)C)c(Cl)c1] | i) A mixture of two diastereomers ii) Methyl ester of Example 24 analytical condition Chiral column IF-3, hexane/IPA = 90/10, Flow rate 1 ml/min, Retention time 8.6 min, 8.7 min |
| 25 | 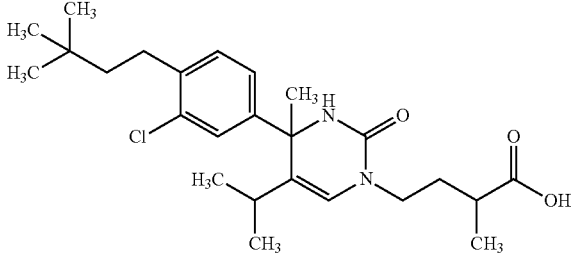 [SMILES: CC(C)C1=CN(CCC(C)C(=O)O)C(=O)NC1(C)c1ccc(CCC(C)(C)C)c(Cl)c1] | i) A mixture of two diastereomers ii) Methyl ester of Example 25 analytical condition Chiral column IF-3, hexane/IPA = 90/10, Flow rate 1 ml/min, Retention time 12.5 min, 13.3 min |

TABLE 1-continued

| Example | Chemical Structural Formula | Structural Information |
|---|---|---|
| 26 | | i) Racemate |
| 27 | | i) Racemate |
| 28 | | i) Racemate |
| 29 | | i) Racemate |
| 30 | | i) Racemate |

TABLE 1-continued

| Example | Chemical Structural Formula | Structural Information |
|---------|----------------------------|------------------------|
| 31 | | i) Enantiomer of Example 32<br>ii) Optical purity of methyl ester of Example 31 was >99% ee<br>Chiral column IA-3,<br>hexane/IPA = 80/20, Flow rate 1 ml/min,<br>Retention time 3.7 min |
| 32 | | i) Enantiomer of Example 31<br>ii) Optical purity of methyl ester of Example 32 was >99% ee<br>Chiral column IA-3,<br>hexane/IPA = 80/20, Flow rate 1 ml/min,<br>Retention time 4.6 min |
| 33 | | i) A mixture of two diastereomers<br>ii) Chiral column AS-3R,<br>$H_2O$/MeCN/TFA = 40/60/0.1, 0.5 ml/min, Retention time 12.60 min |
| 34 | | i) A mixture of two diastereomers<br>ii) Chiral column AS-3R,<br>$H_2O$/MeCN/TFA = 40/60/0.1, 0.5 ml/min, Retention time 13.25 min, 14.05 min |
| 35 | | i) Enantiomer of Example 36<br>ii) Optical purity was >99.5% ee<br>Chiral column IA-3,<br>IPA/Hex/TFA = 5/95/0.1, 1 ml/min,<br>Retention time 4.91 min |

TABLE 1-continued

| Example | Chemical Structural Formula | Structural Information |
|---|---|---|
| 36 | | i) Enantiomer of Example 35<br>ii) Optical purity was >99.5% ee<br>Chiral column IA-3,<br>IPA/Hex/TFA = 5/95/0.1, 1 ml/min,<br>Retention time 8.08 min |
| 37 | | i) Enantiomer of Example 38<br>ii) 92% ee<br>Chiral column AD-3R,<br>H$_2$O/MeCN/HCOOH = 30/70/0.1, Flow rate 0.5 ml/min, Retention time 6.5 min |
| 38 | | i) Enantiomer of Example 37<br>ii) >99% ee<br>Chiral column AD-3R,<br>H$_2$O/MeCN/HCOOH = 30/70/0.1, Flow rate 0.5 ml/min, Retention time 10.0 min<br>$[\alpha]_D^{25}$ = +106.5° (C = 1.00, MeOH) |
| 39 | | i) Enantiomer of Example 40<br>ii) Optical purity of methyl ester of Example 39 was >99% ee<br>Chiral column IA-3,<br>IPA/Hex/TFA = 10/90/0.1,<br>1 ml/min, Retention time 6.32 min |
| 40 | | i) Enantiomer of Example 39<br>ii) Optical purity of methyl ester of Example 40 was >99% ee<br>Chiral column IA-3,<br>IPA/Hex/TFA = 10/90/0.1,<br>1 ml/min, Retention time 9.27 min |

TABLE 1-continued

| Example | Chemical Structural Formula | Structural Information |
|---|---|---|
| 41 | | i) Enantiomer of Example 42<br>ii) Optical purity of methyl ester of Example 41 was >99% ee<br>Chiral column IA-3,<br>hexane/IPA = 90/10, Flow rate 1 ml/min,<br>Retention time 4.8 min |
| 42 | | i) Enantiomer of Example 41<br>ii) Optical purity of methyl ester of Example 42 was >99% ee<br>Chiral column IA-3,<br>hexane/IPA = 90/10, Flow rate 1 ml/min,<br>Retention time 10.2 min |
| 43 | | i) Enantiomer of Example 44<br>ii) Analytical condition of methyl ester of Example 43<br>Chiral column IA-3,<br>hexane/IPA = 90/10, Flow rate 1 ml/min,<br>Retention time 4.0 min |
| 44 | | i) Enantiomer of Example 43<br>ii) Analytical condition of methyl ester of Example 44<br>Chiral column IA-3,<br>hexane/IPA = 90/10, Flow rate 1 ml/min,<br>Retention time 4.0 min |
| 45 | | i) Enantiomer of Example 46<br>ii) Optical purity of methyl ester of Example 45 was >99% ee<br>Chiral column IA-3,<br>hexane/IPA = 90/10, Flow rate 1 ml/min,<br>Retention time 4.4 min |

TABLE 1-continued

| Example | Chemical Structural Formula | Structural Information |
|---|---|---|
| 46 | | i) Enantiomer of Example 45<br>ii) Optical purity of methyl ester of Example 46 was >99% ee<br>Chiral column IA-3,<br>hexane/IPA = 90/10, Flow rate 1 ml/min,<br>Retention time 6.7 min |
| 47 | | i) Enantiomer of Example 48<br>ii) Optical purity of methyl ester of Example 47 was >99% ee<br>Chiral column IA-3,<br>hexane/IPA = 90/10, Flow rate 1 ml/min,<br>Retention time 5.3 min |
| 48 | | i) Enantiomer of Example 47<br>ii) Optical purity of methyl ester of Example 48 was >99% ee<br>Chiral column IA-3,<br>hexane/IPA = 90/10, Flow rate 1 ml/min,<br>Retention time 7.3 min |
| 49 | | i) Enantiomer of Example 50<br>ii) Optical purity of methyl ester of Example 49 was >99% ee<br>Chiral column IA-3,<br>hexane/IPA = 80/20, Flow rate 1 ml/min,<br>Retention time 5.3 min |
| 50 | | i) Enantiomer of Example 49<br>ii) Optical purity of methyl ester of Example 50 was >99% ee<br>Chiral column IA-3,<br>hexane/IPA = 80/20, Flow rate 1 ml/min,<br>Retention time 7.3 min |

TABLE 1-continued

| Example | Chemical Structural Formula | Structural Information |
|---|---|---|
| 51 | | i) Enantiomer of Example 52<br>ii) Optical purity of methyl ester was >99% ee<br>Chiral column IA-3,<br>hexane/IPA = 90/10, Flow rate 1 ml/min,<br>Retention time 6.0 min |
| 52 | | i) Enantiomer of Example 51<br>ii) Optical purity of methyl ester of Example 52 was >99% ee<br>Chiral column IA-3,<br>hexane/IPA = 90/10, Flow rate 1 ml/min,<br>Retention time 7.9 min |
| 53 | | i) Racemate |
| 54 | | i) Enantiomer of Example 55<br>ii) Optical purity of methyl ester of Example 54 was >99% ee<br>Chiral column IA-3,<br>IPA/Hex/TFA = 10/90/0.1,<br>1 ml/min, Retention time 3.65 min |
| 55 | | i) Enantiomer of Example 54<br>ii) Optical purity of methyl ester of Example 55 was >99% ee<br>Chiral column IA-3,<br>IPA/Hex/TFA = 10/90/0.1,<br>1 ml/min, Retention time 6.01 min |
| 56 | | i) Enantiomer of Example 57<br>ii) Optical purity of methyl ester of Example 56 was >99% ee<br>Chiral column IA-3,<br>hexane/IPA = 90/10, Flow rate 1 ml/min,<br>Retention time 5.8 min |

TABLE 1-continued

| Example | Chemical Structural Formula | Structural Information |
|---|---|---|
| 57 | | i) Enantiomer of Example 58<br>ii) Optical purity of methyl ester of Example 57 was >99% ee<br>Chiral column IA-3,<br>hexane/IPA = 90/10, Flow rate 1 ml/min,<br>Retention time 8.5 min |
| 58 | | i) Enantiomer of Example 59<br>ii) Optical purity of methyl ester of Example 57 was >99% ee<br>Chiral column IA-3,<br>hexane/IPA = 90/10, Flow rate 1 ml/min,<br>Retention time 5.2 min |
| 59 | | i) Enantiomer of Example 58<br>ii) Optical purity of methyl ester was >99% ee<br>Chiral column IA-3,<br>hexane/IPA = 90/10, Flow rate 1 ml/min,<br>Retention time 8.1 min |
| 60 | | i) Enantiomer of Example 61<br>ii) Optical purity of methyl ester of Example 60 was >99% ee<br>Chiral column IA-3,<br>hexane/IPA = 90/10, Flow rate 1 ml/min,<br>Retention time 6.1 min |
| 61 | | i) Enantiomer of Example 60<br>ii) Optical purity of methyl ester of Example 61 was >99% ee<br>Chiral column IA-3,<br>hexane/IPA = 90/10, Flow rate 1 ml/min,<br>Retention time 936 min |
| 62 | | i) Racemate |

TABLE 1-continued

| Example | Chemical Structural Formula | Structural Information |
|---|---|---|
| 63 | | i) Single enantiomer<br>Stereochemistry of cyclopentane ring not determined<br>ii) Optical purity of methyl ester of Example 63 was >99% ee<br>Chiral column IA-3,<br>hexane/IPA = 90/10, Flow rate 1 ml/min,<br>Retention time 4.3 min |
| 64 | | i) Single enantiomer<br>Stereochemistry of cyclopentane ring not determined<br>Examples 64, 278, 279, and 280 are a diastereomer with each other<br>ii) Optical purity of methyl ester of Example 64 was >99% ee<br>Chiral column IA-3,<br>hexane/IPA = 90/10, Flow rate 1 ml/min,<br>Retention time 6.3 min<br>Optical purity of Example 64 was >99% ee<br>Analytical condition of Example 64<br>JAIGEL-ODS-AP-A,<br>MeCN/H$_2$O/HCO$_2$H = 90/10/0.1, Flow rate 1 ml/min, Retention time 9.6 min. |
| 65 | | i) Racemate |
| 66 | | i) Enantiomer of Example 67<br>ii) Optical purity of methyl ester of Example 66 was >98% ee<br>Chiral column IF-3,<br>IPA/Hex/TFA = 10/90/0.1,<br>1 ml/min, Retention time 8.69 min |
| 67 | | i) Enantiomer of Example 66<br>ii) Optical purity of methyl ester of Example 67 was >98% ee<br>Chiral column IF-3,<br>IPA/Hex/TFA = 10/90/0.1,<br>1 ml/min, Retention time 10.26 min |

TABLE 1-continued

| Example | Chemical Structural Formula | Structural Information |
|---|---|---|
| 68 | | i) Enantiomer of Example 69<br>ii) Optical purity of methyl ester of Example 68 was >99% ee<br>Chiral column IA-3,<br>hexane/IPA = 90/10, Flow rate 1 ml/min,<br>Retention time 5.3 min |
| 69 | | i) Enantiomer of Example 68<br>ii) Optical purity of methyl ester of Example 69 was >99% ee<br>Chiral column IA-3,<br>hexane/IPA = 90/10, Flow rate 1 ml/min,<br>Retention time 8.4 min |
| 70 | | i) Racemate |
| 71 | | i) Enantiomer of Example 72<br>ii) Optical purity of methyl ester of Example 71 was >99% ee<br>Chiral column IA-3,<br>hexane/IPA = 90/10, Flow rate 1 ml/min,<br>Retention time 4.2 min |
| 72 | | i) Enantiomer of Example 71<br>ii) Optical purity of methyl ester of Example 72 was >99% ee<br>Chiral column IA-3,<br>hexane/IPA = 90/10, Flow rate 1 ml/min,<br>Retention time 6.5 min |
| 73 | | i) Diastereomer mixture<br>ii) Analytical condition of methyl ester of Example 73<br>Chiral column 1A-3,<br>hexane/IPA = 90/10, Flow rate 1 ml/min.<br>Retention time 3.6 min, 4.6 min, 7.0 min, 7.7 min<br>Example 73 was prepared by hydrolysis of two diastereomer mixtures with 7.0 min and 7.7 min of retention times among the isomers. |

TABLE 1-continued

| Example | Chemical Structural Formula | Structural Information |
|---|---|---|
| 74 | | i) Enantiomer of Example 75<br>ii) Optical purity of methyl ester of Example 74 was >99% ee<br>Chiral column IA-3,<br>hexane/IPA = 90/10, Flow rate 1 ml/min,<br>Retention time 3.8 min |
| 75 | | i) Enantiomer of Example 74<br>ii) Optical purity of methyl ester of Example 75 was >99% ee<br>Chiral column IA-3,<br>hexane/IPA = 90/10, Flow rate 1 ml/min,<br>Retention time 5.0 min |
| 76 | | i) Enantiomer of Example 77<br>ii) Optical purity of methyl ester of Example 76 was >99% ee<br>Chiral column IA-3,<br>hexane/IPA = 90/10, Flow rate 1 ml/min,<br>Retention time 3.7 min |
| 77 | | i) Enantiomer of Example 76<br>ii) Optical purity of methyl ester of Example 77 was >99% ee<br>Chiral column IA-3,<br>hexane/IPA = 90/10, Flow rate 1 ml/min,<br>Retention time 6.1 min |
| 78 | | i) Enantiomer of Example 79<br>ii) Optical purity of methyl ester of Example 78 was >99.5% ee<br>Chiral column IA-3,<br>IPA/Hex/TFA = 10/90/0.1,<br>1 ml/min, Retention time 5.27 min |

TABLE 1-continued

| Example | Chemical Structural Formula | Structural Information |
|---|---|---|
| 79 | | i) Enantiomer of Example 78<br>ii) Optical purity of methyl ester of Example 79 was >99.5% ee<br>Chiral column IA-3,<br>IPA/Hex/TFA = 10/90/0.1,<br>1 ml/min, Retention time 9.25 min |
| 80 | | i) Racemate |
| 81 | | i) Racemate |
| 82 | | i) Enantiomer of Example 83<br>ii) Optical purity of methyl ester of Example 82 was >99% ee<br>Chiral column IA-3,<br>hexane/IPA = 80/20, Flow rate 1 ml/min,<br>Retention time 4.2 min |
| 83 | | i) Enantiomer of Example 82<br>ii) Optical purity of methyl ester of Example 83 was >99% ee<br>Chiral column IA-3,<br>hexane/IPA = 80/20, Flow rate 1 ml/min,<br>Retention time 6.3 min |

TABLE 1-continued

| Example | Chemical Structural Formula | Structural Information |
|---|---|---|
| 84 | | i) Racemate |
| 85 | | i) Racemate |
| 86 | | i) Enantiomer of Example 87<br>ii) Optical purity of ethyl ester was >99% ee<br>Analytical condition of ethyl ester of Example 86<br>Chiral column IA-3,<br>hexane/IPA = 90/10. Flow rate 1 ml/min, Retention time 4.9 min<br>Optical purity of Example 86 was >99% ee<br>Analytical condition of Example 86<br>Chiral column AD-3R,<br>$H_2O$/MeCN/HCOOH = 30/70/0.1, Flow rate 0.5 ml/min, Retention time 6.0 min |
| 87 | | i) Enantiomer of Example 86<br>ii) Optical purity of ethyl ester was >99% ee<br>Analytical condition of ethyl ester of Example 87<br>Chiral column IA-3,<br>hexane/IPA = 90/10. Flow rate 1 ml/min, Retention time 7.1 min<br>Optical purity of Example 87 was >99% ee<br>Analytical condition of Example 87<br>Chiral column AD-3R,<br>$H_2O$/MeCN/HCOOH = 30/70/0.1, Flow rate 0.5 ml/min,<br>Retention time 6.0 min<br>$[\alpha]_D^{25}$ = +112.6° (C = 1.00, MeOH) |
| 88 | | i) Diastereomer of Example 89<br>ii) Optical purity of methyl ester of Example 88 was >99% ee<br>Chiral column IA-3,<br>hexane/IPA = 80/20, Flow rate 1 ml/min, Retention time 3.7 min |

| Example | Chemical Structural Formula | Structural Information |
|---|---|---|
| 89 | | i) Diastereomer of Example 88<br>ii) Optical purity of methyl ester of Example 89 was >99% ee<br>Chiral column IA-3,<br>hexane/IPA = 80/20, Flow rate 1 ml/min,<br>Retention time 5.6 min |
| 90 | | i) Racemate |
| 91 | | i) Enantiomer of Example 92<br>ii) Optical purity of methyl ester of Example 91 was >99% ee<br>Chiral column IA-3,<br>hexane/IPA = 80/20, Flow rate 1 ml/min,<br>Retention time 4.5 min |
| 92 | | i) Enantiomer of Example 91<br>ii) Optical purity of methyl ester of Example 92 was >99% ee<br>Chiral column IA-3,<br>hexane/IPA = 80/20, Flow rate 1 ml/min,<br>Retention time 7.5 min |
| 93 | | i) Enantiomer of Example 94<br>ii) Optical purity of methyl ester of Example 93 was >99% ee<br>Chiral column IA-3,<br>hexane/IPA = 90/10, Flow rate 1 ml/min,<br>Retention time 5.3 min |

TABLE 1-continued

| Example | Chemical Structural Formula | Structural Information |
|---|---|---|
| 94 | | i) Enantiomer of Example 93<br>ii) Optical purity of methyl ester of Example 94 was >99% ee<br>Chiral column IA-3,<br>hexane/IPA = 90/10, Flow rate 1 ml/min,<br>Retention time 6.8 min |
| 95 | | i) Enantiomer of Example 96<br>ii) Analytical condition of methyl ester of Example 95<br>Chiral column IA-3,<br>hexane/IPA = 90/10, Flow rate 1 ml/min,<br>Retention time 5.0 min |
| 96 | | i) Enantiomer of Example 95<br>ii) Analytical condition of methyl ester of Example 96<br>Chiral column IA-3,<br>hexane/IPA = 90/10, Flow rate 1 ml/min,<br>Retention time 9.7 min |
| 97 | | i) Enantiomer of Example 98<br>ii) Optical purity of ethyl ester of Example 97 was >99% ee<br>Chiral column IA-3,<br>hexane/IPA = 90/10, Flow rate 1 ml/min,<br>Retention time 4.2 min |
| 98 | | i) Enantiomer of Example 97<br>ii) Optical purity of ethyl ester of Example 98 was >99% ee<br>Chiral column IA-3,<br>hexane/IPA = 90/10, Flow rate 1 ml/min,<br>Retention time 6.2 min |

TABLE 1-continued

| Example | Chemical Structural Formula | Structural Information |
|---|---|---|
| 99 | | i) Enantiomer of Example 100<br>ii) Optical purity of methyl ester of Example 99 was >99% ee<br>Chiral column IA-3,<br>hexane/IPA = 80/20, Flow rate 1 ml/min,<br>Retention time 4.3 min |
| 100 | | i) Enantiomer of Example 99<br>ii) Optical purity of methyl ester of Example 100 was >99% ee<br>Chiral column IA-3,<br>hexane/IPA = 80/20, Flow rate 1 ml/min,<br>Retention time 8.9 min |
| 101 | | i) Enantiomer of Example 102<br>ii) Analytical condition of methyl ester of Example 101<br>Chiral column IA-3,<br>hexane/IPA = 80/20, Flow rate 1 ml/min,<br>Retention time 7.3 min |
| 102 | | i) Enantiomer of Example 101<br>ii) Analytical condition of methyl ester of Example 102<br>Chiral column IA-3,<br>hexane/IPA = 80/20, Flow rate 1 ml/min,<br>Retention time 7.9 min |
| 103 | | i) Enantiomer of Example 104<br>ii) Optical purity of methyl ester of Example 103 was >99% ee<br>Chiral column IA-3,<br>hexane/IPA = 90/10, Flow rate 1 ml/min,<br>Retention time 4.7 min |

TABLE 1-continued

| Example | Chemical Structural Formula | Structural Information |
|---|---|---|
| 104 | | i) Enantiomer of Example 103<br>ii) Optical purity of methyl ester of Example 104 was >99% ee<br>Chiral column IA-3,<br>hexane/IPA = 90/10, Flow rate 1 ml/min,<br>Retention time 12.4 min |
| 105 | | i) Racemate |
| 106 | | i) Racemate |
| 107 | | i) Enantiomer of Example 108<br>ii) Optical purity of methyl ester of Example 107 was >99% ee<br>Chiral column IA-3,<br>hexane/IPA = 80/10, Flow rate 1 ml/min,<br>Retention time 3.4 min<br>The relative configuration of substituents on the cyclobutane ring was estimated as trans-isomer |
| 108 | | i) Enantiomer of Example 107<br>ii) Optical purity of methyl ester of Example 108 was >99% ee<br>Chiral column IA-3,<br>hexane/IPA = 80/10, Flow rate 1 ml/min,<br>Retention time 4.9 min |
| 109 | | i) Enantiomer of Example 110<br>ii) Analytical condition of methyl ester of Example 109<br>Chiral column IA-3,<br>hexane/IPA = 90/10, Flow rate 1 ml/min,<br>Retention time 5.7 min |

TABLE 1-continued

| Example | Chemical Structural Formula | Structural Information |
|---------|----------------------------|------------------------|
| 110 | | i) Enantiomer of Example 109<br>ii) Analytical condition of methyl ester of Example 110<br>Chiral column IA-3,<br>hexane/IPA = 90/10, Flow rate 1 ml/min,<br>Retention time 9.3 min |
| 111 | | i) Enantiomer of Example 112<br>ii) Optical purity of ethyl ester of Example 111 was 86.6% ee<br>Chiral column IA-3,<br>hexane/IPA = 90/10, Flow rate 1 ml/min,<br>Retention time 3.8 min |
| 112 | | i) Enantiomer of Example 111<br>ii) Optical purity of ethyl ester of Example 112 was 98.8% ee<br>Chiral column IA-3,<br>hexane/IPA = 90/10, Flow rate 1 ml/min,<br>Retention time 4.3 min |
| 113 | | i) Optically active product (optical purity not determined) |
| 114 | | i) Racemate |

TABLE 1-continued

| Example | Chemical Structural Formula | Structural Information |
|---|---|---|
| 115 | | i) Enantiomer of Example 116<br>ii) Optical purity was >99% ee<br>Analytical condition of ethyl ester of Example 115<br>Chiral column IA-3,<br>hexane/IPA = 90/10, Flow rate 1 ml/min, Retention time 4.1 min<br>Analytical condition of Example 115<br>Chiral column AD-3R,<br>$H_2O$/MeCN/HCOOH = 30/70/0.1, Flow rate 0.5 ml/min, Retention time 6.0 min |
| 116 | | i) Enantiomer of Example 115<br>ii) Optical purity was >99% ee<br>Analytical condition of ethyl ester of Example 116<br>Chiral column IA-3,<br>hexane/IPA = 90/10, Flow rate 1 ml/min, Retention time 6.4 min<br>Analytical condition of Example 116<br>Chiral column AD-3R,<br>$H_2O$/MeCN/HCOOH = 30/70/0.1, Flow rate 0.5 ml/min, Retention time 9.2 min<br>$[\alpha]_D^{25}$ = +106.1° (C = 1.00, MeOH) |
| 117 | | i) Enantiomer of Example 118<br>ii) Prepared by hydrolysis of ethyl ester of Example 117<br>Analytical condition of ethyl ester<br>Chiral column IA-3,<br>hexane/IPA = 90/10, Flow rate 1 ml/min, Retention time 4.1 min |
| 118 | | i) Enantiomer of Example 117<br>ii) Synthesized by hydrolysis of ethyl ester of Example 118<br>Analytical condition of ethyl ester<br>Chiral column IA-3,<br>hexane/IPA = 90/10, Flow rate 1 ml/min, Retention time 6.4 min |
| 119 | | i) Enantiomer of Example 120<br>ii) Analytical condition of ethyl ester of Example 119<br>Chiral column IA-3,<br>hexane/IPA = 90/10, Flow rate 1 ml/min, Retention time 4.8 min |

TABLE 1-continued

| Example | Chemical Structural Formula | Structural Information |
|---|---|---|
| 120 | | i) Enantiomer of Example 119<br>ii) Analytical condition of ethyl ester of Example 120<br>Chiral column IA-3,<br>hexane/IPA = 90/10, Flow rate 1 ml/min,<br>Retention time 8.9 min |
| 121 | | i) Enantiomer of Example 122<br>ii) Analytical condition of ethyl ester of Example 121<br>Chiral column IA-3,<br>hexane/IPA = 90/10, Flow rate 1 ml/min,<br>Retention time 4.7 min |
| 122 | | i) Enantiomer of Example 121<br>ii) Analytical condition of ethyl ester of Example 122<br>Chiral column IA-3,<br>hexane/IPA = 90/10, Flow rate 1 ml/min,<br>Retention time 7.8 min |
| 123 | | i) Enantiomer of Example 124<br>ii) Analytical condition of ethyl ester of Example 123<br>Chiral column IA-3,<br>hexane/IPA = 90/10, Flow rate 1 ml/min,<br>Retention time 4.2 min |
| 124 | | i) Enantiomer of Example 123<br>ii) Analytical condition of ethyl ester of Example 124<br>Chiral column IA-3,<br>hexane/IPA = 90/10, Flow rate 1 ml/min,<br>Retention time 6.7 min |
| 125 | | i) Optically active product (optical purity not determined) |

TABLE 1-continued

| Example | Chemical Structural Formula | Structural Information |
|---|---|---|
| 126 | | i) Optically active product (optical purity not determined) |
| 127 | | i) Optically active product (optical purity not determined) |
| 128 | | i) Enantiomer of Example 129<br>ii) Analytical condition of ethyl ester of Example 128<br>Chiral column IA-3,<br>hexane/IPA = 90/10, Flow rate 1 ml/min,<br>Retention time 5.1 min |
| 129 | | i) Enantiomer of Example 129<br>ii) Analytical condition of ethyl ester of Example 128<br>Chiral column IA-3,<br>hexane/IPA = 90/10, Flow rate 1 ml/min,<br>Retention time 11.1 min |
| 130 | | i) Optically active product (optical purity not determined) |
| 131 | | i) Enantiomer of Example 132<br>ii) Analytical condition of ethyl ester of Example 131<br>Chiral column IA-3,<br>hexane/IPA = 90/10, Flow rate 1 ml/min,<br>Retention time 5.0 min |

TABLE 1-continued

| Example | Chemical Structural Formula | Structural Information |
|---|---|---|
| 132 | | i) Enantiomer of Example 131<br>ii) Analytical condition of ethyl ester of Example 132<br>Chiral column IA-3,<br>hexane/IPA = 90/10, Flow rate 1 ml/min,<br>Retention time 8.7 min |
| 133 | | i) Enantiomer of Example 134<br>ii) Analytical condition of ethyl ester of Example 133<br>Chiral column IA-3,<br>hexane/IPA = 90/10, Flow rate 1 ml/min,<br>Retention time 4.4 min |
| 134 | | i) Enantiomer of Example 133<br>ii) Analytical condition of ethyl ester of Example 134<br>Chiral column IA-3,<br>hexane/IPA = 90/10, Flow rate 1 ml/min,<br>Retention time 5.9 min |
| 135 | | i) Enantiomer of Example 136<br>Prepared by reduction of ethyl ester of Example 133<br>ii) Analytical condition of ethyl ester of Example 135<br>Chiral column IA-3,<br>hexane/IPA = 90/10, Flow rate 1 ml/min,<br>Retention time 4.4 min |
| 136 | | i) Enantiomer of Example 135<br>Prepared by reduction of ethyl ester of Example 134<br>ii) Analytical condition of ethyl ester of Example 136<br>Chiral column IA-3,<br>hexane/IPA = 90/10, Flow rate 1 ml/min,<br>Retention time 5.9 min |

TABLE 1-continued

| Example | Chemical Structural Formula | Structural Information |
|---|---|---|
| 137 | 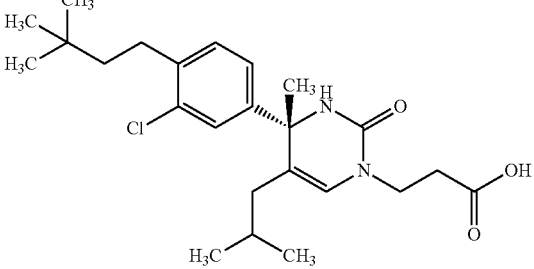 | i) Optically active product<br>ii) Chiral column AD-3R,<br>$H_2O$/MeCN/HCOOH = 30/70/0.1, Flow rate 0.5 ml/min<br>Retention time 9.2 min<br>$[\alpha]_D^{25}$ = +113.4° (C = 0.5, MeOH) |
| 138 | 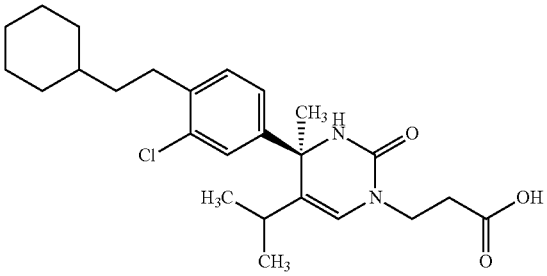 [SMILES: CC(C)C1=CN(CCC(=O)O)C(=O)N[C@]1(C)c1ccc(CCC2CCCCC2)c(Cl)c1] | i) Enantiomer of Example 139<br>ii) Optical purity of methyl ester of Example 138 was >99% ee<br>Chiral column IA-3,<br>hexane/IPA = 90/10, Flow rate 1 ml/min,<br>Retention time 4.9 min |
| 139 | 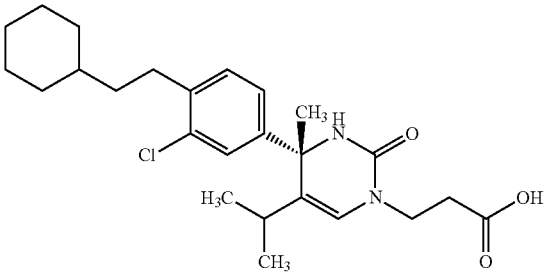 [SMILES: CC(C)C1=CN(CCC(=O)O)C(=O)N[C@@]1(C)c1ccc(CCC2CCCCC2)c(Cl)c1] | i) Enantiomer of Example 138<br>ii) Optical purity of methyl ester of Example 139 was >99% ee<br>Chiral column IA-3,<br>hexane/IPA = 90/10, Flow rate 1 ml/min,<br>Retention time 8.7 min |
| 140 | 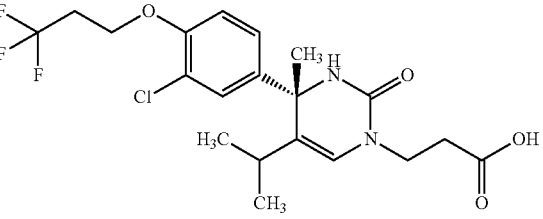 | i) Optically active product (optical purity not determined) |
| 141 | 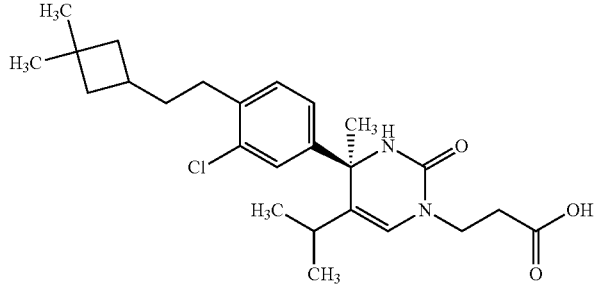 [SMILES: CC(C)C1=CN(CCC(=O)O)C(=O)N[C@]1(C)c1ccc(CCC2CC(C)(C)C2)c(Cl)c1] | i) Enantiomer of Example 142<br>ii) Analytical condition of ethyl ester of Example 141<br>Chiral column IA-3,<br>hexane/IPA = 90/10, Flow rate 1 ml/min,<br>Retention time 4.1 min |

TABLE 1-continued

| Example | Chemical Structural Formula | Structural Information |
|---|---|---|
| 142 | | i) Enantiomer of Example 141<br>ii) Analytical condition of ethyl ester of Example 142<br>Chiral column IA-3,<br>hexane/IPA = 90/10, Flow rate 1 ml/min,<br>Retention time 7.5 min |
| 143 | | i) Enantiomer of Example 144<br>ii) Analytical condition of ethyl ester of Example 143<br>Chiral column IA-3,<br>hexane/IPA = 90/10, Flow rate 1 ml/min,<br>Retention time 6.0 min |
| 144 | | i) Enantiomer of Example 143<br>ii) Analytical condition of ethyl ester of Example 144<br>Chiral column IA-3,<br>hexane/IPA = 90/10, Flow rate 1 ml/min,<br>Retention time 11.1 min |
| 145 | | i) Enantiomer of Example 146<br>ii) Optical purity of methyl ester of Example 145 was >99% ee<br>Chiral column IA-3,<br>hexane/IPA = 90/10, Flow rate 1 ml/min,<br>Retention time 5.1 min |
| 146 | | i) Enantiomer of Example 145<br>ii) Optical purity of methyl ester of Example 146 was >99% ee<br>Chiral column IA-3,<br>hexane/IPA = 90/10, Flow rate 1 ml/min,<br>Retention time 8.6 min |

TABLE 1-continued

| Example | Chemical Structural Formula | Structural Information |
|---|---|---|
| 147 | | i) Optically active product (optical purity not determined) |
| 148 | | i) Enantiomer of Example 149<br>ii) Analytical condition of ethyl ester of Example 148<br>Chiral column IA-3,<br>hexane/IPA = 90/10, Flow rate 1 ml/min,<br>Retention time 4.9 min |
| 149 | | i) Enantiomer of Example 148<br>ii) Analytical condition of ethyl ester of Example 149<br>Chiral column IA-3,<br>hexane/IPA = 90/10, Flow rate 1 ml/min,<br>Retention time 8.7 min |
| 150 | | i) Optically active product (optical purity not determined) |
| 151 | | i) Optically active product<br>ii) Analytical condition of ethyl ester of Example 151<br>Chiral column IA-3,<br>hexane/IPA = 90/10, Flow rate 1 ml/min,<br>Prepared from a fraction with 6.1 min of retention time among fractions with retention times of 4.2 min and 6.1 min |
| 152 | | i) Optically active product<br>ii) Analytical condition of ethyl ester of Example 152<br>Chiral column IA-3,<br>hexane/IPA = 90/10, Flow rate 1 ml/min,<br>Retention time 5.1 min |

TABLE 1-continued

| Example | Chemical Structural Formula | Structural Information |
|---|---|---|
| 153 | | i) Optically active product<br>ii) Analytical condition of ethyl ester of Example 153<br>Chiral column IA-3,<br>hexane/IPA = 90/10, Flow rate 1 ml/min,<br>Retention time 7.5 min |
| 154 | | i) Optically active product<br>ii) Chiral column AD-3R,<br>$H_2O$/MeCN/HCOOH = 30/70/0.1, Flow rate 0.5 ml/min, Retention time 12.1 min<br>$[\alpha]_D^{25}$ = +141.2° (C = 0.05, MeOH) |
| 155 | | i) Enantiomer of Example 156<br>Same absolute configuration as Example 148 (prepared by reduction of ethyl ester of Example 148) |
| 156 | | i) Enantiomer of Example 155<br>Same absolute configuration as Example 149 (prepared by reduction of ethyl ester of Example 149) |
| 157 | | i) Optically active product (optical purity not determined) |

TABLE 1-continued

| Example | Chemical Structural Formula | Structural Information |
|---|---|---|
| 158 | 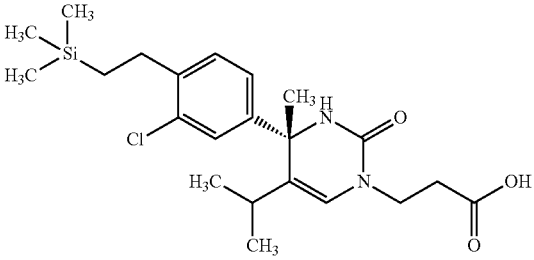 | i) Optically active product (optical purity not determined) |
| 159 | 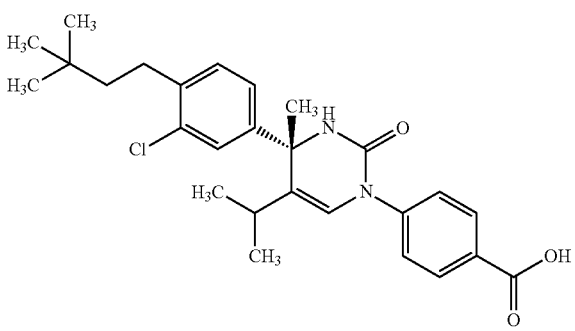 [SMILES: CC(C)C1=CN(c2ccc(C(=O)O)cc2)C(=O)N[C@@]1(C)c1ccc(CCC(C)(C)C)c(Cl)c1] | i) Optically active product<br>ii) Chiral column AD-3R, H$_2$O/MeCN/HCOOH = 30/70/0.1, Flow rate 0.5 ml/min, Retention time 16.2 min<br>$[\alpha]_D^{25}$ = +87.5° (C = 0.25, MeOH) |
| 160 | 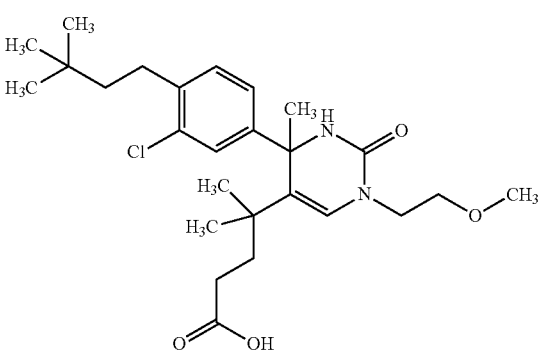 [SMILES: COCCN1C=C(C(C)(C)CCC(=O)O)C(C)(c2ccc(CCC(C)(C)C)c(Cl)c2)NC1=O] | i) Optically active product (optical purity not determined) |
| 161 | 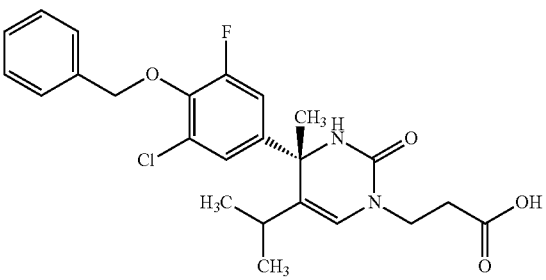 [SMILES: CC(C)C1=CN(CCC(=O)O)C(=O)N[C@@]1(C)c1cc(F)c(OCc2ccccc2)c(Cl)c1] | i) Optically active product (optical purity not determined) |
| 162 | 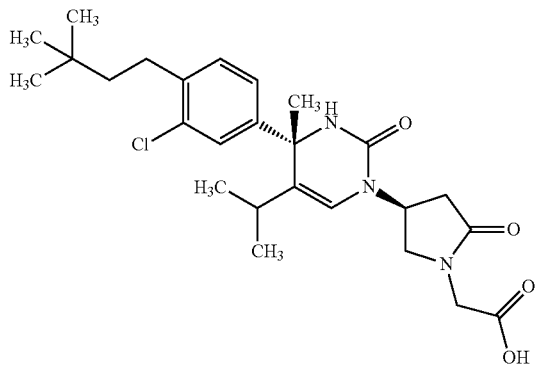 [SMILES: CC(C)C1=CN([C@H]2CC(=O)N(CC(=O)O)C2)C(=O)N[C@@]1(C)c1ccc(CCC(C)(C)C)c(Cl)c1] | i) Optically active product (optical purity not determined) |

TABLE 1-continued

| Example | Chemical Structural Formula | Structural Information |
|---|---|---|
| 163 | | i) Optically active product (optical purity not determined) |
| 164 | | i) Optically active product (optical purity not determined) |
| 165 | | i) Optically active product (optical purity not determined) |
| 166 | | i) Single enantiomer Example 166 and Example 167 are a diastereomer with each other ii) Ethyl ester of Example 166 was prepared by reduction of ethyl ester of Example 151 (Chiral column IA-3, hexane/IPA = 90/10, Flow rate 1 ml/min, the compound in a fraction with 6.9 min of retention time). Prepared from the ethyl ester (Chiral column IA-3, hexane/IPA = 80/20, Flow rate 1 ml/min, the compound in a fraction of 3.8 min with retention time) |
| 167 | | i) Single enantiomer Example 166 and Example 167 are a diastereomer with each other ii) Ethyl ester of Example 167 was prepared by reduction of ethyl ester of Example 151 (Chiral column IA-3, hexane/IPA = 90/10, Flow rate 1 ml/min, the compound in a fraction with 6.9 min of retention time). Prepared from the ethyl ester (Chiral column IA-3, hexane/IPA = 80/20, Flow rate 1 ml/min, the compound in a fraction of 4.6 min with retention time) |

TABLE 1-continued

| Example | Chemical Structural Formula | Structural Information |
|---|---|---|
| 168 | | i) Optically active product (optical purity not determined) |
| 169 | | i) Single enantiomer Stereochemistry of the cyclopropane ring was estimated as trans-isomer Example 169 and Example 170 are a diastereomer with each other ii) Analytical condition of ethyl ester of Example 169 Chiral column IA-3, hexane/IPA = 90/10, Flow rate 1 ml/min, Retention time 6.7 min |
| 170 | | i) Single enantiomer Stereochemistry of the cyclopropane ring was estimated as trans-isomer Example 169 and Example 170 are a diastereomer with each other ii) Analytical condition of ethyl ester of Example 170 Chiral column IA-3, hexane/IPA = 90/10, Flow rate 1 ml/min, Retention time 7.1 min |
| 171 | | i) Optically active product ii) Analytical condition of ethyl ester of Example 171 Chiral column IA-3, hexane/IPA = 90/10, Flow rate 1 ml/min, Prepared from a fraction with 6.6 min of retention time among fractions with 4.8 min and 6.6 min of retention times. |
| 172 | | i) Optically active product (optical purity not determined) |

TABLE 1-continued

| Example | Chemical Structural Formula | Structural Information |
|---|---|---|
| 173 | | i) Optically active product (optical purity not determined) |
| 174 | | i) Single enantiomer Stereochemistry of the cyclopropane ring was estimated as trans-isomer ii) Analytical condition of ethyl ester of Example 174 Chiral column IA-3, hexane/IPA = 90/10, Flow rate 1 ml/min, Retention time 14.5 min |
| 175 | | i) Optically active product (optical purity not determined) |
| 176 | | i) Optically active product (optical purity not determined) |
| 177 | | i) Optically active product (optical purity not determined) |
| 178 | | i) Optically active product (optical purity not determined) |

TABLE 1-continued

| Example | Chemical Structural Formula | Structural Information |
|---|---|---|
| 179 | 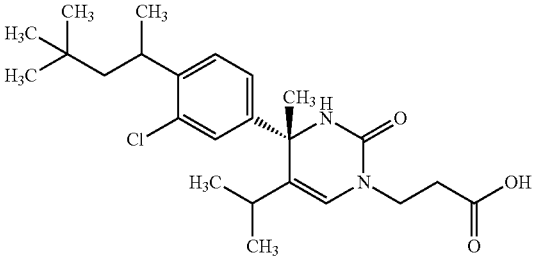 [SMILES: CC(C)C1=CN(CCC(=O)O)C(=O)N[C@@]1(C)c1ccc(C(C)CC(C)(C)C)c(Cl)c1] | i) Diastereomer mixture of 3-{(S)-4-[3-chloro-4-((S)-1,3,3-trimethyl-butyl)-phenyl]-5-isopropyl-4-methyl-2-oxo-3,4-dihydro-2H-pyrimidin-1-yl}-propionic acid and 3-{(S)-4-[3-chloro-4-((R)-1,3,3-trimethyl-butyl)-phenyl]-5-isopropyl-4-methyl-2-oxo-3,4-dihydro-2H-pyrimidin-1-yl}-propionic acid |
| 180 | 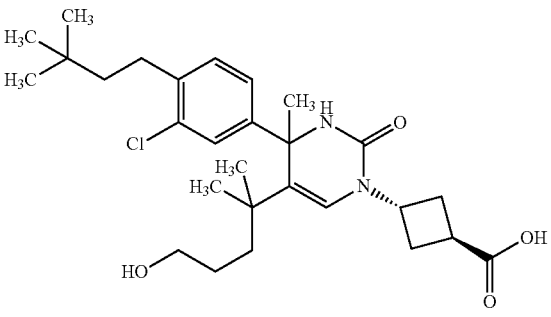 [SMILES: CC(C)(C)CCc1ccc(C2(C)NC(=O)N([C@H]3C[C@H](C(=O)O)C3)C=C2C(C)(C)CCCO)cc1Cl] | i) Optically active product (optical purity not determined) |
| 181 | 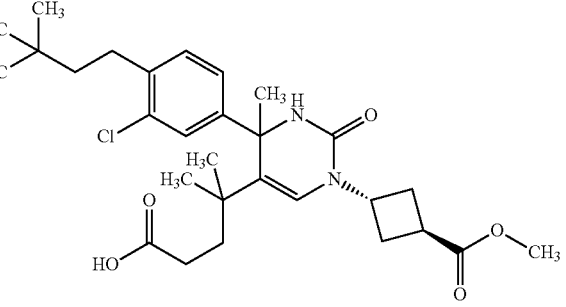 | i) Optically active product (optical purity not determined) |
| 182 | 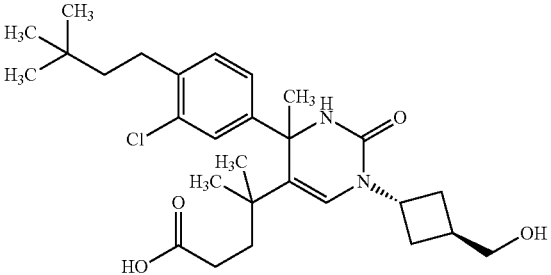 [SMILES: CC(C)(C)CCc1ccc(C2(C)NC(=O)N([C@H]3C[C@H](CO)C3)C=C2C(C)(C)CCC(=O)O)cc1Cl] | i) Optically active product (optical purity not determined) |
| 183 | 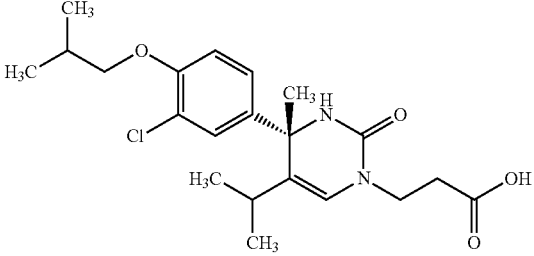 [SMILES: CC(C)COc1ccc([C@]2(C)NC(=O)N(CCC(=O)O)C=C2C(C)C)cc1Cl] | i) Optically active product (optical purity not determined) |

TABLE 1-continued
| Example | Chemical Structural Formula | Structural Information |
|---|---|---|
| 184 | 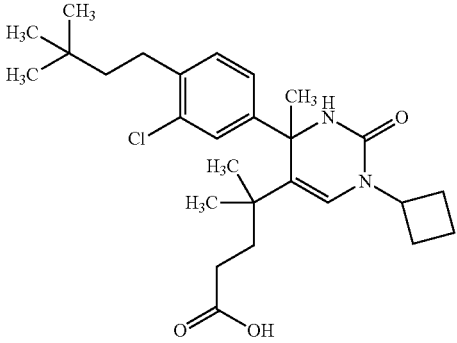 [SMILES: CC(C)(C)CCc1ccc(C2(C)NC(=O)N(C3CCC3)C=C2C(C)(C)CCC(=O)O)cc1Cl] | i) Optically active product (optical purity not determined) |
| 185 | 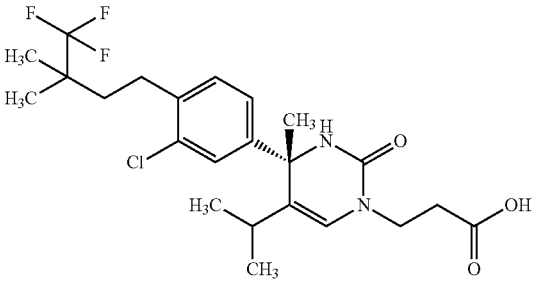 [SMILES: CC(C)C1=CN(CCC(=O)O)C(=O)N[C@@]1(C)c1ccc(CCC(C)(C)C(F)(F)F)c(Cl)c1] | i) Optically active product (optical purity not determined) |
| 186 | 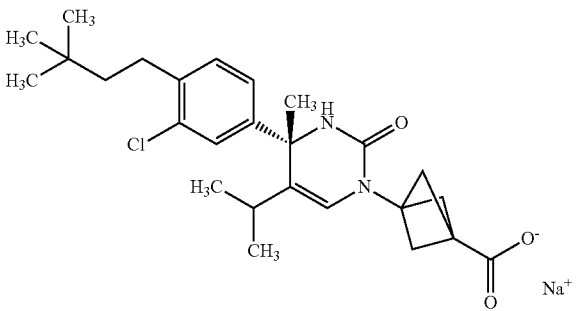 [SMILES: CC(C)C1=CN(C23CC(C(=O)[O-])(C2)C3)C(=O)N[C@@]1(C)c1ccc(CCC(C)(C)C)c(Cl)c1 ; [Na+]] | i) Optically active product (optical purity not determined)<br>ii) Na salt of Example 77 |
| 187 | 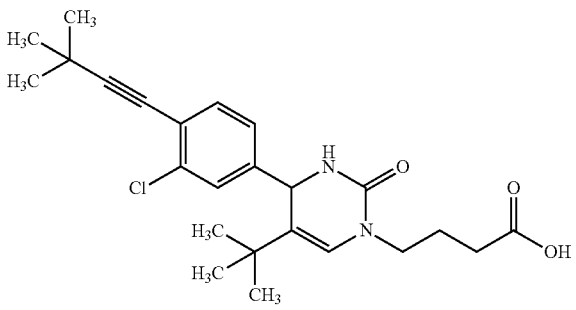 [SMILES: CC(C)(C)C#Cc1ccc(C2NC(=O)N(CCCC(=O)O)C=C2C(C)(C)C)cc1Cl] | i) Racemate |
| 188 | 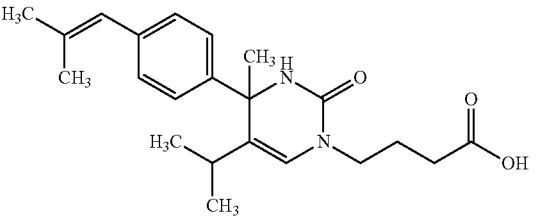 [SMILES: CC(C)=Cc1ccc(C2(C)NC(=O)N(CCCC(=O)O)C=C2C(C)C)cc1] | i) Racemate |

TABLE 1-continued

| Example | Chemical Structural Formula | Structural Information |
|---|---|---|
| 189 | (structure) | i) Optically active product (optical purity not determined) |

TABLE 2

| Example | Chemical Structural Formula | Structural Information |
|---|---|---|
| 190 | (structure) | i) Optically active product (optical purity not determined)<br>ii) Analytical condition<br>Chiral column IA-3, hexane/IPA = 80/20,<br>Flow rate 1 ml/min, Retention time 4.7 min |
| 191 | (structure) | i) Optically active product (optical purity not determined)<br>ii) Analytical condition<br>Chiral column IA-3, hexane/IPA = 80/20,<br>Flow rate 1 ml/min, Retention time 10.7 min |
| 192 | (structure) | i) Optically active product (optical purity not determined) |

TABLE 2-continued

| Example | Chemical Structural Formula | Structural Information |
|---|---|---|
| 193 | | i) Optically active product (optical purity not determined) |
| 194 | | i) Optically active product (optical purity not determined) |
| 195 | | i) Optically active product (optical purity not determined) |
| 196 | | i) Optically active product (optical purity not determined) |
| 197 | | i) Optically active product (optical purity not determined)<br>ii) Optical purity of alcohol, a synthetic precursor, was >99% ee<br>Analytical condition of alcohol of Example 197<br>Chiral column IA-3, hexane/IPA = 80/20, Flow rate 1 ml/min, Retention time 6.3 min |

TABLE 2-continued

| Example | Chemical Structural Formula | Structural Information |
|---|---|---|
| 198 | | i) Optically active product (optical purity not determined) |
| 199 | | i) Optically active product (optical purity not determined)<br>ii) Optical purity of alcohol, a synthetic precursor, was >99% ee<br>Analytical condition of alcohol of Example 199<br>Chiral column IA-3, hexane/IPA = 80/20, Flow rate 1 ml/min, Retention time 5.7 min |
| 200 | | i) Optically active product (optical purity not determined)<br>ii) Optical purity of alcohol, a synthetic precursor, was >99% ee<br>Analytical condition of alcohol of Example 200<br>Chiral column IA-3, hexane/IPA = 80/20, Flow rate 1 ml/min, Retention time 6.0 min |
| 201 | | i) Optically active product (optical purity not determined) |
| 202 | | i) Optically active product (optical purity not determined) |

TABLE 2-continued

| Example | Chemical Structural Formula | Structural Information |
|---|---|---|
| 203 | | i) Optically active product (optical purity not determined) |
| 204 | | i) Optically active product (optical purity not determined) |
| 205 | | i) Optically active product (optical purity not determined)<br>ii) Analytical condition of methyl ester of Example 205<br>Chiral column IA-3, hexane/IPA = 80/20, Flow rate 1 ml/min, Retention time 8.8 min |
| 206 | | i) Optically active product (optical purity not determined) |
| 207 | | i) Optically active product (optical purity not determined) |

TABLE 2-continued

| Example | Chemical Structural Formula | Structural Information |
|---|---|---|
| 208 | | i) Optically active product (optical purity not determined) |
| 209 | | i) Optically active product (optical purity not determined) |
| 210 | | i) Optically active product (optical purity not determined) |
| 211 | | i) Optically active product (optical purity not determined) |
| 212 | | i) Enantiomer of Example 213<br>ii) Optical purity of ethyl ester was >99% ee Chiral column IA-3, hexane/IPA = 90/10, Flow rate 1 ml/min, Retention time 5.2 min |

TABLE 2-continued

| Example | Chemical Structural Formula | Structural Information |
|---|---|---|
| 213 | | i) Enantiomer of Example 212<br>ii) Optical purity of ethyl ester was >99% ee<br>Chiral column IA-3, hexane/IPA = 90/10,<br>Flow rate 1 ml/min, Retention time 8.3 min |
| 214 | | i) Optically active product (optical purity not determined) |
| 215 | | i) A mixture of two diastereomers |
| 216 | | i) Optically active product (optical purity not determined) |
| 217 | | i) A mixture of two diastereomers |
| 218 | | i) Optically active product (optical purity not determined) |

| Example | Chemical Structural Formula | Structural Information |
|---|---|---|
| 219 | | i) Optically active product (optical purity not determined) |
| 220 | | i) Optically active product (optical purity not determined) |
| 221 | | i) Optically active product (optical purity not determined) |
| 222 | | i) Optically active product (optical purity not determined) |
| 223 | | i) A mixture of two diastereomers |

TABLE 2-continued

| Example | Chemical Structural Formula | Structural Information |
|---------|----------------------------|------------------------|
| 224 | | i) Optically active product (optical purity not determined) |
| 225 | | i) Optically active product (optical purity not determined) |
| 226 | | i) Optically active product (optical purity not determined) |
| 227 | | i) Optically active product (optical purity not determined) |
| 228 | | i) Optically active product (optical purity not determined) |

TABLE 2-continued

| Example | Chemical Structural Formula | Structural Information |
|---|---|---|
| 229 | | i) Optically active product (optical purity not determined) |
| 230 | | i) Optically active product (optical purity not determined) |
| 231 | | i) Optically active product (optical purity not determined) |
| 232 | | i) Single enantiomer (optical purity not determined)<br>Example 232 and Example 233 are a diastereomer with each other |

TABLE 2-continued

| Example | Chemical Structural Formula | Structural Information |
|---|---|---|
| 233 | | i) Single enantiomer (optical purity not determined)<br>Example 232 and Example 233 are a diastereomer with each other |
| 234 | | i) Optically active product (optical purity not determined) |
| 235 | | i) Optically active product (optical purity not determined) |
| 236 | | i) Optically active product (optical purity not determined) |
| 237 | | i) Single enantiomer (optical purity not determined)<br>Stereochemistry of the pyrrolidine ring was estimated as trans-isomer |

TABLE 2-continued

| Example | Chemical Structural Formula | Structural Information |
|---|---|---|
| 238 | | i) Optically active product (optical purity not determined)<br>Stereochemistry of the pyrrolidine ring was estimated as trans-isomer |
| 239 | | i) Single enantiomer (optical purity not determined)<br>Stereochemistry of the pyrrolidine ring was estimated as trans-isomer |
| 240 | | i) Single enantiomer (optical purity not determined)<br>Stereochemistry of the pyrrolidine ring was estimated as trans-isomer |
| 241 | | i) Optically active product (optical purity not determined) |
| 242 | | i) Single enantiomer (optical purity not determined)<br>Stereochemistry of the cyclopentane ring was estimated as trans-isomer<br>Example 242 and Example 243 are a diastereomer with each other |

TABLE 2-continued

| Example | Chemical Structural Formula | Structural Information |
|---|---|---|
| 243 | | i) Single enantiomer (optical purity not determined)<br>Stereochemistry of the cyclopentane ring was estimated as trans-isomer<br>Example 242 and Example 243 are a diastereomer with each other |
| 244 | | i) Single enantiomer (optical purity not determined)<br>Stereochemistry of the pyrrolidine ring was estimated as trans-isomer<br>Example 244 and Example 245 are a diastereomer with each other |
| 245 | | i) Single enantiomer (optical purity not determined)<br>Stereochemistry of the pyrrolidine ring was estimated as trans-isomer<br>Example 244 and Example 245 are a diastereomer with each other |
| 246 | | i) Optically active product (optical purity not determined) |
| 247 | | i) Optically active product (optical purity not determined) |

TABLE 2-continued

| Example | Chemical Structural Formula | Structural Information |
|---|---|---|
| 248 | | i) Optically active product (optical purity not determined) |
| 249 | | i) Optically active product (optical purity not determined) |
| 250 | | i) Optically active product (optical purity not determined) |
| 251 | | i) Optically active product (optical purity not determined) |
| 252 | | i) Optically active product (optical purity not determined) |

TABLE 2-continued

| Example | Chemical Structural Formula | Structural Information |
|---|---|---|
| 253 | | i) Optically active product (optical purity not determined) |
| 254 | | i) Single enantiomer (optical purity not determined)<br>Stereochemistry of the cyclohexane ring was estimated as trans-isomer<br>Example 254, Example 255, Example 256, and Example 257 are a diastereomer with each other<br>ii) Optical purity of Example 254 was >99% ee<br>Analytical condition of Example 254<br>JAIGEL-ODS-AP-A,<br>MeCN/H$_2$O/HCO$_2$H = 90/10/0.1, Flow rate 1 ml/min, Retention time 10.2 min. |
| 255 | | i) Single enantiomer (optical purity not determined)<br>Stereochemistry of the cyclohexane ring was estimated as cis-isomer<br>Example 254, Example 255, Example 256, and Example 257 are a diastereomer with each other<br>ii) Optical purity of Example 255 was >99% ee<br>Analytical condition of Example 255<br>JAIGEL-ODS-AP-A,<br>MeCN/H$_2$O/HCO$_2$H = 90/10/0.1, Flow rate 1 ml/min, Retention time 13.2 min. |
| 256 | | i) Single enantiomer (optical purity not determined)<br>Stereochemistry of the cyclohexane ring was estimated as trans-isomer<br>Example 254, Example 255, Example 256, and Example 257 are a diastereomer with each other<br>ii) Optical purity of Example 256 was >99% ee<br>Analytical condition of Example 256<br>JAIGEL-ODS-AP-A,<br>MeCN/H$_2$O/HCO$_2$H = 90/10/0.1, Flow rate 1 ml/min, Retention time 11.7 min. |
| 257 | | i) Single enantiomer (optical purity not determined)<br>Stereochemistry of the cyclohexane ring was estimated as cis-isomer<br>Example 254, Example 255, Example 256, and Example 257 are a diastereomer with each other<br>ii) Optical purity of Example 257 was >99% ee<br>Analytical condition of Example 257<br>JA1GEL ODS-AP-A,<br>MeCN/H$_2$O/HCO$_2$H = 90/10/0.1, Flow rate 1 ml/min, Retention time 14.0 min. |

TABLE 2-continued

| Example | Chemical Structural Formula | Structural Information |
|---|---|---|
| 258 | | i) Optically active product (optical purity not determined) |
| 259 | | i) Optically active product (optical purity not determined) |
| 260 | | i) Optically active product (optical purity not determined) |
| 261 | | i) Optically active product (optical purity not determined) |
| 262 | | i) Optically active product (optical purity not determined) |

TABLE 2-continued

| Example | Chemical Structural Formula | Structural Information |
|---|---|---|
| 263 | | i) Optically active product (optical purity not determined) |
| 264 | | i) Optically active product (optical purity not determined) |
| 265 | | i) Optically active product (optical purity not determined) |
| 266 | | i) Optically active product (optical purity not determined) |
| 267 | | i) Optically active product (optical purity not determined) |
| 268 | | i) Optically active product (optical purity not determined) |

TABLE 2-continued

| Example | Chemical Structural Formula | Structural Information |
|---|---|---|
| 269 | | i) Optically active product (optical purity not determined) |
| 270 | | i) Optically active product (optical purity not determined) |
| 271 | | i) Optically active product (optical purity not determined) |
| 272 | | i) Optically active product (optical purity not determined) |
| 273 | | i) Optically active product (optical purity not determined) |

TABLE 2-continued

| Example | Chemical Structural Formula | Structural Information |
|---|---|---|
| 274 | | i) Optically active product (optical purity not determined) |
| 275 | | i) Optically active product (optical purity not determined) |
| 276 | | i) Single enantiomer (optical purity not determined)<br>Stereochemistry of the cyclobutane ring not determined |
| 277 | | i) Single enantiomer (optical purity not determined)<br>Stereochemistry of the cyclobutane ring not determined |
| 278 | | i) Single enantiomer<br>Stereochemistry of the cyclopentane ring not determined<br>Examples 64, 278, 279, and 280 are a diastereomer with each other<br>ii) Optical purity of Example 278 was >99% ee<br>Analytical condition of Example 278<br>JAIGEL-ODS-AP-A,<br>MeCN/H$_2$O/HCO$_2$H = 90/10/0.1, Flow rate 1 ml/min, Retention time 9.1 min. |

TABLE 2-continued

| Example | Chemical Structural Formula | Structural Information |
|---------|---|---|
| 279 | | i) Single enantiomer<br>Stereochemistry of the cyclopentane ring not determined<br>Examples 64, 278, 279, and 280 are a diastereomer with each other<br>ii) Optical purity of Example 279 was >99% ee<br>Analytical condition of Example 279<br>JAIGEL-ODS-AP-A,<br>MeCN/H$_2$O/HCO$_2$H = 90/10/0.1, Flow rate 1 ml/min, Retention time 10.4 min. |
| 280 | | i) Single enantiomer<br>Stereochemistry of the cyclopentane ring not determined<br>Examples 64, 278, 279, and 280 are a diastereomer with each other<br>ii) Optical purity of Example 280 was >99% ee<br>Analytical condition of Example 280<br>JAJGEL-ODS-AP-A,<br>MeCN/H$_2$O/HCO$_2$H = 90/10/0.1, Flow rate 1 ml/min, Retention time 10.8 min. |
| 281 | | i) Optically active product (optical purity not determined) |
| 282 | | i) Optically active product (optical purity not determined) |
| 283 | | i) Optically active product (optical purity not determined) |

TABLE 2-continued

| Example | Chemical Structural Formula | Structural Information |
|---|---|---|
| 284 | | i) Optically active product (optical purity not determined) |
| 285 | | i) Optically active product (optical purity not determined) |
| 286 | | i) Optically active product (optical purity not determined) |
| 287 | | i) Optically active product (optical purity not determined) |
| 288 | | i) Optically active product (optical purity not determined) |
| 289 | | i) Optically active product (optical purity not determined) |

TABLE 2-continued

| Example | Chemical Structural Formula | Structural Information |
|---|---|---|
| 290 | (structure) | i) Optically active product (optical purity not determined) |
| 291 | (structure) | i) Optically active product (optical purity not determined) |
| 292 | (structure) | i) Optically active product (optical purity not determined) |
| 293 | (structure) | i) Optically active product (optical purity not determined) |
| 294 | (structure) | i) Optically active product (optical purity not determined) |
| 295 | (structure) | i) Optically active product (optical purity not determined) |

TABLE 2-continued

| Example | Chemical Structural Formula | Structural Information |
|---|---|---|
| 296 | | i) Optically active product (optical purity not determined) |
| 297 | | i) Optically active product (optical purity not determined) |
| 298 | | i) Optically active product (optical purity not determined) |
| 299 | | i) Single enantiomer<br>Example 299 and Example 300 are a diastereomer with each other<br>ii) Optical purity of Example 299 was >99% ee<br>Analytical condition of Example 299<br>JAIGEL-ODS-AP-A,<br>MeCN/H$_2$O/HCO$_2$H = 80/20/0.1, Flow rate 1 ml/min, Retention time 14.7 min. |
| 300 | | i) Single enantiomer<br>Example 299 and Example 300 are a diastereomer with each other<br>ii) Optical purity of Example 300 was >99% ee<br>Analytical condition of Example 300<br>JAIGEL-ODS-AP-A,<br>MeCN/H$_2$O/HCO$_2$H = 80/20/0.1, Flow rate 1 ml/min, Retention time 15.3 min. |

TABLE 2-continued

| Example | Chemical Structural Formula | Structural Information |
|---|---|---|
| 301 | | i) Optically active product (optical purity not determined) |
| 302 | | i) Optically active product (optical purity not determined) |
| 303 | | i) Optically active product (optical purity not determined) |
| 304 | | i) Optically active product (optical purity not determined)<br>Diastereomer mixture |
| 305 | | i) Single enantiomer (optical purity not determined)<br>Example 305 and Example 306 are a diastereomer with each other |

TABLE 2-continued

| Example | Chemical Structural Formula | Structural Information |
|---|---|---|
| 306 | 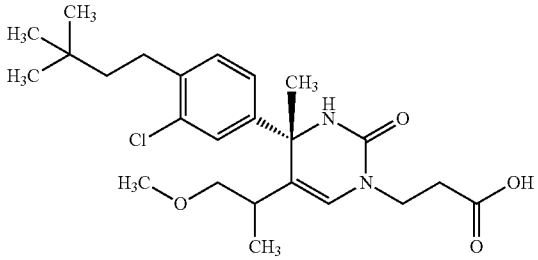 [SMILES: COCC(C)C1=CN(CCC(=O)O)C(=O)N[C@@]1(C)c1ccc(CCC(C)(C)C)c(Cl)c1] | i) Single enantiomer (optical purity not determined)<br>Example 305 and Example 306 are a diastereomer with each other |
| 307 | 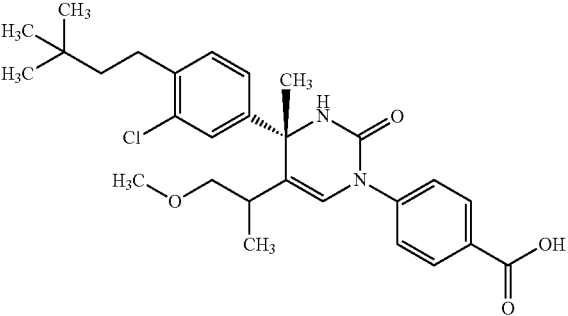 [SMILES: COCC(C)C1=CN(c2ccc(C(=O)O)cc2)C(=O)N[C@@]1(C)c1ccc(CCC(C)(C)C)c(Cl)c1] | i) Single enantiomer (optical purity not determined)<br>Example 307 and Example 308 are a diastereomer with each other |
| 308 | 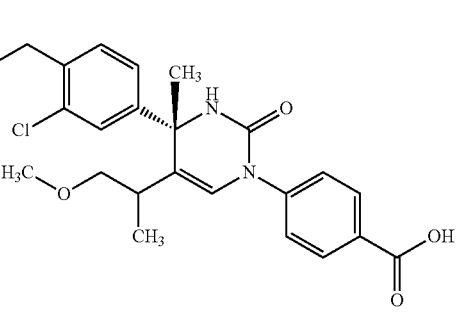 | i) Single enantiomer (optical purity not determined)<br>Example 307 and Example 308 are a diastereomer with each other |
| 309 | 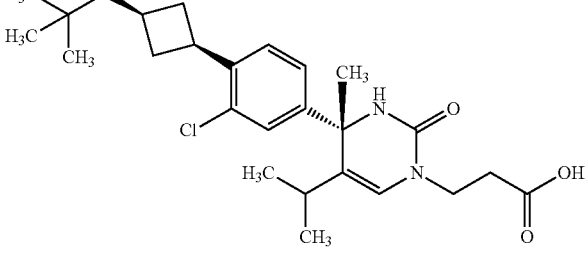 | i) Optically active product (optical purity not determined) |
| 310 | 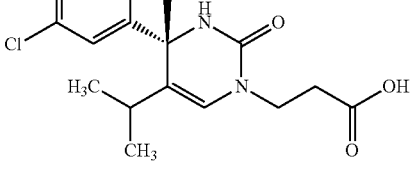 | i) Single enantiomer (optical purity not determined)<br>Example 310 and Example 311 are a diastereomer with each other |

TABLE 2-continued

| Example | Chemical Structural Formula | Structural Information |
|---|---|---|
| 311 | 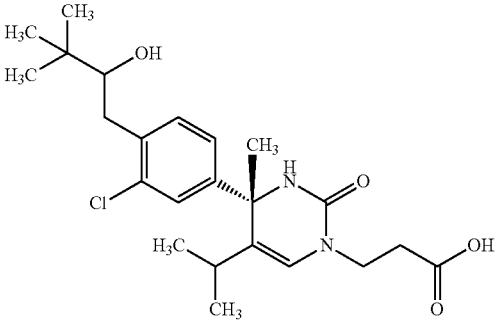 [SMILES: CC(C)C1=CN(CCC(=O)O)C(=O)N[C@@]1(C)c1ccc(CC(O)C(C)(C)C)c(Cl)c1] | i) Single enantiomer (optical purity not determined)<br>Stereochemistry of hydroxyl not determined |
| 312 | 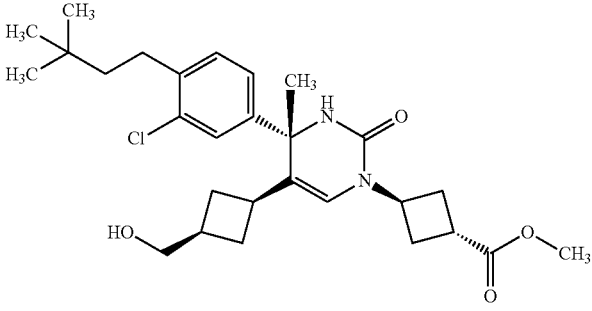 [SMILES: COC(=O)[C@H]1C[C@H](N2C=C([C@H]3C[C@@H](CO)C3)[C@](C)(c3ccc(CCC(C)(C)C)c(Cl)c3)NC2=O)C1] | i) Single enantiomer, >99% ee<br>Analytical condition of Example 312<br>Chiral column IA-3, hexane/IPA = 80/20,<br>Flow rate 1 ml/min, Retention time 8.8 min |
| 313 | 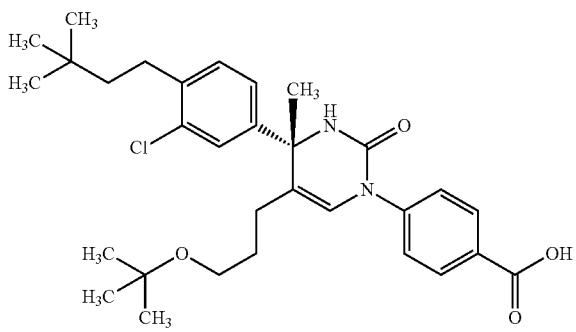 [SMILES: CC(C)(C)CCc1ccc([C@]2(C)NC(=O)N(c3ccc(C(=O)O)cc3)C=C2CCCOC(C)(C)C)cc1Cl] | i) Optically active product (optical purity not determined) |
| 314 | 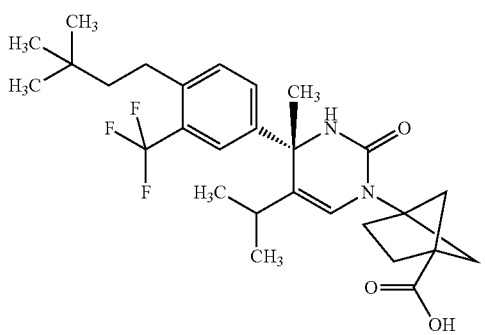 [SMILES: CC(C)C1=CN(C23CCC(C(=O)O)(C2)C3)C(=O)N[C@@]1(C)c1ccc(CCC(C)(C)C)c(C(F)(F)F)c1] | i) Optically active product (optical purity not determined) |

TABLE 2-continued

| Example | Chemical Structural Formula | Structural Information |
|---|---|---|
| 315 | | i) Optically active product (optical purity not determined) |
| 316 | | i) Optically active product (optical purity not determined) |
| 317 | | i) Optically active product (optical purity not determined) |
| 318 | | i) Optically active product (optical purity not determined) |

TABLE 2-continued

| Example | Chemical Structural Formula | Structural Information |
|---|---|---|
| 319 | | i) Optically active product (optical purity not determined) |
| 320 | | i) Optically active product (optical purity not determined) |
| 321 | | i) Optically active product (optical purity not determined) |
| 322 | | i) Optically active product (optical purity not determined) |
| 323 | | i) Optically active product (optical purity not determined) |

TABLE 2-continued

| Example | Chemical Structural Formula | Structural Information |
|---|---|---|
| 324 | | i) Optically active product (optical purity not determined) |
| 325 | | i) Optically active product (optical purity not determined) |
| 326 | | i) Optically active product (optical purity not determined) |
| 327 | | i) Optically active product (optical purity not determined) |
| 328 | | i) Optically active product (optical purity not determined) |

TABLE 2-continued

| Example | Chemical Structural Formula | Structural Information |
|---|---|---|
| 329 | | i) Optically active product (optical purity not determined) |
| 330 | | i) Optically active product (optical purity not determined) |
| 331 | | i) Optically active product (optical purity not determined) |
| 332 | | i) Optically active product (optical purity not determined) |

TABLE 2-continued

| Example | Chemical Structural Formula | Structural Information |
|---|---|---|
| 333 | | i) Optically active product (optical purity not determined) |
| 334 | | i) Optically active product (optical purity not determined) |
| 335 | | i) Optically active product (optical purity not determined) |
| 336 | | i) Optically active product (optical purity not determined) |
| 337 | | i) Optically active product (optical purity not determined) |

TABLE 2-continued

| Example | Chemical Structural Formula | Structural Information |
|---|---|---|
| 338 | 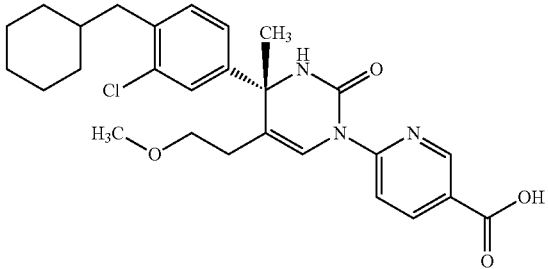 [SMILES: COCCC1=CN(c2ccc(C(=O)O)cn2)C(=O)N[C@@]1(C)c1ccc(CC2CCCCC2)c(Cl)c1] | i) Optically active product (optical purity not determined) |
| 339 | 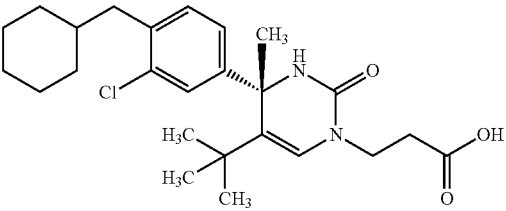 [SMILES: CC(C)(C)C1=CN(CCC(=O)O)C(=O)N[C@@]1(C)c1ccc(CC2CCCCC2)c(Cl)c1] | i) Optically active product (optical purity not determined) |
| 340 | 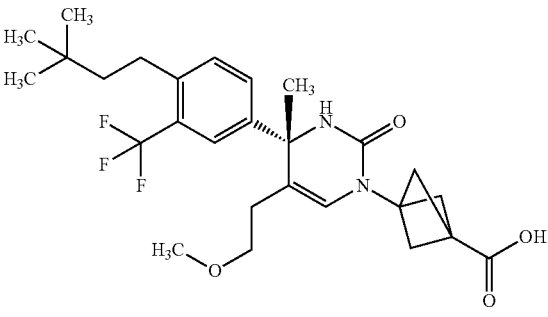 [SMILES: COCCC1=CN(C23CC(C(=O)O)(C2)C3)C(=O)N[C@@]1(C)c1ccc(CCC(C)(C)C)c(C(F)(F)F)c1] | i) Optically active product (optical purity not determined) |
| 341 | 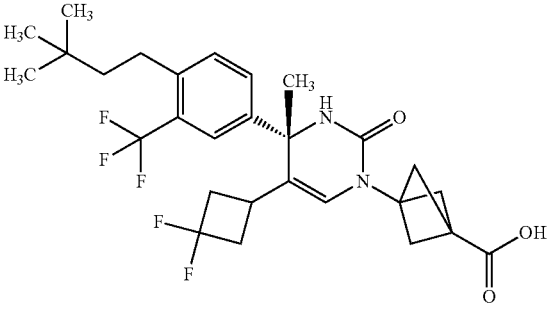 [SMILES: CC(C)(C)CCc1ccc([C@]2(C)NC(=O)N(C34CC(C(=O)O)(C3)C4)C=C2C2CC(F)(F)C2)cc1C(F)(F)F] | i) Optically active product (optical purity not determined) |
| 342 | 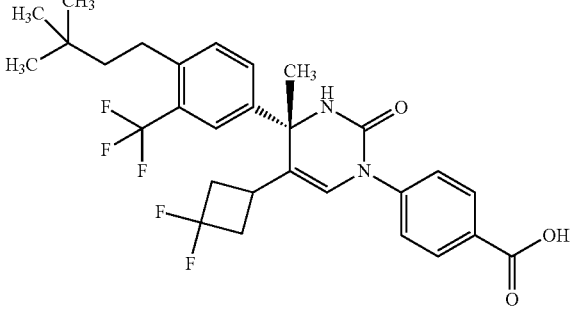 | i) Optically active product (optical purity not determined) |

US 10,196,363 B2

TABLE 2-continued

| Example | Chemical Structural Formula | Structural Information |
|---|---|---|
| 343 | 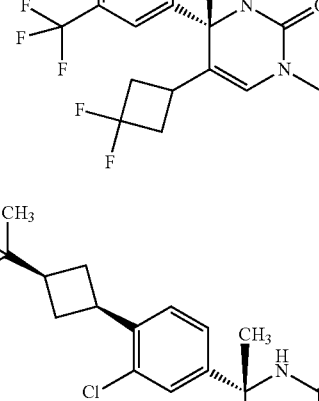 | i) Optically active product (optical purity not determined) |
| 344 | 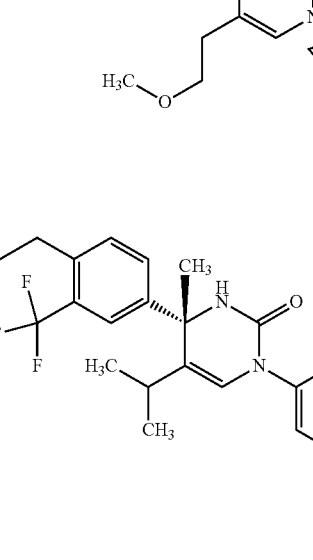 | i) Single enantiomer (optical purity not determined)<br>Stereochemistry of the cyclobutane ring was estimated as cis-isomer |
| 345 | 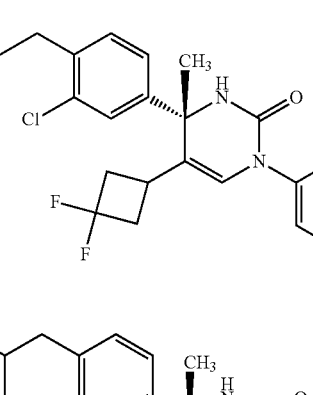 | i) Optically active product (optical purity not determined) |
| 346 | 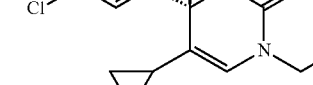 | i) Optically active product (optical purity not determined) |
| 347 |  | i) Optically active product (optical purity not determined) |

TABLE 2-continued

| Example | Chemical Structural Formula | Structural Information |
|---|---|---|
| 348 | | i) Optically active product (optical purity not determined) |
| 349 | | i) Optically active product (optical purity not determined) |
| 350 | | i) Optically active product (optical purity not determined) |
| 351 | | i) Single enantiomer (optical purity not determined) Example 351 and Example 352 are a diastereomer with each other |
| 352 | | i) Single enantiomer (optical purity not determined) Example 351 and Example 352 are a diastereomer with each other |

TABLE 2-continued

| Example | Chemical Structural Formula | Structural Information |
|---|---|---|
| 353 | | i) Optically active product (optical purity not determined) |
| 354 | | i) Optically active product (optical purity not determined) |
| 355 | | i) Optically active product (optical purity not determined) |
| 356 | | i) Optically active product (optical purity not determined) |
| 357 | | i) Optically active product (optical purity not determined) |

In the following table, compounds of Examples 38, 87, and 116 were synthesized by a preparation method using Claisen reaction and measured.

TABLE 3

| | | MS | |
|---|---|---|---|
| Example | $^1$H-NMR | M + H or M—+ H | M − H or M—Na − H |
| 1 | (400 MHz, CDCl$_3$) 0.98 (s, 9H), 1.06 (s, 9H), 1.88-2.04 (m, 2H), 2.32-2.44 (m, 2H), 3.37-3.44 (m, 1H), 3.61 (s, 2H), 3.69-3.76 (m, 1H), 4.82 (d, J = 2.65 Hz, 1H), 5.75-5.81 (m, 1H), 6.09 (s, 1H), 6.82 (d, J = 8.60 Hz, 1H), 7.06 (dd, J = 8.49, 2.32 Hz, 1H), 7.23 (d, J = 2.21 Hz, 1H) | 437 | 435 |
| 2 | (400 MHz, DMSO-D$_6$) 0.96 (s, 3H), 1.02 (s, 9H), 1.20 (s, 3H), 3.68 (s, 2H), 4.72 (d, J = 3.24 Hz, 1H), 6.22 (d, J = 5.32 Hz, 1H), 7.06 (t, J = 8.21 Hz, 2H), 7.14 (dd, J = 8.32, 2.08 Hz, 1H), 7.26 (d, J = 2.08 Hz, 1H), 8.21 (s, 1H), 12.14 (s, 1H) | 381 | 379 |
| 3 | (400 MHz, CDCl$_3$) 0.98 (s, 9H), 1.14-1.31 (m, 3H), 1.49-1.59 (m, 2H), 1.64-1.78 (m, 8H), 1.90-2.03 (m, 2H), 2.32-2.45 (m, 2H), 3.39-3.46 (m, 1H), 3.68-3.75 (m, 1H), 4.03 (t, J = 6.73 Hz, 2H), 4.82 (d, J = 2.65 Hz, 1H), 5.58 (d, J = 2.21 Hz, 1H), 6.09 (s, 1H), 6.85 (d, J = 8.38 Hz, 1H), 7.06 (dd, J = 8.49, 2.10 Hz, 1H), 7.22 (d, J = 1.98 Hz, 1H) | 477 | 475 |
| 4 | (400 MHz, DMSO-D6) 0.88 (s, 3H), 1,02 (s, 9H), 1.08 (s, 3H), 2.15 (d, J = 13.87 Hz, 1H), 2.29 (d, J = 14.33 Hz, 1H), 3.68 (s, 2H), 4.77 (d, J = 3.24 Hz, 1H), 6.15 (d, J = 5.32 Hz, 1H), 7.03 (s, 1H), 7.05 (d, J = 8.55 Hz, 1H), 7.19 (dd, J = 8.44, 2.20 Hz, 1H), 7.33 (d, J = 2.08 Hz, 1H), 8.09 (d, J = 3.24 Hz, 1H), 11.92 (s, 1H) | 395 | 393 |
| 5 | (400 MHz, CDCl3) 0.98 (s, 9H), 1.06 (s, 9H), 1.90-2.03 (m, 2H), 2.32-2.45 (m, 2H), 3.38-3.45 (m, 1H), 3.61 (s, 2H), 3.68-3.75 (m, 1H), 4.82 (d, J = 2.65 Hz, 1H), 5.62 (brs, 1H), 6.09 (s, 1H), 6.82 (d, J = 8.16 Hz, 1H), 7.05 (dd, J = 8.49, 2.32 Hz, 1H), 7.23 (d, J = 2.21 Hz, 1H) | 437 | 435 |
| 6 | (400 MHz, CDCl3) 0.99 (s, 9H), 1.07 (s, 9H), 1.91-2.03 (m, 2H), 2.33-2.45 (m, 2H), 3.39-3.46 (m, 1H), 3.62 (s, 2H), 3.69-3.76 (m, 1H), 4.82 (d, J = 2.65 Hz, 1H), 5.50-5.60 (brm, 1H), 6.09 (s, 1H), 6.83 (d, J = 8.38 Hz, 1H), 7.05 (dd, J = 8.38, 2.21 Hz, 1H), 7.23 (d, J = 2.21 Hz, 1H) | 437 | 435 |
| 7 | (400 MHz, DMSO-D6) 0.72 (s, 3H), 0.96 (s, 3H), 1.00 (s, 9H), 1.37-1.46 (m, 1H), 1.61-1.69 (m, 1H), 1.95-2.10 (m, 2H), 3.68 (s, 2H), 4.64 (d, J = 3.24 Hz, 1H), 6.08 (d, J = 5.32 Hz, 1H), 7.01 (s, 1H), 7.05 (d, J = 8.44 Hz, 1H), 7.19 (dd, J = 8.44, 2.20 Hz, 1H), 7.32 (d, J = 2.31 Hz, 1H), 8.14 (d, J = 4.86 Hz, 1H), 11.96 (s, 1H) | 409 | 407 |
| 8 | (400 MHz, CDCl3) 0.97 (s, 9H), 0.98 (s, 9H), 1.24-1.30 (m, 2H), 1.41-1.46 (m, 2H), 1.89-2.02 (m, 2H), 2.36-2.40 (m, 2H), 2.62-2.67 (m, 2H), 3.37-3.44 (m, 1H), 3.68-3.75 (m, 1H), 4.84 (d, J = 2.87 Hz, 1H), 5.82 (brs, 1H), 6.10 (s, 1H), 7.04 (dd, J = 7.72, 1.76 Hz, 1H), 7.16 (d, J = 7.94 Hz, 1H), 7.20 (d, J = 1.76 Hz, 1H) | 435 | 433 |
| 9 | (400 MHz, DMSO-D6) 0.73 (d, J = 6.94 Hz, 3H), 1.03 (s, 9H), 1.05 (d, J = 6.94 Hz, 3H), 1.61 (s, 3H), 1.65-1.76 (m, 2H), 1.92-1.99 (m, 1H), 2.19 (t, J = 7.40 Hz, 2H), 2.40-2.50 (m, 1H), 3.40-3.50 (m, 1H), 3.70 (s, 2H), 6.05 (s, 1H), 6.98 (s, 1H), 7.07 (d, J = 8.79 Hz, 1H), 7.27 (dd, J = 8.67, 2.43 Hz, 1H), 7.37 (d, J = 2.31 Hz, 1H), 12.07 (s, 1H) | 437 | 435 |
| 10 | (400 MHz, DMSO-D6) 0.92 (s, 9H), 0.93 (s, 9H), 1.34-1.38 (m, 2H), 1.62-1.79 (m, 2H), 2.18 (t, J = 7.40 Hz, 2H), 2.57-2.61 (m, 2H), 3.11-3.18 (m, 1H), 3.59-3.66 (m, 1H), 4.76 (d, J = 3.01 Hz, 1H), 6.25 (s, 1H), 7.13 (dd, J = 7.86, 1.62 Hz, 1H), 7.16 (d, J = 3.24 Hz, 1H), 7.25 (d, J = 7.86 Hz, 1H), 7.28 (d, J = 1.85 Hz, 1H), 12.05 (brs, 1H) | 435 | 433 |
| 11 | (400 MHz, DMSO-D6) 0.92 (s, 9H), 0.93 (s, 9H), 1.34-1.38 (m, 2H), 1.62-1.78 (m, 2H), 2.18 (t, J = 7.40 Hz, 2H), 2.57-2.61 (m, 2H), 3.11-3.18 (m, 1H), 3.59-3.66 (m, 1H), 4.76 (d, J = 3.01 Hz, 1H), 6.25 (s, 1H), 7.13 (dd, J = 7.86, 1.62 Hz, 1H), 7.16 (d, J = 3.24 Hz, 1H), 7.25 (d, J = 7.86 Hz, 1H), 7.28 (d, J = 1.85 Hz, 1H), 12.05 (brs, 1H) | 435 | 433 |

TABLE 3-continued

| Example | ¹H-NMR | MS M + H or M—+ H | M − H or M—Na − H |
|---|---|---|---|
| 12 | (400 MHz, DMSO-D6) 0.72 (d, J = 6.76 Hz, 3H), 1.00 (d, J = 13.28 Hz, 9H), 1.04 (d, J = 6.76 Hz, 3H), 1.60 (s, 3H), 1.66-1.73 (m, 2H), 1.95 (dd, J = 13.52, 6.76 Hz, 1H), 2.19 (t, J = 7.49 Hz, 2H), 3.27-3.34 (m, 1H), 3.41-3.48 (m, 1H), 3.69 (s, 2H), 6.04 (s, 1H), 6.97 (s, 1H), 7.06 (d, J = 8.69 Hz, 1H), 7.26 (dd, J = 8.57, 2.29 Hz, 1H), 7.37 (d, J = 2.41 Hz, 1H), 12.06 (s, 1H) | 437 | 435 |
| 13 | (400 MHz, DMSO-D6) 0.72 (d, J = 7.00 Hz, 3H), 1.02 (s, 9H), 1.04 (t, J = 5.80 Hz, 3H), 1.60 (s, 3H), 1.66-1.73 (m, 2H), 1.91-1.97 (m, 1H), 2.19 (t, J = 7.49 Hz, 2H), 3.27-3.34 (m, 1.H), 3.41-3.48 (m, 1H), 3.69 (s, 2H), 6.04 (s, 1H), 6.97 (s, 1H), 7.06 (d, J = 8.69 Hz, 1H), 7.26 (dd, J = 8.57, 2.29 Hz, 1H), 7.37 (d, J = 2.41 Hz, 1H), 12.06 (s, 1H) | 437 | 435 |
| 14 | (400 MHz, DMSO-D6) 0.71 (d, J = 6.94 Hz, 3H), 0.95 (s, 9H), 1.04 (d, J = 6.70 Hz, 3H), 1.36-1.40 (m, 2H), 1.61 (s, 3H), 3.66-1.73 (m, 2H), 1.94-2.01 (m, 1H), 2.17 (t, J = 7.63 Hz, 2H), 2.56-2.66 (m, 2H), 3.25-3.35 (m, 1H), 3.41-3.48 (m, 1H), 6.05 (s, 1H), 7.01 (s, 1H), 7.26 (dd, J = 7.98, 1.73 Hz, 1H), 7.29 (d, J = 8.09 Hz, 1H), 7.35 (d, J = 1.62 Hz, 1H), 12.08 (s, 1H) | 435 | 433 |
| 15 | (400 MHz, DMSO-D6) 0.71 (d, J = 6.94 Hz, 3H), 0.94 (s, 9H), 1.04 (d, J = 6.70 Hz, 3H), 1.36-1.40 (m, 2H), 1.61 (s, 3H), 1.65-1.73 (m, 2H), 1.94-2.01 (m, 1H), 2.17 (t, J = 7.40 Hz, 2H), 2.60-2.67 (m, 2H), 3.25-3.35 (m, 1H), 3.41-3.48 (m, 1H), 6.05 (s, 1H), 7.01 (s, 1H), 7.26 (dd, J = 7.98, 1.73 Hz, 1H), 7.29 (d, J = 8.09 Hz, 1H), 7.35 (d, J = 1.62 Hz, 1H), 12.08 (s, 1H) | 435 | 433 |
| 16 | (400 MHz, DMSO-D6) 0.76 (d, J = 7.00 Hz, 3H), 1.01 (s, 9H), 1.07 (d, J = 6.40 Hz, 3H), 1.60 (s, 3H), 1.98-2.05 (m, 1H), 2.22-2.31 (m, 2H), 2.35-2.40 (m, 2H), 2.70-2.78 (m, 1H), 3.69 (s, 2H), 4.65-4.74 (m, 1H), 6.26 (s, 1H), 7.06 (s, 1H), 7.09 (s, 1H), 7.24 (dd, J = 8.69, 2.41 Hz, 1H), 7.34 (d, J = 2.41 Hz, 1H), 12.22 (s, 1H) | 449 | 447 |
| 17 | (400 MHz, DMSO-D6) 0.78 (d, J = 7.49 Hz, 3H), 1.03 (s, 9H), 1.09 (d, J = 6.76 Hz, 3H), 1.60 (s, 3H), 1.95-2.02 (m, 1H), 2.24-2.30 (m, 2H), 2.46-2.54 (m, 2H), 2.88-2.90 (m, 1H), 3.69 (s, 2H), 4.92-5.01 (m, 1H), 6.32 (s, 1H), 7.07 (t, J = 4.35 Hz, 2H), 7.24 (dd, J = 8.57, 2.29 Hz, 1H), 7.33 (d, J = 2.17 Hz, 1H), 12.25 (s, 1H) | 449 | 447 |
| 18 | (400 MHz, DMSO-D6) 0.71 (d, J = 6.76 Hz, 3H), 1.01 (s, 9H), 1.03 (d, J = 7.00 Hz, 3H), 1.47-1.48 (m, 4H), 1.60 (s, 3H), 1.91-1.98 (m, 1H), 2.24 (t, J = 6.64 Hz, 2H), 3.25-3.32 (m, 1H), 3.41-3.44 (m, 1H), 3.69 (s, 2H), 6.05 (s, 1H), 6.93 (s, 1H), 7.06 (d, J = 8.69 Hz, 1H), 7.26 (dd, J = 8.69, 2.41 Hz, 1H), 7.36 (d, J = 2.41 Hz, 1H), 11.99 (s, 1H) | 451 | 449 |
| 19 | (400 MHz, DMSO-D6) 0.70 (d, J = 6.94 Hz, 3H), 1.00 (s, 9H), 1.02 (d, J = 6.70 Hz, 4H), 1.08 (d, J = 6.94 Hz, 3H), 1.47 (td, J = 13.76, 7.32 Hz, 1H), 1.58 (s, 3H), 1.79 (td, J = 13.70, 7.24 Hz, 1H), 1.89-1.95 (m, 1H), 2.28 (dt, J = 16.49, 4.74 Hz, 1H), 3.32-3.43 (m, 1H), 3.68 (s, 2H), 6.02 (s, 1H), 6.95 (s, 1H), 7.05 (d, J = 8.79 Hz, 1H), 7.25 (dd, J = 8.55, 2.31 Hz, 1H), 7.35 (d, J = 2.31 Hz, 1H), 12.11 (s, 1H) | 451 | 449 |
| 20 | (400 MHz, DMSO-D6) 0.71 (d, J = 6.70 Hz, 3H), 1.00 (s, 9H), 1.02 (d, J = 6.70 Hz, 3H), 1.07 (d, J = 6.94 Hz, 3H), 1.47-1.50 (m, 1H), 1.58 (s, 3H), 1.75-1.79 (m, 1H), 1.95-1.97 (m, 1H), 2.26-2.28 (m, 1H), 3.20-3.27 (m, 1H), 3.47-3.54 (m, 1H), 3.67 (s, 2H), 6.01 (s, 1H), 6.96 (s, 1H), 7.04 (d, J = 8.79 Hz, 1H), 7.24 (dd, J = 8.55, 2.3 1 Hz, 1H), 7.35 (d, J = 2.31 Hz, 1H), 12.11 (s, 1H) | 451 | 449 |
| 21 | (400 MHz, DMSO-D6) 0.70 (dd, J = 6.94, 3.24 Hz, 3H), 1.00 (s, 9H), 1.02 (d, J = 7.40 Hz, 3H), 1.07 (dd, J = 6.94, 4.16 Hz, 3H), 1.42-1.53 (m, 1H), 1.58 (s, 3H), 1.73-1.84 (m, 1H), 1.89-1.98 (m, 1H), 2.23-2.33 (m, 1H), 3.17-3.57 (m, 2H), 3.68 (s, 2H), 6.02 (d, J = 3.70 Hz, 1H), 6.96 (d, J = 4.86 Hz, 1H), 7.05 (dd, J = 8.67, 2.20 Hz, 1H), 7.25 (dt, J = 8.79, 2.14 Hz, 1H), 7.35 (d, J = 2.31 Hz, 1H), 12.11 (s, 1H) | 451 | 449 |
| 22 | (400 MHz, DMSO-D6) 0.94 (s, 9H), 0.94 (s, 9H), 1.36-1.40 (m, 2H), 1.70-1.72 (m, 2H), 1.78 (s, 3H), 2.19 (t, J = 7.46 Hz, 2H), 2.60-2.64 (m, 2H), 3.26-3.28 (m, | 449 | 447 |

TABLE 3-continued

| Example | ¹H-NMR | MS M + H or M—+ H | MS M − H or M—Na − H |
|---|---|---|---|
| | 1H), 3.48-3.55 (m, 1H), 6.23 (s, 1H), 6.85 (s, 1H), 7.27 (s, 2H), 7.36 (s, 1H), 12.09 (brs, 1H) | | |
| 23 | (400 MHz, DMSO-D6) 0.82 (s, 9H), 0.94 (s, 9H), 1.35-1.39 (m, 2H), 1.54 (s, 3H), 1.65-1.69 (m, 2H), 1.79 (d, J = 4.16 Hz, 2H), 2.13 (t, J = 7.46 Hz, 2H), 2.59-2.63 (m, 2H), 3.25-3.27 (m, 1H), 3.43-3.50 (m, 1H), 6.06 (s, 1H), 7.13 (s, 1H), 7.24-7.27 (m, 2H), 7.34 (d, J = 1.73 Hz, 1H), 12.06 (brs, 1H) | 463 | 461 |
| 24 | (400 MHz, DMSO-D6) 0.70-0.72 (m, 3H), 0.90-0.98 (m, 9H), 1.05-1.07 (m, 6H), 1.36-1.40 (m, 2H), 1.47-1.50 (m, 1H), 1.61 (s, 3H), 1.76-1.83 (m, 1H), 1.95-2.01 (m, 1H), 2.26-2.31 (m, 1H), 2.60-2.64 (m, 2H), 3.23-3.27 (m, 1H), 3.35-3.54 (m, 1H), 6.04 (d, J = 4.39 Hz, 1H), 7.02 (d, J = 5.78 Hz, 1H), 7.23-7.32 (m, 2H), 7.34 (d, J = 1.62 Hz, 1H), 12.12 (s, 1H) | 449 | 447 |
| 25 | (400 MHz, DMSO-D6) 0.70-0.72 (m, 3H), 0.90-0.98 (m, 9H), 1.05-1.07 (m, 6H), 1.36-1.40 (m, 2H), 1.47-1.50 (m, 1H), 1.61 (s, 3H), 1.76-1.83 (m, 1H), 1.95-2.01 (m, 1H), 2.26-2.31 (m, 1H), 2.60-2.64 (m, 2H), 3.23-3.27 (m, 1H), 3.35-3.54 (m, 1H), 6.04 (d, J = 4.39 Hz, 1H), 7.02 (d, J = 5.78 Hz, 1H), 7.23-7.32 (m, 2H), 7.34 (d, J = 1.62 Hz, 1H), 12.12 (s, 1H) | 449 | 447 |
| 26 | (400 MHz, CDCl3) δ: 0.70 (t, J = 6.65 Hz, 3H), 0.94 (d, J = 12.89 Hz, 9H), 1.05 (q, J = 3.49 Hz, 3H), 1.45-1.50 (m, 2H), 1.72 (d, J = 9.67 Hz, 3H), 1.92 (dd, J = 10.88, 6.85 Hz, 3H), 2.37 (t, J = 6.85 Hz, 2H), 2.53-2.57 (m, 2H), 3.55 (q, J = 6.31 Hz, 2H), 5.36-5.49 (m, 1H), 5.78 (s, 1H), 7.14 (d, J = 8.46 Hz, 2H), 7.31 (dd, J = 8.26, 4.23 Hz, 2H). | 401 | 399 |
| 27 | (400 MHz, CDCl3) δ: 0.71 (dd, J = 12.69, 6.65 Hz, 3H), 0.93 (dd, J = 14.51, 11.69 Hz, 6H), 1.06 (dd, J = 20.75, 13.90 Hz, 3H), 1.48 (dt, J = 17.19, 7.45 Hz, 2H), 1.61 (td, J = 13.30, 6.85 Hz, 1H), 1.69 (d, J = 14.10 Hz, 3H), 1.87-1.94 (m, 3H), 2.38 (t, J = 6.85 Hz, 2H), 2.67-2.71 (m, 2H), 3.55 (dq, J = 25.39, 6.58 Hz, 2H), 5.47 (s, 1H), 5.80 (d, J = 11.69 Hz, 1H), 7.17 (d, J = 8.06 Hz, 1H), 7.24 (dd, J = 8.06, 2.01 Hz, 1H), 7.37 (d, J = 2.01 Hz, 1H). | 421 | 419 |
| 28 | (400 MHz, CDCl3) δ: 0.72 (d, J = 6.85 Hz, 3H), 0.94 (t, J = 7.25 Hz, 3H), 1.06 (d, J = 6.85 Hz, 3H), 1.37 (t, J = 7.45 Hz, 2H), 1.57 (dd, J = 15.51, 7.86 Hz, 2H), 1.72 (s, 3H), 1.93 (dt, J = 18.67, 6.95 Hz, 3H), 2.41 (t, J = 6.85 Hz, 2H), 2.71 (t, J = 7.66 Hz, 2H), 3.58 (dd, J = 7.66, 5.64 Hz, 2H), 4.97 (s, 1H), 5.81 (s, 1H), 7.19 (d, J = 7.66 Hz, 1H), 7.23 (d, J = 2.01 Hz, 1H), 7.38 (d, J = 1.61 Hz, 1H). | 407 | 405 |
| 29 | (400 MHz, DMSO-D6) 0.74 (d, J = 6.94 Hz, 3H), 0.94 (s, 9H), 1.06 (d, J = 6.94 Hz, 3H), 1.34-1.43 (m, 4H), 1.54-1.65 (m, 7H), 1.95-2.05 (m, 3H), 2.20-2.27 (m, 1H), 2.59-2.64 (m, 2H), 4.03-4.09 (m, 1H), 6.13 (s, 1H), 7.01 (s, 1H), 7.24 (dd, J = 8.09, 1.85 Hz, 1H), 7.29 (d, J = 8.09 Hz, 1H), 7.33 (d, J = 1.85 Hz, 1H), 12.05 (s, 1H) | 475 | 473 |
| 30 | (400 MHz, DMSO-D6) 0.70 (d, J = 6.94 Hz, 3H), 0.94 (s, 9H), 1.03 (d, J = 6.70 Hz, 3H), 1.24-1.25 (m, 1H), 1.38 (dt, J = 10.33, 3.41 Hz, 2H), 1.44-1.60 (m, 9H), 2.02-2.13 (m, 3H), 2.60-2.62 (m, 2H), 4.07-4.09 (m, 1H), 5.91 (s, 1H), 7.03 (s, 1H), 7.23 (dd, J = 7.98, 1.97 Hz, 1H), 7.29 (d, J = 7.86 Hz, 1H), 7.33 (d, J = 1.85 Hz, 1H) | 475 | 473 |
| 31 | (400 MHz, CDCl3) 0.87-0.94 (m, 2H), 0.96 (s, 9H), 1.02-1.18 (m, 4H), 1.41-1.45 (m, 2H), 1.47-1.59 (m, 3H), 1.67 (s, 3H), 1.68-1.79 (m, 2H), 1.87-1.94 (m, 2H), 2.35 (t, J = 6.94 Hz, 2H), 2.63-2.68 (m, 2H), 3.52 (t, J = 6.47 Hz, 2H), 5.20 (s, 1H), 5.76 (s, 1H), 7.15 (d, J = 8.09 Hz, 1H), 7.21 (dd, J = 7.98, 1.97 Hz, 1H), 7.35 (d, J = 1.85 Hz, 1H) | 475 | 473 |
| 32 | (400 MHz, CDCl3) 0.89-0.95 (m, 2H), 0.96 (s, 9H), 1.04-1.17 (m, 4H), 1.41-1.45 (m, 2H), 1.47-1.59 (m, 3H), 1.68 (s, 3H), 1.70-1.79 (m, 2H), 1.89-1.96 (m, 2H), 2.38 (t, J = 6.94 Hz, 2H), 2.64-2.68 (m, 2H), 3.55 (t, J = 6.59 Hz, 2H), 5.05 (s, 1H), 5.77 (s, 1H), 7.16 (d, J = 8.09 Hz, 1H), 7.21 (dd, J = 8.09, 2.08 Hz, 1H), 7.35 (d, J = 2.08 Hz, 1H) | 475 | 473 |

TABLE 3-continued

| Example | ¹H-NMR | MS M + H or M—+ H | M − H or M—Na − H |
|---|---|---|---|
| 33 | (400 MHz, DMSO-D6) 0.38 (t, J = 7.34 Hz, 1.5H), 0.61 (d, J = 6.82 Hz, 1.5H), 0.83 (t, J = 7.34 Hz, 1.5H), 0.94 (s, 4.5H), 0.95 (s, 4.5H), 1.02 (d, J = 6.70 Hz, 1.5H), 1.04-1.06 (m, 1H), 1.24-1.31 (m, 0.5H), 1.37 (dt, J = 12.48, 5.12 Hz, 2H), 1.42-1.49 (m, 0.5H), 1.58 (s, 1.5H), 1.61 (s, 1.5H), 1.69-1.71 (m, 3H), 2.17-2.18 (m, 2H), 2.61-2.63 (m, 2H), 3.23-3.53 (m, 3H), 5.93 (s, 0.5H), 5.96 (s, 0.5H), 7.00 (s, 0.5H), 7.02 (s, 0.5H), 7.26-7.28 (m, 2H), 7.34 (d, J = 1.62 Hz, 0.5H), 7.35 (d, J = 1.50 Hz, 0.5H), 12.09 (brs, 1H) | 449 | 447 |
| 34 | (400 MHz, DMSO-D6) 0.38 (t, J = 7.28 Hz, 1.5H), 0.61 (d, J = 6.82 Hz, 1.5H), 0.83 (t, J = 7.34 Hz, 1.5H), 0.94 (s, 4.5H), 0.95 (s, 4.5H), 1.02 (d, J = 6.82 Hz, 1.5H), 1.05-1.07 (m, 1H), 1.24-1.31 (m, 0.5H), 1.36-1.39 (m, 2H), 1.42-1.49 (m, 0.5H), 1.58 (s, 1.5H), 1.61 (s, 1.5H), 1.69-1.72 (m, 3H), 2.17-2.19 (m, 2H), 2.61-2.63 (m, 2H), 3.23-3.53 (m, 3H), 5.93 (s, 0.5H), 5.97 (s, 0.5H), 7.00 (s, 0.5H), 7.02 (s, 0.5H), 7.26-7.28 (m, 2H), 7.34 (d, J = 1.62 Hz, 0.5H), 7.35 (d, J = 1.50 Hz, 0.5H), 12.10 (brs, 1H) | 449 | 447 |
| 35 | (400 MHz, DMSO-D6) 0.76 (d, J = 6.82 Hz, 3H), 0.87 (s, 3H), 0.89 (s, 3H), 0.94 (s, 9H), 1.04 (d, J = 6.82 Hz, 3H), 1.35-1.40 (m, 2H), 1.61 (s, 3H), 2.02-2.07 (m, 3H), 2.60-2.64 (m, 2H), 3.17 (d, J = 13.99 Hz, 1H), 3.56 (d, J = 13.99 Hz, 1H), 6.08 (s, 1H), 7.17 (bs, 1H), 7.29-7.29 (m, 2H), 7.39 (s, 1H), 12.09 (bs, 1H) | 463 | 461 |
| 36 | (400 MHz, DMSO-D6) 0.76 (d, J = 6.82 Hz, 3H), 0.87 (s, 3H), 0.89 (s, 3H), 0.94 (s, 9H), 1.04 (d, J = 6.82 Hz, 3H), 1.35-1.40 (m, 2H), 1.61 (s, 3H), 2.02-2.07 (m, 3H), 2.60-2.64 (m, 2H), 3.17 (d, J = 13.99 Hz, 1H), 3.56 (d, J = 13.99 Hz, 1H), 6.08 (s, 1H), 7.17 (bs, 1H), 7.29-7.29 (m, 2H), 7.39 (s, 1H), 12.09 (bs, 1H) | 463 | 461 |
| 37 | (400 MHz, DMSO-D6) 0.72-0.79 (m, 6H), 0.95 (s, 9H), 1.35-1.40 (m, 2H), 1.45-1.50 (m, 1H), 1.55-1.58 (m, 4H), 1.65-1.72 (m, 3H), 2.16 (t, J = 7.51 Hz, 2H), 2.60-2.64 (m, 2H), 3.27-3.31 (m, 1H), 3.42-3.48 (m, 1H), 5.94 (s, 1H), 7.05 (s, 1H), 7.25-7.28 (m, 2H), 7.35 (d, J = 1.73 Hz, 1H), 12.08 (brs, 1H) | 449 | 447 |
| 38 | (400 MHz, DMSO-D6) 0.73-0.76 (m, 6H), 0.95 (s, 9H), 1.35-1.40 (m, 2H), 1.45-1.49 (m, 1H), 1.55-1.58 (m, 4H), 1.68-1.70 (m, 3H), 2.16 (t, J = 7.51 Hz, 2H), 2.60-2.64 (m, 2H), 3.27-3.30 (m, 1H), 3.41-3.48 (m, 1H), 5.94 (s, 1H), 7.05 (s, 1H), 7.25-7.28 (m, 2H), 7.35 (d, J = 1.73 Hz, 1H), 12.08 (brs, 1H) | 449 | 447 |
| 39 | (400 MHz, DMSO-D6) 0.69 (d, J = 6.70 Hz, 3H), 0.95 (s, 9H), 1.03 (d, J = 6.70 Hz, 3H), 1.38 (dt, J = 8.79, 3.73 Hz, 2H), 1.61 (s, 3H), 1.93-1.96 (m, 1H), 2.62 (dt, J = 10.40, 3.73 Hz, 2H), 3.44-3.62 (m, 4H), 3.92 (s, 2H), 6.12 (s, 1H), 7.02 (bs, 1H), 7.27-7.30 (m, 2H), 7.34-7.36 (m, 1H) | 451 | 449 |
| 40 | (400 MHz, DMSO-D6) 0.69 (d, J = 6.70 Hz, 3H), 0.95 (s, 9H), 1.03 (d, J = 6.70 Hz, 3H), 1.38 (dt, J = 8.79, 3.73 Hz, 2H), 1.61 (s, 3H), 1.93-1.96 (m, 1H), 2.62 (dt, J = 10.40, 3.73 Hz, 2H), 3.44-3.62 (m, 4H), 3.92 (s, 2H), 6.12 (s, 1H), 7.02 (bs, 1H), 7.27-7.30 (m, 2H), 7.34-7.36 (m, 1H) | 451 | 449 |
| 41 | (400 MHz, DMSO-D6) 0.67-0.79 (m, 3H), 0.94 (s, 9H), 1.03-1.13 (m, 3H), 1.32-1.43 (m, 2H), 1.54-1.61 (m, 3H), 1.93-2.05 (m, 1H), 2.14-2.35 (m, 5H), 2.54-2.69 (m, 2H), 4.83-4.99 (m, 1H), 6.27 (s, 1H), 6.99 (s, 1H), 7.17-7.35 (m, 3H) | 447 | 445 |
| 42 | (400 MHz, DMSO-D6) 0.67-0.79 (m, 3H), 0.94 (s, 9H), 1.03-1.13 (m, 3H), 1.32-1.43 (m, 2H), 1.54-1.61 (m, 3H), 1.93-2.05 (m, 1H), 2.14-2.35 (m, 5H), 2.54-2.69 (m, 2H), 4.83-4.99 (m, 1H), 6.27 (s, 1H), 6.99 (s, 1H), 7.17-7.35 (m, 3H) | 447 | 445 |
| 43 | (400 MHz, DMSO-D6) 0.74-0.77 (m, 6H), 0.94 (s, 9H), 1.01-1.10 (m, 1H), 1.14-1.23 (m, 1H), 1.38-1.41 (m, 3H), 1.57 (s, 3H), 1.63-1.71 (m, 3H), 1.83-1.90 (m, 1H), 2.14 (t, J = 7.46 Hz, 2H), 2.60-2.64 (m, 2H), 3.25-3.27 (m, 1H), 3.40-3.47 (m, 1H), 5.94 (s, 1H), 7.05 (s, 1H), 7.24 (dd, J = 7.98, 1.85 Hz, 1H), 7.29 (d, J = 7.98 Hz, 1H), 7.34 (d, J = 1.85 Hz, 1H), 12.08 (brs, 1H) | 463 | 461 |

TABLE 3-continued

| Example | ¹H-NMR | MS M + H or M—+ H | MS M − H or M—Na − H |
|---|---|---|---|
| 44 | (400 MHz, DMSO-D6) 0.74-0.77 (m, 6H), 0.94 (s, 9H), 1.02-1.06 (m, 1H), 1.15-1.21 (m, 1H), 1.38-1.41 (m, 3H), 1.57 (s, 3H), 1.64-1.68 (m, 3H), 1.84-1.88 (m, 1H), 2.13 (t, J = 7.46 Hz, 2H), 2.60-2.64 (m, 2H), 3.25-3.27 (m, 1H), 3.40-3.47 (m, 1H), 5.94 (s, 1H), 7.05 (s, 1H), 7.24 (dd, J = 8.03, 1.79 Hz, 1H), 7.29 (d, J = 8.09 Hz, 1H), 7.34 (d, J = 1.85 Hz, 1H) | 463 | 461 |
| 45 | (400 MHz, DMSO-D6) 0.69-0.77 (m, 3H), 0.93 (s, 9H), 1.02-1.10 (m, 3H), 1.30-1.43 (m, 2H), 1.61 (s, 3H), 1.95-2.06 (m, 1H), 2.18-2.39 (m, 5H), 2.57-2.65 (m, 2H), 2.66-2.77 (m, 1H), 4.59-4.73 (m, 1H), 6.25 (s, 1H), 7.09 (s, 1H), 7.17-7.33 (m, 3H), 12.23 (brs, 1H) | 447 | 445 |
| 46 | (400 MHz, DMSO-D6) 0.69-0.77 (m, 3H), 0.93 (s, 9H), 1.02-1.10 (m, 3H), 1.30-1.43 (m, 2H), 1.61 (s, 3H), 1.95-2.06 (m, 1H), 2.18-2.39 (m, 5H), 2.57-2.65 (m, 2H), 2.66-2.77 (m, 1H), 4.59-4.73 (m, 1H), 6.25 (s, 1H), 7.09 (s, 1H), 7.17-7.33 (m. 3H), 12.23 (brs, 1H) | 447 | 445 |
| 47 | (400 MHz, DMSO-D6) 0.64-0.72 (m, 3H), 0.93 (s, 9H), 1.00-1.05 (m, 3H), 1.31-1.40 (m, 2H), 1.40-1.51 (m, 4H), 1.59 (s, 3H), 1.90-2.00 (m, 1H), 2.18-2.25 (m, 2H), 2.55-2.65 (m, 2H), 3.21-3.28 (m, 1H), 3.38-3.46 (m, 1H), 6.04 (s, 1H), 6.95 (brs, 1H), 7.21-7.29 (m, 2H), 7.31-7.34 (m, 1H), 11.94 (brs, 1H) | 449 | 447 |
| 48 | (400 MHz, DMSO-D6) 0.64-0.72 (m, 3H), 0.93 (s, 9H), 1.00-1.05 (m, 3H), 1.31-1.40 (m, 2H), 1.40-1.51 (m, 4H), 1.59 (s, 3H), 1.90-2.00 (m, 1H), 2.18-2.25 (m, 2H), 2.55-2.65 (m, 2H), 3.21-3.28 (m, 1H), 3.38-3.46 (m, 1H), 6.04 (s, 1H), 6.95 (brs, 1H), 7.21-7.29 (m, 2H), 7.31-7.34 (m, 1H), 11.94 (brs, 1H) | 449 | 447 |
| 49 | (400 MHz, DMSO-D6) 0.47-0.54 (m, 3H), 0.86-0.91 (m, 3H), 0.94 (s, 9H), 1.33-1.42 (m, 2H), 1.54 (s, 3H), 1.75-1.88 (m, 1H), 2.57-2.65 (m, 2H), 2.81-2.90 (m, 2H), 3.49-3.59 (m, 1H), 3.70-3.81 (m, 1H), 5.78 (s, 1H), 6.96 (s, 1H), 7.09-7.15 (m, 1H), 7.21-7.27 (m, 1H), 7.27-7.34 (m, 3H), 7.80-7.86 (m, 2H), 12.75 (brs, 1H) | 497 | 495 |
| 50 | (400 MHz, DMSO-D6) 0.47-0.54 (m, 3H), 0.86-0.91 (m, 3H), 0.94 (s, 9H), 1.33-1.42 (m, 2H), 1.54 (s, 3H), 1.75-1.88 (m, 1H), 2.57-2.65 (m, 2H), 2.81-2.90 (m, 2H), 3.49-3.59 (m, 1H), 3.70-3.81 (m, 1H), 5.78 (s, 1H), 6.96 (s, 1H), 7.09-7.15 (m, 1H), 7.21-7.27 (m, 1H), 7.27-7.34 (m, 3H), 7.80-7.86 (m, 2H), 12.75 (brs, 1H) | 497 | 495 |
| 51 | (400 MHz, DMSO-D6) 0.15-0.19 (m, 1H), 0.51-0.41 (m, 3H), 0.79 (s, 3H), 0.94 (s, 9H), 1.36-1.40 (m, 2H), 1.66-1.71 (m, 2H), 1.74 (s, 3H), 2.16 (t, J = 7.49 Hz, 2H), 2.60-2.64 (m, 2H), 3.16-3.27 (m, 1H), 3.47-3.55 (m, 1H), 6.25 (s, 1H), 7.08 (s, 1H), 7.27 (d, J = 0.97 Hz, 2H), 7.38 (s, 1H), 12.05 (brs, 1H) | 447 | 445 |
| 52 | (400 MHz, DMSO-D6) 0.16-0.19 (m. 1H), 0.41-0.51 (m, 3H), 0.79 (s, 3H), 0.94 (s, 9H), 1.36-1.40 (m, 2H), 1.66-1.71 (m, 2H), 1.73 (s, 3H), 2.19-2.13 (m, 2H), 2.60-2.64 (m, 2H), 3.18-3.25 (m, 1H), 3.47-3.55 (m, 1H), 6.25 (s, 1H), 7.08 (s, 1H), 7.27 (s, 2H), 7.38 (s, 1H), 12.04 (brs, 1H) | 447 | 445 |
| 53 | (400 MHz, CDCl3) δ: 0.72 (d, J = 6.85 Hz, 3H), 0.90 (t, J = 6.85 Hz, 3H), 1.06 (d, J = 6.85 Hz, 3H), 1.35 (t, J = 3.63 Hz, 4H), 1.60 (t, J = 7.45 Hz, 2H), 1.73 (d, J = 8.06 Hz, 3H), 1.93 (tt, J = 17.93, 5.31 Hz, 3H), 2.41 (t, J = 7.05 Hz, 2H), 2.70 (t, J = 7.66 Hz, 2H), 3.58 (td, J = 6.55, 3.49 Hz, 2H), 5.06 (s, 1H), 5.82 (s, 1H), 7.18 (d, J = 8.06 Hz, 1H), 7.23 (d, J = 2.01 Hz, 1H), 7.38 (d, J = 2.01 Hz, 1H). | 421 | 419 |
| 54 | (400 MHz, DMSO-D6) 0.70 (d, J = 6.82 Hz, 3H), 0.95 (s, 9H), 1.04 (d, J = 6.82 Hz, 3H), 1.12 (s, 6H), 1.36-1.40 (m, 2H), 1.60 (s, 3H), 1.63-1.68 (m, 2H), 1.97-1.98 (m, 1H), 2.60-2.64 (m, 2H), 3.27-3.41 (m, 4H), 6.00 (s, 1H), 7.00 (bs, 1H), 7.26 (dd, J = 8.09, 1.85 Hz, 1H), 7.30 (d, J = 8.09 Hz, 1H), 7.34 (d, J = 1.85 Hz, 1H), 12.18 (bs, 1H) | 463 | 461 |
| 55 | (400 MHz, DMSO-D6) 0.70 (d, J = 6.82 Hz, 3H), 0.95 (s, 9H), 1.04 (d, J = 6.82 Hz, 3H), 1.12 (s, 6H), 1.36-1.40 (m, 2H), 1.60 (s, 3H), 1.63-1.68 (m, 2H), 1.97-1.98 | 463 | 461 |

TABLE 3-continued

| Example | ¹H-NMR | MS M + H or M—+ H | MS M − H or M—Na − H |
|---|---|---|---|
| | (m, 1H), 2.60-2.64 (m, 2H), 3.27-3.41 (m, 4H), 6.00 (s, 1H), 7.00 (bs, 1H), 7.26 (dd, J = 8.09, 1.85 Hz, 1H), 7.30 (d, J = 8.09 Hz, 1H), 7.34 (d, J = 1.85 Hz, 1H), 12.18 (bs, 1H) | | |
| 56 | (400 MHz, CDCl3) 0.20-0.26 (m, 1H), 0.27-0.32 (m, 1H), 0.38-0.45 (m, 1H), 0.60-0.67 (m, 1H), 0.86-0.92 (m, 1H), 0.98 (s, 9H), 1.42-1.47 (m, 2H), 1.80 (s, 3H), 1.89-1.96 (m, 2H), 2.39 (t, J = 7.05 Hz, 2H), 2.65-2.69 (m, 2H), 3.54 (ddd, J = 6.85, 6.85, 2.82 Hz, 2H), 5.09 (s, 1H), 5.65 (d, J = 1.61 Hz, 1H), 7.19 (d, J = 8.06 Hz, 1H), 7.27 (dd, J = 4.43, 2.01 Hz, 1H), 7.41 (d, J = 2.01 Hz, 1H) | 433 | 431 |
| 57 | (400 MHz, CDCl3) 0.20-0.26 (m, 1H), 0.27-0.32 (m, 1H), 0.38-0.45 (m, 1H), 0.60-0.67 (m, 1H), 0.86-0.92 (m, 1H), 0.98 (s, 9H), 1.42-1.47 (m, 2H), 1.80 (s, 3H), 1.89-1.96 (m, 2H), 2.39 (t, J = 7.05 Hz, 2H), 2.65-2.69 (m, 2H), 3.54 (ddd, J = 6.85, 6.85, 2.82 Hz, 2H), 5.09 (s, 1H), 5.65 (d, J = 1.61 Hz, 1H), 7.19 (d, J = 8.06 Hz, 1H), 7.27 (dd, 3 = 4.43, 2.01 Hz, 1H), 7.41 (d, J = 2.01 Hz, 1H) | 433 | 431 |
| 58 | (400 MHz, CDCl3) 0.98 (s, 9H), 1.42-1.47 (m, 2H), 3.52-1.67 (m, 3H), 1.64 (s, 3H), 1.69-1.76 (m, 1H), 1.80-1.88 (m, 1H), 1.92-2.03 (m, 3H), 2.40 (t, J = 7.25 Hz, 2H), 2.51-2.59 (m, 1H), 2.64-2.68 (m, 2H), 3.57 (ddd, J = 14.91, 12.89, 8.06 Hz, 2H), 5.32 (s, 1H), 5.77 (d, J = 1.21 Hz, 1H), 7.16 (d, J = 8.06 Hz, 1H), 7.20 (dd, J = 8.06, 2.01 Hz, 1H), 7.34 (d, J = 1.61 Hz, 1H) | 447 | 445 |
| 59 | (400 MHz, CDCl3) 0.98 (s, 9H), 1.42-1.47 (m, 2H), 1.52-1.67 (m, 3H), 1.64 (s, 3H), 1.69-1.76 (m, 1H), 1.80-1.88 (m, 1H), 1.92-2.03 (m, 3H), 2.40 (t, J = 7.25 Hz, 2H), 2.51-2.59 (m, 1H), 2.64-2.68 (m, 2H), 3.57 (ddd, J = 14.91, 12.89, 8.06 Hz, 2H), 5.32 (s, 1H), 5.77 (d, J = 1.21 Hz, 1H), 7.16 (d, J = 8.06 Hz, 1H), 7.20 (dd, J = 8.06, 2.01 Hz, 1H), 7.34 (d, J = 1.61 Hz, 1H) | 447 | 445 |
| 60 | (400 MHz, CDCl3) 0.98 (s, 9H), 1.42-1.45 (m, 2H), 1.46 (d, J = 1.61 Hz, 3H), 1.70 (s, 3H), 1.90-1.97 (m, 2H), 2.40 (t, J = 6.85 Hz, 2H), 2.65-2.69 (m, 2H), 3.55 (t, J = 6.85 Hz, 2H), 5.04 (s, 1H), 5.76 (d, J = 1.21 Hz, 1H), 7.21-7.20 (m, 2H), 7.36 (d, J = 1.61 Hz, 1H) | 407 | 405 |
| 61 | (400 MHz, CDCl3) 0.98 (s, 9H), 1.42-1.45 (m, 2H), 1.46 (d, J = 1.61 Hz, 3H), 1.70 (s, 3H), 1.90-1.97 (m, 2H), 2.40 (t, J = 6.85 Hz, 2H), 2.65-2.69 (m, 2H), 3.55 (t, J = 6.85 Hz, 2H), 5.04 (s, 1H), 5.76 (d, J = 1.21 Hz, 1H), 7.21-7.20 (m, 2H), 7.36 (d, J = 1.61 Hz, 1H) | 407 | 405 |
| 62 | (400 MHz, DMSO-D6) 1.02 (s, 9H), 1.89-2.01 (m, 3H), 2.14-2.20 (m, 1H), 2.63-2.72 (m, 1H), 2.75-2.81 (m, 1H), 3.69 (s, 2H), 4.66 (s, 1H), 5.95 (d, J = 4.35 Hz, 1H), 7.01 (s, 1H), 7.08 (d, J = 8.69 Hz, 1H), 7.13 (dd, J = 8.45, 1.93 Hz, 1H), 7.25 (d, J = 1.69 Hz, 1H), 8.11 (d, J = 3.38 Hz, 1H) | 393 | 391 |
| 63 | (400 MHz, DMSO-D6) 0.68-0.77 (m, 3H), 0.93 (s, 9H), 1.00-1.08 (m, 3H), 1.32-1.40 (m, 2H), 1.59 (s, 3H), 1.66-1.91 (m, 4H), 1.91-2.06 (m, 2H), 2.57-2.64 (m, 2H), 2.67-2.79 (m, 1H), 4.63-4.77 (m, 1H), 6.18 (s, 1H), 7.02 (s, 1H), 7.19-7.37 (m, 3H), 12.21 (brs, 1H) | 461 | 459 |
| 64 | (400 MHz, DMSO-D6) 0.68-0.77 (m, 3H), 0.93 (s, 9H), 1.00-1.08 (m, 3H), 1.32-1.40 (m, 2H), 1.59 (s, 3H), 1.66-1.91 (m, 4H), 1.91-2.06 (m, 2H), 2.57-2.64 (m, 2H), 2.67-2.79 (m, 1H), 4.63-4.77 (m, 1H), 6.18 (s, 1H), 7.02 (s, 1H), 7.19-7.37 (m, 3H), 12.21 (brs, 1H) | 461 | 459 |
| 65 | (400 MHz, CDCl3) δ: 0.70 (t, J = 7.66 Hz, 3H), 0.98 (d, J = 7.25 Hz, 9H), 1.05 (d, J = 6.85 Hz, 3H), 1.28 (d, J = 15.72 Hz, 2H), 1.37-1.42 (m, 2H), 1.72 (d, J = 5.24 Hz, 3H), 1.88-1.98 (m, 3H), 2.29 (s, 3H), 2.41 (t, J = 6.85 Hz, 2H), 2.51-2.55 (m, 2H), 3.57 (ddd, J = 14.81, 8.36, 5.94 Hz, 2H), 5.12 (s, 1H), 5.78 (s, 1H), 7.08 (d, J = 7.66 Hz, 1H), 7.16 (d, J = 7.66 Hz, 2H). | 415 | 413 |
| 66 | (400 MHz, DMSO-D6) 0.70 (d, J = 6.94 Hz, 3H), 0.94 (s, 9H), 1.03 (d, J = 6.70 Hz, 3H), 1.24-1.25 (m, 1H), 1.38 (dt, J = 10.33, 3.41 Hz, 2H), 1.44-1.60 (m, 9H), 2.02-2.13 (m, 3H), 2.60-2.62 (m, 2H), 4.07-4,09 (m, 1H), 5.91 (s, 1H), 7.03 (s, 1H), 7.23 (dd, J = 7.98, 1.97 Hz, 1H), 7.29 (d, J = 7.86 Hz, 1H), 7.33 (d, J = 1.85 Hz, 1H) | 475 | 473 |

TABLE 3-continued

| Example | ¹H-NMR | MS M + H or M—+ H | MS M − H or M—Na − H |
|---|---|---|---|
| 67 | (400 MHz, DMSO-D6) 0.70 (d, J = 6.94 Hz, 3H), 0.94 (s, 9H), 1.03 (d, J = 6.70 Hz, 3H), 1.24-1.25 (m, 1H), 1.38 (dt, J = 10.33, 3.41 Hz, 2H), 1.44-1.60 (m, 9H), 2.02-2.13 (m, 3H), 2.60-2.62 (m, 2H), 4.07-4.09 (m, 1H), 5.91 (s, 1H), 7.03 (s, 1H), 7.23 (dd, J = 7.98, 1.97 Hz, 1H), 7.29 (d, J = 7.86 Hz, 1H), 7.33 (d, J = 1.85 Hz, 1H) | 475 | 473 |
| 68 | (400 MHz, CDCl3) 0.93 (t, J = 7.25 Hz, 3H), 0.98 (s, 9H), 1.42-1.47 (m, 2H), 1.59-1.68 (m, 1H), 1.69 (s, 3H), 1.91-1.84 (m, 1H), 1.99-1.92 (m, 2H), 2.40 (t, J = 7.05 Hz, 2H), 2.69-2.64 (m, 2H), 3.58 (t, J = 6.45 Hz, 2H), 5.06 (s, 1H), 5.71 (t, J = 1.61 Hz, 1H), 7.18 (d, J = 8.06 Hz, 1H), 7.22 (dd, J = 7.66, 2.01 Hz, 1H), 7.35 (d, J = 1.61 Hz, 1H) | 421 | 419 |
| 69 | (400 MHz, CDCl3) 0.93 (t, J = 7.25 Hz, 3H), 0.98 (s, 9H), 1.42-1.47 (m, 2H), 1.59-1.68 (m, 1H), 1.69 (s, 3H), 1.91-1.84 (m, 1H), 1.99-1.92 (m, 2H), 2.40 (t, J = 7.05 Hz, 2H), 2.69-2.64 (m, 2H), 3.58 (t, J = 6.45 Hz, 2H), 5.06 (s, 1H), 5.71 (t, J = 1.61 Hz, 1H), 7.18 (d, J = 8.06 Hz, 1H), 7.22 (dd, J = 7.66, 2.01 Hz, 1H), 7.35 (d, J = 1.61 Hz, 1H) | 421 | 419 |
| 70 | (400 MHz, CDCl3) δ: 0.72 (d, J = 6.85 Hz, 3H), 0.91 (q, J = 8.19 Hz, 3H), 1.06 (d, J = 6.85 Hz, 3H), 1.30-1.40 (m, 2H), 1.57 (dt, J = 16.12, 7.05 Hz, 2H), 1.72 (d, J = 9.67 Hz, 3H), 1.93 (td, J = 13.00, 6.45 Hz, 3H), 2.39 (t, J = 6.85 Hz, 2H), 2.61 (t, J = 7.66 Hz, 2H), 3.49-3.60 (m, 2H), 5.33 (s, 1H), 5.81 (s, 1H), 7.11 (dq, J = 24.48, 6.18 Hz, 3H). | 391 | 389 |
| 71 | (400 MHz, DMSO-D6) 0.61-0.72 (m, 5H), 0.93 (s, 9H), 0.98-1.04 (m, 5H), 1.32-1.40 (m, 2H), 1.59 (s, 3H), 1.61-1.67 (m, 2H), 1.87-1.98 (m, 1H), 2.57-2.65 (m, 2H), 3.44-3.58 (m, 2H), 5.93 (s, 1H), 6.95 (s, 1H), 7.22-7.31 (m, 2H), 7.31-7.39 (m, 1H), 12.09 (brs, 1H) | 461 | 459 |
| 72 | (400 MHz, DMSO-D6) 0.61-0.72 (m, 5H), 0.93 (s, 9H), 0.98-1.04 (m, 5H), 1.32-1.40 (m, 2H), 1.59 (s, 3H), 1.61-1.67 (m, 2H), 1.87-1.98 (m, 1H), 2.57-2.65 (m, 2H), 3.44-3.58 (m, 2H), 5.93 (s, 1H), 6.95 (s, 1H), 7.22-7.31 (m, 2H), 7.31-7.39 (m, 1H), 12.09 (brs, 1H) | 461 | 459 |
| 73 | (400 MHz, CDCl3) 0.68-0.75 (m, 3H), 0.95 (s, 9H), 0.99-1.07 (m, 3H), 1.13-1.28 (m, 3H), 1.37-1.48 (m, 2H), 1.65 (s, 3H), 1.72-1.98 (m, 4H), 2.19-2.36 (m, 1H), 2.58-2.68 (m, 2H), 4.56 (brs, 1H), 5.82 (s, 1H), 7.08-7.22 (m, 2H), 7.32-7.39 (m, 1H) | 449 | 447 |
| 74 | (400 MHz, DMSO-D6) 0.70-0.72 (m, 3H), 0.94 (s, 9H), 0.98 (s, 6H), 1.01-1.09 (m, 3H), 1.26-1.45 (m, 6H), 1.59 (s, 3H), 1.91-2.03 (m, 1.H), 2.59-2.66 (m, 2H), 3.14-3.23 (m, 1H), 3.36-3.47 (m, 1H), 6.01 (s, 1H), 6.92 (s, 1H), 7.23-7.32 (m, 2H), 7.33-7.39 (m, 1H) | 477 | 475 |
| 75 | (400 MHz, DMSO-D6) 0.70-0.72 (m, 3H), 0.94 (s, 9H), 0.98 (s, 6H), 1.01-1.09 (m, 3H), 1.26-1.45 (m, 6H), 1.59 (s, 3H), 1.91-2.03 (m, 1H), 2.59-2.66 (m, 2H), 3.14-3.23 (m, 1H), 3.36-3.47 (m, 1H), 6.01 (s, 1H), 6.92 (s, 1H), 7.23-7.32 (m, 2H), 7.33-7.39 (m, 1H) | 477 | 475 |
| 76 | (400 MHz, DMSO-D6) 0.63-0.72 (m, 3H), 0.93 (s, 9H), 0.98-1.05 (m, 2H), 1.30-1.43 (m, 2H), 1.57 (s, 3H), 1.89-1.99 (m, 1H), 2.06 (brs, 6H), 2.57-2.68 (m, 2H), 5.93 (s, 1H), 6.94 (brs, 1H), 7.19-7.35 (m, 3H) | 459 | 457 |
| 77 | (400 MHz, DMSO-D6) 0.63-0.72 (m, 3H), 0.93 (s, 9H), 0.98-1.05 (m, 2H), 1.30-1.43 (m, 2H), 1.57 (s, 3H), 1.89-1.99 (m, 1H), 2.06 (brs, 6H), 2.57-2.68 (m, 2H), 5.93 (s, 1H), 6.94 (brs, 1H), 7.19-7.35 (m, 3H) | 459 | 457 |
| 78 | (400 MHz, DMSO-D6) 0.74 (d, J = 6.94 Hz, 3H), 0.94 (s, 9H), 1.06 (d, J = 6.94 Hz, 3H), 1.34-1.43 (m, 4H), 1.54-1.65 (m, 7H), 1.95-2.05 (m, 3H), 2,20-2.27 (m, 1H), 2.59-2.64 (m, 2H), 4.03-4.09 (m, 1H), 6.13 (s, 1H), 7.01 (s, 1H), 7.24 (dd, J = 8.09, 1.85 Hz, 1H), 7.29 (d, J = 8.09 Hz, 1H), 7.33 (d, J = 1.85 Hz, 1H), 12.05 (s, 1H) | 475 | 473 |

TABLE 3-continued

| Example | ¹H-NMR | MS M + H or M—+ H | MS M − H or M—Na − H |
|---|---|---|---|
| 79 | (400 MHz, DMSO-D6) 0.74 (d, J = 6.94 Hz, 3H), 0.94 (s, 9H), 1.06 (d, J = 6.94 Hz, 3H), 1.34-1.43 (m, 4H), 1.54-1.65 (m, 7H), 1.95-2.05 (m, 3H), 2.20-2.27 (m, 1H), 2.59-2.64 (m, 2H), 4.03-4.09 (m, 1H), 6.13 (s, 1H), 7.01 (s, 1H), 7.24 (dd, J = 8.09, 1.85 Hz, 1H), 7.29 (d, J = 8.09 Hz, 1H), 7.33 (d, J = 1.85 Hz, 1H), 12.05 (s, 1H) | 475 | 473 |
| 80 | (400 MHz, DMSO-D6) 0.72 (d, J = 6.82 Hz, 3H), 0.94 (s, 9H), 1.04 (d, J = 6.82 Hz, 3H), 1.37 (dt, J = 8.71, 3.67 Hz, 2H), 1.60 (s, 3H), 1.88-2.01 (m, 3H), 2.12-2.15 (m, 2H), 2.62 (dt, J = 10.17, 3.67 Hz, 2H), 2.97-3.00 (m, 1H), 3.26-3.28 (m, 1H), 3.62 (dd, J = 13.64, 7.40 Hz, 1H), 6.11 (s, 1H), 7.01 (bs, 1H), 7.24 (dd, J = 8.09, 1.85 Hz, 1H), 7.28 (d, J = 8.09 Hz, 1H), 7.32 (d, J = 1.85 Hz, 1H), 12.06 (bs, 1H) | 461 | 459 |
| 81 | (400 MHz, CDCl3) 0.98 (s, 9H), 1.42-1.46 (m, 2H), 1.64 (s, 3H), 1.93-2.00 (m, 2H), 2.40 (t J = 7.25 Hz, 2H), 2.65-2.69 (m, 2H), 2.80 (s, 3H), 2.88-2.96 (m, 1H), 3.29 (t, J = 7.25 Hz, 1H), 3.45 (t, J = 7.66 Hz, 1H), 3.50-3.57 (m, 1H), 3.63-3.70 (m, 1H), 3.84 (d, J = 7.66 Hz, 2H), 5.57 (s, 1H), 6.03 (s, 1H), 7.20 (s, 2H), 7.33 (s, 1H) | 526 | 524 |
| 82 | (400 MHz, DMSO-D6) 0.52-0.57 (m, 3H), 0.89-0.92 (m, 3H), 0.94 (s, 9H), 1.31-1.42 (m, 2H), 1.55 (s, 3H), 1.78-1.89 (m, 1H), 2.58-2.64 (m, 2H), 3.05-3.18 (m, 2H), 3.50-3.59 (m, 1H), 3.61-3.70 (m, 1H), 5.77 (s, 1H), 6.94 (s, 1H), 7.15-7.24 (m, 2H), 7.25-7.34 (m, 3H), 7.36-7.45 (m, 1H), 7.77-7.84 (m, 1H), 12.91 (brs, 1H) | 497 | 495 |
| 83 | (400 MHz, DMSO-D6) 0.52-0.57 (m, 3H), 0.89-0.92 (m, 3H), 0.94 (s, 9H), 1.31-1.42 (m, 2H), 1.55 (s, 3H), 1.78-1.89 (m, 1H), 2.58-2.64 (m, 2H), 3.05-3.18 (m, 2H), 3.50-3.59 (m, 1H), 3.61-3.70 (m, 1H), 5.77 (s, 1H), 6.94 (s, 1H), 7.15-7.24 (m, 2H), 7.25-7.34 (m, 3H), 7.36-7.45 (m, 1H), 7.77-7.84 (m, 1H), 12.91 (brs, 1H) | 497 | 495 |
| 84 | (400 MHz, DMSO-D6) 0.66 (d, J = 6.94 Hz, 3H), 0.88 (t, J = 7.40 Hz, 3H), 1.03 (d, J = 6.94 Hz, 3H), 1.28 (qt, J = 7.40, 7.20 Hz, 2H), 1.53 (tt, J = 7.63, 7.20 Hz, 2H), 1.61 (s, 3H), 1.70 (tt, J = 7.40, 6.80 Hz, 2H), 1.94 (sep, J = 6.94 Hz, 1H), 2.18 (t, J = 7.40 Hz, 2H), 2.54 (t, J = 7.63 Hz, 2H), 3.31 (dt, J = 13.60, 6.80 Hz, 1H), 3.43 (dt, J = 13.60, 6.80 Hz, 1H), 5.99 (s, 1H), 6.87 (s, 1H), 7.14 (d, J = 8.32 Hz, 2H), 7.29 (d, J = 8.32 Hz, 2H), 12.07 (brs, 1H) | 373 | 371 |
| 85 | (400 MHz, CDCl3) δ: 0.61 (d, J = 6.85 Hz, 3H), 0.92 (t, J = 7.25 Hz, 3H), 1.01 (d, J = 6.85 Hz, 3H), 1.36 (d, J = 7.25 Hz, 2H), 1.69 (s, 3H), 1.96 (d, J = 6.45 Hz, 3H), 2.42 (t, J = 6.65 Hz, 2H), 2.66 (s, 2H), 3.58 (d, J = 6.45 Hz, 2H), 4.82 (s, 1H), 5.08 (d, J = 7.25 Hz, 2H), 5.74 (s, 1H), 6.92 (d, J = 6.45 Hz, 2H), 7.11 (d, J = 8.46 Hz, 1H), 7.38 (dt, J = 13.70, 5.84 Hz, 5H). | 479 | 477 |
| 86 | (400 MHz, DMSO-D6) 0.66-0.71 (m, 3H), 0.94 (s, 9H), 1.00-1.07 (m, 3H), 1.34-1.43 (m, 2H), 1.60 (s, 3H), 1.86-1.99 (m, 1H), 2.38-2.46 (m, 2H), 2.59-2.66 (m, 2H), 3.46-3.56 (m, 3H), 3.56-3.66 (m, 1H), 6.11 (s, 1H), 7.01 (s, 1H), 7.23-7.31 (m, 2H), 7.32-7.35 (m, 1H), 12.27 (brs, 1H) | 421 | 419 |
| 87 | (400 MHz, DMSO-D6) 0.66-0.71 (m, 3H), 0.94 (s, 9H), 1.00-1.07 (m, 3H), 1.34-1.43 (m, 2H), 1.60 (s, 3H), 1.86-1.99 (m, 1H), 2.38-2.46 (m, 2H), 2.59-2.66 (m, 2H), 3.46-3.56 (m, 1H), 3.56-3.66 (m, 1H), 6.11 (s, 1H), 7.01 (s, 1H), 7.23-7.31 (m, 2H), 7.32-7.35 (m, 1H), 12.27 (brs, 1H) | 421 | 419 |
| 88 | (400 MHz, DMSO-D6) 0.65-0.73 (m, 2H), 0.95 (s, 9H), 1.00-1.07 (m, 2H), 1.34-1.42 (m, 2H), 1.54-1.68 (m, 4H), 1.84-2.01 (m, 2H), 2.59-2.66 (m, 2H), 3.40-3.52 (m, 2H), 3.77-3.88 (m, 1H), 6.04 (s, 1H), 7.01 (s, 1H), 7.23-7.32 (m, 2H), 7.32-7.37 (m, 1H) | 451 | 449 |
| 89 | (400 MHz, DMSO-D6) 0.65-0.73 (m, 2H), 0.95 (s, 9H), 1.00-1.07 (m, 2H), 1.34-1.42 (m, 2H), 1.54-1.68 (m, 4H), 1.84-2.01 (m, 2H), 2.59-2.66 (m, 2H), 3.40-3.52 (m, 2H), 3.77-3.88 (m, 1H), 6.04 (s, 1H), 7.01 (s, 1H), 7.23-7.32 (m, 2H), 7.32-7.37 (m, 1H) | 451 | 449 |

TABLE 3-continued

| Example | ¹H-NMR | MS M + H or M—+ H | M − H or M—Na − H |
|---|---|---|---|
| 90 | (400 MHz, CDCl3) 0.80 (d, J = 7.25 Hz, 3H), 0.97 (s, 9H), 1.14 (d, J = 7.25 Hz, 3H), 1.42-1.47 (m, 2H), 1.65 (s, 3H), 1.84-1.91 (m, 2H), 2.04-1.96 (m, 1H), 2.00 (s, 3H), 2.36 (t, J = 6.85 Hz, 2H), 2.68-2.64 (m, 2H), 3.78-3.61 (m, 2H), 5.52 (s, 1H), 7.16 (d, J = 8.06 Hz, 1H), 7.24 (dd, J = 8.06, 1.61 Hz, 1H), 7.37 (d, J = 1.61 Hz, 1H) | 449 | 447 |
| 91 | (400 MHz, CDCl3) 0.93-1.02 (m, 2H), 0.98 (s, 9H), 1.29-1.39 (m, 1H), 1.42-1.47 (m, 2H), 1.51-1.76 (m, 2H), 1.71 (s, 3H), 1.90-1.96 (m, 2H), 2.37 (t, J = 7.25 Hz, 2H), 2.64-2.69 (m, 2H), 3.08 (dd, J = 12.09, 11.69 Hz, 1H), 3.29 (dd, J = 11.69, 12.49 Hz, 1H), 3.48-3.61 (m, 2H), 3.80 (dd, J = 11.69, 3.63 Hz, 1H), 3.95 (dd, J = 11.28, 2.82 Hz, 1H), 5.65 (s, 1H), 5.86 (s, 1H), 7.18 (d, J = 8.06 Hz, 1H), 7.24 (dd, J = 8.06, 2.01 Hz, 1H), 7.38 (d, J = 1.61 Hz, 1H) | 477 | 475 |
| 92 | (400 MHz, CDCl3) 0.93-1.02 (m, 2H), 0.98 (s, 9H), 1.29-1.39 (m, 1H), 1.42-1.47 (m, 2H), 1.51-1.76 (m, 2H), 1.71 (s, 3H), 1.90-1.96 (m, 2H), 2.37 (t, J = 7.25 Hz, 2H), 2.64-2.69 (m, 2H), 3.08 (dd, J = 12.09, 11.69 Hz, 1H), 3.29 (dd, J = 11.69, 12.49 Hz, 1H), 3.48-3.61 (m, 2H), 3.80 (dd, J = 11.69, 3.63 Hz, 1H), 3.95 (dd, J = 11.28, 2.82 Hz, 1H), 5.65 (s, 1H), 5.86 (s, 1H), 7.18 (d, J = 8.06 Hz, 1H), 7.24 (dd, J = 8.06, 2.01 Hz, 1H), 7.38 (d, J = 1.61 Hz, 1H) | 477 | 475 |
| 93 | (400 MHz, DMSO-D6) 0.60-0.68 (m, 3H), 0.93 (s, 9H), 0.98-1.02 (m, 3H), 1.31-1.40 (m, 2H), 1.63 (s, 3H), 1.85-1.96 (m, 1H), 2.57-2.66 (m, 2H), 3.91-4.02 (m, 1H), 4.05-4.15 (m, 1H), 6.06 (s, 1H), 7.05 (s, 1H), 7.22-7.29 (m, 1H), 7.31-7.38 (m, 1H), 7.43-7.48 (m, 1H), 12.41-12.73 (m, 1H) | 407 | 405 |
| 94 | (400 MHz, DMSO-D6) 0.60-0.68 (m, 3H), 0.93 (s, 9H), 0.98-1.02 (m, 3H), 1.31-1.40 (m, 2H), 1.63 (s, 3H), 1.85-1.96 (m, 1H), 2.57-2.66 (m, 2H), 3.91-4.02 (m, 1H), 4.05-4.15 (m, 1H), 6.06 (s, 1H), 7.05 (s, 1H), 7.22-7.29 (m, 1H), 7.31-7.38 (m, 1H), 7.43-7.48 (m, 1H), 12.41-12.73 (m, 1H) | 407 | 405 |
| 95 | (400 MHz, DMSO-D6) 0.93 (s, 9H), 1.21-1.23 (m, 1H), 1.34-1.38 (m, 2H), 1.54 (s, 3H), 2.21-2.32 (m, 3H), 2.52-2.63 (m, 7H), 2.64-2.66 (m, 1H), 4.92-4.96 (m, 1H), 6.38 (s, 1H), 7.20-7.22 (m, 2H), 7.29 (d, J = 8.09 Hz, 1H), 7.31 (d, J = 1.85 Hz, 1H) | 495 | 493 |
| 96 | (400 MHz, DMSO-D6) 0.93 (s, 9H), 1.21-1.23 (m, 1H), 1.34-1.38 (m, 2H), 1.54 (s, 3H), 2.23-2.32 (m, 3H), 2.51-2.66 (m, 7H), 2.84-2.90 (m, 1H), 4.90-4.98 (m, 1H), 6.38 (s, 1H), 7.21 (dd, J = 7.98, 1.97 Hz, 1H), 7.23 (s, 1H), 7.29 (d, J = 8.09 Hz, 1H), 7.31 (d, J = 1.85 Hz, 1H) | 495 | 493 |
| 97 | (400 MHz, DMSO-D6) 0.65-0.69 (m, 3H), 0.86-0.91 (m, 2H), 0.93 (s, 9H), 0.99-1.06 (m, 5H), 1.32-1.40 (m, 2H), 1.59 (s, 3H), 1.91-2.01 (m, 1H), 2.57-2.64 (m, 2H), 3.65-3.74 (m, 2H), 6.26 (s, 1H), 7.02 (s, 1H), 7.21-7.30 (m, 2H), 7.32-7.36 (m, 1H), 12.38 (brs, 1H) | 447 | 445 |
| 98 | (400 MHz, DMSO-D6) 0.65-0.69 (m, 3H), 0.86-0.91 (m, 2H), 0.93 (s, 9H), 0.99-1.06 (m, 5H), 1.32-1.40 (m, 2H), 1.59 (s, 3H), 1.91-2.01 (m, 1H), 2.57-2.64 (m, 2H), 3.65-3.74 (m, 2H), 6.26 (s, 1H), 7.02 (s, 1H), 7.21-7.30 (m, 2H), 7.32-7.36 (m, 1H), 12.38 (brs, 1H) | 447 | 445 |
| 99 | (400 MHz, CDCl3) 0.93-1.05 (m, 2H), 0.98 (s, 9H), 1.35-1.47 (m, 3H), 1.56-1.77 (m, 2H), 1.70 (s, 3H), 2.56-2.69 (m, 6H), 3.00-3.05 (m, 1H), 3.10 (t, J = 11.69 Hz, 1H), 3.30 (t, J = 11.28 Hz, 1H), 3.81 (d, J = 12.09 Hz, 1H), 3.96 (d, J = 11.28 Hz, 1H), 4.99-5.08 (m, 1H), 5.61 (s, 1H), 6.06 (s, 1H), 7.18 (d, J = 8.06 Hz, 1H), 7.24 (d, J = 10.07 Hz, 1H), 7.37 (s, 1H) | 489 | 487 |
| 100 | (400 MHz, CDCl3) 0.93-1.05 (m, 2H), 0.98 (s, 9H), 1.35-1.47 (m, 3H), 1.56-1.77 (m, 2H), 1.70 (s, 3H), 2.56-2.69 (m, 6H), 3.00-3.05 (m, 1H), 3.10 (t, J = 11.69 Hz, 1H), 3.30 (t, J = 11.28 Hz, 1H), 3.81 (d, J = 12.09 Hz, 1H), 3.96 (d, J = 11.28 Hz, 1H), 4.99-5.08 (m, 1H), 5.61 (s, 1H), 6.06 (s, 1H), 7.18 (d, J = 8.06 Hz, 1H), 7.24 (d, J = 10.07 Hz, 1H), 7.37 (s, 1H) | 489 | 487 |
| 101 | (400 MHz, CDCl3) 0.97 (s, 9H), 1.01 (s, 9H), 1.41-1.45 (m, 2H), 2.62-2.69 (m, 6H), 3.06-3.13 (m, 1H), | 447 | 445 |

TABLE 3-continued

| | | MS | |
|---|---|---|---|
| Example | ¹H-NMR | M + H or M—+ H | M − H or M—Na − H |
| | 4.77 (d, J = 2.90 Hz, 1H), 4.91-5.00 (m, 1H), 5.31-5.36 (m, 1H), 6.27 (s, 1H), 7.02 (dd, J = 7.85, 1.81 Hz, 1H), 7.15 (d, J = 7.73 Hz, 1H), 7.17 (d, J = 1.69 Hz, 1H) | | |
| 102 | (400 MHz, CDCl3) 0.97 (s, 9H), 1.01 (s, 9H), 1.41-1.45 (m, 2H), 2.62-2.68 (m, 6H), 3.05-3.12 (m, 1H), 4.77 (d, J = 3.14 Hz, 1H), 4.91-5.00 (m, 1H), 5.39 (d, J = 2.41 Hz, 1H), 6.27 (s, 1H), 7.02 (dd, J = 7.73, 1.93 Hz, 1H), 7.15 (d, J = 7.97 Hz, 1H), 7.17 (d, J = 1.93 Hz, 1H) | 447 | 445 |
| 103 | (400 MHz, DMSO-D6) 0.70-0.77 (m, 3H), 0.93 (s, 9H), 1.03-1.10 (m, 3H), 1.33-1.42 (m, 2H), 1.61 (s, 3H), 1.85-1.95 (m, 1H), 2.17-2.29 (m, 2H), 2.36-2.47 (m, 2H), 2.55-2.63 (m, 2H), 2.81-2.89 (m, 1H), 4.88-5.01 (m, 1H), 6.26 (s, 1H), 6.98 (s, 1H), 7.11-7.20 (m, 1H), 7.27-7.33 (m, 1H), 12.18 (brs, 1H) | 465 | 463 |
| 104 | (400 MHz, DMSO-D6) 0.70-0.77 (m, 3H), 0.93 (s, 9H), 1.03-1.10 (m, 3H), 1.33-1.42 (m, 2H), 1.61 (s, 3H), 1.85-1.95 (m, 1H), 2.17-2.29 (m, 2H), 2.36-2.47 (m, 2H), 2.55-2.63 (m, 2H), 2.81-2.89 (m, 1H), 4.88-5.01 (m, 1H), 6.26 (s, 1H), 6.98 (s, 1H), 7.11-7.20 (m, 1H), 7.27-7.33 (m, 1H), 12.18 (brs, 1H) | 465 | 463 |
| 105 | (400 MHz, DMSO-D6) 0.68 (d, J = 6.45 Hz, 3H), 1.03 (d, J = 6.45 Hz, 3H), 1.61 (s, 3H), 1.66-1.74 (m, 2H), 1.93 (qq, J = 6.45, 6.45 Hz, 1H), 2.18 (t, J = 7.45 Hz, 2H), 2.71-2.83 (m, 2H), 3.27-3.34 (m, 1H), 3.39-3.46 (m, 1H), 4.18 (t, J = 5.84 Hz, 2H), 6.00 (s, 1H), 6.87 (s, 1H), 6.91 (d, J = 8.87 Hz, 2H), 7.31 (d, J = 8.87 Hz, 2H) | 429 | 427 |
| 106 | (400 MHz, DMSO-D6) 0.63 (d, J = 6.85 Hz, 3H), 0.84 (d, J = 6.45 Hz, 6H), 1.02 (d, J = 6.85 Hz, 3H), 1.62 (s, 3H), 1.66-1.74 (m, 2H), 1.80 (tsep, J = 6.45, 7.25 Hz, 1H), 1.94 (qq, J = 6.85, 6.85 Hz, 1H), 2.18 (t, J = 7.66 Hz, 2H), 2.42 (d, J = 7.25 Hz, 2H), 3.28-3.34 (m, 1H), 3.40-3.47 (m, 1H), 5.99 (s, 1H), 6.89 (s, 1H), 7.10 (d, J = 8.46 Hz, 2H), 7.29 (d, J = 8.46 Hz, 2H), 12.07 (brs, 1H) | 373 | 371 |
| 107 | (400 Mz, DMSO-D6) 0.76 (d, J = 6.76 Hz, 1H), 0.96 (d, J = 12.56 Hz, 9H), 1.09 (d, J = 6.76 Hz, 1H), 1.35-1.40 (m, 2H), 1.60 (s, 3H), 1.86-1.89 (m, 2H), 2.00-2.03 (m, 1H), 2.34-2.43 (m, 5H), 2.61-2.65 (m, 2H), 4.87-4.89 (m, 1H), 6.30 (s, 1H), 7.05 (s, 1H), 7.22-7.24 (m, 1H), 7.29-7.31 (m, 2H). | 461 | 459 |
| 108 | (400 Mz, DMSO-D6) 0.76 (d, J = 6.76 Hz, 1H), 0.96 (d, J = 12.56 Hz, 9H), 1.09 (d, J = 6.76 Hz, 1H), 1.35-1.40 (m, 2H), 1.60 (s, 3H), 1.86-1.89 (m, 2H), 2.00-2.03 (m, 1H), 2.34-2.43 (m, 5H), 2.61-2.65 (m, 2H), 4.87-4.89 (m, 1H), 6.30 (s, 1H), 7.05 (s, 1H), 7.22-7.24 (m, 1H), 7.29-7.31 (m, 2H). | 461 | 459 |
| 109 | (400 MHz, DMSO-D6) 0.70 (d, J = 6.94 Hz, 3H), 1.04 (d, J = 6.70 Hz, 3H), 1.57-1.84 (m, 8H), 1.61 (s, 3H), 1.94-2.04 (m, 3H), 2.17 (t, J = 7.51 Hz, 2H), 2.20-2.28 (m, 1H), 2.56 (dd, J = 8.79, 6.94 Hz, 2H), 3.27-3.34 (m, 1H), 3.42-3.49 (m, 1H), 6.05 (s, 1H), 6.99 (s, 1H), 7.27 (s, 2H), 7.35 (s, 1H), 12.04 (s, 1H) | 433 | 431 |
| 110 | (400 MHz, DMSO-D6) 0.71 (d, J = 6.94 Hz, 3H), 1.04 (d, J = 6.70 Hz, 3H), 1.57-1.84 (m, 8H), 3.61 (s, 3H), 1.94-2.05 (m, 3H), 2.37 (t, J = 7.51 Hz, 2H), 2.20-2.26 (m, 1H), 2.56 (dd, J = 8.67, 6.82 Hz, 2H), 3.27-3.34 (m, 1H), 3.42-3.49 (m, 1H), 6.05 (s, 1H), 7.00 (s, 1H), 7.27 (s, 2H), 7.35 (s, 1H), 12.06 (s, 1H) | 433 | 431 |
| 111 | (400 MHz, DMSO-D6) 0.70-0.78 (m, 3H), 0.93 (s, 9H), 1.02-1.09 (m, 3H), 1.30-1.42 (m, 5H), 1.60 (s, 3H), 1.96-2.12 (m, 3H), 2.50-2.54 (m, 2H), 2.58-2.67 (m, 2H), 4.78-4.95 (m, 1H), 6.30 (s, 1H), 7.11 (s, 1H), 7.18-7.35 (m, 3H), 12.32 (brs, 1H) | 461 | 459 |
| 112 | (400 MHz, DMSO-D6) 0.70-0.78 (m, 3H), 0.93 (s, 9H), 1.02-1.09 (m, 3H), 1.30-1.42 (m, 5H), 1.60 (s, 3H), 1.96-2.12 (m, 3H), 2.50-2.54 (m, 2H), 2.58-2.67 (m, 2H), 4.78-4.95 (m, 1H), 6.30 (s, 1H), 7.11 (s, 1H), 7.18-7.35 (m, 3H), 12.32 (brs, 1H) | 461 | 459 |
| 113 | (400 MHz, DMSO-D6) 0.64 (d, J = 6.70 Hz, 3H), 1.01 (d, J = 6.70 Hz, 3H), 1.09 (s, 3H), 1.10 (s, 3H), 1.60 (s, 3H), 1.89 (sep, J = 6.70 Hz, 1H), 2.45 (t, J = 6.94 Hz, 2H), 2.62-2.67 (m, 4H), 3.52 (dt, J = 14.00, 6.94 Hz, 1H), 3.62 (dt, J = 14.00, 6.94 Hz, 1H), 6.03 (s, 1H), 6.86 (s, 1H), 7.09 (d, J = 7.86 Hz, 1H), 7.12 (d, J = 7.86 Hz, 1H), 7.19 (s, 1H), 12.24 (s, 1H) | 371 | 369 |

TABLE 3-continued

| Example | ¹H-NMR | MS M + H or M—+ H | MS M − H or M—Na − H |
|---|---|---|---|
| 114 | (400 MHz, DMSO-D6) 0.69 (d, J = 6.85 Hz, 3H), 1.04 (d, J = 6.85 Hz, 3H), 1.31 (t, J = 7.25 Hz, 3H), 1.64 (s, 3H), 1.96 (qq, J = 6.85, 6.85 Hz, 1H), 2.45 (dd, J = 6.85, 6.85 Hz, 2H), 3.51 (dt, J = 13.50, 6.85 Hz, 1H), 3.65 (dt, J = 13.50, 6.85 Hz, 1H), 4.32 (q, J = 7.25 Hz, 2H), 6.15 (s, 1H), 7.16 (s, 1H), 7.46 (dd, J = 8.06, 2.01 Hz, 1H), 7.50 (d, J = 2.01 Hz, 1H), 7.77 (d, J = 8.06 Hz, 1H) | 409 | 407 |
| 115 | (400 MHz, DMSO-D6) 0.71 (d, J = 6.76 Hz, 3H), 0.98 (s, 6H), 1.03 (d, J = 6.76 Hz, 3H), 1.45 (t, J = 6.52 Hz, 2H), 1.61 (s, 3H), 1.92-1.99 (m, 3H), 2.21-2.26 (m, 2H), 2.45 (t, J = 7.00 Hz, 2H), 3.49-3.56 (m, 1H), 3.58-3.65 (m, 1H), 5.54-5.56 (m, 1H), 6.12 (s, 1H), 7.04 (s, 1H), 7.19 (d, J = 7.97 Hz, 1H), 7.29 (dd, J = 7.97, 1.93 Hz, 1H), 7.36 (d, J = 1.93 Hz, 1H), 12.25 (brs, 1H) | 445 | 443 |
| 116 | (400 MHz, DMSO-D6) 0.71 (d, J = 7.00 Hz, 3H), 0.98 (s, 6H), 1.03 (d, J = 6.76 Hz, 3H), 1.46 (t, J = 6.52 Hz, 2H), 1.61 (s, 3H), 1.92-1.99 (m, 3H), 2.22-2.26 (m, 2H), 2.45 (t, J = 7.00 Hz, 2H), 3.49-3.56 (m, 1H), 3.59-3.66 (m, 1H), 5.54-5.56 (m, 1H), 6.13 (s, 1H), 7.04 (s, 1H), 7.19 (d, J = 7.97 Hz, 1H), 7.29 (dd, J = 8.09, 1.81 Hz, 1H), 7.36 (d, J = 1.93 Hz, 1H), 12.26 (brs, 1H) | 445 | 443 |
| 117 | (400 MHz, DMSO-D6) 0.69 (d, J = 6.76 Hz, 3H), 0.94 (s, 3H), 0.97 (s, 3H), 1.03 (d, J = 7.00 Hz, 3H), 1.29-1.37 (m, 2H), 1.42-1.49 (m, 2H), 1.55-1.60 (m, 7H), 1.90-1.97 (m, 1H), 2.45 (t, J = 7.00 Hz, 3H), 2.76-2.84 (m, 1H), 3.48-3.55 (m, 1H), 3.58-3.65 (m, 1H), 6.11 (s, 1H), 7.02 (s, 1H), 7.30 (dd, J = 7.97, 1.93 Hz, 1H), 7.34 (d, J = 1.93 Hz, 1H), 7.39 (d, J = 8.21 Hz, 1H), 12.26 (brs, 1H) | 447 | 445 |
| 118 | (400 MHz, DMSO-D6) 0.69 (d, J = 7.00 Hz, 3H), 0.94 (s, 3H), 0.97 (s, 3H), 1.03 (d, J = 5.80 Hz, 3H), 1.29-1.37 (m, 2H), 1.45-1.48 (m, 2H), 1.55-1.58 (m, 4H), 1.60 (s, 3H), 1.90-1.97 (m, 1H), 2.45 (t, J = 7.00 Hz, 2H), 2.76-2.84 (m, 1H), 3.48-3.55 (m, 1H), 3.58-3.65 (m, 1H), 6.11 (s, 1H), 7.02 (s, 1H), 7.30 (dd, J = 8.09, 1.81 Hz, 1H), 7.34 (d, J = 1.93 Hz, 1H), 7.39 (d, J = 8.21 Hz, 1H), 12.26 (brs, 1H) | 447 | 445 |
| 119 | (400 MHz, DMSO-D6) 0.68 (d, J = 6.94 Hz, 3H), 1.03 (d, J = 6.70 Hz, 3H), 1.07-1.19 (m, 2H), 1.42-1.60 (m, 6H), 1.61 (s, 3H), 1.71-1.81 (m, 3H), 1.93 (t, J = 6.70 Hz, 1H), 2.45 (t, J = 6.94 Hz, 2H), 2.65-2.69 (m, 2H), 3.54 (dd, J = 13.76, 6.82 Hz, 1H), 3.62 (dd, J = 13.76, 6.82 Hz, 1H), 6.11 (s, 1H), 7.02 (s, 1H), 7.27 (dd, J = 7.98, 1.73 Hz, 1H), 7.30 (d, J = 8.09 Hz, 1H), 7.35 (d, J = 1.62 Hz, 1H), 12.30 (s, 1H) | 433 | 431 |
| 120 | (400 MHz, DMSO-D6) 0.68 (d, J = 6.94 Hz, 3H), 1.02 (d, J = 6.70 Hz, 3H), 1.06-1.19 (m, 2H), 1.46-1.58 (m, 6H), 1.60 (s, 3H), 1.70-1.80 (m, 3H), 1.89-1.96 (m, 1H), 2.44 (t J = 7.05 Hz, 2H), 2.64-2.68 (m, 2H), 3.48-3.55 (m, 1H), 3.58-3.65 (m, 1H), 6.10 (s, 1H), 7.01 (s, 1H), 7.26 (dd, J = 8.09, 1.85 Hz, 1H), 7.29 (d, J = 8.09 Hz, 1H), 7.34 (d, J = 1.62 Hz, 1H), 12.33 (s, 1H) | 433 | 431 |
| 121 | (400 MHz, DMSO-D6) 0.69 (d, J = 6.94 Hz, 3H), 1.03 (d, J = 6.94 Hz, 3H), 1.57-1.66 (m, 4H), 1.60 (s, 3H), 1.75-1.82 (m, 2H), 1.90-1.97 (m, 1H), 1.97-2.05 (m, 2H), 2.24 (t, J = 7.74 Hz, 1H), 2.30-2.36 (m, 2H), 2.56 (t, J = 7.86 Hz, 2H), 3.45-3.54 (m, 1H), 3.55-3.64 (m, 1H), 6.11 (s, 1H), 6.97 (s, 1H), 7.26 (d, J = 0.92 Hz, 2H), 7.33 (s, 1H), 12.44 (s, 1H) | 419 | 417 |
| 122 | (400 MHz, DMSO-D6) 0.69 (d, J = 6.94 Hz, 3H), 1.03 (d, J = 6.70 Hz, 3H), 1.57-1.66 (m, 4H), 1.60 (s, 3H), 1.79 (dt, J = 12.02, 5.20 Hz, 2H), 1.94 (dd, J = 12.72, 5.55 Hz, 1H), 1.98-2.02 (m, 2H), 2.24 (t, J = 7.74 Hz, 1H), 2.29-2.36 (m, 2H), 2.56 (dd, J = 12.95, 4.86 Hz, 2H), 3.45-3.54 (m, 1H), 3.55-3.64 (m, 1H), 6.11 (s, 1H), 6.96 (s, 1H), 7.26 (d, J = 0.92 Hz, 2H), 7.33 (s, 1H), 12.35 (s, 1H) | 419 | 417 |
| 123 | (400 MHz, DMSO-D6) 0.67 (d, J = 6.94 Hz, 3H), 0.84 (s, 9H), 1.02 (d, J = 6.70 Hz, 3H), 1.17-1.23 (m, 2H), 1.47-1.55 (m, 2H), 1.60 (s, 3H), 1.93 (t, J = 7.05 Hz, 1H), 2.35-2.44 (m, 2H), 2.63 (t, J = 7.74 Hz, 2H), 3.52 (dd, J = 14.10, 6.94 Hz, 1H), 3,60 (dd, J = 14.10, 6.94 Hz, 1H), 6.10 (s, 1H), 7.00 (s, 1H), 7.26 (dd, J = 7.60, 1.40 Hz, 1H), 7.29 (d, J = 7.60 Hz, 1H), 7.35 (d, J = 1.39 Hz, 1H), 12.40 (s, 1H) | 435 | 433 |

TABLE 3-continued

| Example | ¹H-NMR | MS M + H or M→+ H | MS M − H or M—Na − H |
|---|---|---|---|
| 124 | (400 MHz, DMSO-D6) 0.67 (d, J = 6.70 Hz, 3H), 0.84 (s, 9H), 1.02 (d, J = 6.94 Hz, 3H), 1.20 (dd, J = 11.10, 5.78 Hz, 2H), 1.47-1.55 (m, 2H), 1.60 (s, 3H), 1.92 (dd, J = 11.79, 4.86 Hz, 1H), 2.43 (t, J = 7.05 Hz, 2H), 2.63 (t, J = 7.63 Hz, 2H), 3.51 (dd, J = 13.87, 6.94 Hz, 1H), 3.61 (dd, J = 13.87, 6.94 Hz, 1H), 6.10 (s, 1H), 7.02 (s, 1H), 7.27 (dd, J = 8.09, 1.62 Hz, 1H), 7.29 (d, J = 8.09 Hz, 1H), 7.35 (d. J = 1.39 Hz, 1H), 12.39 (s, 1H) | 435 | 433 |
| 125 | (400 MHz, CDCl3) 0.67-0.73 (m, 3H), 1.00 (s, 9H), 1.02-1.06 (m, 3H), 1.69 (s, 3H), 1.75-1.81 (m, 2H), 1.82-1.91 (m, 1H), 2.61-2.68 (m, 2H), 3.70-3.84 (m, 2H), 4.04-4.11 (m, 2H), 5.45 (s, 1H), 5.85 (s, 1H), 6.83-6.91 (m, 1H), 7.27-7.30 (m, 1H), 7.41-7.43 (m, 1H) | 437 | 435 |
| 126 | (400 MHz, CDCl3) 0.68-0.74 (m, 3H), 1.01-1.06 (m, 3H), 1.08 (s, 9H), 1.69 (s, 3H), 1.82-1.90 (m, 1H), 2.63-2.71 (m, 2H), 3.64 (s, 2H), 3.71-3.82 (m, 2H), 5.24 (s, 1H), 5.86 (s, 1H), 6.81-6.87 (m, 1H), 7.22-7.28 (m, 1H), 7.39-7.44 (m, 1H) | 423 | 421 |
| 127 | (400 MHz, CDCl3) 0.65-0.73 (m, 3H), 1.00-1.06 (m, 3H), 1.68 (s, 3H), 1.80-1.90 (m, 1H), 2.59-2.69 (m, 2H), 3.47 (s, 3H), 3.72-3.78 (m, 2H), 3.78-3.83 (m, 2H), 4.13-4.20 (m, 2H), 5.32-5.52 (m, 1H), 5.84 (s, 1H), 6.87-6.92 (m, 1H), 7.26-7.30 (m, 1H), 7.40-7.44 (m, 1H) | 411 | 409 |
| 128 | (400 MHz, DMSO-D6) 0.67 (d, J = 6.85 Hz, 3H), 1.02 (d, J = 6.85 Hz, 3H), 1.61 (s, 3H), 1.72-1.80 (m, 2H), 1.93 (qq, J = 6.85, 6.85 Hz, 1H), 2.22-2.35 (m, 2H), 2.44 (dd, J = 6.85, 6.85 Hz, 2H), 2.76 (t, J = 7.86 Hz, 2H), 3.52 (dt, J = 13.50, 6.85 Hz, 1H), 3.62 (dt, J = 13.50, 6.85 Hz, 1H), 6.11 (s, 1H), 7.03 (s, 1H), 7.30 (dd, J = 8.06, 1.61 Hz, 1H), 7.33 (d, J = 8.06 Hz, 1H), 7.38 (d, J = 1.61 Hz, 1H) | 447 | 445 |
| 129 | (400 MHz, DMSO-D6) 0.67 (d, J = 6.85 Hz, 3H), 1.02 (d, J = 6.85 Hz, 3H), 1.61 (s, 3H), 1.72-1.80 (m, 2H), 1.93 (qq, J = 6.85, 6.85 Hz, 1H), 2.22-2.35 (m, 2H), 2.44 (dd, J = 6.85, 6.85 Hz, 2H), 2.76 (t, J = 7.86 Hz, 2H), 3.52 (dt, J = 13.50, 6.85 Hz, 1H), 3.62 (dt, J = 13.50, 6.85 Hz, 1H), 6.11 (s, 1H), 7.04 (s, 1H), 7.30 (dd, J = 8.06, 1.61 Hz, 1H), 7.33 (d, J = 8.06 Hz, 1H), 7.38 (d, J = 1.61 Hz, 1H) | 447 | 445 |
| 130 | (400 MHz, DMSO-D6) 0.73 (s, 3H), 0.92 (s, 3H), 0.95 (s, 9H), 1.27-1.35 (m, 1H), 1.36-1.41 (m, 2H), 1.66-1.72 (m, 1H), 1.74 (s, 3H), 1.98-2.13 (m, 2H), 2.59-2.64 (m, 2H), 6.00 (d, J = 5.24 Hz, 1H), 6.77 (d, J = 2.01 Hz, 1H), 7.28 (s, 2H), 7.36 (s, 1H), 8.22 (dd J = 5.24, 2.42 Hz, 1H), 11.96 (br s, 1H) | 421 | 419 |
| 131 | (400 MHz, CDCl3) 0.24-0.30 (m, 4H), 0.71 (d, J = 6.76 Hz, 3H), 1.05 (d, J = 6.76 Hz, 3H), 1.12 (s, 3H), 1.47-1.51 (m, 2H), 1.71 (s, 3H), 1.85-1.92 (m, 1H), 2.69 (t, J = 6.40 Hz, 2H), 2.76-2.80 (m, 2H), 3.77 (t, J = 6.52 Hz, 2H), 5.89 (s, 1H), 6.00 (brs, 1H), 7.17 (d, J = 8.21 Hz, 1H), 7.23 (dd, J = 7.97, 1.93 Hz, 1H), 7.35 (d, J = 1.93 Hz, 1H) | 419 | 417 |
| 132 | (400 MHz, CDCl3) 0.24-0.29 (m, 4H), 0.72 (d, J = 7.00 Hz, 3H), 1.05 (d, J = 7.00 Hz, 3H), 1.12 (s, 3H), 1.47-1.52 (m, 2H), 1.72 (s, 3H), 1.86-1.93 (m, 1H), 2.70 (t, J = 6.40 Hz, 2H), 2.76-2.80 (m, 2H), 3.77 (t, J = 6.52 Hz, 2H), 5.90 (s, 1H), 6.31 (brs, 1H), 7.18 (d, J = 7.97 Hz, 1H), 7.22 (dd, J = 7.97, 1.93 Hz, 1H), 7.34 (d, J = 1.93 Hz, 1H) | 419 | 417 |
| 133 | (400 MHz, DMSO-D6) 0.71 (d, J = 6.76 Hz, 3H), 1.03 (d, J = 6.76 Hz, 3H), 1.60-1.65 (m, 5H), 1.67-1.73 (m, 2H), 1.92-1.99 (m, 1H), 2.11-2.16 (m, 2H), 2.20-2.24 (m, 2H), 2.45 (t, J = 6.88 Hz, 3H), 3.48-3.56 (m, 1H), 3.58-3.65 (m, 1H), 5.62-5.65 (m, 1H), 6.12 (s, 1H), 7.04 (s, 1H), 7.18 (d, J = 8.21 Hz, 1H), 7.29 (dd, J = 7.97, 1.93 Hz, 1H), 7.36 (d, J = 1.93 Hz, 1H), 12.26 (brs, 1H) | 417 | 415 |
| 134 | (400 MHz, DMSO-D6) 0.71 (d, J = 6.76 Hz, 3H), 1.03 (d, J = 6.76 Hz, 3H), 1.61-1.65 (m, 5H), 1.67-1.73 (m, 2H), 1.92-1.99 (m, 1H), 2.12-2.16 (m, 2H), 2.20-2.24 (m, 2H), 2.45 (t, J = 6.88 Hz, 2H), 3.49-3.56 (m, 1H), 3.58-3.65 (m, 1H), 5.62-5.64 (m, 1H), 6.12 (s, 1H), 7.04 (s, 1H), 7.18 (d, J = 7.97 Hz, 1H), 7.29 (dd, | 417 | 415 |

TABLE 3-continued

| Example | ¹H-NMR | MS M + H or M—+ H | MS M − H or M—Na − H |
|---|---|---|---|
| | J = 8.09, 1.81 Hz, 1H), 7.36 (d, J = 1.93 Hz, 1H), 12.26 (brs, 1H) | | |
| 135 | (400 MHz, DMSO-D6) 0.69 (d, J = 7.00 Hz, 3H), 1.02 (d, J = 6.76 Hz, 3H), 1.19-1.44 (m, 5H), 1.60 (s, 3H), 1.70-1.81 (m, 5H), 1.90-1.97 (m, 1H), 2.45 (t J = 7.00 Hz, 3H), 2.85-2.91 (m, 1H), 3.48-3.55 (m, 1H), 3.58-3.65 (m, 1H), 6.11 (s, 1H), 7.01 (s, 1H), 7.31-7.32 (m, 2H), 7.34 (d, J = 1.69 Hz, 1H), 12.26 (brs, 1H) | 419 | 417 |
| 136 | (400 MHz, DMSO-D6) 0.69 (d, J = 6.76 Hz, 3H), 1.02 (d, J = 6.76 Hz, 3H), 1.18-1.44 (m, 5H), 1.60 (s, 3H), 1.70-1.81 (m, 5H), 1.90-1.97 (m, 1H), 2.45 (t, J = 6.88 Hz, 2H), 2.85-2.91 (m, 1H), 3.48-3.55 (m, 1H), 3.58-3.65 (m, 1H), 6.11 (s, 1H), 7.01 (s, 1H), 7.31-7.32 (m, 2H), 7.34 (d, J = 1.45 Hz, 1H), 12.26 (brs, 1H) | 419 | 417 |
| 137 | (400 MHz, DMSO-D6) 0.72 (d, J = 6.28 Hz, 3H), 0.76 (d, J = 6.28 Hz, 3H), 0.95 (s, 9H), 1.36-1.40 (m, 2H), 1.42-1.52 (m, 2H), 1.55 (s, 3H), 1.62-1.68 (m, 1H), 2.44 (t, J = 6.76 Hz, 2H), 2.60-2.64 (m, 2H), 3.48-3.55 (m, 1H), 3.58-3.64 (m, 1H), 5.99 (s, 1H), 7.06 (s, 1H), 7.25 (dd, J = 7.97, 1.69 Hz, 1H), 7.28 (d, J = 7.97 Hz, 1H), 7.33 (d, J = 1.69 Hz, 1H) | 435 | 433 |
| 138 | (400 MHz, DMSO-D6) 0.67 (d, J = 6.76 Hz, 3H), 0.86-0.96 (m, 2H), 1.02-1.04 (m, 4H), 1.16-1.21 (m, 4H), 1.40-1.43 (m, 2H), 1.60 (s, 3H), 1.66-1.74 (m, 4H), 1.89-1.96 (m, 1H), 2.45 (t, J = 6.88 Hz, 2H), 2.64-2.68 (m, 2H), 3.48-3.65 (m, 2H), 6.10 (s, 1H), 7.02 (s, 1H), 7.26-7.27 (m, 2H), 7.34 (s, 1H), 12.30 (br s, 1H). | 447 | 445 |
| 139 | (400 MHz, DMSO-D6) 0.67 (d, J = 6.76 Hz, 3H), 0.86-0.96 (m, 2H), 1.02-1.04 (m, 4H), 1.16-1.21 (m, 4H), 1.40-1.43 (m, 2H), 1.60 (s, 3H), 1.66-1.74 (m, 4H), 1.89-1.96 (m, 1H), 2.45 (t, J = 6.88 Hz, 2H), 2.64-2.68 (m, 2H), 3.48-3.65 (m, 2H), 6.10 (s, 1H), 7.02 (s, 1H), 7.26-7.27 (m, 2H), 7.34 (s, 1H), 12.30 (br s, 1H). | 447 | 445 |
| 140 | (400 MHz, DMSO-D6) 0.70 (d, J = 6.85 Hz, 3H), 1.02 (d, J = 6.85 Hz, 3H), 1.60 (s, 3H), 1.92 (qq, J = 6.85, 6.85 Hz, 1H), 2.45 (dd, J = 6.85, 6.85 Hz, 2H), 2.76-2.87 (m, 2H), 3.52 (dt, J = 13.50, 6.85 Hz, 1H), 3.63 (dt, J = 13.50, 6.85 Hz, 1H), 4.27 (t, J = 5.84 Hz, 2H), 6.10 (s, 1H), 7.01 (s, 1H), 7.14 (d, J = 8.46 Hz, 1H), 7.29 (dd, J = 8.46, 2.42 Hz, 1H), 7.38 (d, J = 2.42 Hz, 1H) | 449 | 447 |
| 141 | (400 MHz, DMSO-D6) 0.67 (d, J = 6.94 Hz, 3H), 1.01 (s, 3H), 1.02 (d, J = 6.01 Hz, 3H), 1.09 (s, 3H), 1.38 (dd, J = 11.68, 8.67 Hz, 2H), 1.57-1.65 (m, 2H), 1.60 (s, 3H), 1.81 (td, J = 8.84, 2.77 Hz, 2H), 1.92 (dd, J = 8.90, 4.51 Hz, 1H), 2.16 (t, J = 8.09 Hz, 1H), 2.45 (t, J = 6.94 Hz, 2H), 2.56 (t, J = 7.74 Hz, 2H), 3.53 (dd, J = 13.76, 6.82 Hz, 1H), 3.61 (dd, J = 13.76, 6.82 Hz, 1H), 6.10 (s, 1H), 7.02 (s, 1H), 7.26 (d, J = 1.16 Hz, 2H), 7.34 (s, 1H), 12.25 (s, 1H) | 447 | 445 |
| 142 | (400 MHz, DMSO-D6) 0.67 (d, J = 6.94 Hz, 3H), 1.01 (s, 3H), 1.02 (d, J = 5.78 Hz, 3H), 1.09 (s, 3H), 1.38 (dd, J = 11.44, 8.90 Hz, 2H), 1.57-1.65 (m, 2H), 1.60 (s, 3H), 1.81 (dt, J = 13.18, 4.16 Hz, 2H), 1.92 (dd, J = 9.02, 4.62 Hz, 1H), 2.16 (t, J = 8.21 Hz, 1H), 2.45 (dd, J = 9.02, 5.09 Hz, 2H), 2.56 (dd, J = 10.06, 5.43 Hz, 2H), 3.53 (q, J = 6.86 Hz, 1H), 3.61 (dd, J = 13.76, 6.82 Hz, 1H), 6.10 (s, 1H), 7.02 (s, 1H), 7.26 (d, J = 1.16 Hz, 2H), 7.34 (s, 1H), 12.25 (s, 1H) | 447 | 445 |
| 143 | (400 MHz, DMSO-D6) 0.69 (d, J = 6.94 Hz, 3H), 1.04 (d, J = 6.70 Hz, 3H), 1.61 (s, 3H), 1.93 (dd, J = 11.10, 4.39 Hz, 1H), 2.45 (dd, J = 9.83, 4.28 Hz, 2H), 2.85 (dd, J = 9.83, 5.90 Hz, 2H), 2.96 (dd, J = 9.71, 5.55 Hz, 2H), 3.53 (t, J = 6.82 Hz, 1H), 3.63 (t, J = 6.94 Hz, 1H), 6.11 (s, 1H), 7.03 (s, 1H). 7.17-7.23 (m, 3H), 7.26-7.29 (m, 4H), 7.38 (d, J = 1.39 Hz, 1H), 12.30 (s, 1H) | 441 | 439 |
| 144 | (400 MHz, DMSO-D6) 0.69 (d, J = 6.70 Hz, 3H), 1.03 (d, J = 6.94 Hz, 3H), 1.60 (s, 3H), 1.90-1.97 (m, 1H), 2.29-2.35 (m, 2H), 2.84 (dd, J = 9.71, 5.55 Hz, 2H), 2.94 (dd, J = 9.59, 5.43 Hz, 2H), 3.53 (t, J = 6.82 Hz, 1H), 3.63 (t, J = 6.94 Hz, 1H), 6.11 (s, 1H), 6.98 (s, 1H), 7.16-7.21 (m, 3H), 7.23-7.29 (m, 4H), 7.37 (d, J = 1.62 Hz, 1H), 12.50 (s, 1H) | 441 | 439 |

TABLE 3-continued

| Example | ¹H-NMR | MS M + H or M—+ H | MS M − H or M—Na − H |
|---|---|---|---|
| 145 | (400 MHz, CDCl3) 0.98 (s, 9H), 1.42-1.47 (m, 2H), 1.68 (s, 3H), 1.93-2.07 (m, 3H), 2.08-2.18 (m, 1H), 2.32-2.46 (m, 4H), 2.60-2.69 (m, 3H), 3.67-3.53 (m, 2H), 5.20 (s, 1H), 5.85 (d, J = 1.21 Hz, 1H), 7.20 (s, 2H), 7.36 (s, 1H) | 483 | 481 |
| 146 | (400 MHz, CDCl3) 0.98 (s, 9H), 1.42-1.47 (m, 2H), 1.68 (s, 3H), 1.93-2.07 (m, 3H), 2.08-2.18 (m, 1H), 2.32-2.46 (m, 4H), 2.60-2.69 (m, 3H), 3.67-3.53 (m, 2H), 5.20 (s, 1H), 5.85 (d, J = 1.21 Hz, 1H), 7.20 (s, 2H), 7.36 (s, 1H) | 483 | 481 |
| 147 | (400 MHz, DMSO-D6) 0.64-0.71 (m, 3H), 0.99-1.04 (m, 3H), 1.22 (s, 9H), 1.59 (s, 3H), 1.87-1.96 (m, 1H), 2.40-2.46 (m, 2H), 3.42-3.56 (m, 1H), 3.56-3.69 (m, 1H), 4.42 (s, 2H), 6.09 (s, 1H), 7.02 (s, 1H), 7.27-7.38 (m, 2H), 7.40-7.49 (m, 1H), 12.24 (brs, 1H) | 423 | 421 |
| 148 | (400 MHz, DMSO-D6) 0.72 (d, J = 6.70 Hz, 3H), 1.04 (d, J = 6.70 Hz, 3H), 1.61 (s, 3H), 1.90-1.98 (m, 3H), 2.42-2.53 (m, 4H), 2.67-2.72 (m, 2H), 3.48-3.55 (m, 1H), 3.62 (dd, J = 13.87, 6.94 Hz, 1H), 6.13 (s, 1H), 6.14-6.16 (m, 1H), 7.05 (s, 1H), 7.30 (dd, J = 8.21, 1.73 Hz, 1H), 7.33 (d, J = 7.86 Hz, 1H), 7.38 (d, J = 1.62 Hz, 1H), 12.26 (s, 1H) | 403 | 401 |
| 149 | (400 MHz, DMSO-D6) 0.72 (d, J = 6.94 Hz, 3H), 1.03 (d, J = 6.70 Hz, 3H), 1.61 (s, 3H), 1.95 (dt, J = 20.88, 6.59 Hz, 3H), 2.42-2.51 (m, 4H), 2.69 (td, J = 7.51, 2.00 Hz, 2H), 3.48-3.55 (m, 1H), 3.59-3.66 (m, 1H), 6.13 (s, 1H), 6.15 (dd, J = 4.16, 2.31 Hz, 1H), 7.05 (s, 1H), 7.30 (dd, J = 8.21, 1.73 Hz, 1H), 7.33 (d, J = 8.09 Hz, 1H), 7.38 (d, J = 1.62 Hz, 1H), 12.31 (s, 1H) | 403 | 401 |
| 150 | (400 MHz, DMSO-D6) 0.69 (d, J = 6.85 Hz, 3H), 0.93 (d, J = 6.45 Hz, 6H), 1.02 (d, J = 6.85 Hz, 3H), 1.59 (s, 3H), 1.63 (dt, J = 6.65, 6.70 Hz, 2H), 1.81 (tsep, J = 6.70, 6.45 Hz, 1H), 1.92 (qq, J = 6.85, 6.85 Hz, 1H), 2.44 (dd, J = 7.05, 7.05 Hz, 2H), 3.51 (dt, J = 13.50, 7.05 Hz, 1H), 3.62 (dt, J = 13.50, 7.05 Hz, 1H), 4.06 (t, J = 6.65 Hz, 2H), 6.09 (s, 1H), 6.98 (s, 1H), 7.10 (d, J = 8.87 Hz, 1H), 7.27 (dd, J = 8.87, 2.42 Hz, 1H), 7.35 (d, J = 2.42 Hz, 1H) | 423 | 421 |
| 151 | (400 MHz, DMSO-D6) 0.71 (d, J = 6.76 Hz, 3H), 1.03 (s, 6H), 1.03 (d, J = 6.76 Hz, 3H), 1.46-1.49 (m, 2H), 1.61 (s, 3H), 1.68-1.74 (m, 2H), 1.91-1.98 (m, 1H), 2.16 (t, J = 5.92 Hz, 2H), 2.45 (t, J = 6.88 Hz, 2H), 3.48-3.55 (m, 1H), 3.59-3.66 (m, 1H), 5.37 (s, 1H), 6.12 (s, 1H), 7.04 (s, 1H), 7.16 (d, J = 7.97 Hz, 1H), 7.29 (dd, J = 7.97, 1.45 Hz, 1H), 7.36 (d, J = 1.21 Hz, 1H), 12.24 (brs, 1H) | 445 | 443 |
| 152 | (400 MHz, DMSO-D6) 0.69 (d, J = 7.00 Hz, 3H), 1.03 (d, J = 6.76 Hz, 3H), 1.61 (s, 3H), 1.75-1.82 (m, 1H), 1.90-2.10 (m, 4H), 2.30-2.37 (m, 2H), 2.45 (t, J = 7.00 Hz, 2H), 3.48-3.55 (m, 1H), 3.59-3.74 (m, 2H), 6.11 (s, 1H), 7.02 (s, 1H), 7.31-7.33 (m, 2H), 7.37 (d, J = 8.93 Hz, 1H), 12.26 (brs, 1H) | 391 | 389 |
| 153 | (400 MHz, DMSO-D6) 0.69 (d, J = 7.00 Hz, 3H), 1.03 (d, J = 6.76 Hz, 3H), 1.60 (s, 3H), 1.75-1.82 (m, 1H), 1.90-2.10 (m, 4H), 2.30-2.36 (m, 2H), 2.45 (t, J = 7.00 Hz, 2H), 3.48-3.55 (m, 1H), 3.59-3.74 (m, 2H), 6.11 (s, 1H), 7.02 (s, 1H), 7.32 (dd, J = 7.49, 1.69 Hz, 1H), 7.33 (s, 1H), 7.37 (d, J = 8.69 Hz, 1H), 12.25 (brs, 1H) | 391 | 389 |
| 154 | (400 MHz, DMSO-D6) 0.72 (d, J = 6.82 Hz, 3H), 0.94 (s, 9H), 1.04 (d, J = 6.82 Hz, 3H), 1.37 (dt, J = 8.71, 3.67 Hz, 2H), 1.60 (s, 3H), 1.88-2.01 (m, 3H), 2.12-2.15 (m, 2H), 2.62 (dt, J = 10.17, 3.67 Hz, 2H), 2.97-3.00 (m, 1H), 3.26-3.28 (m, 1H), 3.62 (dd, J = 13.64, 7.40 Hz, 1H), 6.11 (s, 1H), 7.01 (bs, 1H), 7.24 (dd, J = 8.09, 1.85 Hz, 1H), 7.28 (d, J = 8.09 Hz, 1H), 7.32 (d, J = 1.85 Hz, 1H), 12.06 (bs, 1H) | 461 | 459 |
| 155 | (400 MHz, DMSO-D6) 0.70 (d, J = 6.94 Hz, 3H), 1.03 (d, J = 6.70 Hz, 3H), 1.50-1.57 (m, 2H), 1.61 (s, 3H), 1.61-1.70 (m, 2H), 1.72-1.81 (m, 2H), 1.90-2.02 (m, 3H), 2.44 (t, J = 6.94 Hz, 2H), 3.28-3.34 (m, 1H), 3.52 (q, J = 7.01 Hz, 1H), 3.61 (dd, J = 13.87, 6.94 Hz, 1H), 6.11 (s, 1H), 7.01 (s, 1H), 7.29 (dd, J = 8.21, | 405 | 403 |

TABLE 3-continued

| Example | ¹H-NMR | MS M + H or M→+ H | MS M − H or M—Na − H |
|---|---|---|---|
| | 1.97 Hz, 1H), 7.35 (d, J = 1.95 Hz, 1H), 7.35 (d, J = 8.21 Hz, 1H), 12.27 (s, 1H) | | |
| 156 | (400 MHz, DMSO-D6) 0.71 (d, J = 6.94 Hz, 3H), 1.03 (d, J = 6.94 Hz, 3H), 1.47-1.57 (m, 2H), 1.60 (s, 3H), 1.62-1.70 (m, 2H), 1.73-1.79 (m, 2H), 1.93-2.00 (m, 3H), 2.35-2.41 (m, 2H), 3.28-3.34 (m, 1H), 3.51 (dd, J = 13.87, 7.17 Hz, 1H), 3.59 (dd, J = 13.87, 7.17 Hz, 1H), 6.12 (s, 1H), 6.98 (s, 1H), 7.29 (dd, J = 8.09, 1.85 Hz, 1H), 7.35 (d, J = 1.94 Hz, 1H), 7.35 (d, J = 8.21 Hz, 1H), 12.39 (s, 1H) | 405 | 403 |
| 157 | (400 MHz, CDCl3) 0.67-0.75 (m, 3H), 1.00-1.08 (m, 3H), 1.21-1.28 (m, 6H), 1.70 (s, 3H), 1.82-1.95 (m, 1H), 2.60-2.66 (m, 2H), 3.68-3.82 (m, 3H), 4.56 (s, 2H), 5.40-5.66 (m, 1H), 5.88 (s, 1H), 7.31-7.42 (m, 2H), 7.45-7.52 (m, 1H) | 409 | 407 |
| 158 | (400 MHz, CDCl3) δ: 0.03 (d, J = 2.82 Hz, 9H), 0.70 (d, J = 6.85 Hz, 3H), 0.81-0.85 (m, 2H), 1.04 (d, J = 6.85 Hz, 3H), 1.70 (s, 3H), 1.83-1.90 (m, 1H), 2.67 (dt, J = 14.78, 5.44 Hz, 4H), 3.71-3.82 (m, 2H), 5.50 (s, 1H), 5.87 (s, 1H), 7.20 (d, J = 8.06 Hz, 1H), 7.25 (d, J = 2.01 Hz, 2H), 7.37 (d, J = 2.01 Hz, 1H). | 437 | 435 |
| 159 | (400 MHz, DMSO-D6) 0.73-0.78 (m, 3H), 0.96 (s, 9H), 1.07-1.13 (m, 3H), 1.35-1.44 (m, 2H), 1.72 (s, 3H), 2.01-2.09 (m, 1H), 2.60-2.70 (m, 2H), 6.39 (s, 1H), 7.30-7.40 (m, 2H), 7.41-7.47 (m, 3H), 7.54-7.59 (m, 1H), 7.91-7.96 (m, 2H) | 469 | 467 |
| 160 | (400 MHz, CDCl3) 0.79 (s, 3H), 0.90 (m, 9H), 1.04 (d, J = 9.02 Hz, 3H), 1.11-1.39 (m, 3H), 1.43 (m, 2H), 1.94 (s, 3H), 2.19 (m, 1H), 2.27-2.34 (m, 1H), 2.61-2.65 (m, 2H), 3.38 (mz, 4H), 3.48-3.54 (m, 2H), 6.11 (s, 1H), 6.66 (s, 1H), 7.11 (d, J = 8.09 Hz, 1H), 7.25 (m, 2H), 7.38 (d, J = 1.85 Hz, 1H) | 479 | 477 |
| 161 | (400 MHz, DMSO-D6) 0.69 (d, J = 6.85 Hz, 3H), 1.03 (d, J = 6.85 Hz, 3H), 1.59 (s, 3H), 1.95 (qq, J = 6.85, 6.85 Hz, 1H), 2.44 (dd, J = 6.85, 6.85 Hz, 2H), 3.50 (dt, J = 13.50, 6.85 Hz, 1H), 3.64 (dt, J = 13.50, 6.85 Hz, 1H), 5.12 (s, 2H), 6.12 (s, 1H), 7.09 (s, 1H), 7.22 (dd, J = 12.40, 2.50 Hz, 2H), 7.25 (dd, J = 2.50, 1.41 Hz, 2H), 7.34-7.40 (m, 3H), 7.43-7.46 (m, 2H) | 461 | 459 |
| 162 | (400 MHz, DMSO-D6) 0.71 (d, J = 6.85 Hz, 3H), 0.95 (s, 9H), 1.03 (d, J = 6.85 Hz, 3H), 1.36-1.40 (m, 2H), 1.62 (s, 3H), 1.98 (qq, J = 6.85, 6.85 Hz, 1H), 2.26-2.32 (m, 1H), 2.60-2.65 (m, 2H), 2.65-2.71 (m, 1H), 3.35-3.38 (m, 1H), 3.67-3.72 (m, 1H), 3.85 (d, J = 17.33 Hz, 1H), 4.07 (d, J = 17.33 Hz, 1H), 5.02-5.09 (m, 1H), 6.22 (s, 1H), 7.19 (s, 1H), 7.27 (dd, J = 8.06, 2.01 Hz, 1H), 7.30 (d, J = 8.06 Hz, 1H), 7.35 (d, J = 2.01 Hz, 1H) | 490 | 488 |
| 163 | (400 MHz, DMSO-D6) 0.73 (d, J = 6.85 Hz, 3H), 0.95 (s, 9H), 1.07 (d, J = 6.85 Hz, 3H), 1.36-1.41 (m, 2H), 1.62 (s, 3H), 1.98 (qq, J = 6.85, 6.85 Hz, 1H), 2.18-2.24 (m, 1H), 2.60-2.65 (m, 2H), 2.67-2.74 (m, 1H), 3.35-3.39 (m, 1H), 3.68-3.73 (m, 1H), 3.83 (d, J = 17.73 Hz, 1H), 4.10 (d, J = 17.73 Hz, 1H), 5.03-5.09 (m, 1H), 6.28 (s, 1H), 7.21 (s, 1H), 7.25 (dd, J = 8.06, 2.01 Hz, 1H), 7.31 (d, J = 8.06 Hz, 1H), 7.34 (d, J = 2.01 Hz, 1H) | 490 | 488 |
| 164 | (400 MHz, DMSO-D6) 0.72 (d, J = 6.85 Hz, 3H), 1.02 (s, 9H), 1.03 (d, J = 6.85 Hz, 3H), 1.60 (s, 3H), 1.97 (qq, J = 6.85, 6.85 Hz, 1H), 2.43 (dd, J = 7.05, 7.05 Hz, 2H), 3.50 (dt, J = 13.50, 7.05 Hz, 1H), 3.64 (dt, J = 13.50, 7.05 Hz, 1H), 3.73 (s, 2H), 6.13 (s, 1H), 7.09 (s, 1H), 7.21 (dd, J = 12.49, 2.42 Hz, 1H), 7.25 (dd, J = 2.42, 1.21 Hz, 1H) | 441 | 439 |
| 165 | (400 MHz, DMSO-D6) 0.72 (d, J = 6.85 Hz, 3H), 0.94 (s, 9H), 1.03 (d, J = 6.85 Hz, 3H), 1.60 (s, 3H), 1.67 (t, J = 7.45 Hz, 2H), 1.97 (qq, J = 6.85, 6.85 Hz, 1H), 2.44 (dd, J = 6.85, 6.85 Hz, 2H), 3.50 (dt, J = 13.50, 6.85 Hz, 1H), 3.64 (dt, J = 13.50, 6.85 Hz, 1H), 4.09 (t, J = 7.45 Hz, 2H), 6.13 (s, 1H), 7.09 (s, 1H), 7.22 (dd, J = 12.29, 2.22 Hz, 1H), 7.26 (dd, J = 2.22, 1.41 Hz, 1H) | 455 | 453 |
| 166 | (400 MHz, DMSO-D6) 0.69 (d, J = 7.00 Hz, 3H), 0.93 (s, 3H), 1.01 (s, 3H), 1.02 (d, J = 7.00 Hz, 3H), 1.17-1.35 (m, 3H), 1.38-1.46 (m, 2H), 1.55-1.74 (m, 6H), 1.89-1.96 (m, 1.H), 2,45 (t, J = 6.76 Hz, 2H), 3.07-3.15 | 447 | 445 |

TABLE 3-continued

| Example | ¹H-NMR | MS M + H or M—+ H | M − H or M—Na − H |
|---|---|---|---|
| | (m, 1H), 3.48-3.55 (m, 1H), 3.58-3.65 (m, 1H), 6.11 (s, 1H), 7.02 (s, 1H), 7.28-7.34 (m, 3H), 12.25 (brs, 1H) | | |
| 167 | (400 MHz, DMSO-D6) 0.69 (d, J = 6.76 Hz, 3H), 0.93 (s, 3H), 1.01 (s, 3H), 1.02 (d, J = 6.76 Hz, 3H), 1.15-1.35 (m, 3H), 1.38-1.46 (m, 2H), 1.54-1.74 (m, 6H), 1.89-1.96 (m, 1H), 2.45 (t, J = 6.76 Hz, 3H), 3.08-3.17 (m, 1H), 3.48-3.55 (m, 1H), 3.58-3.65 (m, 1H), 6.11 (s, 1H), 7.01 (s, 1H), 7.28-7.34 (m, 3H), 12.25 (brs, 1H) | 447 | 445 |
| 168 | (400 MHz, CDCl3) 0.97 (s, 9H), 1.41-1.50 (m, 2H), 1.63 (s, 3H), 1.76-1.96 (m, 3H), 2.03-2.18 (m, 1H), 2.24-2.35 (m, 1H), 2.38-2.51 (m, 1H), 2.61-2.71 (m, 2H), 2.74-2,88 (m, 1H), 3.38 (s, 3H), 3.53-3.60 (m, 2H), 3.61-3.75 (m, 2H), 5.08-5.42 (m, 1H), 5.93 (s, 1H), 7.12-7.24 (m, 2H), 7.35-7.39 (m, 1H) | 463 | 461 |
| 169 | (400 MHz, DMSO-D6) 0.70 (d, J = 6.94 Hz, 3H), 0.86-0.94 (m, 3H), 0.90 (s, 9H), 1.02 (d, J = 6.94 Hz, 3H), 1.59 (s, 3H), 1.90-1.95 (m, 1H), 1.99-2.05 (m, 1H), 2.44 (t, J = 6.70 Hz, 2H), 3.47-3.54 (m, 1H), 3.58-3.65 (m, 1H), 6.11 (s, 1H), 6.97 (d, J = 8.55 Hz, 1H), 6.98 (s, 1H), 7.23 (dd, J = 8.21, 1.97 Hz, 1H), 7.33 (d, J = 2.08 Hz, 1H), 12.28 (s, 1H) | 433 | 431 |
| 170 | (400 MHz, DMSO-D6) 0.71 (d, J = 6.94 Hz, 3H), 0.85-0.94 (m, 3H), 0.90 (s, 9H), 1.03 (d, J = 6.70 Hz, 3H), 1.59 (s, 3H), 1.94 (t, J = 6.94 Hz, 1H), 1.99-2.04 (m, 1H), 2.35-2.40 (m, 2H), 3.50 (dd, J = 13.99, 6.82 Hz, 1H), 3.59 (dd, J = 13.99, 6.82 Hz, 1H), 6.11 (s, 1H), 6.96 (d, J = 8.28 Hz, 1H), 6.97 (s, 1H), 7.22 (dd, J = 8.09, 1.85 Hz, 1H), 7.34 (d, J = 1.85 Hz, 1H), 12.35 (s, 1H) | 433 | 431 |
| 171 | (400 MHz, CDCl3) 0.30-0.40 (m, 2H), 0.51 (m, 1H), 0.78 (s, 3H), 0.92-1.00 (m, 9H), 1.40-1.45 (m, 2H), 1.79 (s, 4H), 2.65 (m, 5H), 3.67-3.78 (m, 1H), 5.31 (s, 1H), 6.11 (s, 1H), 7.14 (d, J = 8.09 Hz, 1H), 7.21 (d, J = 2.08 Hz, 1H), 7.24 (m, 1H), 7.37 (d, J = 2.08 Hz, 1H) | 433 | 431 |
| 172 | (400 MHz, CDCl3) 0.85 (s, 3H), 0.97 (s, 9H), 1.13 (s, 3H), 1.21 (d, J = 4.84 Hz, 3H), 1.23 (d, J = 4.84 Hz, 3H), 1.34-1.39 (m, 1H), 1.42-1.46 (m, 2H), 1.97 (s, 3H), 2.12-2.25 (m, 2H), 2.35-2.27 (m, 1H), 2.66-2.62 (m, 2H), 4.59-4.52 (m, 1H), 6.16 (s, 1H), 6.58 (s, 1H), 7.13 (d, J = 8.06 Hz, 1H), 7.23 (dd, J = 8.06, 2.01 Hz, 1H), 7.36 (d, J = 2.01 Hz, 1H) | 463 | 461 |
| 173 | (400 MHz, DMSO-D6) 0.69 (d, J = 6.94 Hz, 3H), 1.02 (d, J = 6.70 Hz, 3H), 1.60 (s, 3H), 1.77-2.04 (m, 7H), 2.12 (t, J = 6,82 Hz, 2H), 2.38-2.47 (m, 4H), 3.46-3.56 (m, 2H), 3.62 (dt, J = 13.60, 6.80 Hz, 1H), 6.11 (s, 1H), 7.01 (s, 1H), 7.28-7.33 (m, 3H), 12.27 (brs, 1H) | 431 | 429 |
| 174 | (400 MHz, DMSO-D6) 0.70 (d, J = 6.70 Hz, 3H), 0.78-0.88 (m, 2H), 0.88-0.95 (m, 1H), 0.98 (d, J = 6.70 Hz, 3H), 1.02 (t, J = 6.13 Hz, 6H), 1.14-1.21 (m, 1H), 1.59 (s, 3H), 1.93 (dd, J = 12.37, 6.13 Hz, 2H), 2.35-2.43 (m, 2H), 3.50 (dd, J = 13.76, 6.59 Hz, 1H), 3.59 (dd, J = 13.76, 7.05 Hz, 1H), 6.11 (s, 1H), 6.93 (d, J = 8.32 Hz, 1H), 6.96 (s, 1H), 7.22 (dd, J = 8.21, 1.97 Hz, 1H), 7.33 (d, J = 2.08 Hz, 1H), 12.46 (s, 1H) | 419 | 417 |
| 175 | (400 MHz, DMSO-D6) 0.71 (d, J = 6.85 Hz, 3H), 0.95 (s, 9H), 1.03 (d, J = 6.85 Hz, 3H), 1.31-1.35 (m, 2H), 1.60 (s, 3H), 1.97 (qq, J = 6.85, 6.85 Hz, 1H), 2.43 (dd, J = 6.85, 6.85 Hz, 2H), 2.64-2.69 (m, 2H), 3.50 (dt, J = 13.50, 6.85 Hz, 1H), 3.63 (dt, J = 13.50, 6.85 Hz, 1H), 6.14 (s, 1H), 7.09 (s, 1H), 7.12 (dd, J = 11.08, 1.81 Hz, 1H), 7.24 (dd, J = 1.81, 1.01 Hz, 1H) | 439 | 437 |
| 176 | (400 MHz, DMSO-D6) 0.67 (d, J = 6.85 Hz, 3H), 0.93 (s, 9H), 1.02 (d, J = 6.85 Hz, 3H), 1.38-1.42 (m, 2H), 1.60 (s, 3H), 1.94 (qq, J = 6.85, 6.85 Hz, 1H), 2.44 (dd, J = 6.85, 6.85 Hz, 2H), 2.52-2.55 (m, 2H), 3.51 (dt, J = 13.50, 6.85 Hz, 1H), 3.62 (dt, J = 13.50, 6.85 Hz, 1H), 6.09 (s, 1H), 6.99 (s, 1H), 7.07 (dd, J = 11.89, 2.01 Hz, 1H), 7.12 (dd, J = 8.06, 2.01 Hz, 1H), 7.23 (dd, J = 8.06, 4.03 Hz, 1H) | 405 | 403 |
| 177 | (400 MHz, DMSO-D6) 0.65 (d, J = 6.82 Hz, 3H), 0.84 (t, J = 7.51 Hz, 6H), 1.02 (d, J = 6.82 Hz, 3H), 1.20-1.30 (m, 4H), 1.53-1.56 (m, 1H), 1.61 (s, 3H), 1.88-1.95 (m, 1H), 2.45 (t, J = 6.80 Hz, 2H), 2.59 (d, J = 7.17 Hz, 2H), 3.52 (dt, J = 14.00, 6.80 Hz, 2H), 3.62 (dt, J = 14.00, | 421 | 419 |

TABLE 3-continued

| Example | ¹H-NMR | MS M + H or M—+ H | MS M − H or M—Na − H |
|---|---|---|---|
|  | 6.80 Hz, 2H), 6.09 (s, 1H), 7.04 (bs, 1H), 7.24 (d, J = 8.09 Hz, 2H), 7.27 (dd, J = 8.09, 1.74 Hz, 2H), 7.35 (d, J = 1.74 Hz, 1H), 12.31 (bs, 1H) |  |  |
| 178 | (400 MHz, DMSO-D6) 0.63 (d, J = 6.94 Hz, 3H), 0.81 (t, J = 6.70 Hz, 6H), 1.01 (d, J = 6.94 Hz, 3H), 1.13-1.35 (m, 8H), 1.61 (s, 3H), 1.67-1.70 (m, 1H), 1.87-1.94 (m, 1H), 2.45 (t, J = 6.80 Hz, 2H), 2.59 (d, J = 7.17 Hz, 2H), 3.53 (dt, J = 14.00, 6.80 Hz, 1H), 3.62 (dt, J = 14.00, 6.80 Hz, 1H), 6.08 (s, 1H), 7.05 (bs, 1H), 7.23 (t, J = 3.93 Hz, 1H), 7.25-7.29 (m, 1H), 7.35 (d, J = 1.85 Hz, 1H), 12.29 (bs, 1H) | 449 | 447 |
| 179 | (400 MHz, DMSO-D6) 0.598 (d, J = 7.20 Hz, 1.5H), 0.600 (d, J = 7.20 Hz, 1.5H), 0.99 (d, J = 6.70 Hz, 3H), 1.11 (d, J = 7.20 Hz, 1.5H), 1.12 (d, J = 7.20 Hz, 1.5H), 1.46 (ddd, J = 14.05, 3.93, 0.92 Hz, 1H), 1.58 (s, 3H), 1.75 (dd, J = 14.05, 8.79 Hz, 1H), 1.87-1.90 (m, 1H), 2.42-2.44 (m, 2H), 2.48-2.49 (m, 1H), 3.51 (dt, J = 14.00, 6.80 Hz, 1H), 3.61 (dt, J = 14.00, 6.80 Hz, 1H), 6.06 (s, 1H), 6.98 (s, 0.5H), 7.00 (s, 0.5H), 7.27-7.31 (m, 2H), 7.36-7.38 (m, 1H) | 435 | 433 |
| 180 | (400 MHz, CDCl3) 0.90 (s, 3H), 0.96-1.02 (m, 18H), 1.29-1.52 (m, 4H), 1.80 (s, 3H), 2.51-2.72 (m, 8H), 2.96-3.10 (m, 1H), 3.44-3.60 (m, 2H), 4.94-5.06 (m, 1H), 5.07-5.18 (m, 1H), 6.16 (s, 1H), 7.13-7.20 (m, 2H), 7.21-7.28 (m, 1H), 7.40-7.45 (m, 1H) | 505 | 503 |
| 181 | (400 MHz, CDCl3) 0.82 (s, 3H), 0.96 (s, 9H), 1.15 (s, 3H), 1.36-1.47 (m, 2H), 1.99 (s, 3H), 2.18-2.36 (m, 2H), 2.50-2.78 (m, 8H), 2.97-3.10 (m, 1H), 3.72 (s, 3H), 4.77-4.90 (m, 1H), 6.24 (s, 1H), 7.02 (brs, 1H), 7.08-7.14 (m, 1H), 7.17-7.21 (m, 1H), 7.31-7.33 (m, 1H) | 533 | 531 |
| 182 | (400 MHz, CDCl3) 0.77 (s, 3H), 0.94 (s, 9H), 1.13 (s, 3H), 1.33-1.50 (m, 3H), 1.97 (s, 3H), 2.07-2.50 (m, 6H), 2.57-2.71 (m, 2H), 3.70-3.75 (m, 2H), 4.78-4.89 (m, 1H), 6.31 (s, 1H), 6.91 (brs, 1H), 7.07-7.13 (m, 1H), 7.13-7.21 (m, 1H), 7.29-7.35 (m, 1H) | 505 | 503 |
| 183 | (400 MHz, DMSO-D6) 0.69 (d, J = 6.85 Hz, 3H), 0.99 (d, J = 6.45 Hz, 6H), 1.02 (d, J = 6.85 Hz, 3H), 1.59 (s, 3H), 1.92 (qq, J = 6.85, 6.85 Hz, 1H), 2.03 (tsep, J = 6.45, 6.45 Hz, 1H), 2.45 (dd, J = 7.05, 7.05 Hz, 2H), 3.52 (dt, J = 13.50, 7.05 Hz, 1H), 3.62 (dt, J = 13.50, 7.05 Hz, 1H), 3.81 (d, J = 6.45 Hz, 2H), 6.09 (s, 1H), 6.98 (s, 1H), 7.07 (d, J = 8.87 Hz, 1H), 7.26 (dd, J = 8.87, 2.42 Hz, 1H), 7.36 (d, J = 2.42 Hz, 1H) | 409 | 407 |
| 184 | (400 MHz, CDCl3) 0.85 (d, J = 15.26 Hz, 3H), 0.96 (s, 9H), 1.10 (s, 6H), 1.24-1.77 (m, 8H), 1.90 m, 2H), 2.14-2.31 (m, 2H), 2.61-2.65 (m, 2H), 4.72 (m, 1H), 6.08 (s, 1H), 6.30 (s, 1H), 7.12 (d, J = 7.63 Hz, 1H), 7.21 (t, J = 3.93 Hz, 1H), 7.25 (t, J = 1.50 Hz, 1H), 7.35 (s, 1H) | 475 | 473 |
| 185 | (400 MHz, DMSO-D6) 0.64-0.70 (m, 3H), 0.98-1.03 (m, 3H), 1.16 (s, 6H), 1.58 (s, 3H), 1.60-1.67 (m, 2H), 1.85-1.99 (m, 1H), 2.35-2.42 (m, 2H), 2.66-2.74 (m, 2H), 3.43-3.55 (m, 1H), 3.55-3.65 (m, 1H), 6.10 (s, 1H), 7.00 (s, 1H), 7.21-7.39 (m, 3H) | 475 | 473 |
| 186 | (400 MHz, DMSO-D6) 0.64-0.70 (m, 3H), 0.94 (s, 9H), 0.99-1.04 (m, 3H), 1.33-1.41 (m, 2H), 1.58 (s, 3H), 1.85-2.00 (m, 7H), 2.58-2.64 (m, 2H), 4.00-4.35 (m, 1H), 5.93 (s, 1H), 6.86 (s, 1H), 7.19-7.34 (m, 3H) | 459 | 457 |
| 187 | (400 MHz, CDCl3) 0.97 (s, 9H), 1.33 (s, 9H), 1.90-2.03 (m, 2H), 2.32-2.45 (m, 1H), 3.40-3.47 (m, 1H), 3.67-3.74 (m, 1H), 4.84 (d, J = 2.87 Hz, 1H), 5.50-5.59 (brm, 1H), 6.11 (s, 1H), 7.05 (dd, J = 7.94, 1.76 Hz, 1H), 7.25 (d, J = 1.76 Hz, 1H), 7.38 (d, J = 7.94 Hz, 1H) | 431 | 429 |
| 188 | (400 MHz, DMSO-D6) 0.67 (d, J = 6.85 Hz, 3H), 1.03 (d, J = 6.85 Hz, 3H), 1.63 (s, 3H), 1.67-1.74 (m, 2H), 1.82 (s, 3H), 1.87 (s, 3H), 1.96 (qq, J = 6.85, 6.85 Hz, 1H), 2.18 (t, J = 7.45 Hz, 2H), 3.28-3.34 (m, 1H), 3.40-3.47 (m, 1H), 6.01 (s, 1H), 6.24 (s, 1H), 6.91 (s, 1H), 7.18 (d, J = 8.46 Hz, 2H), 7.34 (d, J = 8.46 Hz, 2H) | 371 | 369 |
| 189 | (400 MHz, DMSO-D6) 0.72 (d, J = 6.85 Hz, 3H), 1.04 (d, J = 6.85 Hz, 3H), 1.11 (s, 9H), 1.61 (s, 3H), 1.98 (qq, J = 6.85, 6.85 Hz, 1H), 2.44 (dd, J = 7.05, 7.05 Hz, 2H), 3.51 (dt, J = 13.50, 7.05 Hz, 1H), 3.64 (dt, J = 13.50, | 437 | 435 |

TABLE 3-continued

| | | MS | |
|---|---|---|---|
| Example | ¹H-NMR | M + H or M—+ H | M − H or M—Na − H |
| | 7.05 Hz, 1H), 6.14 (s, 1H), 6.29 (d, J = 16.52 Hz, 1H), 6.44 (d, J = 16.52 Hz, 1H), 7.13 (s, 1H), 7.17 (dd, J = 12.29, 1.81 Hz, 1H), 7.28 (d, J = 1.81 Hz, 1H) | | |

TABLE 4

| | | MS | |
|---|---|---|---|
| Example | ¹H-NMR | M + H or M—Na + H | M − H or M—Na − H |
| 190 | (400 MHz, CDCl₃) 0.90 (s, 3H), 0.97 (s, 9H), 1.00 (s, 3H), 1.24-1.40 (m, 2H), 1.40-1.51 (m, 3H), 1.79 (s, 3H), 2.56-2.73 (m, 6H), 3.00-3.11 (m, 1H), 3.43-3.60 (m, 2H), 3.73 (s, 3H), 4.48-4.53 (m, 1H), 4.89-5.03 (m, 1H), 6.14 (s, 1H), 7.14-7.18 (m, 1H), 7.24-7.29 (m, 1H), 7.42-7.46 (m, 1H) | 519 | 517 |
| 191 | (400 MHz, CDCl₃) 0.90 (s, 3H), 0.97 (s, 9H), 1.00 (s, 3H), 1.24-1.40 (m, 2H), 1.40-1.51 (m, 3H), 1.79 (s, 3H), 2.56-2.73 (m, 6H), 3.00-3.11 (m, 1H), 3.43-3.60 (m, 2H), 3.73 (s, 3H), 4.48-4.53 (m, 1H), 4.89-5.03 (m, 1H), 6.34 (s, 1H), 7.14-7.18 (m, 1H), 7.24-7.29 (m, 1H), 7.42-7.46 (m, 1H) | 519 | 517 |
| 192 | (400 MHz, DMSO-D₆) 0.73-0.79 (m, 3H), 0.88-0.93 (m, 6H), 1.05-1.11 (m, 3H), 1.55-1.63 (m, 2H), 1.70 (s, 3H), 1.77-1.88 (m, 1H), 2.02-2.13 (m, 1H), 4.05-4.11 (m, 2H), 6.35 (s, 1H), 7.27-7.38 (m, 4H), 7.51-7.55 (m, 1H), 7.85-7.91 (m, 2H) | 489 | 487 |
| 193 | (400 MHz, DMSO-D₆) 0.72-0.78 (m, 3H), 1.01 (s, 9H), 1.06-1.10 (m, 3H), 1.70 (s, 3H), 2.03-2.12 (m, 1H), 3.73-3.75 (m, 2H), 6.33 (s, 1H), 7.24-7.36 (m, 4H), 7.46-7.52 (m, 1H), 7.82-7.89 (m, 2H) | 489 | 487 |
| 194 | (400 MHz, DMSO-D₆) 0.72 (d, J = 6.85 Hz, 3H), 0.99 (d, J = 6.45 Hz, 6H), 1.03 (d, J = 6.45 Hz, 3H), 1.60 (s, 3H), 1.93-2.05 (m, 2H), 2.44 (t, J = 7.05 Hz, 2H), 3.50 (dt, J = 13.50, 7.05 Hz, 1H), 3.64 (dt, J = 13.50, 7.05 Hz, 1H), 3.83 (d, J = 6.25 Hz, 2H), 6.13 (s, 1H), 7.09 (s, 1H), 7.21 (dd, J = 12.29, 2.22 Hz, 1H), 7.25 (dd, J = 2.22, 1.41 Hz, 1H) | 427 | 425 |
| 195 | (400 MHz, DMSO-D₆) 0.72 (d, J = 6.85 Hz, 3H), 0.92 (d, J = 6.85 Hz, 6H), 1.03 (d, J = 6.85 Hz, 3H), 1.57-1.62 (m, 2H), 1.60 (s, 3H), 1.78-1.88 (m, 1H), 1.93-2.00 (m, 1H), 2.44 (t, J = 6.85 Hz, 2H), 3.50 (dt, J = 13.50, 6.85 Hz, 1H), 3.64 (dt, J = 13.50, 6.85 Hz, 1H), 4.07 (t, J = 6.45 Hz, 2H), 6.13 (s, 1H), 7.09 (s, 1H), 7.22 (dd, J = 12.29, 2.22 Hz, 1H), 7.26 (dd, J = 2.22, 1.41 Hz, 1H) | 441 | 439 |
| 196 | (400 MHz, DMSO-D₆) 0.71-0.77 (m, 3H), 1.06-1.11 (m, 3H), 1.14-1.18 (m, 6H), 1.61-1.69 (m, 2H), 1.72 (s, 3H), 2.01-2.09 (m, 1H), 2.68-2.77 (m, 2H), 6.39 (s, 1H), 7.36-7.40 (m, 2H), 7.41-7.49 (m, 3H), 7.55-7.58 (m, 1H), 7.91-7.95 (m, 2H), 12.86 (brs, 1H) | 523 | 521 |
| 197 | (400 MHz, CDCl₃) 0.83 (s, 3H), 0.97 (s, 9H), 1.14 (s, 3H), 1.33-1.40 (m, 1H), 1.41-1.48 (m, 2H), 1.97 (s, 3H), 2.11-2.34 (m, 3H), 2.34-2.46 (m, 3H), 2.46-2.57 (m, 1H), 2.59-2.69 (m, 2H), 3.26 (s, 3H), 3.97-4.04 (m, 1H), 4.77-4.87 (m, 1H), 6.22 (s, 1H), 6.81 (brs, 1H), 7.10-7.15 (m, 1H), 7.19-7.22 (m, 1H), 7.32-7.35 (m, 1H) | 505 | 503 |
| 198 | (400 MHz, DMSO-D₆) 0.81 (s, 3H), 0.94 (s, 9H), 0.98 (s, 3H), 1.35-1.40 (m, 3H), 1.74 (s, 3H), 1.76-1.83 (m, 1H), 1.93-1.99 (m, 2H), 2.04-2.08 (m, 2H), 2.25-2.40 (m, 3H), 2.59-2.63 (m, 2H), 3.28 (s, 3H), 3.40 (d, J = 6.45 Hz, 2H), 4.88-4.80 (m, 1H), 6.34 (s, 1H), 6.92 (s, 1H), 7.22 (dd, J = 8.06, 2.01 Hz, 1H), 7.27 (d, J = 8.06 Hz, 1H), 7.32 (d, J = 2.01 Hz, 1H) | 519 | 517 |
| 199 | (400 MHz, CDCl₃) 0.77-0.91 (m, 2H), 0.96-0.99 (m, 9H), 1.40-1.49 (m, 2H), 1.61-1.66 (m, 3H), 1.69-1.76 (m, 1H), 1.77-1.94 (m, 2H), 2.09-2.19 (m, 1H), 2.27-2.37 (m, 1H), 2.43-2.53 (m, 1H), 2.61-2.71 (m, 1H), 2.78-2.92 (m, 1H), 3.47-3.57 (m, 2H), 4.01-4.11 (m, 2H), 4.51-4.63 (m, 1H), 5.12 (brs, | 489 | 487 |

TABLE 4-continued

| Example | ¹H-NMR | MS | |
|---|---|---|---|
| | | M + H or M—Na + H | M − H or M—Na − H |
| | 1H), 5.96 (brs, 1H), 7.15-7.19 (m, 2H), 7.33-7.34 (m, 1H) | | |
| 200 | (400 MHz, CDCl₃) 0.98 (s, 9H), 1.41-1.47 (m, 2H), 1.62-1.66 (m, 3H), 1.79-1.98 (m, 3H), 2.09-2.21 (m, 1H), 2.39-2.54 (m, 5H), 2.62-2.71 (m, 2H), 2.81-2.92 (m, 1H), 3.26-3.30 (m, 3H), 3.99-4.06 (m, 1H), 4.84-4.90 (m, 1H), 4.92-5.02 (m, 1H), 5.98-6.00 (m, 1H), 7.14-7.23 (m, 2H), 7.33-7.36 (m, 1H) | 489 | 487 |
| 201 | (400 MHz, CDCl₃) 0.74-0.85 (m, 6H), 1.05 (s, 9H), 1.47-1.63 (m, 2H), 1.66-1.75 (m, 4H), 2.61-2.68 (m, 2H), 3.59-3.66 (m, 2H), 3.67-3.77 (m, 2H), 5.30 (brs, 1H), 5.79 (s, 1H), 6.56-6.62 (m, 1H), 7.03-7.10 (m, 1H) | 455 | 453 |
| 202 | (400 MHz, CDCl₃) 0.74-0.85 (m, 6H), 0.91-1.01 (m, 6H), 1.45-2.09 (m, 9H), 2.60-2.69 (m, 2H), 3.68-3.78 (m, 2H), 4.00-4.07 (m, 2H), 5.19 (brs, 1H), 5.79 (s, 1H), 6.58-6.65 (m, 1H), 7.03-7.12 (m, 1H) | 455 | 453 |
| 203 | (400 MHz, DMSO-D₆) 0.75-0.80 (m, 3H), 1.09-1.13 (m, 3H), 1.24 (s, 9H), 1.74 (s, 3H), 2.03-2.13 (m, 1H), 4.45 (s, 2H), 6.41 (s, 1H), 7.41-7.54 (m, 5H), 7.58-7.62 (m, 1H), 7.92-7.97 (m, 2H), 12.88 (brs, 1H) | 471 | 469 |
| 204 | (400 MHz, DMSO-D₆) 0.64-0.72 (m, 3H), 0.94 (s, 9H), 0.98-1.03 (m, 3H), 1.35-1.38 (m, 2H), 1.96-2.05 (m, 3H), 2.57-2.65 (m, 2H), 4.48-4.57 (m, 1H), 4.70-4.79 (m, 2H), 6.14 (s, 1H), 7.17-7.36 (m, 6H), 7.84-7.89 (m, 2H), 12.88 (brs, 1H) | 483 | 481 |
| 205 | (400 MHz, DMSO-D₆) 0.95 (s, 9H), 1.34-1.41 (m, 2H), 1.43-1.51 (m, 1H), 1.51-1.54 (m, 3H), 1.57-1.67 (m, 2H), 2.02-2.15 (m, 2H), 2.23-2.34 (m, 4H), 2.58-2.65 (m, 2H), 2.84-2.95 (m, 1H), 3.23-3.28 (m, 2H), 4.32-4.37 (m, 1H), 4.88-4.99 (m, 1H), 6.17 (s, 1H), 7.12-7.14 (m, 1H), 7.18-7.24 (m, 1H), 7.26-7.31 (m, 2H), 12.24 (brs, 1H) | 489 | 487 |
| 206 | (400 MHz, CDCl₃) 0.94-1.01 (m, 9H), 1.40-1.49 (m, 2H), 1.53-1.68 (m, 5H), 2.05-2.17 (m, 1H), 2.17-2.29 (m, 1H), 2.29-2.43 (m, 1H), 2.58-2.69 (m, 5H), 3.20-3.24 (m, 2H), 3.27-3.30 (m, 3H), 3.66-3.79 (m, 1H), 3.79-3.90 (m, 1H), 5.53-5.64 (m, 1H), 5.79-5.82 (m, 1H), 7.12-7.23 (m, 2H), 7.31-7.36 (m, 1H) | 477 | 475 |
| 207 | (400 MHz, DMSO-D₆) 0.68-0.72 (m, 3H), 0.96 (s, 9H), 1.03-1.09 (m, 3H), 1.37-1.43 (m, 2H), 1.73 (s, 3H), 1.98-2.08 (m, 1H), 2.61-2.69 (m, 2H), 6.20 (s, 1H), 7.32-7.46 (m, 3H), 7.46-7.49 (m, 1H), 7.51-7.56 (m, 1H), 7.65-7.72 (m, 1H), 7.72-7.78 (m, 1H) | 487 | 485 |
| 208 | (400 MHz, CDCl₃) 0.68-0.79 (m, 3H), 0.98 (brs, 9H), 1.03-1.09 (m, 3H), 1.39-1.49 (m, 2H), 1.72-1.80 (m, 3H), 1.87-2.00 (m, 1H), 2.61-2.72 (m, 2H), 5.51-5.77 (m, 1H), 6.00-6.10 (m, 1H), 7.00-7.12 (m, 1H), 7.14-7.24 (m, 1H), 7.28-7.35 (m, 1H), 7.37-7.51 (m, 2H), 7.84-7.99 (m, 1H) | 487 | 485 |
| 209 | (400 MHz, DMSO-D₆) 0.75-0.79 (m, 3H), 0.79-0.83 (m, 3H), 0.95 (s, 9H), 1.34-1.44 (m, 4H), 1.66 (s, 3H), 1.84-1.95 (m, 2H), 2.60-2.67 (m, 2H), 3.15 (s, 3H), 3.24-3.29 (m, 2H), 6.39 (s, 1H), 7.32-7.36 (m, 2H), 7.41-7.44 (m, 2H), 7.44-7.46 (m, 1H), 7.64-7.69 (m, 1H), 7.91-7.97 (m, 2H) | 541 | 539 |
| 210 | (400 MHz, DMSO-D₆) 0.96 (s, 9H), 1.35-1.43 (m, 2H), 1.69 (s, 3H), 1.96-2.09 (m, 1H), 2.13-2.22 (m, 1H), 2.60-2.69 (m, 2H), 3.12 (s, 3H), 3.18-3.29 (m, 2H), 6.39 (s, 1H), 7.32-7.39 (m, 2H), 7.42-7.48 (m, 3H), 7.63-7.67 (m, 1H), 7.90-7.97 (m, 2H), 12.89 (brs, 1H) | 485 | 483 |
| 211 | (400 MHz, CDCl₃) 0.98 (s, 9H), 1.40-1.48 (m, 2H), 1.68 (s, 3H), 1.84-1.95 (m, 1H), 2.00-2.11 (m, 1H), 2.59-2.70 (m, 4H), 3.14-3.27 (m, 5H), 3.67-3.88 (m, 2H), 5.53 (brs, 1H), 5.91-5.93 (m, 1H), 7.15-7.19 (m, 1H), 7.22-7.26 (m, 1H), 7.37-7.39 (m, 1H) | 437 | 435 |
| 212 | (400 MHz, DMSO-D₆) 0.72 (d, J = 6.94 Hz, 3H), 0.92 (s, 9H), 1.03 (d, J = 6.94 Hz, 3H), 1.32-1.38 (m, 2H), 1.61 (s, 3H), 1.91-1.98 (m, 1H), 2.43-2.49 (m, 4H), 3.45-3.52 (m, 1H), 3.61-3.69 (m, 1H), 3.75 (s, 3H), 6.08 (s, 1H), 6.87 (dd, J = 7.74, 1.73 Hz, 1H), 6.89-6.92 (m, 2H), 7.05 (d, J = 7.86 Hz, 1H), 12.24 (s, 1H) | 417 | 415 |

TABLE 4-continued

| Example | ¹H-NMR | MS M + H or M—Na + H | MS M − H or M—Na − H |
|---|---|---|---|
| 213 | (400 MHz, DMSO-D₆) 0.72 (d, J = 6.94 Hz, 3H), 0.92 (s, 9H), 1.03 (d, J = 6.94 Hz, 3H), 1.32-1.38 (m, 2H), 1.61 (s, 3H), 1.94 (t, J = 6.70 Hz, 1H), 2.43-2.49 (m, 4H), 3.45-3.52 (m, 1H), 3.62-3.69 (m, 1H), 3.75 (s, 3H), 6.08 (s, 1H), 6.87 (dd, J = 7.74, 1.73 Hz, 1H), 6.89-6.92 (m, 2H), 7.05 (d, J = 7.86 Hz, 1H), 12.26 (s, 1H) | 417 | 415 |
| 214 | (400 MHz, CDCl₃) 0.70 (d, J = 6.94 Hz, 3H), 1.03 (t, J = 5.20 Hz, 6H), 1.06 (d, J = 6.70 Hz, 6H), 1.88 (tt, J = 19.19, 6.40 Hz, 2H), 2.66 (t, J = 6.24 Hz, 2H), 2.80 (d, J = 6.94 Hz, 2H), 3.76 (t, J = 6.47 Hz, 2H), 5.19 (s, 1H), 5.86 (s, 1H), 7.18 (d, J = 8.32 Hz, 1H), 7.28 (dd, J = 8.44, 1.97 Hz, 1H), 7.39 (d, J = 2.08 Hz, 1H) | 425 | 423 |
| 215 | (400 MHz, CDCl₃) 0.69 (t, J = 6.59 Hz, 3H), 1.06 (d, J = 6.70 Hz, 6H), 1.20 (d, J = 6.70 Hz, 6H), 1.88 (dt, J = 19.34, 6.70 Hz, 2H), 2.60 (tt, J = 17.11, 5.39 Hz, 2H), 2.83 (dd, J = 12.95, 9.94 Hz, 2H), 3.76 (ddd, J = 44.74, 20.46, 12.60 Hz, 2H), 5.69 (d, J = 27.51 Hz, 1H), 5.91 (s, 1H), 7.45 (dd, J = 18.84, 1.73 Hz, 1H), 7.58 (ddd, J = 20.29, 8.38, 1.79 Hz, 1H), 7.86 (dd, J = 10.52, 8.21 Hz, 1H) | 441 | 439 |
| 216 | ¹H-NMR (CDCl₃) δ: 0.71 (d, J = 6.94 Hz, 3H), 0.87 (t, J = 3.24 Hz, 6H), 1.07 (d, J = 6.94 Hz, 6H), 1.51-1.68 (m, 2H), 1.86 (dd, J = 13.64, 6.70 Hz, 2H), 2.58 (dt, J = 8.71, 3.29 Hz, 2H), 3.36-3.40 (m, 2H), 3.69-3.85 (m, 2H), 5.82 (s, 1H), 5.92 (s, 1H), 7.54 (dd, J = 8.32, 1.85 Hz, 1H), 7.63 (d, J = 1.85 Hz, 1H), 8.06 (d, J = 8.32 Hz, 1H). | 471 | 469 |
| 217 | (400 MHz, CDCl₃) 0.71 (d, J = 6.94 Hz, 3H), 0.87 (t, J = 3.24 Hz, 6H), 1.07 (d, J = 6.94 Hz, 6H), 1.51-1.68 (m, 2H), 1.86 (dd, J = 13.64, 6.70 Hz, 2H), 2.58 (dt, J = 8.71, 3.29 Hz, 2H), 3.36-3.40 (m, 2H), 3.69-3.85 (m, 2H), 5.82 (s, 1H), 5.92 (s, 1H), 7.54 (dd, J = 8.32, 1.85 Hz, 1H), 7.63 (d, J = 1.85 Hz, 1H), 8.06 (d, J = 8.32 Hz, 1H) | 455 | 453 |
| 218 | (400 MHz, CDCl₃) 0.70 (d, J = 6.70 Hz, 3H), 0.93 (d, J = 6.70 Hz, 6H), 1.04 (d, J = 6.94 Hz, 3H), 1.57 (dd, J = 15.37, 6.82 Hz, 5H), 1.72-1.89 (m, 2H), 2.66 (t, J = 6.36 Hz, 2H), 2.92 (t, J = 7.74 Hz, 2H), 3.76 (td, J = 6.30, 2.62 Hz, 2H), 5.24 (s, 1H), 5.86 (s, 1H), 7.19 (d, J = 8.32 Hz, 1H), 7.29 (dd, J = 8.32, 2.08 Hz, 1H), 7.40 (d, J = 1.85 Hz, 1H) | 439 | 437 |
| 219 | (400 MHz, CDCl₃) 0.71 (d, J = 6.94 Hz, 3H), 0.99-1.08 (m, 9H), 1.83-1.90 (m, 3H), 2.18-2.28 (m, 2H), 2.52-2.60 (m, 2H), 3.28 (d, J = 6.47 Hz, 2H), 3.67-3.86 (m, 2H), 5.92 (d, J = 5.32 Hz, 2H), 7.54 (dd, J = 8.44, 1.73 Hz, 1H), 7.62 (d, J = 1.85 Hz, 1H), 8.07 (d, J = 8.32 Hz, 1H) | 457 | 455 |
| 220 | (400 MHz, DMSO-D₆) 0.61-0.77 (m, 3H), 0.95 (s, 9H), 0.99-1.10 (m, 3H), 1.35-1.43 (m, 2H), 1.71 (s, 3H), 2.02-2.18 (m, 4H), 2.60-2.69 (m, 2H), 5.91-6.04 (m, 1H), 6.95-7.05 (m, 1H), 7.18-7.45 (m, 3H), 7.46-7.49 (m, 1H), 7.62-7.67 (m, 1H), 7.67-7.75 (m, 1H) | 483 | 481 |
| 221 | (400 MHz, DMSO-D₆) 0.65-0.70 (m, 3H), 0.94 (s, 9H), 1.00-1.06 (m, 3H), 1.36-1.43 (m, 2H), 1.71 (s, 3H), 1.95-2.05 (m, 1H), 2.60-2.68 (m, 2H), 3.87 (s, 3H), 5.98 (s, 1H), 7.29-7.36 (m, 3H), 7.37-7.44 (m, 1H), 7.52-7.60 (m, 1H), 13.03 (brs, 1H) | 499 | 497 |
| 222 | (400 MHz, CDCl₃) 0.71-0.77 (m, 3H), 0.98 (s, 9H), 1.03-1.10 (m, 3H), 1.40-1.49 (m, 2H), 1.71 (s, 3H), 1.87-1.97 (m, 1H), 2,63-2.72 (m, 2H), 4.17-4.26 (m, 3H), 4.27-4.35 (m, 3H), 5.35 (brs, 1H), 5.91 (s, 1H), 7.14-7.21 (m, 1H), 7.23-7.28 (m, 1H), 7.38-7.41 (m, 1H) | 495 | 493 |
| 223 | (400 MHz, CDCl₃) 0.66 (dd, J = 9.02, 6.94 Hz, 3H), 1.05 (dd, J = 6.82, 1.50 Hz, 3H), 1.31-2.07 (m, 20H), 2.61-2.67 (m, 2H), 3.42 (t, J = 7.86 Hz, 1H), 3.70-3.84 (m, 2H), 5.53 (d, J = 15.95 Hz, 1H), 5.90 (d, J = 3.24 Hz, 1H), 7.44 (dd, J = 17.57, 1.85 Hz, 1H), 7.54 (tt, J = 13.18, 3.74 Hz, 1H), 7.78 (dd, J = 10.06, 8.21 Hz, 1H) | 453 | 451 |
| 224 | (400 MHz, CDCl₃) 0.70 (d, J = 6.94 Hz, 3H), 1.04 (d, J = 6.94 Hz, 3H), 1.54-1.89 (m, 0H), 2.10 (t, J = 7.86 Hz, 2H), 2.67 (t, J = 6.24 Hz, 2H), 3.76 (t, J = 6.24 Hz, 2H), | 437 | 435 |

TABLE 4-continued

| Example | ¹H-NMR | MS M + H or M—Na + H | MS M − H or M—Na − H |
|---|---|---|---|
| | 5.19 (s, 1H), 5.87 (s, 1H), 7.28 (t, J = 2.08 Hz, 2H), 7.39 (s, 1H) | | |
| 225 | (400 MHz, CDCl₃) 0.97 (s, 9H), 1.41-1.49 (m, 2H), 1.71 (s, 3H), 2.63-2.70 (m, 2H), 3.39 (s, 3H), 3.54-3.63 (m, 3H), 3.82-3.95 (m, 1H), 5.43-5.55 (m, 1H), 6.44 (s, 1H), 6.96-7.01 (m, 2H), 7.15-7.21 (m, 1H), 7.25-7.30 (m, 1H), 7.43-7.46 (m, 1H), 7.83-7.87 (m, 2H) | 485 | 483 |
| 226 | (400 MHz, CDCl₃) 0.76-0.81 (m, 3H), 0.99 (s, 9H), 1.10-1.14 (m, 3H), 1.42-1.49 (m, 2H), 1.82 (s, 3H), 1.95-2.04 (m, 1H), 2.66-2.72 (m, 2H), 4.11 (s, 3H), 4.93 (brs, 1H), 6.23 (s, 3H), 7.00-7.05 (m, 1H), 7.20-7.25 (m, 1H), 7.29-7.34 (m, 1H), 7.36-7.40 (m, 1H), 7.45-7.48 (m, 1H), 8.20-8.25 (m, 1H) | 499 | 497 |
| 227 | (400 MHz, CDCl₃) 0.70 (d, J = 6.94 Hz, 3H), 1.07 (d, J = 6.70 Hz, 3H), 1.64 (d, J = 7.17 Hz, 5H), 1.83 (dt, J = 17.42, 7.63 Hz, 4H), 2.05 (t, J = 11.33 Hz, 2H), 2.57 (dd, J = 9.13, 6.59 Hz, 2H), 3.77 (ddd, J = 25.72, 13.24, 6.65 Hz, 2H), 4.07 (t, J = 7.40 Hz, 1H), 5.83 (s, 1H), 5.91 (s, 1H), 7.50-7.54 (m, 1H), 7.62 (d, J = 1.85 Hz, 1H), 8.06 (d, J = 8.32 Hz, 1H) | 469 | 467 |
| 228 | (400 MHz, CDCl₃) 0.74 (d, J = 6.85 Hz, 3H), 0.96-1.10 (m, 4H), 0.98 (s, 9H), 1.07 (d, J = 6.85 Hz, 3H), 1.46-1.42 (m, 2H), 1.68 (s, 3H), 1.87-1.93 (m, 1H), 2.64-2.69 (m, 2H), 2.72 (s, 2H), 5.45 (s, 1H), 5.98 (s, 1H), 7.18 (d, J = 8.06 Hz, 1H), 7.21 (dd, J = 8.06, 1.61 Hz, 1H), 7.33 (d, J = 1.61 Hz, 1H) | 447 | 445 |
| 229 | (400 MHz, CDCl₃) 0.98 (s, 9H), 1.42-1.47 (m, 2H), 1.64 (s, 3H), 1.81-1.92 (m, 2H), 2.09-2.17 (m, 1H), 2.28-2.38 (m, 1H), 2.45-2.54 (m, 1H), 2.65-2.69 (m, 2H), 2.78-2.91 (m, 3H), 2.94-3.04 (m, 2H), 4.66-4.76 (m, 1H), 4.99 (s, 1H), 5.95 (s, 1H), 7.21-7.17 (m, 2H), 7.34 (s, 1H) | 495 | 493 |
| 230 | (400 MHz, CDCl₃) 0.98 (s, 9H), 1.14-1.19 (m, 6H), 1.40-1.48 (m, 2H), 1.67 (s, 3H), 1.99-2.11 (m, 1H), 2.13-2.37 (m, 3H), 2.61-2.70 (m, 2H), 4.59-4.70 (m, 1H), 5.83 (s, 1H), 5.90 (s, 1H), 7.13-7.22 (m, 2H), 7.32-7.37 (m, 1H) | 421 | 419 |
| 231 | (400 MHz, MeOH-D₄) 1.01 (s, 9H), 1.44-1.51 (m, 2H), 1.84 (s, 3H), 2.19-2.38 (m, 4H), 2.70-2.76 (m, 2H), 6.50 (s, 1H), 7.27-7.33 (m, 1H), 7.38-7.43 (m, 1H), 7.48-7.51 (m, 1H), 7.56-7.60 (m, 2H), 8.49-8.55 (m, 2H) | 456 | 454 |
| 232 | (400 MHz, DMSO-D₆) 0.70-0.76 (m, 3H), 0.93 (s, 9H), 1.03-1.07 (m, 3H), 1.32-1.41 (m, 2H), 1.57 (s, 3H), 1.91-2.26 (m, 9H), 2.57-2.63 (m, 2H), 4.46-4.59 (m, 1H), 6.15 (s, 1H), 7.01 (brs, 1H), 7.19-7.23 (m, 1H), 7.25-7.32 (m, 2H) | 487 | 475 |
| 233 | (400 MHz, DMSO-D₆) 0.69-0.75. (m, 3H), 0.93 (s, 9H), 1.02-1.08 (m, 3H), 1.32-1.40 (m, 2H), 1.58 (s, 3H), 1.84-2.20 (m, 9H), 2.56-2.64 (m, 2H), 4.46-4.58 (m, 1H), 6.14 (s, 1H), 7.00 (brs, 1H), 7.18-7.24 (m, 1H), 7.24-7.31 (m, 2H) | 487 | 485 |
| 234 | (400 MHz, CDCl₃) 0.75 (d, J = 6.85 Hz, 3H), 0.98 (s, 9H), 1.08 (d, J = 6.85 Hz, 3H), 1.42-1.46 (m, 2H), 1.71 (s, 3H), 1.74-1.89 (m, 3H), 1.94-2.11 (m, 4H), 2.63-2.68 (m, 2H), 2.80 (td, J = 8.46, 8.06 Hz, 1H), 4.89 (td, J = 7.25, 8.06 Hz, 1H), 5.27 (s, 1H), 5.93 (s, 1H), 7.17 (d, J = 8.06 Hz, 1H), 7.23 (dd, J = 8.06, 2.01 Hz, 1H), 7.36 (d, J = 2.01 Hz, 1H) | 461 | 459 |
| 235 | (400 MHz, DMSO-D₆) 0.65 (d, J = 6.85 Hz, 3H), 0.95 (s, 9H), 1.01 (d, J = 6.85 Hz, 3H), 1.22-1.46 (m, 5H), 1.55 (s, 3H), 1.57-1.67 (m, 3H), 1.69-1.78 (m, 1H), 1.79-1.94 (m, 2H), 2.45-2.53 (m, 1H), 2.60-2.65 (m, 2H), 4.11-4.26 (m, 1H), 6.10 (s, 1H), 6.79 (s, 1H), 7.26 (dd, J = 8.06, 1.61 Hz, 1H), 7.29 (d, J = 8.06 Hz, 1H), 7.34 (d, J = 1.61 Hz, 1H) | 475 | 473 |
| 236 | (400 MHz, DMSO-D₆) 0.67-0.74 (m, 3H), 0.95 (s, 9H), 1.01-1.06 (m, 3H), 1.14-1.20 (m, 3H), 1.34-1.42 (m, 2H), 1.58 (s, 3H), 1.87-1.99 (m, 1H), 2.52-2.57 (m, 2H), 2.58-2.66 (m, 2H), 4.55-4.70 (m, 1H), 6.11 (s, 1H), 6.93-6.96 (m, 1H), 7.23-7.32 (m, 2H), 7.32-7.36 (m, 1H), 12.21 (brs, 1H) | 435 | 433 |
| 237 | (400 MHz, DMSO-D₆) 0.65-0.73 (m, 3H), 0.95 (s, 9H), 1.02-1.07 (m, 3H), 1.35-1.40 (m, 2H), 1.42 (s, | 562 | 560 |

TABLE 4-continued

| Example | ¹H-NMR | MS M + H or M—Na + H | MS M − H or M—Na − H |
|---|---|---|---|
| | 9H), 1.56-1.64 (m, 3H), 1.86-1.97 (m, 1H), 2.59-2.66 (m, 2H), 3.24-3.43 (m, 4H), 3.45-3.56 (m, 1H), 3.56-3.67 (m, 1H), 4.85-5.03 (m, 1H), 6.18-6.30 (m, 1H), 7.11-7.18 (m, 1H), 7.23-7.39 (m, 3H), 12.63 (brs, 1H) | | |
| 238 | (400 MHz, DMSO-D₆) 0.65-0.73 (m, 3H), 0.95 (s, 9H), 1.02-1.08 (m, 3H), 1.35-1.42 (m, 2H), 1.59-1.68 (m, 3H), 2.59-2.66 (m, 2H), 3.25-3.52 (m, 5H), 3.58-3.68 (m, 1H), 4.77-5.03 (m, 1H), 6.20-6.29 (m, 1H), 7.24-7.42 (m, 4H), 8.87-9.22 (m, 1H) | 462 | 460 |
| 239 | (400 MHz, DMSO-D₆) 0.64-0.71 (m, 3H), 0.94 (s, 9H), 1.00-1.07 (m, 3H), 1.32-1.41 (m, 2H), 1.56-1.63 (m, 3H), 1.83-1.96 (m, 4H), 2.57-2.65 (m, 2H), 3.30-3.36 (m, 1H), 3.39-3.64 (m, 2H), 3.66-3.89 (m, 2H), 4.80-5.13 (m, 1H), 6.13-6.32 (m, 1H), 7.10-7.16 (m, 1H), 7.22-7.39 (m, 2H), 12.62 (brs, 1H) | 504 | 502 |
| 240 | (400 MHz, DMSO-D₆) 0.65-0.72 (m, 3H), 0.93 (s, 9H), 1.00-1.06 (m, 3H), 1.33-1.41 (m, 2H), 1.60 (s, 3H), 1.86-2.00 (m, 1H), 2.57-2.64 (m, 2H), 2.91-2.96 (m, 3H), 3.08-3.26 (m, 2H), 3.38-3.52 (m, 2H), 3.52-3.59 (m, 1H), 4.81-5.02 (m, 1H), 6.19 (s, 1H), 7.08-7.15 (m, 1H), 7.22-7.31 (m, 2H), 7.31-7.37 (m, 1H) | 540 | 538 |
| 241 | (400 MHz, DMSO-D₆) 0.95 (s, 9H), 1.30-1.40 (m, 3H), 1.48-1.59 (m, 2H), 1.52 (s, 3H), 2.02-2.09 (m, 2H), 2.35-2.43 (m, 3H), 2.60-2.64 (m, 2H), 3.22 (d, J = 5.64 Hz, 2H), 3.48-3.55 (m, 1H), 3.57-3.65 (m, 1H), 6.03 (s, 1H), 7.02 (s, 1H), 7.22 (dd, J = 8.06, 2.01 Hz, 1H), 7.28 (d, J = 8.06 Hz, 1H), 7.31 (d, J = 2.01 Hz, 1H) | 463 | 461 |
| 242 | (400 MHz, DMSO-D₆) 0.68-0.73 (m, 3H), 0.95 (s, 9H), 1.02-1.07 (m, 3H), 1.33-1.42 (m, 2H), 1.47-2.00 (m, 9H), 2.53-2.57 (m, 2H), 2.58-2.66 (m, 2H), 4.67-4.78 (m, 1H), 6.04-6.08 (m, 1H), 6.90-6.95 (m, 1H), 7.22-7.36 (m, 3H) | 461 | 459 |
| 243 | (400 MHz, DMSO-D₆) 0.68-0.73 (m, 3H), 0.95 (s, 9H), 1.02-1.07 (m, 3H), 1.33-1.42 (m, 2H), 1.47-2.00 (m, 9H), 2.53-2.57 (m, 2H), 2.58-2.66 (m, 2H), 4.67-4.78 (m, 1H), 6.04-6.08 (m, 1H), 6.90-6.95 (m, 1H), 7.22-7.36 (m, 3H) | 461 | 459 |
| 244 | (400 MHz, CDCl₃) 0.85-0.89 (m, 3H), 0.97 (s, 9H), 1.08-1.13 (m, 3H), 1.29-1.35 (m, 3H), 1.40-1.47 (m, 2H), 1.85 (s, 3H), 2.59-2.69 (m, 2H), 3.28-3.66 (m, 5H), 3.77-3.92 (m, 1H), 4.20-4.30 (m, 2H), 4.30-4.38 (m, 1H), 5.95 (s, 1H), 7.12-7.20 (m, 1H), 7.28-7.36 (m, 1H), 7.60-7.69 (m, 1H), 8.66 (brs, 1H), 11.57 (brs, 1H) | 490 | 488 |
| 245 | (400 MHz, CDCl₃) 0.78-0.82 (m, 3H), 0.97 (s, 9H), 1.04-1.12 (m, 3H), 1.22-1.35 (m, 3H), 1.38-1.52 (m, 2H), 1.80 (s, 3H), 2.57-2.72 (m, 3H), 3.36-3.71 (m, 5H), 3.72-3.91 (m, 1H), 4.20-4.30 (m, 2H), 4.35-4.47 (m, 1H), 5.95 (s, 1H), 7.03-7.10 (m, 1H), 7.13-7.20 (m, 1H), 7.23-7.26 (m, 1H), 7.30-7.35 (m, 1H), 8.79 (brs, 1H), 10.94 (brs, 1H) | 490 | 488 |
| 246 | (400 MHz, DMSO-D₆) 0.95 (s, 9H), 1.35-1.40 (m, 2H), 1.53 (s, 3H), 1.58-1.70 (m, 2H), 1.74-2.11 (m, 9H), 2.23-2.31 (m, 1H), 2.55 (d, J = 9.27 Hz, 1H), 2.60-2.64 (m, 2H), 2.73-2.82 (m, 1H), 4.27-4.20 (m, 1H), 5.97 (s, 1H), 7.18 (s, 1H), 7.21 (dd, J = 7.86, 1.81 Hz, 1H), 7.29 (d, J = 8.06 Hz, 1H), 7.31 (d, J = 2.01 Hz, 1H) | 523 | 521 |
| 247 | (400 MHz, DMSO-D₆) 0.67-0.73 (m, 3H), 0.92 (s, 9H), 1.01-1.06 (m, 3H), 1.13-1.19 (m, 3H), 1.32-1.41 (m, 2H), 1.58 (s, 3H), 1.89-2.01 (m, 1H), 2.50-2.54 (m, 2H), 2.56-2.67 (m, 2H), 4.54-4.69 (m, 1H), 6.10 (s, 1H), 6.92-6.98 (m, 1H), 7.21-7.29 (m, 2H), 7.29-7.35 (m, 1H), 12.16 (brs, 1H) | 435 | 433 |
| 248 | (400 MHz, CDCl₃) 0.98 (s, 9H), 1.42-1.46 (m, 2H), 1.63 (s, 3H), 1.82-1.91 (m, 2H), 2.11 (q, J = 10.21 Hz, 1H), 2.29-2.55 (m, 5H), 2.61-2.72 (m, 4H), 2.81-2.90 (m, 1H), 3.63 (d, J = 7.25 Hz, 2H), 5.09 (s, 1H), 5.83 (s, 1H), 7.18-7.16 (m, 2H), 7.32 (s, 1H) | 509 | 507 |
| 249 | (400 MHz, DMSO-D₆) 0.95 (s, 9H), 1.36-1.40 (m, 2H), 1.53 (s, 3H), 1.70 (t, J = 10.00 Hz, 2H), 1.89-1.96 (m, 1H), 2.18-2.25 (m, 1H), 2.29-2.35 (m, 2H), 2.43- | 476 | 474 |

TABLE 4-continued

| Example | $^1$H-NMR | MS M + H or M—Na + H | MS M − H or M—Na − H |
|---|---|---|---|
| | 2.53 (m, 1H), 2.60-2.75 (m, 3H), 3.49-3.56 (m, 1H), 3.58-3.66 (m, 1H), 6.03 (s, 1H), 6.86 (s, 1H), 7.06 (s, 1H), 7.23 (dd, J = 1.61, 8.06 Hz, 1H), 7.29 (d, J = 8.06 Hz, 1H), 7.31 (d, J = 2.01 Hz, 1H), 7.37 (s, 1H) | | |
| 250 | (400 MHz, DMSO-D$_6$) 0.72-0.85 (m, 4H), 0.95 (s, 9H), 1.35-1.40 (m, 2H), 1.52 (s, 3H), 1.67 (q, J = 10.21 Hz, 1H), 1.73-1.81 (m, 1H), 1.91 (q, J = 10.07 Hz, 1H), 2.21-2.29 (m, 1H), 2.46-2.53 (m, 1H), 2.60-2.64 (m, 2H), 2.72-2.78 (m, 1H), 3.28 (s, 3H), 3.34-3.44 (m, 2H), 5.93 (s, 1H), 7.03 (s, 1H), 7.21 (dd, J = 2.01, 8.06 Hz, 1H), 7.29-7.27 (m, 2H) | 489 | 487 |
| 251 | (400 MHz, CDCl$_3$) 0.98 (s, 9H), 1.17 (s, 3H), 1.21 (s, 3H), 1.42-1.46 (m, 2H), 1.62 (s, 3H), 1.83-1.97 (m, 4H), 2.10-2.18 (m, 3H), 2.28-2.36 (m, 1H), 2.44-2.52 (m, 1H), 2.63-2.68 (m, 2H), 2.80-2.89 (m, 1H), 4.79-4.88 (m, 1H), 5.27 (s, 1H), 6.06 (s, 1H), 7.15 (d, J = 8.06 Hz, 1H), 7.19 (dd, J = 8.06, 1.61 Hz, 1H), 7.33 (d, J = 1.61 Hz, 1H) | 487 | 485 |
| 252 | (400 MHz, CDCl$_3$) 0.98 (s, 9H), 1.41-1.48 (m, 2H), 1.79 (s, 3H), 1.98-2.24 (m, 2H), 2.32-2.57 (m, 2H), 2.61-2.74 (m, 3H), 5.45 (brs, 1H), 6.20 (s, 1H), 7.20-7.24 (m, 1H), 7.26-7.31 (m, 1H), 7.40-7.55 (m, 3H), 8.05-8.20 (m, 2H) | 517 | 515 |
| 253 | (400 MHz, DMSO-D$_6$) 0.64 (d, J = 6.70 Hz, 3H), 0.93 (s, 9H), 1.01 (d, J = 6.70 Hz, 3H), 1.42 (dt, J = 8.55, 4.16 Hz, 2H), 1.60 (s, 3H), 1.86-1.94 (m, 1H), 2.42-2.54 (m, 4H), 3.48-3.56 (m, 1H), 3.57-3.65 (m, 1H), 6.05 (s, 1H), 6.90 (s, 1H), 7.14 (d, J = 8.09 Hz, 2H), 7.28 (d, J = 8.09 Hz, 2H), 12.26-12.29 (m, 1H) | 387 | 385 |
| 254 | (400 MHz, DMSO-D$_6$) 0.67-0.73 (m, 3H), 0.93 (s, 9H), 1.00-1.06 (m, 3H), 1.32-1.54 (m, 4H), 1.55-1.66 (m, 4H), 1.70-1.81 (m, 1H), 1.83-2.02 (m, 3H), 2.56-2.63 (m, 2H), 2.74-2.80 (m, 1H), 4.21-4.33 (m, 1H), 6.09 (s, 1H), 6.94 (s, 1H), 7.19-7.25 (m, 1H), 7.25-7.29 (m, 1H), 7.30-7.33 (m, 1H), 12.18 (brs, 1H) | 475 | 473 |
| 255 | (400 MHz, DMSO-D$_6$) 0.68-0.74 (m, 3H), 0.93 (s, 9H), 1.01-1.07 (m, 3H), 1.31-1.44 (m, 4H), 1.44-1.54 (m, 2H), 1.55-1.67 (m, 4H), 1.70-1.81 (m, 1H), 1.83-2.02 (m, 3H), 2.57-2.64 (m, 2H), 4.22-4.33 (m, 1H), 6.10 (s, 1H), 6.94 (s, 1H), 7.19-7.24 (m, 1H), 7.24-7.29 (m, 1H), 7.29-7.33 (m, 1H), 12.19 (brs, 1H) | 475 | 473 |
| 256 | (400 MHz, DMSO-D$_6$) 0.67-0.73 (m, 3H), 0.93 (s, 9H), 1.00-1.06 (m, 3H), 1.32-1.54 (m, 4H), 1.55-1.66 (m, 4H), 1.70-1.81 (m, 1H), 1.83-2.02 (m, 3H), 2.56-2.63 (m, 2H), 2.74-2.80 (m, 1H), 4.21-4.33 (m, 1H), 6.09 (s, 1H), 6.94 (s, 1H), 7.19-7.25 (m, 1H), 7.25-7.29 (m, 1H), 7.30-7.33 (m, 1H), 12.18 (brs, 1H) | 475 | 473 |
| 257 | (400 MHz, DMSO-D$_6$) 0.68-0.74 (m, 3H), 0.93 (s, 9H), 1.01-1.07 (m, 3H), 1.31-1.44 (m, 4H), 1.44-1.54 (m, 2H), 1.55-1.67 (m, 4H), 1.70-1.81 (m, 1H), 1.83-2.02 (m, 3H), 2.57-2.64 (m, 2H), 4.22-4.33 (m, 1H), 6.10 (s, 1H), 6.94 (s, 1H), 7.19-7.24 (m, 1H), 7.24-7.29 (m, 1H), 7.29-7.33 (m, 1H), 12.19 (brs, 1H) | 475 | 473 |
| 258 | (400 MHz, DMSO-D$_6$) 0.69 (d, J = 6.70 Hz, 3H), 0.80 (d, J = 6.70 Hz, 6H), 1.02 (d, J = 6.70 Hz, 3H), 1.37-1.48 (m, 1H), 1.60-1.69 (m, 2H), 1.60 (s, 3H), 1.83-1.97 (m, 2H), 2.38-2.48 (m, 4H), 3.37-3.46 (m, 1H), 3.52 (ddd, J = 6.80, 7.20, 14.00 Hz, 1H), 3.62 (ddd, J = 6.80, 7.20, 14.00 Hz, 1H), 6.11 (s, 1H), 7.03 (s, 1H), 7.29-7.34 (m, 3H), 12.30 (brs, 1H) | 433 | 431 |
| 259 | (400 MHz, CDCl$_3$) 0.75 (d, J = 6.85 Hz, 3H), 0.98 (s, 9H), 1.04 (d, J = 6.85 Hz, 3H), 1.42-1.47 (m, 2H), 1.56 (s, 3H), 1.58 (s, 3H), 1.67 (s, 3H), 1.90-1.97 (m, 1H), 2.64-2.69 (m, 2H), 3.11 (d, J = 14.51 Hz, 1H), 3.19 (d, J = 14.91 Hz, 1H), 4.97 (s, 1H), 6.16 (s, 1H), 7.18 (d, J = 8.06 Hz, 1H), 7.25 (d, J = 8.06 Hz, 1H), 7.38 (d, J = 2.01 Hz, 1H) | 449 | 447 |
| 260 | (400 MHz, CDCl$_3$) 0.71 (d, J = 6.94 Hz, 3H), 0.98 (s, 6H), 1.05 (d, J = 6.94 Hz, 3H), 1.49-1.54 (m, 2H), 1.70 (s, 3H), 1.84-1.91 (m, 1H), 2.70-2.65 (m, 4H), 3.40 (s, 2H), 3.75-3.77 (m, 2H), 5.28 (s, 1H), 5.87 (s, 1H), | 437 | 435 |

TABLE 4-continued

| Example | ¹H-NMR | MS M + H or M—Na + H | MS M − H or M—Na − H |
|---|---|---|---|
| | 7.19 (d, J = 8.09 Hz, 1H), 7.26 (dd, J = 8.09, 1.85 Hz, 1H), 7.38 (d, J = 1.85 Hz, 1H) | | |
| 261 | (400 MHz, CDCl₃) 0.99 (d, J = 6.94 Hz, 3H), 1.13-1.11 (m, 6H), 1.16 (s, 3H), 1.39-1.66 (m, 2H), 1.80 (s, 3H), 1.91-1.96 (m, 1H), 2.14-2.23 (m, 1H), 2.53-2.58 (m, 1H), 3.31-3.19 (m, 2H), 3.96-4.00 (m, 1H), 6.12 (s, 1H), 6.66-6.69 (m, 1H), 7.13-7.16 (m, 1H), 7.26 (s, 1H) | 451 | 449 |
| 262 | (400 MHz, DMSO-D₆) 0.68-0.76 (m, 3H), 0.93 (s, 9H), 0.99-1.10 (m, 5H), 1.32-1.40 (m, 2H), 1.46-1.62 (m, 7H), 1.63-1.81 (m, 3H), 1.94-2.03 (m, 1H), 2.07-2.11 (m, 2H), 2.57-2.64 (m, 2H), 3.99-4.10 (m, 1H), 6.13 (s, 1H), 6.97 (brs, 1H), 7.20-7.29 (m, 2H), 7.29-7.33 (m, 1H) | 489 | 487 |
| 263 | (400 MHz, CDCl₃) 0.69 (d, J = 6.85 Hz, 3H), 1.05 (d, J = 6.85 Hz, 3H), 1.17-1.26 (m, 2H), 1.50-1.56 (m, 2H), 1.62-1.68 (m, 4H), 1.70 (s, 3H), 1.84-1.91 (m, 1H), 2.13-2.21 (m, 1H), 2.66 (t, J = 6.25 Hz, 2H), 2.71 (d, J = 7.25 Hz, 2H), 3.70-3.84 (m, 2H), 5.28 (s, 1H), 5.86 (s, 1H), 7.17 (d, J = 8.06 Hz, 1H), 7.26-7.24 (m, 1H), 7.38 (d, J = 2.01 Hz, 1H) | 419 | 417 |
| 264 | (400 MHz, CDCl₃) 0.71 (d, J = 6.85 Hz, 3H), 1.05 (d, J = 6.85 Hz, 3H), 1.68-1.77 (m, 4H), 1.71 (s, 3H), 1.85-1.92 (m, 1H), 2.45 (t, J = 7.05 Hz, 2H), 2.53 (t, J = 6.85 Hz, 2H), 2.67 (t, J = 6.25 Hz, 2H), 3.84-3.71 (m, 2H), 5.30 (s, 1H), 5.87 (s, 1H), 6.55 (t, J = 2.01 Hz, 1H), 7.29 (dd, J = 8.06, 2.42 Hz, 1H), 7.39 (d, J = 8.87 Hz, 1H), 7.41 (d, J = 2.01 Hz, 1H) | 417 | 415 |
| 265 | (400 MHz, CDCl₃) 0.98 (s, 9H), 1.44-1.48 (m, 2H), 1.67 (s, 3H), 2.65-2.70 (m, 2H), 2.72 (t, J = 6.04 Hz, 2H), 3.91-3.75 (m, 2H), 5.49 (s, 1H), 6.25 (s, 1H), 6.87 (dd, J = 8.06, 1.61 Hz, 2H), 7.25-7.14 (m, 5H), 7.38 (d, J = 2.01 Hz, 1H) | 455 | 453 |
| 266 | (400 MHz, DMSO-D₆) 0.69-0.76 (m, 3H), 0.94 (s, 9H), 1.04-1.10 (m, 3H), 1.34-1.42 (m, 2H), 1.70 (s, 3H), 1.96-2.09 (m, 1H), 2.43-2.53 (m, 3.H), 2.60-2.67 (m, 2H), 6.29 (s, 1H), 7.06-7.18 (m, 2H), 7.29-7.39 (m, 2H), 7.40-7.46 (m, 2H), 7.64-7.75 (m, 1H) | 483 | 481 |
| 267 | (400 MHz, CDCl₃) 0.71 (d, J = 6.85 Hz, 3H), 1.05 (d, J = 6.85 Hz, 3H), 1.54-1.69 (m, 6H), 1.71 (s, 3H), 1.86-1.93 (m, 1H), 2.22 (t, J = 5.64 Hz, 2H), 2.30 (t, J = 5.64 Hz, 2H), 2.65 (t, J = 6.25 Hz, 2H), 3.71-3.82 (m, 2H), 5.45 (s, 1H), 5.88 (s, 1H), 6.18 (s, 1H), 7.18 (d, J = 8.06 Hz, 1H), 7.28 (dd, J = 8.06, 1.61 Hz, 1H), 7.41 (d, J = 1.61 Hz, 1H) | 431 | 429 |
| 268 | (400 MHz, CDCl₃) 0.69 (d, J = 6.85 Hz, 3H), 0.95-0.98 (m, 2H), 1.04 (d, J = 6.85 Hz, 3H), 1.13-1.22 (m, 3H), 1.60-1.68 (m, 6H), 1.70 (s, 3H), 1.84-1.91 (m, 1H), 2.58 (d, J = 6.85 Hz, 2H), 2.64 (t, J = 6.45 Hz, 2H), 3.83-3.70 (m, 2H), 5.49 (s, 1H), 5.86 (s, 1H), 7.12 (d, J = 8.06 Hz, 1H), 7.24 (dd, J = 8.06, 2.01 Hz, 1H), 7.38 (d, J = 2.01 Hz, 1H) | 433 | 431 |
| 269 | (400 MHz, DMSO-D₆) 0.68-0.74 (m, 3H), 0.94 (s, 9H), 1.00-1.06 (m, 3H), 1.31-1.46 (m, 4H), 1.46-1.53 (m, 2H), 1.57 (s, 3H), 1.71-1.81 (m, 2H), 1.81-1.91 (m, 2H), 1.99-2.05 (m, 1H), 2.08-2.19 (m, 2H), 2.56-2.64 (m, 2H), 6.09 (s, 1H), 6.80 (brs, 1H), 7.20-7.31 (m, 2H), 7.31-7.37 (m, 1H) | 487 | 485 |
| 270 | (400 MHz, DMSO-D₆) 0.62-0.69 (m, 3H), 0.93 (s, 9H), 0.99-1.05 (m, 3H), 1.36-1.43 (m, 2H), 1.63 (s, 3H), 1.84-1.94 (m, 1H), 2.39-2.45 (m, 2H), 2.62-2.69 (m, 2H), 3.45-3.54 (m, 1H), 3.57-3.67 (m, 1H), 6.13 (s, 1H), 7.07 (s, 1H), 7.38-7.43 (m, 1H), 7.54-7.61 (m, 2H), 12.28 (brs, 1H) | 455 | 453 |
| 271 | (400 MHz, DMSO-D₆) 0.70-0.74 (m, 3H), 0.93 (s, 9H), 1.06-1.12 (m, 3H), 1.36-1.44 (m, 2H), 1.75 (s, 3H), 1.98-2.08 (m, 1H), 2.63-2.72 (m, 2H), 6.42 (s, 1H), 7.42-7.50 (m, 3H), 7.60-7.63 (m, 1H), 7.65-7.70 (m, 2H), 7.90-7.96 (m, 2H), 12.89 (brs, 1H) | 503 | 501 |
| 272 | (400 MHz, DMSO-D₆) 0.67-0.73 (m, 3H), 0.95 (s, 9H), 1.01-1.06 (m, 3H), 1.34-1.43 (m, 2H), 1.60 (s, 3H), 1.62-1.84 (m, 8H), 1.95-2.06 (m, 1H), 2.59-2.66 (m, 2H), 5.91 (s, 1H), 6.90 (brs, 1H), 7.22-7.37 (m, 3H) | 473 | 471 |

TABLE 4-continued

| Example | ¹H-NMR | MS M + H or M—Na + H | MS M − H or M—Na − H |
|---|---|---|---|
| 273 | (400 MHz, CDCl₃) 0.98 (s, 9H), 1.44-1.48 (m, 2H), 1.71 (s, 3H), 2.66-2.71 (m, 2H), 3.41 (s, 3H), 3.57-3.61 (m, 3H), 3.88-3.94 (m, 1H), 5.46 (s, 1H), 6.35 (s, 1H), 7.01 (dt, J = 8.46, 2.01 Hz, 1H), 7.19-7.30 (m, 3H), 7.45 (d, J = 2.01 Hz, 1H), 7.74 (t, J = 1.61 Hz, 1H), 7.90 (dt, J = 7.66, 1.41 Hz, 1H) | 485 | 483 |
| 274 | (400 MHz, DMSO-D₆) 0.94 (s, 9H), 1.32-1.41 (m, 2H), 1.55 (s, 3H), 1.73-1.84 (m, 6H), 1.85-1.89 (m, 2H), 1.90-1.99 (m, 1H), 2.01-2.12 (m, 1H), 2.57-2.64 (m, 2H), 3.10 (s, 3H), 3.11-3.25 (m, 2H), 5.93 (s, 1H), 7.04 (brs, 1H), 7.22-7.27 (m, 1H), 7.27-7.32 (m, 1H), 7.32-7.36 (m, 1H), 12.30 (brs, 1H) | 489 | 487 |
| 275 | (400 MHz, DMSO-D₆) 0.95 (s, 9H), 1.38-1.43 (m, 2H), 1.62 (s, 3H), 2.64-2.68 (m, 2H), 3.28 (s, 3H), 3.41-3.53 (m, 3H), 3.80-3.87 (m, 1H), 6.79 (s, 1H), 7.34 (dd, J = 8.06, 1.61 Hz, 1H), 7.37 (d, J = 8.46 Hz, 1H), 7.47 (d, J = 1.21 Hz, 1H), 7.54 (s, 1H), 7.71 (t, J = 2.22 Hz, 1H), 8.39 (d, J = 1.61 Hz, 1H), 8.85 (d, J = 1.21 Hz, 1H) | 486 | 484 |
| 276 | (400 MHz, CDCl₃) 0.97 (s, 9H), 1.39-1.48 (m, 2H), 1.71-1.84 (m, 5H), 2.07-2.23 (m, 2H), 2.63-2.71 (m, 2H), 2.83-2.96 (m, 1H), 3.17 (s, 3H), 3.76-3.85 (m, 1H), 5.45 (brs, 1H), 6.19-6.22 (m, 1H), 7.16-7.22 (m, 1H), 7.23-7.29 (m, 1H), 7.38-7.44 (m, 1H), 7.46-7.53 (m, 2H), 8.08-8.16 (m, 2H) | 511 | 509 |
| 277 | (400 MHz, CDCl₃) 0.98 (s, 9H), 1.41-1.48 (m, 2H), 1.48-1.58 (m, 1H), 1.72-1.81 (m, 4H), 1.90-2.00 (m, 1H), 2.01-2.13 (m, 1H), 2.39-2.49 (m, 1H), 2.63-2.71 (m, 2H), 3.16 (s, 3H), 3.52-3.64 (m, 1H), 5.33 (s, 1H), 6.17-6.21 (m, 1H), 7.18-7.23 (m, 1H), 7.26-7.31 (m, 1H), 7.40-7.43 (m, 1H), 7.47-7.52 (m, 2H), 8.07-8.14 (m, 2H) | 511 | 509 |
| 278 | (400 MHz, DMSO-D₆) 0.70-0.75 (m, 3H), 0.93 (s, 9H), 1.01-1.07 (m, 3H), 1.32-1.41 (m, 2H), 1.51-1.66 (m, 4H), 1.66-1.92 (m, 4H), 1.92-2.05 (m, 2H), 2.57-2.64 (m, 2H), 2.69-2.80 (m, 1H), 4.65-4.77 (m, 1H), 6.18 (s, 1H), 7.03 (brs, 1H), 7.19-7.26 (m, 1H), 7.25-7.34 (m, 2H), 12.17 (brs, 1H) | 461 | 459 |
| 279 | (400 MHz, DMSO-D₆) 0.67-0.74 (m, 3H), 0.93 (s, 9H), 1.01-1.09 (m, 3H), 1.30-1.41 (m, 2H), 1.53-1.64 (m, 4H), 1.67-1.93 (m, 4H), 1.93-2.05 (m, 2H), 2.56-2.64 (m, 2H), 2.69-2.81 (m, 1H), 4.65-4.78 (m, 1H), 6.19 (s, 1H), 7.02 (s, 1H), 7.19-7.34 (m, 3H), 12.20 (brs, 1H) | 461 | 459 |
| 280 | (400 MHz, CDCl₃) 0.71-0.78 (m, 3H), 0.97 (s, 9H), 1.03-1.10 (m, 3H), 1.40-1.49 (m, 2H), 1.64-1.76 (m, 4H), 1.81-1.99 (m, 3H), 2.04-2.16 (m, 2H), 2.23-2.34 (m, 1H), 2.61-2.71 (m, 2H), 2.91-3.03 (m, 1H), 4.82-4.96 (m, 1H), 5.63 (brs, 1H), 5.86 (brs, 1H), 7.14-7.19 (m, 1H), 7.20-7.25 (m, 1H), 7.34-7.38 (m, 1H) | 461 | 459 |
| 281 | (400 MHz, DMSO-D₆) 0.76 (d, J = 6.85 Hz, 3H), 0.95 (s, 9H), 1.12 (d, J = 6.85 Hz, 3H), 1.36-1.40 (m, 2H), 1.74 (s, 3H), 2.06-2.13 (m, 2H), 2.62-2.66 (m, 2H), 7.29 (s, 1H), 7.32-7.36 (m, 2H), 7.41 (s, 1H), 7.91 (s, 1H), 8.06 (dd, J = 8.87, 0.81 Hz, 1H), 8.22 (dd, J = 8.87, 2.42 Hz, 1H), 8.90 (dd, J = 2.42, 0.81 Hz, 1H), 13.20 (s, 1H) | 470 | 468 |
| 282 | (400 MHz, CDCl₃) 0.68 (d, J = 6.85 Hz, 3H), 1.05 (d, J = 6.85 Hz, 3H), 1.71 (s, 3H), 1.83-1.90 (m, 1H), 2.22-2.34 (m, 2H), 2.47-2.56 (m, 1H), 2.58-2.69 (m, 4H), 2.90 (d, J = 7.66 Hz, 2H), 3.82-3.70 (m, 2H), 5.68 (s, 1H), 5.87 (s, 1H), 7.13 (d, J = 8.06 Hz, 1H), 7.29 (dd, J = 8.06, 2.01 Hz, 1H), 7.42 (d, J = 2.01 Hz, 1H) | 441 | 439 |
| 283 | (400 MHz, DMSO-D₆) 0.69-0.75 (m, 3H), 0.94 (s, 9H), 1.05-1.10 (m, 3H), 1.34-1.42 (m, 2H), 1.71 (s, 3H), 1.97-2.08 (m, 1H), 2.59-2.68 (m, 2H), 6.38 (s, 1H), 7.30-7.39 (m, 2H), 7.42-7.45 (m, 1H), 7.46-7.72 (m, 4H) | 537 | 535 |
| 284 | (400 MHz, DMSO-D₆) 0.69 (d, J = 12.49 Hz, 1H), 0.80 (s, 3H), 0.91 (s, 3H), 0.94 (s, 9H), 1.07 (s, 3H), 1.09-1.23 (m, 2H), 1.12 (s, 3H), 1.32-1.37 (m, 2H), 1.53 (d, J = 12.09 Hz, 1H), 1.61 (s, 3H), 1.99-2.06 (m, 1H), 2.44 (t, J = 6.85 Hz, 2H), 2.61-2.65 (m, 2H), 3.51-3.62 (m, 2H), 6.06 (s, 1H), 7.09 (s, 1H), 7.29 (d, | 519 | 517 |

TABLE 4-continued

| Example | $^1$H-NMR | MS M + H or M—Na + H | MS M − H or M—Na − H |
|---|---|---|---|
| | J = 8.06 Hz, 1H), 7.32 (dd, J = 8.06, 1.61 Hz, 1H), 7.40 (d, J = 1.61 Hz, 1H) | | |
| 285 | (400 MHz, CDCl$_3$) 0.70 (d, J = 6.85 Hz, 3H), 0.98 (s, 6H), 1.04 (d, J = 6.85 Hz, 3H), 1.34 (t, J = 6.25 Hz, 2H), 1.46 (t, J = 6.25 Hz, 2H), 1.69 (s, 3H), 1.85-1.92 (m, 1H), 2.24 (t, J = 6.04 Hz, 2H), 2.32 (t, J = 6.04 Hz, 2H), 2.63 (t, J = 6.45 Hz, 2H), 3.68-3.82 (m, 2H), 5.80 (s, 1H), 5.87 (s, 1H), 6.19 (s, 1H), 7.18 (d, J = 8.06 Hz, 1H), 7.27 (dd, J = 8.06, 2.01 Hz, 1H), 7.40 (d, J = 2.01 Hz, 1H) | 459 | 457 |
| 286 | (400 MHz, CDCl$_3$) 0.68 (d, J = 6.85 Hz, 3H), 0.87 (s, 3H), 0.88 (s, 3H), 1.03 (d, J = 6.85 Hz, 3H), 1.08-1.23 (m, 4H), 1.33-1.36 (m, 2H), 1.45-1.56 (m, 3H), 1.68 (s, 3H), 1.83-1.90 (m, 1H), 2.60-2.63 (m, 4H), 3.67-3.82 (m, 2H), 5.85 (s, 1H), 5.86 (s, 1H), 7.12 (d, J = 8.06 Hz, 1H), 7.24 (dd, J = 8.06, 2.01 Hz, 1H), 7.37 (d, J = 2.01 Hz, 1H) | 461 | 459 |
| 287 | (400 MHz, DMSO-D$_6$) 0.93 (s, 9H), 1.02 (d, J = 6.24 Hz, 1H), 1.12, (s, 3H), 1.14 (s, 3H), 1.22 (s, 1H), 1.34-1.38 (m, 2H), 1.48 (s, 3H), 1.83-1.85 (m, 2H), 1.89-2.05 (m, 4H), 2.22-2.25 (m, 1H), 2.59-2.63 (m, 2H), 2.79 (t, J = 8.55 Hz, 1H), 3.52 (brs, 1H), 4.65-4.74 (m, 1H), 6.15 (s, 1H), 7.07 (s, 1H), 7.14-7.16 (m, 1H), 7.25-7.26 (m, 2H) | 487 | 485 |
| 288 | (400 MHz, CDCl$_3$) 0.71 (d, J = 6.85 Hz, 3H), 1.04 (d, J = 6.85 Hz, 3H), 1.70 (s, 3H), 1.84-1.91 (m, 1H), 2.08-2.17 (m, 2H), 2.67 (t, J = 6.25 Hz, 2H), 2.92 (t, J = 7.66 Hz, 2H), 2.99 (t, J = 8.06 Hz, 2H), 3.71-3.83 (m, 2H), 5.28 (s, 1H), 5.87 (s, 1H), 6.41 (t, J = 2.22 Hz, 1H), 7.26-7.27 (m, 2H), 7.40 (d, J = 1.21 Hz, 1H) | 403 | 401 |
| 289 | (400 MHz, CDCl$_3$) 0.72 (d, J = 6.85 Hz, 3H), 1.06 (d, J = 6.85 Hz, 3H), 1.72 (s, 3H), 1.93-1.87 (m, 1H), 2.37 (t, J = 5.04 Hz, 2H), 2.44 (t, J = 5.04 Hz, 2H), 2.66 (t, J = 6.25 Hz, 2H), 3.67 (t, J = 5.44 Hz, 2H), 3.75-3.82 (m, 4H), 5.34 (s, 1H), 5.89 (s, 1H), 6.30 (s, 1H), 7.17 (d, J = 8.06 Hz, 1H), 7.29 (dd, J = 8.46, 2.42 Hz, 1H), 7.44 (d, J = 2.01 Hz, 1H) | 433 | 431 |
| 290 | (400 MHz, CDCl$_3$) 0.69 (d, J = 6.85 Hz, 3H), 1.05 (d, J = 6.85 Hz, 3H), 1.33-1.43 (m, 2H), 1.50-1.54 (m, 2H), 1.71. (s, 3H), 1.81-1.91 (m, 2H), 2.61-2.67 (m, 4H) 3.33 (td, J = 11.69, 1.61 Hz, 2H), 3.76 (dt, J = 20.42, 7.25 Hz, 2H), 3.94 (dd, J = 11.28, 2.82 Hz, 2H), 5.56 (s, 1H), 5.87 (s, 1H), 7.13 (d, J = 8.06 Hz, 1H), 7.27 (dd, J = 8.06, 2.01 Hz, 1H), 7.41 (d, J = 2.01 Hz, 1H) | 435 | 433 |
| 291 | (400 MHz, CDCl$_3$) 0.68 (d, J = 6.85 Hz, 3H), 1.04 (d, J = 6.85 Hz, 3H), 1.69 (s, 3H), 1.71-1.77 (m, 2H), 1.81-1.90 (m, 3H), 1.99-2.08 (m, 2H), 2.60-2.68 (m, 3H), 2.80 (d, J = 7.66 Hz, 2H), 3.70-3.83 (m, 2H), 5.32 (s, 1H), 5.86 (s, 1H), 7.12 (d, J = 8.06 Hz, 1H), 7.24 (dd, J = 8.06, 2.01 Hz, 1H), 7.38 (d, J = 2.01 Hz, 1H) | 405 | 403 |
| 292 | (400 MHz, CDCl$_3$) 0.96 (s, 12H), 1.40-1.45 (m, 2H), 1.66 (s, 3H), 1.80 (s, 3H), 2.61-2.71 (m, 4H), 3.69-3.87 (m, 2H), 4.45 (s, 1H), 4.69 (s, 1H), 5.23 (s, 1H), 6.24 (s, 1H), 7.14 (d, J = 7.86 Hz, 1H), 7.22 (dd, J = 7.86, 1.62 Hz, 1H), 7.36 (d, J = 1.62 Hz, 1H) | 419 | 417 |
| 293 | (400 MHz, CDCl$_3$) 0.71 (d, J = 6.88 Hz, 3H), 1.05 (d, J = 6.88 Hz, 3H), 1.26 (s, 1H), 1.30 (s, 6H), 1.70 (s, 3H), 1.71-1.76 (m, 2H), 1.85-1.92 (m, 1H), 2.59-2.72 (m, 2H), 2.76-2.81 (m, 2H), 3.69-3.82 (m, 2H), 5.46 (s, 1H), 5.87 (s, 1H), 7.19 (d, J = 8.07 Hz, 1H), 7.26 (dd, J = 8.07, 2.09 Hz, 1H), 7.38 (d, J = 2.09 Hz, 1H) | 423 | 421 |
| 294 | (400 MHz, CDCl$_3$) 0.70 (d, J = 6.88 Hz, 3H), 1.05 (d, J = 6.88 Hz, 3H), 1.40 (s, 3H), 1.46 (s, 3H), 1.71 (s, 3H), 1.84-1.93 (m, 3H), 2.66 (t, J = 6.28 Hz, 2H), 2.79-2.84 (m, 2H), 3.71-3.84 (m, 2H), 5.40 (brs, 1H), 5.88 (s, 1H), 7.20 (d, J = 8.07 Hz, 1H), 7.28 (dd, J = 8.07, 2.09 Hz, 1H), 7.40 (d, J = 1.79 Hz, 1H) | 425 | 423 |
| 295 | (400 MHz, DMSO-D$_6$) 0.73 (d, J = 6.82 Hz, 3H), 0.95 (s, 9H), 1.10 (d, J = 6.82 Hz, 3H), 1.35-1.41 (m, 2H), 1.73 (s, 3H), 2.02-2.10 (m, 1H), 2.61-2.67 (m, 2H), 6.79 (s, 1H), 7.30-7.41 (m, 4H), 8.01 (s, 1H) | 460 | 458 |
| 296 | (400 MHz, CDCl$_3$) 0.98 (s, 9H), 1.41-1.46 (m, 2H), 1.66 (s, 6H), 1.67 (s, 3H), 2.66-2.71 (m, 2H), 3.39 (s, 3H), 3.56-3.65 (m, 3H), 3.74-3.81 (m, 1H), 5.15 (s, 1H), 6.23 (s, 1H), 6.80 (s, 1H), 7.09 (s, 1H), 7.19 (d, | 517 | 515 |

TABLE 4-continued

| Example | ¹H-NMR | MS M + H or M—Na + H | MS M − H or M—Na − H |
|---|---|---|---|
| | J = 8.06 Hz, 1H), 7.28 (dd, J = 8.06, 2.01 Hz, 1H), 7.43 (d, J = 1.61 Hz, 1H) | | |
| 297 | (400 MHz, DMSO-D₆) 0.70 (d, J = 6.90 Hz, 3H), 0.94 (s, 9H), 1.05 (d, J = 6.90 Hz, 3H), 1.36-1.41 (m, 2H), 1.71 (s, 3H), 2.61-2.66 (m, 2H), 3.55 (s, 3H), 6.11 (s, 1H), 6.32 (brs, 1H), 7.35 (brs, 2H), 7.43 (brs, 1H), 7.67 (brs, 1H) | 473 | 471 |
| 298 | (400 MHz, CDCl₃) 0.72 (d, J = 6.94 Hz, 3H), 1.05 (d, J = 6.94 Hz, 3H), 1.10 (s, 3H), 1.28 (s, 3H), 1.70 (s, 3H), 1.85-1.92 (m, 3H), 2.21-2.26 (m, 2H), 2.69 (t, J = 6.24 Hz, 2H), 3.66-3.83 (m, 3H), 5.20 (brs, 1H), 5.88 (s, 1H), 7.25 (d, J = 8.21 Hz, 1H), 7.30 (dd, J = 8.21, 2.08 Hz, 1H), 7.36 (d, J = 2.08 Hz, 1H) | 419 | 417 |
| 299 | (400 MHz, CDCl₃) 0.61-0.71 (m, 3H), 0.95 (s, 9H), 0.99-1.06 (m, 3H), 1.11-1.17 (m, 3H), 1.38-1.47 (m, 2H), 1.67 (brs, 3H), 1.78-1.90 (m, 1H), 2.59-2.67 (m, 2H), 2.72-2.85 (m, 1H), 3.46-3.60 (m, 1H), 3.62-3.75 (m, 1H), 5.76-5.85 (m, 2H), 7.11-7.17 (m, 1H), 7.21-7.25 (m, 1H), 7.33-7.38 (m, 1H) | 435 | 433 |
| 300 | (400 MHz, CDCl₃) 0.61-0.71 (m, 3H), 0.95 (s, 9H), 0.99-1.06 (m, 3H), 1.11-1.17 (m, 3H), 1.38-1.47 (m, 2H), 1.67 (brs, 3H), 1.78-1.90 (m, 1H), 2.59-2.67 (m, 2H), 2.72-2.85 (m, 1H), 3.46-3.60 (m, 1H), 3.62-3.75 (m, 1H), 5.76-5.85 (m, 2H), 7.11-7.17 (m, 1H), 7.21-7.25 (m, 1H), 7.33-7.38 (m, 1H) | 435 | 433 |
| 301 | (400 MHz, CDCl₃) 0.71 (d, J = 6.94 Hz, 3H), 1.05 (d, J = 6.94 Hz, 3H), 1.58-1.67 (m, 4H), 1.71 (s, 3H), 1.80-1.91 (m, 3H), 1.94-2.04 (m, 4H), 2.68 (t, J = 6.24 Hz, 2H), 2.86-2.90 (m, 2H), 3.72-3.83 (m, 2H), 5.24 (s, 1H), 5.88 (s, 1H), 7.21 (d, J = 8.09 Hz, 1H), 7.27 (dd, J = 8.09, 2.08 Hz, 1H), 7.40 (d, J = 2.08 Hz, 1H) | 451 | 449 |
| 302 | (400 MHz, DMSO-D₆) 0.65-0.71 (m, 3H), 0.79 (s, 9H), 0.99-1.03 (m, 3H), 1.58 (s, 3H), 1.68-1.81 (m, 2H), 1.87-1.97 (m, 1H), 2.04-2.15 (m, 1H), 2.17-2.33 (m, 4H), 3.30-3.40 (m, 1H), 3.40-3.50 (m, 1H), 3.51-3.61 (m, 1H), 6.10 (s, 1H), 6.91 (brs, 1H), 7.27-7.32 (m, 3H) | 447 | 445 |
| 303 | (400 MHz, DMSO-D₆) 1.03 (s, 9H), 1.36-1.41 (m, 2H), 1.61 (s, 3H), 2.03-2.11 (m, 1H), 2.21.-2.29 (m, 1H), 2.46 (t, J = 7.17 Hz, 2H), 2.61-2.65 (m, 2H), 2.92 (s, 3H), 2.93-2.98 (m, 1H), 3.15-3.22 (m, 1H), 3.48-3.65 (m, 2H), 6.16 (s, 1H), 7.20 (s, 1H), 7.26 (dd, J = 8.09, 1.85 Hz, 1H), 7.31 (d, J = 8.09 Hz, 1H), 7.37 (d, J = 1.85 Hz, 1H), 12.26 (brs, 1H) | 485 | 483 |
| 304 | (400 MHz, CDCl₃) 0.83 (s, 9H), 0.96-1.03 (m, 3H), 1.65-1.69 (m, 3H), 1.70-1.84 (m, 3H), 1.91-2.06 (m, 1H), 2.08-2.21 (m, 1H), 2.24-2.36 (m, 2H), 2.58-2.66 (m, 2H), 2.89-3.05 (m, 1H), 3.14-3.18 (m, 3H), 3.35-3.48 (m, 1H), 3.66-3.88 (m, 2H), 5.66-5.72 (m, 1H), 5.93-5.99 (m, 1H), 7.20-7.24 (m, 1H), 7.27-7.32 (m, 1H), 7.35-7.38 (m, 1H) | 477 | 475 |
| 305 | (400 MHz, DMSO-D₆) 0.69 (d, J = 6.94 Hz, 3H), 0.95 (s, 9H), 1.35-1.41 (m, 2H), 1.58 (s, 3H), 1.90-2.00 (m, 1H), 2.45 (t, J = 6.94 Hz, 2H), 2.60-2.66 (m, 2H), 3.08 (t, J = 9.02 Hz, 1H), 3.21 (s, 3H), 3.46-3.65 (m, 2H), 6.11 (s, 1H), 7.07 (s, 1H), 7.25-7.31 (m, 2H), 7.33-7.36 (m, 1H) | 451 | 449 |
| 306 | (400 MHz, DMSO-D₆) 0.95 (s, 9H), 1.02 (d, J = 6.94 Hz, 3H), 1.34-1.40 (m, 2H), 1.60 (s, 3H), 1.93-2.02 (m, 1H), 2.42 (t, J = 7.05 Hz, 2H), 2.56-2.66 (m, 3H), 2.85 (t, J = 9.36 Hz, 1H), 2.90 (s, 3H), 3.48-3.63 (m, 2H), 6.08 (s, 1H), 7.05 (s, 1H), 7.26-7.31 (m, 2H), 7.36 (s, 1H) | 451 | 449 |
| 307 | (400 MHz, DMSO-D₆) 0.73 (d, J = 6.94 Hz, 3H), 0.95 (s, 9H), 1.37-1.43 (m, 2H), 1.69 (s, 3H), 2.05-2.11 (m, 1H), 2.63-2.68 (m, 2H), 3.19 (t, J = 8.90 Hz, 1H), 3.23 (s, 3H), 3.33-3.37 (m, 2H), 6.30 (s, 1H), 7.17 (d, J = 8.32 Hz, 2H), 7.33-7.46 (m, 4H), 7.83 (d, J = 8.32 Hz, 2H) | 499 | 497 |
| 308 | (400 MHz, DMSO-D₆) 0.95 (s, 9H), 1.09 (d, J = 6.70 Hz, 3H), 1.36-1.41 (m, 2H), 1.73 (s, 3H), 2.08-2.14 (m, 1H), 2.62-2.71 (m, 3H), 2.92 (s, 3H), 2.96 (t, J = 9.13 Hz, 1H), 6.37 (s, 1H), 7.33-7.48 (m, 5H), 7.58 (s, 1H), 7.91-7.94 (m, 2H) | 499 | 497 |

TABLE 4-continued

| Example | ¹H-NMR | MS M + H or M—Na + H | MS M − H or M—Na − H |
|---|---|---|---|
| 309 | (400 MHz, DMSO-D₆) 0.69 (d, J = 6.82 Hz, 3H), 0.87 (s, 9H), 1.02 (d, J = 6.82 Hz, 3H), 1.32 (d, J = 6.70 Hz, 2H), 1.60 (s, 3H), 1.65 (d, J = 32.60 Hz, 2H), 1.93 (sep, J = 6.82 Hz, 1H), 2.28-2.40 (m, 1H), 2.43-2.46 (m, 2H), 2.48-2.54 (m, 2H), 3.44-3.56 (m, 2H), 3.62 (ddd, J = 6.80, 7.20, 14.00 Hz, 1H), 6.11 (s, 1H), 7.01 (s, 1H), 7.29-7.33 (m, 3H), 12.32 (brs, 1H) | 461 | 459 |
| 310 | (400 MHz, DMSO-D₆) 0.73 (d, J = 6.82 Hz, 3H), 0.91 (s, 9H), 1.04 (d, J = 6.82 Hz, 3H), 1.61 (s, 3H), 1.93-2.00 (m, 1H), 2.36-2.46 (m, 3H), 2.93-2.98 (m, 1H), 3.47-3.55 (m, 1H), 3.58-3.66 (m, 1H), 4.38 (brs, 1H), 6.12 (s, 1H), 7.01 (s, 1H), 7.24 (dd, J = 7.98, 1.97 Hz, 1H), 7.31-7.34 (m, 2H) | 437 | 435 |
| 311 | (400 MHz, DMSO-D₆) 0.73 (d, J = 6.82 Hz, 3H), 0.91 (s, 9H), 1.04 (d, J = 6.82 Hz, 3H), 1.61 (s, 3H), 1.92-2.00 (m, 1H), 2.36-2.45 (m, 3H), 2.96 (dd, J = 13.76, 1.50 Hz, 1H), 3.47-3.55 (m, 1H), 3.58-3.66 (m, 1H), 4.39 (brs, 1H), 6.12 (s, 1H), 7.00 (s, 1H), 7.24 (dd, J = 8.09, 1.85 Hz, 1H), 7.31-7.35 (m, 2H) | 437 | 435 |
| 312 | (400 MHz, CDCl₃) 0.97 (s, 9H), 1.39-1.47 (m, 2H), 1.52-1.68 (m, 5H), 2.07-2.26 (m, 2H), 2.36-2.47 (m, 1H), 2.56-2.68 (m, 6H), 2.98-3.08 (m, 1H), 3.46-3.51 (m, 2H), 3.72 (s, 3H), 4.64-4.69 (m, 1H), 4.89-5.01 (m, 1H), 5.90-5.94 (m, 1H), 7.12-7.21 (m, 2H), 7.32-7.35 (m, 1H) | 503 | 501 |
| 313 | (400 MHz, CDCl₃) 0.98 (s, 9H), 1.12 (s, 9H), 1.37-1.74 (m, 6H), 1.80 (s, 3H), 2.65-2.73 (m, 2H), 3.19-3.29 (m, 2H), 5.15 (s, 1H), 6.18 (s, 1H), 7.19-7.33 (m, 2H), 7.42-7.52 (m, 3H), 8.07-8.13 (m, 2H) | 541 | 539 |
| 314 | (400 MHz, DMSO-D₆) 0.66-0.71 (m, 3H), 0.94 (s, 9H), 1.02-1.07 (m, 3H), 1.37-1.44 (m, 2H), 1.65 (s, 3H), 1.78-1.82 (m, 2H), 1.81-1.87 (m, 4H), 1.91-1.96 (m, 2H), 1.96-2.05 (m, 1H), 2.64-2.71 (m, 2H), 5.96 (s, 1H), 7.04 (s, 1H), 7.40-7.47 (m, 1H), 7.56-7.63 (m, 2H), 12.27 (brs, 1H) | 507 | 505 |
| 315 | (400 MHz, DMSO-D₆) 0.79 (s, 9H), 1.68 (s, 3H), 1.70-1.81 (m, 2H), 1.96-2.08 (m, 1H), 2.08-2.17 (m, 2H), 2.17-2.28 (m, 2H), 3.11 (s, 3H), 3.16-3.44 (m, 3H), 6.38 (s, 1H), 7.32-7.48 (m, 5H), 7.61-7.65 (m, 1H), 7.89-7.96 (m, 2H), 12.86 (brs, 1H) | 511 | 509 |
| 316 | (400 MHz, DMSO-D₆) 0.93 (s, 9H), 1.33-1.40 (m, 2H), 1.54 (brs, 3H), 2.15 (brs, 6H), 2.17-2.27 (m, 2H), 2.38-2.46 (m, 2H), 2.58-2.64 (m, 2H), 2.65-2.77 (m, 1H), 6.01 (brs, 1H), 7.14 (brs, 1H), 7.18-7.24 (m, 1H), 7.27-7.33 (m, 2H) | 507 | 505 |
| 317 | (400 MHz, DMSO-D₆) 0.66 (d, J = 6.94 Hz, 3H), 1.02 (d, J = 6.94 Hz, 3H), 1.30 (s, 9H), 1.61 (s, 3H), 1.89-1.95 (m, 1H), 2.45 (t, J = 6.94 Hz, 2H), 3.48-3.67 (m, 2H), 6.12 (s, 1H), 7.10 (s, 1H), 7.31 (dd, J = 8.09, 1.85 Hz, 1H), 7.43 (d, J = 8.09 Hz, 1H), 7.43 (d, J = 1.85 Hz, 1H), 12.25 (brs, 1H) | 417 | 415 |
| 318 | (400 MHz, DMSO-D₆) 0.81 (d, J = 6.70 Hz, 6H), 1.38-1.49 (m, 1H), 1.63-1.69 (m, 2H), 1.69 (s, 3H), 1.84-1.96 (m, 1H), 1.99-2.08 (m, 1H), 2.13-2.23 (m, 1H), 2.40-2.48 (m, 2H), 3.13 (s, 3H), 3.20-3.29 (m, 2H), 3.44 (tt, J = 9.66, 7.33 Hz, 1H), 6.39 (s, 1H), 7.35-7.44 (m, 3H), 7.46 (dt, J = 8.94, 2.20 Hz, 2H), 7.65 (s, 1H), 7.94 (dt, J = 8.94, 2.20 Hz, 2H), 12.91 (brs, 1H) | 497 | 495 |
| 319 | (400 MHz, CDCl₃) 0.96 (s, 9H), 1.40-1.46 (m, 2H), 1.89-2.16 (m, 3H), 2.26-2.45 (m, 2H), 2.56-2.70 (m, 4H), 3.69-3.78 (m, 1H), 3.78-3.88 (m, 1H), 5.65 (brs, 1H), 5.89-5.93 (m, 1H), 7.13-7.22 (m, 2H), 7.33-7.36 (m, 1H) | 469 | 467 |
| 320 | (400 MHz, DMSO-D₆) 0.94 (s, 9H), 1.33-1.41 (m, 2H), 1.69 (s, 3H), 2.14-2.36 (m, 2H), 2.56-2.67 (m, 3H), 2.75-2.90 (m, 1H), 3.23-3.44 (m, 1H), 7.23-7.35 (m, 3H), 7.39-7.42 (m, 1H), 7.97-8.03 (m, 2H), 8.19-8.25 (m, 2H), 8.87-8.92 (m, 1H) | 518 | 516 |
| 321 | (400 MHz, DMSO-D₆) 0.23-0.32 (m, 2H), 0.32-0.40 (m, 1H), 0.54-0.62 (m, 1H), 0.87-0.94 (m, 1H), 0.97 (s, 6H), 1.41-1.47 (m, 2H), 1.67 (s, 3H), 1.90-1.94 (m, 2H), 2.20-2.26 (m, 2H), 2.34-2.42 (m, 2H), 3.40-3.50 (m, 1H), 3.51-3.62 (m, 1H), 5.52-5.55 (m, 1H), 5.92-5.96 (m, 1H), 7.11-7.15 (m, 1H), 7.15- | 443 | 441 |

TABLE 4-continued

| Example | ¹H-NMR | MS M + H or M—Na + H | MS M − H or M—Na − H |
|---|---|---|---|
| | 7.17 (m, 1H), 7.17-7.20 (m, 1H), 7.27-7.33 (m, 1H), 7.35-7.39 (m, 1H) | | |
| 322 | (400 MHz, DMSO-D₆) 0.64-0.69 (m, 3H), 0.93 (s, 9H), 1.00-1.05 (m, 3H), 1.36-1.42 (m, 2H), 1.64 (s, 3H), 1.90-1.98 (m, 1H), 2.28 (s, 6H), 2.62-2.71 (m, 2H), 5.99 (s, 1H), 7.12 (brs, 1H), 7.39-7.45 (m, 1H), 7.52-7.61 (m, 2H), 12.41 (brs, 1H) | 493 | 491 |
| 323 | (400 MHz, DMSO-D₆) 0.95 (s, 9H), 1.38-1.46 (m, 2H), 1.73 (s, 3H), 1.98-2.10 (m, 1H), 2.13-2.24 (m, 1H), 2.66-2.73 (m, 2H), 3.09 (s, 3H), 3.16-3.25 (m, 2H), 6.42 (s, 1H), 7.41-7.46 (m, 2H), 7.46-7.51 (m, 1H), 7.66-7.74 (m, 3H), 7.91-7.96 (m, 2H) | 519 | 517 |
| 324 | (400 MHz, DMSO-D₆) 0.92 (s, 9H), 1.35-1.43 (m, 2H), 1.60 (s, 3H), 1.74-1.79 (m, 2H), 1.79-1.83 (m, 4H), 1.87-1.91 (m, 2H), 1.91-1.99 (m, 1H), 2.03-2.13 (m, 1H), 2.62-2.70 (m, 2H), 3.06 (s, 3H), 3.08-3.21 (m, 2H), 5.97 (s, 1H), 7.10 (brs, 1H), 7.38-7.44 (m, 1H), 7.53-7.59 (m, 1H), 7.60-7.65 (m, 1H), 12.27 (brs, 1H) | 523 | 521 |
| 325 | (400 MHz, DMSO-D₆) 0.94 (s, 9H), 1.30-1.44 (m, 4H), 1.49-1.57 (m, 2H), 1.56-1.64 (m, 5H), 1.91-2.05 (m, 3H), 2.07-2.24 (m, 2H), 2.63-2.71 (m, 2H), 3.09 (s, 3H), 3.10-3.25 (m, 2H), 3.96-4.09 (m, 1H), 6.16 (s, 1H), 7.18 (brs, 1H), 7.40-7.44 (m, 1H), 7.54-7.59 (m, 1H), 7.61-7.64 (m, 1H), 12.07 (brs, 1H) | 525 | 523 |
| 326 | (400 MHz, CDCl₃) 0.69-0.76 (m, 3H), 0.97 (s, 9H), 1.04-1.10 (m, 3H), 1.42-1.50 (m, 2H), 1.76 (s, 3H), 1.84-1.94 (m, 1H), 2.68-2.77 (m, 2H), 4.19-4.27 (m, 3H), 4.28-4.35 (m, 3H), 5.18 (brs, 1H), 5.94 (s, 1H), 7.28-7.32 (m, 1H), 7.52-7.58 (m, 1H), 7.62-7.67 (m, 1H) | 529 | 527 |
| 327 | (400 MHz, DMSO-D₆) 0.72 (d, J = 6.94 Hz, 3H), 1.04 (d, J = 6.94 Hz, 3H), 1.62 (s, 3H), 1.93-1.99 (m, 1H), 2.10-2.20 (m, 2H), 2.45 (t, J = 6.82 Hz, 2H), 2.66-2.75 (m, 2H), 3.48-3.66 (m, 2H), 5.54-5.58 (m, 1H), 6.13 (s, 1H), 7.06 (s, 1H), 7.23 (d, J = 8.09 Hz, 1H), 7.32 (dd, J = 8.09, 2.08 Hz, 1H), 7.39 (d, J = 2.08 Hz, 1H), 12.25 (brs, 1H) | 453 | 451 |
| 328 | (400 MHz, DMSO-D₆) 0.69 (d, J = 6.94 Hz, 3H), 1.03 (d J = 6.94 Hz, 3H), 1.61 (s, 3H), 1.63-1.70 (m, 2H), 1.83-1.87 (m, 2H), 1.91-2.15 (m, 5H), 2.45 (t, J = 6.94 Hz, 2H), 3.03-3.11 (m, 1H), 3.48-3.65 (m, 2H), 6.12 (s, 1H), 7.03 (s, 1H), 7.30-7.38 (m, 3H), 12.25 (brs, 1H) | 455 | 453 |
| 329 | (400 MHz, DMSO-D₆) 0.80 (d, J = 6.58 Hz, 6H), 1.40-1.45 (m, 1H), 1.55 (s, 3H), 1.62-1.67 (m, 2H), 1.85-1.90 (m, 1H), 2.22-2.28 (m, 3H), 2.41-2.45 (m, 3H), 2.55-2.60 (m, 4H), 2.69-2.75 (m, 1H), 2.88 (t, J = 9.87 Hz, 1H), 3.37-3.46 (m, 1H), 4.91-5.01 (m, 1H), 6.41 (s, 1H), 7.25 (s, 1H), 7.27-7.35 (m, 3H), 12.23 (s, 1H) | 507 | 505 |
| 330 | (400 MHz, DMSO-D₆) 0.80 (d, J = 6.70 Hz, 6H), 1.38-1.48 (m, 1H), 1.57 (s, 3H), 1.60-1.70 (m, 2H), 1.77-1.99 (m, 6H), 1.83 (s, 4H), 2.04-2.13 (m, 1H), 2.39-2.47 (m, 2H), 3.12 (s, 3H), 3.13-3.19 (m, 1H), 3.20-3.27 (m, 1H), 3.37-3.47 (m, 1H), 5.94 (s, 1H), 7.06 (s, 1H), 7.28-7.36 (m, 3H), 12.30 (brs, 1H) | 501 | 499 |
| 331 | (400 MHz, DMSO-D₆) 0.98 (s, 6H), 1.46 (t, J = 6.40 Hz, 2H), 1.58 (s, 3H), 1.86-1.95 (m, 3H), 2.03-2.11 (m, 1H), 2.21-2.27 (m, 2H), 2.44 (t, J = 6.94 Hz, 2H), 3.12-3.28 (m, 5H), 3.47-3.62 (m, 2H), 5.54-5.56 (m, 1H), 6.07 (s, 1H), 7.14 (s, 1H), 7.19 (d, J = 7.98 Hz, 1H), 7.29 (dd, J = 7.98, 1.85 Hz, 1H), 7.37 (d, J = 1.85 Hz, 1H), 12.24 (brs, 1H) | 461 | 459 |
| 332 | (400 MHz, DMSO-D₆) 0.98 (s, 6H), 1.46 (t, J = 6.36 Hz, 2H), 1.70 (s, 3H), 1.91-1.96 (m, 2H), 2.01-2.10 (m, 1H), 2.15-2.28 (m, 3H), 3.12 (s, 3H), 3.20-3.29 (m, 2H), 5.55-5.58 (m, 1H), 6.40 (s, 1H), 7.25 (d, J = 7.91 Hz, 1H), 7.40 (dd, J = 7.91, 1.97 Hz, 1H), 7.44-7.49 (m, 3H), 7.67 (s, 1H), 7.91-7.96 (m, 2H), 12.90 (brs, 1H) | 509 | 507 |
| 333 | (400 MHz, DMSO-D₆) 0.98 (s, 6H), 1.46 (t, J = 6.36 Hz, 2H), 1.70 (s, 3H), 1.92-1.95 (m, 2H), 2.00-2.08 (m, 1H), 2.13-2.28 (m, 3H), 3.12 (s, 3H), 3.20-3.30 (m, 2H), 3.82 (s, 3H), 5.55-5.58 (m, 1H), 6.39 | 539 | 537 |

TABLE 4-continued

| Example | ¹H-NMR | MS M + H or M—Na + H | MS M − H or M—Na − H |
|---|---|---|---|
| | (s, 1H), 6.96 (dd, J = 8.32, 1.85 Hz, 1H) 7.07 (d, J = 1.62 Hz, 1H), 7.25 (d, J = 7.86 Hz, 1H), 7.40 (dd, J = 7.98, 1.97 Hz, 1H), 7.48 (d, J = 1.85 Hz, 1H), 7.62 (s, 1H), 7.66 (d, J = 8.55 Hz, 1H), 12.50 (s, 0H) | | |
| 334 | (400 MHz, DMSO-D₆) 0.98 (s, 6H), 1.46 (t, J = 6.36 Hz, 2H), 1.70 (s, 3H), 1.91-1.95 (m, 2H), 2.05-2.13 (m, 1H), 2.19-2.27 (m, 3H), 3.14 (s, 3H), 3.22-3.26 (m, 2H), 5.55-5.57 (m, 1H), 7.17 (s, 1H), 7.23 (d, J = 8.04 Hz, 1H), 7.37 (dd, J = 8.04, 1.91 Hz, 1H), 7.45 (d, J = 1.91 Hz, 1H), 7.81-7.86 (m, 2H), 8.14 (dd, J = 8.67, 2.03 Hz, 1H), 8.81 (d, J = 2.03 Hz, 1H) | 510 | 508 |
| 335 | (400 MHz, DMSO-D₆) 0.92-1.03 (m, 2H), 1.09-1.18 (m, 3H), 1.50-1.68 (m, 9H), 1.85-1.93 (m, 1H), 2.00-2.09 (m, 1H), 2.44 (t, J = 6.94 Hz, 2H), 2.56 (d, J = 6.94 Hz, 2H), 3.05-3.12 (m, 4H), 3.15-3.22 (m, 1H), 3.47-3.63 (m, 2H), 6.06 (s, 1H), 7.11 (s, 1H), 7.22-7.28 (m, 2H), 7.36 (d, J = 1.39 Hz, 1H), 12.25 (brs, 1H) | 449 | 447 |
| 336 | (400 MHz, DMSO-D₆) 0.95-1.05 (m, 2H), 1.10-1.17 (m, 3H), 1.53-1.70 (m, 9H), 1.99-2.07 (m, 1H), 2.13-2.21 (m, 1H), 2.58 (d, J = 6.70 Hz, 2H), 3.10 (s, 3H), 3.13-3.28 (m, 2H), 6.39 (s, 1H), 7.28-7.31 (m, 1H), 7.35-7.37 (m, 1H), 7.45-7.49 (m, 3H), 7.64 (s, 1H), 7.92-7.96 (m, 2H), 12.89 (s, 1H) | 497 | 495 |
| 337 | (400 MHz, DMSO-D₆) 0.96-1.03 (m, 2H), 1.10-1.18 (m, 3H), 1.53-1.71 (m, 9H), 1.98-2.06 (m, 1H), 2.12-2.20 (m, 1H), 2.58 (d, J = 6.70 Hz, 2H), 3.10 (s, 3H), 3.12-3.28 (m, 2H), 3.82 (s, 3H), 6.38 (s, 1H), 6.93-6.97 (m, 1H), 7.05-7.07 (m, 1H), 7.30 (d, J = 8.15 Hz, 1H), 7.37 (dd, J = 8.15, 2.14 Hz, 1H), 7.46 (d, J = 2.14 Hz, 1H), 7.59 (s, 1H), 7.63-7.67 (m, 1H) | 527 | 525 |
| 338 | (400 MHz, DMSO-D₆) 0.93-1.04 (m, 2H), 1.09-1.18 (m, 3H), 1.52-1.72 (m, 9H), 2.02-2.11 (m, 1H), 2.17-2.26 (m, 1H), 2.57 (d, J = 6.00 Hz, 2H), 3.11 (s, 3H), 3.21 (d, J = 14.57 Hz, 2H), 7.24-7.34 (m, 3H), 7.42 (d, J = 1.85 Hz, 1H), 7.95 (s, 1H), 8.04 (dd, J = 8.79, 0.69 Hz, 1H), 8.22 (dd, J = 8.79, 2.54 Hz, 1H), 8.87-8.89 (m, 1H) | 498 | 496 |
| 339 | (400 MHz, DMSO-D₆) 0.88-1.03 (m, 2H), 0.91 (s, 9H), 1.09-1.18 (m, 3H), 1.52-1.69 (m, 6H), 1.77 (s, 3H), 2.41-2.47 (m, 2H), 2.55 (d, J = 6.45 Hz, 2H), 3.47-3.54 (m, 1H), 3.71-3.64 (m, 1H), 6.29 (s, 1H), 6.85 (s, 1H), 7.20 (d, J = 8.06 Hz, 1H), 7.25 (dd, J = 8.46, 2.01 Hz, 1H), 7.35 (d, J = 2.01 Hz, 1H) | 447 | 445 |
| 340 | (400 MHz, DMSO-D₆) 0.94 (s, 9H), 1.37-1.44 (m, 2H), 1.61 (s, 3H), 1.87-1.98 (m, 1H), 2.02-2.13 (m, 1H), 2.25 (s, 6H), 2.64-2.72 (m, 2H), 3.05-3.14 (m, 4H), 3.14-3.22 (m, 1H), 6.03 (s, 1H), 7.20-7.24 (m, 1H), 7.42-7.47 (m, 1H), 7.54-7.59 (m, 1H), 7.59-7.64 (m, 1H), 12.49 (brs, 1H) | 509 | 507 |
| 341 | (400 MHz, CDCl₃) 0.96 (s, 9H), 1.41-1.48 (m, 2H), 1.70 (s, 3H), 1.87-2.13 (m, 2H), 2.28-2.44 (m, 2H), 2.50 (s, 6H), 2.57-2.68 (m, 1H), 2.68-2.76 (m, 2H), 5.18 (brs, 1H), 5.86 (s, 1H), 7.27-7.32 (m, 1H), 7.44-7.50 (m, 1H), 7.57-7.61 (m, 1H) | 541 | 539 |
| 342 | (400 MHz, CDCl₃) 0.98 (s, 9H), 1.44-1.51 (m, 2H), 1.84 (s, 3H), 1.96-2.24 (m, 2H), 2.37-2.57 (m, 2H), 2.63-2.81 (m, 3H), 5.44 (brs, 1H), 6.24 (s, 1H), 7.32-7.40 (m, 1H), 7.45-7.54 (m, 2H), 7.55-7.63 (m, 1H), 7.67-7.72 (m, 1H), 8.08-8.18 (m, 2H) | 551 | 549 |
| 343 | (400 MHz, CDCl₃) 0.96-1.00 (m, 9H), 1.42-1.50 (m, 2H), 1.71 (s, 3H), 1.88-2.13 (m, 2H), 2.29-2.45 (m, 2H), 2.59-2.67 (m, 2H), 2.68-2.77 (m, 2H), 3.69-3.75 (m, 1H), 3.75-3.88 (m, 2H), 5.81 (brs, 1H), 5.95 (s, 1H), 7.28-7.33 (m, 1H), 7.48-7.54 (m, 1H), 7.60-7.63 (m, 1H) | 503 | 501 |
| 344 | (400 MHz, CDCl₃) 0.82 (s, 9H), 1.65-1.69 (m, 3H), 1.71-1.85 (m, 3H), 1.85-1.97 (m, 2H), 1.98-2.03 (m, 3H), 2.03-2.18 (m, 6H), 2.24-2.37 (m, 2H), 3.14-3.26 (m, 5H), 3.35-3.47 (m, 1H), 4.88 (brs, 1H), 5.84 (s, 1H), 7.18-7.28 (m, 2H), 7.32-7.37 (m, 1H) | 515 | 513 |
| 345 | (400 MHz, CDCl₃) 0.73-0.78 (m, 3H), 0.96 (s, 9H), 1.09-1.14 (m, 3H), 1.43-1.49 (m, 2H), 1.85 (s, 3H), 1.90-2.00 (m, 1H), 2.69-2.78 (m, 2H), 4.10 (s, 3H), 4.92 (s, 1H), 6.24 (s, 1H), 6.99-7.04 (m, 1H), 7.30- | 533 | 531 |

TABLE 4-continued

| Example | $^1$H-NMR | MS M + H or M—Na + H | MS M − H or M—Na − H |
|---|---|---|---|
| | 7.37 (m, 2H), 7.56-7.62 (m, 1H), 7.69-7.72 (m, 1H), 8.18-8.25 (m, 1H), 10.44-10.67 (m, 1H) | | |
| 346 | (400 MHz, CDCl$_3$) 0.97 (s, 9H), 1.41-1.49 (m, 2H), 1.78 (s, 3H), 1.97-2.26 (m, 2H), 2.33-2.59 (m, 2H), 2.62-2.76 (m, 3H), 4.10 (s, 3H), 4.98 (brs, 1H), 6.19-6.23 (m, 1H), 7.00-7.07 (m, 1H), 7.20-7.29 (m, 2H), 7.30-7.34 (m, 1H), 7.42-7.45 (m, 1H), 8.20-8.26 (m, 1H), 10.51 (brs, 1H) | 547 | 545 |
| 347 | (400 MHz, CDCl$_3$) 0.16-0.24 (m, 1H), 0.25-0.32 (m, 1H), 0.33-0.43 (m, 1H), 0.56-0.65 (m, 1H), 0.82-0.91 (m, 1H), 0.91-1.06 (m, 2H), 1.09-1.30 (m, 4H), 1.55-1.76 (m, 6H), 1.79 (s, 3H), 2.54-2.65 (m, 4H), 3.65-3.81 (m, 2H), 5.66 (brs, 1H), 5.70-5.72 (m, 1H), 7.11-7.15 (m, 1H), 7.25-7.29 (m, 1H), 7.40-7.44 (m, 1H) | 431 | 429 |
| 348 | (400 MHz, DMSO-D$_6$) 0.94 (d, J = 6.47 Hz, 6H), 1.63 (t, J = 6.82 Hz, 2H), 1.67 (s, 3H), 1.76-1.86 (m, 1H), 2.21-2.40 (m, 2H), 2.56-2.67 (m, 3H), 4.09 (t, J = 6.59 Hz, 2H), 6.49 (d, J = 0.92 Hz, 1H), 7.16 (d, J = 8.79 Hz, 1H), 7.36 (dd, J = 8.67, 2.43 Hz, 1H), 7.47 (d, J = 2.54 Hz, 1H), 7.50-7.53 (m, 2H), 7.67 (s, 1H), 7.94-7.96 (m, 2H), 12.90 (brs, 1H) | 519 | 517 |
| 349 | (400 MHz, DMSO-D$_6$) 0.93 (d, J = 6.47 Hz, 6H), 1.55 (s, 3H), 1.65-1.60 (m, 2H), 1.75-1.86 (m, 1H), 2.18-2.28 (m, 2H), 2.32 (s, 6H), 2.42-2.55 (m, 2H), 2.66-2.75 (m, 1H), 4.07 (t, J = 6.59 Hz, 2H), 6.03 (d, J = 1.16 Hz, 1H), 7.13 (d, J = 8.70 Hz, 1H), 7.21 (s, 1H), 7.24 (dd, J = 8.70, 2.43 Hz, 1H), 7.35 (d, J = 2.43 Hz, 1H), 12.46 (brs, 1H) | 509 | 507 |
| 350 | (400 MHz, DMSO-D$_6$) 0.12-0.16 (m, 2H), 0.41-0.46 (m, 2H), 0.81-0.89 (m, 1H), 1.64 (t, J = 6.47 Hz, 2H), 1.68 (s, 3H), 2.21-2.37 (m, 2H), 2.54-2.74 (m, 3H), 4.12 (t, J = 6.47 Hz, 2H), 6.49 (d, J = 0.92 Hz, 1H), 7.16 (d, J = 8.70 Hz, 1H), 7.37 (dd, J = 8.70, 2.50 Hz, 1H), 7.47 (d, J = 2.50 Hz, 1H), 7.50-7.53 (m, 2H), 7.67 (s, 1H), 7.93-7.97 (m, 2H), 12.90 (brs, 1H) | 517 | 515 |
| 351 | (400 MHz, DMSO-D$_6$) 0.70 (d, J = 6.94 Hz, 3H), 0.95 (s, 9H), 1.35-1.41 (m, 2H), 1.56-1.77 (m, 11H), 1.99-2.06 (m, 1H), 2.61-2.65 (m, 2H), 3.11 (t, J = 8.90 Hz, 1H), 3.22 (s, 4H), 5.93 (s, 1H), 6.91 (s, 1H), 7.25-7.35 (m, 3H) | 503 | 501 |
| 352 | (400 MHz, DMSO-D$_6$) 0.95 (s, 10H), 1.03 (d, J = 6.70 Hz, 3H), 1.35-1.40 (m, 2H), 1.61-1.79 (m, 11H), 2.00-2.06 (m, 1H), 2.61-2.67 (m, 3H), 2.86-2.91 (m, 1H), 2.93 (s, 3H), 5.90 (s, 1H), 6.95 (s, 1H), 7.25-7.32 (m, 2H), 7.37 (d, J = 1.85 Hz, 1H) | 503 | 501 |
| 353 | (400 MHz, DMSO-D$_6$) 1.03 (s, 9H), 1.67 (s, 3H), 2.38-2.21 (m, 2H), 2.54-2.79 (m, 3H), 3.72 (s, 2H), 6.49 (d, J = 0.92 Hz, 1H), 7.12 (d, J = 8.79 Hz, 1H), 7.36 (dd J = 8.55, 2.31 Hz, 1H), 7.47 (d, J = 2.31 Hz, 1H), 7.50-7.53 (m, 2H), 7.67 (s, 1H), 7.93-7.97 (m, 2H), 12.90 (brs, 1H) | 519 | 517 |
| 354 | (400 MHz, DMSO-D$_6$) 0.16-0.12 (m, 2H), 0.45-0,41 (m, 2H), 0.81-0.88 (m, 1H), 1.56 (s, 3H), 1.61-1.67 (m, 2H), 2.19-2.28 (m, 2H), 2.32 (s, 6H), 2.44-2.57 (m, 2H), 2.66-2,74 (m, 1H), 4.10 (t, J = 6.47 Hz, 2H), 6.03 (d, J = 1.16 Hz, 1H), 7.12 (d, J = 8.79 Hz, 1H), 7.21 (s, 1H), 7.24 (dd, J = 8.67, 2.43 Hz, 1H), 7.35 (d J = 2.54 Hz, 1H), 12.44 (brs, 1H) | 507 | 505 |
| 355 | (400 MHz, DMSO-D$_6$) 1.02 (s, 9H), 1.55 (s, 3H), 2.28-2.19 (m, 2H), 2.32 (s, 6H), 2.44-2.52 (m, 2H), 2.66-2.74 (m, 1H), 3.70 (s, 2H), 6.04 (d, J = 1.16 Hz, 1H), 7.08 (d, J = 8.55 Hz, 1H), 7.21 (s, 1H), 7.23 (dd, J = 8.55, 2.31 Hz, 1H), 7.35 (d, J = 2.31 Hz, 1H), 12.44 (brs, 1H) | 509 | 507 |
| 356 | (400 MHz, DMSO-D$_6$) 0.70-0.76 (m, 3H), 0.94 (s, 9H), 1.06-1.11 (m, 3H), 1.37-1.46 (m, 2H), 1.71 (s, 3H), 2.02-2.10 (m, 1H), 2.52-2.61 (m, 2H), 6.26 (s, 1H), 7.14-7.21 (m, 3H), 7.21-7.27 (m, 1H), 7.27-7.34 (m, 1H), 7.80-7.87 (m, 2H) | 453 | 451 |
| 357 | (400 MHz, DMSO-D$_6$) 1.55 (s, 3H), 1.73-1.64 (m, 2H), 1.76-1.87 (m, 4H), 2.01-2.08 (m, 2H), 2.17-2.28 (m, 2H), 2.32 (s, 6H), 2.41-2.51 (m, 3H), 2.66-2.74 (m, 1H), 3.98 (t, J = 6.47 Hz, 2H), 6.03 (d, J = 1.16 Hz, 1H), 7.09 (d, J = 8.79 Hz, 1H), 7.21 (s, 1H), | 521 | 519 |

TABLE 4-continued

| | | MS | |
|---|---|---|---|
| Example | $^1$H-NMR | M + H or M—Na + H | M − H or M—Na − H |
| | 7.23 (dd, J = 8.67, 2.43 Hz, 1H), 7.34 (d, J = 2.31 Hz, 1H), 12.45 (brs, 1H) | | |

Formulation examples of the present invention include for example the following, but the present invention should not be construed as being limited thereto.

| 1) Compound of Example 1 | 30 mg |
|---|---|
| 2) Microcrystalline cellulose | 10 mg |
| 3) Lactose | 19 mg |
| 4) Magnesium stearate | 1 mg |

1), 2), 3), and 4) are mixed and filled in a gelatin capsule.

Formulation Example 1

Preparation of a Capsule

| 1) Compound of Example 1 | 10 g |
|---|---|
| 2) Lactose | 50 g |
| 3) Corn starch | 15 g |
| 4) Carmellose calcium | 44 g |
| 5) Magnesium stearate | 1 g |

The entire amounts of 1), 2) and 3) and 30 g of 4) are mixed with water and dried in vacuo and then granulated. The granulated powder is mixed with 14 g of 4) and 1 g of 5) and tableted by a tableting machine. In this way, 1000 tablets can be obtained, each of which contains 10 mg of Compound of Example 1.

Test Example 1

Pharmacological effects of the typical compounds of the present invention were observed.

In Vitro Assay of Inhibitory Effect Against RORγ Transcriptional Activity

Inhibitory effect of a test article on transcriptional activity of RORγ was measured by means of the following reporter gene assay.

cDNA encoding human and mouse RORγ ligand binding domain (LBD) were obtained based on the sequences of human RORγ (Genebank registered number NM_005060.3) and mouse RORγ (Genebank registered number NM_011281.2) (LBD sequence: human RORγ, from Ser253 to Lys518; mouse RORγ, from Ile251 to Lys516).

The LBD cDNA of human or mouse RORγ was inserted into pFA-CMV vector (Strategene), which expresses GAL4-DNA binding domain fusion protein. The resulting plasmids are hereinafter referred to as GAL4-hRORγ plasmid and GAL4-mRORγ plasmid, respectively.

GAL4-hRORγ plasmid or GAL4-mRORγ plasmid was transiently co-transfected into Chinese hamster ovary cells (CHO cells) with pG5-Luc (Promega), a reporter plasmid expressing firefly luciferase depending on GAL4.

TransIT (Registered trademark) CHO transfection reagent (Mirus) was used to co-transfect GAL4-hRORγ plasmid or GAL4-mRORγ plasmid into CHO cells with pG5-Luc plasmid. One day before the assay, CHO cells were suspended in HAM F-12 Nutrient medium containing 10 v/v % fetal bovine serum and seeded at $6\times10^6$ cells per 175 cm$^2$ cell culture flask. Fifty four micro litters of TransIT (Registered trademark) CHO reagent was added into a 15 ml tube containing 1.16 mL of HAM F-12 Nutrient medium without fetal bovine serum, and mixed and incubated at room temperature for 10 min. Thirty six micro litters of plasmid solution containing the GAL4-hRORγ plasmid (400 ng), pG5-Luc plasmid (9000 ng) and pcDNA3 plasmid (8600 ng) were added into the tube and mixed gently. In case of mouse assay, a plasmid solution containing the GAL4-mRORγ plasmid (250 ng), pG5-Luc plasmid (9000 ng) and pcDNA3 plasmid (8750 ng) was added, instead. The mixture was incubated at room temperature for 10 min. Nine micro litters of CHO Mojo Reagent were then added into each tube and mixed gently. The mixture was incubated at room temperature for 10 min. The resultant transfection reagent was applied to the cell culture. After incubation at 37° C., 5% $CO_2$ for 4 hours, the plasmid-transfected CHO cells were harvested with a trypsin treatment. The collected cells were resuspended in HAM F-12 Nutrient medium supplemented with 10 v/v % fetal bovine serum and plated into a 384-well-white plate at 8,000 cells/50 μL/well. The plate was incubated at room temperature for 1 hour and then further incubated at 37° C., 5% $CO_2$ for 3 hours. The test articles were dissolved in dimethylsulfoxide (DMSO) to obtain a concentration of 10 mM. The resulting solution was diluted with a medium just before use and added to the cells in the plate to prepare 8 different concentrations of the test article. The final concentration of DMSO was 0.2 v/v %. After the addition of the test articles, the cells were incubated at 37° C., 5% $CO_2$ for 2 days.

Cell viability was tested by a fluorescence method using Resazurin (invitrogen). Two days after the addition of the test article, Resazurin was diluted with a medium to make the 20 μM resazurin solution. Ten micro litters of the diluted Resazurin solution was added into the 384-well-plate. Then, the fluorescence was measured immediately at 615 nm with the excitation wavelength of 570 nm (0 hr reading). After incubation at 37° C., 5% $CO_2$ for 2 hours, the fluorescence was measured at 615 nm with the excitation wavelength of 570 nm again (2 hour reading). The fluorescence counts (2 hr–0 hr) were calculated by subtracting the 0 hr readings from the 2 hr readings. The luminescence count (2 h-0 h) in the cells treated with 0.2% DMSO alone was defined as 100%, and the cell viability in the test article was calculated as a percentage (%-of-control) based on the value of 0.2% DMSO alone. When the cell viability is 70% or less, it was judged that the test article has cytotoxicity.

RORγ transcriptional activity was detected as the intracellular luciferase activity using SteadyLite HTS Reporter Gene Assay System (Perkin Elmer). StedyLite Reagent was diluted five-fold into a solution containing Extension reagent (10 mM Tricine, 0.2% w/v BSA, 0.02% v/v Tween-20) to obtain the luciferase substrate solution. After the measurement of the cell viability using Resazurin, the culture media in the plate were removed, and then the luciferase substrate solution was added into each well. After the incubation at room temperature for 10 minutes, luminescence of each well was measured by a microplate reader. The luciferase activity derived from the luminescence count in the vehicle-control well treated with 0.2% DMSO alone was defined as 100%, and the luciferase activity in the test article was calculated as a percentage (%-of-control) based on the value of the vehicle-control. $EC_{50}$ value of test article was calculated by curve fitting with GraphPad Prism. The luminescence counts at the concentration of the test article where the cytotoxicity was observed were excluded from the data analysis.

The results are shown in the table below.

The values with % is the activity of the test article which was calculated as a percentage (%-of-control) based on the value of the vehicle-control treated with 0.2% DMSO alone (100%).

In the following table, compounds of Examples 38, 87, and 116 were synthesized by a preparation method using Claisen reaction and measured.

TABLE 5

| Example | LUC $EC_{50}$ (μM) | |
| --- | --- | --- |
| | hRORγ | mRORγ |
| 1 | 0.088 | 0.060 |
| 2 | >20 (55%) | 13.060 |
| 3 | 0.182 | 0.061 |
| 4 | 1.443 | 0.675 |
| 5 | 0.034 | 0.024 |
| 6 | >8 (76%) | >8 (75%) |
| 7 | 0.152 | 0.110 |
| 8 | 0.021 | 0.022 |
| 9 | 0.055 | 0.032 |
| 10 | 0.009 | 0.017 |
| 11 | >8 (87%) | >8 (79%) |
| 12 | 0.023 | 0.017 |
| 13 | 6.572 | 5.926 |
| 14 | >8 (69%) | >8 (59%) |
| 15 | 0.012 | 0.012 |
| 16 | 0.362 | 0.137 |
| 17 | 0.206 | 0.153 |
| 18 | 0.051 | 0.028 |
| 19 | 2.285 | 1.209 |
| 20 | 2.935 | 2.519 |
| 21 | 0.019 | 0.024 |
| 22 | 0.017 | 0.029 |
| 23 | 0.042 | 0.041 |
| 24 | 2.938 | 2.934 |
| 25 | <0.032 | <0.032 |
| 26 | 0.364 | 0.217 |
| 27 | 0.025 | 0.016 |
| 28 | 0.187 | 0.082 |
| 29 | 0.036 | 0.049 |
| 30 | 0.060 | 0.047 |
| 31 | 3.074 | >3.2 (52%) |
| 32 | 0.026 | 0.046 |
| 33 | 0.435 | 0.617 |
| 34 | 0.013 | 0.021 |
| 35 | >3.2 (51%) | >3.2 (52%) |
| 36 | 0.021 | 0.024 |
| 37 | 0.154 | 0.282 |
| 38 | 0.011 | 0.015 |
| 39 | 0.020 | 0.026 |
| 40 | 0.152 | 0.198 |
| 41 | >8 (59%) | >8 (61%) |
| 42 | 0.031 | 0.028 |
| 43 | 0.564 | 0.835 |
| 44 | 0.051 | 0.090 |
| 45 | 7.330 | 7.508 |
| 46 | 0.017 | 0.016 |
| 47 | 1.103 | 0.764 |
| 48 | 0.012 | 0.016 |
| 49 | 0.983 | 0.832 |
| 50 | 0.007 | 0.013 |
| 51 | 1.181 | 1.083 |
| 52 | 0.010 | 0.015 |
| 53 | 0.036 | 0.021 |
| 54 | >8 (92%) | >8 (81%) |
| 55 | 0.022 | 0.026 |
| 56 | 5.163 | 4.291 |
| 57 | 0.031 | 0.022 |
| 58 | 1.249 | 1.654 |
| 59 | 0.012 | 0.020 |
| 60 | 15.270 | 12.430 |
| 61 | 0.143 | 0.046 |
| 62 | 0.665 | 0.520 |
| 63 | >8 (51%) | >8 (70%) |
| 64 | 0.019 | 0.016 |
| 65 | 0.028 | 0.021 |
| 66 | 3.609 | 2.681 |
| 67 | 0.023 | 0.017 |
| 68 | 1.236 | 1.756 |
| 69 | 0.020 | 0.017 |
| 70 | 0.251 | 0.133 |
| 71 | 0.505 | 0.758 |
| 72 | 0.013 | 0.017 |
| 73 | 0.803 | 0.657 |
| 74 | 0.986 | 1.103 |
| 75 | 0.296 | 0.316 |
| 76 | 3.472 | 6.358 |
| 77 | 0.015 | 0.024 |
| 78 | 6.490 | 10.760 |
| 79 | 0.016 | 0.018 |
| 80 | 0.016 | 0.017 |
| 81 | 2.579 | 2.487 |
| 82 | 0.980 | 0.790 |
| 83 | 0.040 | 0.043 |
| 84 | 0.746 | 0.502 |
| 85 | 0.545 | 0.368 |
| 86 | 6.770 | >8 (51%) |
| 87 | 0.011 | 0.015 |
| 88 | 0.443 | 0.422 |
| 89 | 0.016 | 0.016 |
| 90 | 0.015 | 0.018 |
| 91 | 0.539 | 1.152 |
| 92 | 0.013 | 0.020 |
| 93 | 2.144 | 2.544 |
| 94 | 0.152 | 0.142 |
| 95 | >3.2 (66%) | 5.685 |
| 96 | 0.033 | 0.026 |
| 97 | 1.344 | 3.097 |
| 98 | 0.013 | 0.018 |
| 99 | 1.507 | 2.886 |
| 100 | 0.020 | 0.035 |
| 101 | 0.032 | 0.021 |
| 102 | >8 (76%) | >8 (76%) |
| 103 | >3.2 (65%) | >3.2 (50%) |
| 104 | 0.050 | 0.031 |
| 105 | 2.792 | 1.691 |
| 106 | 1.162 | 0.616 |
| 107 | 3.930 | 1.976 |
| 108 | 0.016 | 0.021 |
| 109 | >8 (60%) | >8 (67%) |
| 110 | 0.011 | 0.010 |
| 111 | 0.405 | 0.481 |
| 112 | 0.021 | 0.019 |
| 113 | 3.031 | 1.399 |
| 114 | 14.880 | 10.960 |
| 115 | >8 (110%) | >8 (100%) |
| 116 | 0.015 | 0.022 |
| 117 | >3.2 (106%) | >8 (76%) |
| 118 | 0.019 | 0.017 |
| 119 | >8 (74%) | >8 (76%) |
| 120 | 0.061 | 0.014 |
| 121 | >8 (62%) | >8 (85%) |
| 122 | 0.028 | 0.015 |
| 123 | >3.2 (109%) | >3.2 (100%) |
| 124 | >0.512 (54%) | 0.030 |
| 125 | <0.032 | <0.032 |
| 126 | 0.037 | 0.027 |

TABLE 5-continued

| Example | LUC EC$_{50}$(μM) hRORγ | LUC EC$_{50}$(μM) mRORγ |
|---|---|---|
| 127 | 2.940 | 1.950 |
| 128 | >20 (66%) | >20 (54%) |
| 129 | 0.047 | <0.032 |
| 130 | 0.010 | 0.019 |
| 131 | >8 (77%) | >8 (81%) |
| 132 | 0.018 | 0.014 |
| 133 | >8 (71%) | >8 (88%) |
| 134 | 0.070 | 0.027 |
| 135 | >8 (90%) | >8 (84%) |
| 136 | 0.094 | 0.049 |
| 137 | 0.015 | 0.011 |
| 138 | >8 (85%) | >8 (96%) |
| 139 | >0.512 (110%) | 0.027 |
| 140 | 0.209 | 0.139 |
| 141 | >8 (57%) | >8 (52%) |
| 142 | >0.512 (102%) | 0.049 |
| 143 | >8 (90%) | >8 (100%) |
| 144 | >0.512 (60%) | 0.037 |
| 145 | 2.038 | 3.973 |
| 146 | 0.014 | 0.012 |
| 147 | 0.059 | 0.030 |
| 148 | >8 (57%) | >8 (69%) |
| 149 | 1.014 | 0.245 |
| 150 | 0.021 | 0.012 |
| 151 | 0.018 | 0.023 |
| 152 | >20 (56%) | >20 (57%) |
| 153 | 0.327 | 0.116 |
| 154 | 0.010 | 0.014 |
| 155 | >8 (83%) | >8 (81%) |
| 156 | 0.520 | 0.166 |
| 157 | 0.497 | 0.255 |
| 158 | 0.030 | 0.023 |
| 159 | 0.021 | 0.023 |
| 160 | 0.015 | 0.040 |
| 161 | 0.154 | 0.047 |
| 162 | 0.172 | 0.275 |
| 163 | 0.143 | 0.267 |
| 164 | 0.018 | 0.011 |
| 165 | 0.027 | 0.017 |
| 166 | 0.014 | 0.029 |
| 167 | 0.065 | 0.049 |
| 168 | 0.012 | 0.018 |
| 169 | 0.008 | 0.015 |
| 170 | 0.058 | 0.040 |
| 171 | 0.012 | 0.014 |
| 172 | 0.013 | 0.018 |
| 173 | 0.022 | 0.011 |
| 174 | 0.014 | 0.011 |
| 175 | 0.009 | 0.012 |
| 176 | 0.022 | 0.013 |
| 177 | 0.017 | 0.017 |
| 178 | 0.019 | 0.021 |
| 179 | 0.064 | 0.027 |
| 180 | 0.032 | 0.050 |
| 181 | 0.018 | 0.032 |
| 182 | 0.027 | 0.076 |
| 183 | 0.118 | 0.078 |
| 184 | 0.011 | 0.022 |
| 185 | 0.009 | 0.014 |
| 186 | 0.091 | 0.116 |
| 187 | 0.172 | 0.063 |
| 188 | 2.606 | 1.129 |
| 189 | 0.030 | 0.022 |

TABLE 6

| Example | LUC EC$_{50}$(μM) hRORγ | LUC EC$_{50}$(μM) mRORγ |
|---|---|---|
| 190 | >8 (74%) | >8 (66%) |
| 191 | 0.045 | 0.071 |
| 192 | 0.017 | 0.011 |
| 193 | 0.018 | 0.019 |
| 194 | 0.058 | 0.028 |
| 195 | 0.018 | 0.012 |
| 196 | 0.009 | 0.017 |
| 197 | 0.013 | 0.023 |
| 198 | 0.012 | 0.026 |
| 199 | 0.070 | 0.136 |
| 200 | 0.014 | 0.023 |
| 201 | 0.060 | 0.051 |
| 202 | 0.087 | 0.052 |
| 203 | 0.030 | 0.021 |
| 204 | 0.014 | 0.017 |
| 205 | 0.281 | 0.427 |
| 206 | 0.081 | 0.117 |
| 207 | 0.009 | 0.018 |
| 208 | 0.021 | 0.040 |
| 209 | 0.051 | 0.074 |
| 210 | 0.006 | 0.007 |
| 211 | 0.011 | 0.008 |
| 212 | >8 (68%) | >8 (81%) |
| 213 | 0.131 | 0.056 |
| 214 | 0.169 | 0.100 |
| 215 | >20 (77%) | >20 (70%) |
| 216 | >20 (86%) | >20 (76%) |
| 217 | >20 (90%) | >20 (77%) |
| 218 | 0.376 | 0.122 |
| 219 | >20 (88%) | >20 (86%) |
| 220 | 0.022 | 0.029 |
| 221 | 0.025 | 0.024 |
| 222 | 0.020 | 0.040 |
| 223 | >20 (78%) | >20 (70%) |
| 224 | 0.343 | 0.123 |
| 225 | 0.101 | 0.072 |
| 226 | 0.017 | 0.020 |
| 227 | >20 (89%) | >20 (87%) |
| 228 | 0.032 | 0.032 |
| 229 | 0.009 | 0.018 |
| 230 | 0.225 | 0.076 |
| 231 | 0.692 | 0.458 |
| 232 | 0.015 | 0.019 |
| 233 | 0.069 | 0.072 |
| 234 | 0.964 | 0.534 |
| 235 | >3.2 (70%) | 1.610 |
| 236 | 0.020 | 0.015 |
| 237 | 0.719 | 0.673 |
| 238 | 0.715 | 0.666 |
| 239 | 4.562 | 3.065 |
| 240 | 0.108 | 0.147 |
| 241 | 0.112 | 0.247 |
| 242 | 0.078 | 0.058 |
| 243 | 1.219 | 0.543 |
| 244 | 0.176 | 0.269 |
| 245 | 0.261 | 0.301 |
| 246 | 0.010 | 0.022 |
| 247 | 0.018 | 0.016 |
| 248 | 0.010 | 0.021 |
| 249 | 0.412 | 0.779 |
| 250 | 0.042 | 0.114 |
| 251 | 0.013 | 0.028 |
| 252 | 0.020 | 0.028 |
| 253 | 0.075 | 0.034 |
| 254 | 0.028 | 0.028 |
| 255 | 0.273 | 0.296 |
| 256 | 0.022 | 0.026 |
| 257 | 0.165 | 0.115 |
| 258 | 0.022 | 0.016 |
| 259 | 0.057 | 0.043 |
| 260 | 0.439 | 0.492 |
| 261 | >20 (90%) | >20 (100%) |
| 262 | 0.022 | 0.022 |
| 263 | 0.026 | 0.018 |
| 264 | 0.045 | 0.033 |
| 265 | 0.037 | 0.071 |
| 266 | 0.012 | 0.017 |
| 267 | 0.030 | 0.033 |
| 268 | 0.015 | 0.014 |

TABLE 6-continued

| | LUC EC$_{50}$(μM) | |
|---|---|---|
| Example | hRORγ | mRORγ |
| 269 | 0.019 | 0.023 |
| 270 | 0.052 | 0.026 |
| 271 | 0.043 | 0.047 |
| 272 | 0.017 | 0.036 |
| 273 | 0.025 | 0.075 |
| 274 | 0.008 | 0.008 |
| 275 | 0.542 | 1.215 |
| 276 | 0.028 | 0.047 |
| 277 | 0.023 | 0.038 |
| 278 | 0.013 | 0.013 |
| 279 | 0.016 | 0.022 |
| 280 | 0.026 | 0.042 |
| 281 | 0.014 | 0.021 |
| 282 | 0.378 | 0.187 |
| 283 | 0.018 | 0.028 |
| 284 | 2.785 | 1.503 |
| 285 | 1.353 | 0.030 |
| 286 | 0.270 | 0.038 |
| 287 | 0.036 | 0.034 |
| 288 | 1.491 | 0.917 |
| 289 | 1.117 | 0.773 |
| 290 | 0.463 | 0.259 |
| 291 | 1.085 | 0.138 |
| 292 | 0.089 | 0.073 |
| 293 | 1.095 | 1.019 |
| 294 | 0.068 | 0.034 |
| 295 | 0.134 | 0.366 |
| 296 | 3.721 | 4.533 |
| 297 | 0.044 | 0.061 |
| 298 | 0.022 | 0.018 |
| 299 | 0.011 | 0.016 |
| 300 | 0.010 | 0.014 |
| 301 | 0.027 | 0.010 |
| 302 | 0.028 | 0.030 |
| 303 | 1.399 | 1.308 |
| 304 | 0.021 | 0.019 |
| 305 | 0.003 | 0.006 |
| 306 | 0.063 | 0.027 |
| 307 | 0.005 | 0.013 |
| 308 | 0.032 | 0.025 |
| 309 | >3.2 (63%) | 0.071 |
| 310 | 0.476 | 0.277 |
| 311 | 0.086 | 0.094 |
| 312 | 0.248 | 0.538 |
| 313 | 0.260 | 0.366 |
| 314 | 0.038 | 0.032 |
| 315 | 0.013 | 0.019 |
| 316 | 0.018 | 0.019 |
| 317 | 0.040 | 0.024 |
| 318 | 0.017 | 0.014 |
| 319 | 0.013 | 0.014 |
| 320 | 0.023 | 0.027 |
| 321 | 0.060 | 0.048 |
| 322 | 0.021 | 0.019 |
| 323 | 0.051 | 0.023 |
| 324 | 0.047 | 0.036 |
| 325 | 0.174 | 0.060 |
| 326 | 0.032 | 0.036 |
| 327 | 0.058 | 0.040 |
| 328 | 0.035 | 0.019 |
| 329 | 0.074 | 0.050 |
| 330 | 0.019 | 0.014 |
| 331 | 0.014 | 0.008 |
| 332 | 0.012 | 0.013 |
| 333 | 0.023 | 0.013 |
| 334 | 0.022 | 0.014 |
| 335 | 0.026 | 0.011 |
| 336 | 0.010 | 0.007 |
| 337 | 0.022 | 0.014 |
| 338 | 0.013 | 0.012 |
| 339 | 0.017 | 0.015 |
| 340 | 0.123 | 0.043 |
| 341 | 0.067 | 0.032 |
| 342 | 0.043 | 0.028 |
| 343 | 0.038 | 0.019 |
| 344 | 0.013 | 0.012 |
| 345 | 0.042 | 0.023 |
| 346 | 0.026 | 0.018 |
| 347 | 0.109 | 0.035 |
| 348 | 0.046 | 0.039 |
| 349 | 0.063 | 0.045 |
| 350 | 0.109 | 0.052 |
| 351 | 0.004 | 0.011 |
| 352 | 0.063 | 0.051 |
| 353 | 0.059 | 0.045 |
| 354 | 0.239 | 0.144 |
| 355 | 0.113 | 0.052 |
| 356 | 0.021 | 0.015 |
| 357 | 0.034 | 0.029 |

INDUSTRIAL APPLICABILITY

The compound of Formula [I] or a pharmaceutically acceptable salt thereof is useful in treating or preventing autoimmune disease such as rheumatoid arthritis, psoriasis, inflammatory bowel disease such as Crohn's disease and ulcerative colitis, multiple sclerosis, systemic lupus erythematosus, ankylosing spondylitis, uveitis, polymyalgia rheumatica, type I diabetes, and graft versus host disease; allergic disease such as asthma; dry eye; fibrosis such as pulmonary fibrosis and primary biliary cirrhosis; and metabolic disease such as diabetes.

The invention claimed is:
1. A compound selected from the group consisting of:

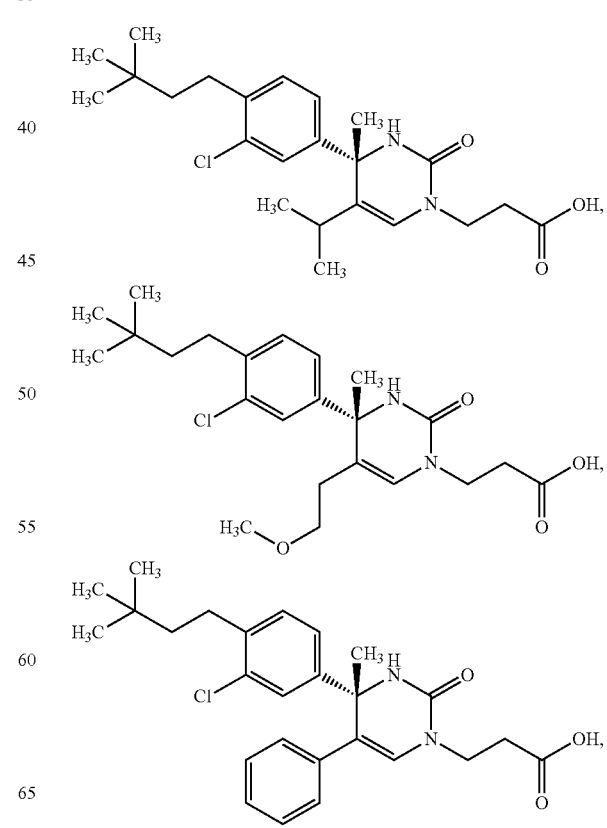

-continued

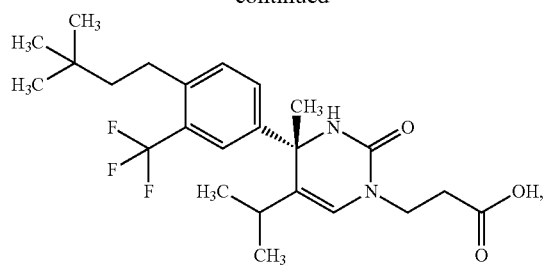

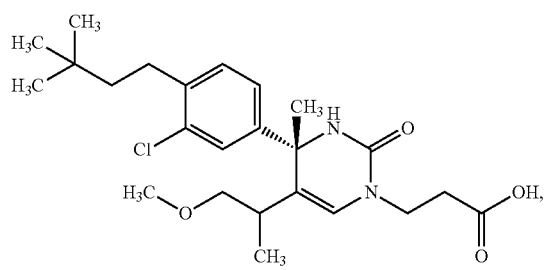

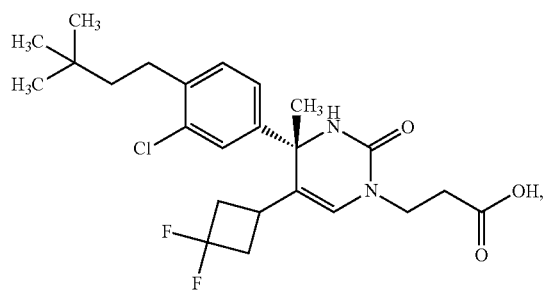

and

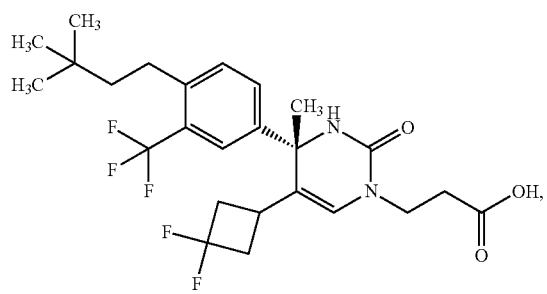

or a pharmaceutically acceptable salt of any of the foregoing.

2. The compound of claim 1, wherein the compound is:

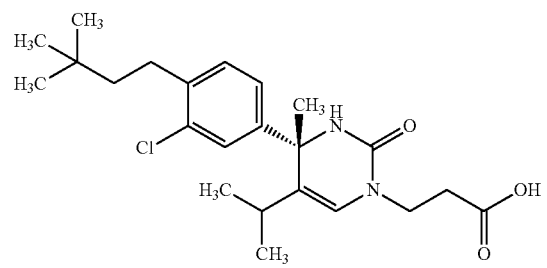 [SMILES: CC(C)C1=CN(CCC(=O)O)C(=O)N[C@@]1(C)c1ccc(CCC(C)(C)C)c(Cl)c1]

or a pharmaceutically acceptable salt thereof.

3. The compound of claim 1, wherein the compound is:

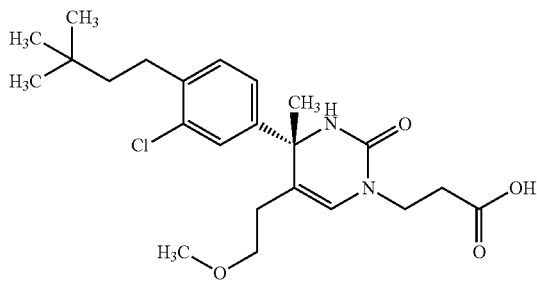 [SMILES: COCCC1=CN(CCC(=O)O)C(=O)N[C@@]1(C)c1ccc(CCC(C)(C)C)c(Cl)c1]

or a pharmaceutically acceptable salt thereof.

4. The compound of claim 1, wherein the compound is:

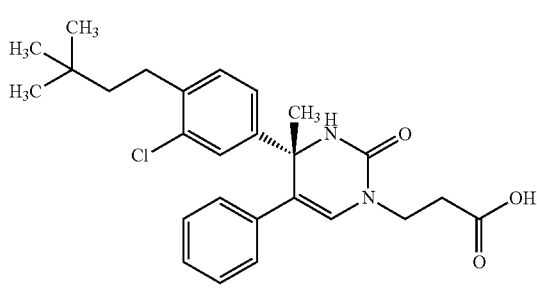 [SMILES: CC(C)(C)CCc1ccc([C@]2(C)NC(=O)N(CCC(=O)O)C=C2c2ccccc2)cc1Cl]

or a pharmaceutically acceptable salt thereof.

5. The compound of claim 1, wherein the compound is:

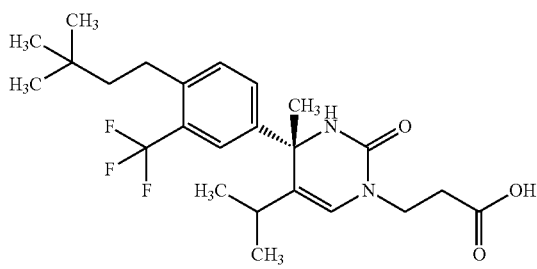 [SMILES: CC(C)C1=CN(CCC(=O)O)C(=O)N[C@@]1(C)c1ccc(CCC(C)(C)C)c(C(F)(F)F)c1]

or a pharmaceutically acceptable salt thereof.

6. The compound of claim 1, wherein the compound is:

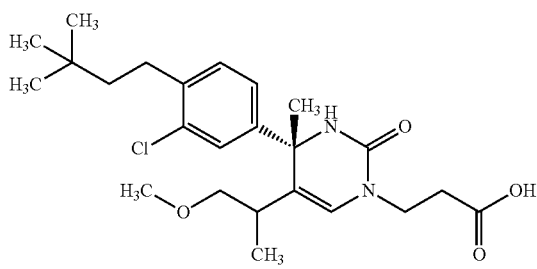 [SMILES: COCC(C)C1=CN(CCC(=O)O)C(=O)N[C@@]1(C)c1ccc(CCC(C)(C)C)c(Cl)c1]

or a pharmaceutically acceptable salt thereof.

7. The compound of claim 1, wherein the compound is:

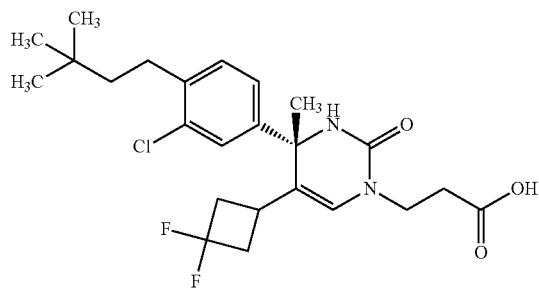 [SMILES: CC(C)(C)CCc1ccc([C@]2(C)NC(=O)N(CCC(=O)O)C=C2C2CC(F)(F)C2)cc1Cl]

or a pharmaceutically acceptable salt thereof.

8. The compound of claim 1, wherein the compound is:

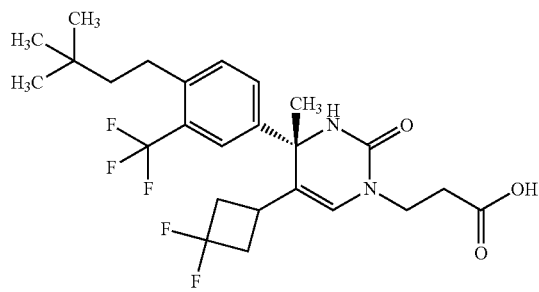 [SMILES: CC(C)(C)CCc1ccc([C@]2(C)NC(=O)N(CCC(=O)O)C=C2C2CC(F)(F)C2)cc1C(F)(F)F]

or a pharmaceutically acceptable salt thereof.

9. A pharmaceutical composition comprising a compound of claims 1 and 2-8, or a pharmaceutically acceptable salt thereof, and a pharmaceutically acceptable carrier.

10. A method of treating an autoimmune disease selected from the group consisting of rheumatoid arthritis, psoriasis, inflammatory bowel disease, multiple sclerosis, systemic lupus erythematosus, ankylosing spondylitis, uveitis, polymyalgia rheumatica, type I diabetes, and graft versus host disease comprising administering to a human an effective amount of a compound of any one of claims 1 and 2-8, or a pharmaceutically acceptable salt thereof.

11. The method of claim 10, wherein the autoimmune disease is inflammatory bowel disease wherein the inflammatory bowel disease is Crohn's disease.

12. The method of claim 10, wherein the autoimmune disease is inflammatory bowel disease wherein the inflammatory bowel disease is ulcerative colitis.

13. A method of treating diabetes comprising administering to a human an effective amount of a compound of any one of claims 1 and 2-8, or a pharmaceutically acceptable salt thereof.

14. The method of claim 10, wherein the autoimmune disease is psoriasis.

15. A compound selected from the group consisting of:

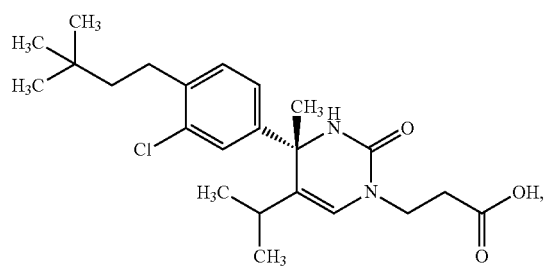 [SMILES: CC(C)C1=CN(CCC(=O)O)C(=O)N[C@@]1(C)c1ccc(CCC(C)(C)C)c(Cl)c1]

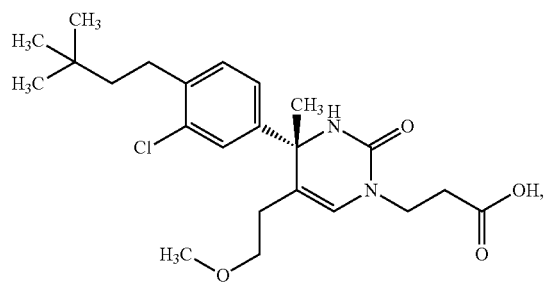 [SMILES: COCCC1=CN(CCC(=O)O)C(=O)N[C@@]1(C)c1ccc(CCC(C)(C)C)c(Cl)c1]

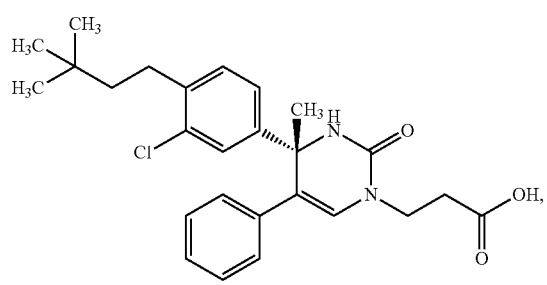 [SMILES: CC(C)(C)CCc1ccc([C@]2(C)NC(=O)N(CCC(=O)O)C=C2c2ccccc2)cc1Cl]

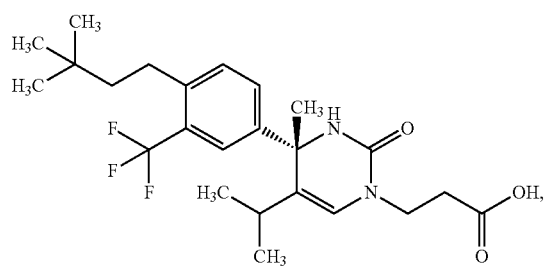 [SMILES: CC(C)C1=CN(CCC(=O)O)C(=O)N[C@@]1(C)c1ccc(CCC(C)(C)C)c(C(F)(F)F)c1]

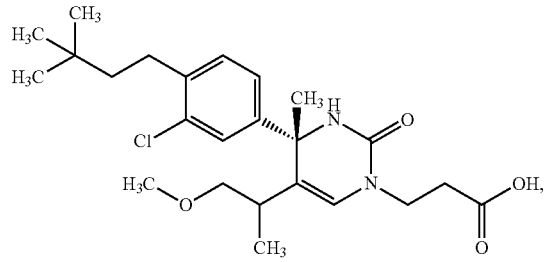

-continued
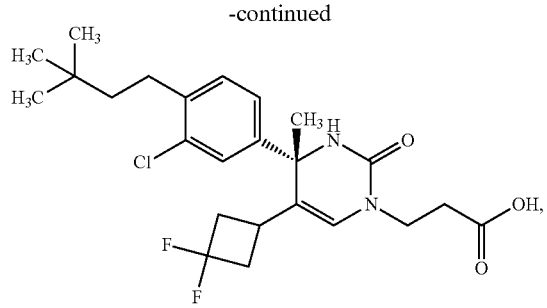
and
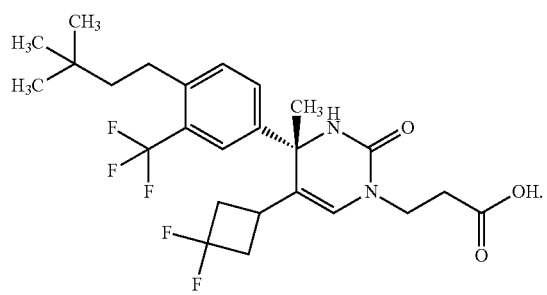 [SMILES: CC(C)(C)CCc1ccc([C@]2(C)NC(=O)N(CCC(=O)O)C=C2C2CC(F)(F)C2)cc1C(F)(F)F]
16. The compound of claim 15, wherein the compound is:
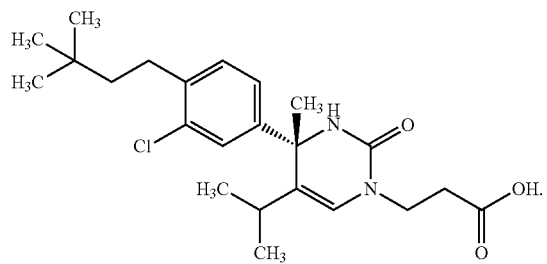
17. The compound of claim 15, wherein the compound is:
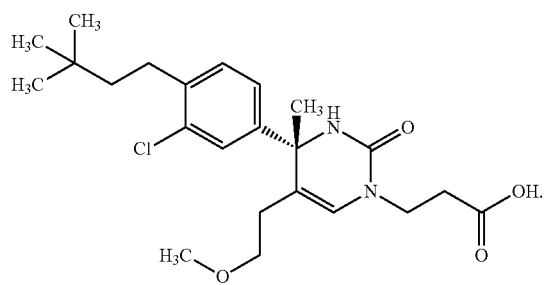
18. The compound of claim 15, wherein the compound is:
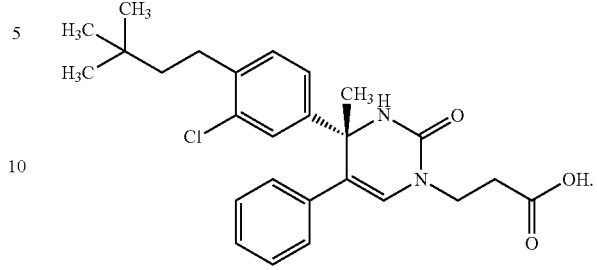
19. The compound of claim 15, wherein the compound is:
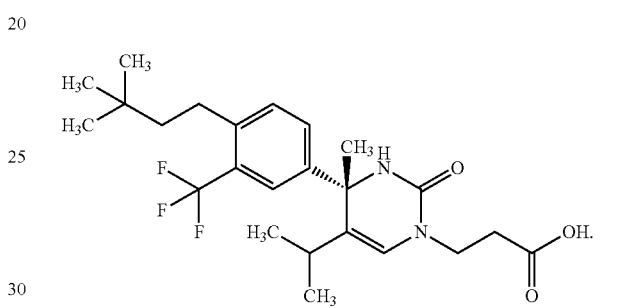
20. The compound of claim 15, wherein the compound is:
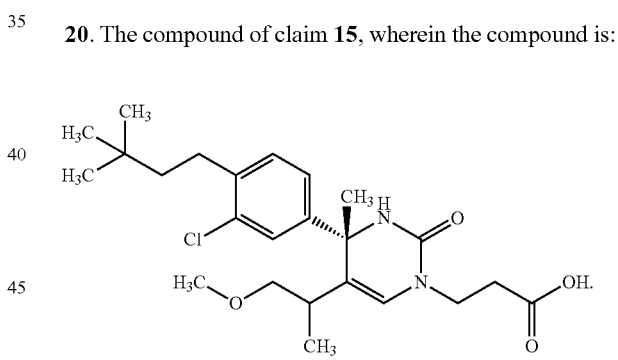
21. The compound of claim 15, wherein the compound is:
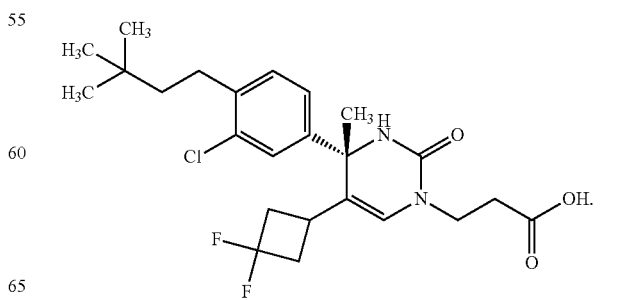

22. The compound of claim 15, wherein the compound is:

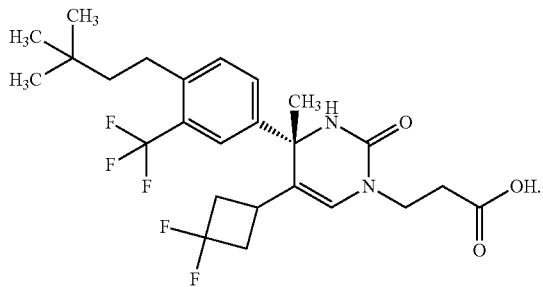

23. A pharmaceutical composition comprising a compound of any one of claims 15-22, and a pharmaceutically acceptable carrier.

24. A method of treating an autoimmune disease selected from the group consisting of rheumatoid arthritis, psoriasis, inflammatory bowel disease, multiple sclerosis, systemic lupus erythematosus, ankylosing spondylitis, uveitis, polymyalgia rheumatica, type I diabetes, and graft versus host disease comprising administering to a human an effective amount of a compound of any one of claims 15-22.

25. The method of claim 24, wherein the autoimmune disease is inflammatory bowel disease wherein the inflammatory bowel disease is Crohn's disease.

26. The method of claim 24, wherein the autoimmune disease is inflammatory bowel disease wherein the inflammatory bowel disease is ulcerative colitis.

27. The method of claim 24, wherein the autoimmune disease is psoriasis.

28. A method of treating diabetes comprising administering to a human an effective amount of a compound of any one of claims 15-22.

* * * * *